(12) United States Patent
Barawkar et al.

(10) Patent No.: US 9,115,133 B2
(45) Date of Patent: Aug. 25, 2015

(54) SUBSTITUTED FUSED TRICYCLIC COMPOUNDS, COMPOSITIONS AND MEDICINAL APPLICATIONS THEREOF

(75) Inventors: Dinesh Barawkar, Hinjewadi (IN); Tanushree Bende, Pune (IN); Robert Zahler, Pennington, NJ (US); Anish Bandyopadhyay, Pune (IN); Robindro Singh Sarangthem, Pune (IN); Jignesh Doshi, Pune (IN); Yogesh Waman, Pune (IN); Rushikesh Jadhav, Pune (IN); Umesh Prasad Singh, Pune (IN)

(73) Assignee: Advinus Therapeutics Limited, Bangalore, IN (US)

( * ) Notice: Subject to any disclaimer, the term of this patent is extended or adjusted under 35 U.S.C. 154(b) by 0 days.

(21) Appl. No.: 14/006,630

(22) PCT Filed: Mar. 21, 2012

(86) PCT No.: PCT/IN2012/000191
§ 371 (c)(1),
(2), (4) Date: Sep. 20, 2013

(87) PCT Pub. No.: WO2012/127506
PCT Pub. Date: Sep. 27, 2012

(65) Prior Publication Data
US 2014/0023614 A1    Jan. 23, 2014

(30) Foreign Application Priority Data
Mar. 22, 2011   (IN) .............................. 891/CHE/2011

(51) Int. Cl.
| C07D 471/14 | (2006.01) |
| A61K 31/4375 | (2006.01) |
| A61K 31/5025 | (2006.01) |
| A61K 31/5377 | (2006.01) |
| A61K 31/519 | (2006.01) |

(Continued)

(52) U.S. Cl.
CPC .......... *C07D 471/14* (2013.01); *A61K 31/4375* (2013.01); *A61K 31/496* (2013.01); *A61K 31/5025* (2013.01); *A61K 31/519* (2013.01); *A61K 31/5377* (2013.01); *A61K 45/06* (2013.01)

(58) Field of Classification Search
CPC .......................... C07D 471/14; A61K 31/4375
USPC .............................. 514/293; 546/82
See application file for complete search history.

(56) References Cited
U.S. PATENT DOCUMENTS
2010/0048552 A1 *  2/2010  Ren et al. .................... 514/232.8
2010/0239526 A1 *  9/2010  Ali et al. ...................... 424/85.4
2011/0311474 A1 * 12/2011  Wishart et al. ............... 424/85.2

FOREIGN PATENT DOCUMENTS
WO       WO0056719       *  9/2000

OTHER PUBLICATIONS
Baelen; Bioorganic & Medicinal Chemistry 17 (2009) 7209-7217.*
(Continued)

*Primary Examiner* — John Mabry
*Assistant Examiner* — Daniel Carcanague
(74) *Attorney, Agent, or Firm* — Perkins Coie LLP

(57) ABSTRACT

The present invention relates to substituted fused tricyclic compounds of formula (I) or (Ia), their tautomers, polymorphs, stereoisomers, prodrugs, solvates, co-crystals, pharmaceutically acceptable salts, pharmaceutical compositions containing them and methods of treating conditions and diseases that are mediated by JAK activity. The compounds of the present invention are useful in the treatment, prevention or suppression of diseases and disorders mediated by JAK activity. Such conditions include, but not limited to, arthritis, Alzheimer's disease, autoimmune thyroid disorders, cancer, diabetes, leukemia, T-cell prolymphocytic leukemia, lymphoma, myeloproliferation disorders, lupus, multiple myeloma, multiple sclerosis, osteoarthritis, sepsis, psoriatic arthritis, prostate cancer, T-cell autoimmune disease, inflammatory diseases, chronic and acute allograft transplant rejection, bone marrow transplant, stroke, asthma, chronic obstructive pulmonary disease, allergy, bronchitis, viral diseases, or Type I diabetes, complications from diabetes, rheumatoid arthritis, asthma, Crohn's disease, dry eye, uveitis, inflammatory bowel disease, organ transplant rejection, psoriasis and ulcerative colitis. The present disclosure also relates to process for the preparation of such compounds, and to pharmaceutical compositions containing them.

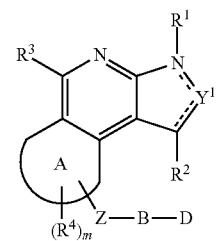

I

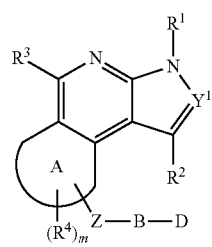

Ia

5 Claims, No Drawings

(51) Int. Cl.
　　　*A61K 45/06*　　　(2006.01)
　　　*A61K 31/496*　　(2006.01)

(56) References Cited

OTHER PUBLICATIONS

Banker, "Modern Pharmaceutics, 3ed.", Marcel Dekker, New York, 1996, pp. 451 and 596.*
Wolff, "Burger's Medicinal Chemistry, 5ed, Part I", John Wiley & Sons, 1995, pp. 975-977.*
Dorwald; "Side Reactions in Organic Synthesis: A Guide to Successful Synthesis Design" 2005 Wiley-VCH Verlag GmbH & Co. KGaA, Wienheim, chapter 1.*
Quintas-Cardama; Nat Rev Drug Discov, 2011, 10, 127-140.*
Jachak; Journal of Heterocyclic Chemistry, 2011, 48, 295-300.*
Patil; Journal of Fluorescence, 2011, 21, 461-471.*
Bagul; Monatshefte fur Chemie, 2011, 142, 169-175.*
Yu; Journal of Medicinal Chemistry, 2003, 46, 457-460.*
Kendre; Tetrahedron, 2007, 63, 11000-11004.*
Rao; ARKIVOC, 2002, 61-66.*
Paronikyan; Pharmaceutical Chemistry Journal, 2001, 35, 8-10.*

* cited by examiner

SUBSTITUTED FUSED TRICYCLIC COMPOUNDS, COMPOSITIONS AND MEDICINAL APPLICATIONS THEREOF

FIELD OF THE INVENTION

The present invention relates to substituted fused tricyclic compounds, their tautomers, polymorphs, stereoisomers, prodrugs, solvates, co-crystals, pharmaceutically acceptable salts, pharmaceutical compositions containing them and methods of treating conditions and diseases that are mediated by JAK activity.

BACKGROUND OF THE INVENTION

Protein phosphorylation catalyzed by protein kinases is one of the most common modes of regulation of protein function. By adding phosphate groups to substrate proteins, protein kinases alter the activity, localization and overall function of many proteins and influence almost all cellular processes. At least 30% of the human proteome is estimated to be phosphorylated by protein kinases. Protein phosphorylation is particularly prominent in signal transduction. Protein kinases are implicated in a variety of diseases including inflammation, cancer, neurodegenerative disorders, diabetes, infectious diseases, and so on. The human genome is estimated to encode 518 protein kinases. Based on the residue they phosphorylate, protein kinases are classified into 2 major groups: 1) protein tyrosine kinases or PTKs (~90 members) and 2) protein serine/threonine kinases (~378 members). The rest are 'atypical' kinases. The kinase domain of all typical protein kinases is highly conserved and consists of two lobes (N-lobe and C-lobe) that surround the nucleotide binding site.

Among the PTKs, a small subfamily known as Janus family kinases (JAKs) consists of four members namely JAK1, JAK2, JAK3, and Tyk2. They are cytoplasmic protein tyrosine kinases that play essential and specific roles in immune cell development and function by participating in the cytokine receptor signal transduction. Binding of cytokines activates the JAKs which in turn phosphorylate and activate a set of transcription factors known as STAT (signal transducers and activators of transcription) proteins. The STAT proteins form homo- or heterodimers and translocate to the nucleus where they induce transcription of genes. The central role of the JAK/STAT pathways in relaying the signals from many cytokine receptors, and the involvement of several cytokines in a range of pathologies such as diseases of the immune system and cancer, makes them attractive targets for drug discovery.

Among the JAKs, JAK3 has particularly selective functions. Unlike the other members of the JAK family, which show wide tissue distribution, JAK3 expression is restricted to the cells of hematopoietic lineage. Unlike the other members of the JAK family which associate with multiple cytokine receptors, JAK3 associates uniquely with γc-chain, the common signaling subunit of receptor complexes for six cytokines namely interleukin (IL)-2, IL-4, IL-7, IL-9, IL-15 and IL-21. These ILs play a pivotal role in the lymphoid development and function. JAK3 is inducible in T and B cells and expressed at high levels in NK cells and normally in thymocytes, platelets, mast cells. JAK3, through its association with the IL-2 receptor, is critical for lymphocyte survival, differentiation, and function. In humans, mutations in either JAK3 or γc-chain are associated with rare and inherited disorder known as severe combined immunodeficiency (SCID) indicating their critical role in the development and function of lymphocytes. These patients do not have deficits outside the immune system and hematopoietic stem cell transplants are curative, suggesting very discrete functions for JAK3.

The SCID phenotype was also observed in JAK3 knockout mice. JAK3 deficiency in humans results in the lack of T cells and NK cell development; B cells are present but their function is not normal. Unlike humans, JAK3 knockout mice show the lack of B cells and have relatively small numbers of T cells. The reason for this difference in the role of JAK3 in B cell development between mice and humans is not clear but it could be due to species-specific cytokine usage. However, similar to humans, JAK3 knockout mice did not display any effect on the development of myeloid or erythroid cells confirming the restriction of JAK3 function to lymphocyte development.

Though initially it was believed that the primary function of JAK3 is regulation of function of T and B cells through cytokine dependent pathway, recent studies using JAK3 knockout mice and JAK3 specific inhibitors suggest that JAK3 can transduce signals in non-cytokine-dependent manner in mast cells and that JAK3 plays a key role in mast cell mediated inflammatory responses. The enzymatic activity of JAK3 is increased by IgE receptor cross-linking in mast cells.

Other JAK family members Tyk2, JAK1 and JAK2 have functions within and outside immune cells. Mutations of Tyk2 cause autosomal recessive hyperIgE syndrome and JAK2 gain-of-function mutations (V617F) underlie a subset of disorders collectively referred to as myeloproliferative diseases. In some contexts, both JAK1 and JAK3 play dual and equal roles in receptor phosphorylation events indicating potential synergistic effects due to suppressing both JAK3 and JAK1 signaling.

JAK family members have been implicated in additional conditions including myeloproliferative disorders (O'Sullivan et al, 2007, Mol Immunol. 44(10):2497-506), where mutations in JAK2 have been identified. This indicates that inhibitors of JAK in particular JAK2 may also be of use in the treatment of myeloproliferative disorders. Additionally, the JAK family, in particular JAK1, JAK2 and JAK3, has been linked to cancers, in particular leukaemias e.g. acute myeloid leukaemia (O'Sullivan et al, 2007, Mol Immunol. 44(10):2497-506; Xiang et al, 2008, "Identification of somatic JAK1 mutations in patients with acute myeloid leukemia" Blood First Edition Paper, prepublished online Dec. 26, 2007; DOI 10.1 182/blood-2007-05-090308) and acute lymphoblastic leukaemia (Mullighan et al, 2009) or solid tumours e.g. uterine leiomyosarcoma (Constantinescu et al, 2007, Trends in Biochemical Sciences 33(3): 122-131), prostate cancer (Tarn et al, 2007, British Journal of Cancer, 97, 378-383). These results indicate that inhibitors of JAK, in particular of JAK1 and/or JAK2, may also have utility in the treatment of cancers (leukaemias and solid tumours e.g. uterine leiomyosarcoma, prostate cancer).

JAK1 is a novel target in the immuno-inflammatory disease area. JAK1 heterodimerizes with the other JAKs to transduce cytokine-driven pro-inflammatory signaling. Therefore, inhibition of JAK1 and/or other JAKs is expected to be of therapeutic benefit for a range of inflammatory conditions as well as for other diseases driven by JAK-mediated signal transduction.

Vandeghinste et al. (WO 2005/124342) discovered JAK1 as a target whose inhibition might have therapeutic relevance for several diseases including OA. Knockout of the JAK1 gene in mice demonstrated that JAK1 plays essential and non-redundant roles during development: JAK1−/− mice died within 24h after birth and lymphocyte development was severely impaired. Moreover, JAK1−/− cells were not, or less, reactive to cytokines that use class II cytokine receptors, cytokine receptors that use the gamma-c subunit for signaling and the family of cytokine receptors that use the gp130 subunit for signaling (Rodig et al, 1998).

Various groups have implicated JAK-STAT signaling in chondrocyte biology. Li et al JAK1 was initially identified in a screen for novel kinases (Wilks A. F., 1989, Proc. Natl. Acad. Sci. U.S.A. 86:1603-1607). Genetic and biochemical studies have shown that JAK1 is functionally and physically associated with the type I interferon (e.g., IFNalpha), type II interferon (e.g., IFNgamma), IL-2 and IL-6 cytokine receptor complexes (Kisseleva et al., 2002, gene 285:1-24; Levy et al., 2005, Nat. Rev. Mol. Cell. Biol. 3:651-662; O'Shea et al., 2002, Cell, 109 (suppl.): S121-S131). JAK1 knockout mice die perinatally due to defects in LIF receptor signaling (Kisseleva et al., 2002, gene 285:1-24; O'Shea et al., 2002, Cell, 109 (suppl.): S121-S131). Characterization of tissues derived from JAK1 knockout mice demonstrated critical roles for this kinase in the IFN, IL-10, IL-2/IL-4, and IL-6 pathways. A humanized monoclonal antibody targeting the IL-6 pathway (Tocilizumab) was recently approved by the European Commission for the treatment of moderate-to-severe rheumatoid arthritis (Scheinecker et al., 2009, Nat. Rev. Drug Discov. 8:273-274).

TYK2 is a potential target for immuno-inflammatory diseases, being validated by human genetics and mouse knockout studies (Levy D. and Loomis C. (2007)).

TYK2 associates with the type I interferon (e.g., IFNalpha), IL-6, IL-10, IL-12 and IL-23 cytokine receptor complexes (Kisseleva et al., 2002, gene 285:1-24; Watford, W. T. & O'Shea, J. J., 2006, Immunity 25:695-697). Consistent with this, primary cells derived from a TYK2 deficient human are defective in type I interferon, IL-6, IL-10, IL-12 and IL-23 signaling. A fully human monoclonal antibody targeting the shared p40 subunit of the IL-12 and 11-23 cytokines (Ustekinumab) was recently approved by the European Commission for the treatment of moderate-to-severe plaque psoriasis (Krueger et al., 2007, N. Engl. J. Med. 356:580-92; Reich et al., 2009, Nat. Rev. Drug Discov. 8:355-356). In addition, an antibody targeting the IL-12 and IL-23 pathways underwent clinical trials for treating Crohn's Disease (Mannon et al., 2004, N. Engl. J. Med. 351:2069-79).

The role of TYK2 in the biological response to cytokines was first characterized using a mutant human cell line that was resistant to the effects of Type I interferons (IFNs) and the demonstration that IFNa responsiveness could be restored by genetic complementation of TYK2 (Velazquez et al, 1992. Cell 70, 313-322). Further in vitro studies implicated TYK2 in the signaling pathways of multiple other cytokines involved in both innate and adaptive immunity. Analysis of TYK-2 " " mice however revealed less profound immunological defects than were anticipated (Karaghiosoff et al, 2000. Immunity 13, 549-560; Shimoda et al, 2000. Immunity 13, 561-671). Surprisingly, TYK2 deficient mice display merely reduced responsiveness to IFNα/β and signal normally to interleukin 6 (IL-6) and interleukin 10 (IL-10), both of which activate TYK2 in vitro. In contrast, TYK2 was shown to be essential for IL-12 signaling with the absence of TYK2 resulting in defective STAT4 activation and the failure of T cells from these mice to differentiate into IFNy-producing Th1 cells. Consistent with the involvement of TYK2 in mediating the biological effects of Type I IFNs and IL-12, TYK2-/- mice were more susceptible to viral and bacterial infections.

US 20100105661, WO 2007077949, WO 2007007919, WO 199965909, WO 200142246, WO 200200661, WO 2005060972 discloses JAK3 inhibitors. US 20030078277, WO 2005009389, WO 2005105788, WO2011068881, EP2420502, discloses tricyclic derivatives where as WO2011068881, EP2420502, WO0142246, WO03068157, WO9965908, WO2004047843, WO2004058749, WO2004099204, WO2004099205, WO2005037843, WO200505393, WO2005095400, WO2006096270, WO2007007919, WO2007070514, WO2007084557, WO2007117494, WO2007140222, WO2009054941, WO2009071701, WO2009155156, WO2010039939, WO2010051781,WO2010085684, WO2011003418, WO201103155 discloses bicyclic derivatives.

In aggregate, because of its restricted distribution and function within the hematopoietic cells, JAK3 has been viewed as an attractive therapeutic target for the development novel class of immunosuppressive drugs. JAK3 inhibitors would be useful in treating many autoimmune and inflammatory diseases such as, but not limited to rheumatoid arthritis, psoriasis, psoriatic arthritis, transplantation rejection, graft-versus-host disease, multiple sclerosis, inflammatory bowel disease, systemic lupus erythematosus, allergic diseases and asthma, and type 1 diabetes. Since JAK3-SCID patients do not exhibit pathology outside the immune system, in principle, a selective JAK3 inhibitor should have very limited and specific effects. Many of the currently used immunosuppressive drugs such as anti-metabolites, corticosteroids, and the inhibitors of calcineurin and mTOR target widely expressed molecules and hence are associated with adverse effects causing morbidity and mortality as the treatment is chronic. Similarly biologic anti-inflammatory agents such as TNF-alpha blockers are also associated with adverse events such as increase in the rate of serious infections, including tuberculosis and other opportunistic infections, injection site/infusion-related reactions, increased risk of lymphoma, the development of autoantibodies and a higher rate of congestive heart failure (CHF) in patients who already are known to have an increased risk of CHF. As a result, potent and selective JAK3 inhibitors are expected to have significant advantages over current regimens.

SUMMARY OF THE INVENTION

The present invention provides compounds of formula (I), their tautomers, polymorphs, stereoisomers, prodrugs, solvates, co-crystals, pharmaceutically acceptable salts, pharmaceutical compositions containing them and methods of treating conditions and diseases that are mediated by JAK activity,

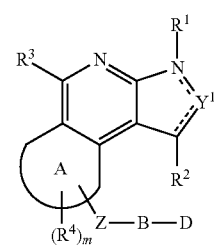

wherein,
=== represents a single bond or a double bond;
$Y^1$ represents N or CR' wherein R' is H or alkyl;
A represents a six or seven membered ring which is saturated, unsaturated or partially unsaturated optionally having up to three heteroatoms selected from O, N or S;
$R^1$ is selected from hydrogen, alkyl, cycloalkyl, aryl, heterocyclyl or heteroaryl;

R² is selected from the group consisting of hydrogen, halogen, hydroxyl, cyano, alkyl, alkenyl, alkynyl, haloalkyl, hydroxyalkyl, carboxyalkyl, cycloalkyl, cycloalkenyl, cycloalkylalkyl, aryl, arylalkyl, heterocyclyl, heterocyclylalkyl, heteroaryl and heteroarylalkyl;
  wherein alkyl, alkenyl, alkynyl, cycloalkyl, cycloalkylalkyl, arylalkyl, aryl, heteroaryl, heteroarylalkyl, heterocyclyl, and heterocyclylalkyl are independently unsubstituted or substituted with up to four substituents independently selected from alkyl, alkenyl, alkynyl, alkoxy, acyl, acyloxy, acylamino, amino, halogen, hydroxy, hydroxyalkyl, keto, thiocarbonyl, carboxy, alkylcarboxy, carboxyalkyl, —SO₃H, aminocarbonyl, aminocarbonylamino, alkoxycarbonylamino, hydroxyamino, alkoxyamino, nitro, azido, cyano, cycloalkyl, cycloalkylalkyl, aryl, arylalkyl, heterocyclyl, heterocyclylalkyl, heteroaryl and heteroarylalkyl cycloalkenyl, cycloalkylamino, arylamino, heterocyclylamino, heteroarylamino, cycloalkyloxy, aryloxy, heterocyclyloxy or heteroaryloxy;
R³ is selected from the group consisting of hydrogen, hydroxyalkyl, amino, monoalkylamino, dialkylamino, halogen, perhaloalkyl, cyano, nitro, alkoxyalkyl, carboxy, carboxyalkyl, acyl, aminocarbonyl, alkyl, alkenyl, alkynyl, hydroxyalkyl, carboxyalkyl, haloalkyl and haloalkyloxy;
R⁴ is selected from hydrogen, alkyl, alkenyl, alkynyl, alkoxy, acyl, acylamino, acyloxy, —(CRᵃRᵇ)ₙC(O)R⁵, —(CRᵃRᵇ)ₙNR⁶R⁷, aminocarbonyl, alkoxycarbonylamino, alkylsulfonylamino, aminocarbonylamino, hydroxyamino, alkoxyamino, azido, cyano, halogen, hydroxy, hydroxyalkyl, haloalkyl, perhaloalkyl, thiocarbonyl, carboxy, alkylcarboxy, carboxyalkyl, carboxyalkyloxy, alkylcarboxyalkyloxy —SO₃H, alkylthio, aminosulfonyl, alkylsulfonyl, or nitro;
Z is a bond or is a group selected from cycloalkylene, cycloalkylenealkyl, cycloalkenylene, cycloalkyleneoxo, cycloalkyleneamino, arylene, arylenealkyl, arylenethio, aryleneoxy, aryleneamino, arylenealkoxycarbonylamino, arylenesulfonyl, arylenesulfonylamino, heterocyclylene, heterocyclylenealkyl, heterocyclyleneoxy, heterocyclylenealkyloxy, heterocyclyleneamino, heterocyclylenethio, heterocyclylenealkylamino heteroarylene, heteroarylenealkyl, heteroaryleneoxy, heteroaryleneamino, spirocyclyl, (C₁₋₆) alkylene, (C₁₋₆)alkenylene or (C₁₋₆)alkynylene wherein one or more than one methylene groups from alkylene, alkenylene or alkynylene are optionally replaced by hetero atoms or groups such as —O—, —S(O)p, —N(R⁵)—, or —C(O);
B is a bond or is a group selected from cycloalkylene, cycloalkenylene, cycloalkylenecarbonyl, cycloalkylenealkoxy, cycloalkyleneamino, arylene, arylenecarbonyl, arylenealkoxycarbonyl, arylenealkoxycarbonylamino, aryleneaminocarbonyl, heterocyclylene, heterocyclylenealkyl, heterocyclylenecarbonyl, heterocyclylenealkylamino, heteroarylene, heteroarylenecarbonyl, heteroarylenealkylamino, (C₁₋)alkylene, (C₁₋₆)alkenylene or (C₁₋₆)alkynylene wherein one or more than one methylene groups from alkylene, alkenylene or alkynylene are optionally replaced by hetero atoms or groups such as —O—, —S(O)p-, —N(R⁵)—, —C(O) or —C(═NR")— wherein R" is H, alkyl, cyano, hydroxy, hydroxyalkyl, haloalkyl or perhaloalkyl;
D is selected from hydrogen, hydroxy, alkoxy, alkoxyalkyl, cyano, halogen, haloalkyl, perhaloalkyl, alkyl, alkenyl, alkynyl, carboxy, carboxyalkyl, cyanoalkyl, acyl, cyanoalkylarbonyl, cyanoalkenylcarbonyl, —(CRᵃRᵇ)ₙOR⁵, —SR⁵, —(CRᵃRᵇ)ₙCOOR⁵, —(CRᵃRᵇ)ₙNR⁶R⁷, —(CRᵃRᵇ)ₙC(O)NR⁶R⁷, —(CRᵃRᵇ)ₙNR⁵C(O)NR⁶R⁷, thiocarbonyl, S(O)₂NR⁶R⁷, —NR⁵S(O)₂R⁵, —S(O)ₚR⁵, —SO₃H, cycloalkyl, cycloalkenyl, cycloalkylalkyl, cycloalkyloxy, cycloalkylamino, aryl, arylalkyl, aryloxy, arylamino, heterocyclyl, heterocyclylalkyl, heterocyclyloxy, heterocycloalkylamino, heteroaryl, heteroarylalkyl, heteroaryloxy, or heteroarylamino;
R⁵ is selected from the group consisting of hydrogen, —(CRᵃRᵇ)ₙOR⁵, halogen, haloalkyl, —(CRᵃRᵇ)ₙC(O)R⁵, alkyl, alkenyl, alkynyl, aryl, arylalkyl, heteroaryl, heteroarylalkyl, cycloalkyl, cycloalkylalkyl, heterocyclyl and heterocyclylalkyl;
  wherein alkyl, alkenyl, alkynyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, OR⁵, —OC(O)R⁵, —(CRᵃRᵇ)ₙC(O)NR⁶R⁷, —NR⁵C(O)R⁵, —SR⁵, —S(O)ₚR⁵, —S(O)₂NR⁶R⁷ or —NR⁵S(O)₂R⁵;
R⁶ and R⁷ are independently selected from the group consisting of hydrogen, —(CRᵃRᵇ)ₙOR⁵, haloalkyl, —(CRᵃRᵇ)ₙC(O)R⁵, alkyl, alkenyl, alkynyl, aryl, arylalkyl, heteroaryl, heteroarylalkyl, cycloalkyl, cycloalkylalkyl, heterocyclyl and heterocyclylalkyl, or
R⁶ and R⁷ taken together form a monocyclic or a bicyclic ring system which is saturated or partially unsaturated and optionally have additional heteroatoms selected from O, N or S, the said ring system is further optionally substituted with 1 to 4 substituents independently selected from halo, alkyl, alkenyl, alkynyl, nitro, cyano, —(CRᵃRᵇ)ₙOR⁵, —SR⁵, —(CRᵃRᵇ)ₙNR⁶R⁷, oxo, alkylsulfonyl, —(CRᵃRᵇ)ₙCOOR⁵, —(CRᵃRᵇ)ₙC(O)NR⁶R⁷, cycloalkyl, cycloalkylalkyl, aryl, arylalkyl, heterocyclyl, heterocyclyalkyl, heteroaryl, and heteroarylalkyl;
Z, B and D may be optionally substituted with one or more substituents independently selected from cyano, nitro, keto, oxo, halogen, haloalkyl, perhaloalkyl, hydroxyamino, —(CRᵃRᵇ)ₙOR⁵, —(CRᵃRᵇ)ₙC(O)R⁵, —OC(O)R⁵, —SR⁵, —(CRᵃRᵇ)ₙCOOR⁵, —(CRᵃRᵇ)ₙNR⁶R⁷, —(CRᵃRᵇ)ₙC(O)NR⁶R⁷, —(CRᵃRᵇ)ₙNR⁵C(O)NR⁶R⁷, —NR⁵C(O)R⁵, thiocarbonyl, —S(O)2NR⁶R⁷, —NR⁵S(O)₂R⁵, —S(O)ₚR⁵, —SO₃H, —OP(O)(R⁸)_q, alkyl, alkenyl, alkynyl, cycloalkyl, cyclkenyl, cycloalkylalkyl, aryl, heterocyclyl and heteroaryl;
  wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)R⁵, —(CRᵃRᵇ)ₙC(O)NR⁶R⁷, —NR⁵C(O)R⁵, —SR⁵, —S(O)ₚR⁵, —S(O)₂NR⁶R⁷ or —NR⁵S(O)₂R⁵;
R⁸ is selected from the group consisting of hydroxy and alkoxy;
Rᵃ and Rᵇ are independently selected from the group consisting of hydrogen, —OR⁵, halogen, haloalkyl, perhaloalkyl and alkyl;
n is 0-6;
m is 0, 1 or 2;
p is 0, 1 or 2; and
q is 1 or 2;
with the proviso that when ring A is phenyl, then Y¹ cannot be N.

DETAILED DESCRIPTION OF THE INVENTION

Definitions

In the structural formulae given herein and throughout the present disclosure, the following terms have the indicated meaning, unless specifically stated otherwise.

The term "optionally substituted" as used herein means that the group in question is either unsubstituted or substituted with one or more of the substituents specified. When the group in question is substituted with more than one substituent, the substituent may be same or different.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methyl, ethyl, n-propyl, iso-propyl, n-butyl, iso-butyl, t-butyl, n-hexyl, n-decyl, tetradecyl, and the like.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

The term "substituted alkyl" or "substituted alkylene" refers to: 1) an alkyl group or alkylene group as defined above, having 1, 2, 3, 4 or 5 substituents, preferably 1, 2 or 3 substituents, selected from the group consisting of alkenyl, alkynyl, alkoxy, cycloalkyl, cycloalkenyl, acyl, acylamino, acyloxy, amino, monoalkylamino, dialkylamino, arylamino, heteroarylamino, aminocarbonyl, alkoxycarbonylamino, azido, cyano, halogen, hydroxy, hydroxyalkyl, keto, thiocarbonyl, carboxy, carboxyalkyl, —$SO_3H$, aryl, aryloxy, heteroaryl, aminocarbonylamino, heteroaryloxy, heterocyclyl, heterocyclyloxy, hydroxy amino, alkoxyamino, nitro, —$S(O)_2NR^aR^a$, —$NR^aS(O)_2R^a$ and —$S(O)_pR^b$, where each $R^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; heterocyclyloxy where $R^b$ is hydrogen, alkyl, aryl, heteroaryl or heterocyclyl. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, $CF_3$, amino, substituted amino, cyano, and —$S(O)_pR^c$, where $R^c$ is alkyl, aryl, or heteroaryl and p is 0, 1 or 2; or 2) an alkyl group or alkylene group as defined above that is interrupted by 1, 2, 3, 4, 5, 6, 7, 8, 9 or 10 atoms independently selected from oxygen, sulphur and $NR^d$, where $R^d$ is selected from hydrogen, alkyl, cycloalkyl, cycloalkenyl, aryl, heteroaryl and heterocyclyl, carbonylalkyl, carboxyester, carboxyamide and sulfonyl. All substituents may be optionally further substituted by alkyl, alkoxy, halogen, $CF_3$, amino, substituted amino, cyano, or —$S(O)_pR^e$, in which $R^e$ is alkyl, aryl, or heteroaryl and p is 0, 1, or 2;

or 3) an alkyl or alkylene as defined above that has 1, 2, 3, 4 or 5 substituents as defined above, as well as interrupted by 1, 2, 3, 4, 5, 6, 7, 8, 9 or 10 atoms as defined above.

The term "alkenyl" refers to a monoradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 double bond (vinyl), preferably 1 double bond. Preferred alkenyl groups include ethenyl or vinyl (—$CH=CH_2$), 1-propylene or allyl (—$CH_2CH=CH_2$), isopropylene (—$C(CH_3)=CH_2$), bicyclo [2.2.1]heptene, and the like.

The term "alkenylene" refers to a diradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 double bond (vinyl), preferably 1 double bond.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, thiocarbonyl, carboxy, carboxyalkyl, $SO_3H$, aryl, aryloxy, heteroaryl, aminocarbonylamino, heteroaryloxy, heterocyclyl, heterocyclyloxy, hydroxyamino, alkoxyamino, nitro, —$S(O)_2NR^aR^a$, —$NR^aS(O)_2R^a$ and —$S(O)_pR^b$ where each $R^a$ is independently selected from the group consisting of hydrogen, alkyl, cycloalkyl, cycloalkylalkyl, aryl, arylalkyl, heteroaryl heteroarylalkyl, heterocyclyl, heterocyclylalkyl and heterocyclyloxy, where $R^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, $CF_3$, amino, substituted amino, cyano, and —$S(O)_pR^c$, where $R^c$ is alkyl, aryl, or heteroaryl and p is 0, 1 or 2.

The term "alkynyl" refers to a monoradical of an unsaturated hydrocarbon, preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 sites of acetylene (triple bond) unsaturation, preferably 1 triple bond. Preferred alkynyl groups include ethynyl, (—C≡CH), propargyl (or prop-1-yn-3-yl, —$CH_2C≡CH$), homopropargyl (or but-1-yn-4-yl, —$CH_2CH_2C≡CH$) and the like.

The term "alkynylene" refers to a diradical of a branched or an unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 sites of acetylene (triple bond) unsaturation, preferably 1 triple bond.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, —$SO_3H$, aryl, aryloxy, heteroaryl, aminocarbonylamino, heteroaryloxy, heterocyclyl, heterocyclyloxy, hydroxyamino, alkoxyamino, nitro, —$S(O)_2NR^aR^a$, —$NR^aS(O)_2R^a$ and —$S(O)_pR^b$, where each $R^a$ is independently selected from the group consisting of hydrogen, alkyl, cycloalkyl, cycloalkylalkyl, aryl, arylalkyl, heteroaryl heteroarylalkyl, heterocyclyl, heterocyclylalkyl and heterocyclyloxy, where $R^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, $CF_3$, amino, substituted amino, cyano, and —$S(O)_pR^c$ where $R^c$ is alkyl, aryl, or heteroaryl and p is 0, 1 or 2.

The term "cycloalkyl" refers to unless otherwise mentioned, carbocyclic groups of from 3 to 20 carbon atoms having a single cyclic ring or multiple condensed rings or spirocyclic rings or bridged rings which may be saturated or partially unsaturated. Such cycloalkyl groups include, by way of example, single ring structures such as cyclopropyl, cyclobutyl, cyclopentyl, cyclopentenyl, cyclohexyl, cyclohexenyl, cyclooctyl, and the like, or multiple ring structures such as adamantanyl, bicyclo[2.2.1]heptane, bicyclo[2.2.2] octane, 1,3,3-trimethylbicyclo[2.2.1]hept-2-yl, (2,3,3-trimethylbicyclo[2.2.1]hept-2-yl), or carbocyclic groups to which is fused an aryl group, for example indane, and the like.

The term "substituted cycloalkyl" refers to cycloalkyl groups having 1, 2, 3, 4 or 5 substituents, and preferably 1, 2, or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, oxo, thiocarbonyl, aryl, aryloxy, heteroaryl, aminosulfonyl, aminocarbonylamino, heteroaryloxy, heterocyclyl, heterocyclyloxy, hydroxyamino, alkoxyamino, nitro, —C(O)R and —S(O)$_p$R$^b$, where R is hydrogen, hydroxyl, alkoxy, alkyl and cyclocalkyl, heterocyclyloxy where R$^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF$_3$, amino, substituted amino, cyano, and —S(O)$_p$R$^c$, where R$^c$ is alkyl, aryl, or heteroaryl and p is 0, 1 or 2.

"Halo" or "Halogen", alone or in combination with any other term means halogens such as chloro (Cl), fluoro (F), bromo (Br) and iodo (I).

"Haloalkyl" refers to a straight chain or branched chain haloalkyl group with 1 to 6 carbon atoms. The alkyl group may be partly or totally halogenated. Representative examples of haloalkyl groups include but are not limited to fluoromethyl, chloromethyl, bromomethyl, difluoromethyl, dichloromethyl, dibromomethyl, trifluoromethyl, trichloromethyl, 2-fluoroethyl, 2-chloroethyl, 2-bromoethyl, 2,2,2-trifluoroethyl, 3-fluoropropyl, 3-chloropropyl, 3-bromopropyl and the like.

The term "alkoxy" refers to the group R'"—O—, where R'" is optionally substituted alkyl or optionally substituted cycloalkyl, or optionally substituted alkenyl or optionally substituted alkynyl; or optionally substituted cycloalkenyl, where alkyl, alkenyl, alkynyl, cycloalkyl and cycloalkenyl are as defined herein. Representative examples of alkoxy groups include but are not limited to methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "aminocarbonyl" refers to the group —C(O) NR'R' where each R' is independently hydrogen, alkyl, aryl, heteroaryl, heterocyclyl or both R' groups are joined to form a heterocyclic group (e. g. morpholino). Unless otherwise constrained by the definition, all substituents may optionally be further substituted by 1-3 substituents selected from alkyl, carboxy, carboxyalkyl, aminocarbonyl, hydroxy, alkoxy, halogen, CF$_3$, amino, substituted amino, cyano, and —S(O)$_p$R$^c$, where R$^c$ is alkyl, aryl, or heteroaryl and p is 0, 1 or 2.

The term "acylamino" refers to the group —NR"C(O)R" where each R" is independently hydrogen, alkyl, aryl, heteroaryl, or heterocyclyl. Unless otherwise constrained by the definition, all substituents may optionally be further substituted by 1-3 substituents selected from alkyl, carboxy, carboxyalkyl, aminocarbonyl, hydroxy, alkoxy, halogen, CF$_3$, amino, substituted amino, cyano, and —S(O)$_p$R$^c$, where R$^c$ is alkyl, aryl, or heteroaryl and p is 0, 1 or 2.

The term "acyloxy" refers to the groups —OC(O)-alkyl, —OC(O)-cycloalkyl, —OC(O)— aryl, —OC(O)-heteroaryl, and —OC(O)-heterocyclyl. Unless otherwise constrained by the definition, all substituents may be optionally further substituted by alkyl, carboxy, carboxyalkyl, aminocarbonyl, hydroxy, alkoxy, halogen, CF$_3$, amino, substituted amino, cyano, or —S(O)$_p$R$^e$, where R$^e$ is alkyl, aryl, or heteroaryl and p is 0, 1 or 2.

"Alkoxyalkyl" refers to alkyl groups as defined above wherein at least one of the hydrogen atoms of the alkyl group is replaced by an alkoxy group as defined above. Representative examples of alkoxyalkyl groups include but are not limited to methoxymethyl, methoxyethyl, ethoxymethyl and the like.

"Aryloxyalkyl" refers to the group -alkyl-O-aryl. Representative examples of aryloxyalkyl include but are not limited to phenoxymethyl, naphthyloxymethyl, phenoxyethyl, naphthyloxyethyl and the like.

"Di alkylamino" refers to an amino group, to which two same or different straight chain or branched chain alkyl groups with 1 to 6 carbon atoms are bound. Representative examples of di alkylamino include but are not limited to dimethylamino, diethylamino, methylethylamino, dipropylamino, dibutylamino and the like.

"Cycloalkylalkyl" refers to an alkyl radical as defined above which is substituted by a cycloalkyl radical as defined above. Representative examples of cycloalkylalkyl include but are not limited to cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

"Aminoalkyl" refers to an amino group that is attached to (C$_{1-6}$)alkylene as defined herein. Representative examples of aminoalkyl include but are not limited to aminomethyl, aminoethyl, 1-aminopropyl, 2-aminopropyl, and the like. The amino moiety of aminoalkyl may be substituted once or twice with alkyl to provide alkylaminoalkyl and dialkylaminoalkyl respectively. Representative examples of alkylaminoalkyl include but are not limited to methylaminomethyl, methylaminoethyl, methylaminopropyl, ethylaminoethyl and the like. Representative examples of dialkylaminoalkyl include but are not limited to dimethylaminomethyl, dimethylaminoethyl, dimethylaminopropyl, N-methyl-N-ethylaminoethyl and the like.

The term "aryl" refers to an aromatic carbocyclic group of 6 to 20 carbon atoms having a single ring (e.g. phenyl) or multiple rings (e.g. biphenyl), or multiple condensed (fused) rings (e.g. naphthyl or anthranyl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained the aryl or arylene groups may optionally be substituted with 1, 2, 3 4 or 5 substituents, preferably 1, 2 or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, carboxy, carboxyalkyl, —SO$_3$H, aryl, aryloxy, heteroaryl, aminosulfonyl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$ where each R$^a$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl; where R$^b$ is hydrogen, alkyl, aryl, heterocyclyl or heteroaryl and p is 0, 1 or 2. Unless otherwise constrained by the definition, all substituents may optionally be further substituted by 1, 2 or 3 substituents selected from alkyl, carboxy, carboxyalkyl, aminocarbonyl, hydroxy, alkoxy, halogen, $CF_3$, amino, substituted amino, cyano, and —$S(O)_pR^e$ where $R^e$ is hydrogen, alkyl, aryl, or heteroaryl and p is 0, 1 or 2.

The term "arylalkyl" refers to an aryl group covalently linked to an alkylene group, where aryl and alkylene are defined herein.

"Optionally substituted arylalkyl" refers to an optionally substituted aryl group covalently linked to an optionally substituted alkylene group. Such arylalkyl groups are exemplified by benzyl, phenethyl, naphthylmethyl, and the like.

The term "aryloxy" refers to the group aryl-O— wherein the aryl group is as defined above, and includes optionally substituted aryl groups as also defined above.

The term "arylthio" refers to the group —S-aryl, where aryl is as defined herein including optionally substituted aryl groups as also defined above.

The term "substituted amino" refers to the group —NR'R' where each R' is independently selected from the group consisting of hydrogen, alkyl, cycloalkyl, carboxyalkyl, alkoxycarbonyl, aryl, heteroaryl and heterocyclyl. Unless otherwise constrained by the definition, all substituents may optionally be further substituted by 1, 2 or 3 substituents selected from alkyl, carboxy, carboxyalkyl, aminocarbonyl, hydroxy, alkoxy, halogen, $CF_3$, amino, substituted amino, cyano, and —$S(O)_pR^c$, where $R^c$ is alkyl, aryl, or heteroaryl and p is 0, 1 or 2.

The term "carboxyalkyl" refers to the groups -alkylene-C(O)OH.

The term "alkylcarboxyalkyl" refers to the groups -alkylene-C(O)$OR^d$ where $R^d$ is alkyl, cycloalkyl, where alkyl, cycloalkyl are as defined herein, and may be optionally further substituted by alkyl, halogen, $CF_3$, amino, substituted amino, cyano, or —$S(O)_pR^c$, in which Re is alkyl, aryl, or heteroaryl and p is 0, 1 or 2.

The term "heteroaryl" refers to an aromatic cyclic group having 1, 2, 3, 4, 5, 6, 7, 8, 9, 10, 11, 12, 13, 14, or 15 carbon atoms and 1, 2, 3 or 4 heteroatoms selected from oxygen, nitrogen and sulphur within at least one ring. Such heteroaryl groups can have a single ring (e.g. pyridyl or furyl) or multiple condensed rings (e.g. indolizinyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, quinoxaline, quinazoline, cinnoline, pteridine, carbazole, carboline, phenanthridine, acridine, phenanthroline, isothiazole, phenazine, isoxazole, phenoxazine, phenothiazine, furan, thiophene, oxazole, thiazole, triazole, triazine and the like.

The term "heteroarylene" refers to a diradical of a heteroaryl group as defined above. Unless otherwise constrained the heteroaryl or heterarylene groups can be optionally substituted with 1, 2, 3, 4 or 5 substituents, preferably 1, 2 or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, thiocarbonyl, carboxy, carboxyalkyl, —$SO_3H$, aryl, aryloxy, heteroaryl, aminocarbonylamino, heteroaryloxy, heterocyclyl, heterocyclyloxy, hydroxyamino, alkoxyamino, nitro, —$S(O)_2NR^aR^a$, —$NR^aS(O)_2R^a$ and —$S(O)_pR^b$, where each $R^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; where $R^b$ is hydrogen, alkyl, aryl, heterocyclyl or heteroaryl, and p is 0, 1 or 2. Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and —$S(O)_nR^c$, where $R^c$ is alkyl, aryl, or heteroaryl and n is 0, 1 or 2.

The term "heteroarylalkyl" refers to a heteroaryl group covalently linked to an alkylene group, where heteroaryl and alkylene are defined herein.

"Optionally substituted heteroarylalkyl" refers to an optionally substituted heteroaryl group covalently linked to an optionally substituted alkylene group. Such heteroarylalkyl groups are exemplified by 3-pyridylmethyl, quinolin-8-ylethyl, 4-methoxythiazol-2-ylpropyl, and the like.

The term "heterocyclyl" refers to a saturated or partially unsaturated group having a single ring or multiple condensed rings or spirocyclic rings, or bridged rings unless otherwise mentioned, having from 1 to 40 carbon atoms and from 1 to 10 hetero atoms, preferably 1, 2, 3 or 4 heteroatoms, selected from nitrogen, sulphur, phosphorus, and/or oxygen within the ring. Heterocyclic groups can have a single ring or multiple condensed rings, and include tetrahydrofuranyl, morpholinyl, piperidinyl, piperazinyl, dihydropyridinyl, tetrahydroquinolinyl and the like. Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, oxo, —C(O)R where R is hydrogen, hydroxyl, alkoxy, alkyl and cycloalkyl, thiocarbonyl, carboxy, carboxyalkyl, aryl, aryloxy, heteroaryl, aminosulfonyl, aminocarbonylamino, heteroaryloxy, heterocyclyl, heterocyclyloxy, hydroxyamino, alkoxyamino, nitro, and —$S(O)_pR^b$, where $R^b$ is hydrogen, alkyl, aryl, heterocyclyl or heteroaryl and p is 0, 1 or 2. Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and —$S(O)R^e$, where $R^e$ is alkyl, aryl, or heteroaryl and n is 0, 1 or 2. The term "heterocyclylalkyl" refers to a heterocyclyl group covalently linked to an alkylene group, where heterocyclyl and alkylene are defined herein.

"Optionally substituted heterocyclylalkyl" refers to an optionally substituted heterocyclyl group covalently linked to an optionally substituted alkylene group.

The term "heteroaryloxy" refers to the group heteroaryl-O—.

The term "thiol" refers to the group —SH.

The term "substituted alkylthio" refers to the group —S-substituted alkyl.

The term "heteroarylthio" refers to the group —S-heteroaryl wherein the heteroaryl group is as defined above including optionally substituted heteroaryl groups as also defined above.

The term "sulfoxide" refers to a group —S(O).

"Substituted sulfoxide" refers to a group —S(O)R, in which R is substituted alkyl, substituted aryl, or substituted heteroaryl, as defined herein.

The term "sulfone" refers to a group —$S(O)_2R$.

The term "substituted sulfone" refers to a group —$S(O)_2R$, in which R is alkyl, aryl, or heteroaryl.

The compounds of the present invention may have the ability to crystallize in more than one form, a characteristic known as polymorphism, and all such polymorphic forms ("polymorphs") are encompassed within the scope of the invention. Polymorphism generally can occur as a response to changes in temperature or pressure or both, and can also result from variations in the crystallization process. Polymorphs can be distinguished by various physical characteristics, and typically the x-ray diffraction patterns, solubility behavior, and melting point of the compound are used to distinguish polymorphs.

The compounds described herein may contain one or more chiral centers and/or double bonds and therefore, may exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof. Accordingly, the chemical structures depicted herein encompass all possible tautomeric forms of the illustrated or identified compounds.

Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated within the scope of the invention are congeners, analogs, hydrolysis products, metabolites and precursor or prodrugs of the compound. In general, unless otherwise indicated, all physical forms are equivalent for the uses contemplated herein and are intended to be within the scope of the present invention.

"Prodrug" refers to a derivative of a drug molecule as, for example, esters, carbonates, carbamates, ureas, amides or phosphates that requires a transformation within the body to release the active drug. Prodrugs are frequently, although not necessarily, pharmacologically inactive until converted to the parent drug. Prodrugs may be obtained by bonding a promoiety (defined herein) typically via a functional group, to a drug.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach or the agent may be supplied exogenously.

"Pharmaceutically acceptable salt" embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the invention are quaternary ammonium compounds wherein an equivalent of an anion (M−) is associated with the positive charge of the N atom. M− may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. M− is preferably an anion selected from chloride, bromide, iodide, sulphate, nitrate, acetate, maleate, oxalate, succinate or trifluoroacetate. More preferably M− is chloride, bromide, trifluoroacetate or methanesulphonate.

"Co-crystal" refers to a crystalline material comprising two or more compounds at ambient temperature (20 to 25[deg.]C., preferably 20[deg.]C.), of which at least two are held together by weak interaction, wherein at least one of the compounds is a co-crystal former. Weak interaction is being defined as an interaction which is neither ionic nor covalent and includes for example: hydrogen bonds, van der Waals forces, and interactions.

"Pharmaceutical composition" refers to one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

"Carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

"drug or pharmaceutically active agent" includes a drug or pharmaceutical agent that will elicit the biological or medical response of a tissue, system, animal or human that is being sought, for instance, by a researcher or clinician.

"Combined" or "in combination" or "combination" should be understood as a functional coadministration, wherein some or all compounds may be administered separately, in different formulations, different modes of administration (for example subcutaneous, intravenous or oral) and different times of administration. The individual compounds of such combinations may be administered either sequentially in separate pharmaceutical compositions as well as simultaneously in combined pharmaceutical compositions.

"Therapeutically effective amount" is an amount of a compound of Formula (I)/(Ia) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

The present invention provides compounds of formula (I), their tautomers, polymorphs, stereoisomers, prodrugs, solvates, co-crystals, pharmaceutically acceptable salts, pharmaceutical compositions containing them and methods of treating conditions and diseases that are mediated by JAK activity,

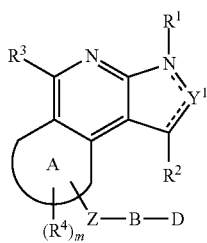

I wherein,
=== represents a single bond or a double bond;
$Y^1$ represents N or CR' wherein R' is H or alkyl;
A represents a six or seven membered ring which is saturated, unsaturated or partially unsaturated optionally having up to three heteroatoms selected from O, N or S;
$R^1$ is selected from hydrogen, alkyl, cycloalkyl, aryl, heterocyclyl and heteroaryl;
$R^2$ is selected from the group consisting of hydrogen, halogen, hydroxyl, cyano, alkyl, alkenyl, alkynyl, haloalkyl, hydroxyalkyl, carboxyalkyl, cycloalkyl, cycloalkenyl, cycloalkylalkyl, aryl, arylalkyl, heterocyclyl, heterocyclylalkyl, heteroaryl and heteroarylalkyl;
  wherein alkyl, alkenyl, alkynyl, cycloalkyl, cycloalkylalkyl, arylalkyl, aryl, heteroaryl, heteroarylalkyl, heterocyclyl, and heterocyclylalkyl are independently unsubstituted or substituted with up to four substituents independently selected from alkyl, alkenyl, alkynyl, alkoxy, acyl, acyloxy, acylamino, amino, halogen, hydroxy, hydroxyalkyl, keto, thiocarbonyl, carboxy, alkylcarboxy, carboxyalkyl, —$SO_3H$, aminocarbonyl, aminocarbonylamino, alkoxycarbonylamino, hydroxyamino, alkoxyamino, nitro, azido, cyano, cycloalkyl, cycloalkylalkyl, aryl, arylalkyl, heterocyclyl, heterocyclylalkyl, heteroaryl and heteroarylalkyl cycloalkenyl, cycloalkylamino, arylamino, heterocyclylamino, heteroarylamino, cycloalkyloxy, aryloxy, heterocyclyloxy and heteroaryloxy;
$R^3$ is selected from the group consisting of hydrogen, hydroxyalkyl, amino, monoalkylamino, dialkylamino, halogen, perhaloalkyl, cyano, nitro, alkoxyalkyl, carboxy, carboxyalkyl, acyl, aminocarbonyl, alkyl, alkenyl, alkynyl, hydroxyalkyl, carboxyalkyl, haloalkyl and haloalkyloxy;
$R^4$ is selected from hydrogen, alkyl, alkenyl, alkynyl, alkoxy, acyl, acylamino, acyloxy, —$(CR^aR^b)_nC(O)R^5$, —$(CR^aR^b)_nNR^6R^7$, aminocarbonyl, alkoxycarbonylamino, alkylsulfonylamino, aminocarbonylamino, hydroxyamino, alkoxyamino, azido, cyano, halogen, hydroxy, hydroxyalkyl, haloalkyl, perhaloalkyl, thiocarbonyl, carboxy, alkylcarboxy, carboxyalkyl, carboxyalkyloxy, alkylcarboxyalkyloxy —$SO_3H$, alkylthio, aminosulfonyl, alkylsulfonyl, and nitro;
Z is a bond or is a group selected from cycloalkylene, cycloalkylenealkyl, cycloalkenylene, cycloalkyleneoxo, cycloalkyleneamino, arylene, arylenealkyl, arylenethio, aryleneoxy, aryleneamino, arylenealkoxycarbonylamino, arylenesulfonyl, arylenesulfonylamino, heterocyclylene, heterocyclylenealkyl, heterocyclyleneoxy, heterocyclylenealkyloxy, heterocyclyleneamino, heterocyclylenethio, heterocyclylenealkylamino heteroarylene, heteroarylenealkyl, heteroaryleneoxy, heteroaryleneamino, spirocyclyl, ($C_{1-6}$)alkylene, ($C_{1-6}$)alkenylene or ($C_{1-6}$)alkynylene wherein one or more than one methylene groups from alkylene, alkenylene or alkynylene are optionally replaced by hetero atoms or groups such as —O—, —S(O)p-, —N($R^5$)—, and —C(O);
B is a bond or is a group selected from cycloalkylene, cycloalkenylene, cycloalkylenecarbonyl, cycloalkylenealkoxy, cycloalkyleneamino, arylene, arylenecarbonyl, arylenealkoxycarbonyl, arylenealkoxycarbonylamino, aryleneaminocarbonyl, heterocyclylene, heterocyclylenealkyl, heterocyclylenecarbonyl, heterocyclylenealkylamino, heteroarylene, heteroarylenecarbonyl, heteroarylenealkylamino, ($C_{1-6}$)alkylene, ($C_{1-6}$)alkenylene or ($C_{1-6}$)alkynylene wherein one or more than one methylene groups from alkylene, alkenylene or alkynylene are optionally replaced by hetero atoms or groups such as —O—, —S(O)p-, —N($R^5$)—, —C(O) or —C(=NR")— wherein R" is H, alkyl, cyano, hydroxy, hydroxyalkyl, haloalkyl or perhaloalkyl;
D is selected from hydrogen, hydroxy, alkoxy, alkoxyalkyl, cyano, halogen, haloalkyl, perhaloalkyl, alkyl, alkenyl, alkynyl, carboxy, carboxyalkyl, cyanoalkyl, acyl, cyanoalkylarbonyl, cyanoalkenylcarbonyl, —$(CR^aR^b)_nOR^5$, —$SR^5$, —$(CR^aR^b)_nCOOR^5$, —$(CR^aR^b)_nNR^6R^7$, —$(CR^aR^b)_nC(O)NR^6R^7$, —$(CR^aR^b)_nNR^5C(O)NR^6R^7$, thiocarbonyl, $S(O)_2NR^6R^7$, —$NR^5S(O)_2R^5$, —$S(O)_pR^5$, —$SO_3H$, cycloalkyl, cycloalkenyl, cycloalkylalkyl, cycloalkyloxy, cycloalkylamino, aryl, arylalkyl, aryloxy, arylamino, heterocyclyl, heterocyclylalkyl, heterocyclyloxy, heterocycloalkylamino, heteroaryl, heteroarylalkyl, heteroaryloxy, and heteroarylamino;
$R^5$ is selected from the group consisting of hydrogen, —$(CR^aR^b)_nOR^5$, halogen, haloalkyl, —$(CR^aR^b)_nC(O)R^5$, alkyl, alkenyl, alkynyl, aryl, arylalkyl, heteroaryl, heteroarylalkyl, cycloalkyl, cycloalkylalkyl, heterocyclyl and heterocyclylalkyl;
  wherein alkyl, alkenyl, alkynyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, OR$^5$, —OC(O)R$^5$, —(CR$^a$R$^b$)$_n$C(O)NR$^6$R$^7$, —NR$^5$C(O)R$^5$, —SR$^5$, —S(O)$_p$R$^5$, —S(O)$_2$NR$^6$R$^7$ or —NR$^5$S(O)$_2$R$^5$;

R$^6$ and R$^7$ are independently selected from the group consisting of hydrogen, —(CR$^a$R$^b$)$_n$OR$^5$, haloalkyl, —(CR$^a$R$^b$)$_n$C(O)R$^5$, alkyl, alkenyl, alkynyl, aryl, arylalkyl, heteroaryl, heteroarylalkyl, cycloalkyl, cycloalkylalkyl, heterocyclyl and heterocyclylalkyl, or R$^6$ and R$^7$ taken together form a monocyclic or a bicyclic ring system which is saturated or partially unsaturated and optionally have additional heteroatoms selected from O, N or S, the said ring system is further optionally substituted with 1 to 4 substituents independently selected from halo, alkyl, alkenyl, alkynyl, nitro, cyano, —(CR$^a$R$^b$)$_n$OR$^5$, —SR$^5$, —(CR$^a$R$^b$)$_n$NR$^6$R$^7$, oxo, alkylsulfonyl, —(CR$^a$R$^b$)$_n$COOR$^5$, —(CR$^a$R$^b$)$_n$C(O)NR$^6$R$^7$, cycloalkyl, cycloalkylalkyl, aryl, arylalkyl, heterocyclyl, heterocyclylalkyl, heteroaryl, and heteroarylalkyl;

Z, B and D may be optionally substituted with one or more substituents independently selected from cyano, nitro, keto, oxo, halogen, haloalkyl, perhaloalkyl, hydroxyamino, —(CR$^a$R$^b$)$_n$OR$^5$, —(CR$^a$R$^b$)$_n$C(O)R$^5$OC(O)R$^5$, —SR$^5$, —(CR$^a$R$^b$)$_n$COOR$^5$, —(CR$^a$R$^b$)$_n$NR$^6$R$^7$, —(CR$^a$R$^b$)$_n$C(O)NR$^6$R$^7$, —(CR$^a$R$^b$)$_n$NR$^5$C(O)NR$^6$R$^7$, —NR$^5$C(O)R$^5$, thiocarbonyl, S(O)$_2$NR$^6$R$^7$, —NR$^5$S(O)$_2$R$^5$, —S(O)$_p$R$^5$, —SO$_3$H, —OP(O)(R$^8$)$_q$, alkyl, alkenyl, alkynyl, cycloalkyl, cyclkenyl, cycloalkylalkyl, aryl, heterocyclyl and heteroaryl;

wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)R$^5$, —(CR$^a$R$^b$)$_n$C(O)NR$^6$R$^7$, —NR$^5$C(O)R$^5$, —SR$^5$, —S(O)$_p$R$^5$, —S(O)$_2$NR$^6$R$^7$ and —NR$^5$S(O)$_2$R$^5$;

R$^8$ is selected from the group consisting of hydroxy or alkoxy;

R$^a$ and R$^b$ are independently selected from the group consisting of hydrogen, —OR$^5$, halogen, haloalkyl, perhaloalkyl and alkyl;

n is 0-6;

m is 0, 1 or 2;

p is 0, 1 or 2;

q is 1 or 2;

with the proviso that when ring A is phenyl, then Y$^1$ cannot be N.

According to another embodiment, the present disclosure relates to compounds of formula (Ia) or its tautomers, polymorphs, stereoisomers, prodrugs, solvate, co-crystals or a pharmaceutically acceptable salts thereof,

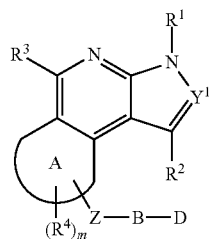

Ia wherein, Y$^1$ represents N or CR' wherein R' is H or alkyl;

A represents a six or seven membered ring which is saturated, unsaturated or partially unsaturated optionally having up to three heteroatoms selected from O, N or S;

R$^1$ is selected from hydrogen, alkyl, cycloalkyl, aryl, heterocyclyl and heteroaryl;

R$^2$ is selected from the group consisting of hydrogen, halogen, hydroxyl, cyano, alkyl, alkenyl, alkynyl, haloalkyl, hydroxyalkyl, carboxyalkyl, cycloalkyl, cycloalkenyl, cycloalkylalkyl, aryl, arylalkyl, heterocyclyl, heterocyclylalkyl, heteroaryl and heteroarylalkyl;

wherein alkyl, alkenyl, alkynyl, cycloalkyl, cycloalkylalkyl, arylalkyl, aryl, heteroaryl, heteroarylalkyl, heterocyclyl, and heterocyclylalkyl are independently unsubstituted or substituted with up to four substituents independently selected from alkyl, alkenyl, alkynyl, alkoxy, acyl, acyloxy, acylamino, amino, halogen, hydroxy, hydroxyalkyl, keto, thiocarbonyl, carboxy, alkylcarboxy, carboxyalkyl, —SO$_3$H, aminocarbonyl, aminocarbonylamino, alkoxycarbonylamino, hydroxyamino, alkoxyamino, nitro, azido, cyano, cycloalkyl, cycloalkylalkyl, aryl, arylalkyl, heterocyclyl, heterocyclylalkyl, heteroaryl and heteroarylalkyl cycloalkenyl, cycloalkylamino, arylamino, heterocyclylamino, heteroarylamino, cycloalkyloxy, aryloxy, heterocyclyloxy and heteroaryloxy;

R$^3$ is selected from the group consisting of hydrogen, hydroxyalkyl, amino, monoalkylamino, dialkylamino, halogen, perhaloalkyl, cyano, nitro, alkoxyalkyl, carboxy, carboxyalkyl, acyl, aminocarbonyl, alkyl, alkenyl, alkynyl, hydroxyalkyl, carboxyalkyl, haloalkyl and haloalkyloxy;

R$^4$ is selected from hydrogen, alkyl, alkenyl, alkynyl, alkoxy, acyl, acylamino, acyloxy, —(CR$^a$R$^b$)$_n$C(O)R$^5$, —(CR$^a$R$^b$)$_n$NR$^6$R$^7$, aminocarbonyl, alkoxycarbonylamino, alkylsulfonylamino, aminocarbonylamino, hydroxyamino, alkoxyamino, azido, cyano, halogen, hydroxy, hydroxyalkyl, haloalkyl, perhaloalkyl, thiocarbonyl, carboxy, alkylcarboxy, carboxyalkyl, carboxyalkyloxy, alkylcarboxyalkyloxy —SO$_3$H, alkylthio, aminosulfonyl, alkylsulfonyl, and nitro;

Z is a bond or is a group selected from cycloalkylene, cycloalkylenealkyl, cycloalkenylene, cycloalkyleneoxo, cycloalkyleneamino, arylene, arylenealkyl, arylenethio, aryleneoxy, aryleneamino, arylenealkoxycarbonylamino, arylenesulfonyl, arylenesulfonylamino, heterocyclylene, heterocyclylenealkyl, heterocyclyleneoxy, heterocyclylenealkyloxy, heterocyclyleneamino, heterocyclylenethio, heterocyclylenealkylamino heteroarylene, heteroarylenealkyl, heteroaryleneoxy, heteroaryleneamino, spirocyclyl, (C$_{1-6}$)alkylene, (C$_{1-6}$)alkenylene or (C$_{1-6}$)alkynylene wherein one or more than one methylene groups from alkylene, alkenylene or alkynylene are optionally replaced by hetero atoms or groups such as —O—, —S(O)p-, —N(R$^5$)—, and —C(O);

B is a bond or is a group selected from cycloalkylene, cycloalkenylene, cycloalkylenecarbonyl, cycloalkylenealkoxy, cycloalkyleneamino, arylene, arylenecarbonyl, arylenealkoxycarbonyl, arylenealkoxycarbonylamino, aryleneaminocarbonyl, heterocyclylene, heterocyclylenealkyl, heterocyclylenecarbonyl, heterocyclylenealkylamino, heteroarylene, heteroarylenecarbonyl, heteroarylenealkylamino, (C$_{1-6}$)alkylene, (C$_{1-6}$)alkenylene or (C$_{1-6}$)alkynylene wherein one or more than one methylene groups from alkylene, alkenylene or alkynylene are optionally replaced by hetero atoms or groups such as —O—, —S(O)p-, —N(R$^5$)—, —C(O) or —C(=NR")— wherein R" is H, alkyl, cyano, hydroxy, hydroxyalkyl, haloalkyl or perhaloalkyl;

D is selected from hydrogen, hydroxy, alkoxy, alkoxyalkyl, cyano, halogen, haloalkyl, perhaloalkyl, alkyl, alkenyl, alkynyl, carboxy, carboxyalkyl, cyanoalkyl, acyl, cyanoalkylarbonyl, cyanoalkenylcarbonyl, —(CR$^a$R$^b$)$_n$OR$^5$, —SR$^5$, —(CR$^a$R$^b$)$_n$COOR$^5$, —(CR$^a$R$^b$)$_n$NR$^6$R$^7$, —(CR$^a$R$^b$)$_n$C(O)

NR$^6$R$^7$, —(CR$^a$R$^b$)$_n$NR$^5$C(O)NR$^6$R$^7$, thiocarbonyl, S(O)$_2$NR$^6$R$^7$, —NR$^5$S(O)$_2$R$^5$, —S(O)$_p$R$^5$, —SO$_3$H, cycloalkyl, cycloalkenyl, cycloalkylalkyl, cycloalkyloxy, cycloalkylamino, aryl, arylalkyl, aryloxy, arylamino, heterocyclyl, heterocyclylalkyl, heterocyclyloxy, heterocycloalkylamino, heteroaryl, heteroarylalkyl, heteroaryloxy, and heteroarylamino;

R$^5$ is selected from the group consisting of hydrogen, —(CR$^a$R$^b$)$_n$OR$^5$, halogen, haloalkyl, —(CR$^a$R$^b$)$_n$C(O)R$^5$, alkyl, alkenyl, alkynyl, aryl, arylalkyl, heteroaryl, heteroarylalkyl, cycloalkyl, cycloalkylalkyl, heterocyclyl and heterocyclylalkyl;

wherein alkyl, alkenyl, alkynyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, OR$^5$, —OC(O)R$^5$, —(CR$^a$R$^b$)$_n$C(O)NR$^6$R$^7$, —NR$^5$C(O)R$^5$, —SR$^5$, —S(O)$_p$R$^5$, —S(O)$_2$NR$^6$R$^7$ and —NR$^5$S(O)$_2$R$^5$;

R$^6$ and R$^7$ are independently selected from the group consisting of hydrogen, —(CR$^a$R$^b$)$_n$OR$^5$, haloalkyl, —(CR$^a$R$^b$)$_n$C(O)R$^5$, alkyl, alkenyl, alkynyl, aryl, arylalkyl, heteroaryl, heteroarylalkyl, cycloalkyl, cycloalkylalkyl, heterocyclyl and heterocyclylalkyl, or R$^6$ and R$^7$ taken together form a monocyclic or a bicyclic ring system which is saturated or partially unsaturated and optionally have additional heteroatoms selected from O, N or S, the said ring system is further optionally substituted with 1 to 4 substituents independently selected from halo, alkyl, alkenyl, alkynyl, nitro, cyano, —(CR$^a$R$^b$)$_n$OR$^5$, —SR$^5$, —(CR$^a$R$^b$)$_n$NR$^6$R$^7$, oxo, alkylsulfonyl, —(CR$^a$R$^b$)$_n$COOR$^5$, —(CR$^a$R$^b$)$_n$C(O)NR$^6$R$^7$, cycloalkyl, cycloalkylalkyl, aryl, arylalkyl, heterocyclyl, heterocyclylalkyl, heteroaryl, and heteroarylalkyl;

Z, B and D may be optionally substituted with one or more substituents independently selected from cyano, nitro, keto, oxo, halogen, haloalkyl, perhaloalkyl, hydroxyamino, —(CR$^a$R$^b$)$_n$OR$^5$, —(CR$^a$R$^b$)$_n$C(O)R$^5$OC(O)R$^5$, —SR$^5$, —(CR$^a$R$^b$)$_n$COOR$^5$, —(CR$^a$R$^b$)$_n$NR$^6$R$^7$, —(CR$^a$R$^b$)$_n$C(O)NR$^6$R$^7$, —(CR$^a$R$^b$)$_n$NR$^5$C(O)NR$^6$R$^7$, —NR$^5$C(O)R$^5$, thiocarbonyl, S(O)$_2$NR$^6$R$^7$, —NR$^5$S(O)$_2$R$^5$, —S(O)$_p$R$^5$, —SO$_3$H, —OP(O)(R$^8$)$_q$, alkyl, alkenyl, alkynyl, cycloalkyl, cyclkenyl, cycloalkylalkyl, aryl, heterocyclyl and heteroaryl;

wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)R$^5$, —(CR$^a$R$^b$)$_n$C(O)NR$^6$R$^7$, —NR$^5$C(O)R$^5$, —SR$^5$, —S(O)$_p$R$^5$, —S(O)$_2$NR$^6$R$^7$ and —NR$^5$S(O)$_2$R$^5$;

R$^8$ is selected from the group consisting of hydroxy and alkoxy;

R$^a$ and R$^b$ are independently selected from the group consisting of hydrogen, —OR$^5$, halogen, haloalkyl, perhaloalkyl and alkyl;

n is 0-6;
m is 0, 1 or 2;
p is 0, 1 or 2; and
q is 1 or 2;
with the proviso that when ring A is phenyl, then Y$^1$ cannot be N.

According to another embodiment, the present disclosure relates to compounds of formula (Ia) or its tautomers, polymorphs, stereoisomers, prodrugs, solvate, co-crystals or a pharmaceutically acceptable salts thereof, wherein, Y$^1$ represents N or CR' wherein R' is H or alkyl;
A represents a six membered ring which is saturated, unsaturated or partially unsaturated optionally having up to three heteroatoms selected from O, N or S;
R$^1$ is selected from hydrogen and alkyl;
R$^2$ is selected from the group consisting of hydrogen, halogen, hydroxyl, cyano and alkyl;
R$^3$ is selected from the group consisting of hydrogen, hydroxyalkyl, amino, monoalkylamino, dialkylamino, halogen, perhaloalkyl, cyano, nitro, alkoxyalkyl, carboxy, carboxyalkyl, acyl, aminocarbonyl and alkyl;
R$^4$ is selected from hydrogen, alkyl, alkoxy, acyl, acylamino, acyloxy, —(CR$^a$R$^b$)$_n$C(O)R$^5$, —(CR$^a$R$^b$)$_n$NR$^6$R$^7$, aminocarbonyl, hydroxyamino, alkoxyamino, azido, cyano, halogen, hydroxy, hydroxyalkyl, haloalkyl, perhaloalkyl, carboxy, alkylcarboxy, carboxy alkyl, carboxyalkyloxy, alkylcarboxyalkyloxy and nitro;
Z is a bond or is a group selected from cycloalkylene, arylene, heterocyclylene, heterocyclylenealkyl, heteroarylene, spirocyclyl, (C$_{1-6}$)alkylene, (C$_{1-6}$)alkenylene or (C$_{1-6}$)alkynylene wherein one or more than one methylene groups from alkylene, alkenylene or alkynylene are optionally replaced by hetero atoms or groups such as —O—, —S(O)p-, —N(R$^5$)—, and —C(O);
B is a bond or is a group selected from cycloalkylene, cycloalkenylene, arylene, heterocyclylene, heteroarylene, (C$_{1-6}$)alkylene, (C$_{1-6}$)alkenylene or (C$_{1-6}$)alkynylene wherein one or more than one methylene groups from alkylene, alkenylene or alkynylene are optionally replaced by hetero atoms or groups such as —O—, —S(O)p-, —N(R$^5$)—, —C(O) or —C(=NR")— wherein R" is H, alkyl, cyano, hydroxy, hydroxyalkyl, haloalkyl or perhaloalkyl;
D is selected from hydrogen, hydroxy, alkoxy, alkoxyalkyl, cyano, halogen, haloalkyl, perhaloalkyl, alkyl, alkenyl, alkynyl, carboxy, carboxyalkyl, cyanoalkyl, acyl, cyanoalkylarbonyl, cyanoalkenylcarbonyl, —(CR$^a$R$^b$)$_n$OR$^5$, —SR$^5$, —(CR$^a$R$^b$)$_n$COOR$^5$, —(CR$^a$R$^b$)$_n$NR$^6$R$^7$, —(CR$^a$R$^b$)$_n$C(O)NR$^6$R$^7$, —(CR$^a$R$^b$)$_n$NR$^5$C(O)NR$^6$R$^7$, thiocarbonyl, S(O)$_2$NR$^6$R$^7$, —NR$^5$S(O)$_2$R$^5$, —S(O)$_p$R$^5$, —SO$_3$H, cycloalkyl, cycloalkenyl, cycloalkylalkyl, cycloalkyloxy, cycloalkylamino, aryl, arylalkyl, aryloxy, arylamino, heterocyclyl, heterocyclylalkyl, heterocyclyloxy, heterocycloalkylamino, heteroaryl, heteroarylalkyl, heteroaryloxy, and heteroarylamino;

R$^5$ is selected from the group consisting of hydrogen, —(CR$^a$R$^b$)$_n$OR$^5$, halogen, haloalkyl, —(CR$^a$R$^b$)$_n$C(O)R$^5$, alkyl, alkenyl, alkynyl, aryl, arylalkyl, heteroaryl, heteroarylalkyl, cycloalkyl, cycloalkylalkyl, heterocyclyl and heterocyclylalkyl;

wherein alkyl, alkenyl, alkynyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, OR$^5$, —OC(O)R$^5$, —(CR$^a$R$^b$)$_n$C(O)NR$^6$R$^7$, —NR$^5$C(O)R$^5$, —SR$^5$, —S(O)$_p$R$^5$, —S(O)$_2$NR$^6$R$^7$ and —NR$^5$S(O)$_2$R$^5$;

R$^6$ and R$^7$ are independently selected from the group consisting of hydrogen, —(CR$^a$R$^b$)$_n$OR$^5$, haloalkyl, —(CR$^a$R$^b$)$_n$C(O)R$^5$, alkyl, alkenyl, alkynyl, aryl, arylalkyl, heteroaryl, heteroarylalkyl, cycloalkyl, cycloalkylalkyl, heterocyclyl and heterocyclylalkyl, or R$^6$ and R$^7$ taken together form a monocyclic or a bicyclic ring system which is saturated or partially unsaturated and optionally have additional heteroatoms selected from O, N or S, the said ring system is further optionally substituted with 1 to 4 substituents independently selected from halo, alkyl, alkenyl, alkynyl, nitro, cyano, —(CR$^a$R$^b$)$_n$OR$^5$, —SR$^5$, —(CR$^a$R$^b$)$_n$NR$^6$R$^7$, oxo, alkylsulfonyl, —(CR$^a$R$^b$)$_n$COOR$^5$, —(CR$^a$R$^b$)$_n$C(O)NR$^6$R$^7$, cycloalkyl, cycloalkylalkyl, aryl, arylalkyl, heterocyclyl, heterocyclylalkyl, heteroaryl, and heteroarylalkyl;

Z, B and D may be optionally substituted with one or more substituents independently selected from cyano, nitro, keto, oxo, halogen, haloalkyl, perhaloalkyl, hydroxyamino, —(CR$^a$R$^b$)$_n$OR$^5$, —(CR$^a$R$^b$)$_n$C(O)R$^5$OC(O)R$^5$, —SR$^5$, —(CR$^a$R$^b$)$_n$COOR$^5$, —(CR$^a$R$^b$)$_n$NR$^6$R$^7$, —(CR$^a$R$^b$)$_n$C(O)NR$^6$R$^7$, —(CR$^a$R$^b$)$_n$NR$^5$C(O)NR$^6$R$^7$, —NR$^5$C(O)R$^5$, thiocarbonyl, S(O)$_2$NR$^6$R$^7$, —NR$^5$S(O)$_2$R$^5$, —S(O)$_p$R$^5$, —SO$_3$H, —OP(O)(R$^8$)$_q$, alkyl, alkenyl, alkynyl, cycloalkyl, cyclkenyl, cycloalkylalkyl, aryl, heterocyclyl and heteroaryl;

wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)R$^5$, —(CR$^a$R$^b$)$_n$C(O)NR$^6$R$^7$, —NR$^5$C(O)R$^5$, —SR$^5$, —S(O)$_p$R$^5$, —S(O)$_2$NR$^6$R$^7$ and —NR$^5$S(O)$_2$R$^5$;

R$^8$ is selected from the group consisting of hydroxy and alkoxy;

R$^a$ and R$^b$ are independently selected from the group consisting of hydrogen, —OR$^5$, halogen, haloalkyl, perhaloalkyl and alkyl;

n is 0-6;
m is 0, 1 or 2;
p is 0, 1 or 2; and
q is 1 or 2;
with the proviso that when ring A is phenyl, then Y$^1$ cannot be N.

According to another embodiment, the present disclosure relates to compounds of formula (Ia) or its tautomers, polymorphs, stereoisomers, prodrugs, solvate, co-crystals or a pharmaceutically acceptable salts thereof, wherein,
Y$^1$ represents N or CR' wherein R' is H or alkyl;
A is selected from

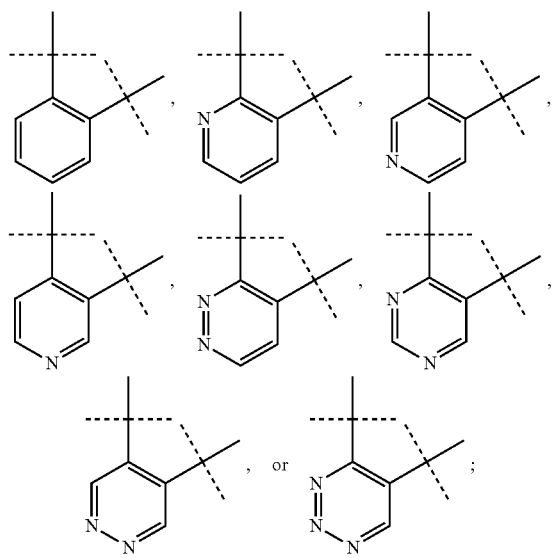

R$^1$ is selected from hydrogen or alkyl;
R$^2$ is selected from hydrogen or alkyl;
R$^3$ is selected from hydrogen or alkyl;

R$^4$ is selected from hydrogen, alkyl, alkoxy, acyl, acylamino, acyloxy, —(CR$^a$R$^b$)$_n$C(O)R$^5$, —(CR$^a$R$^b$)$_n$NR$^6$R$^7$, aminocarbonyl, hydroxyamino, alkoxyamino, azido, cyano, halogen, hydroxy, hydroxyalkyl, haloalkyl, perhaloalkyl, carboxy, alkylcarboxy, carboxyalkyl, carboxyalkyloxy, alkylcarboxyalkyloxy and nitro;

Z is a bond or is a group selected from cycloalkylene, arylene, heterocyclylene, heterocyclylenealkyl, heteroarylene, spirocyclyl, (C$_{1-6}$)alkylene, (C$_{1-6}$)alkenylene or (C$_{1-6}$)alkynylene wherein one or more than one methylene groups from alkylene, alkenylene or alkynylene are optionally replaced by hetero atoms or groups such as —O—, —S(O)p-, —N(R$^5$)—, and —C(O);

B is a bond or is a group selected from cycloalkylene, cycloalkenylene, arylene, heterocyclylene, heteroarylene, (C$_{1-6}$)alkylene, (C$_{1-6}$)alkenylene or (C$_{1-6}$)alkynylene wherein one or more than one methylene groups from alkylene, alkenylene or alkynylene are optionally replaced by hetero atoms or groups such as —O—, —S(O)p-, —N(R$^5$)—, —C(O) or —C(=NR")— wherein R" is H, alkyl, cyano, hydroxy, hydroxyalkyl, haloalkyl or perhaloalkyl;

D is selected from hydrogen, hydroxy, alkoxy, alkoxyalkyl, cyano, halogen, haloalkyl, perhaloalkyl, alkyl, alkenyl, alkynyl, carboxy, carboxyalkyl, cyanoalkyl, acyl, cyanoalkylarbonyl, cyanoalkenylcarbonyl, —(CR$^a$R$^b$)$_n$OR$^5$, —SR$^5$, —(CR$^a$R$^b$)$_n$COOR$^5$, —(CR$^a$R$^b$)$_n$NR$^6$R$^7$, —(CR$^a$R$^b$)$_n$C(O)NR$^6$R$^7$, —(CR$^a$R$^b$)$_n$NR$^5$C(O)NR$^6$R$^7$, thiocarbonyl, S(O)$_2$NR$^6$R$^7$, —NR$^5$S(O)$_2$R$^5$, —S(O)$_p$R$^5$, —SO$_3$H, cycloalkyl, cycloalkenyl, cycloalkylalkyl, cycloalkyloxy, cycloalkylamino, aryl, arylalkyl, aryloxy, arylamino, heterocyclyl, heterocyclylalkyl, heterocyclyloxy, heterocycloalkylamino, heteroaryl, heteroarylalkyl, heteroaryloxy, and heteroarylamino;

R$^5$ is selected from the group consisting of hydrogen, —(CR$^a$R$^b$)$_n$OR$^5$, halogen, haloalkyl, —(CR$^a$R$^b$)$_n$C(O)R$^5$, alkyl, alkenyl, alkynyl, aryl, arylalkyl, heteroaryl, heteroarylalkyl, cycloalkyl, cycloalkylalkyl, heterocyclyl and heterocyclylalkyl;

wherein alkyl, alkenyl, alkynyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, OR$^5$, —OC(O)R$^5$, —(CR$^a$R$^b$)$_n$C(O)NR$^6$R$^7$, —NR$^5$C(O)R$^5$, —SR$^5$, —S(O)$_p$R$^5$, —S(O)$_2$NR$^6$R$^7$ and —NR$^5$S(O)$_2$R$^5$;

R$^6$ and R$^7$ are independently selected from the group consisting of hydrogen, —(CR$^a$R$^b$)$_n$OR$^5$, haloalkyl, —(CR$^a$R$^b$)$_n$C(O)R$^5$, alkyl, alkenyl, alkynyl, aryl, arylalkyl, heteroaryl, heteroarylalkyl, cycloalkyl, cycloalkylalkyl, heterocyclyl and heterocyclylalkyl, or R$^6$ and R$^7$ taken together form a monocyclic or a bicyclic ring system which is saturated or partially unsaturated and optionally have additional heteroatoms selected from O, N or S, the said ring system is further optionally substituted with 1 to 4 substituents independently selected from halo, alkyl, alkenyl, alkynyl, nitro, cyano, —(CR$^a$R$^b$)$_n$OR$^5$, —SR$^5$, —(CR$^a$R$^b$)$_n$NR$^6$R$^7$, oxo, alkylsulfonyl, —(CR$^a$R$^b$)$_n$COOR$^5$, —(CR$^a$R$^b$)$_n$C(O)NR$^6$R$^7$, cycloalkyl, cycloalkylalkyl, aryl, arylalkyl, heterocyclyl, heterocyclylalkyl, heteroaryl, and heteroarylalkyl;

Z, B and D may be optionally substituted with one or more substituents independently selected from cyano, nitro, keto, oxo, halogen, haloalkyl, perhaloalkyl, hydroxyamino, —(CR$^a$R$^b$)$_n$OR$^5$, —(CR$^a$R$^b$)$_n$C(O)R$^5$, OC(O)R$^5$, —SR$^5$, —(CR$^a$R$^b$)$_n$COOR$^5$, —(CR$^a$R$^b$)$_n$NR$^6$R$^7$, —(CR$^a$R$^b$)$_n$C(O)NR$^6$R$^7$, —(CR$^a$R$^b$)$_n$NR$^5$C(O)NR$^6$R$^7$, —NR$^5$C(O)R$^5$, thiocarbonyl, S(O)₂NR⁶R⁷, —NR⁵S(O)₂R⁵, —S(O)ₚR⁵, —SO₃H, —OP(O)(R⁸)_q, alkyl, alkenyl, alkynyl, cycloalkyl, cyclkenyl, cycloalkylalkyl, aryl, heterocyclyl and heteroaryl;
  wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)R⁵, —(CRᵃRᵇ)ₙC(O)NR⁶R⁷, —NR⁵C(O)R⁵, —SR⁵, —S(O)ₚR⁵, —S(O)₂NR⁶R⁷ and —NR⁵S(O)₂R⁵;
R⁸ is selected from the group consisting of hydroxy and alkoxy;
Rᵃ and Rᵇ are independently selected from the group consisting of hydrogen, —OR⁵, halogen, haloalkyl, perhaloalkyl and alkyl;
n is 0-6;
m is 0, 1 or 2;
p is 0, 1 or 2; and
q is 1 or 2;
with the proviso that when ring A is phenyl, then Y¹ cannot be N.

According to another embodiment, the present disclosure relates to compounds of formula (Ia) or its tautomers, polymorphs, stereoisomers, prodrugs, solvate, co-crystals or a pharmaceutically acceptable salts thereof, wherein,
Y¹ represents N or CR' wherein R' is H or alkyl;
A is selected from

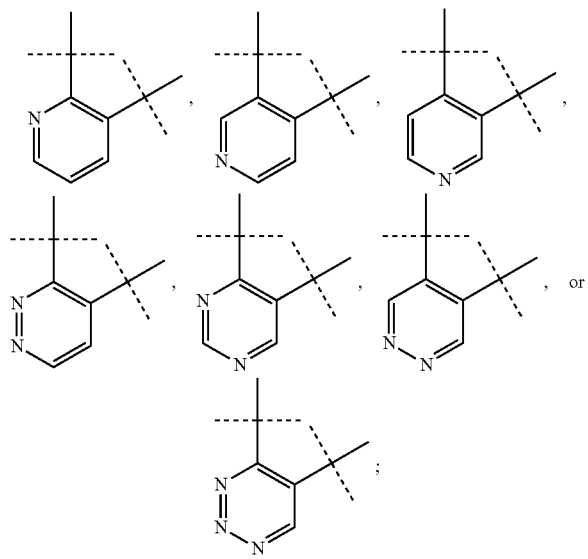

R¹ is selected from hydrogen or alkyl;
R² is selected from hydrogen or alkyl;
R³ is selected from hydrogen or alkyl;
R⁴ is selected from hydrogen, alkyl, alkoxy, cyano, halogen, hydroxy, hydroxyalkyl, haloalkyl, perhaloalkyl, carboxy, alkylcarboxy, carboxyalkyl, carboxyalkyloxy, alkylcarboxyalkyloxy and nitro;
Z is a bond or is a group selected from cycloalkylene, arylene, heterocyclylene, heterocyclylenealkyl, heteroarylene, spirocyclyl, (C₁₋₆)alkylene, (C₁₋₆)alkenylene or (C₁₋₆)alkynylene wherein one or more than one methylene groups from alkylene, alkenylene or alkynylene are optionally replaced by hetero atoms or groups such as —O—, —S(O)p-, —N(R⁵)—, or —C(O);

B is a bond or is a group selected from cycloalkylene, cycloalkenylene, arylene, heterocyclylene, heteroarylene, (C₁₋₆)alkylene, (C₁₋₆)alkenylene or (C₁₋₆)alkynylene wherein one or more than one methylene groups from alkylene, alkenylene or alkynylene are optionally replaced by hetero atoms or groups such as —O—, —S(O)p-, —N(R⁵)—, —C(O) or —C(=NR")— wherein R" is H, alkyl, cyano, hydroxy, hydroxyalkyl, haloalkyl or perhaloalkyl;
D is selected from hydrogen, hydroxy, alkoxy, alkoxyalkyl, cyano, halogen, haloalkyl, perhaloalkyl, alkyl, alkenyl, alkynyl, carboxy, carboxyalkyl, cyanoalkyl, acyl, cyanoalkylarbonyl, cyanoalkenylcarbonyl, —(CRᵃRᵇ)ₙOR⁵, —SR⁵, —(CRᵃRᵇ)ₙCOOR⁵, —(CRᵃRᵇ)ₙNR⁶R⁷, —(CRᵃRᵇ)ₙC(O)NR⁶R⁷, —(CRᵃRᵇ)ₙNR⁵C(O)NR⁶R⁷, thiocarbonyl, S(O)₂NR⁶R⁷, —NR⁵S(O)₂R⁵, —S(O)ₚR⁵, —SO₃H, cycloalkyl, cycloalkenyl, cycloalkylalkyl, cycloalkyloxy, cycloalkylamino, aryl, arylalkyl, aryloxy, arylamino, heterocyclyl, heterocyclylalkyl, heterocyclyloxy, heterocycloalkylamino, heteroaryl, heteroarylalkyl, heteroaryloxy, and heteroarylamino;
R⁵ is selected from the group consisting of hydrogen, —(CRᵃRᵇ)ₙOR⁵, halogen, haloalkyl, —(CRᵃRᵇ)ₙC(O)R⁵, alkyl, alkenyl, alkynyl, aryl, arylalkyl, heteroaryl, heteroarylalkyl, cycloalkyl, cycloalkylalkyl, heterocyclyl and heterocyclylalkyl;
  wherein alkyl, alkenyl, alkynyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, OR⁵, —OC(O)R⁵, —(CRᵃRᵇ)ₙC(O)NR⁶R⁷, —NR⁵C(O)R⁵, —SR⁵, —S(O)ₚR⁵, —S(O)₂NR⁶R⁷ or —NR⁵S(O)₂R⁵;
R⁶ and R⁷ are independently selected from the group consisting of hydrogen, —(CRᵃRᵇ)ₙOR⁵, haloalkyl, —(CRᵃRᵇ)ₙC(O)R⁵, alkyl, alkenyl, alkynyl, aryl, arylalkyl, heteroaryl, heteroarylalkyl, cycloalkyl, cycloalkylalkyl, heterocyclyl and heterocyclylalkyl, or
R⁶ and R⁷ taken together form a monocyclic or a bicyclic ring system which is saturated or partially unsaturated and optionally have additional heteroatoms selected from O, N or S, the said ring system is further optionally substituted with 1 to 4 substituents independently selected from halo, alkyl, alkenyl, alkynyl, nitro, cyano, —(CRᵃRᵇ)ₙOR⁵, —SR⁵, —(CRᵃRᵇ)ₙNR⁶R⁷, oxo, alkylsulfonyl, —(CRᵃRᵇ)ₙCOOR⁵, —(CRᵃRᵇ)ₙC(O)NR⁶R⁷, cycloalkyl, cycloalkylalkyl, aryl, arylalkyl, heterocyclyl, heterocyclylalkyl, heteroaryl, and heteroarylalkyl;
Z, B and D may be optionally substituted with one or more substituents independently selected from cyano, nitro, keto, oxo, halogen, haloalkyl, perhaloalkyl, hydroxyamino, —(CRᵃRᵇ)ₙOR⁵, —(CRᵃRᵇ)ₙC(O)R⁵OC(O)R⁵, —SR⁵, —(CRᵃRᵇ)ₙCOOR⁵, —(CRᵃRᵇ)ₙNR⁶R⁷, —(CRᵃRᵇ)ₙC(O)NR⁶R⁷, —(CRᵃRᵇ)ₙNR⁵C(O)NR⁶R⁷, —NR⁵C(O)R⁵, thiocarbonyl, S(O)₂NR⁶R⁷, —NR⁵S(O)₂R⁵, —S(O)ₚR⁵, —SO₃H, —OP(O)(R⁸)_q, alkyl, alkenyl, alkynyl, cycloalkyl, cyclkenyl, cycloalkylalkyl, aryl, heterocyclyl and heteroaryl;
  wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)R⁵, —(CRᵃRᵇ)ₙC(O)NR⁶R⁷, —NR⁵C(O)R⁵, —SR⁵, —S(O)ₚR⁵, —S(O)₂NR⁶R⁷ or —NR⁵S(O)₂R⁵;
R⁸ is selected from the group consisting of hydroxy and alkoxy;

$R^a$ and $R^b$ are independently selected from the group consisting of hydrogen, —$OR^5$, halogen, haloalkyl, perhaloalkyl or alkyl;

n is 0-6;
m is 0, 1 or 2;
p is 0, 1 or 2; and
q is 1 or 2.

According to another embodiment, the present disclosure relates to compounds of formula (Ia) or its tautomers, polymorphs, stereoisomers, prodrugs, solvate, co-crystals or a pharmaceutically acceptable salts thereof, wherein,
$Y^1$ is N;
A is selected from

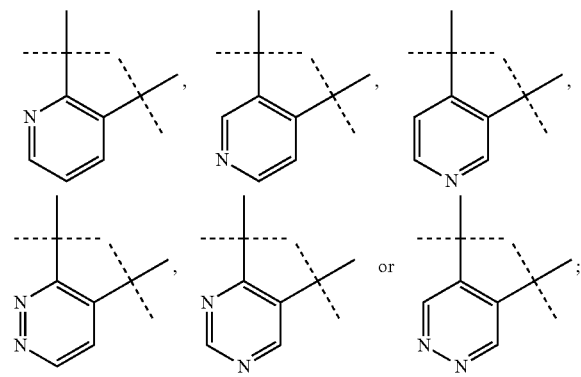

$R^1$ is selected from hydrogen or alkyl;
$R^2$ is selected from hydrogen or alkyl;
$R^3$ is selected from hydrogen or alkyl;
$R^4$ is selected from hydrogen, alkyl, alkoxy, cyano, halogen, hydroxy, hydroxyalkyl, haloalkyl or perhaloalkyl;
Z is a bond or is a group selected from cycloalkylene, heterocyclylene, heterocyclylenealkyl or $(C_{1-6})$alkylene, wherein one or more than one methylene groups from alkylene is optionally replaced by hetero atoms or groups such as —O—, —S(O)p-, —N($R^5$)—, or —C(O);
B is a bond or is a group selected from cycloalkylene, heterocyclylene or $(C_{1-6})$alkylene, wherein one or more than one methylene groups from alkylene is optionally replaced by hetero atoms or groups such as —O—, —S(O)p-, —N($R^5$)—, —C(O) or —C(=NR")— wherein R" is H, alkyl, cyano, hydroxy, hydroxyalkyl, haloalkyl or perhaloalkyl;
D is selected from hydrogen, hydroxy, alkoxy, alkoxyalkyl, cyano, halogen, haloalkyl, perhaloalkyl, alkyl, alkenyl, alkynyl, cyanoalkyl, acyl, cyanoalkylarbonyl, —$(CR^aR^b)_nOR^5$, —$SR^5$, —$(CR^aR^b)_nCOOR^5$, —$(CR^aR^b)_nNR^6R^7$, —$(CR^aR^b)_nC(O)NR^6R^7$, —$(CR^aR^b)_nNR^5C(O)NR^6R^7$, thiocarbonyl, $S(O)_2NR^6R^7$, —$NR^5S(O)_2R^5$, —$S(O)_pR^5$, —$SO_3H$, cycloalkyl, cycloalkenyl, cycloalkylalkyl, aryl, arylalkyl, heterocyclyl, heterocyclylalkyl, heteroaryl or heteroarylalkyl;
$R^5$ is selected from the group consisting of hydrogen, —$(CR^aR^b)_nOR^5$, halogen, haloalkyl, —$(CR^aR^b)_nC(O)R^5$, alkyl, alkenyl, alkynyl, aryl, arylalkyl, heteroaryl, heteroarylalkyl, cycloalkyl, cycloalkylalkyl, heterocyclyl and heterocyclylalkyl;
wherein alkyl, alkenyl, alkynyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, $OR^5$, —$OC(O)R^5$, —$(CR^aR^b)_nC(O)NR^6R^7$, —$NR^5C(O)R^5$, —$SR^5$, —$S(O)_pR^5$, —$S(O)_2NR^6R^7$ or —$NR^5S(O)_2R^5$;
$R^6$ and $R^7$ are independently selected from the group consisting of hydrogen, haloalkyl, —$(CR^aR^b)_nC(O)R^5$, alkyl, alkenyl, alkynyl, arylalkyl, heteroarylalkyl, cycloalkyl, cycloalkylalkyl, heterocyclyl and heterocyclylalkyl, or
$R^6$ and $R^7$ taken together form a monocyclic or a bicyclic ring system which is saturated or partially unsaturated and optionally have additional heteroatoms selected from O, N or S;
Z, B and D may be optionally substituted with one or more substituents independently selected from cyano, nitro, keto, oxo, halogen, haloalkyl, perhaloalkyl, hydroxyamino, —$(CR^aR^b)_nOR^5$, —$(CR^aR^b)_nC(O)R^5OC(O)R^5$, —$SR^5$, —$(CR^aR^b)_nCOOR^5$, —$(CR^aR^b)_nNR^6R^7$, —$(CR^aR^b)_nC(O)NR^6R^7$, —$(CR^aR^b)_nNR^5C(O)NR^6R^7$, —$NR^5C(O)R^5$, thiocarbonyl, $S(O)_2NR^6R^7$, —$NR^5S(O)_2R^5$, —$S(O)_pR^5$, —$SO_3H$, —$OP(O)(R^8)_q$, alkyl, alkenyl, alkynyl, cycloalkyl, cyclkenyl, cycloalkylalkyl, aryl, heterocyclyl and heteroaryl;
wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —$OC(O)R^5$, —$(CR^aR^b)_nC(O)NR^6R^7$, —$NR^5C(O)R^5$, —$SR^5$, —$S(O)_pR^5$, —$S(O)_2NR^6R^7$ or —$NR^5S(O)_2R^5$;
$R^8$ is selected from the group consisting of hydroxy and alkoxy;
$R^a$ and $R^b$ are independently selected from the group consisting of hydrogen, —$OR^5$, halogen, haloalkyl, perhaloalkyl and alkyl;
n is 0-6;
m is 0, 1 or 2;
p is 0, 1 or 2; and
q is 1 or 2.

According to another embodiment, the present disclosure relates to compounds of formula (Ia) or its tautomers, polymorphs, stereoisomers, prodrugs, solvate, co-crystals or a pharmaceutically acceptable salts thereof, wherein,
$Y^1$ is N;
A is selected from

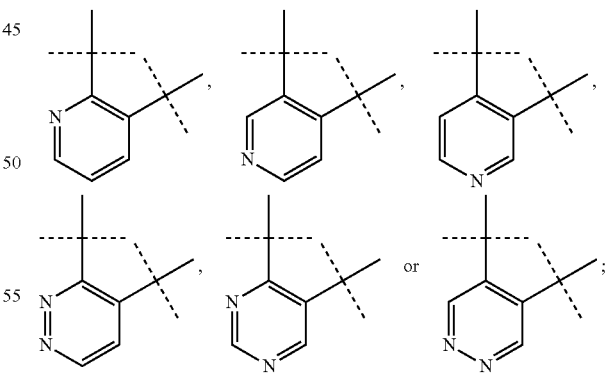

$R^1$, $R^2$ and $R^3$ are independently selected from hydrogen or alkyl;
$R^4$ is selected from hydrogen, alkyl, alkoxy, cyano, halogen, hydroxy, hydroxyalkyl, haloalkyl or perhaloalkyl;
Z is a bond or is a group selected from cycloalkylene and heterocyclylene;
B is a bond or is $(C_{1-6})$alkylene, wherein one or more than one methylene groups from alkylene is optionally replaced by hetero atoms or groups such as —O—, —S(O)p-, —N(R⁵)—, —C(O) or —C(=NR")— wherein R" is H, alkyl, cyano, hydroxy, hydroxyalkyl, haloalkyl or perhaloalkyl;

D is selected from hydrogen, hydroxy, alkoxy, alkoxyalkyl, cyano, halogen, haloalkyl, perhaloalkyl, alkyl, —(CRᵃRᵇ)ₙOR⁵, —SR⁵, —(CRᵃRᵇ)ₙCOOR⁵, —(CRᵃRᵇ)ₙNR⁶R⁷, —(CRᵃRᵇ)ₙC(O)NR⁶R⁷, —(CRᵃRᵇ)ₙNR⁵C(O)NR⁶R⁷, S(O)₂NR⁶R⁷, —NR⁵S(O)₂R⁵, —S(O)ₚR⁵, —SO₃H, cycloalkyl, cycloalkenyl, aryl, heterocyclyl or heteroaryl;

R⁵ is selected from a group consisting of hydrogen, —(CRᵃRᵇ)ₙOR⁵, halogen, haloalkyl, —(CRᵃRᵇ)ₙC(O)R⁵, alkyl, aryl, heteroaryl, cycloalkyl or heterocyclyl;

wherein alkyl, aryl, heteroaryl, cycloalkyl or heterocyclyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, OR⁵, —OC(O)R⁵, —(CRᵃRᵇ)ₚC(O)NR⁶R⁷, —NR⁵C(O)R⁵, —SR⁵, —S(O)ₚR⁵, —S(O)₂NR⁶R⁷ or —NR⁵S(O)₂R⁵;

R⁶ and R⁷ are independently selected from the group consisting of hydrogen, haloalkyl or alkyl, or
R⁶ and R⁷ taken together form a monocyclic or a bicyclic ring system which is saturated or partially unsaturated and optionally have additional heteroatoms selected from O, N or S;

Z, B and D may be optionally substituted with one or more substituents independently selected from cyano, nitro, keto, oxo, halogen, haloalkyl, perhaloalkyl, hydroxyamino, —(CRᵃRᵇ)ₙOR⁵, —(CRᵃRᵇ)ₙC(O)R⁵OC(O)R⁵, —SR⁵, —(CRᵃRᵇ)ₙCOOR⁵, —(CRᵃRᵇ)ₙNR⁶R⁷, —(CRᵃRᵇ)ₙC(O)NR⁶R⁷, —(CRᵃRᵇ)ₙNR⁵C(O)NR⁶R⁷, —NR⁵C(O)R⁵, thiocarbonyl, S(O)₂NR⁶R⁷, —NR⁵S(O)₂R⁵, —S(O)ₚR⁵, —SO₃H, —OP(O)(R⁸)_q, alkyl, alkenyl, alkynyl, cycloalkyl, cyclkenyl, cycloalkylalkyl, aryl, heterocyclyl and heteroaryl;

wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)R⁵, —(CRᵃRᵇ)ₙC(O)NR⁶R⁷, —NR⁵C(O)R⁵, —SR⁵, —S(O)ₚR⁵, —S(O)₂NR⁶R⁷ or —NR⁵S(O)₂R⁵;

R⁸ is selected from the group consisting of hydroxy and alkoxy;

Rᵃ and Rᵇ are independently selected from the group consisting of hydrogen, halogen, haloalkyl, perhaloalkyl or alkyl;

n is 0-6;
m is 0, 1 or 2;
p is 0, 1 or 2; and
q is 1 or 2.

According to another embodiment, the present disclosure relates to compounds of formula (Ia) or its tautomers, polymorphs, stereoisomers, prodrugs, solvate, co-crystals or a pharmaceutically acceptable salts thereof, wherein,
Y¹ represents N or CR' wherein R' is H or alkyl;
A is selected from

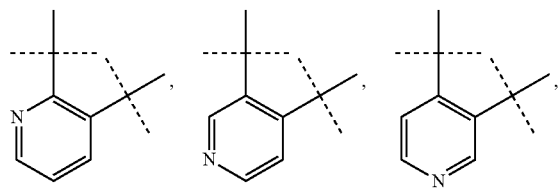

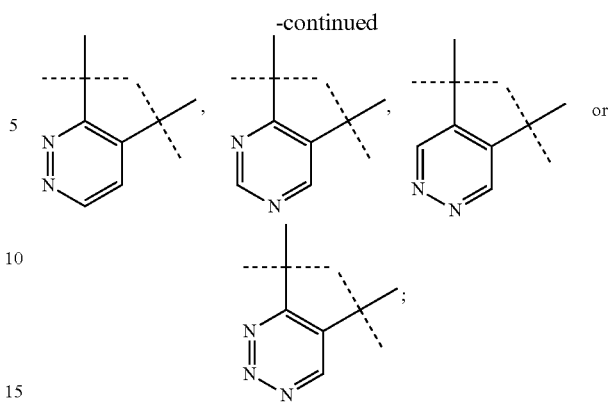

R¹ is selected from hydrogen or alkyl;
R² is selected from hydrogen or alkyl;
R³ is selected from hydrogen or alkyl;
R⁴ is selected from hydrogen, alkyl, alkoxy, cyano, halogen, hydroxy, hydroxyalkyl, haloalkyl, perhaloalkyl, carboxy, alkylcarboxy, carboxyalkyl, carboxyalkyloxy, alkylcarboxyalkyloxy or nitro;
Z is selected from

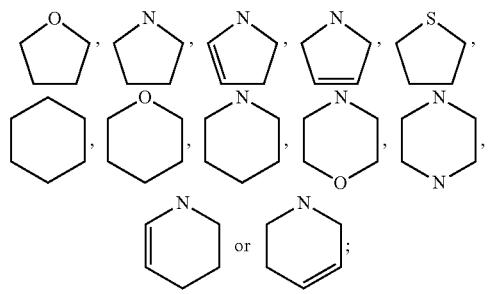

B is a bond or (C₁₋₆)alkylene wherein one or more than one methylene groups are optionally replaced by hetero atoms or groups such as —O—, —S(O)p-, —N(R⁵)—, —C(O) or —C(=NR")— wherein R" is H, alkyl, cyano, hydroxy, hydroxyalkyl, haloalkyl or perhaloalkyl;

D is selected from hydrogen, hydroxy, alkoxy, alkoxyalkyl, cyano, halogen, haloalkyl, perhaloalkyl, alkyl, alkenyl, alkynyl, carboxy, carboxyalkyl, cyanoalkyl, acyl, cyanoalkylarbonyl, cyanoalkenylcarbonyl, —(CRᵃRᵇ)ₙOR⁵, —SR⁵, —(CRᵃRᵇ)ₙCOOR⁵, —(CRᵃRᵇ)ₙNR⁶R⁷, —(CRᵃRᵇ)ₙC(O)NR⁶R⁷, —(CRᵃRᵇ)ₙNR⁵C(O)NR⁶R⁷, thiocarbonyl, S(O)₂NR⁶R⁷, —NR⁵S(O)₂R⁵, —S(O)ₚR⁵, —SO₃H, cycloalkyl, cycloalkenyl, cycloalkylalkyl, cycloalkyloxy, cycloalkylamino, aryl, arylalkyl, aryloxy, arylamino, heterocyclyl, heterocyclylalkyl, heterocyclyloxy, heterocycloalkylamino, heteroaryl, heteroarylalkyl, heteroaryloxy, or heteroarylamino;

R⁵ is selected from the group consisting of hydrogen, —(CRᵃRᵇ)ₙOR⁵, halogen, haloalkyl, —(CRᵃRᵇ)ₙC(O)R⁵, alkyl, alkenyl, alkynyl, aryl, arylalkyl, heteroaryl, heteroarylalkyl, cycloalkyl, cycloalkylalkyl, heterocyclyl and heterocyclylalkyl;

wherein alkyl, alkenyl, alkynyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OR⁵, —OC(O)R⁵, —(CᵃRᵇ)ₙC(O)NR⁶R⁷, —NR⁵C(O)R⁵, —SR⁵, —S(O)ₚR⁵, —S(O)₂NR⁶R⁷ or —NR⁵S(O)₂R⁵;

R⁶ and R⁷ are independently selected from the group consisting of hydrogen, —(CᵃRᵇ)ₙOR⁵, haloalkyl, —(CᵃRᵇ)ₙC(O)R⁵, alkyl, alkenyl, alkynyl, aryl, arylalkyl, heteroaryl, heteroarylalkyl, cycloalkyl, cycloalkylalkyl, heterocyclyl or heterocyclylalkyl, or R⁶ and R⁷ taken together form a monocyclic or a bicyclic ring system which is saturated or partially unsaturated and optionally have additional heteroatoms selected from O, N or S, the said ring system is further optionally substituted with 1 to 4 substituents independently selected from halo, alkyl, alkenyl, alkynyl, nitro, cyano, —(CᵃRᵇ)ₙOR⁵, —SR⁵, —(CᵃRᵇ)ₙNR⁶R⁷, oxo, alkylsulfonyl, —(CᵃRᵇ)ₙCOOR⁵, —(CᵃRᵇ)ₙC(O)NR⁶R⁷, cycloalkyl, cycloalkylalkyl, aryl, arylalkyl, heterocyclyl, heterocyclylalkyl, heteroaryl, or heteroarylalkyl;

Z, B and D may be optionally substituted with one or more substituents independently selected from cyano, nitro, keto, oxo, halogen, haloalkyl, perhaloalkyl, hydroxyamino, —(CᵃRᵇ)ₙOR⁵, —(CᵃRᵇ)ₙC(O)R⁵OC(O)R⁵, —SR⁵, —(CᵃRᵇ)ₙCOOR⁵, —(CᵃRᵇ)ₙNR⁶R⁷, —(CᵃRᵇ)ₙC(O)NR⁶R⁷, —(CᵃRᵇ)ₙNR⁵C(O)NR⁶R⁷, —NR⁵C(O)R⁵, thiocarbonyl, S(O)₂NR⁶R⁷, —NR⁵S(O)₂R⁵, —S(O)ₚR⁵, —SO₃H, —OP(O)(R⁸)_q, alkyl, alkenyl, alkynyl, cycloalkyl, cyclkenyl, cycloalkylalkyl, aryl, heterocyclyl or heteroaryl;

wherein alkyl, alkenyl, alkynyl, cycloalkyl, cyclkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)R⁵, —(CᵃRᵇ)ₙC(O)NR⁶R⁷, —NR⁵C(O)R⁵, —SR⁵, —S(O)ₚR⁵, —S(O)₂NR⁶R⁷ or —NR⁵S(O)₂R⁵;

R⁸ is selected from the group consisting of hydroxy and alkoxy;

Rᵃ and Rᵇ are independently selected from the group consisting of hydrogen, —OR⁵, halogen, haloalkyl, perhaloalkyl and alkyl;

n is 0-6;

m is 0, 1 or 2;

p is 0, 1 or 2; and q is 1 or 2.

According to another embodiment, the present disclosure relates to compounds of formula (Ia) or its tautomers, polymorphs, stereoisomers, prodrugs, solvate, co-crystals or a pharmaceutically acceptable salts thereof, wherein, Y¹ is N;

A is selected from

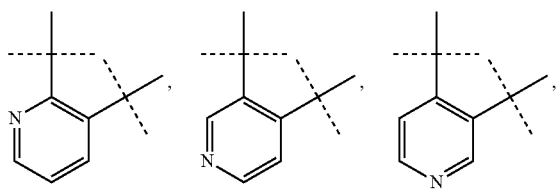

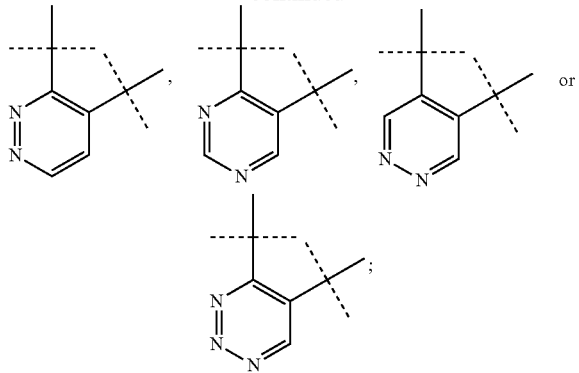

R¹ is selected from hydrogen or alkyl;
R² is selected from hydrogen or alkyl;
R³ is selected from hydrogen or alkyl;
R⁴ is selected from hydrogen, alkyl, alkoxy, cyano, halogen, hydroxy, hydroxyalkyl, haloalkyl, perhaloalkyl, carboxy, alkylcarboxy, carboxyalkyl, carboxyalkyloxy, alkylcarboxyalkyloxy or nitro;

Z is selected from

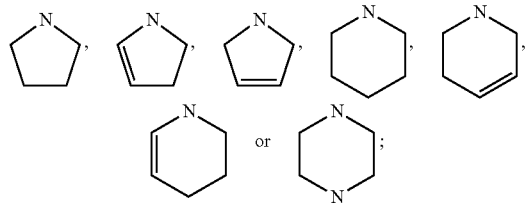

B is a bond or (C₁₋₆)alkylene wherein one or more than one methylene groups are optionally replaced by hetero atoms or groups such as —O—, —S(O)p-, —N(R⁵)—, —C(O) or —C(=NR")— wherein R" is H, alkyl, cyano, hydroxy, hydroxyalkyl, haloalkyl or perhaloalkyl;

D is selected from hydrogen, hydroxy, alkoxy, alkoxyalkyl, cyano, halogen, haloalkyl, perhaloalkyl, alkyl, alkenyl, alkynyl, carboxy, carboxyalkyl, cyanoalkyl, acyl, cyanoalkylarbonyl, cyanoalkenylcarbonyl, —(CᵃRᵇ)ₙOR⁵, —SR⁵, —(CᵃRᵇ)ₙCOOR⁵, —(CᵃRᵇ)ₙNR⁶R⁷, —(CᵃRᵇ)ₙC(O)NR⁶R⁷, —(CᵃRᵇ)ₙNR⁵C(O)NR⁶R⁷, thiocarbonyl, S(O)₂NR⁶R⁷, —NR⁵S(O)₂R⁵, —S(O)ₚR⁵ or —SO₃H;

R⁵ is selected from the group consisting of hydrogen, —(CᵃRᵇ)ₙOR⁵, halogen, haloalkyl, —(CᵃRᵇ)ₙC(O)R⁵, alkyl, alkenyl, alkynyl, aryl, arylalkyl, heteroaryl, heteroarylalkyl, cycloalkyl, cycloalkylalkyl, heterocyclyl or heterocyclylalkyl;

wherein alkyl, alkenyl, alkynyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OR⁵, —OC(O)R⁵, —(CᵃRᵇ)ₙC(O)NR⁶R⁷, —NR⁵C(O)R⁵, —SR⁵, —S(O)ₚR⁵, —S(O)₂NR⁶R⁷ or —NR⁵S(O)₂R⁵;

R⁶ and R⁷ are independently selected from the group consisting of hydrogen, —(CᵃRᵇ)ₙOR⁵, haloalkyl, —(CᵃRᵇ)ₙC(O)R⁵, alkyl, alkenyl, alkynyl, aryl, arylalkyl, heteroaryl, heteroarylalkyl, cycloalkyl, cycloalkylalkyl, heterocyclyl or heterocyclylalkyl;

Z, B and D may be optionally substituted with one or more substituents independently selected from cyano, nitro, keto, oxo, halogen, haloalkyl, perhaloalkyl, hydroxyamino, —$(CR^aR^b)_nOR^5$, —$(CR^aR^b)_nC(O)R^5OC(O)R^5$, —$SR^5$, —$(CR^aR^b)_nCOOR^5$, —$(CR^aR^b)_nNR^6R^7$, —$(CR^aR^b)_nC(O)NR^6R^7$, —$(CR^aR^b)_nNR^5C(O)NR^6R^7$, —$NR^5C(O)R^5$, thiocarbonyl, $S(O)_2NR^6R^2$, —$NR^5S(O)_2R^5$, —$S(O)_pR^5$, —$SO_3H$, —$OP(O)(R^8)_q$, alkyl;

$R^8$ is selected from the group consisting of hydroxy and alkoxy;

$R^a$ and $R^b$ are independently selected from the group consisting of hydrogen, halogen, haloalkyl, perhaloalkyl and alkyl;

n is 0-6;

m is 0, 1 or 2;

p is 0, 1 or 2; and q is 1 or 2.

The present disclosure further relates to the process of preparation of compounds of formula (I) or (Ia) or its tautomers, polymorphs, stereoisomers, prodrugs, solvate, co-crystals or pharmaceutically acceptable salts thereof.

The compounds of formula (Ia) may be prepared as outlined in the Scheme 1 below:

Scheme 1:

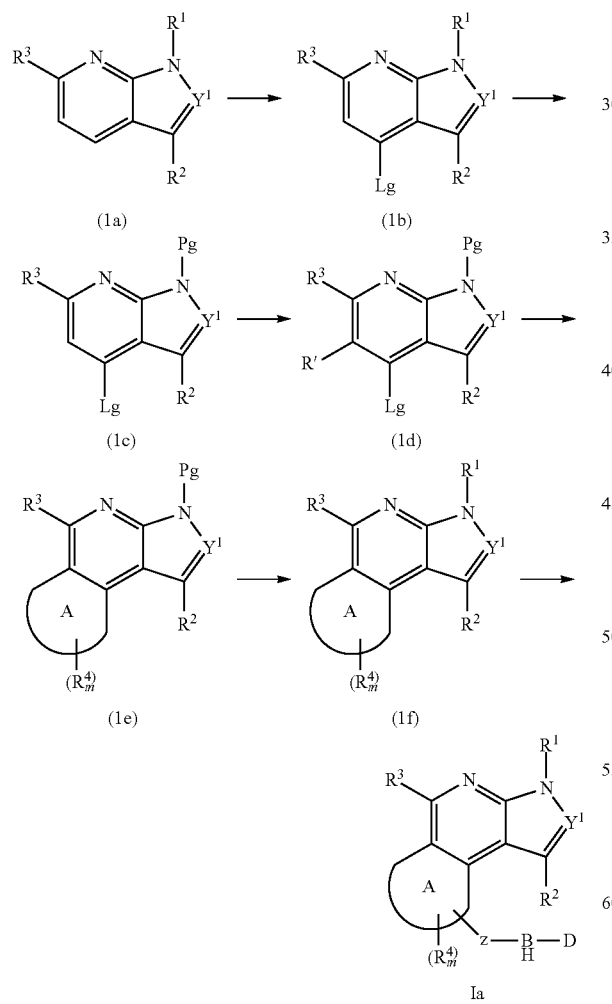

As exemplified in scheme 1 above, compound of formula (1a), wherein $R^1$, $R^2$, $R^3$ and Y are defined herein above, which is available commercially or can be prepared by well known methods in the art, may be converted to compounds of formula (1b) wherein Lg is a leaving group selected from halogen, triflate, tosylate or mesylate, preferably halogen and more preferably chlorine. Compounds of formula (1b) may be protected to obtain compounds of formula (1c) by methods well known in the art, wherein Pg is a protecting group such as p-toluene sulphonyl (Ts), methane sulphonyl (Ms), triisopropylsilyl (TIPS), p-methoxy benzyl (PMB), 2-(trimethylsilyl) ethoxymethyl (SEM), Methoxymethyl (MOM) and the like. Compound of formula (1c) may be converted to compounds of formula (1d) wherein R' is selected from —C(O)H, —C(O)OCH$_3$, —C(O)CH=CH$_2$, or —OH. Compound of formula (1d) may be cyclised to obtained compounds of formula (1e), wherein all symbols are defined herein above, which on deprotection reaction may provide compounds of formula (1f) wherein all symbols are defined herein above. Compounds of formula (1f) may be converted to compounds of formula (Ia) wherein all symbols are defined herein above. Schemes 2-11 further describes synthesis of compounds of formula (Ia)

Scheme 2: Compound of formula (Ia) wherein A is

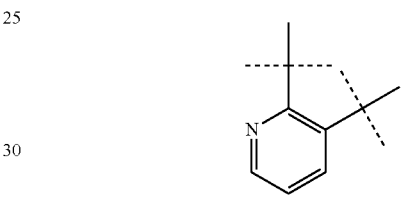

and all other symbols are defined herein above.

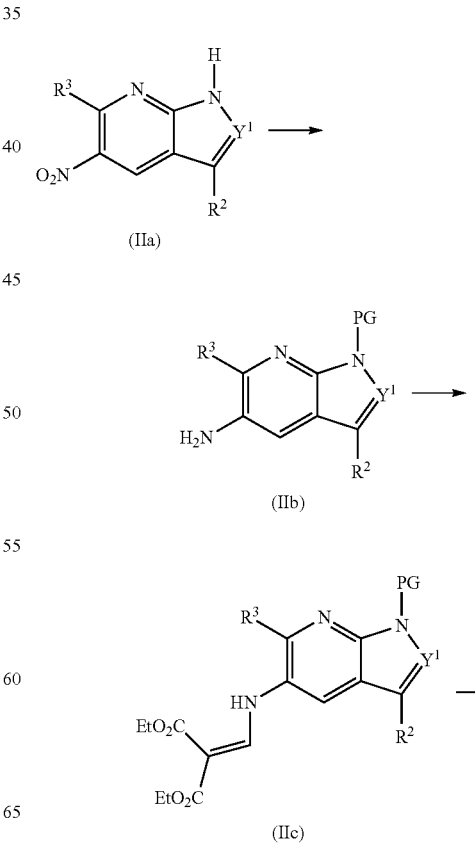

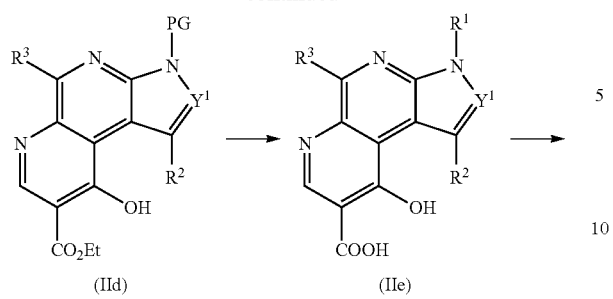

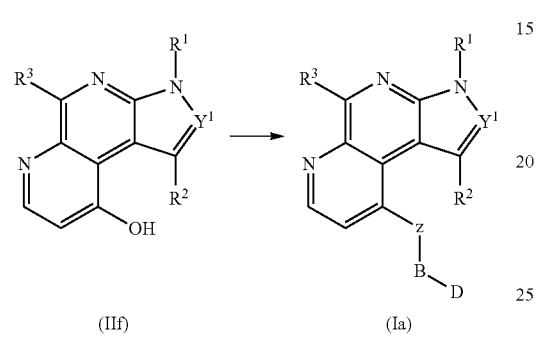

Compound of formula (IIa) was protected and reduced to obtain compound of formula (IIb) wherein PG is a protective group such as tosylate, benzenesulphonate, tri-isopropyl silyl and all other symbols are defined herein above. Compound of formula (IIb) was reacted with diethyl 2-(methoxymethylene) propanedioate to obtain compound of formula (IIc) which was cyclised to obtain compound of formula (IId). Compound of formula (IId) was hydrolysed to obtain compound of formula (IIe) which was further decarboxylated to obtain compounds of formula (IIf). Compound of formula (IIf) was coupled to provide compound of formula (Ia) wherein A is pyridine and all other symbols are defined herein above.

Scheme 3: Compound of formula (Ia) wherein A is

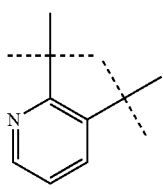

and all other symbols are defined herein above.

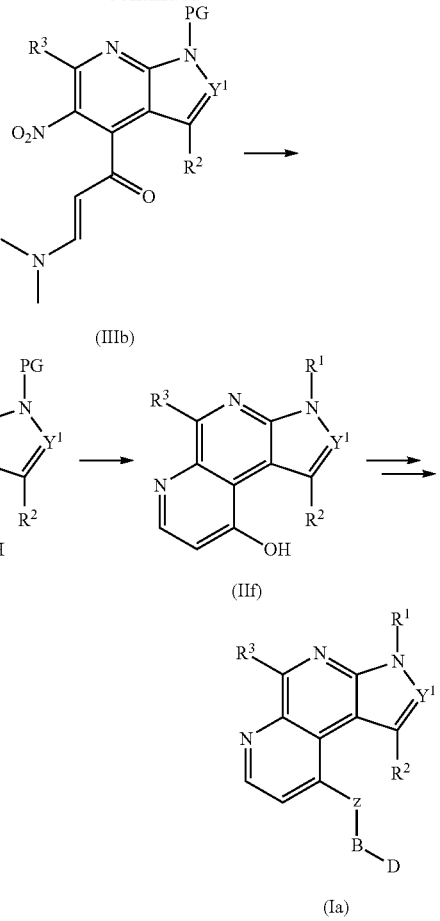

Compound of formula (IIIa) wherein PG is a protecting group and all other symbols are defined herein above is converted to compound of formula (IIIb) which was reduced followed by cyclisation to obtain compound of formula (IIIc). Compound of formula (IIIc) was deprotected to obtain compound of formula (IIf) which was converted to compound of formula (Ia) as described in scheme 2.

Scheme 4: Compound of formula (Ia) wherein A is

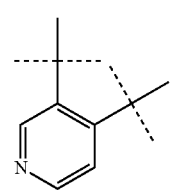

and all other symbols are defined herein above.

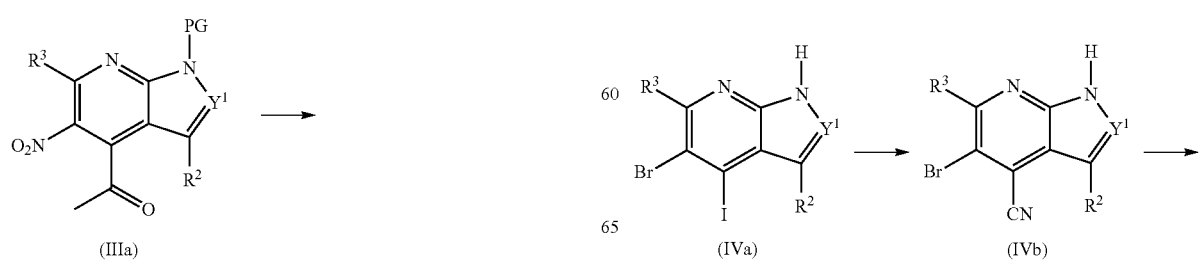

compound of formula (IVh) wherein in LG is a leaving group selected from halogen such as Br, Cl, I or triflate. Compound of formula (IVh) was coupled to provide compound of formula (Ia) wherein A is pyridine and all other symbols are defined herein above.

Scheme 5: Compound of formula (Ia) wherein A is

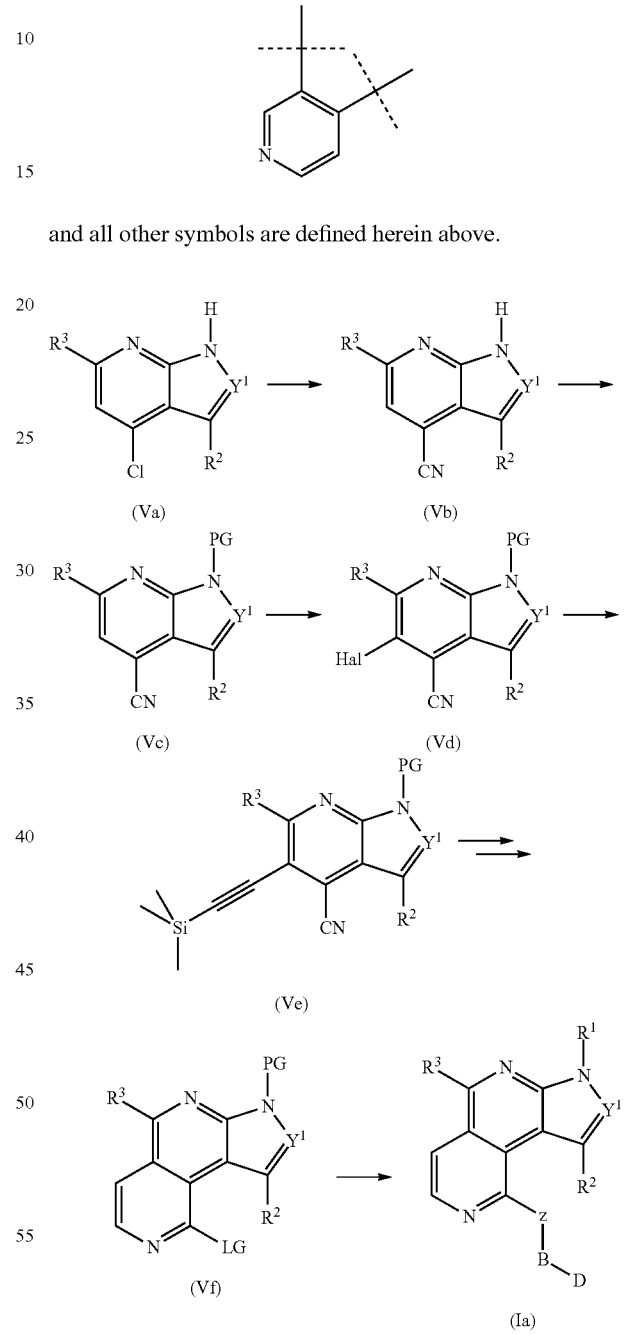

and all other symbols are defined herein above.

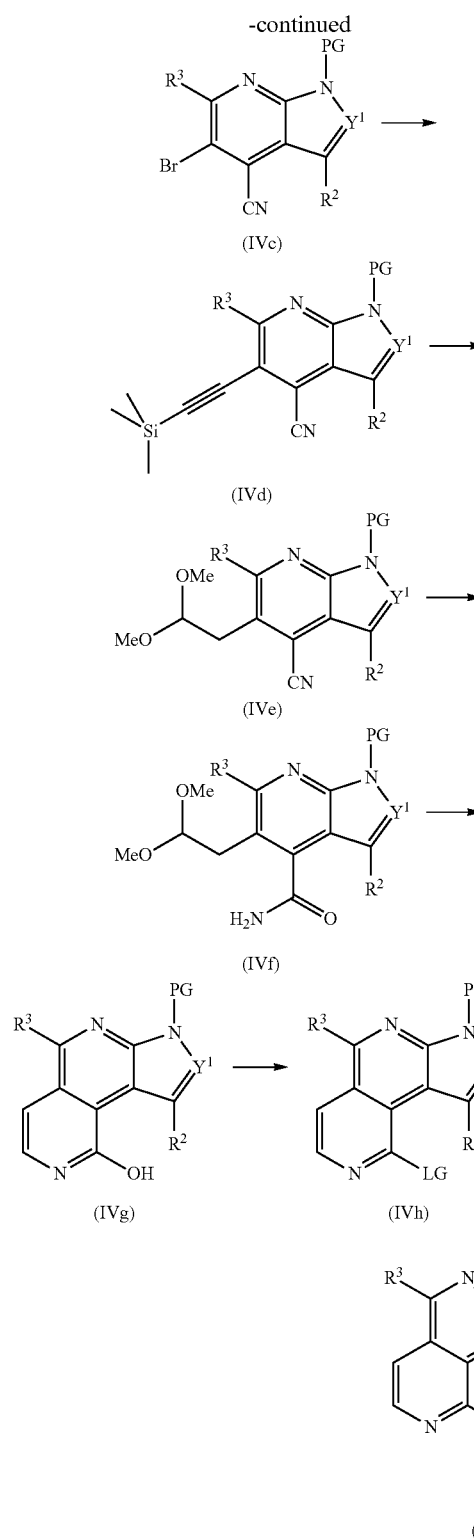

Compound of formula (IVa) is converted to compound of formula (IVb). Compound of formula (IVb) is protected to obtain compound of formula (IVc) which is then coupled with tri-methyl silyl acetylene to obtain compound of formula (IVd). Compound of formula (IVd) is converted to compound of formula (IVe) which is hydrolysed to provide compound of formula (IVf). Compound of formula (IVf) is cyclised to obtain compound of formula (IVg) which is converted to Compound of formula (Va) is converted to compound of formula (Vb). Compound of formula (Vb) is protected to obtain compound of formula (Vc). Compound of formula (Vc) is halogenated to obtain compound of formula (Vd) which is then coupled with tri-methyl silyl acetylene to obtain compound of formula (Ve). Compound of formula (Ve) is converted to compound of formula (Vf) wherein in LG is a leaving group selected from halogen such as Br, Cl, I or triflate in an analogous manner as described in scheme 4. Compound of formula (Vf) was coupled to provide compound of formula (Ia) wherein A is pyridine and all other symbols are defined herein above.

Scheme 6: Compound of formula (Ia) wherein A is

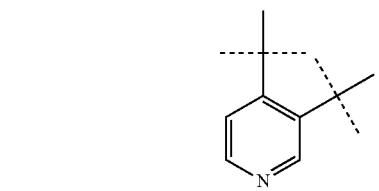

and all other symbols are defined herein above.

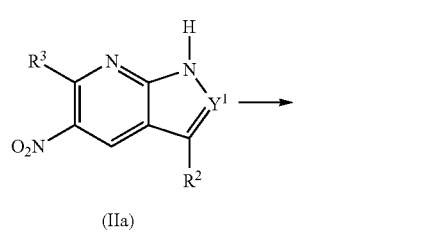
(IIa)

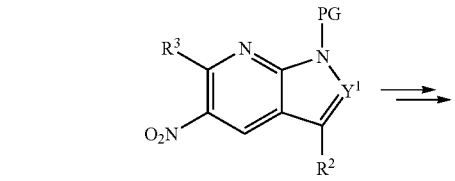
(VIa)

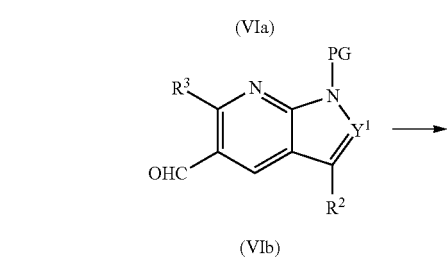
(VIb)

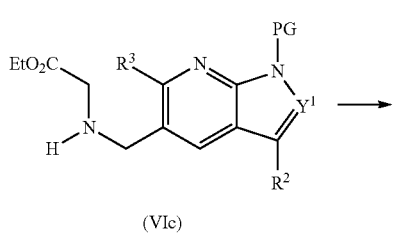
(VIc)

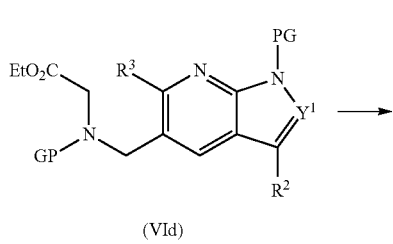
(VId)

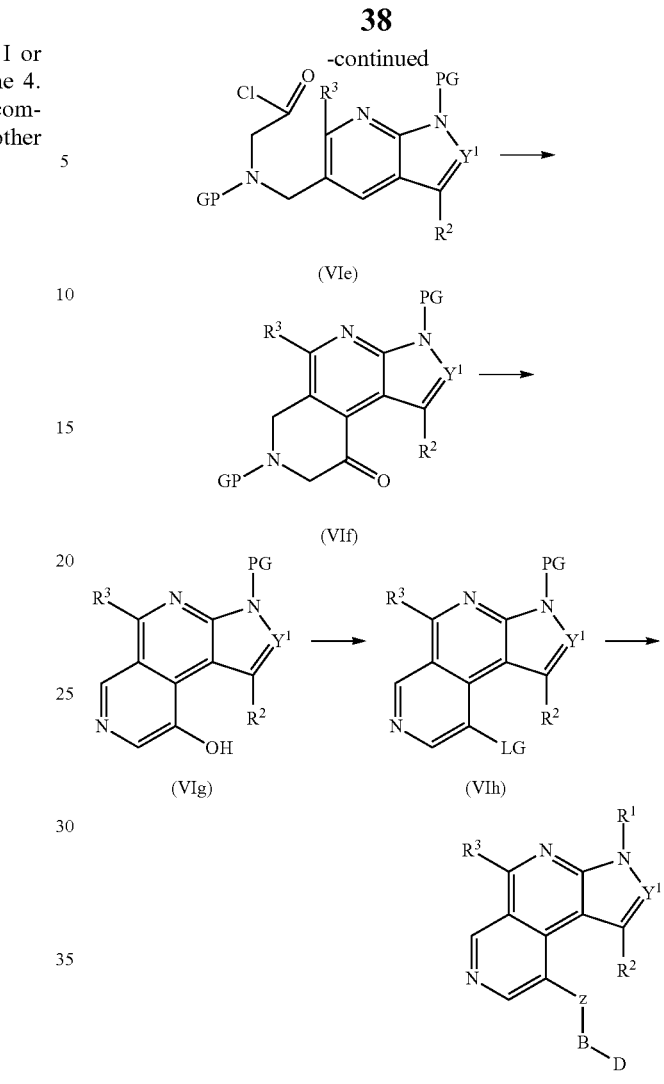

Compound of formula (IIa) is protected to obtain compound of formula (VIa). Compound of formula (VIa) was converted to the aldehyde of formula (VIb) by known methods. Aldehyde of formula (VIb) was converted compound of formula (VIc) by reductive amination. Compound of formula (VIc) was protedted to obtain compound of formula (VId) which was converted to the corresponding acid chloride (VIe) by known methods. Compound of formula (VIe) was cyclised to obtain compound of formula (VIf) which was deprotected and aromatized to obtain compound of formula (VIg). Compound of formula (VIg) was protected to obtain compound of formula (VIh). Compound of formula (VIh) was coupled to provide compound of formula (Ia) wherein A is pyridine and all other symbols are defined herein above.

Scheme 7: Compound of formula (Ia) wherein A is

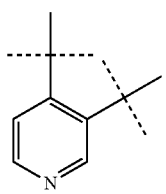

and all other symbols are defined herein above.

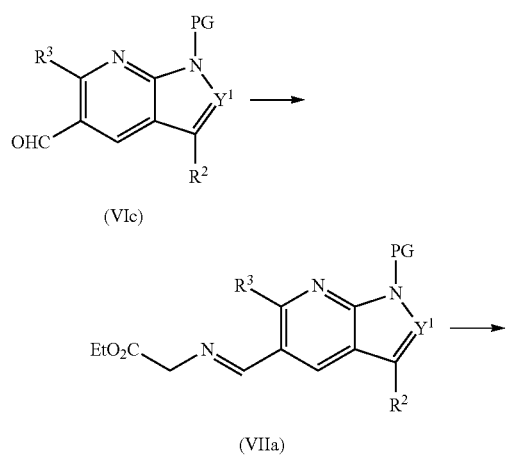

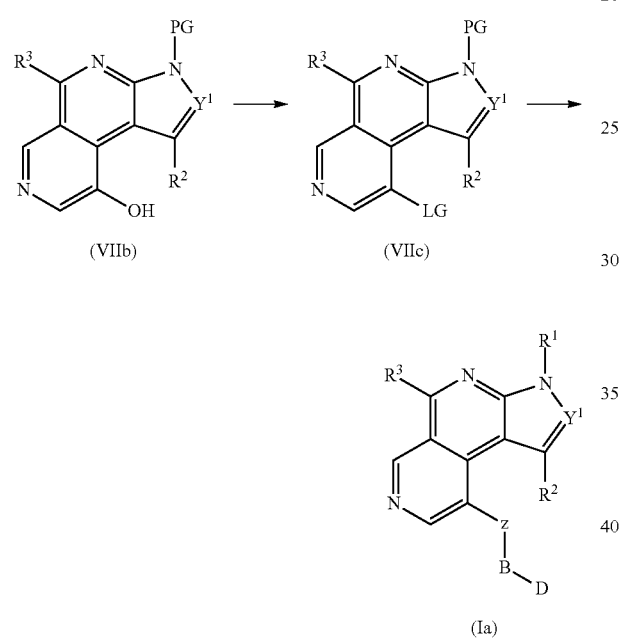

Aldehyde of formula (VIc) obtained in scheme 6 was coupled with glycine ethyl ester to provide imine of formula (VIIa) which was cyclised to obtain compound of formula (VIIb). Compound of formula (VIIb) was protected to obtain compound of formula (VIIc). Compound of formula (VIIc) was coupled to provide compound of formula (Ia) wherein A is pyridine and all other symbols are defined herein above.

Scheme 8: Compound of formula (Ia) wherein A is phenyl and all other symbols are defined herein above.

Isoquinoline of formula (VIIIa) was halogenated to obtain compound of formula (VIIIb) wherein Hal is a halogen selected from Br or I. Compound of formula (VIIIb) was coupled with Trimethyl silyl acetylene to obtain compound of formula (VIIIc) which was deprotected and cyclised to obtain compound of formula (VIIId). Compound of formula (VIIId) was protected to obtain compound of formula (VIIIe). Compound of formula (VIIIe) was coupled to provide compound of formula (Ia) wherein A is pyridine and all other symbols are defined herein above.

Scheme 9: Compound of formula (Ia) wherein A is phenyl and all other symbols are defined herein above.

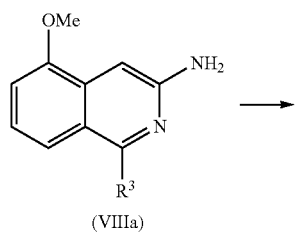

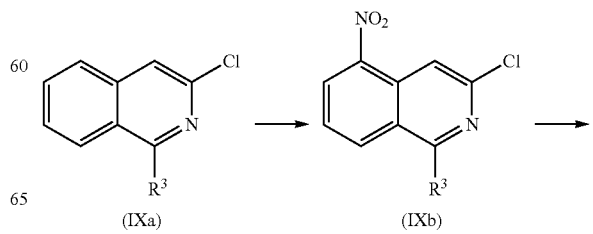

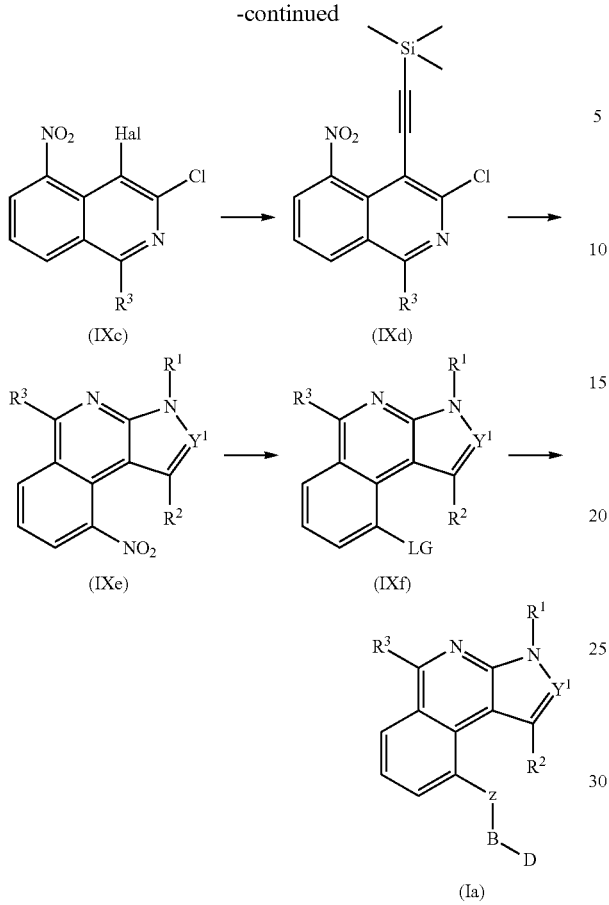

Isoquinoline of formula (IXa) was nitrated to obtain compound of formula (IXb) which was halogenated to obtain compound of formula (IXc) wherein Hal is a halogen selected from Br or I. Compound of formula (IXc) was coupled with Trimethyl silyl acetylene to obtain compound of formula (IXd) which was deprotected and cyclised to obtain compound of formula (IXe). Compound of formula (IXe) was converted to obtain compound of formula (IXf) wherein LG is a leaving group selected from halogen such as Br or I. Compound of formula (IXf) was coupled to provide compound of formula (Ia) wherein A is pyridine and all other symbols are defined herein above.

Scheme 10: Compound of formula (Ia) wherein Z is

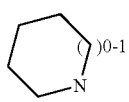

and all other symbols are defined herein above.

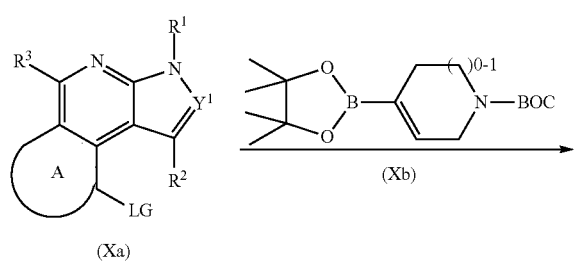

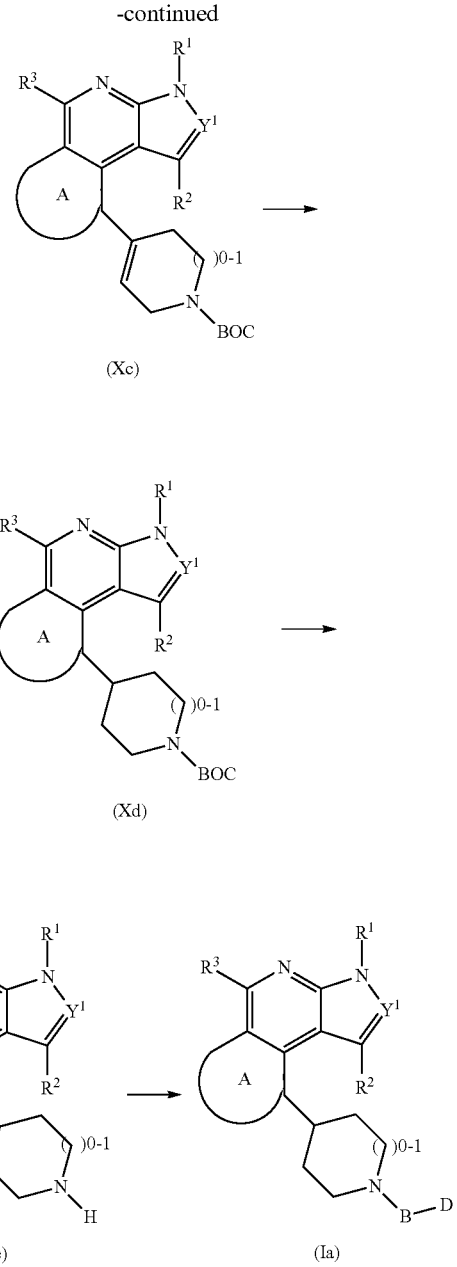

Compound of formula (Xa) was coupled with boronate ester of formula (Xb) to obtain compound of formula (Xc) which was hydrogenated to obtain compound of formula (Xd) followed by deprotection to obtain compound of formula (Xe). Compound of formula (Xe) was coupled to obtain compound of formula (Ia).

Scheme 11: Compound of formula (Ia) wherein Z is

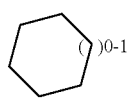

and all other symbols are defined herein above.

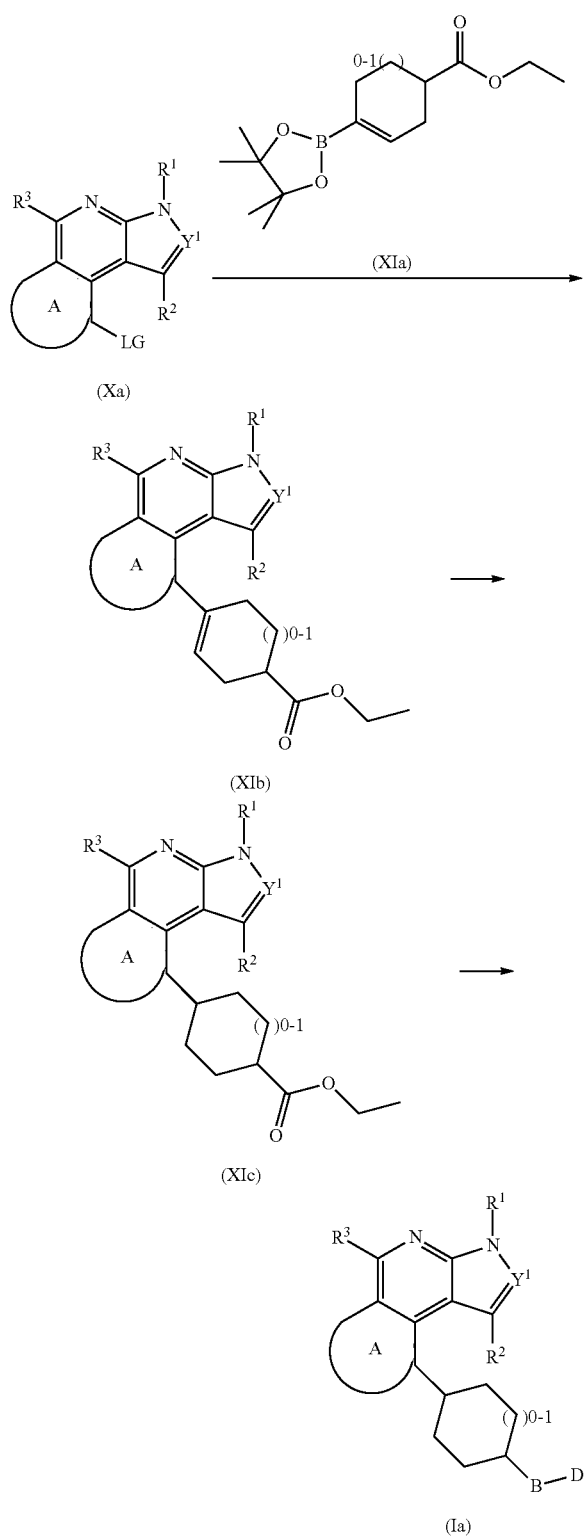

Compound of formula (Xa) was coupled with boronate ester of formula (XIa) to obtain compound of formula (XIb) which was hydrogenated to obtain compound of formula (XIc). Compound of formula (XIc) was coupled to obtain compound of formula (Ia).

Above mentioned conditions, for the respective functional group transformations, are only to illustrated the type of synthesis. More specific conditions for above transformations are well documented and referred in the literature (R. C. Larock in Comprehensive Organic Transformations, Wiley-VCH Publication; B. M. Trost and I. Fleming Ed. Comprehensive Organic Synthesis, Elsevier Publication)

In the reactions described in the schemes herein above, any reactive group present, such as hydroxyl, amino, carbonyl, imino and the like, may be protected during the reaction by conventional protecting groups such as trimethylsilyl, ter-butylmethylsilyl, benzyl, acetal, ketal and the like, which are cleaved again after the reaction.

It will be appreciated that the compounds of formula (Ia) may be prepared by derivatisation of formula (Ia) by transformations well known to those skilled in the art, e.g functional groups as $R^3$ may be transformed to different functional groups such as an ester function being converted to an acid, amide, hydroxyalkyl, keto, aldehyde as well as an ester. The said conversions may be carried out using reagents and conditions well documented in the literature.

Wherever desired or necessary, in any of the above mentioned processes, any of the compounds of formula (Ia) may be converted into a pharmaceutically acceptable salt or vice versa or converting one salt form into another pharmaceutically acceptable salt form.

According to another embodiment the present invention provides co-crystals comprising a compound of formula (I) or (Ia) wherein compounds of formula (I) and (Ia) that contain groups capable of acting as donors and/or acceptors for hydrogen bonds may be capable of forming co-crystals with suitable co-crystal formers. These co-crystals may be prepared from compounds of Formula (I) or (Ia) by known co-crystal forming procedures. Such procedures include grinding, heating, co-subliming, co-melting, or contacting in solution compounds of formula I with the co-crystal former under crystallization conditions and isolating co-crystals thereby formed.

According to another embodiment the present invention provides pharmaceutical compositions comprising a compound of formula (I) or (Ia) or a pharmaceutically acceptable salt thereof as active ingredient together with a pharmaceutically acceptable carrier, optionally in combination with one or more other pharmaceutical compositions.

Yet another embodiment of the present invention is the use of a compound of the present invention or a pharmaceutically acceptable salt thereof for the manufacture of a medicament for the treatment or prophylaxis of diseases and disorders associated with JAK.

According to another embodiment compositions can be prepared by mixing one or more compounds described herein, or pharmaceutically acceptable salts or tautomers thereof, with pharmaceutically acceptable carriers or the like, to treat or ameliorate a variety of JAK related conditions. The pharmaceutical compositions of the present disclosure can be manufactured by methods well known in the art such as conventional granulating, mixing, dissolving, encapsulating, lyophilizing, emulsifying or levigating processes, among others. The compositions can be in the form of, for example, granules, powders, tablets, capsule syrup, suppositories, injections, emulsions, elixirs, suspensions or solutions. The instant compositions can be formulated for various routes of administration, for example, by oral administration, transmucosal administration, rectal administration, topical administration or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation.

Besides those representative dosage forms described above, pharmaceutically acceptable excipients and carries are generally known to those skilled in the art and are thus included in the instant invention. Such excipients and carriers are described, for example, in "Remington's Pharmaceutical Sciences" Mack Pub. Co., New Jersey (1991).

The formulations of the invention can be designed for to be short-acting, fast-releasing, long-acting, and sustained-releasing. Thus, the pharmaceutical formulations can also be formulated for controlled release or for slow release.

The pharmaceutical compositions of the present disclosure can also comprise, for example, micelles or liposomes, or some other encapsulated form, or can be administered in an extended release form to provide a prolonged storage and/or delivery effect. Therefore, the pharmaceutical formulations can be compressed into pellets or cylinders and implanted intramuscularly or subcutaneously as depot injections or as implants such as stents. Such implants can employ known materials such as silicones and biodegradable polymers.

The pharmaceutical compositions may contain, for example, from about 0.1% by weight, to about 90% or more by weight, of the active material, depending on the method of administration. Where the compositions comprise dosage units, each unit can contain, for example, from about 0.1 to 500 mg or more of the active ingredient. The dosage as employed for adult human treatment can range, for example, from about 0.1 to 1000 mg per day, depending on the route and frequency of administration.

Specific dosages can be adjusted depending on conditions of the JAK related condition, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention. Generally, the total daily dose can typically range from about 1 mg/kg/day to about 500 mg/kg/day in single or in divided doses. Typically, dosages for humans can range from about 5 mg to about 100 mg per day, in a single or multiple doses.

A therapeutically effective dose or amount can vary depending upon the route of administration and dosage form. Some compositions of the instant invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ can be determined by standard pharmaceutical procedures in animal cell cultures or experimental models.

Also provided is an article of manufacture a pharmaceutical composition comprising a provided compound contained within a packaging material and a label or package insert which indicates that said pharmaceutical composition can be used for treating a JAK related condition, as described herein.

According to another embodiment, compounds of Formula (I) or (Ia) of the invention can be used alone or in combination with one or more additional therapeutic agent selected from the group consisting of cytokine suppressive anti-inflammatory drugs, antibodies to or antagonists of other human cytokines or growth factors, IL-1, IL-2, IL-3, IL-4, IL-5, IL-6, IL-7, IL-8, IL-12, IL-15, IL-16, IL-21, IL-23, interferons, EMAP-II, GM-CSF, FGF, PDGF, CTLA or their ligands including CD154, Adalimumab, infliximab, golimumab, Certolizumab Pegol, Tocilizumab, CDP 571, soluble p55 or p75 TNF receptors, Etanercept, Lenercept, TNFa converting enzyme inhibitors, IL-1 inhibitors, Interleukin 11, IL-18 antagonists, IL-12 antagonists, IL-12 antibodies, soluble IL-12 receptors, IL-12 binding proteins, non-depleting anti-CD4 inhibitors FK506, rapamycin, mycophenolate mofetil, leflunomide, NSAIDs, ibuprofen, corticosteroids, phosphodiesterase inhibitors, adensosine agonists, antithrombotic agents, complement inhibitors, adrenergic agents, IL-Iβ converting enzyme inhibitors, T-cell signalling kinase inhibitors, metalloproteinase inhibitors, sulfasalazine, 6-mercaptopurines, derivatives p75TNFRIgG, sIL-1RI, sIL-1RII, sIL-6R, celecoxib, hydroxychloroquine sulfate, rofecoxib, infliximab, naproxen, valdecoxib, sulfasalazine, meloxicam, acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, anti-IL15, VX-740, Roflumilast, IC-485, CDC-801, S1P1 agonists, FTY720, PKC family inhibitors, Ruboxistaurin, AEB-071, Mesopram, methotrexate, leflunomide, corticosteroids, budenoside, dexamethasone, sulfasalazine, 5-aminosalicylic acid, olsalazine, IL-Iβ converting enzyme inhibitors, IL-1ra, T cell signaling inhibitors, tyrosine kinase inhibitors, 6-mercaptopurines, IL-11, mesalamine, prednisone, azathioprine, mercaptopurine, infliximab, methylprednisolone sodium succinate, diphenoxy late/atrop sulfate, loperamide hydrochloride, omeprazole, folate, ciprofloxacin/dextrose-water, hydrocodone, bitartrate/apap, tetracycline hydrochloride, fluocinonide, metronidazole, thimerosal/boric acid, cholestyramine/sucrose, ciprofloxacin hydrochloride, hyoscyamine sulfate, meperidine hydrochloride, midazolam hydrochloride, oxycodone HCl/acetaminophen, promethazine hydrochloride, sodium phosphate, sulfamethoxazole/trimethoprim, polycarbophil, propoxyphene napsylate, hydrocortisone, multivitamins, balsalazide disodium, codeine phosphate/apap, colesevelam HCl, cyanocobalamin, folic acid, levofloxacin, natalizumab, interferon-gamma, methylprednisolone, azathioprine, cyclophosphamide, cyclosporine, methotrexate, 4-aminopyridine, tizanidine, interferon-ia, interferon Beta-1A, interferon-ib, interferon Beta-1B, interferon a-n3, interferon-a, interferon βIA-IF, Peginterferon a 2b, Copolymer 1, glatiramer acetate, hyperbaric oxygen, intravenous immunoglobulin, cladribine, cyclosporine, FK506, mycophenolate mofetil, leflunomide, NSAIDs, corticosteroids, prednisolone, phosphodiesterase inhibitors, adensosine agonists, antithrombotic agents, complement inhibitors, adrenergic agents, antiinflammatory cytokines, interferon-β, IFN ia, IFN ib, Copaxone, corticosteroids, caspase inhibitors, inhibitors of caspase-1, antibodies to CD40 ligand and CD80, alemtuzumab, dronabinol, daclizumab, mitoxantrone, xaliproden hydrochloride, fampridine, glatiramer acetate, natalizumab, sinnabidol, a-immunokine NNS03, ABR-215062, AnergiX.MS, chemokine receptor antagonists, BBR-2778, calagualine, CPI-1189, liposome encapsulated mitoxantrone, THC.CBD, cannabinoid agonists, MBP-8298, mesopram, MNA-715, anti-IL-6 receptor antibody, neurovax, pirfenidone allotrap 1258 (RDP-1258), sTNF-RI, talampanel, teriflunomide, TGF-beta2, tiplimotide, VLA-4 antagonists, interferon gamma antagonist, IL-4 agonists, Diclofenac, Misoprostol, naproxen, Meloxicam, indomethacin, Diclofenac, Methotrexate, Azathioprine, Minocycline, prednisone, etanercept, Rofecoxib, Sulfasalazine, naproxen, leflunomide, methylprednisolone acetate, indomethacin, hydroxychloroquine sulfate, prednisone, sulindac, betamethasone diprop augmented, infliximab, Methotrexate, folate, Triamcinolone acetonide, Diclofenac, dimethylsulfoxide, Piroxicam, Diclofenac Sodium, ketoprofen, Meloxicam, methylprednisolone, nabumetone, tolmetin Sodium, calcipotriene, cyclosporine, Diclofenac Sodium/Misoprostol, fluocinonide, glucosamine sulfate, Sodium gold thiomalate, hydrocodone bitartrate/Apap, Sodium risedronate, sulfadiazine, thioguanine, valdecoxib, alefacept, and efalizumab, Diclofenac, naproxen, ibuprofen, Piroxicam, indomethacin, COX2 Inhibitors, Rofecoxib, valdecoxib, hydroxychloroquine, Steroids, Prednisolone, budenoside, Dexamethasone, cytotoxics, Azathioprine, cyclophosphamide, mycophenolate mofetil, Inhibitors of PDE4, purine synthesis Inhibitor, Sulfasalazine, 5-aminosalicylic acid, olsalazine, azathioprine, CTLA-4-IgG, anti-B7 family antibodies, anti-PD-1 family antibodies, anti-cytokine antibodies, fonotolizumab, Antibody anti-IFNg, anti-receptor receptor antibodies, anti-IL-6 receptor Antibody, antibodies to B-cell Surface molecules, LJP 394, rituximab, anti-CD20 Antibody and B-lymphostat.

In one embodiment, the invention provides methods of treating or preventing a condition associated with JAK in a subject, such as a mammal, i.e., a human or non-human mammal, comprising administering an effective amount of one or more compounds described herein to the subject. The JAK associated condition can be related to JAK1, JAK2, JAK3, and/or Tyk2. Suitable non-human subjects that can be treated include domestic or wild animals, companion animals, such as dogs, cats and the like; livestock, including horses, cows and other ruminants, pigs, poultry, rabbits and the like; primates, for example monkeys, such as macaques including rhesus monkeys and cynomolgus monkeys, marmosets, tamarins and the like, apes, including chimpanzees and orangutans; and rodents, such as rats, mice, gerbils, guinea pigs and the like.

In one embodiment, the compound is administered in a pharmaceutically acceptable form, optionally in a pharmaceutically acceptable carrier.

JAK3 in particular has been implicated in a variety of biological processes. For example, the proliferation and survival of murine mast cells induced by IL-4 and IL-9 have been shown to be dependent on JAK3 and gamma chain-signaling. Suzuki et al., (2000), Blood 96:2172-2180. JAK3 also plays a crucial role in IgE receptor-mediated mast cell degranulation responses (Malaviya et al., (1999), Biochem. Biophys. Res. Commun. 257:807-813), and inhibition of JAK3 kinase has been shown to prevent type I hypersensitivity reactions, including anaphylaxis (Malaviya et al., (1999), J. Biol. Chem. 274:27028-27038). JAK3 inhibition has also been shown to result in immune suppression for allograft rejection (Kirken, (2001), Transpl. Proc. 33:3268-3270). JAK3 kinases have also been implicated in the mechanism involved in early and late stages of rheumatoid arthritis (Muller-Ladner et al., (2000), J. Immunal. 164:3894-3901); familial amyotrophic lateral sclerosis (Trieu et al., (2000), Biochem Biophys. Res. Commun. 267:22-25); leukemia (Sudbeck et al., (1999), Clin. Cancer Res. 5:1569-1582); mycosis fungoides, a form of T-cell lymphoma (Nielsen et al., (1997), Prac. Natl. Acad. Sci. USA 94:6764-6769); and abnormal cell growth (Yu et al., (1997), J. Immunol. 159:5206-5210; Catlett-Falcone et al., (1999), Immunity 10:105-115).

The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), Mol. Cell. Biol. 16:4710-6; Jurlander et al., (1997), Blood 89:4146-52; Kaneko et al., (1997), Clin. Exp. Immun. 109:185-193; and Nakamura et al., (1996), J. Biol. Chem. 271: 19483-8). They are also known to be important to lymphocyte differentiation, function and survival. JAK-3 in particular plays an essential role in the function of lymphocytes, macrophages, and mast cells. Given the importance of this JAK kinase, compounds which modulate the JAK pathway, including those selective for JAK3, can be useful for treating conditions where the function of lymphocytes, macrophages, or mast cells is involved (Kudlacz et al., (2004) Am. J. Transplant 4:51-57; Changelian (2003) Science 302:875-878).

Conditions in which targeting of the JAK pathway or modulation of the JAK kinases, are contemplated to be therapeutically useful include, arthritis, asthma, autoimmune diseases, cancers or tumors, diabetes, certain eye diseases, disorders or conditions, inflammation, intestinal inflammations, allergies or conditions, neurodegenerative diseases, psoriasis, transplant rejection, and viral infection.

Accordingly, the described compounds, pharmaceutically acceptable salts and pharmaceutical compositions can be used to treat a variety of conditions such as the following.

In some embodiments, the methods and compositions of the present invention encompass the treatment of the connective tissue and joint disorders such as arthritis, rheumatoid arthritis, ankylosing spondylitis, fibromyalgia, spondyloarthopathies, gouty arthritis, lumbar spondylarthrosis, carpal tunnel syndrome, psoriatic arthritis, sclerodoma, canine hip dysplasia, systemic lupus erythematosus, juvenile arthritis, osteoarthritis, tendonitis and bursitis.

In other embodiments, the methods and compositions of the present invention encompass the treatment of neuroinflammation and neurodegenerative disorders such as Alzheimer's disease, multiple sclerosis (MS), Parkinson's disease, motor neuron disease, amyotrophic lateral sclerosis, Huntington's disease, cerebral ischemia, neurodegenerative disease caused by traumatic injury, the neurological complications of AIDS, spinal cord injury, and some peripheral neuropathies and neurodegenerative disorders.

In other embodiments, the methods and compositions of the present invention encompass the treatment of autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be O-cell (humoral) based or T-cell based, including Cogan's syndrome, Wegener's granulomatosis, autoimmune alopecia, and thyroiditis.

In other embodiments, the methods and compositions of the present invention encompass the treatment of diabetes, including Type I diabetes, juvenile onset diabetes and complications from diabetes.

In other embodiments, the methods and compositions of the present invention encompass the treatment of respiratory disorders such as asthma, bronchitis, chronic obstructive pulmonary disease (COPD), airway hyper-responsiveness, bronchial asthma, allergic asthma, intrinsic asthma, extrinsic asthma, dust asthma, cystic fibrosis, pulmonary edema, pulmonary embolism, pneumonia, pulmonary sarcoisosis, silicosis, pulmonary fibrosis, respiratory failure, acute respiratory distress syndrome and emphysema.

In other embodiments, the methods and compositions of the present invention encompass the treatment of the surgical disorders such as pain and swelling following surgery, infection following surgery and inflammation following surgery.

In other embodiments, the methods and compositions of the present invention encompass the treatment of the gastrointestinal disorders such as inflammatory bowel disease, irritable bowel syndrome, Crohn's disease, gastritis, irritable bowel syndrome, diarrhea, constipation, dysentery, ulcerative colitis, gastric esophageal reflux, gastric ulcers, gastric varices, ulcers, heartburn, coeliac diseases, proctitis, eosinophilic gastroenteritis, and mastocytosis.

In other embodiments, the methods and compositions of the present invention encompass the treatment of pain, including but not limited to chronic pain, acute pain, joint pain, nociceptive pain, neuropathic pain, allodynia, hyperalgesia, burn pain, menstrual cramps, kidney stones, headache, migraine headache, sinus headaches, tension headaches, dental pain, myasthenia gravis, multiple sclerosis, sarcoidosis, Behcet's syndrome, myositis, polymyositis, gingivitis, hypersensitivity, swelling occurring after injury, closed head injury, endometriosis, vasculitis, sepsis, glutamate neurotoxicity or hypoxia; ischemic/reperfusion injury in stroke, myocardial ischemica, renal ischemia, heart attacks, stroke, cardiac hypertrophy, coronary artery disease, atherosclerosis and arteriosclerosis, organ hypoxia, and platelet aggregation, stroke, and the like.

Another embodiment provides a method of inhibiting a JAK enzyme, including JAK-1, JAK-2, JAK-3 and/or Tyk-2, that includes contacting the JAK enzyme with either a non-therapeutic amount or a therapeutically effective amount of one or more of the present compounds. Such methods can occur in vivo or in vitro. In vitro contact can involve a screening assay to determine the efficacy of the one or more compounds against a selected enzyme at various amounts or concentrations. In vivo contact with a therapeutically effective amount of the one or more compounds can involve treatment of a described condition or prophylaxis of organ transplant rejection in the animal in which the contact occurs. The effect of the one or more compounds on the JAK enzyme and/or host animal can also be determined or measured.

EXAMPLES

The invention is further illustrated by the following examples which in no way should be construed as being further limiting. One skilled in the art will readily appreciate that the specific methods and results described are merely illustrative.

Preparation 1:
9-chloro-3H-pyrrolo[3,2-f][1,7]naphthyridine (11)

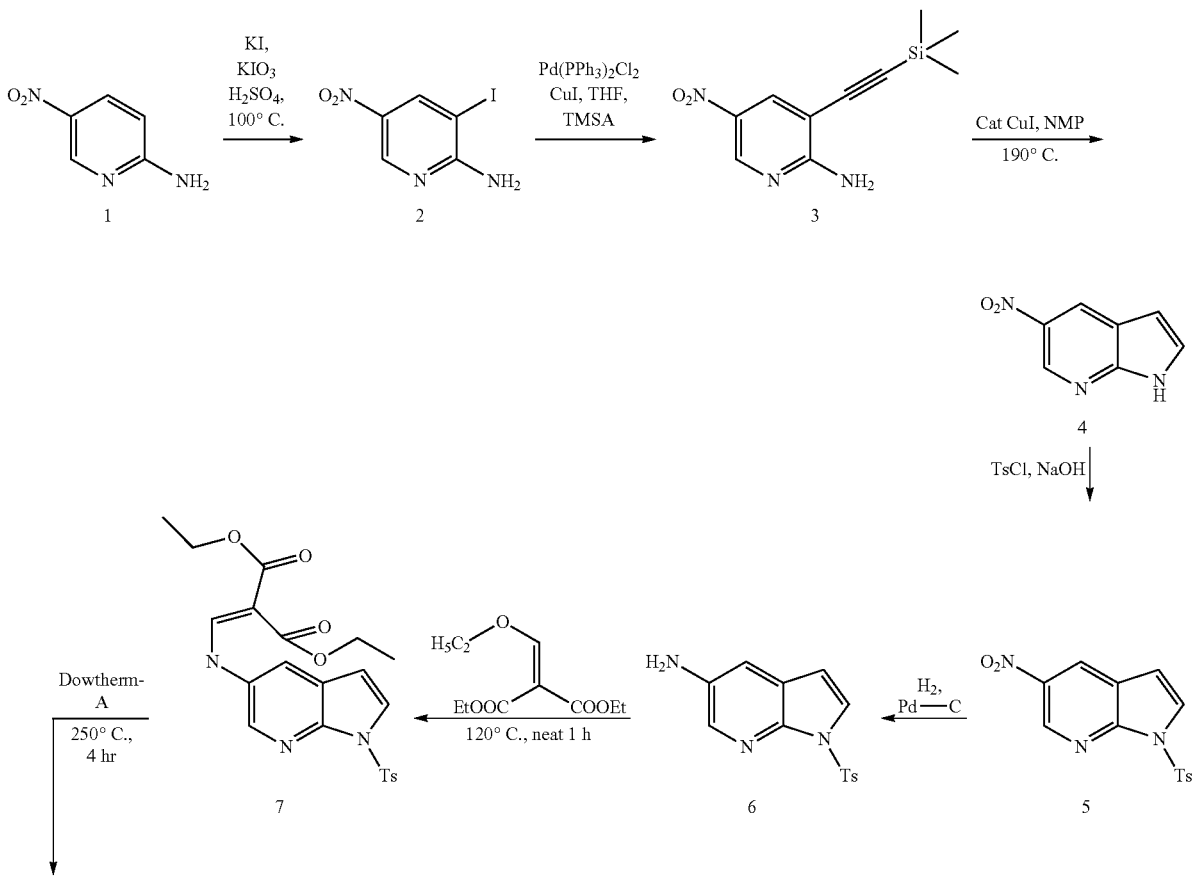

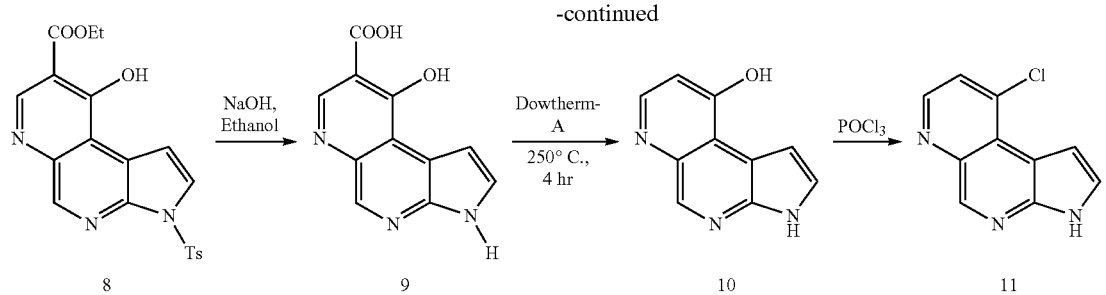

Step 1: 3-iodo-5-nitro-pyridin-2-amine (2)

To a solution of compound 1 (50 g, 359.71 mmol) in H$_2$SO$_4$ (2 M, 750 mL) potassium periodate (30.79 g, 143.88 mmol) was added portion-wise at room temperature. It was heated under reflux and aqueous potassium iodide was added dropwise over 1 h and heating continued further for 1.5 h. Reaction mixture was cooled to room temperature and neutralized by solid sodium bicarbonate. The reaction mixture was diluted with water (200 mL) and dichloromethane (200 mL). To this solid sodium thiosulphate was added with stirring. A green colored solid that separated out was filtered and dried to get 3-iodo-5-nitro-pyridin-2-amine (85 g, 89.4%). $^1$HNMR (400 MHz, DMSO-d$_6$): δ 7.15 (br s, 2H), 8.56 (d, J=2.8 Hz, 1H), 8.84 (d, J=2.8 Hz, 1H).

Step 2: 5-nitro-3-(2-trimethylsilylethynyl)pyridine-2-amine (3)

A mixture of compound 2 (95 g, 358.49 mmol), triethyl amine (100 mL), tetrahydrofuran (200 mL) and N, N-diethylacetamide (400 mL) was degassed for 30 min. with nitrogen. To this copper (I) iodide (1.36 g, 7.169 mmol) and dichlorobis triphenyl phosphine palladium (II) (5.02 g, 7.169 mmol) were added. The mixture was stirred and trimethylsilylacetylene (73 mL, 537.73 mmol) was added. It was stirred for 2 h. Reaction mixture was filtered and filtrate was concentrated under vacuum to minimum quantity and refiltered, washed with dichloromethane and hexane (1:5). This treatment was repeated for three more times to get 5-nitro-3-(2 trimethylsilylethynyl)pyridine-2-amine as yellow solid (60 g, 71.22%). $^1$HNMR (400 MHz, DMSO-d$_6$): δ 0.25 (s, 9H), 7.15 (br s, 2H), 8.18 (d, J=3.2 Hz, 1H), 8.85 (d, J=2.4 Hz, 1H).

Step 3: 5-nitro-1H-pyrrolo[2,3-b]pyridine (4)

To a suspension of compound 3 (54 g, 229.78 mmol) in N,N-dimethylformamide (400 mL) was added copper(I) iodide (21.88 g, 114.89 mmol) under nitrogen atmosphere followed by heating for 2 h in preheated oil bath at 135° C. Reaction mixture was cooled and filtered through celite pad and washed with hot ethyl acetate. Filtrate was concentrated under vacuum and residue obtained was purified by column chromatography to get 5-nitro-1H-pyrrolo[2,3-b]pyridine (17.7 g, 47.26%). $^1$HNMR (400 MHz, DMSO-d$_6$): δ 6.74 (d, J=3.2 Hz, 1H), 7.71 (s, 1H), 8.88 (d, J=2.4 Hz, 1H), 9.1 (d, J=2.4 Hz, 1H), 12.49 (s, 1H).

Step 4: 5-nitro-1-(p-tolylsulfonyl)pyrrolo[2,3-b]pyridine (5)

To a solution of compound 4 (17.7 g, 108.5 mmol) in acetone (450 mL), p-toluenesulphonyl chloride (22.61 g, 118.71 mmol) and aqueous 2M sodium hydroxide (5.6 g, 141 mmol) was added at 0° C. and the reaction was stirred overnight. Acetone was concentrated under vacuum and water was added into the reaction mixture. Light brown solid precipitated which was filtered and dried to obtain 5-nitro-1-(p-tolylsulfonyl)pyrrolo[2,3-b]pyridine (24.8 g, 72.51%). $^1$HNMR (400 MHz, DMSO-d$_6$): δ 2.35 (s, 3H), 7.03 (d, J=3.6 Hz, 1H), 7.45 (d, J=8.4 Hz, 2H), 8.04 (d, J=8.4 Hz, 1H), 8.17 (d, J=4.4 Hz, 1H), 8.95 (d, J=2.4 Hz, 1H), 9.2 (d, J=2.4 Hz, 1H).

Step 5: 1-(p-tolylsulfonyl)pyrrolo[2,3-b]pyridine-5-amine (6)

To a suspension of compound 5 (24.7 g, 78.16 mmol) in methanol (240 mL) and dichloromethane (350 mL), Pd-C 10% (24.7 g) was added at room temperature and stirred overnight under H$_2$ pressure. The reaction mixture was filtered through celite pad and organic solvent was evaporated. Residue obtained was purified by column chromatography to get 1-(p-tolylsulfonyl)pyrrolo[2,3-b]pyridine-5-amine (14.7 g, 69.7%). $^1$HNMR (400 MHz, DMSO-d$_6$): δ 2.32 (s, 3H), 5.15 (s, 2H), 6.56 (d, J=3.6 Hz, 1H), 7.07 (d, J=2.4 Hz, 1H), 7.37 (d, J=8.0 Hz, 2H), 7.63 (d, J=4.4 Hz, 1H), 7.75 (d, J=2.4 Hz, 1H), 7.88 (d, J=8.4 Hz, 1H).

Step 6: Diethyl 2-[[[1-(p-tolylsulfonyl)pyrrolo[2,3-b]pyridin-5-yl]amino]ethylene]propanedioate (7)

A mixture of 6 (2 g, 6.96 mmol) and diethyl 2-(methoxymethylene) propanedioate (1.4 g, 0.696 mmol) was heated at 130° C. for 4 h. Reaction mixture was evaporated and residue was purified by column chromatography to get diethyl 2-[[[1-(p-tolylsulfonyl)pyrrolo[2,3-b]pyridin-5-yl]amino]ethylene] propanedioate (1.8 g, 56%) as oil. $^1$HNMR (400 MHz, DMSO-d$_6$): δ 1.21-1.27 (m, 6H), 2.34 (s, 3H), 4.11 (q, J=7.2 Hz, 2H), 4.20 (q, J=7.2 Hz, 2H), 6.81 (d, J=3.6, 1H), 7.42 (d, J=8.4 Hz, 2H), 7.36 (d, J=4 Hz, 1H), 7.97 (d, J=8.4 Hz, 2H), 8.09 (d, J=2.4 Hz, 1H), 8.34 (d, J=14 Hz, 1H), 8.44 (d, J=2 Hz, 1H), 10.76 (d, J=14 Hz, 1H).

Step 7: Ethyl 9-hydroxy-3-(p-tolylsulfonyl)pyrrolo[3,2-f][1,7]naphthyridine-8-carboxylate (8)

A mixture of compound 7 (1.8 g, 0.382 mmol) in Dowtherm-A (60 mL) was heated at 250° C. for 3 h. It was poured into hexane (500 mL) to provide a light brown solid precipitate which was filtered and purified by column chromatography to get ethyl 9-hydroxy-3-(p-tolylsulfonyl)pyrrolo[3,2-f][1,7]naphthyridine-8-carboxylate (1.1 g, 68.32%) as a white solid. $^1$HNMR (400 MHz, DMSO-d6): δ 1.27-1.33 (m, 3H), 2.33 (s, 3H), 4.23 (q, J=7.2 Hz, 2H), 6.96 (d, J=4 Hz, 1H), 7.42 (d, J=8.4 Hz, 2H), 7.65 (d, J=3.6 Hz, 1H), 8.01 (d, J=8.4 Hz, 2H), 8.15 (d, J=4 Hz, 1H), 8.25 (d, J=8.8 Hz, 1H), 8.67 (s, 1H), 8.83 (s, 1H), 12.45 (br s, 1H).

Step 8: 9-hydroxy-3H-pyrrolo[3,2-f][1,7]naphthyridine-8-carboxylic acid (9)

To a suspension of 8 (1.1 g, 4.803 mmol) in ethanol (50 mL), aqueous sodium hydroxide (2M, 25 mL) was added and refluxed for overnight. Reaction mixture was concentrated and water was added to it. It was acidified by concentrated HCl. White solid precipitated was filtered and dried to get 9-hydroxy-3H-pyrrolo[3,2-f][1,7]naphthyridine-8-carboxylic acid (0.3 g, 49%) as off white solid. $^1$HNMR (400 MHz, DMSO-$d_6$): δ 7.37 (br s, 1H), 7.80 (br s, 1H), 8.87 (s, 1H), 8.94 (s, 1H), 12.5 (s, 1H), 13.84 (br s, 1H), 15.61 (br s, 1H).

Step 9: 3H-pyrrolo[3,2-f][1,7]naphthyridin-9-ol (10)

A mixture of compound 9 (0.3 g, 1.31 mmol) in Dowtherm-A (15 mL) was heated at 250° C. for 3 h. It was poured into hexane (150 mL) and light brown solid precipitated was filtered. It was purified by column chromatography to get 3H-pyrrolo[3,2-f][1,7]naphthyridin-9-ol (0.12 g, 50%) as white solid. $^1$HNMR (400 MHz, DMSO-$d_6$): δ 6.14 (d, J=7.2 Hz, 1H), 7.31 (br s, 1H), 7.56 (s, 1H), 7.95 (t, J=6 Hz, 1H), 8.60 (s, 1H), 12.05 (br s, 1H).

Step 10: 9-chloro-3H-pyrrolo[3,2-f][1,7]naphthyridine (11)

To a solution of compound 10 (1.5 g, 8.11 mmol) in chlorobenzene (25 mL) was added phosphorous oxychloride (11.3 mL, 121.62 mmol) and it was heated to stirred overnight at 100° C. The reaction mixture was concentrated, diluted with water (40 mL) and aq. ammonia was added to make it basic. The solid separated was filtered and filtrate was extracted with ethyl acetate (5×100 mL), the organic layer was washed with brine solution (100 mL), dried over sodium sulphate and concentrated and the residue was added to solid obtained above. The combined crude was purified by column chromatography to obtain 9-chloro-3H-pyrrolo[3,2-f][1,7]naphthyridine (1 g, 61%) as yellow solid. $^1$HNMR (400 MHz, DMSO $d_6$): δ 7.40-7.43 (m, 1H), 7.70 (t, J=2.8 Hz, 1H), 7.97 (d, J=2.4 Hz, 1H), 8.83 (d, J=2.4 Hz, 1H), 9.07 (s, 1H), 12.55 (br s, 1H).

Alternate preparation of 3H-pyrrolo[3,2-f][1,7]naphthyridin-9-ol (10)

Step 1: 1-(Benzenesulfonyl)-4-chloro-pyrrolo[2,3-b]pyridine

A stirred suspension of 4-chloro-1H-pyrrolo[2,3-b]pyridine (25.0 g, 163.8 mmol) in dichloromethane (1.25 L) was treated with 4-(dimethylamino)pyridine (2.0 g, 16.3 mmol), triethylamine (34.2 mL, 245.7 mmol) and benzenesulfonyl chloride (23.1 mL, 180.2 mmol) at ambient temperature. The reaction mixture was stirred overnight at room temperature. Reaction mixture was washed with 1M aqueous HCl solution and saturated sodium hydrogen carbonate solution, water, brine, dried over sodium sulphate and concentrated under reduced pressure. The residue was triturated with diethyl ether to afford 1-(benzenesulfonyl)-4-chloro-pyrrolo[2,3-b]pyridine as off-white solid (43.5 gm, 91%). $^1$H NMR (400 MHz, DMSO-$d_6$): δ 8.35 (d, J=5.2 Hz, 1H), 8.13 (d, J=7.6 Hz, 2H), 8.07 (d, J=4.0 Hz, 1H), 7.76-7.73 (m, 1H), 7.66-7.62 (m, 2H), 7.49 (d, J=5.2 Hz, 1H), 6.91 (d, J=4.0 Hz, 1H).

Step 2: 1-Benzenesulfonyl-4-chloro-5-nitro-1H-pyrrolo[2,3-b]pyridine

To a stirred solution of 1-(benzenesulfonyl)-4-chloro-pyrrolo[2,3-b]pyridine (50 g 170.8 mmol), in dichloromethane (750 mL) at −5° C. tetra-methyl ammonium nitrate (29.0 g, 213.5 mmol) was added in portions followed by drop wise addition of trifluoroacetic anhydride (31.4 mL, 222.0 mmol), stirring was continued below 0° C. for 30 min and another 16 h at room temperature. Tetramethyl ammonium nitrate (5.8 g, 42.7 mmol) was added in portions followed by dropwise addition of trifluoroacetic anhydride (7.25 mL, 51.2 mmol) and stirring for another 4 h at room temperature. Reaction mixture was diluted with dichloromethane, washed with water, dried over sodium sulphate and concentrated under reduced pressure. The residue was triturated with methanol and filtered through buchnor funnel to afford 1-benzenesulfonyl-4-chloro-5-nitro-1H-pyrrolo[2,3-b]pyridine as yellow solid (55 gm, 95%). $^1$H NMR (400 MHz, DMSO-$d_6$): δ 9.0 br s, 1H), 8.28 (d, J=4.0 Hz, 1H), 8.17 (d, J=7.6 Hz, 2H), 7.80-7.77 (m, 1H), 7.69-7.65 (m, 2H), 7.11 (d, J=4.0 Hz, 1H).

Step 3: 1-(Benzenesulfonyl)-4-(1-ethoxyvinyl)-5-nitro-pyrrolo[2,3-b]pyridine To a solution of 1-benzenesulfonyl-4-chloro-5-nitro-1H-pyrrolo[2,3-b]pyridine (0.5 g, 1.48 mmol) and ethoxy vinyl tri n-butyl tin (0.58 g, 1.63 mmol) in dioxane (15 mL) was added Pd(PPh$_3$)$_2$Cl$_2$ (0.104 g, 0.148 mmol) under nitrogen atmosphere. It was heated under reflux overnight. Water was added to it and extracted with ethyl acetate. The organic layer was dried over sodium sulphate, filtered and concentrated under vacuum. Residue obtained was purified by column chromatography to get 1-(benzenesulfonyl)-4-(1-ethoxyvinyl)-5-nitro-pyrrolo[2,3-b]pyridine (0.32 gm, 57.86%) as yellow oil. $^1$H NMR (400 MHz, CDCl$_3$): δ 1.28 (t, J=6.8 Hz, 3H), 3.92 (q, J=6.8 Hz, 2H), 4.57 (d, J=2.8 Hz, 1H), 4.67 (d, J=2.4 Hz, 1H), 6.85 (d, J=4.4 Hz, 1H), 7.51-7.55 (m, 2H), 7.62-7.65 (m, 1H), 7.90 (d, J=3.6 Hz, 1H), 8.19 (d, J=8 Hz, 2H), 8.88 (s, 1H).

Step 4: 1-[1-(Benzenesulfonyl)-5-nitro-pyrrolo[2,3-b]pyridin-4-yl]ethanone

To a solution of 1-(benzenesulfonyl)-4-(1-ethoxyvinyl)-5-nitro-pyrrolo[2,3-b]pyridine (0.3 g, 0.80 mmol) in acetone (3 mL) was added 1M aq. HCl (0.7 mL) and refluxed for 2 h. Reaction mixture was concentrated and aqueous sodium bicarbonate was added into it. It was extracted with ethyl acetate. The organic layer was dried over sodium sulphate, filtered and concentrated under vacuum. Residue obtained was purified by column chromatography to get 1-[1-(benzenesulfonyl)-5-nitro-pyrrolo[2,3-b]pyridin-4-yl]ethanone (0.2 gm, 72.20%) as yellow solid. $^1$H NMR (400 MHz, CDCl$_3$): δ 2.61 (s□□ 6.63 (d, J=4.4 Hz, 1H), 7.53-7.57 (m, 2H), 7.65-7.68 (m, 1H), 7.97 (d, J=4.4 Hz, 1H), 8.22 (d, J=7.6 Hz, 2H), 9.24 (s, 1H).

Step 5: [4-[(E)-3-(dimethylamino)prop-2-enoyl]-1-(p-tolylsulfonyl)pyrrolo[2,3-b]pyridin-5-yl]ammonium A solution of 1-[1-(benzenesulfonyl)-5-nitro-pyrrolo[2,3-b]pyridin-4-yl]ethanone (700 mg, 2.02 mmol) and N,N-dimethylformamide diethyl acetal (446 mg, 3.0 mmol) in toluene (15 ml) was heated to 85° C. for 15 h and then the reaction mixture was concentrated. The residue was purified on silica gel column to get [4-[(E)-3-(dimethylamino)prop-2-enoyl]-1-(p-tolylsulfonyl)pyrrolo[2,3-b]pyridin-5-yl]ammonium (810 mg) as pale yellow solid. $^1$H NMR (400 MHz, CDCl$_3$): δ 2.87 (s☐☐ 3.10 (br s, 3H), 5.25 (br s, 1H), 6.72 (d, J=3.2 Hz, 1H), 7.50-7.65 (m, 4H), 7.87 (d, J=3.6 Hz, 1H), 8.19 (d, J=8 Hz, 2H), 9.14 (s, 1H).

Step 6: 3-(benzenesulfonyl)pyrrolo[3,2-f][1,7]naphthyridin-9-ol

A mixture of [4-[(E)-3-(dimethylamino)prop-2-enoyl]-1-(p-tolylsulfonyl)pyrrolo[2,3-b]pyridin-5-yl]ammonium (800 mg, 2 mmol) and palladium on carbon 10% (200 mg) in ethanol (15 ml) was stirred under hydrogen atmosphere (Bladder) for 2 h. The catalyst was removed by filtration through a pad of Celite and the solvent was concentrated. The resulting residue was dissolved in ethanol (20 mL) and refluxed for 1 h. The reaction mixture was concentrated and washed with pentane to get 3-(benzenesulfonyl)pyrrolo[3,2-f][1,7]naphthyridin-9-ol (500 mg). $^1$H NMR (400 MHz, DMSO-d6): δ 6.23 (d, J=7.6 Hz, 1H), 7.60-7.73 (m, 4H), 8.01-8.12 (m, 4H), 8.79 (s, 1H), 11.32 (br s, 1H).

Step 7: 3H-pyrrolo[3,2-f][1,7]naphthyridin-9-ol (10)

LiOH.H$_2$O (40 mg, 0.96 mmol) was added to solution of 3-(benzenesulfonyl)pyrrolo[3,2-f][1,7]naphthyridin-9-ol (80 mg, 0.24 mmol) in tetrahydrofuran-MeOH-water (5 mL, 4:0.5:0.5). The reaction mixture was heated under reflux for 5 h. The reaction mixture was concentrated and diluted with water. The aqueous layer was extracted with 5% methanol in ethyl acetate. The combined organic layer was washed with brine, dried over sodium sulphate, concentrated under reduced pressure, and purified on silica-gel column to obtain 3H-pyrrolo[3,2-f][1,7]naphthyridin-9-ol with 50% yield. $^1$HNMR (400 MHz, DMSO-d$_6$): δ 6.19 (d, J=6.4 Hz, 1H), 7.33 (s, 1H), 7.57 (s, 1H), 7.99 (d, J=7.2 Hz, 1H), 8.63 (s, 1H), 12.04 (br s, 1H).

Preparation 2: 9-chloro-3-(toluene-4-sulfonyl)-3H-3,4,6,8-tetraaza-cyclopenta[a]naphthalene (20)

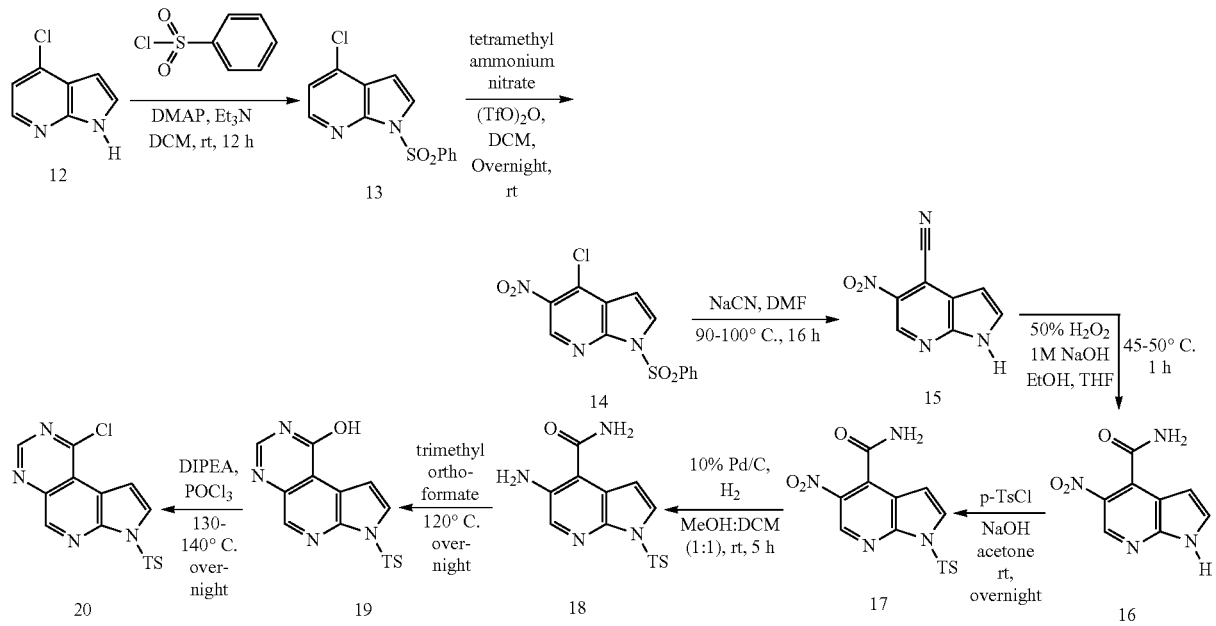

Step 1: 1-(benzenesulfonyl)-4-chloro-pyrrolo[2,3-b]pyridine (13)

A stirred suspension of compound 12 (25.0 g, 163.8 mmol) in dichloromethane (1.25 L) was treated with 4-(dimethylamino)pyridine (2.0 g, 16.3 mmol), triethylamine (34.2 mL, 245.7 mmol) and benzenesulfonyl chloride (23.1 mL, 180.2 mmol) at ambient temperature. The reaction mixture was stirred overnight at room temperature. Reaction mixture washed with 1M aqueous HCl solution and saturated sodium hydrogen carbonate solution, water, brine, dried over sodium sulphate and concentrated under reduced pressure. The residue was triturated with diethyl ether to afford off-white solid 43.5 g (91%). $^1$HNMR (400 MHz, DMSO-d$_6$): δ 8.35 (d, J=5.2 Hz, 1H), 8.13 (d, J=7.6 Hz, 2H), 8.07 (d, J=4.0 Hz, 1H), 7.76-7.73 (m, 1H), 7.66-7.62 (m, 2H), 7.49 (d, J=5.2 Hz, 1H), 6.91 (d, J=4.0 Hz, 1H).

Step 2: 1-benzenesulfonyl-4-chloro-5-nitro-1H-pyrrolo[2,3-b]pyridine (14)

To a stirred solution of compound 13 (50 g 170.8 mmol), in dichloromethane (750 mL) at −5° C. tetra-methyl ammonium nitrate (29.0 g, 213.5 mmol) was added in portions followed by drop wise addition of trifluoroacetic anhydride (31.4 mL, 222.0 mmol), stirring was continued below 0° C. for 30 min and another 16 h at room temperature. Tetramethyl ammonium nitrate (5.8 g, 42.7 mmol) was added in portions followed by dropwise addition of trifluoroacetic anhydride (7.25 mL, 51.2 mmol) and stirring for another 4 h at room temperature. Reaction mixture was diluted with dichloromethane, washed with water, dried over sodium sulphate and concentrated under reduced pressure. The residue was triturated with methanol and filtered through buchnor funnel to afford yellow solid 55 g (95%). ¹HNMR (400 MHz, DMSO-$d_6$): δ 9.0☐☐ br s, 1H), 8.28 (d, J=4.0 Hz, 1H), 8.17 (d, J=7.6 Hz, 2H), 7.80-7.77 (t, J=7.6 Hz 1H), 7.69-7.65 (t, J=7.6 Hz 2H), 7.11 (d, J=4.0 Hz, 1H).

Step 3:
5-nitro-1H-pyrrolo[2,3-b]pyridine-4-carbonitrile (15)

A stirred solution of compound 14 (55 g, 162.8 mmol) in DMF (300 mL) was treated with sodium cyanide (24.0 g, 488.5 mmol), and continued stirring at 100° C. for 16 h. Reaction mixture was allowed to cool to room temperature, quenched with water (300 mL), extracted with ethyl acetate, washed with brine, dried over sodium sulphate, and concentrated under reduced pressure to afford off-white solid 17.5 g (57%). ¹HNMR (400 MHz, DMSO-$d_6$): δ☐☐☐.12☐☐br s, 1H), 9.24 μs, 1H), 8.14 (d, J=3.6 Hz, 1H), 6.90 (d, J=3.2 Hz, 1H).

Step 4:
5-nitro-1H-pyrrolo[2,3-b]pyridine-4-carboxylic acid amide (16)

A stirred solution of compound 15 (17.5 g, 93.0 mmol), in 1:1 ethanol: tetrahydrofuran (680 mL) was treated with 50% hydrogen peroxide (170 mL), 1N sodium hydroxide solution (85 mL) followed by additional tetrahydrofuran (340 mL). The reaction was heated to 40-45° C. for 1 h, allowed to cool to room temperature, quenched with 5% HCl solution. This was extracted with dichloromethane, combined organic extracts were dried over sodium sulphate, concentrated under reduced pressure, triturated with methanol to afford yellow solid 10 g (52%). ¹HNMR (400 MHz, DMSO-$d_6$): δ☐☐☐.59 ☐☐br s, 1H), 9.01 ☐☐s, 1H), 8.☐0 ☐☐br s, 1H), 7.96 ☐☐br s, 1H), 7.81-7.79 (m, 1H), 6.59-6.58 (m, 1H).

Step 5: 5-nitro-1-(toluene-4-sulfonyl)-1H-pyrrolo[2,3-b]pyridine-4-carboxylic acid amide (17)

A stirred suspension of compound 16 (10.0 g, 48.5 mmol) in acetone (120 mL) was treated with p-tolunesulfonyl chloride (13.87 g, 72.7 mmol), sodium hydroxide (3.88 g, 97.0 mmol) at 0° C. and stirring continued at room temperature for 16 h. Solvent was evaporated under reduced pressure; water was added to the residue and filtered through buchner funnel to afford off-white solid 16.5 g (95%). ¹HNMR (400 MHz, DMSO-$d_6$): δ 9.12 (s, 1H), 8.25 (br s, 1H), 8.19 (d, J=4.0 Hz, 1H), 8.10 (br s, 1H), 8.05 (d, J=8.4 Hz, 2H), 7.46 (d, J=8.4 Hz, 2H), 6.87 (d, J=4.0 Hz, 1H), 2.36 (s, 3H).

Step 6: 5-Amino-1-(toluene-4-sulfonyl)-1H-pyrrolo[2,3-b]pyridine-4-carboxylic acid amide (18)

A stirred suspension of compound 17 (16.5 g, 45.7 mmol) in 1:1 methanol: DCM (2 L) was purged under vacuum/argon cycles to replace air inside the flask with argon gas by a suction adapter (fitted with a balloon). Following this, 10% palladium on charcoal (3.0 g), was added and the reaction mixture was purged under vacuum/$H_2$ cycles to replace air inside the flask with hydrogen gas by a suction adapter (fitted with a bladder). The reaction mixture was stirred at room temperature for 5 h. The reaction mixture was filtered through a celite pad, washed with 10% methanol in DCM, and concentrated under reduced pressure to afford off-white solid 13.6 g (90%). This was carried forward without further purification.

Step 7: 3-(toluene-4-sulfonyl)-3H-3,4,6,8-tetraaza-cyclopenta[a]naphthalen-9-ol (19)

Compound 18 (13.6 g, 41.1 mmol) taken in trimethyl orthoformate (200 mL) was heated at 120° C. for 16 h. Reaction mixture was allowed to cool to room temperature, the solid precipitate was filtered through buchner funnel and dried under reduced pressure to obtain the product, 5.0 g (36%). ¹HNMR (400 MHz, DMSO-$d_6$): $δ_1$☐.70 (br s, 1H), 8.82 (br s, 1H), 8.12 (d, J=3.6 Hz, 1H), 8.01 (d, J=8.4 Hz, 2H), 7.43 (d, J=8.0 Hz, 2H), 7.38 (d, J=4.0 Hz, 1H), 2.33 (s, 3H).

Step 8: 9-chloro-3-(toluene-4-sulfonyl)-3H-3,4,6,8-tetraaza-cyclopenta[a]naphthalene (20)

Compound 19 (4.6 g, 13.5 mmol) was taken in a mixture of diisopropyl ethylamine (2.91 mL, 16.9 mmol) and $POCl_3$ (18.6 mL, 202.9 mmol) and heated at 130-140° C. for 16 h. Reaction mixture was allowed to cool to room temperature and solvent was concentrated under reduced pressure. Sat. $NaHCO_3$ solution was added to the residue and the solid was filtered through buchner funnel, washed with water, dried under reduced pressure to afford off-white solid 4.7 g (97%). ¹H-NMR (400 MHz, $CDCl_3$): ☐☐.28 (s, 1H), 9.15 (s, 1H), 8.12 (d, J=8.4 Hz, 2H), 8.07 (d, J=4.0 Hz, 1H), 7.60 (d, J=4.0 Hz, 1H), 7.31 (d, J=8.0 Hz, 2H), 2.37 (s, 3H).

Preparation 3: 9-chloro-3H-3,4,7,8-tetraaza-cyclopenta[a]naphthalene (27)

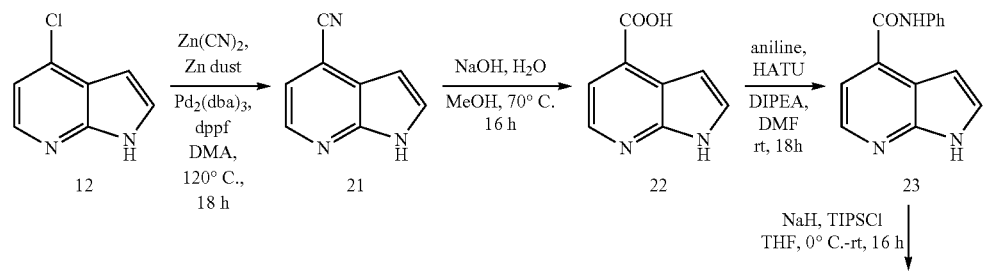

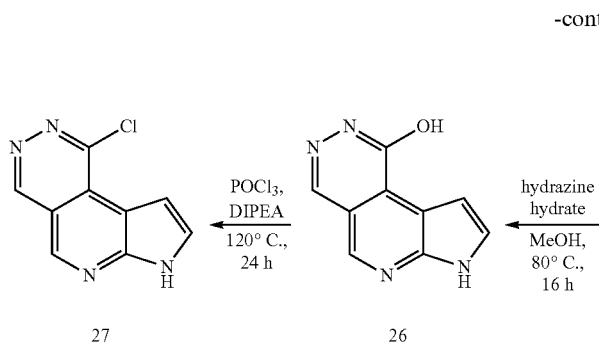
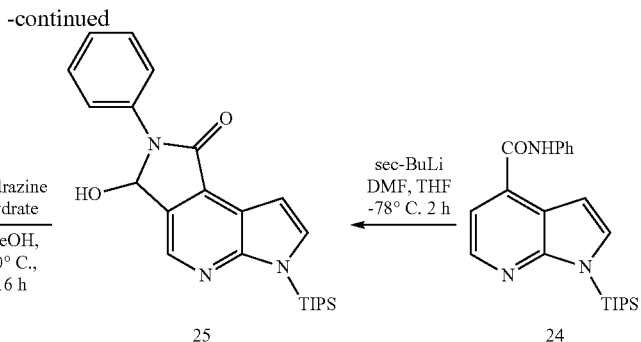

Step 1: 1H-pyrrolo[2,3-b]pyridine-4-carbonitrile (21)

To degassed N,N-dimethylacetamide (200 mL), compound 12 (30.0 g, 196.7 mmol), zinc cyanide (23.1 g, 196.7 mmol), zinc powder (1.28 g, 19.67 mmol), tris(dibenzylideneaceton)-dipalladium (3.6 g, 3.93 mmol) and diphenylphosphinoferrocene (4.36 g, 7.86 mmol) were added and the mixture was heated at 120° C. for 18 h. After cooling to room temperature, reaction mixture was poured on crushed ice (1.5 kg) and resulting solid was filtered. Solid was taken in ethyl acetate (2×1500 mL) and stirred for 0.5 h and filtered. Filtrate was concentrated, residue was crystallized from ethyl acetate and filtered to afford 1H-pyrrolo[2,3-b]pyridine-4-carbonitrile 22.0 g (78%). $^1$HNMR (400 MHz, DMSO-$d_6$): δ 12.20 (br s, 1H), 8.41 (d, J=4.8 Hz, 1H), 7.84 (s, 1H), 7.56 (d, J=4.8 Hz, 1H), 6.65 □d, J=1.6 Hz, 1H).

Step 2: 1H-pyrrolo[2,3-b]pyridine-4-carboxylic acid (22)

A mixture of compound 21 (17 g, 118.7 mmol), NaOH (47 g, 1187.6 mmol), ethanol (170 mL) and water (170 mL) was heated at 80° C. for 16 h. After cooling to room temperature, ethanol was removed under reduced pressure. The residue was diluted with water (200 mL) and washed with ethyl acetate (100 mL). Aqueous layer was acidified with conc. hydrochloric acid, solid precipitated was filtered to afford 1H-pyrrolo[2,3-b]pyridine-4-carboxylic acid 19.0 g (98.5%). $^1$HNMR (400 MHz, DMSO-$d_6$): δ 13.43 (br s, 1H), 11.97 (br s, 1H), 8.34 (d, J=4.8 Hz, 1H), 7.56 (d, J=4.8 Hz, 1H), 6.87-6.86 (m, 1H).

Step 3: 1H-pyrrolo[2,3-b]pyridine-4-carboxylic acid phenyl amide (23)

To a cooled solution of compound 22 (19 g, 117.7 mmol) in DMF (200 mL), aniline (21.4 mL, 234.35 mmol), HATU (89.1 g, 234.35 mmol) and N,N-diisopropylethylamine (60.7 mL, 351.35 mmol) were added under argon atmosphere and stirred at room temperature for 16 h. To the reaction mixture 1N NaOH (40 mL) was added and heated at 80° C. for 4 h, additional 1N NaOH (190 mL) was added and heating continued for 1 h. The reaction mixture was cooled and poured on ice, resulting solid was filtered, crystallized from methanol to afford 1H-pyrrolo[2,3-b]pyridine-4-carboxylic acid phenyl amide 18.7 g (67.2%). $^1$HNMR (400 MHz, DMSO-$d_6$): δ 11.95 (br s, 1H), 10.49 (br s, 1H), 8.38 (d, J=7.2 Hz, 1H), 7.81 (d, J=8.0 Hz, 2H), 7.64 (s, 1H), 7.50 (d, J=7.2 Hz, 1H), 7.38 (t, J=7.6 Hz, 2H), 7.13 (t, J=7.2 Hz, 1H), 6.77 (d, J=1.6 Hz, 1H). LCMS:— M+1=238

Step 4: 1-triisopropylsilanyl-1H-pyrrolo[2,3-b]pyridine-4-carboxylic acid phenyl amide (24)

To a cooled suspension of compound 23 (18.7 g, 78.81 mmol) in THF (300 mL), sodium hydride (4.72 g, 118.22 mmol, 60%(w/w) mineral oil dispersion) was added in portions and stirred for 1 h. To this solution triisopropylsilylchloride (25.3 mL, 118.22 mmol) was added and stirring continued for 12 h at room temperature. Following this, water was added and the mixture was extracted with ethyl acetate (2×500 mL). The combined extracts were washed with brine, dried over sodium sulphate and concentrated under reduced pressure. Residue obtained was crystallized from n-pentane, filtered to afford 1-triisopropylsilanyl-1H-pyrrolo[2,3-b]pyridine-4-carboxylic acid phenyl amide 27.9 g (89.9%). $^1$HNMR (400 MHz, DMSO-$d_6$): δ 10.44 (s, 1H), 8.37 (d, J=7.2 Hz, 1H), 7.78 (d, J=8.0 Hz, 2H), 7.62 (d, J=3.2 Hz, 1H), 7.48 (d, J=7.2 Hz, 1H), 7.36 (t, J=8.0 Hz, 2H), 7.11 (t, J=7.6 Hz, 1H), 6.89 (d, J=3.2 Hz, 1H), 1.95-1.81 (m, 3H), 1.06 (d, J=7.2 Hz, 18H).

Step 5: 3-Hydroxy-2-phenyl-6-triisopropylsilanyl-3,6-dihydro-2H-2,5,6-triaza-as-indacen-1-one (25)

A solution of compound 24 (5.0 g, 12.70 mmol) in THF (60 mL), was cooled to −78° C., sec-BuLi (1.3 M) (20.5 mL, 26.67 mmol) was added under argon and stirring continued for 1 h at −78° C. Mixture was quenched by DMF (1.18 mL, 15.24 mmol) and stirred for 1 h at −40° C. Water was added and the mixture extracted with ethyl acetate (2×250 mL), washed with brine (50 mL), dried over sodium sulphate and concentrated under reduced pressure. Residue obtained was crystallized from diethyl ether:n-hexanes (1:1) (100 mL), filtered to afford 3-hydroxy-2-phenyl-6-triisopropylsilanyl-3,6-dihydro-2H-2,5,6-triaza-as-indacen-1-one 3.1 g (58.5%). $^1$HNMR (400 MHz, DMSO-$d_6$): δ 8.57 (s, 1H), 7.81 (d, J=8.0 Hz, 3H), 7.47 (t, J=7.6 Hz, 2H), 7.24 (t, J=7.6 Hz, 1H), 7.02 (d, J=3.6 Hz, 1H), 6.87 (d, J=10.4 Hz, 1H), 6.71 (d, J=10.4 Hz, 1H), 1.98-1.86 (m, 3H), 1.08 (dd, J=2.8, 7.2 Hz, 18H).

Step 6: 3H-3,4,7,8-Tetraaza-cyclopenta[a]naphthalen-9-ol (26)

A suspension of compound 25 (14.4 g, 34.16 mmol), hydrazine hydrate (72 mL) and methanol (72 mL) was heated at 100° C. for 16 h. Reaction mixture was cooled, filtered, washed with methanol to afford 3H-3,4,7,8-tetraaza-cyclopenta[a]naphthalen-9-ol 5.0 g (78.7%). $^1$HNMR (400 MHz, DMSO-d$_6$): δ 12.85 (br s, 1H), 12.52 (br s, 1H), 8.93 (s, 1H), 8.54 (s, 1H), 7.84 (d, J=3.2 Hz, 1H), 7.27 (d, J=3.2 Hz, 1H).

Step 7: 9-chloro-3H-3,4,7,8-tetraaza-cyclopenta[a]naphthalene (27)

To a cooled mixture of phosphorous oxychloride (25.03 mL, 268.5 mmol) and N,N-diisopropylethylamine (4.67 mL, 26.8 6 mmol), compound 26 (4.0 g, 21.46 mmol) was added and heated at 120° C. for 16 h. After being cooled to room temperature reaction mixture was concentrated under reduced pressure. Residue was quenched with water and basified with solid sodium carbonate, the resulting solid was filtered, washed with water to afford 9-chloro-3H-3,4,7,8-tetraaza-cyclopenta[a]naphthalene 4.7 g (90.9%). $^1$HNMR (400 MHz, DMSO-d$_6$): δ 13.06 (br s, 1H), 9.82 (s, 1H), 9.27 (s, 1H), 7.97 (s, 1H), 7.47-7.46 (m, 1H).

Preparation 4: 3-Benzenesulfonyl-9-chloro-3H-3,4,6,7-tetraaza cyclopenta[a]naphthalene (32)

Step 2: 1-[1-(benzenesulfonyl)-5-nitro-pyrrolo[2,3-b]pyridin-4-yl]ethanone (29)

To a solution of compound 28 (0.3 g, 0.80 mmol) in acetone (3 mL) was added 1M aq. HCl (0.7 mL) and refluxed for 2 h. Reaction mixture was concentrated and aqueous sodium bicarbonate was added into it. It was extracted with ethyl acetate. The organic layer was dried over sodium sulphate, filtered and concentrated under vacuum. Residue obtained was purified by column chromatography to get 1-[1-(benzenesulfonyl)-5-nitro-pyrrolo[2,3-b]pyridin-4-yl]ethanone (0.2 g, 72.20%) as yellow solid. $^1$HNMR (400 MHz, CDCl$_3$): δ 2.61 (s☐☐ 6.63 (d, J=4.4 Hz, 1H), 7.55 (dd, J=7.2 Hz, 2H), 7.66 (dd, J=7.6 Hz, 1H), 7.97 (d, J=4.4 Hz, 1H), 8.22 (d, J=7.6 Hz, 2H), 9.24 (s, 1H).

Step 3: 1-[5-amino-1-(benzenesulfonyl)pyrrolo[2,3-b]pyridin-4-yl]ethanone (30)

To a solution of compound 29 (0.2 g, 0.579 mmol) in methanol (10 mL) was added 10% Pd—C (40 mg, 20% by

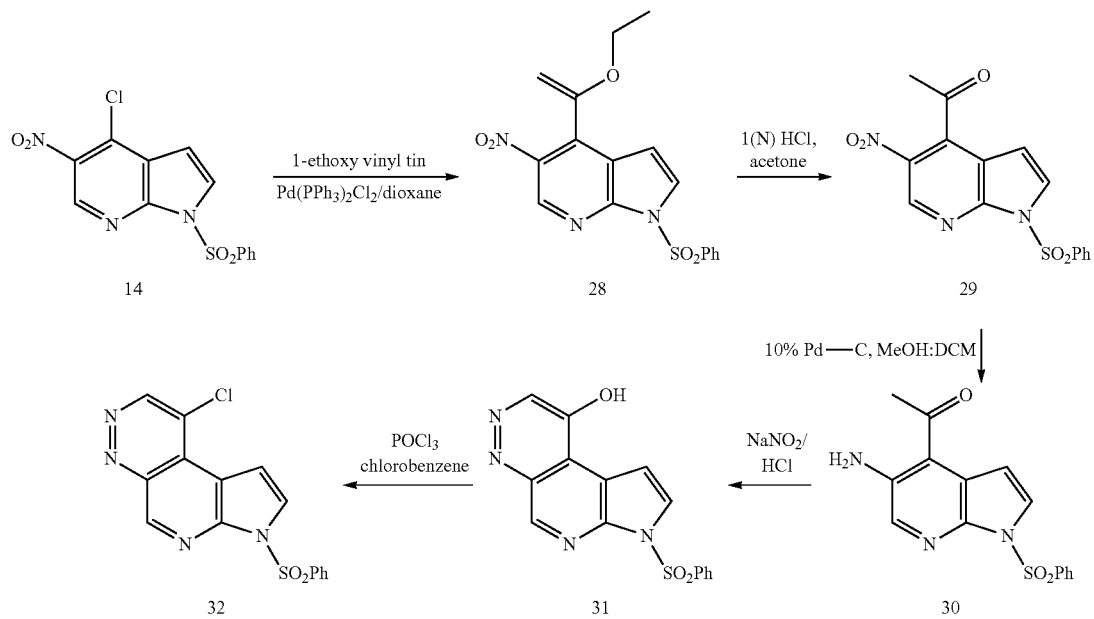

Step 1: 1-(benzenesulfonyl)-4-(1-ethoxyvinyl)-5-nitro-pyrrolo[2,3-b]pyridine (28)

To a solution of compound 14 (0.5 g, 1.48 mmol) and ethoxy vinyl tri n-butyl tin (0.58 g, 1.63 mmol) in dioxane (15 mL) was added Pd(PPh$_3$)$_2$Cl$_2$ (0.104 g, 0.148 mmol) under nitrogen atmosphere. It was heated under reflux overnight. Water was added to it and extracted with ethyl acetate. The organic layer was dried over sodium sulphate, filtered and concentrated under vacuum. Residue obtained was purified by column chromatography to get 1-(benzenesulfonyl)-4-(1-ethoxyvinyl)-5-nitro-pyrrolo[2,3-b]pyridine (0.32 g, 57.86%) as yellow oil. $^1$HNMR (400 MHz, CDCl$_3$): δ 1.28 (t, J=6.8 Hz, 3H), 3.92 (q, J=6.8 Hz, 2H), 4.57 (d, J=2.8 Hz, 1H), 4.67 (d, J=2.4 Hz, 1H), 6.85 (d, J=4.4 Hz, 1H), 7.53 (dd, J=8 Hz, 2H), 7.64 (dd, J=6.4 Hz, 1H), 7.90 (d, J=3.6 Hz, 1H), 8.19 (d, J=8 Hz, 2H), 8.88 (s, 1H).

wt.). It was degassed, purged with hydrogen and stirred under hydrogen atmosphere overnight. Reaction mixture was filtered through celite pad and washed with 10% methanol in CH$_2$Cl$_2$. Organic layer was concentrated and residue was purified by column chromatography to get 1-[5-amino-1-(benzenesulfonyl)pyrrolo[2,3-b]pyridin-4-yl]ethanone (0.11 g, 60.43%) as yellow solid. $^1$HNMR (400 MHz, CDCl$_3$): δ 2.69 (s☐☐6.17 (br s, 2H), ☐6.76☐ (d, J=4 Hz, 1H), 7.47 (d, J=7.2 Hz, 2H), 7.57 (d, J=7.2 Hz, 1H), 7.74 (d, J=4 Hz, 1H), 7.98 (s, 1H), 8.12 (d, J=7.2 Hz, 2H).

Step 4: 3-Benzenesulfonyl-3H-3,4,6,7-tetraaza cyclopenta[a]naphthalen-9-ol (31)

To a suspension of compound 30 (0.1 g, 0.317 mmol) in conc. HCl (2 mL) and water (5 mL); was added sodium nitrite (26 mg, 0.38 mmol) at 0° C. and it was stirred at room temperature for 2 h. The reaction mixture was concentrated and water was added to it, the solid separated out was filtered and it was purified by column chromatography to get 3-benzenesulfonyl-3H-3,4,6,7-tetraaza-cyclopenta[a]naphthalen-9-ol (40 mg, 38.83%) as white solid. $^1$HNMR (400 MHz, DMSO-do): δ 7.49 □ (d, J=3.6 Hz, 1H), 7.63 (d, J=7.6 Hz, 1H), 7.73 (d, J=7.6 Hz, 1H), 7.91 (s, 1H), 8.12-8.14 (m, 3H), 8.86 (s, 1H).

Step 5: 3-Benzenesulfonyl-9-chloro-3H-3,4,6,7-tetraaza cyclopenta[a]naphthalene (32)

To a solution of compound 31 (40 mg, 0.122 mmol) in chlorobenzene (2 mL) was added phosphorous oxychloride (2 mL) and it was heated stirred overnight at 120° C. The reaction mixture was concentrated, diluted with water (4 mL) and to it aq. ammonia was added. The solid separated was filtered and filtrate was extracted with ethyl acetate (3×10 mL). The organic layer was washed with brine solution (10 mL), dried over sodium sulphate and the residue obtained was combined with the solid and purified by column chromatography to obtain 3-benzenesulfonyl-9-chloro-3H-3,4,6,7-tetraazacyclopenta[a]naphthalene (10 mg, 23.80%) as brown solid. $^1$HNMR (400 MHz, CDCl$_3$): δ 7.52-7.56 (m, 2H), 7.61-7.63 (m, 2H), 8.01 (d J=4.4 Hz, 1H), 8.28 (d, J=7.6 Hz, 1H), 9.46 (s, 1H), 9.72 (s, 1H).

Preparation 5: tert-butyl 5-(3H-pyrrolo[3,2-f][1,7]naphthyridin-9-yl)-3,6-dihydro-2H-pyridine-1-carboxylate (36)

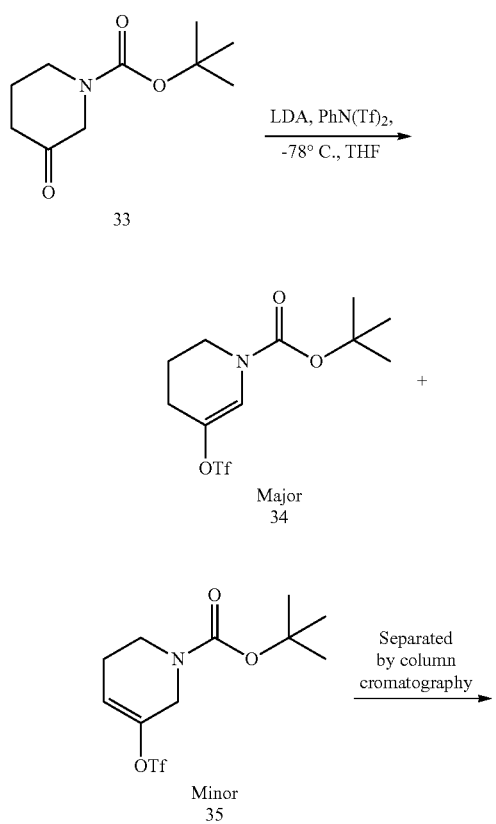

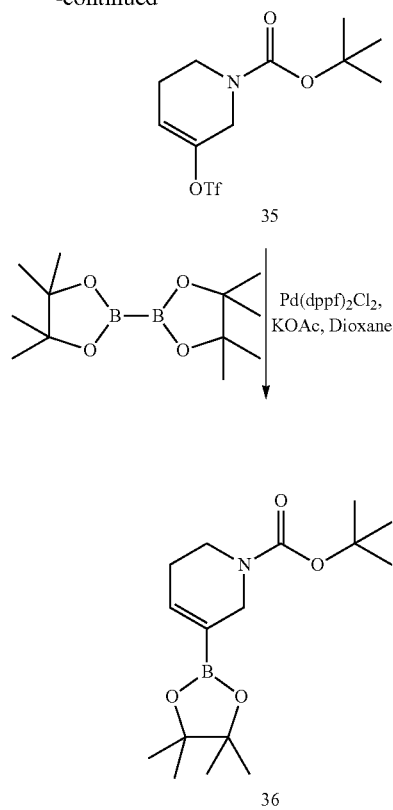

The compound 36 is prepared according to the procedure described in patent applications WO 2007/146838 and WO 2010/059771

Preparation 6: tert-butyl 3-(4,4,5,5-tetramethyl-1,3,2-dioxaborolan-2-yl)-2,5-dihydro-pyrrole-1-carboxylate (39)

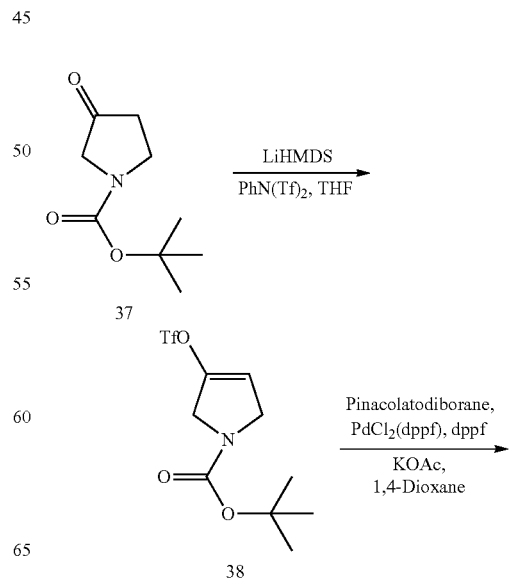

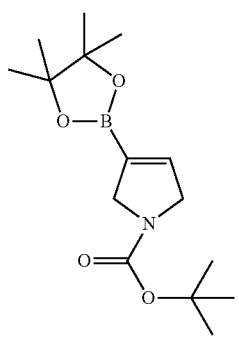

39

The compound 39 is prepared according to the procedure described in patent applications US 2006/0235037 and US 2010/0204265

Preparation 7: 9-(3-piperidyl)-3H-pyrrolo[3,2-f][1,7]naphthyridine core (42)

Method 7A

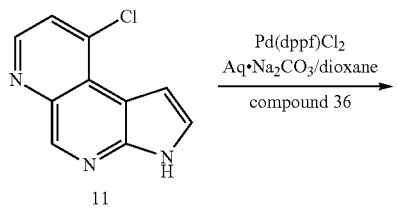

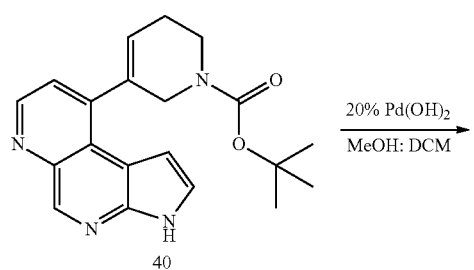

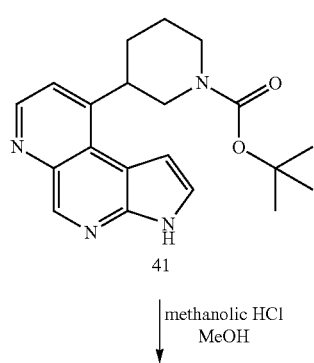

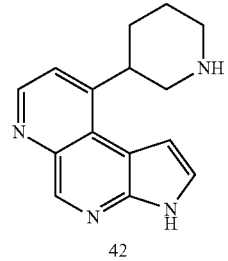

42

Step 1: tert-butyl 5-(3H-pyrrolo[3,2-f][1,7]naphthyridin-9-yl)-3,6-dihydro-2H-pyridine-1-carboxylate (40)

To a degassed solution of compound 11 (4 g, 19.70 mmol), compound 36 (7.61 g, 24.63 mmol) in dioxane (200 mL) was added aq. $Na_2CO_3$ (2.5 M, 59.11 mmol, 24 mL) and Pd(dppf)$Cl_2$ (1.6 g, 1.97 mmol) under nitrogen atmosphere. It was heated at 90° C. overnight. Water was added to it and extracted with ethyl acetate. Organic layer was dried over sodium sulphate filtered and concentrated under vacuum. Residue obtained was purified by column chromatography to get tert-butyl 5-(3H-pyrrolo[3,2-f][1,7]naphthyridin-9-yl)-3,6-dihydro-2H-pyridine-1-carboxylate (5.5 g, 79.82%). $^1$HNMR (400 MHz, $CDCl_3$): $\square_1\square\square$br s, 9H), 2.40-2.54 (m, 2H), 3.40-3.52 (m, 1H), 3.80-3.94 (m, 1H), 4.05-4.29 (m, 1H), 4.46-4.57 (m, 1H), 6.01 (s, 1H), 7.40 (d, J=4.4 Hz, 2H), 8.89 (d, J=4.4 Hz, 1H), 9.20 (s, 1H), 9.55 (br s, 1H).

Step 2: tert-butyl 3-(3H-pyrrolo[3,2-f][1,7]naphthyridin-9-yl)piperidine-1-carboxylate (41)

To a solution of compound 40 (5.5 g, 15.71 mmol) in methanol (250 mL) and DCM (100 mL), 20% Pd(OH)$_2$ (2.75 g, 0.5 wt/wt) was added. It was degassed, purged with hydrogen and stirred under hydrogen atmosphere for overnight. Reaction mixture was filtered through celite pad and it was washed with 10% methanol in $CH_2Cl_2$ (3.5 L). Organic layer was concentrated and residue was purified by column chromatography to get tert-butyl 3-(3H-pyrrolo[3,2-f][1,7]naphthyridin-9-yl)piperidine-1-carboxy late (4.7 g, 84%). $^1$HNMR (400 MHz, DMSO-d6): $\delta_1\square\square$br s, 9H), 1.62-1.75 (m, 1H), 1.79-1.98 (m, 2H), 2.08-2.16 (m, 1H), 2.81-3.09 (m, 2H), 3.61-3.70 (m, 1H), 4.02-4.17 (m, 1H), 4.28-4.31 (m, 1H), 6.97 (s, 1H), 7.66 (d, J=4.4 Hz, 2H), 8.85 (d, J=4.4 Hz, 1H), 9.20 (s, 1H), 12.38 (br s, 1H).

Step 3: 9-(3-piperidyl)-3H-pyrrolo[3,24-f][1,7]naphthyridine (42)

To a solution of compound 41 (3.5 g, 9.943 mmol) in methanol (50 mL) was added methanolic HCl (3N, 50 mL) at 0° C. under nitrogen atmosphere. It was stirred at room temperature for overnight. Reaction mixture was concentrated and excess of aqueous ammonia was added into it till it gets precipitated. Solid separated out was filtered and dried to get 9-(3-piperidyl)-3H-pyrrolo[3,2-f][1,7]naphthyridine (1.9 g) 76% yield. $^1$HNMR (400 MHz, DMSO-d$_6$): δ 1.62-1.85 (m, 3H), 2.08-2.16 (m, 1H), 2.51-2.63 (m, 2H), 3.04-3.07 (m, 1H), 3.25-3.34 (m, 1H), 3.65 (m, 1H), 7.12 (s, 1H), 7.60 (d, J=4 Hz, 2H), 7.65 (s, 1H), 8.81 (d, J=4 Hz, 1H), 8.98 (s, 1H), 12.33 (br s, 1H).

Method 7B

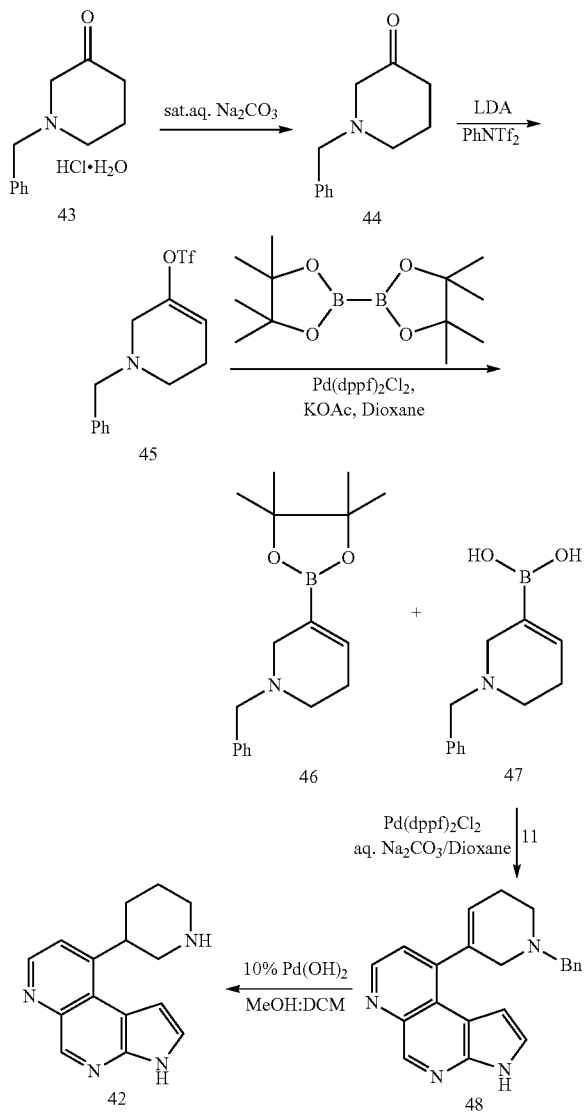

Step 1: 1-benzyl-3-piperidone (44)

Commercially available 1-benzyl-3-piperidone monohydrochloride monohydrated salt (43) was neutralized with saturated sodium carbonate solution, extracted with EtOAc, dried over sodium sulphate, concentrated in vacuum and stripped with dry THF. The liquid mass was used as such for the next step.

Step 2: (1-benzyl-3,6-dihydro-2H-pyridin-5-yl)trifluoromethane sulfonate (45)

To a solution of diisopropylamine (23.69 mL, 169.08 mmol) in THF (100 mL) was added 1.6 M of n-butyllithium (99.07 mL, 158.52 mmol) dropwise at −78° C. This was stirred 30 min and additional 30 min at 0° C. The reaction mixture was cooled to −78° C. and then a solution of compound 44 (20 g, 105.68 mmol) in dry THF (100 mL) was added dropwise. After further stirring for 1 h, a solution of 1,1,1-trifluoro-N-phenyl-N-(trifluoromethylsulfonyl) methanesulfonamide (41.53 g, 116.24 mmol) in THF (100 mL) was added dropwise to the reaction mixture. The reaction mixture was allowed to warm to room temperature and stirred for overnight. The reaction mixture was quenched with water and extracted with diethyl ether (3×400 mL). The combined ether layers were washed with water, brine and dried over sodium sulphate. The solvent was concentrated and purified on silica-gel column (100% hexane followed by 2-4% ethyl acetate/hexane) to get 20.0 g of (1-benzyl-3,6-dihydro-2H-pyridin-5-yl)trifluoromethanesulfonate. $^1$HNMR (400 MHz, CDCl$_3$): δ 7.40-7.24 (m, 5H), 5.84 (t, J=4.4 Hz, 1H), 3.64 (s, 2H), 3.13 (d, J=2 Hz, 2H), 2.61 (t, J=5.6 Hz, 2H), 2.31-2.28 (m, 2H).

Step 3: (1-benzyl-3,6-dihydro-2H-pyridin-5-yl)boronic acid (47)

Compound 45 (3.5 g, 10.89 mmol) was dissolved in 1,4-dioxane (45 mL) and potassium acetate (3.20 g, 32.67 mmol), bis(pinacolanto)diorane (3.32 g, 13.07 mmol), 1,1-bis(diphenylphosphino) ferrocene-palladium(II)dichloride dichloromethane complex (0.355 g, 0.435 mmol) and 1,1-bis (diphenylphosphino)ferrocene (0.241 g, 0.435 mmol) were added. The reaction mixture was degassed and purged with argon, followed by heating at 80° C. for 3 h. The reaction mixture was allowed to cool to room temperature, filtered through celite pad, washed with ethyl acetate, concentrated and residue was used as such for next reaction (LCMS was showing formation of boronic acid 47 in major amount and respective boronate ester 46 as minor product)

Step 4: 9-(1-benzyl-3,6-dihydro-2H-pyridin-5-yl)-3H-pyrrolo[3,2-f][1,7]naphthyridine (48)

To a solution of compound 11 (0.5 g, 2.45 mmol), was added crude material of above step 3, aq. Na$_2$CO$_3$ (2.0 M, 7.36 mmol, 3.7 mL) in degassed dioxane (25 mL) followed by Pd(dppf)Cl$_2$ DCM complex (0.2 g, 0.24 mmol) under argon atmosphere. It was heated at 90° C. for overnight. Water was added to it and extracted with ethyl acetate. Organic layer was dried over sodium sulphate filtered and concentrated in vacuum. Residue obtained was purified by flash column chromatography to get 9-(1-benzyl-3,6-dihydro-2H-pyridin-5-yl)-3H-pyrrolo[3,2-f][1,7]naphthyridine (0.6 g, 71.85%). $^1$HNMR (400 MHz, DMSO-do): δ 12.2 (br s, 1H), 8.97 (s, 1H), 8.80 (d, J=4.4 Hz, 1H), 7.56 (s, 1H), 7.42 (d, J=4.4 Hz, 1H), 7.37 (d, J=7.2 Hz, 2H), 7.28 (t, J=7.2 Hz, 2H), 7.20 (t, J=7.2 Hz, 1H), 7.11 (s, 1H), 5.85 (s, 1H), 3.66-3.60 (m, 2H), 3.40-3.25 (m, 2H), 3.10-2.80 (m, 2H), 2.60-2.30 (m, 2H).

Step 5: 9-(3-piperidyl)-3H-pyrrolo[3,2-f][1,7]naphthyridine (42)

To a solution of compound 48 (0.6 g, 1.76 mmol) in methanol (10 mL) and DCM (10 mL), 20% Pd(OH)$_2$ (0.3 g, 0.5 wt/wt) was added. It was purged with hydrogen and stirred under hydrogen balloon pressure for 24 h. Reaction mixture was filtered through celite pad and washed with 50% methanol in CH$_2$Cl$_2$ (3×100 mL). Organic layer was concentrated to get of 9-(3-piperidyl)-3H-pyrrolo[3,2-f][1,7]naphthyridine (0.42 g, 95%). $^1$HNMR (400 MHz, DMSO-d$_6$): δ 12.44 (br s, 1H), 9.02 (s, 1H), 8.87 (d, J=4.4 Hz, 1H), 7.70-7.55 (m, 3H), 7.28 (s, 1H), 4.22 (t, J=11.2 Hz, 1H), 3.53 (d, J=11.2 Hz, 1H), 3.41 (d, J=12 Hz, 1H), 3.37-3.30 (m, 1H), 3.00 (t, J=12 Hz, 1H), 2.21-2.10 (m, 2H), 2.05-1.95 (m, 1H), 1.90-1.70 (m, 1H).

Preparation 8: 9-pyrrolidin-3-yl-3H-pyrrolo[3,2-f][1,7]naphthyridine (51)

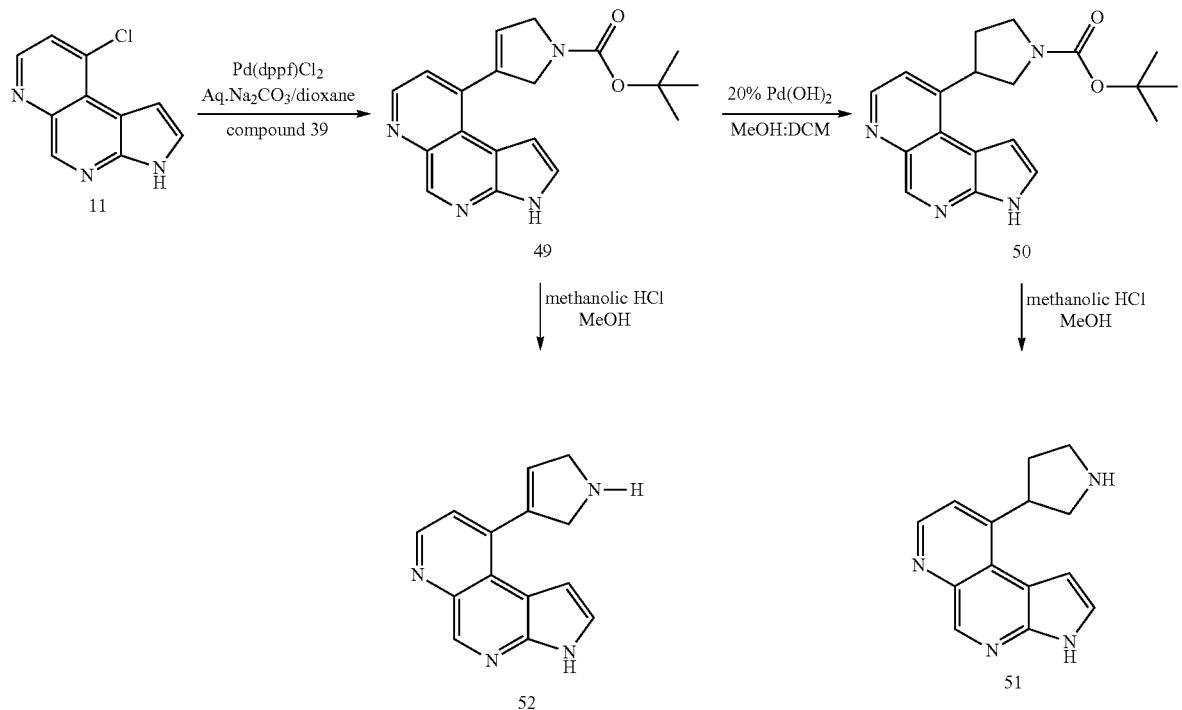

Step 1: tert-butyl 3-(3H-pyrrolo[3,2-f][1,7]naphthyridin-9-yl)-2,5-dihydropyrrole-1-carboxylate (49)

The preparation of compound 49 was carried out in a manner similar to that described for the preparation of compound 40. $^1$HNMR (400 MHz, CDCl$_3$): □$_1$□□$_{11}$□m, 1H), 9.22 (s, 1H), 8.91-8.90 (d, J=4 Hz, 1H), 7.47-7.43 (m, 2H), 6.87-6.86 (m, 1H), 6.05-6.01 (m, 1H), 4.95-4.48 (m, 4H), 1.49 (m, 9H).

Step 2: tert-butyl 3-(3H-pyrrolo[3,2-f][1,7]naphthyridin-9-yl)pyrrolidine-1-carboxylate (50)

The preparation of compound 50 was carried out in a manner similar to that described for the preparation of compound 41. $^1$H NMR (400 MHz, DMSO-d$_6$): δ 12.4 (s, 1H), 9.01 (s, 1H), 8.84 (d, J=4.4 Hz, 1H), 7.67 (s, 1H), 7.56-7.55 (m, 1H), 7.09 (s, 1H), 4.41-4.40 (m, 2H), 3.86-3.84 (m, 2H), 3.62-3.50 (m, 2H), 2.09-2.08 (m, 1H), 1.42 (d, J=7.8 Hz, 9H)

Step 3: 9-pyrrolidin-3-yl-3H-pyrrolo[3,2-f][1,7]naphthyridine (51)

The preparation of compound 51 was carried out in a manner similar to that described for the preparation of compound 42.

Preparation 9: 9-(2,5-dihydro-1H-pyrrol-3-yl)-3H-pyrrolo[3,2-f][1,7]naphthyridine (52)

The preparation of compound 52 is carried out in a manner similar to that described for the preparation of compound 42.

Preparation 10: 9-Piperidin-3-yl-3H-3,4,6,8-tetraaza-cyclopenta[a]naphthalene (56)

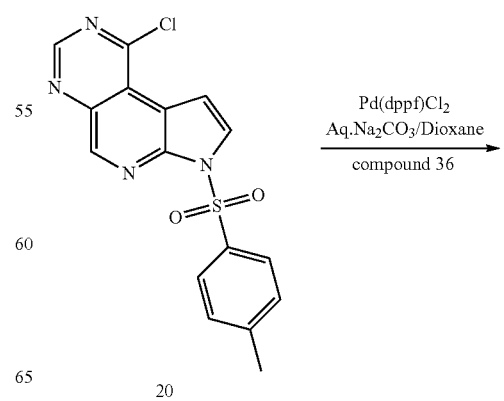

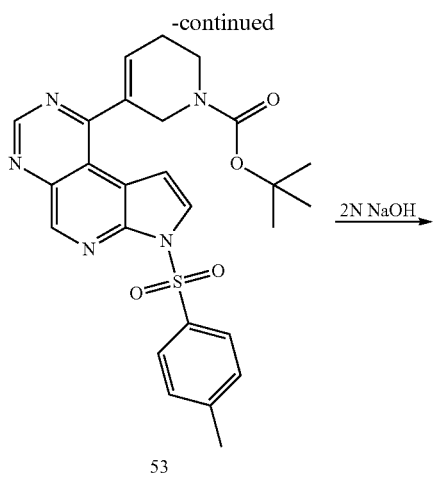

Step 1: 5-[3-(Toluene-4-sulfonyl)-3H-3,4,6,8-tetraaza-cyclopenta[a]naphthalen-9-yl]-3,6-dihydro-2H-pyridine-1-carboxylic acid tert-butyl ester (53)

The preparation of compound 53 was carried out in a manner similar to that described for the preparation of compound 40. ¹HNMR (400 MHz, CDCl₃): □₁□□s, 9H), 2.37 (s, 3H), 2.44-2.48 (m, 2H), 3.73-3.77 (m, 2H), 4.36-4.40 (m, 2H), 6.23-6.25 (m, 1H), 7.04 (d, J=2.4 Hz, 1H), 7.30 (d, J=8.4 Hz, 2H), 7.90 (d, J=2.8 Hz, 1H), 8.12 (d, J=8.4 Hz, 2H), 9.26 (s, 1H), 9.35 (s, 1H).

Step 2: 5-(3H-3,4,6,8-Tetraaza-cyclopenta[a]naphthalen-9-yl)-3,6-dihydro-2H-pyridine-1-carboxylic acid tert-butylester (54)

A stirred solution of compound 53 (4.7 mmol) in tetrahydrofuran (25 mL) was treated with 2N sodium hydroxide (10 mL) and heated under reflux for 2 h. Reaction mixture was allowed to cool to room temperature and the two layers separated. The aqueous layer was extracted with ethyl acetate and combined with organic fraction. This was washed with brine, dried over sodium sulphate, concentrated under reduced pressure, and purified on silica-gel column chromatography to obtain desired product with 45% yield. ¹HNMR (400 MHz, CDCl₃): □₁□□s, 9H), 2.38-2.42 (m, 3H), 3.65-3.69 (m, 2H), 4.34-4.38 (m, 2H), 6.33-6.37 (m, 1H), 6.87-6.89 (m, 1H), 7.70 (s, 1H), 9.04 (s, 1H), 9.29 (s, 1H), 12.59 (s, 1H).

Step 3: 3-(3H-3,4,6,8-Tetraaza-cyclopenta[a]naphthalen-9-yl)-piperidine-1-carboxylic acid tert-butyl ester (55)

The preparation of compound 55 was carried out in a manner similar to that described for the preparation of compound 41. ¹HNMR (400 MHz, DMSO-d₆): δ 1.19-1.51 (m, 10H), 1.67-1.74 (m, 1H), 1.89-2.06 (m, 2H), 2.13-2.18 (m, 1H), 2.90-3.02 (m, 1H), 3.75-3.88 (m, 1H), 4.02 (d, J=12.8 Hz, 1H), 4.25-4.32 (m, 1H), 7.04 (s, 1H), 7.86 (s, 1H), 9.04 (s, 1H), 9.28 (s, 1H), 12.72 (br s, 1H)

Step 4: 9-Piperidin-3-yl-3H-3,4,6,8-tetraaza-cyclopenta[a]naphthalene (56)

The preparation of compound 56 was carried out in a manner similar to that described for the preparation of compound 42.

Preparation 11: 9-Pyrrolidin-3-yl-3H-3,4,6,8-tetraaza-cyclopenta[a]naphthalene (60)

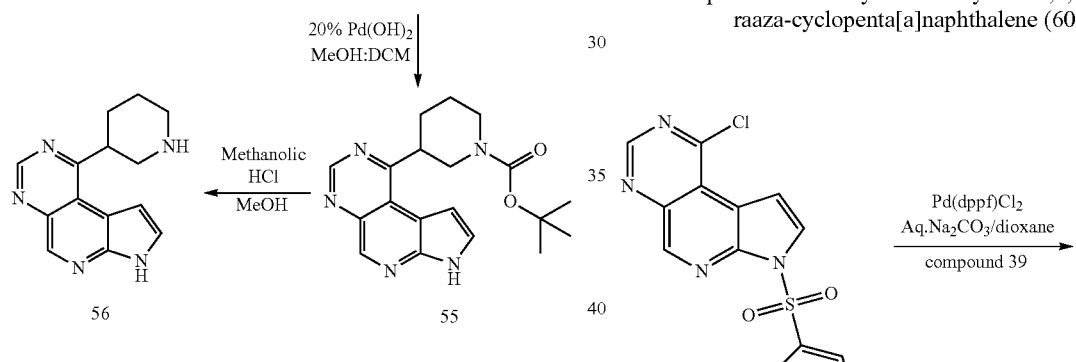

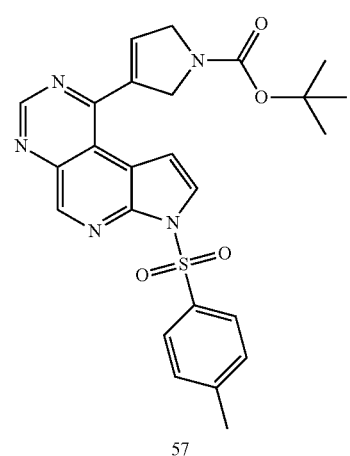

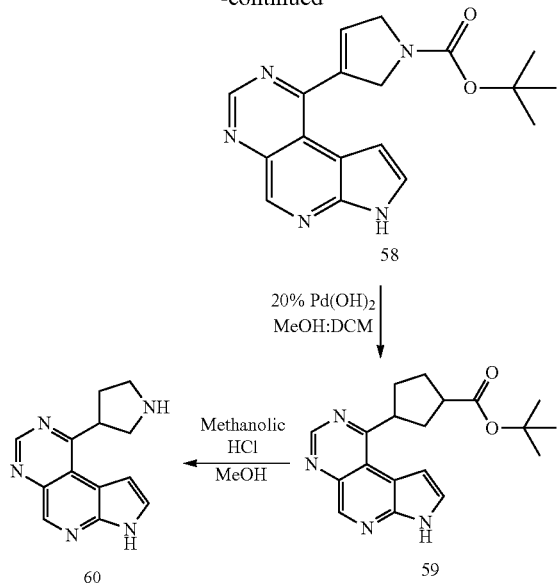

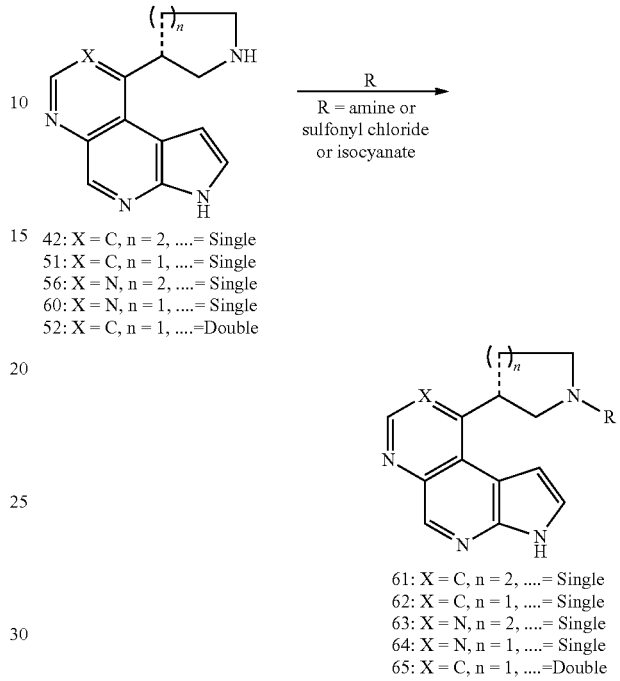

42: X = C, n = 2, .... = Single
51: X = C, n = 1, .... = Single
56: X = N, n = 2, .... = Single
60: X = N, n = 1, .... = Single
52: X = C, n = 1, .... = Double 61: X = C, n = 2, .... = Single
62: X = C, n = 1, .... = Single
63: X = N, n = 2, .... = Single
64: X = N, n = 1, .... = Single
65: X = C, n = 1, .... = Double (s, 1H), 7.26 (s, 1H), 4.77-4.74 (m, 1H), 3.89-3.85 (m, 1H) 3.70-3.61 (m, 1H), 3.54-3.37 (m, 1H), 3.31-3.25 (m, 1H), 2.64-2.57 (m, 1H), 2.27-2.22 (m, 1H).

Preparation of Amides, Sulfonamides and Urea Compounds:

Step 1: 3-[3-(toluene-4-sulfonyl)-3H-3,4,6,8-tetraaza-cyclopenta[a]naphthalen-9-yl]-2,5-dihydro-pyrrole-1-carboxylic acid tert-butyl ester (57)

The preparation of compound 57 was carried out in a manner similar to that described for the preparation of compound 40. $^1$H-NMR (400 MHz, CDCl$_3$): □□.35 (d, J=3.6 Hz, 1H), 9.25 (s, 1H), 8.11 (t, J=7.6 Hz, 2H), 7.91 (t, J=4 Hz, 1H), 7.30 (d, J=8.0 Hz, 2H), 7.09 (dd, J=3.6, 14 Hz, 1H), 6.38 (br s, 1H), 4.73 (br s, 2H), 4.52 (br d, J=19.6 Hz, 2H), 2.37 (s, 3H), 1.58 (s, 9H).

Step 2: 3-(3H-3,4,6,8-Tetraaza-cyclopenta[a]naphthalen-9-yl)-2,5-dihydro-pyrrole-1-carboxylic acid tert-butyl ester (58)

The preparation of compound 58 was carried out in a manner similar to that described for the preparation of compound 54. $^1$H-NMR (400 MHz, CDCl$_3$) □□12.6 (br s, 1H), □.27 (d, J=4.8 Hz, 1H), 9.01 (s, 1H), 7.69 (s, 1H), 7.01 (s, 1H), 6.64 (br s, 1H), 4.63 (br d, 2H) 4.52 (s, 2H), 1.45 (d, J=8.8 Hz, 9H).

Step 3: 3-(3H-3,4,6,8-Tetraaza-cyclopenta[a]naphthalen-9-yl)-pyrrolidine-1-carboxylic acid tert-butyl ester (59)

The preparation of 59 was carried out in a manner similar to that described for the preparation of compound 41. $^1$H-NMR (400 MHz, DMSO-d$_6$) □□12.7 (br s, 1H), □.27 (s, 1H), 9.03 (s, 1H), 7.84 (s, 1H), 7.18 (s, 1H), 4.59-4.60 (m, 1H), 3.95-3.87 (m, 1H) 3.82-3.78 (m, 1H), 3.55-3.49 (m, 1H), 3.45-3.39 (m, 1H), 2.41-2.26 (m, 2H), 1.40 (d, J=3.6 Hz, 9H).

Step 4: 9-Pyrrolidin-3-yl-3H-3,4,6,8-tetraaza-cyclopenta[a]naphthalene (60)

The preparation of compound 60 was carried out in a manner similar to that described for the preparation of compound 42. $^1$HNMR (400 MHz, DMSO-d$_6$): δ 12.80 (br s, 1H), 9.57 (br s, 1H) □.30 (s, 1H), 9.22 (br s, 1H) 9.06 (s, 1H), 7.89

Preparation 12: Amides (Method A1)

A stirred solution of suitable amine compound (0.376 mmol) in 3:1 dichloromethane:tetrahydrofuran (10 mL) was treated with suitable carboxylic acid (0.756 mmol), triethylamine (2.25 mmol), EDCI (0.756 mmol), and stirred for overnight at room temperature. The reaction mixture was concentrated under reduced pressure, residue was dissolved in ethyl acetate, washed with water and separated. The aqueous layer was again extracted with ethyl acetate. The combined organic layer was washed with brine, dried over sodium sulphate. It was concentrated under vacuum and purified on silica-gel column (0-2.5% methanol in dichloromethane) to obtain desired product (40-80%).

Amides (Method A2)

A stirred solution of suitable amine compound (0.376 mmol) in 3:1 dichloromethane:tetrahydrofuran (10 mL) was treated with suitable carboxylic acid (0.756 mmol), triethylamine (2.25 mmol), EDCI (0.756 mmol), HOBt (0.756 mmol) and stirred for overnight at room temperature. Water was added and extracted with 5% MeOH in CH$_2$Cl$_2$ until no product was there in aq. layer. The Combined organic layer was dried over sodium sulfate and filtered and concentrated under vacuum. The residue obtained was purified on silica-gel column chromatography (20-100% hexane in ethyl acetate) to obtain desired product (40-80%).

Preparation 13: Sulfonamides (Method B)

A stirred solution of suitable amine (0.25 mmol) in 3:1 dichloromethane:tetrahydrofuran (10 mL) was treated with suitable sulfonyl chloride (0.376 mmol), triethylamine (1.0 mmol), and stirred for overnight at room temperature. The reaction was quenched with saturated sodium bicarbonate and extracted 5% MeOH in CH$_2$Cl$_2$ The combined organic layer was dried over sodium sulphate, concentrated under vacuum and purified on silica-gel column (0-2.5% methanol in dichloromethane) to obtain desired product (40-80%).

Preparation 14: Urea Compounds (Method C)

To a solution of suitable amine (1.0 mmol) in DCM:THF (3:2 mL) under argon at 0° C. was added a suitable isocyanate (1.0 mmol) and stirred for overnight. Reaction mixture was concentrated and extracted with ethyl acetate and water. Organic layer was dried over sodium sulphate filtered and concentrated under vacuum. Residue obtained was purified by column chromatography to afford desired product.

The compounds in Table 1 were synthesized according to the above general method A1, A2, B or C

TABLE 1

| Ex | Structure | Method of coupling | IUPAC Name | 1H NMR |
|---|---|---|---|---|
| 1 | 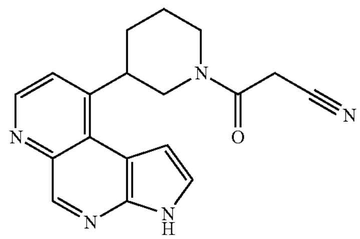 [SMILES: N#CCC(=O)N1CCCC(c2ccnc3cnc4[nH]ccc4c23)C1] | A1 | 3-oxo-3-[3-(3H-pyrrolo[3,2-f][1,7]naphthyridin-9-yl)-1-piperidyl]propanenitrile | $^1$HNMR (400 MHz, DMSO-d6): δ 1.59-1.62 (m, 3H), 2.11-2.35 (m, 1H), 2.62-3.09 (m, 1H), 3.16-3.29 (m, 1H), 3.51-3.69 (m, 1H), 3.77-3.99 (m, 1H), 4.01-4.21 (m, 2H), 4.51-4.70 (m, 1H), 6.98 (d, J = 8.4 Hz, 1H), 7.58-7.69 (m, 2H), 8.85 (d, J = 4.4 Hz, 1H), 9.01 (s, 1H), 12.38 (br s, 1H) |
| 1A | Pure enantiomer | Purified by Chrialpak IC-3 (150 × 4.6 mm, 3μ). Mobile phase EtOH | (R)3-oxo-3-[3-(3H-pyrrolo[3,2-f][1,7]naphthyridin-9-yl)-1-piperidyl]propanenitrile | $^1$HNMR (400 MHz, DMSO-d6): δ 1.59-1.92 (m, 3H), 2.11-2.35 (m, 1H), 2.62-3.09 (m, 1H), 3.16-3.29 (m, 1H), 3.51-3.69 (m, 1H), 3.77-3.99 (m, 1H), 4.01-4.21 (m, 2H), 4.51-4.70 (m, 1H), 6.98 (d, J = 8.4 Hz, 1H), 7.58-7.69 (m, 2H), 8.85 (d, J = 4.4 Hz, 1H), 9.01 (s, 1H), 12.38 (s, 1H) |
| 1B | Pure enantiomer | Purified by Chrialpak IC-3 (150 × 4.6 mm, 3μ). Mobile phase EtOH | (S)3-oxo-3-[3-(3H-pyrrolo[3,2-f][1,7]naphthyridin-9-yl)-1-piperidyl]propanenitrile | $^1$HNMR (400 MHz, DMSO-d6): δ 1.59-1.92 (m, 3H), 2.11-2.35 (m, 1H), 2.62-3.09 (m, 1H), 3.16-3.29 (m, 1H), 3.51-3.69 (m, 1H), 3.77-3.99 (m, 1H), 4.01-4.21 (m, 2H), 4.51-4.70 (m, 1H), 6.98 (d, J = 8.4 Hz, 1H), 7.58-7.69 (m, 2H), 8.85 (d, J = 4.4 Hz, 1H), 9.01 (s, 1H), 12.38 (s, 1H) |
| 2 | 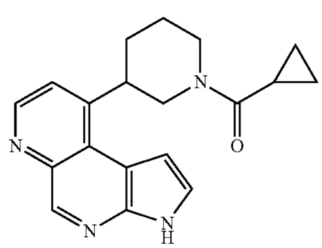 [SMILES: O=C(C1CC1)N1CCCC(c2ccnc3cnc4[nH]ccc4c23)C1] | A1 | cyclopropyl-[3-(3H-pyrrolo[3,2-f][1,7]naphthyridin-9-yl)-1-piperidyl]methanone | $^1$HNMR (400 MHz, DMSO-d6): δ 0.56-0.88 (m, 4H), 1.62-1.99 (m, 4H), 2.05-2.32 (m, 1H), 2.64-3.08 (m, 1H), 3.24-3.44 (m, 1H), 3.54-3.82 (m, 1H), 4.35-4.73 (m, 2H), 6.95 (d, J = 18 Hz, 1H), 7.60-7.72 (m, 2H), 8.85 (s, 1H), 9.00 (s, 1H), 12.37 (br s, 1H) |
| 3 | 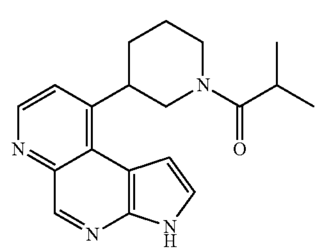 [SMILES: CC(C)C(=O)N1CCCC(c2ccnc3cnc4[nH]ccc4c23)C1] | A1 | 2-methyl-1-[3-(3H-pyrrolo[3,2-f][1,7]naphthyridin-9-yl)-1-piperidyl]propan-1-one | $^1$HNMR (400 MHz, DMSO-d6): δ 0.86-1.16 (m, 6H), 1.64-1.96 (m, 3H), 2.13-2.35 (m, 1H), 2.61-3.05 (m, 2H), 3.16-3.51 (m, 1H), 3.52-3.79 (m, 1H), 4.04-4.25 (m, 1H), 4.48-4.78 (m, 1H), 6.91 (s, 1H), 7.60-7.69 (m, 2H), 8.85 (m, 1H), 9.01 (s, 1H), 12.38 (br s, 1H) |

TABLE 1-continued

| Ex | Structure | Method of coupling | IUPAC Name | 1H NMR |
|---|---|---|---|---|
| 4 | 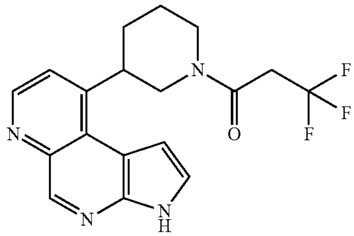 [SMILES: O=C(CC(F)(F)F)N1CCCC(c2ccnc3cnc4[nH]ccc4c23)C1] | A1 | 3,3,3-trifluoro-1-[3-(3H-pyrrolo[3,2-f][1,7]naphthyridin-9-yl)-1-piperidyl]propan-1-one | ¹HNMR (400 MHz, DMSO-d6): δ 1.64-1.76 (m, 1H), 1.79-1.91 (m, 2H), 2.16-2.34 (m, 1H), 3.00-3.26 (m, 1H), 3.36-3.42 (m, 1H), 3.50-3.71 (m, 2H), 3.72-3.84 (m, 1H), 3.96-4.15 (m, 1H), 4.58-4.74 (m, 1H), 6.94 (d, 1H, J = 6.8 Hz), 7.60-7.69 (m, 2H), 8.85 (m, 1H), 9.01 (s, 1H), 12.38 (s, 1H) |
| 4A | Pure enantiomer | Purified by Chiracel OJ-RH (150 × 4.6 mm, 5µ). Mobile phase MeOH: 0.05% formic acid in H₂O (60:40) | (R)3,3,3-trifluoro-1-[3-(3H-pyrrolo[3,2-f][1,7]naphthyridin-9-yl)-1-piperidyl]propan-1-one | ¹HNMR (400 MHz, DMSO-d6) δ 1.64-1.76 (m, 1H), 1.79-1.91 (m, 2H), 2.16-2.34 (m, 1H), 3.00-3.26 (m, 1H), 3.36-3.42 (m, 1H), 3.50-3.71 (m, 2H), 3.72-3.84 (m, 1H), 3.96-4.15 (m, 1H), 4.58-4.75 (m, 1H), 6.94 (d, J = 6.8 Hz, 1H), 7.60-7.69 (m, 2H), 8.85 (d, J = 6.8 Hz, 1H), 9.01 (s, 1H), 12.38 (s, 1H) |
| 4B | Pure enantiomer | Purified by Chiracel OJ-RH (150 × 4.6 mm, 5µ). Mobile phase MeOH: 0.05% formic acid in H₂O (60:40) | (S)3,3,3-trifluoro-1-[3-(3H-pyrrolo[3,2-f][1,7]naphthyridin-9-yl)-1-piperidyl]propan-1-one | ¹HNMR (400 MHz, DMSO-d6) δ 1.64-1.76 (m, 1H), 1.79-1.91 (m, 2H), 2.16-2.34 (m, 1H), 3.00-3.26 (m, 1H), 3.36-3.42 (m, 1H), 3.50-3.71 (m, 2H), 3.72-3.84 (m, 1H), 3.96-4.15 (m, 1H), 4.58-4.75 (m, 1H), 6.94 (d, J = 6.8 Hz, 1H), 7.60-7.69 (m, 2H), 8.85 (d, J = 6.8 Hz, 1H), 9.01 (s, 1H), 12.38 (s, 1H) |
| 5 | 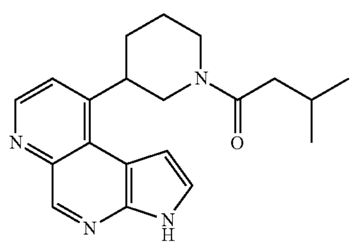 [SMILES: CC(C)CC(=O)N1CCCC(c2ccnc3cnc4[nH]ccc4c23)C1] | A1 | 3-methyl-1-[3-(3H-pyrrolo[3,2-f][1,7]naphthyridin-9-yl)-1-piperidyl]butan-1-one | ¹HNMR (400 MHz, DMSO-d6): δ 0.77-0.99 (m, 6H), 1.67-1.91 (m, 3H), 1.96-2.36 (m, 4H), 2.62-2.99 (m, 1H), 3.13-3.46 (m, 1H), 3.52-3.75 (m, 1H), 4.00-4.18 (m, 1H), 4.56-4.77 (m, 1H), 6.93 (s, 1H), 7.60-7.69 (m, 2H), 8.82-8.88 (m, 1H), 9.00-9.01 (m, 1H), 12.38 (br s, 1H) |
| 6 | 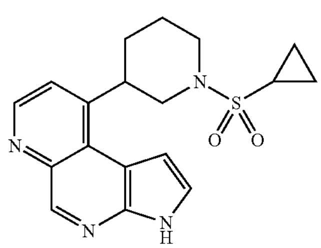 [SMILES: O=S(=O)(C1CC1)N1CCCC(c2ccnc3cnc4[nH]ccc4c23)C1] | B | 9-(1-cyclopropylsulfonyl-3-piperidyl)-3H-pyrrolo[3,2-f][1,7]naphthyridine | ¹HNMR (400 MHz, DMSO-d6): δ 0.82-1.00 (m, 4H), 1.80-2.00 (m, 3H), 2.09-2.18 (m, 1H), 2.61-2.70 (m, 1H), 2.95-3.09 (m, 2H), 3.74 (d, J = 11.2 Hz, 1H), 3.78-3.87 (m, 1H), 3.96 (d, J = 11.2 Hz, 1H), 6.98 (s, 1H), 7.63-7.68 (m, 1H), 7.71 (d, J = 4.4 Hz, 1H), 8.86 (d, J = 4.4 Hz, 1H), 9.01 (s, 1H), 12.39 (br s, 1H) |
| 7 | 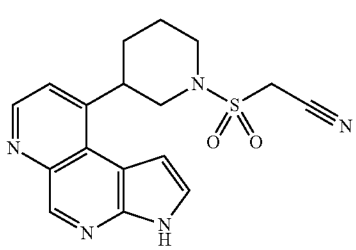 [SMILES: N#CCS(=O)(=O)N1CCCC(c2ccnc3cnc4[nH]ccc4c23)C1] | B | 2-[[3-(3H-pyrrolo[3,2-f][1,7]naphthyridin-9-yl)-1-piperidyl]sulfonyl]acetonitrile | ¹HNMR (400 MHz, DMSO-d6): δ 1.87-1.93 (m, 2H), 1.97-2.01 (m, 1H), 2.13-2.17 (m, 1H), 3.07-3.24 (m, 2H), 3.82-3.89 (m, 2H), 4.00-4.07 (m, 1H), 4.93 (s, 2H), 6.98 (s, 1H), 7.68 (t, J = 4.4 Hz, 2H), 8.87 (d, J = 4.4 Hz, 1H), 9.02 (s, 1H), 12.41 (s, 1H) |

TABLE 1-continued

| Ex | Structure | Method of coupling | IUPAC Name | 1H NMR |
|---|---|---|---|---|
| 8 | 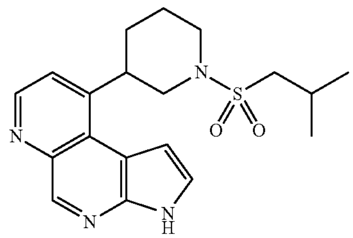 [SMILES: CC(C)CS(=O)(=O)N1CCCC(c2ccnc3cnc4[nH]ccc4c23)C1] | B | 9-(1-isobutylsulfonyl-3-piperidyl)-3H-pyrrolo[3,2-f][1,7]naphthyridine | ¹HNMR (400 MHz, DMSO-d6): δ 0.97-1.05 (m, 6H), 1.80-1.90 (m, 2H), 1.92-1.98 (m, 1H), 2.07-2.16 (m, 2H), 2.86-3.04 (m, 4H), 3.73 (d, J = 11.2 Hz, 1H), 3.76-3.84 (m, 1H), 3.94 (d, J = 11.2 Hz, 1H), 6.99 (s, 1H), 7.66 (t, J = 3.2 Hz, 1H), 7.70 (d, J = 4.4 Hz, 1H), 8.86 (d, J = 4.4 Hz, 1H), 9.01 (s, 1H), 12.39 (s, 1H) |
| 9 | 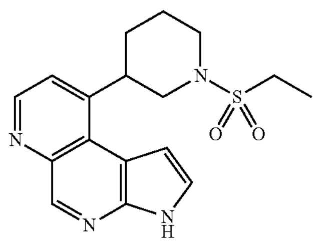 [SMILES: CCS(=O)(=O)N1CCCC(c2ccnc3cnc4[nH]ccc4c23)C1] | B | 9-(1-ethylsulfonyl-3-piperidyl)-3H-pyrrolo[3,2-f][1,7]naphthyridine | ¹HNMR (400 MHz, DMSO-d6): δ 1.19-1.25 (m, 3H), 1.80-1.90 (m, 2H), 1.92-1.98 (m, 1H), 2.11-2.17 (m, 1H), 2.92-3.02 (m, 1H), 3.03-3.13 (m, 3H), 3.71-3.84 (m, 2H), 3.96 (d, J = 11.2 Hz, 1H), 6.99 (s, 1H), 7.67 (t, J = 3.2 Hz, 1H), 7.69 (d, J = 4.4 Hz, 1H), 8.86 (d, J = 4.4 Hz, 1H), 9.01 (s, 1H), 12.39 (s, 1H) |
| 10 | 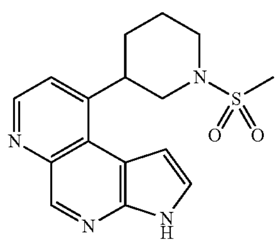 [SMILES: CS(=O)(=O)N1CCCC(c2ccnc3cnc4[nH]ccc4c23)C1] | B | 9-(1-methylsulfonyl-3-piperidyl)-3H-pyrrolo[3,2-f][1,7]naphthyridine | ¹HNMR (400 MHz, DMSO-d6): δ 1.80-1.90 (m, 2H), 1.92-1.98 (m, 1H), 2.11-2.17 (m, 1H), 2.82-2.88 (m, 1H), 2.90 (s, 3H), 2.91-2.98 (m, 1H), 3.69 (d, J = 11.2 Hz, 1H), 3.76-3.86 (m, 1H), 3.92 (d, J = 10.4 Hz, 1H), 6.98 (s, 1H), 7.67 (t, J = 2.8 Hz, 1H), 7.71 (d, J = 4.8 Hz, 1H), 8.86 (d, J = 4.8 Hz, 1H), 9.01 (s, 1H), 12.40 (s, 1H) |
| 10A | Pure enantiomer | Purified by Chiralpak IC-3 (150 × 4.6 mm, 3μ). Mobile phase Hexane:MTBE:MeOH (30:60:10) | (R)9-(1-methylsulfonyl-3-piperidyl)-3H-pyrrolo[3,2-f][1,7]naphthyridine | ¹HNMR (400 MHz, DMSO-d6): δ 12.39 (s, 1H), 9.01 (s, 1H), 8.86 (d, J = 4.7 Hz, 1H), 7.71 (d, J = 4.4 Hz, 1H), 7.67 (t, J = 3 Hz, 1H), 6.98 (s, 1H), 3.92 (d, J = 10.5 Hz, 1H), 3.83-3.81 (m, 1H), 3.69 (d, J = 11.2 Hz, 1H), 2.97-2.84 (m, 2H), 2.90 (s, 3H), 2.16-2.14 (m, 1H), 1.97-1.95 (m, 1H), 1.88-1.82 (m, 2H) |
| 10B | Pure enantiomer | Purified by Chiralpak IC-3 (150 × 4.6 mm, 3μ). Mobile phase Hexane:MTBE:MeOH (30:60:10) | (S)9-(1-methylsulfonyl-3-piperidyl)-3H-pyrrolo[3,2-f][1,7]naphthyridine | ¹HNMR (400 MHz, DMSO-d6): δ 12.39 (s, 1H), 9.01 (s, 1H), 8.86 (d, J = 4.6 Hz, 1H), 7.71 (d, J = 4.4 Hz, 1H), 7.67 (t, J = 2.9 Hz, 1H), 6.98 (s, 1H), 3.92 (d, J = 10.8 Hz, 1H), 3.83-3.81 (m, 1H), 3.69 (d, J = 10.2 Hz, 1H), 2.96-2.86 (m, 2H), 2.90 (s, 3H), 2.16-2.14 (m, 1H), 1.99-1.96 (m, 1H), 1.86-1.84 (m, 2H) |
| 11 | 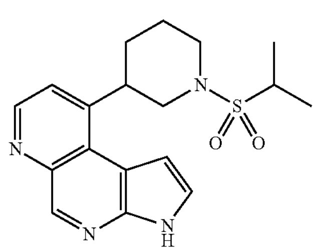 [SMILES: CC(C)S(=O)(=O)N1CCCC(c2ccnc3cnc4[nH]ccc4c23)C1] | B | 9-(1-isopropylsulfonyl-3-piperidyl)-3H-pyrrolo[3,2-][1,7]naphthyridine | ¹HNMR (400 MHz, DMSO-d6): δ 1.22 (t, J = 7.6 Hz, 6H), 1.80-1.93 (m, 3H), 2.14 (d, J = 11.2 Hz, 1H), 3.05 (t, J = 11.2 Hz, 1H), 3.18 (t, J = 11.6 Hz, 1H), 3.29-3.41 (m, 1H), 3.77-3.84 (m, 2H), 3.99 (d, J = 11.2 Hz, 1H), 7.02 (s, 1H), 7.64-7.71 (m, 2H), 8.85 (d, J = 4.4 Hz, 1H), 9.00 (s, 1H), 12.39 (s, 1H) |

TABLE 1-continued

| Ex | Structure | Method of coupling | IUPAC Name | 1H NMR |
|---|---|---|---|---|
| 12 | 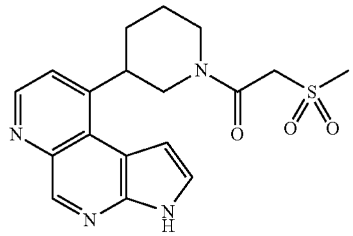 [SMILES: CS(=O)(=O)CC(=O)N1CCCC(c2ccnc3cnc4[nH]ccc4c23)C1] | A1 | 2-methylsulfonyl-1-[3-(3H-pyrrolo[3,2-f][1,7]naphthyridin-9-yl)-1-piperidyl]ethanone | ¹HNMR (400 MHz, DMSO-d6): δ 1.61-1.75 (m, 1H), 1.81-1.92 (m, 2H), 2.15-2.30 (m, 1H), 2.72-3.30 (m, 5H), 3.57-3.86 (m, 1H), 4.11-4.34 (m, 1H), 4.47-4.73 (m, 3H), 6.92 (s, 1H), 7.58-7.69 (m, 2H), 8.83-8.88 (m, 1H), 9.00 (s, 1H), 12.37 (br s, 1H) |
| 13 | 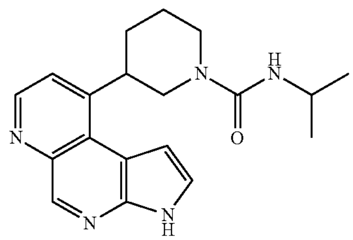 [SMILES: CC(C)NC(=O)N1CCCC(c2ccnc3cnc4[nH]ccc4c23)C1] | C | N-isopropyl-3-(3H-pyrrolo[3,2-f][1,7]naphthyridin-9-yl)piperidine-1-carboxamide | ¹HNMR (400 MHz, DMSO-d6): δ 1.03-1.05 (m, 6H), 1.65-1.84 (m, 3H), 2.15 (d, J = 11.2 Hz, 1H), 2.79 (t, J = 12.8 Hz, 1H), 3.61 (t, J = 10.4 Hz, 1H), 3.75-3.86 (m, 1H), 4.15 (d, J = 13.2 Hz, 1H), 4.29 (d, J = 12.8 Hz, 1H), 6.20 (d, J = 7.6 Hz, 1H), 6.93 (s, 1H), 7.60-7.69 (m, 2H), 8.81 (d, J = 4.8 Hz, 1H), 8.98 (s, 1H), 12.33 (s, 1H) |
| 14 | 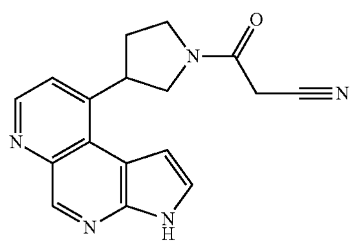 [SMILES: N#CCC(=O)N1CCC(c2ccnc3cnc4[nH]ccc4c23)C1] | A2 | 3-oxo-3-[3-(3H-pyrrolo[3,2-f][1,7]naphthyridin-9-yl)pyrrolidin-1-yl]propanenitrile | ¹HNMR (400 MHz, DMSO-d6): δ 12.40 (s, 1H), 9.01 (s, 1H), 8.85-8.83 (m, 1H), 7.67-7.52 (m, 2H), 7.11 (d, J = 10.8 Hz, 1H), 4.54-4.42 (m, 1H), 4.13-3.91 (m, 3H), 3.81-3.51 (m, 3H), 2.66-2.59 (m, 1H), 2.20-2.07 (m, 1H) |
| 14A | Pure enantiomer | Purified by Chiralpak IA-3 (150 × 4.6 mm, 3µ). Mobile phase EtOH | (R)3-oxo-3-[3-(3H-pyrrolo[3,2-f][1,7]naphthyridin-9-yl)pyrrolidin-1-yl]propanenitrile | ¹HNMR (400 MHz, DMSO-d6): δ 12.40 (s, 1H), 9.01 (s, 1H), 8.85-8.83 (m, 1H), 7.67-7.52 (m, 2H), 7.11 (d, J = 10.8 Hz, 1H), 4.54-4.42 (m, 1H), 4.13-3.91 (m, 3H), 3.81-3.51 (m, 3H), 2.66-2.59 (m, 1H), 2.20-2.07 (m, 1H) |
| 14B | Pure enantiomer | Purified by Chiralpak IA-3 (150 × 4.6 mm, 3µ). Mobile phase EtOH | (S)3-oxo-3-[3-(3H-pyrrolo[3,2-f][1,7]naphthyridin-9-yl)pyrrolidin-1-yl]propanenitrile | ¹HNMR (400 MHz, DMSO-d6): δ 12.40 (s, 1H), 9.01 (s, 1H), 8.85-8.83 (m, 1H), 7.67-7.52 (m, 2H), 7.11 (d, J = 10.8 Hz, 1H), 4.54-4.42 (m, 1H), 4.13-3.91 (m, 3H), 3.81-3.51 (m, 3H), 2.66-2.59 (m, 1H), 2.20-2.07 (m, 1H) |
| 15 | 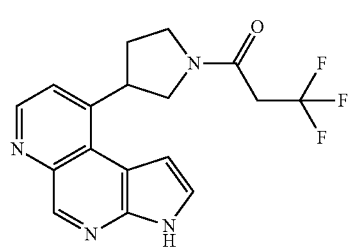 [SMILES: O=C(CC(F)(F)F)N1CCC(c2ccnc3cnc4[nH]ccc4c23)C1] | A2 | 3,3,3-trifluoro-1-[3-(3H-pyrrolo[3,2-f][1,7]naphthyridin-9-yl)pyrrolidin-1-yl]propan-1-one | ¹HNMR (400 MHz, MeOH-d4): δ 9.02 (s, 1H), 8.81 (t, J = 4.4 Hz, 1H), 7.66 (d, J = 4.8 Hz, 1H), 7.60-7.62 (m, 1H), 7.58 (d, J = 4.4 Hz, 1H), 7.17 (d, J = 2.8 Hz, 1H), 4.71-4.58 (m, 1H), 4.23-4.06 (m, 1H), 3.99-3.92 (m, 1H), 3.86-3.47 (m, 3H), 2.80-2.64 (m, 1H), 2.36-2.18 (m, 1H) |

TABLE 1-continued

| Ex | Structure | Method of coupling | IUPAC Name | 1H NMR |
|---|---|---|---|---|
| 15A | Pure enantiomer | Purified by Chiralpak IA-3 (150 × 4.6 mm, 3μ). Mobile phase 0.1% Et₂NH in Hexane:EtOH (80:20) | (R)3,3,3-trifluoro-1-[3-(3H-pyrrolo[3,2-f][1,7]naphthyridin-9-yl)pyrrolidin-1-yl]propan-1-one | ¹HNMR (400 MHz, DMSO-d6): δ 12.41 (br s, 1H), 9.01 (s, 1H), 8.84 (t, J = 4 Hz, 1H), 7.68 (d, J = 2.8 Hz, 1H), 7.63-7.51 (m, 1H), 7.11 (d, J = 9.2 Hz, 1H), 4.53-4.41 (m, 1H), 4.08-3.86 (m, 2H), 3.75-3.61 (m, 4H), 2.67-2.60 (m, 1H), 2.21-2.07 (m, 1H) |
| 15B | Pure enantiomer | Purified by Chiralpak IA-3 (150 × 4.6 mm, 3μ). Mobile phase 0.1% Et₂NH in Hexane:EtOH (80:20) | (S)3,3,3-trifluoro-1-[3-(3H-pyrrolo[3,2-f][1,7]naphthyridin-9-yl)pyrrolidin-1-yl]propan-1-one | ¹HNMR (400 MHz, DMSO-d6): δ 12.41 (br s, 1H), 9.01 (s, 1H), 8.84 (t, J = 4 Hz, 1H), 7.68 (d, J = 2.8 Hz, 1H), 7.63-7.51 (m, 1H), 7.11 (d, J = 9.2 Hz, 1H), 4.53-4.41 (m, 1H), 4.08-3.86 (m, 2H), 3.75-3.61 (m, 4H), 2.67-2.60 (m, 1H), 2.21-2.07 (m, 1H) |
| 16 | 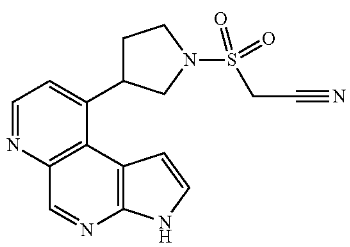 [SMILES: N#CCS(=O)(=O)N1CCC(c2ccnc3cnc4[nH]ccc4c23)C1] | B | 2-[3-(3H-pyrrolo[3,2-f][1,7]naphthyridin-9-yl)pyrrolidin-1-yl]sulfonylacetonitrile | ¹HNMR (400 MHz, DMSO-d6): δ 12.39 (s, 1H), 9.0 (s, 1H), 8.85 (d, J = 4.4 Hz, 1H), 7.68-7.66 (m, 2H), 7.08 (s, 1H), 5.0 (s, 2H), 4.54-4.51 (m, 1H), 4.04-4.0 (m, 1H), 3.76-3.71 (m, 2H), 3.59-3.53 (m, 1H), 2.65-2.59 (m, 1H), 2.22-2.16 (m, 1H) |
| 16A | Pure enantiomer | Purified by Chiralpak IC-3 (150 × 4.6 mm, 3μ). Mobile phase Hexane:MTBE:MeOH (45:45:10) | (R)2-[3-(3H-pyrrolo[3,2-f][1,7]naphthyridin-9-yl)pyrrolidin-1-yl]sulfonylacetonitrile | ¹HNMR (400 MHz, MeOH-d4): δ 9.02 (s, 1H), 8.83 (d, J = 4.4 Hz, 1H), 7.77 (d, J = 4.8 Hz, 1H), 7.61 (d, J = 3.2 Hz, 1H), 7.16 (d, J = 3.2 Hz, 1H), 4.68-4.64 (m, 1H), 4.85-4.82 (m, 2H), 4.18-4.14 (m, 1H), 3.91-3.87 (m, 1H), 3.85-3.80 (m, 1H), 3.71-3.66 (m, 1H), 2.80-2.71 (m, 1H), 2.38-2.30 (m, 1H) |
| 16B | Pure enantiomer | Purified by Chiralpak IC-3 (150 × 4.6 mm, 3μ). Mobile phase Hexane:MTBE:MeOH (45:45:10) | (S)2-[3-(3H-pyrrolo[3,2-f][1,7]naphthyridin-9-yl)pyrrolidin-1-yl]sulfonylacetonitrile | ¹HNMR (400 MHz, MeOH-d4): δ 9.02 (s, 1H), 8.83 (d, J = 4.4 Hz, 1H), 7.77 (d, J = 4.8 Hz, 1H), 7.61 (d, J = 3.2 Hz, 1H), 7.16 (d, J = 3.2 Hz, 1H), 4.68-4.64 (m, 1H), 4.85-4.82 (m, 2H), 4.18-4.14 (m, 1H), 3.91-3.87 (m, 1H), 3.85-3.80 (m, 1H), 3.71-3.66 (m, 1H), 2.80-2.71 (m, 1H), 2.38-2.30 (m, 1H) |

TABLE 1-continued

| Ex | Structure | Method of coupling | IUPAC Name | 1H NMR |
| --- | --- | --- | --- | --- |
| 17 | 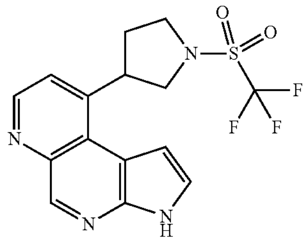 [SMILES: O=S(=O)(N1CCC(c2ccnc3cnc4[nH]ccc4c23)C1)C(F)(F)F] | B | 9-[1-(trifluoromethylsujlfonyl)pyrrolidin-3-yl]-3H-pyrrolo[3,2-f][1,7]naphthyridine | ¹HNMR (400 MHz, DMSO-d6): δ 12.42 (s, 1H), 9.01 (s, 1H), 8.86 (d, 1J = 4.4 Hz, 1H), 7.68-7.65 (m, 2H), 7.08 (s, 1H), 4.62-4.59 (m, 1H), 4.15-4.13 (m, 1H), 3.83-3.70 (m, 3H), 2.68-2.65 (m, 1H), 2.40-2.31 (m, 1H) |
| 18 | 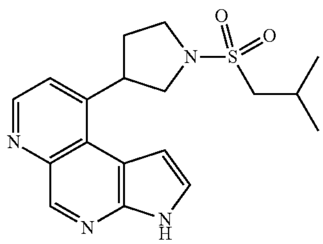 [SMILES: CC(C)CS(=O)(=O)N1CCC(c2ccnc3cnc4[nH]ccc4c23)C1] | B | 9-(1-isobutylsulfonylpyrrolidin-3-yl]-3H-pyrrolo[3,2-f][1,7]naphthyridine | ¹HNMR (400 MHz, DMSO-d6): δ 12.38 (s, 1H), 9.00 (s, 1H), 8.84 (d, J = 4.4 Hz, 1H), 7.70 (d, J = 4.4 Hz, 1H), 7.67-7.65 (m, 1H), 7.06 (s, 1H), 4.47-4.45 (m, 1H), 3.90-3.85 (m, 1H), 3.60-3.50 (m, 2H), 3.46-3.40 (m, 1H), 3.04 (d, J = 6 Hz, 2H), 2.59-2.54 (m, 1H), 2.18-2.09 (m, 2H), 1.03 (d, J = 6.4 Hz, 6H) |
| 19 | 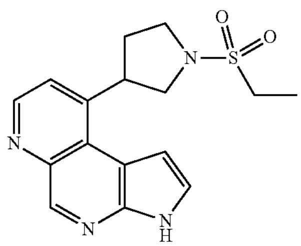 [SMILES: CCS(=O)(=O)N1CCC(c2ccnc3cnc4[nH]ccc4c23)C1] | B | 9-(1-ethylsulfonylpyrrolidin-3-yl)-3H-pyrrolo[3,2-f][1,7]naphthyridine | ¹HNMR (400 MHz, DMSO-d6): δ 12.40 (s, 1H), 9.01 (s, 1H), 8.86 (d, J = 4.4 Hz, 1H), 7.71 (d, J = 4.4 Hz, 1H), 7.68-7.67 (m, 1H), 7.08 (s, 1H), 4.50-4.47 (m, 1H), 3.91 (dd, J = 6.8, 10 Hz, 1H), 3.62-3.56 (m, 2H), 3.48-3.44 (m, 1H), 3.19 (q, J = 7.2 Hz, 2H), 2.62-2.57 (m, 1H), 2.21-2.16 (m, 1H), 1.23 (t, J = 7.6 Hz, 3H) |
| 20 | 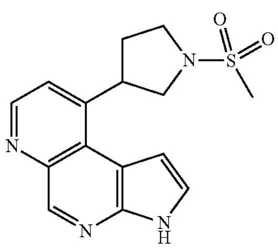 [SMILES: CS(=O)(=O)N1CCC(c2ccnc3cnc4[nH]ccc4c23)C1] | B | 9-(1-methylsulfonylpyrrolidin-3-yl)-3H-pyrrolo[3,2-f][1,7]naphthyridine | ¹HNMR (400 MHz, DMSO-d6): δ 12.41 (s, 1H), 9.02 (s, 1H), 8.86 (d, J = 4.4 Hz, 1H), 7.73 (d, J = 4.6 Hz, 1H), 7.68 (t, J = 2.8 Hz, 1H), 7.08 (s, 1H), 4.50-4.47 (m, 1H), 3.87 (dd, J = 6.8, 10 Hz, 1H), 3.59-3.53 (m, 2H), 3.47-3.42 (m, 1H), 3.00 (s, 3H), 2.67-2.56 (m, 1H), 2.18-2.13 (m, 1H) |
| 21 | 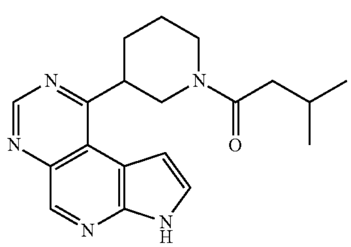 [SMILES: CC(C)CC(=O)N1CCCC(c2ncnc3cnc4[nH]ccc4c23)C1] | A1 | 3-Methyl-1-[3-(3H-3,4,6,8-tetraazacyclopenta[a]naphthalen-9-yl)-piperidin-1-yl]-butan-1-one | ¹HNMR (400 MHz, DMSO-d6): δ 0.78-0.90 (m, 3H), 0.95 (t, J = 7.6 Hz, 3H), 1.69-1.87 (m, 2H), 1.89-2.06 (m, 2H), 2.17-2.35 (m, 3H), 2.65-2.76 (m, 1H), 3.04-3.22 (m, 1H), 3.65-3.86 (m, 1H), 4.01-4.22 (m, 1H), 4.51-4.81 (m, 1H), 6.99-7.04 (m, 1H), 7.83 (s, 1H), 9.03 (s, 1H), 9.28 (s, 1H), 12.70 (s, 1H) |
| 22 | 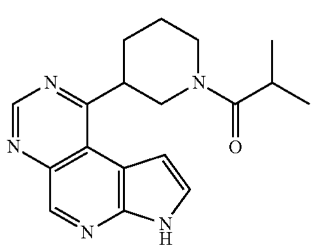 [SMILES: CC(C)C(=O)N1CCCC(c2ncnc3cnc4[nH]ccc4c23)C1] | A1 | 2-Methyl-1-[3-(3H-3,4,6,8-tetraazacyclopenta[a]naphthalen-9-yl)-piperidin-1-yl]-propan-1-one | ¹HNMR (400 MHz, DMSO-d6): δ 0.90-1.13 (m, 6H), 1.69-1.87 (m, 2H), 1.89-2.06 (m, 1H), 2.17-2.33 (m, 1H), 2.50-2.71 (m, 1H), 2.86-3.00 (m, 1H), 3.08-3.23 (m, 1H), 3.67-3.86 (m, 1H), 4.05-4.30 (m, 1H), 4.51-4.81 (m, 1H), 6.99-7.04 (m, 1H), 7.84 (s, 1H), 9.03 (s, 1H), 9.28 (s, 1H), 12.71 (s, 1H) |

TABLE 1-continued

| Ex | Structure | Method of coupling | IUPAC Name | 1H NMR |
|---|---|---|---|---|
| 23 | 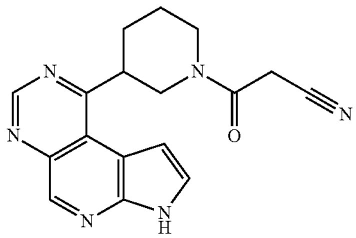 [SMILES: N#CCC(=O)N1CCCC(c2ncnc3cnc4[nH]ccc4c23)C1] | A1 | 3-Oxo-3-[3-(3H-3,4,6,8-tetraazacyclopenta[a]naphthalen-9-yl)-piperidin-1-yl]-propionitrile | ¹HNMR (400 MHz, DMSO-d6): δ 1.59-1.98 (m, 3H), 2.18-2.36 (m, 1H), 2.81-2.83 (m, 1H), 3.13-3.23 (m, 1H), 3.67-3.86 (m, 1H), 3.96-4.05 (m, 1H), 4.09-4.17 (m, 2H), 4.42-4.76 (m, 1H), 7.06 (s, 1H), 7.86 (d, J = 9.2 Hz, 1H), 9.04 (s, 1H), 9.28 (d, J = 6.4 Hz, 1H), 12.72 (d, J = 9.2 Hz, 1H) |
| 23A | Pure enantiomer | Purified by Chiralpak IC-3 (150 × 4.6 mm, 3μ), Mobile phase MeOH | (R)3-Oxo-3-[3-(3H-3,4,6,8-tetraazacyclopenta[a]naphthalen-9-yl)-piperidin-1-yl]-propionitrile | ¹HNMR (400 MHz, CDCl₃): δ 1.79-1.98 (m, 2H), 2.00-2.14 (m, 1H), 2.31-2.52 (m, 1H), 3.02-3.42 (m, 2H), 3.56-3.69 (m, 2H), 3.81-4.09 (m, 2H), 4.51-5.04 (m, 1H), 6.92-7.03 (m, 1H), 7.58-7.65 (m, 1H), 9.09-9.18 (m, 1H), 9.30 (d, J = 4.4 Hz, 1H), 9.74 (br s, 1H) |
| 23B | Pure enantiomer | Purified by Chiralpak IC-3 (150 × 4.6 mm, 3μ), Mobile phase MeOH | (S)3-Oxo-3-[3-(3H-3,4,6,8-tetraazacyclopenta[a]naphthalen-9-yl)-piperidin-1-yl]-propionitrile | ¹HNMR (400 MHz, CDCl₃): δ 1.79-1.98 (m, 2H), 2.00-2.14 (m, 1H), 2.31-2.52 (m, 1H), 3.02-3.42 (m, 2H), 3.56-3.69 (m, 2H), 3.81-4.09 (m, 2H), 4.51-5.04 (m, 1H), 6.92-7.03 (m, 1H), 7.58-7.65 (m, 1H), 9.09-9.18 (m, 1H), 9.30 (d, J = 4.4 Hz, 1H), 9.74 (br s, 1H) |
| 24 | 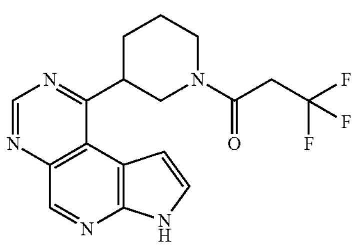 [SMILES: O=C(CC(F)(F)F)N1CCCC(c2ncnc3cnc4[nH]ccc4c23)C1] | A1 | 3,3,3-Trifluoro-1-[3-(3H-3,4,6,8-tetraazacyclopenta[a]naphthalen-9-yl)-piperidin-1-yl]-propan-1-one | ¹HNMR (400 MHz, DMSO-d6): δ 1.59-1.98 (m, 3H), 2.18-2.38 (m, 1H), 2.71-2.81 (m, 1H), 3.13-3.23 (m, 1H), 3.67-3.86 (m, 3H), 3.89-4.15 (m, 1H), 4.48-4.80 (m, 1H), 7.02 (s, 1H), 7.84 (s, 1H), 9.04 (s, 1H), 9.28 (d, J = 6.4 Hz, 1H), 12.71 (d, J = 7.6 Hz, 1H) |
| 24A | Pure enantiomer | Purified by Chiralpak IC-3 (150 × 4.6 mm, 3μ). Mobile phase 0.05% Et₂N in CH₃CN | (R)3,3,3-Trifluoro-1-[3-(3H-3,4,6,8-tetraazacyclopenta[a]naphthalen-9-yl)-piperidin-1-yl]-propan-1-one | ¹HNMR (400 MHz, CDCl₃): δ 1.79-2.11 (m, 3H), 2.31-2.52 (m, 1H), 2.87-2.97 (m, 1H), 3.23-3.49 (m, 3H), 3.73-4.09 (m, 2H), 4.71-5.14 (m, 1H), 6.92-6.97 (m, 1H), 7.55-7.66 (m, 1H), 9.04-9.18 (m, 1H), 9.31 (m, 1H), 9.67-9.78 (m, 1H) |

TABLE 1-continued

| Ex | Structure | Method of coupling | IUPAC Name | 1H NMR |
|---|---|---|---|---|
| 24B | (structure) Pure enantiomer | Purified by Chiralpak IC-3 (150 × 4.6 mm, 3μ). Mobile phase 0.05% Et$_2$N in CH$_3$CN | (S)3,3,3-Trifluoro-1-[3-(3H-3,4,6,8-tetraazacyclopenta[a]naphthalen-9-yl)-piperidin-1-yl]-propan-1-one | $^1$HNMR (400 MHz, CDCl$_3$): δ 1.79-2.11 (m, 3H), 2.31-2.52 (m, 1H), 2.87-2.97 (m, 1H), 3.23-3.49 (m, 3H), 3.73-4.09 (m, 2H), 4.71-5.14 (m, 1H), 6.92-6.97 (m, 1H), 7.55-7.66 (m, 1H), 9.04-9.18 (m, 1H), 9.31 (m, 1H), 9.67-9.78 (m, 1H) |
| 25 | (structure) | A1 | 2-Cyclopropyl-1-[3-(3H-3,4,6,8-tetraazacyclopenta[a]naphthalen-9-yl)-piperidin-1-yl]-ethanone | $^1$HNMR (400 MHz, DMSO-d6): δ 0.13-0.20 (m, 1H), 0.35-0.41 (m, 1H), 0.44-0.54 (m, 1H), 0.89-1.05 (m, 1H), 1.69-1.97 (m, 3H), 2.10-2.43 (m, 4H), 2.65-2.71 (m, 1H), 3.06-3.21 (m, 1H), 3.65-3.87 (m, 1H), 3.95-4.17 (m, 1H), 4.52-4.82 (m, 1H), 7.06 (s, 1H), 7.83-7.89 (m, 1H), 9.04 (s, 1H), 9.28 (d, J = 6.4 Hz, 1H), 12.72 (br s, 1H) |
| 26 | (structure) | A1 | [3-(3H-3,4,6,8-Tetraaza-cyclopenta[a]naphthalen-9-yl)-piperidin-1-yl]-(tetrahydro-furan-3-yl)-mathanone | $^1$HNMR (400 MHz, DMSO-d6): δ 1.05-1.30 (m, 1H), 1.69-1.94 (m, 3H), 1.98-2.14 (m, 1H), 2.18-2.34 (m, 1H), 2.39-2.77 (m, 1H), 3.11-3.23 (m, 1H), 3.35-3.40 (m, 1H), 3.44-3.60 (m, 1H), 3.62-3.97 (m, 4H), 4.06-4.33 (m, 1H), 4.50-4.79 (m, 1H), 7.05 (s, 1H), 7.83 (s, 1H), 9.03 (s, 1H), 9.28 (s, 1H), 12.70 (s, 1H) |
| 27 | (structure) | A1 | 1-[3-(3H-3,4,6,8-Tetraaza-cyclopenta[a]naphthalen-9-yl)-piperidin-1-yl]-propan-1-one | $^1$HNMR (400 MHz, DMSO-d6): δ 0.91-1.08 (m, 3H), 1.71-1.97 (m, 3H), 2.16-2.69 (m, 4H), 3.04-3.17 (m, 1H), 3.63-3.87 (m, 1H), 3.97-4.19 (m, 1H), 4.52-4.82 (m, 1H), 7.02-7.06 (m, 1H), 7.83-7.85 (m, 1H), 9.03 (s, 1H), 9.28 (s, 1H), 12.70 (s, 1H) |
| 28 | (structure) | A1 | 2,2-Dimethyl-1-[3-(3H-3,4,6,8-tetraaza-cyclopenta[a]naphthalen-9-yl)-piperidin-1-yl]-propan-1-one | $^1$HNMR (400 MHz, DMSO-d6): δ 1.14 (s, 9H), 1.74-1.93 (m, 3H), 2.26 (d, J = 11.2 Hz, 1H), 3.04 (t, J = 11.6 Hz, 1H), 3.85 (t, J = 11.6 Hz, 1H), 3.77 (t, J = 11.6 Hz, 1H), 3.77 (t, J = 11.6 Hz, 1H), 4.41 (d, J = 12.8 Hz, 1H), 4.65 (d, J = 12.8 Hz, 1H), 7.03 (s, 1H), 7.83 (s, 1H), 9.03 (s, 1H), 9.29 (s, 1H), 12.71 (s, 1H) |
| 29 | (structure) | A1 | Cyclopropyl-[3-(3H-3,4,6,8-tetraaza-cyclopenta[a]naphthalen-9-yl)-piperidin-1-yl]-methanone | $^1$HNMR (400 MHz, DMSO-d6): δ 0.56-0.88 (m, 4H), 1.62-1.99 (m, 3H), 2.05-2.34 (m, 2H), 2.64-3.18 (m, 2H), 3.64-3.90 (m, 1H), 4.35-4.76 (m, 2H), 7.02 (s, 1H), 7.82 (d, J = 8.4 Hz, 1H), 9.01 (s, 1H), 9.27 (s, 1H), 12.68 (s, 1H) |

TABLE 1-continued

| Ex | Structure | Method of coupling | IUPAC Name | 1H NMR |
|---|---|---|---|---|
| 30 | 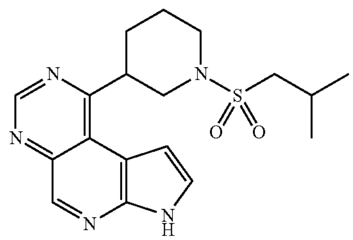 [SMILES: CC(C)CS(=O)(=O)N1CCCC(c2ncnc3cnc4[nH]ccc4c23)C1] | B | 9-[1-(2-Methyl-propane-1-sulfonyl)-piperidin-3-yl]-3H-3,4,6,8-tetraaza-cyclopenta[a]naphthalene | $^1$HNMR (400 MHz, DMSO-d6): δ 0.96-1.06 (m, 6H), 1.75-1.95 (m, 4H), 2.06-2.12 (m, 1H), 2.19 (d, J = 12.4 Hz, 1H), 2.87 (t, J = 10.4 Hz, 1H), 2.94 (d, J = 6.4 Hz, 1H), 3.20 (t, J = 11.2 Hz, 1H), 3.74 (d, J = 10.8 Hz, 1H), 3.91 (t, J = 10.4 Hz, 1H), 3.99 (d, J = 11.6 Hz, 1H), 7.01 (s, 1H), 7.84 (s, 1H), 9.02 (s, 1H), 9.27 (s, 1H), 12.71 (s, 1H) |
| 31 | 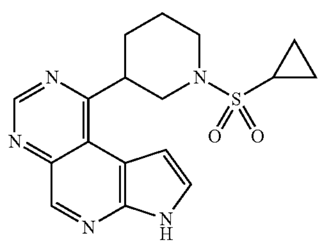 [SMILES: O=S(=O)(C1CC1)N1CCCC(c2ncnc3cnc4[nH]ccc4c23)C1] | B | 9-(1-Cyclopropanesulfonyl-piperidin-3-yl)-3H-3,4,6,8-tetraaza-cyclopenta[a]naphthalene | $^1$HNMR (400 MHz, DMSO-d6): δ 0.87-0.99 (m, 4H), 1.52-2.02 (m, 4H), 2.19 (d, J = 12 Hz, 1H), 2.63-2.68 (m, 1H), 2.89-2.99 (m, 1H), 3.77 (d, J = 10.8 Hz, 1H), 3.88-3.97 (m, 1H), 4.01 (d, J = 11.2 Hz, 1H), 7.00 (d, J = 3.2 Hz, 1H), 9.02 (s, 1H), 9.27 (s, 1H), 12.70 (s, 1H) |
| 32 | 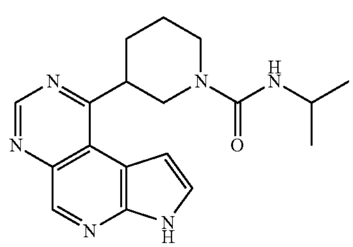 [SMILES: CC(C)NC(=O)N1CCCC(c2ncnc3cnc4[nH]ccc4c23)C1] | C | 3-(3H-3,4,6,8-Tetraaza-cyclopenta[a]naphthalen-9-yl)-piperidine-1-carboxylic acid isopropylamide | $^1$HNMR (400 MHz, DMSO-d6): δ 0.1.03-1.05 (m, 6H), 1.65-1.87 (m, 3H), 2.19 (d, J = 10.8 Hz, 1H), 2.76 (t, J = 11.2 Hz, 1H), 3.21 (t, J = 12.8 Hz, 1H), 3.69-3.83 (m, 2H), 4.17 (d, J = 12.4 Hz, 1H), 4.35 (d, J = 13.6 Hz, 1H), 6.24 (d, J = 7.6 Hz, 1H), 7.05 (d, J = 3.2 Hz, 1H), 7.83 (d, J = 3.2 Hz, 1H), 9.03 (s, 1H), 9.28 (s, 1H), 12.71 (s, 1H) |
| 33 | 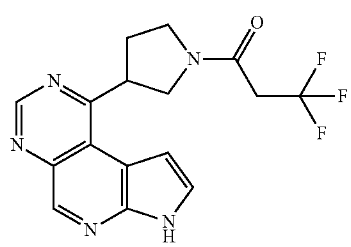 [SMILES: O=C(CC(F)(F)F)N1CCC(c2ncnc3cnc4[nH]ccc4c23)C1] | A1 | 3,3,3-Trifluoro-1-[3-(3H-3,4,6,8-tetraaza-cyclopenta[a]naphthalen-9-yl)-pyrrolidin-1-yl]-propan-1-one | $^1$HNMR (400 MHz, DMSO-d6): δ 12.72 (br s, 1H), 9.28 (d, J = 2.8 Hz, 1H), 9.04 (s, 1H), 7.86 (s, 1H), 7.20 (s, 1H), 4.69-4.61 (m, 1H), 4.14-3.8 (m, 2H), 3.74-3.46 (m, 4H), 2.62-2.50 (m, 1H), 2.36-2.21 (m, 1H) |
| 34 | 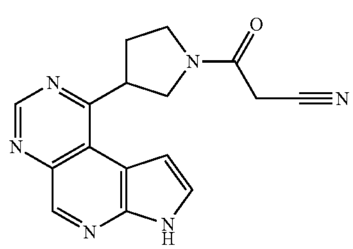 [SMILES: N#CCC(=O)N1CCC(c2ncnc3cnc4[nH]ccc4c23)C1] | A1 | 3-Oxo-3-[3-(3H-3,4,6,8-tetraaza-cyclopenta[a]naphthalen-9-yl)-pyrrolidin-1-yl]-propionitrile | $^1$HNMR (400 MHz, DMSO-d6): δ 12.73 (br s, 1H), 9.28 (d, J = 2.8 Hz, 1H), 9.04 (s, 1H), 7.86 (s, 1H), 7.19 (s, 1H), 4.70-4.61 (m, 1H), 7.09-3.87 (m, 4H), 3.68-3.35 (m, 2H), 2.67-2.50 (m, 1H), 2.36-2.21 (m, 1H) |
| 35 | 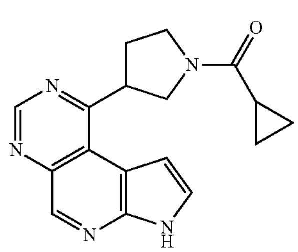 [SMILES: O=C(C1CC1)N1CCC(c2ncnc3cnc4[nH]ccc4c23)C1] | A1 | Cyclopropyl-[3-(3H-3,4,6,8-tetraaza-cyclopenta[a]naphthalen-9-yl)-pyrrolidin-1-yl]-methanone | $^1$HNMR (400 MHz, DMSO-d6): δ 12.71 (br s, 1H), 9.29 (d, J = 4.4 Hz, 1H), 9.04 (d, J = 2.8 Hz, 1H), 7.86 (s, 1H), 7.21 (dd, J = 3.2, 10 Hz, 1H), 4.74-4.59 (m, 1H), 4.35-4.10 (m, 1H), 3.96-3.77 (m, 2H), 3.64-3.38 (m, 1H), 2.66-2.50 (m, 1H), 2.45-2.08 (m, 1H), 1.81-1.78 (m, 1H), 0.85-0.73 (m, 4H) |

TABLE 1-continued

| Ex | Structure | Method of coupling | IUPAC Name | 1H NMR |
|---|---|---|---|---|
| 36 | 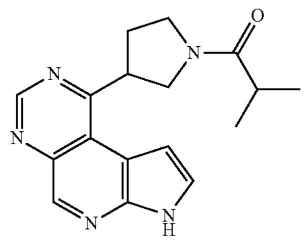 [SMILES: CC(C)C(=O)N1CCC(c2ncnc3cnc4[nH]ccc4c23)C1] | A1 | 2-Methyl-1-[3-(3H-3,4,6,8-tetraaza-cyclopenta[a]naphthalen-9-yl)-pyrrolidin-1-yl]-propan-1-one | ¹HNMR (400 MHz, DMSO-d6): δ 12.69 (br s, 1H), 9.24 (s, 1H), 9.02 (d, J = 1.2 Hz, 1H), 7.83 (s, 1H), 7.18 (s, 1H), 4.6-4.56 (m, 1H), 4.20-3.82 (m, 2H), 3.78-3.36 (m, 2H), 2.73-2.65 (m, 1H), 2.58-2.5 (m, 1H), 2.38-2.11 (m, 1H), 1.03-0.96 (m, 6H) |
| 37 | 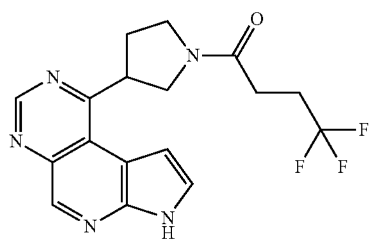 [SMILES: O=C(CCC(F)(F)F)N1CCC(c2ncnc3cnc4[nH]ccc4c23)C1] | A1 | 4,4,4-Trifluoro-1-[3-(3H-3,4,6,8-tetraaza-cyclopenta[a]naphthalen-9-yl)-pyrrolidin-1-yl]-butan-1-one | ¹HNMR (400 MHz, DMSO-d6): δ 12.70 (br s, 1H), 9.25 (d, J = 2.0 Hz, 1H), 9.02 (d, J = 2.0 Hz, 1H), 7.84 (d, J = 2.8 Hz, 1H), 7.18 (d, J = 5.2 Hz, 1H), 4.66-4.56 (m, 1H), 4.12-3.9 (m, 2H), 3.73-3.43 (m, 2H), 2.57-2.50 (m, 4H), 2.39-2.35 (m, 1H), 2.31-2.18 (m, 1H) |
| 38 | 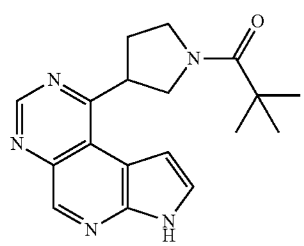 [SMILES: CC(C)(C)C(=O)N1CCC(c2ncnc3cnc4[nH]ccc4c23)C1] | A1 | 2,2-Dimethyl-1-[3-(3H-3,4,6,8-tetraaza-cyclopenta[a]naphthalen-9-yl)-pyrrolidin-1-yl]-propan-1-one | ¹HNMR (400 MHz, DMSO-d6): δ 12.71 (br s, 1H), 9.26 (s, 1H), 9.04 (s, 1H), 7.86 (d, J = 3.6 Hz, 1H), 7.20 (d, J = 2.6 Hz, 1H), 4.57-4.55 (m, 2H), 4.31-4.00 (m, 5H), 1.19 (s, 9H) |
| 39 | 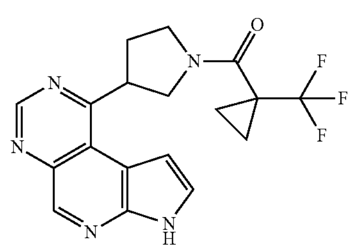 [SMILES: O=C(N1CCC(c2ncnc3cnc4[nH]ccc4c23)C1)C1(C(F)(F)F)CC1] | A1 | [3-(3H-3,4,6,8-Tetraaza-cyclopenta[a]naphthalen-9-yl)-pyrrolidin-1-yl]-(1-trifluoromethyl-cyclopropyl)-methanone | ¹HNMR (400 MHz, DMSO-d6): δ 12.72 (br s, 1H), 9.26 (s, 1H), 9.04 (s, 1H), 7.86 (s, 1H), 7.20 (s, 1H), 4.66-4.61 (m, 1H), 4.34-4.32 (m, 1H), 4.12-4.04 (m, 1H), 3.94-3.90 (m, 1H), 3.60-3.47 (m, 1H), 2.60-2.55 (m, 1H), 2.32-2.23 (m, 1H), 1.35-1.23 (m, 4H) |
| 40 | 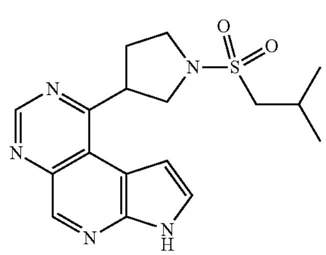 [SMILES: CC(C)CS(=O)(=O)N1CCC(c2ncnc3cnc4[nH]ccc4c23)C1] | B | 9-[1-(2-Methyl-propane-1-sulfonyl)-pyrrolidin-3-yl]-3H-3,4,6,8-tetraaza-cyclopenta[a]naphthalene | ¹HNMR (400 MHz, DMSO-d6): δ 12.73 (br s, 1H), 9.28 (s, 1H), 9.05 (s, 1H), 7.86 (s, 1H), 7.18 (d, J = 3.2 Hz, 1H), 4.69-4.64 (m, 1H), 3.91-3.84 (m, 2H), 3.57-3.51 (m, 1H), 3.46-3.40 (m, 1H), 3.09-2.99 (m, 2H), 2.62-2.50 (m, 1H), 2.32-2.28 (m, 1H), 2.16-2.10 (m, 1H), 1.05 (dd, J = 2.8, 6.4 Hz, 6H) |
| 41 | 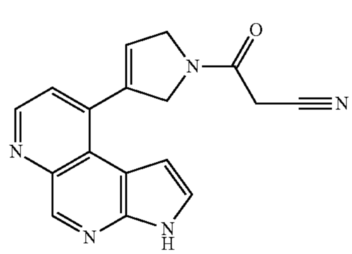 [SMILES: N#CCC(=O)N1CC=C(c2ccnc3cnc4[nH]ccc4c23)C1] | A1 | 3-oxo-3-[3-(3H-pyrrolo[3,2-f][1,7]naphthyridin-9-yl)-2,5-dihydropyrrolo-1-yl]propanenitrile | ¹HNMR (400 MHz, DMSO-d6): δ 4.04-4.16 (m, 2H), 4.48-4.68 (m, 4H), 6.22 (s, 1H), 6.76-6.82 (m, 1H), 7.59-7.66 (m, 2H), 8.91-8.97 (m, 1H), 9.04 (s, 1H), 12.39 (s, 1H) |

TABLE 1-continued

| Ex | Structure | Method of coupling | IUPAC Name | 1H NMR |
|---|---|---|---|---|
| 42 | 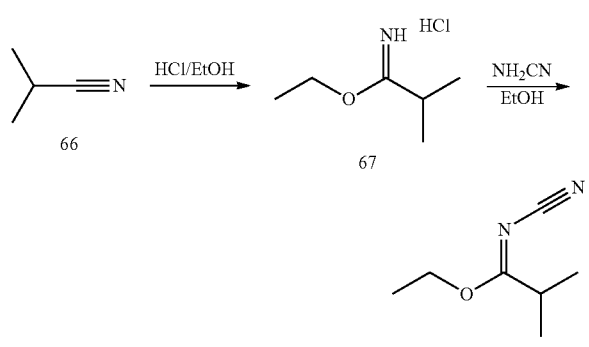 | A1 | 3,3,3-trifluoro-1-[3-(3H-pyrrolo[3,2-f][1,7]naphthyridin-9-yl)-2,5-dihyropyrrol-1-yl]propan-1-one | ¹HNMR (400 MHz, DMSO-d6): δ 3.62-3.84 (m, 2H), 4.44-4.58 (m, 2H), 4.62-4.78 (m, 2H), 6.22 (s, 1H), 6.76-6.82 (m, 1H), 7.59-7.66 (m, 2H), 8.91-8.97 (m, 1H), 9.03 (s, 1H), 12.39 (s, 1H). |

Preparation 15: ethyl (1E)-N-cyano-2-methyl-propanimidate (68)

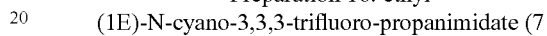

Step 1: ethyl 2-methylpropanimidate hydrochloride (67)

Isobutyronitrile (66) (6.49 mL, 0.072 mol) was taken in dry ether (10 mL) and cooled in an ice-water bath. To this was added ethanol (5.06 mL, 0.086 mol). The resultant solution was stirred for 15 min followed by gradual addition of hydrochloric acid (4.0M in dioxane, 0.144 mol). The reaction was allowed to warm up to room temperature and stirred overnight at room temperature. The reaction mass was then concentrated to a crude residue which upon ether trituration afforded a white solid. The solid was filtered and washed with cold ether to give 6.1 g of desired product. ¹HNMR (400 MHz, DMSO-do): δ 12.06 (br s, 1H), 11.26 (br s, 1H), 4.43 (q, J=6.8 Hz, 2H), 2.99 (sept., J=7.1 Hz, 1H), 1.33 (t, J=7.0 Hz, 3H), 1.16 (d, J=6.8 Hz, 6H).

Step 2: ethyl (1E)-N-cyano-2-methyl-propanimidate (68)

Compound 67 (2.0 g, 0.0132 mol) was taken in dry ethanol (5 mL) followed by addition of cyanamide (0.56 g, 0.0132 mol). The reaction mixture was stirred at room temperature. After 3 h, additional cyanamide (0.220 g, 5 mmol) was added. The solid ammonium chloride was filtered and the filtrate evaporated to give oil. This was diluted with dichloromethane and washed with brine. The organic layer was dried over sodium sulphate and concentrated under vacuum to afford the desired product (0.92 g) as oil. ¹HNMR (400 MHz, DMSO-d₆): δ 4.26 (q, J=6.8 Hz, 2H), 3.12 (sept., J=6.8 Hz, 1H), 1.27 (t, J=7.2 Hz, 3H), 1.18 (d, J=6.8 Hz, 6H).

Preparation 16: ethyl (1E)-N-cyano-3,3,3-trifluoro-propanimidate (71)

The preparation of compound 71 was carried out in a manner similar to that described for the preparation of compound 68. ¹H NMR (400 MHz, DMSO-d₆): 4.38 (q, J=7.1 Hz, 2H), 4.07 (q, J=10.5 Hz, 2H), 1.29 (t, J=7.1 Hz, 3H).

Preparation 17: Amide Surrogates (72)

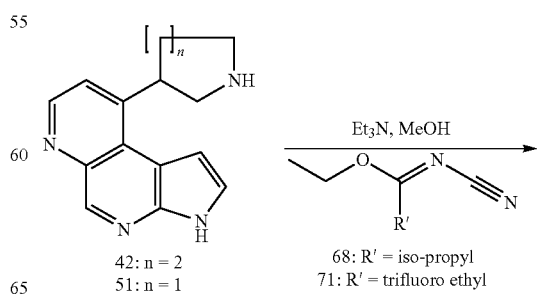

42: n = 2
51: n = 1

68: R' = iso-propyl
71: R' = trifluoro ethyl

-continued

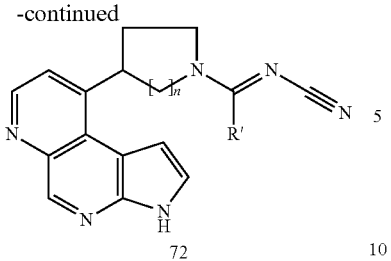

72

Compound 68 or compound 71 (0.24 mmol) was taken in dry MeOH (1 mL), followed by the addition of 42 (0.198 mmol) and triethylamine (0.055 mL, 0.39 mmol). The reaction mixture was then stirred at room temperature under an inert atmosphere overnight. Additional 68 or 71 accordingly (0.24 mmol) was added and the reaction stirred at room temperature for another 4 h. The reaction was then concentrated and residue purified by preparative TLC to afford 72.

The compounds in Table 2 were synthesized according to the above general method

TABLE 2

| Ex. | Structure | IUPAC name | NMR data |
|---|---|---|---|
| 43 | 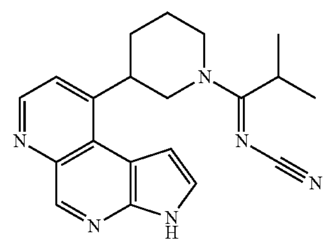 [SMILES: CC(C)/C(=N\C#N)N1CCCC(c2ccnc3cnc4[nH]ccc4c23)C1] | (E)-[2-methyl-1-[3-(3H-pyrrolo[3,2-f][1,7]naphthyridin-9-yl)-1-piperidyl]propylidene]cyanamide | $^1$H NMR (400 MHz, DMSO-d6): 12.40 (br s, 1H), 9.02 (s, 1H), 8.87 (br s, 1H), 7.67-7.64 (m, 2H), 6.96 (br s, 1H), 4.85-4.73 (m, 1H), 4.46-4.33 (m, 1H), 3.82-3.52 (m, 2H), 3.39-3.37 (m, 1H), 3.05-2.98 (m, 1H), 2.27-2.22 (m, 1H), 1.99-1.85 (m, 3H), 1.45 (d, J = 7.2 Hz, 2H), 1.39-1.35 (m, 3H), 1.2 (d, J = 6.8 Hz, 1H) |
| 43A | Pure enantiomer | (R)(E)-[2-methyl-1-[3-(3H-pyrrolo[3,2-f][1,7]naphthyridin-9-yl)-1-piperidyl]propylidene]cyanamide | $^1$H NMR (400 MHz, DMSO-d6): 12.4 (br s, 1H), 8.99 (s, 1H), 8.84 (d, J = 3.4 Hz, 1H), 7.63 (d, J = 4 Hz, 2H), 6.94 (s, 1H), 4.83-4.71 (m, 1H), 4.43-4.31 (m, 1H), 3.80-3.63 (m, 2H), 3.53-3.50 (m, 1H), 3.04-3.0 (m, 1H), 2.22-2.20 (m, 1H), 1.97-1.83 (m, 3H), 1.44-1.34 (m, 4H), 1.22-1.18 (m, 2H) |
| 43B | Pure enantiomer | (S)(E)-[2-methyl-1-[3-(3H-pyrrolo[3,2-f][1,7]naphthyridin-9-yl)-1-piperidyl]propylidene]cyanamide | $^1$H NMR (400 MHz, DMSO-d6): 12.4 (br s, 1H), 8.99 (s, 1H), 8.84 (d, J = 3.4 Hz, 1H), 7.63 (d, J = 4 Hz, 2H), 6.94 (s, 1H), 4.83-4.71 (m, 1H), 4.43-4.31 (m, 1H), 3.80-3.63 (m, 2H), 3.53-3.50 (m, 1H), 3.04-3.0 (m, 1H), 2.22-2.20 (m, 1H), 1.97-1.83 (m, 3H), 1.44-1.34 (m, 4H), 1.22-1.18 (m, 2H) |
| 44 | 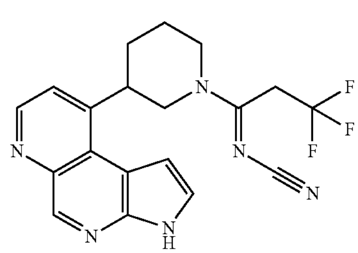 [SMILES: N#C/N=C(\CC(F)(F)F)N1CCCC(c2ccnc3cnc4[nH]ccc4c23)C1] | (E)-[3,3,3-trifluoro-1-[3-(3H-pyrrolo[3,2-f][1,7]naphthyridin-9-yl)-1-piperidyl]propylidene]cyanamide | $^1$H NMR (400 MHz, MeOH-d4): 9.02 (br s, 1H), 8.83 (d, J = 4.4 Hz, 1H), 7.70-7.66 (m, 1H), 7.62-7.59 (m, 1H), 7.05-7.01 (m, 1H), 5.14-5.0 (m, 1H), 4.44-4.29 (m, 1H), 4.15-3.9 (m, 3H), 3.56-3.48 (m, 1H), 3.15 (q, J = 10.8 Hz, 2H), 2.50-2.35 (m, 1H), 2.10-1.92 (m, 2H) |

TABLE 2-continued

| Ex. | Structure | IUPAC name | NMR data |
|---|---|---|---|
| 45 | 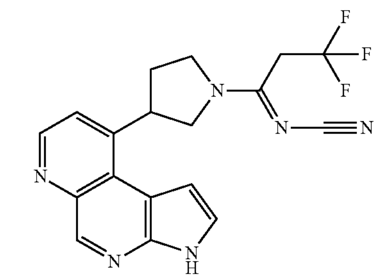 [SMILES: N#C/N=C(\CC(F)(F)F)N1CCC(c2ccnc3cnc4[nH]ccc4c23)C1] | (E)-[3,3,3-trifluoro-1-[3-(3H-pyrrolo[3,2-f][1,7]naphthyridin-9-yl)pyrrolidin-1-yl]propylidene]cyanamide | $^1$H NMR (400 MHz, DMSO-d6): 12.41 (br s, 1H), 9.02 (s, 1H), 8.86-8.84 (m, 1H), 7.69 (s, 1H), 7.62-7.51 (m, 1H), 7.15 (br s, 1H), 4.63-4.54 (m, 1H), 4.33-3.86 (m, 4H), 3.83-3.59 (m, 2H), 2.63-2.59 (m, 1H), 2.25-2.19 (m, 1H) |

Two enantiomers of 72 were separated using Chiralpak IC-3 (150×4.6 mm, 3μ). Mobile phase MeOH:MTBE:Hexane (20:40:40).

Preparation 18: Preparation of Urea Compounds (77)

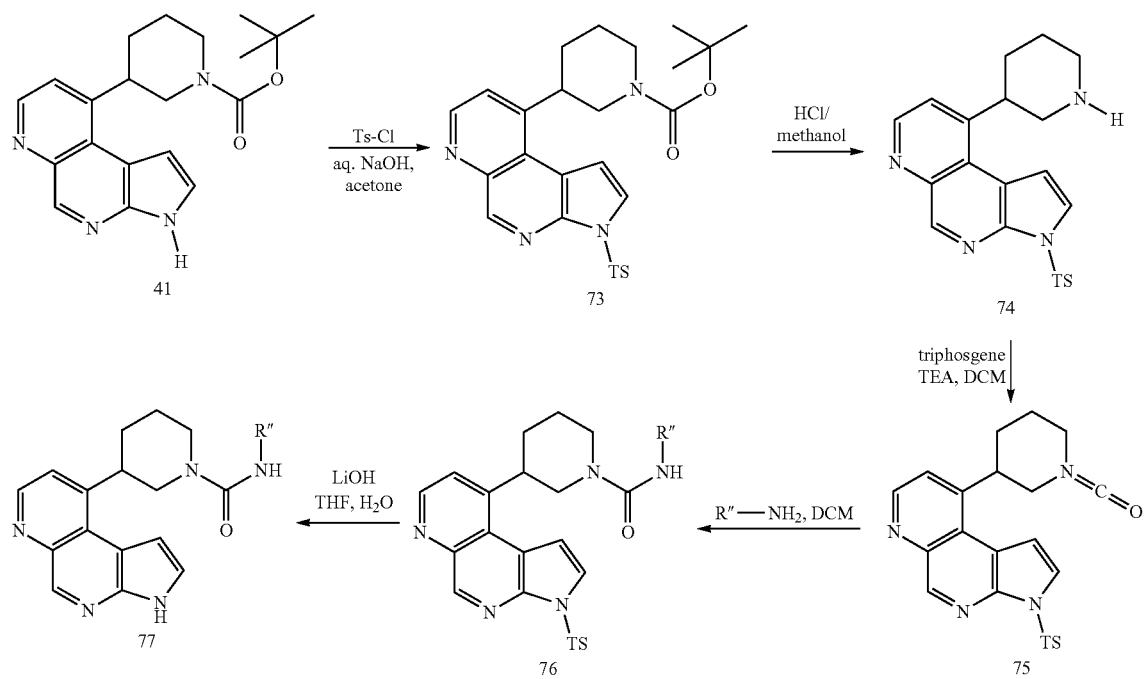

Step 1: tert-Butyl-3-[3-(p-tolylsulfonyl)pyrrolo[3,2f][1,7]naphthyridin-9-yl]piperidine-1-carboxylate (73)

The preparation of compound 73 was carried out in a manner similar to that described for the preparation of compound 17. $^1$HNMR (400 MHz, CDCl$_3$): δ 1.45 (br s, 9H), 1.71-1.98 (m, 3H), 2.15-2.21 (m, 1H), 2.35 (s, 3H), 2.71-2.95 (□□m, 2H), 3.55-3.65 (m, 1H), 4.21-4.49 (m, 2H), 7.15 (d, J=4 Hz, 1H), 7.27 (d, J=10.4 Hz 2H), 7.49 (d, J=4.4 Hz, 1H), 7.93 (d, J=3.6 Hz, 1H), 8.11 (d, J=8.4 Hz, 2H), 8.90 (d, J=4.4 Hz, 1H), 9.28 (s, 1H).

Step 2: 9-(3-piperidyl)-3-(p-tolylsulfonyl)pyrrolo[3,2-f][1,7]naphthyridine (74)

The preparation of compound 74 was carried out in a manner similar to that described for the preparation of compound 42. $^1$HNMR (400 MHz, DMSO-d$_6$): δ 1.74-2.04 (m, 3H), 2.31 (s, 3H), 2.65-2.80 (m, 2H), 2.90-3.00 (m, 1H), 3.14-3.38 (□□m, 2H), 3.83-3.89 (m, 1H), 7.41 (d, J=8.4 Hz, 2H), 7.48 (d, J=4, 1H), 7.71 (d, J=4.4 Hz, 1H), 8.03 (d, J=8 Hz, 2H), 8.15 (d, J=3.6 Hz, 2H), 8.94 (d, J=4.4 Hz, 1H), 9.13 (s, 1H).

Step 3: [3-(3-Benzenesulfonyl-3H-3,4,6,8 tetraazacyclopenta[a]naphthalen-9-yl)-piperidin-1-ylidene]-methanone (75)

A stirred suspension of compound 74 (0.28 g, 0.689 mmol) in dichloromethane (5 mL) was treated with triethylamine (0.2 mL, 1.379 mmol) and triphosgene (0.245 g, 0.826 mmol) at 0° C. The reaction mixture was stirred for overnight. Reaction mixture was diluted with CH$_2$Cl$_2$ and washed with water and brine. Organic layer was dried over sodium sulphate and concentrated under reduced pressure crude residue of 75 was obtained (0.12 g, 40.26%) and used directly for the next step.

Step 4: Urea Coupling (76)

A stirred suspension of compound 75 (0.138 mmol) in 1,2-dichloroethane (3 mL) was treated with suitable amine (R″—NH$_2$) (0.692 mmol) at ambient temperature. The reaction mixture was stirred for overnight. Reaction mixture was triturated with diethyl ether to afford crude tosyl protected urea derivatives.

Step 5: Tosyl Deprotection (77)

To a solution of above crude urea compound (0.059 mmol) in THF (3 mL), MeOH (0.5 mL) and water (1 mL) was added LiOH (10 mg, 0.29 mmol) at 0° C. and the reaction was stirred overnight. Organic solvents were removed by concentrating under vacuum. Residue was diluted with DCM and washed with water and brine. Organic layer was dried over sodium sulphate and concentrated under reduced pressure crude residue was purified by preparative TLC to obtain deprotected urea compound.

The compounds in Table 3 were synthesized according to the above synthetic procedure

TABLE 3

| Ex. | Structure | IUPAC name | NMR data |
|---|---|---|---|
| 46 | 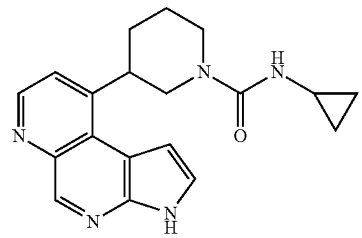 [SMILES: O=C(NC1CC1)N1CCCC(c2ccnc3cnc4[nH]ccc4c23)C1] | N-cyclopropyl-3-(3H-pyrrolo[3,2-f][1,7]naphthyridin-9-yl)piperidine-1-carboxamide | $^1$HNMR (400 MHz, DMSO-d6): δ 12.35 (s, 1H), 9.0 (s, 1H), 8.83 (d, J = 4.7 Hz, 1H) 7.63 (d, J = 4.7 Hz, 2H), 6.93 (s, 1H), 6.62 (s, 1H), 4.23 (d, J = 12 Hz, 1H), 4.11-4.08 (m, 1H), 3.60-3.58 (m, 1H), 3.17 (d, J = 5.2 Hz, 1H), 3.06-3.00 (m, 1H), 2.82-2.76 (m, 1H), 2.15-2.13 (m, 1H), 1.79-1.66 (m, 3H), 0.55-0.50 (m, 2H), 0.37-0.36 (m, 2H) |
| 47 | 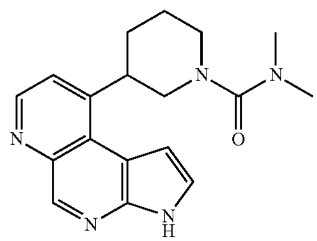 [SMILES: CN(C)C(=O)N1CCCC(c2ccnc3cnc4[nH]ccc4c23)C1] | N,N-dimethyl-3-(3H-pyrrolo[3,2-f][1,7]naphthyridin-9-yl)piperidine-1-carboxamide | $^1$HNMR (400 MHz, DMSO-d6): δ 12.36 (s, 1H), 9.0 (s, 1H), 8.83 (d, J = 4.4 Hz, 1H), 7.65 (s, 1H), 6.99 (s, 1H), 3.85 (d, J = 12.5 Hz, 1H), 3.72-3.68 (m, 2H), 3.03 (t, J = 12 Hz, 1H), 2.89-2.87 (m, 1H), 2.76 (s, 6H), 2.14 (br s, 1H), 1.81 (br s, 3H) |
| 48 | 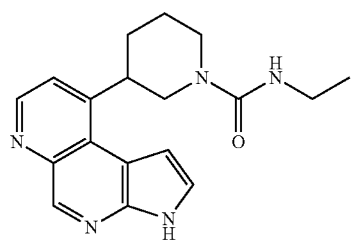 [SMILES: CCNC(=O)N1CCCC(c2ccnc3cnc4[nH]ccc4c23)C1] | N-ethyl-3-(3H-pyrrolo[3,2-f][1,7]naphthyridin-9-yl)piperidine-1-carboxamide | $^1$HNMR (400 MHz, DMSO-d6): δ 12.36 (s, 1H), 9.00 (s, 1H), 8.84 (d, J = 4.4 Hz, 1H), 7.65 (d, J = 4.8 Hz, 2H), 6.95 (s, 1H), 6.53 (t, J = 5.2 Hz, 1H), 4.28 (d, J = 12 Hz, 1H), 4.11 (d, J = 12 Hz, 1H), 3.60-3.61 (m, 1H), 3.07-3.01 (m, 3H), 2.82 (t, J = 11.2 Hz, 1H), 2.17-2.14 (m, 1H), 1.80-1.65 (m, 3H), 1.00 (t, J = 7.2 Hz, 3H) |
| 49 | 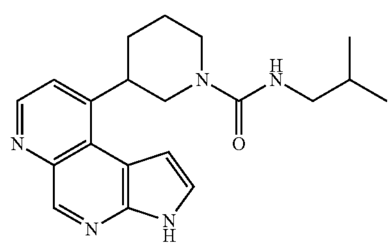 [SMILES: CC(C)CNC(=O)N1CCCC(c2ccnc3cnc4[nH]ccc4c23)C1] | N-isobutyl-3-(3H-pyrrolo[3,2-f][1,7]naphthyridin-9-yl)piperidine-1-carboxamide | $^1$HNMR (400 MHz, DMSO-d6): δ 12.32 (s, 1H), 8.97 (s, 1H), 8.81 (d, J = 4.4 Hz, 1H), 7.62 (d, J = 4.4 Hz, 1H), 7.60 (s, 1H), 6.91 (s, 1H), 6.53 (s, 1H), 4.26 (d, J = 11.6 Hz, 1H), 4.10 (d, J = 13.2 Hz, 1H), 3.61-3.60 (m, 1H), 3.14 (s, 1H), 3.04 (t, J = 11.2 Hz, 1H), 2.83-2.78 (m, 2H), 2.15-2.13 (m, 1H), 1.77-1.63 (m, 4H), 0.79 (d, J = 6.4 Hz, 6H) |
| 50 | 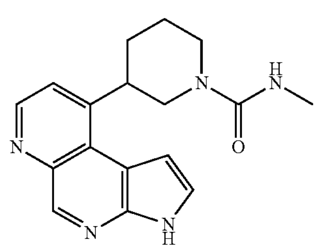 [SMILES: CNC(=O)N1CCCC(c2ccnc3cnc4[nH]ccc4c23)C1] | N-methyl-3-(3H-pyrrolo[3,2-f][1,7]naphthyridin-9-yl)piperidine-1-carboxamide | $^1$HNMR (400 MHz, DMSO-d6): δ 12.35 (s, 1H), 9.00 (s, 1H), 8.82 (d, J = 4.4 Hz, 1H), 7.64 (d, J = 4 Hz, 2H), 6.95 (s, 1H), 6.49 (d, J = 4.0 Hz, 1H), 4.27 (d, J = 12.8 Hz, 1H), 4.06 (d, J = 12.8 Hz, 1H), 3.61-3.60 (m, 1H), 3.03 (t, J = 11.2 Hz, 1H), 2.83 (t, J = 11.2 Hz, 1H), 2.58 (d, J = 4.0 Hz, 3H), 2.16-2.14 (m, 1H), 1.80-1.65 (m, 3H) |

Example 51

2,2,2-trifluoroethyl 3-(3H-pyrrolo[3,2-f][1,7]naph-thyridin-9-yl)piperidine-1-carboxylate (79)

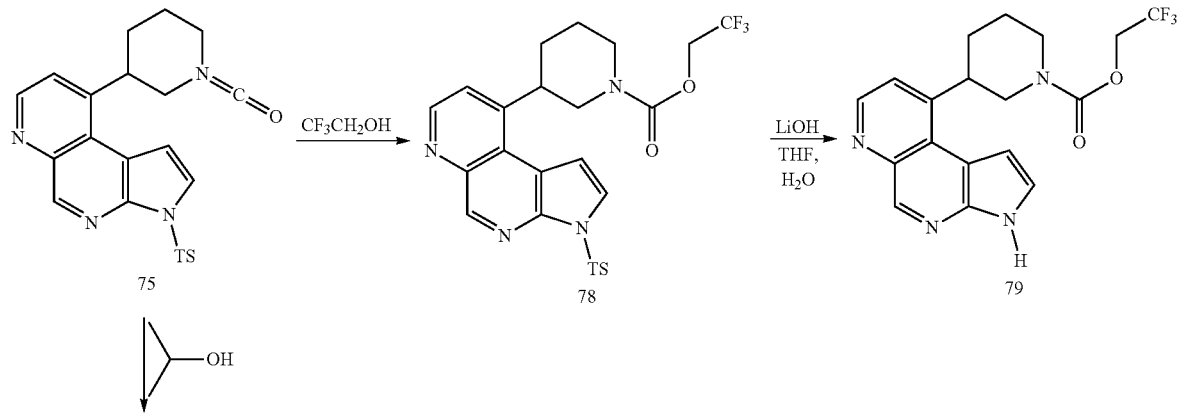

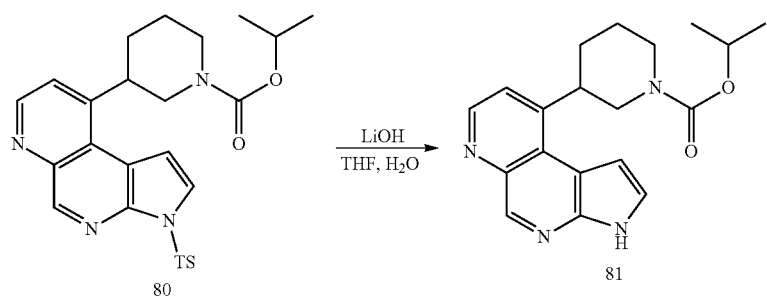

Step 1: 2,2,2-trifluoroethyl 3-[3-(p-tolylsulfonyl)pyrrolo[3,2-f][1,7]naphthyridin-9-yl]piperidine-1-carboxylate (78)

A stirred suspension of compound 75 (30 mg, 0.069 mmol) in trifluoroethanol (4 mL) was heated at 50° C. for overnight. The reaction mixture was triturated with diethyl ether to afford crude 2,2,2-trifluoroethyl-3-[3-(p-tolylsulfonyl)pyrrolo[3,2-f][1,7]naphthyridin-9-yl]piperidine-1-carboxylate (14 mg, 38.88%) as an off-white solid.

Step 2: 2,2,2-trifluoroethyl 3-(3H-pyrrolo[3,2-f][1,7]naphthyridin-9-yl)piperidine-1-carboxylate (79)

To a solution of compound 78 (14 mg, 0.026 mmol) in THF (2 mL), MeOH (0.3 mL) and water (0.5 mL) was added LiOH (10 mg, 0.26 mmol) at 0° C. and the reaction was stirred overnight. Organic solvents were removed by concentrating under vacuum. Residue was diluted with DCM and washed with water and brine. Organic layer was dried over sodium sulphate and concentrated under reduced pressure to a crude residue which was purified by preparative TLC to obtain 2,2,2-trifluoroethyl-3-(3H-pyrrolo[3,2-f][1,7]naphthyridin-9-yl)piperidine-1-carboxylate (5 mg, 50.50%) as white solid. NMR (400 MHz, DMSO-$d_6$): δ 1.78-1.76 (m, 1H), 1.90-1.86 (m, 2H), 2.17-2.15 (m, 1H), 3.31-3.20 (m, 2H), 3.71-3.70 (m, 1H), 4.16-4.14 (m, 1H), 4.32-4.30 (m, 1H), 4.77-4.73 (m, 2H), 6.95 (s, 1H), 7.63 (s, 1H), 7.67 (d, J=4.4 Hz, 1H), 8.85 (d, J=4.8 Hz, 1H), 9.01 (s, 1H), 12.38 (br s, 1H)

Example 52

Isopropyl 3-(3H-pyrrolo[3,2-f][1,7]naphthyridin-9-yl)piperidine-1-carboxylate (81)

Step 1: Isopropyl 3-[3-(p-tolylsulfonyl)pyrrolo[3,2-f][1,7]naphthyridin-9-yl]piperidine-1-carboxylate (80)

The preparation of compound 80 is carried out in a manner similar to that described for the preparation of compound 78.

Step 2: Isopropyl 3-(3H-pyrrolo[3,2-f][1,7]naphthyridin-9-yl)piperidine-1-carboxylate (81)

The preparation of compound 81 is carried out in a manner similar to that described for the preparation of compound 79. $^1$HNMR (400 MHz, DMSO-$d_6$): δ 12.39 (s, 1H), 9.01 (s, 1H), 8.85 (d, J=4.4 Hz, 1H), 7.66 (t, J=4.8 Hz, 2H), 6.98 (s, 1H), 4.83-4.80 (m, 1H), 4.34 (d, J=12.8 Hz, 1H), 4.15-4.13 (m, 1H), 3.68-3.63 (m, 1H), 3.09-3.03 (m, 2H), 2.92-2.90 (m, 1H), 2.12-2.08 (m, 1H), 1.86-1.84 (m, 1H), 1.72-1.68 (m, 1H), 1.23-1.19 (m, 6H)

Example 53

3,3,3-trifluoro-1-[4-(3H-pyrrolo[3,2-f][1,7]naphthyridin-9-yl)-1-piperidyl]propan-1-one (88)

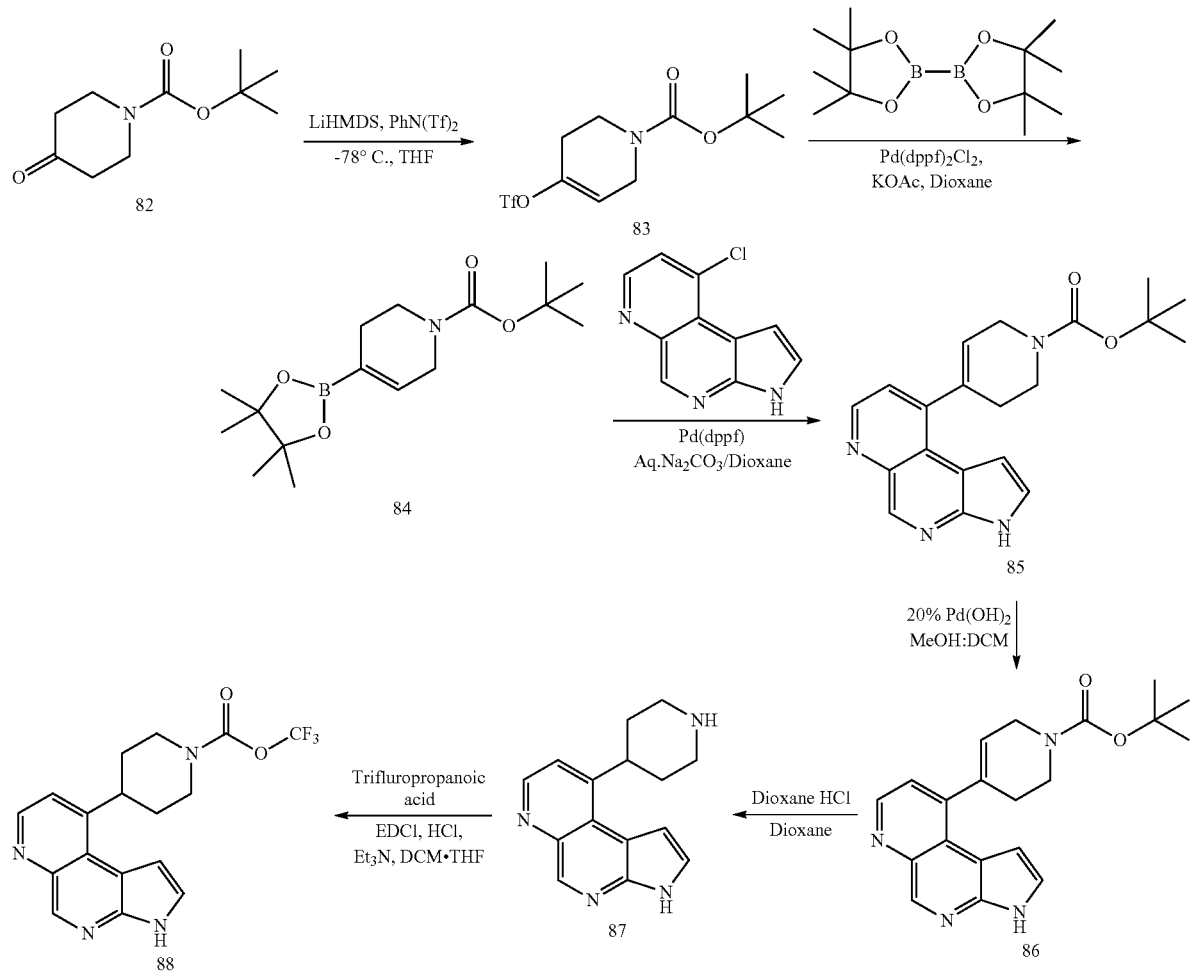

Step 1: tert-butyl 4-(trifluoromethylsulfonyloxy)-3,6-dihydro-2H-pyridine-1-carboxylate (83)

The compound 83 was prepared according to the procedure described in patent application WO 2010/056941.

Step 2: tert-butyl 4-(4,4,5,5-tetramethyl-1,3,2-dioxaborolan-2-yl)-3,6-dihydro-2H-pyridine-1-carboxylate (84)

The compound 84 was prepared according to the procedure described in patent application WO 2010/056941.

$^1$H NMR (400 MHz, CDCl$_3$): δ 1.25 (s, 12H), 1.45 (s, 9H), 2.20-2.22 (m, 2H), 3.41-3.43 (m, 2H), 3.93-3.94 (m, 2H), 6.45 (br s, 1H)

Step 3: tert-butyl 4-(3H-pyrrolo[3,2-f][1,7]naphthyridin-9-yl)-3,6-dihydro-2H-pyridine-1-carboxylate (85)

The synthesis was carried out in a similar manner to that described for the preparation of compound 40 to get the desired compound 85. $^1$HNMR (400 MHz, CD$_3$OD): □$_1$□□s, 9H), 2.40 (br s, 1H), 2.67 (br s, 1H), 3.83-3.85 (m, 2H), 4.20-4.21 (m, 2H), 5.93 (br s, 1H), 6.90 (d, J=3.6 Hz, 1H), 7.47-7.53 (m, 2H), 8.81 (d, J=4.4 Hz, 1H), 9.0 (s, 1H).

Step 4: tert-butyl 4-(3H-pyrrolo[3,2-f][1,7]naphthyridin-9-yl)piperidine-1-carboxylate (86)

The synthesis was carried out in a similar manner to that described for the preparation of compound 41 to get the desired compound 86.

Step 5: 9-(4-piperidyl)-3H-pyrrolo[3,2-f][1,7]naphthyridine (87)

To a solution of 86 (220 mg, 0.62 mmol) in dioxane (0.5 mL) was added dioxane-HCl (4 M, 2 mL) at 0° C. under nitrogen atmosphere. It was stirred at room temperature for 4 h. Reaction mixture was concentrated to get yellow solid and the solid was washed with diethyl ether and dried to obtain as hydrochloride salt of 9-(4-piperidyl)-3H-pyrrolo[3,2-f][1,7]naphthyridine (130 mg).

Step 6: 3,3,3-trifluoro-1-[4-(3H-pyrrolo[3,2-f][1,7]naphthyridin-9-yl)-1-piperidyl]propan-1-one (88)

The compound 88 were synthesized according to the general method A2.
$^1$H NMR (400 MHz, DMSO-d$_6$): δ 9.0 (s, 1H), 8.80 (d, J=4.8 Hz, 1H), 7.66 (d, J=4 Hz, 1H), 7.61 (d, J=4 Hz, 1H), 7.14 (d, J=3.6 Hz, 1H), 4.89-4.82 (m, 1H), 4.20-4.16 (m, 1H), 4.06-4.0 (m, 1H), 4.63-3.52 (m, 3H), 3.09-3.02 (m, 1H), 2.28-2.18 (m, 2H), 1.74-1.19 (m, 2H).

Preparation 19: Method of Coupling (Method D)

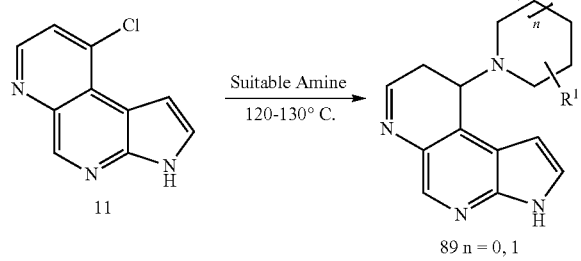

89 n = 0, 1

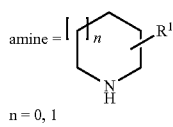

n = 0, 1

A mixture of compound 11 (1.0 mmol) and suitable amine (5.0 mmol) was heated neat at 120-130° C. for 12 h. Reaction mixture was purified by silica gel (100-200) column chromatography to afford the pure product.

The suitable amine compounds are prepared according to the following procedures:

Preparation 20: Amine Series 1 (92)

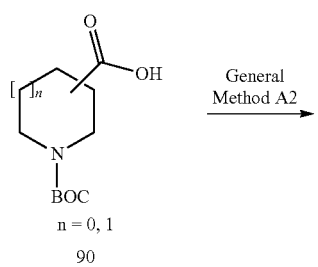

90 n = 0, 1

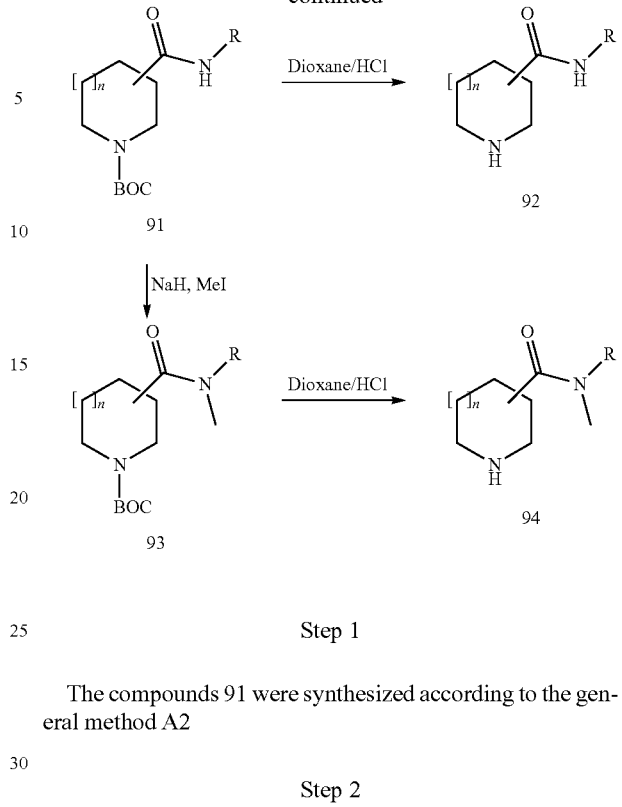

Step 1

The compounds 91 were synthesized according to the general method A2

Step 2

Boc deprotection was carried out in a similar manner to that described for the preparation of compound 87 to get the desired compound 92.

Preparation 21: Amine Series 2 (94)

Step 1

The compounds 91 were synthesized according to the general method A2

Step 2

Under nitrogen atmosphere, compound 91 (2.4 mmol) was taken in dry THF (5 mL) and cooled in ice-water bath. To this was added NaH (3 mmol). The resultant reaction mixture was stirred at room temperature for 1 h. The reaction mixture was cooled in ice-water and methyl iodide (3.6 moles) was added slowly and stirred at room temperature for overnight. The reaction mixture was quenched with water and extracted with ethyl acetate (3×20 mL). The organic layer was concentrated under vacuum and purified on silica gel column to get pure desired compound 93.

Step 3

Boc deprotection was carried out in a similar manner to that described for the preparation of compound 87 to get the desired compound 94.

The side chains in Table 4 were synthesized according to the above scheme.

TABLE 4

| No. | Structure | Name | NMR data |
|---|---|---|---|
| S1 | 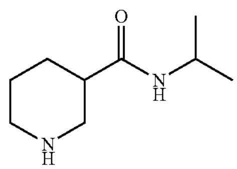 | N-isopropylpiperidine-3-carboxamide | ¹HNMR (400 MHz, CDCl₃): δ 1.11-1.17 (m, 6H), 1.52-1.50 (m, 1H), 1.68-1.86 (m, 3H), 2.31-2.32 (m, 2H), 2.81-3.0 (m, 4H), 7.09 (br, 1H) |
| S2 | 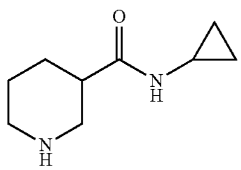 [SMILES: O=C(NC1CC1)C1CCCNC1] | N-cyclopropylpiperidine-3-carboxamide | ¹HNMR (400 MHz, CDCl₃): δ 0.47-0.49 (m, 2H), 0.74-0.78 (m, 2H), 1.46-1.51 (m, 1H), 1.62-1.79 (m, 3H), 1.86-1.89 (m, 1H), 2.32-2.34 (m, 1H), 2.71-2.78 (m, 2H), 2.86-2.92 (m, 2H), 2.99-3.03 (m, 1H), 7.56 (br s, 1H) |
| S3 | 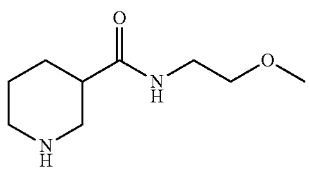 | N-(2-methoxyethyl)piperidine-3-carboxamide | ¹HNMR (400 MHz, CDCl₃): δ 1.46-1.53 (m, 1H), 1.67-1.92 (m, 5H), 2.34-2.39 (m, 1H), 2.81-2.85 (m, 2H), 2.98-3.01 (m, 2H), 3.37 (s, 3H), 3.42-3.50 (m, 3H), 7.42 (bs, 1H) |
| S4 | 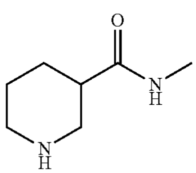 | N-methylpiperidine-3-carboxamide | ¹HNMR (400 MHz, CDCl₃): δ 1.47-1.50 (m, 1H), 1.64-1.75 (m, 2H), 1.86-1.88 (m, 1H), 2.04-2.09 (m, 2H), 2.36-2.40 (m, 1H), 2.76-2.79 (m, 1H), 2.82 (d, J = 4.8 Hz, 3H), 2.86-3.05 (m, 3H) |
| S5 | 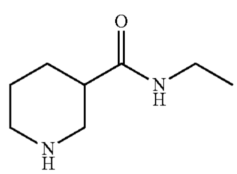 | N-ethylpiperidine-3-carboxamide | ¹HNMR (400 MHz, CDCl₃): δ 1.14 (t, J = 6.8 Hz, 3H), 1.45-1.52 (m, 1H), 1.64-1.79 (m, 2H), 1.84-1.93 (m, 3H), 2.32-2.37 (m, 1H), 2.75-2.89 (m, 2H), 2.92-2.96 (m, 1H), 3.01-3.04 (m, 1H), 3.24-3.35 (m, 2H) |
| S6 | 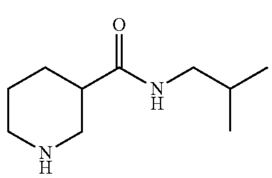 | N-isobutylpiperidine-3-carboxamide | ¹HNMR (400 MHz, CDCl₃): δ 0.92 (d, J = 6.8 Hz, 6H), 1.45-1.52 (m, 1H), 1.63-1.92 (m, 5H), 2.35-2.39 (m, 1H), 2.72-2.78 (m, 1H), 2.88-2.94 (m, 2H), 3.03-3.16 (m, 3H), 7.67 (br s, 1H) |
| S7 | 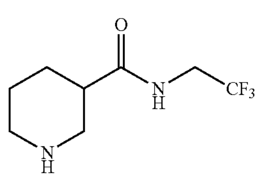 [SMILES: O=C(NCC(F)(F)F)C1CCCNC1] | N-(2,2,2-trifluoroethyl)piperidiNe-3-carboxamide | ¹HNMR (400 MHz, DMSO-d₆): δ 1.28-1.31 (m, 1H), 1.49-1.53 (m, 2H), 1.71-1.73 (m, 1H), 2.23-2.53 (m, 4H), 2.75-2.86 (m, 2H), 3.79-3.88 (m, 2H), 8.48 (br s, 1H) |
| S8 | 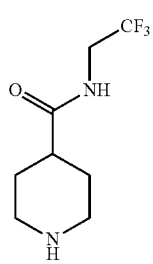 [SMILES: O=C(NCC(F)(F)F)C1CCNCC1] | N-(2,2,2-trifluoroethyl)piperidiNe-4-carboxamide | ¹HNMR (400 MHz, DMSO-d₆): δ 1.36-1.46 (m, 2H), 1.54-1.57 (m, 2H), 2.07-2.10 (m, 1H), 2.21-2.29 (m, 1H), 2.38-2.45 (m, 2H), 2.89-2.93 (m, 2H), 3.81-3.90 (m, 2H), 8.39 (t, J = 6.4 Hz, 1H) |

TABLE 4-continued

| No. | Name | NMR data |
|---|---|---|
| S9 | N-isopropylpiperidiNe-4-carboxamide | $^1$HNMR (400 MHz, DMSO-$d_6$): δ 1.01 (d, J = 6.8 Hz, 6H), 1.38-1.52 (m, 4H), 2.06-2.12 (m, 1H), 2.38-2.43 (m, 2H), 2.89-2.90 (m, 2H), 3.22 (bs, 1H), 3.74-3.82 (m, 1H), 7.52 (br s, 1H) |
| S10 | N-cyclopropylpiperidiNe-4-carboxamide | $^1$HNMR (400 MHz, DMSO-$d_6$): δ 0.32-0.36 (m, 2H), 0.54-0.59 (m, 2H), 1.33-1.51 (m, 4H), 2.02-2.09 (m, 1H), 2.34-2.41 (m, 2H), 2.56-2.60 (m, 1H), 2.88-2.91 (m, 2H), 3.32 (br, 1H), 7.73 (br s, 1H) |
| S11 | N-(2-methoxyethyl)piperidiNe-4-carboxamide | $^1$HNMR (400 MHz, DMSO-$d_6$): δ 1.39-1.54 (m, 4H), 2.16-2.18 (m, 1H), 2.42-2.44 (m, 2H), 2.90-2.92 (m, 1H), 3.16-3.17 (m, 2H), 3.22 (m, 3H), 3.22-3.35 (m, 4H), 7.78 (br s, 1H) |
| S12 | N-cyclopropylpyrrolidiNe-3-carboxamide | $^1$HNMR (400 MHz, DMSO-$d_6$): δ 0.35-0.38 (m, 2H), 0.56-0.60 (m, 2H), 1.70-1.83 (m, 2H), 2.57-2.65 (m, 2H), 2.72-2.85 (m, 3H), 2.89-2.94 (m, 1H), 3.83 (bs, 1H), 7.95 (s, 1H) |
| S13 | N-isopropylpyrrolidiNe-3-carboxamide | $^1$HNMR (400 MHz, DMSO-$d_6$): δ 1.0 (d, J = 6.8 Hz, 6H), 1.64-1.74 (m, 2H), 2.52-2.76 (m, 4H), 2.84 (dd, J = 10.8, 8 Hz, 1H), 3.73-3.82 (m, 1H), 7.65 (bs, 1H) |
| S14 | N-methyl-N-(2,2,2-trifluoroethyl)piperidiNe-4-carboxamide | $^1$HNMR (400 MHz, CDCl$_3$): δ 1.71-1.74 (m, 4H), 2.35-2.77 (m, 6H), 3.18 (s, 3H), 4.04 (q, J = 9.2 Hz, 2H) |

TABLE 4-continued
| No. | Structure | Name | NMR data |
|---|---|---|---|
| S15 | 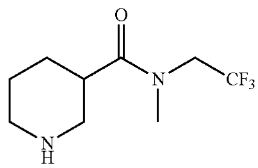 | N-methyl-N-(2,2,2-trifluoroethyl)piperidiNe-3-carboxamide | |
| S16 | 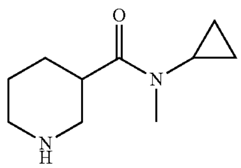 | N-cyclopropyl-N-methyl-piperidiNe-3-carboxamide | |
Preparation 22: Amine Series 3 (97)
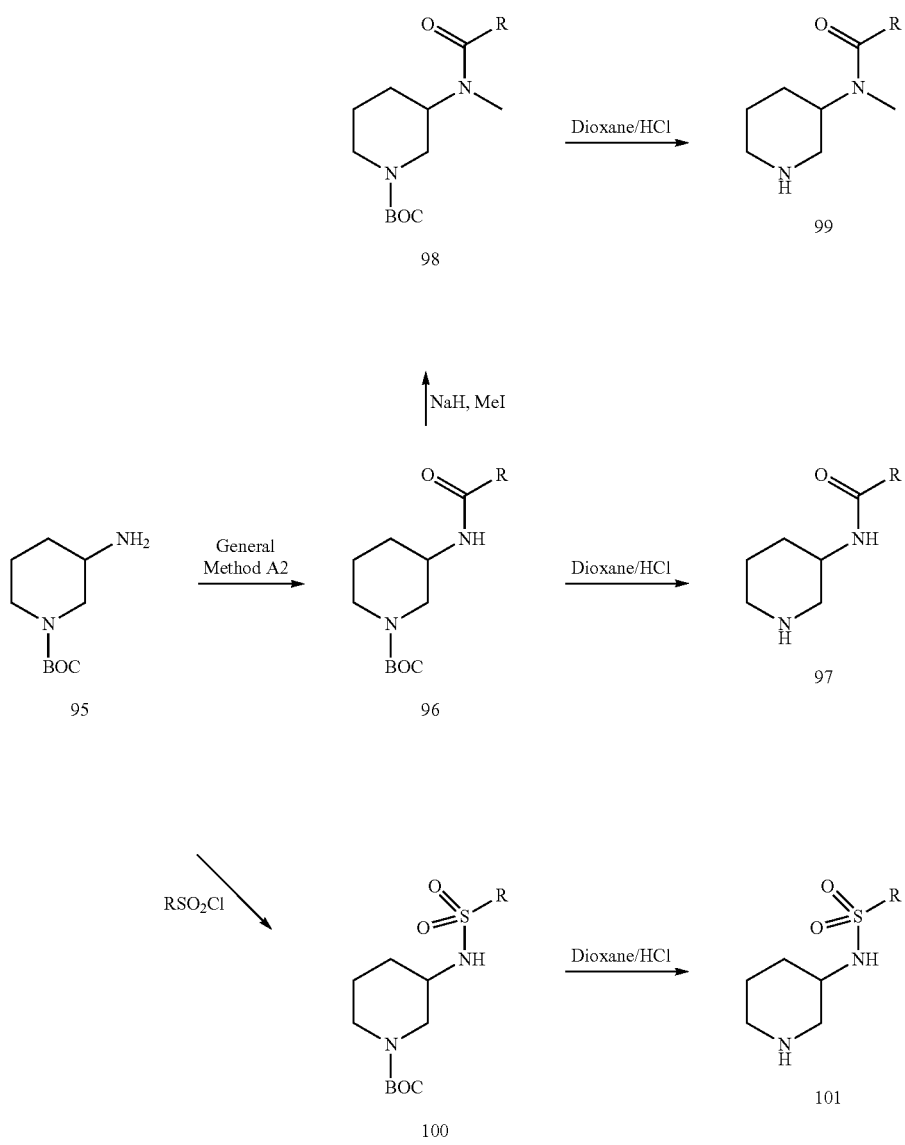

115

Step 1

The compounds 96 were synthesized according to the general method A2

Step 2

Boc deprotection was carried out in a similar manner to that described for the preparation of compound 87 to get the desired compound 97.

Preparation 23: Amine Series 4 (99)

Step 1

The compounds 96 were synthesized according to the general method A2

Step 2

Methylation was carried out in a similar manner to that described for preparation of 93 to get the desired compound 98.

116

Step 3

Boc deprotection was carried out in a similar manner to that described for the preparation of compound 87 to get the desired compound 99.

Preparation 24: Amine Series 5 (101)

Step 1

The compounds 100 were synthesized according to the general method B

Step 2

Boc deprotection was carried out in a similar manner to that described for the preparation of compound 87 to get the desired compound 101.

The side chains in Table 5 were synthesized according to the above scheme.

TABLE 5

| Entry | Structure | Name | NMR data |
|---|---|---|---|
| S17 | 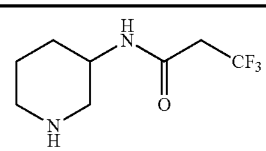 | 3,3,3-trifluoro-N-(3-piperidyl)propanamide | $^1$HNMR (400 MHz, CDCl$_3$): δ 1.65-1.68 (m, 2H), 1.86 (br s, 2H), 2.69-2.76 (m, 2H), 2.82-2.86 (m, 1H), 2.93-2.97 (m, 1H), 3.07 (q, J = 10.8 Hz, 2H), 4.01-4.03 (m, 1H), 5.72 (br s, 1H), 6.57 (br s, 1H) |
| S18 | 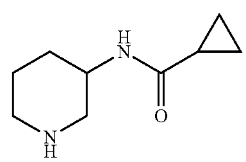 [SMILES: O=C(NC1CCCNC1)C1CC1] | N-(3-piperidyl)cyclopropane-carboxamide | $^1$HNMR (400 MHz, MeOH-d$_4$): δ 0.75-0.86 (m, 4 H), 1.56-1.66 (m, 2H), 1.73-1.84 (m, 1H), 1.98-2.05 (m, 2H), 2.78-2.84 (m, 1H), 2.91-2.98 (m, 1H), 3.25-3.27 (m, 1H), 3.34-3.39 (m, 1H), 3.95-4.03 (m, 1H) |
| S19 | 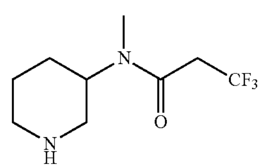 | 3,3,3-trifluoro-N-methyl-N-(3-piperidyl)propanamide | $^1$HNMR (400 MHz, DMSO-d$_6$): δ 1.35-1.72 (m, 2H), 2.27-2.33 (m, 1H), 2.67-2.73 (m, 2H), 2.81 (s, 3H), 3.46-3.72 (m, 6H), 4.63-4.64 (m, 1H) |
| S20 | 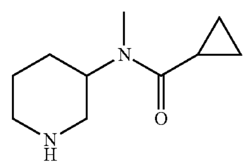 | N-methyl-N-(3-piperidyl)cyclopropane-carboxamide | $^1$HNMR (400 MHz, CDCl$_3$): δ 0.75-0.77 (m, 2H), 0.98-0.99 (m, 2H), 1.58-1.97 (m, 7H), 2.49 (q, J = 12.4 Hz, 1H), 2.59-2.79 (m, 1H), 2.85 (s, 1H), 2.95-3.11 (m, 3H), 4.04-4.44 (m, 1H) |
| S21 | 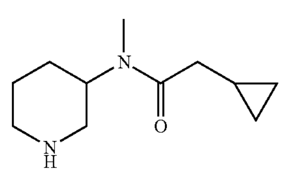 | 2-cyclopropyl-N-methyl-N-(3-piperidyl)acetamide | $^1$HNMR (400 MHz, DMSO-d$_6$): δ 0.07-0.11 (m, 2H), 0.41-0.45 (m, 2H), 0.94-0.95 (m, 1H), 1.43-1.67 (m, 3H), 2.21-2.26 (m, 3H), 2.54-2.61 (m, 1H), 2.68 (s, 2H), 2.77 (s, 3H), 2.80-2.82 (m, 1H), 3.46-3.50 (m, 1H), 3.65-3.72 (m, 1H) |
| S22 | 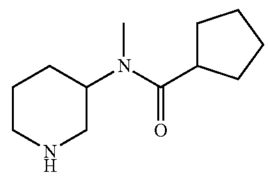 | N-methyl-N-(3-piperidyl)cyclopentane-carboxamide | $^1$HNMR (400 MHz, DMSO-d$_6$): δ 1.53-1.74 (m, 12H), 2.30-2.32 (m, 1H), 2.58-2.70 (m, 2H), 2.84 (s, 3H), 2.92-2.94 (m, 1H), 3.46-3.71 (m, 2H), 4.24-4.26 (m, 1H) |

TABLE 5-continued

| Entry | Structure | Name | NMR data |
|---|---|---|---|
| S23 | 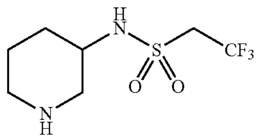 [SMILES: O=S(=O)(CC(F)(F)F)NC1CCCNC1] | 2,2,2-trifluoro-N-(3-piperidyl)ethanesulfonamide | $^1$HNMR (400 MHz, DMSO-$d_6$): δ 1.30-1.33 (m, 2H), 1.82-1.87 (m, 2H), 2.28-2.33 (m, 2H), 2.69-2.96 (m, 4H), 3.18-3.19 (m, 1H), 4.38 (q, J = 9.6 Hz, 2H) |
| S24 | 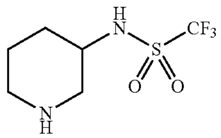 [SMILES: O=S(=O)(NC1CCCNC1)C(F)(F)F] | 1,1,1-trifluoro-N-(3-piperidyl)methanesulfonamide | $^1$HNMR (400 MHz, CDCl$_3$): δ 1.37-1.39 (m, 1H), 1.51-1.49(m, 1H), 1.64-1.66 (m, 1H), 1.86-1.88 (m, 1H), 2.56-2.61 (m, 2H), 2.83-3.0 (m, 3H), 3.37-3.34 (m, 2H) |
| S25 | 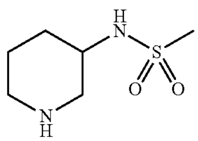 | N-(3-piperidyl)methanesulfonamide | $^1$HNMR (400 MHz, CD$_3$OD): δ 1.36-1.58 (m, 2H), 1.69-1.76 (m, 1H), 2.0-2.04 (m, 1H), 2.39-2.50 (m, 2H), 2.83-2.88 (m, 1H), 2.94 (s, 3H), 3.10-3.14 (m, 1H), 3.23-3.28 (m, 1H) |
| S26 | 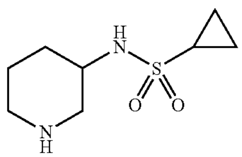 [SMILES: O=S(=O)(NC1CCCNC1)C1CC1] | N-(3-piperidyl)cyclopropanesulfonamide | |

Preparation 25: Amine Series 6 (104)

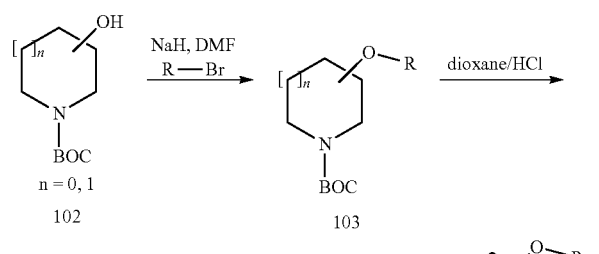

Step 1

NaH (5.96 mmol) was added slowly to the solution of alcohol 102 (2.48 mmol) in dry DMF at 0° C. The reaction mixture was stirred for 1 h at room temperature and alkyl bromide (3.1 mmol) was added at 0° C. and allowed to stir at room temperature for 12 h. The reaction mixture was poured into ice-water and extracted with ethyl acetate (3×25 mL). The combined organic solvent was washed with brine and dried over sodium sulphate, concentrated to a crude oil. The crude material was purified by column chromatography get pure desired compound 103.

Step 2

Boc deprotection of compound 103 was carried out in a similar manner to that described for the preparation of compound 87 to get the desired compound 104.

The side chains in Table 6 were synthesized according to the above scheme.

TABLE 6

| Entry | Structure | Name | NMR data |
|---|---|---|---|
| S27 | 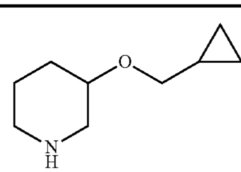 | 3-(cyclopropylmethoxy)piperidine | $^1$HNMR (400 MHz, CDCl$_3$): δ 0.17-0.21 (m, 2H), 0.51-0.55 (m, 2H), 1.01-1.08 (m, 1H), 1.37-1.52 (m, 2H), 1.69-1.77 (m, 3H), 1.92-1.98 (m, 1H), 2.56-2.64 (m, 2H), 2.81-2.86 (m, 1H), 3.07-3.11 (m, 1H), 3.26-3.31 (m, 2H) |
| S28 | 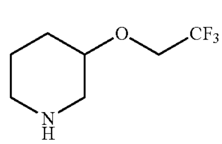 [SMILES: FC(F)(F)COC1CCCNC1] | 3-(2,2,2-trifluoroethoxy)piperidine | |

TABLE 6-continued

| Entry | Structure | Name | NMR data |
|---|---|---|---|
| S29 | 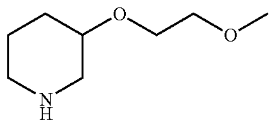 | 3-(2-methoxyethoxy)piperidine | ¹HNMR (400 MHz, CDCl₃): δ 1.67-1.74 (m, 2H), 1.88-1.99 (m, 2H), 2.94-2.99 (m, 2H), 3.04-3.09 (m, 1H), 3.20-3.24 (m, 1H), 3.39 (s, 3H), 3.54-3.56 (m, 2H), 3.62-3.70 (m, 3H), 4.76 (br s, 1H) |
| S30 | 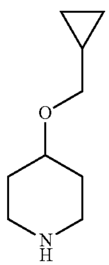 [SMILES: C1CC(OCC2CC2)CCN1] | 4-(cyclopropylmethoxy)piperidine | ¹HNMR (400 MHz, CDCl₃): δ 0.19-0.20 (m, 2H), 0.53-0.54 (m, 2H), 1.02-1.08 (m, 1H), 1.37-1.46 (m, 2H), 1.92-1.94 (m, 2H), 2.57-2.63 (m, 2H), 3.07-3.11 (m, 2H), 3.29 (d, J = 6.8 Hz, 2H), 3.37-3.39 (m, 1H), 3.64-3.76 (m, 1H) |
| S31 | 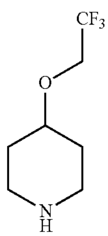 [SMILES: FC(F)(F)COC1CCNCC1] | 4-(2,2,2-trifluoroethoxy)piperidine | |
| S32 | 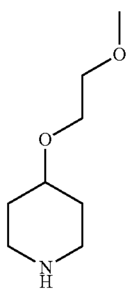 | 4-(2-methoxyethoxy)piperidine | |
| S33 | 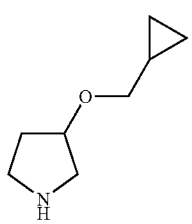 | 3-(cyclopropylmethoxy)pyrrolidine | ¹HNMR (400 MHz, CDCl₃): δ 0.16-0.21 (m, 2H), 0.51-0.55 (m, 2H), 0.98-1.08 (m, 1H), 1.78-1.94 (m, 2H), 2.76-2.94 (m, 3H), 2.98-3.15 (m, 2H), 3.17-3.30 (m, 2H), 4.02(br s, 1H) |

Preparation 26: Amine S34:
4-(3-piperidyl)morpholine (106)

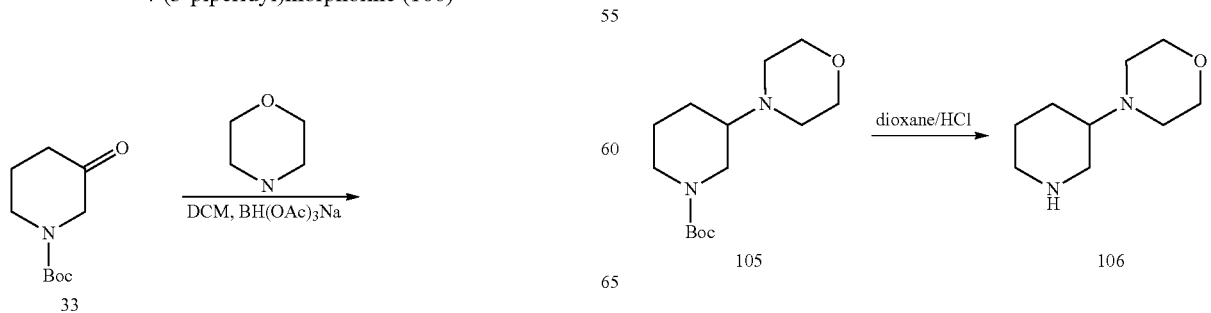

Step 1: tert-butyl 3-morpholinopiperidine-1-carboxylate (105)

A mixture compound 33 (1 gm, 5 mmol) and morpholine (0.65 ml, 7.5 mmol) in 1,2-dichloroethane was stirred for 5 min followed by addition of glacial acetic acid (0.28 mL) followed by sodium triacetoxyborohydride (3.18 gm, 15 mmol). The reaction mixture was stirred 16 h at room temperature and quenched with 1 N sodium hydroxide and stirred for 10 min. The reaction mixture was extracted with ethyl acetate, concentrated, purified on silica gel column to afford the pure product (0.9 gm).

Step 2

Boc deprotection of compound 105 was carried out in a similar manner to that described for the preparation of compound 87 to get the desired compound 106. $^1$H NMR (400 MHz, CDCl$_3$): δ 1.29-1.47 (m, 2H), 1.74-1.99 (m, 3H), 2.20-2.25 (m, 1H), 2.47-2.58 (m, 6H), 2.92-2.97 (m, 1H), 3.18-3.21 (m, 1H), 3.67-3.72 (m, 4H)

Preparation 27: Amine S35: N-(cyclopropylmethyl)-N-methyl-pyrrolidin-3-amine (109)

Step 1: tert-butyl 3-(methylamino)pyrrolidine-1-carboxylate (107)

A mixture compound 37 (1 gm, 5.4 mmol) and methyl amine (4 mL, 2.0 M in tetrahydrofuran) in 1,2-dichloroethane was stirred for 5 min followed by addition of glacial acetic acid (0.28 mL) followed by sodium triacetoxyborohydride (3.18 gm, 15 mmol). The reaction mixture was stirred 16 h at room temperature and quenched with 1 N sodium hydroxide and stirred for 10 min. The reaction mixture was extracted with ethyl acetate, concentrated, purified on silica gel column to afford the pure product (0.9 gm).

Step 2: tert-butyl 3-[cyclopropylmethyl(methyl)amino]pyrrolidine-1-carboxylate (108)

NaH (238 mg, 5.96 mmol) was added slowly to the solution of compound 107 (496 mg, 2.48 mmol) in dry DMF at 0° C. The reaction mixture was stirred for 1 h at room temperature and bromomethylcyclopropane (418.5 mg, 3.1 mmol) was added at 0° C. and allowed to stir at room temperature for 12 h. The reaction mixture was poured into ice-water and extracted with ethyl acetate (3×25 mL). The combined organic solvent was washed with brine and dried over sodium sulphate, concentrated to a crude oil. The crude material was purified by column chromatography get pure desired compound 108.

Step 3

Boc deprotection of compound 108 is carried out in a similar manner to that described for the preparation of compound 87 to get the desired compound 109. $^1$HNMR (400 MHz, CDCl$_3$): δ 0.07-0.12 (m, 2H), 0.52-0.54 (m, 2H), 0.86-0.84 (m, 1H), 1.66-1.71 (m, 1H), 2.23-2.32 (m, 2H), 2.34 (s, 3H), 2.72-2.82 (m, 2H), 2.94-3.0 (m, 2H), 3.05-3.17 (m, 2H)

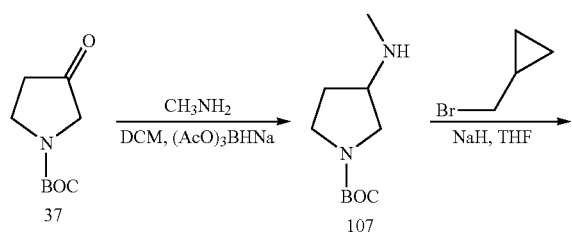

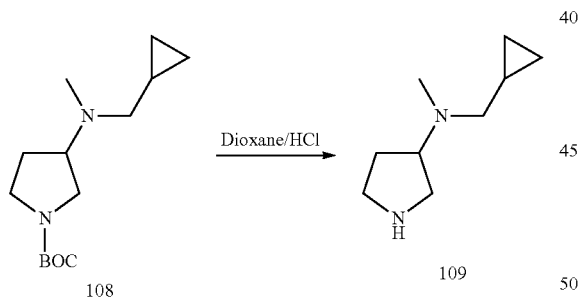

Preparation 28: Amine S36 (A): cis N-cyclopropyl-6-methyl-piperidine-3-carboxamide (118)

Amine S36 (B): trans N-cyclopropyl-6-methyl-piperidine-3-carboxamide (119)

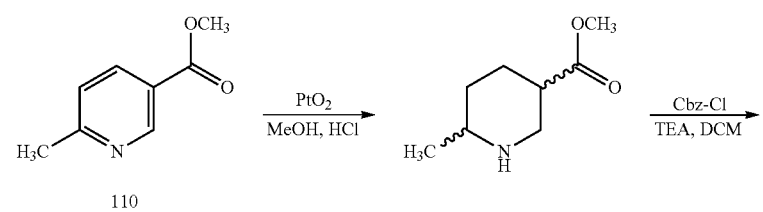

-continued

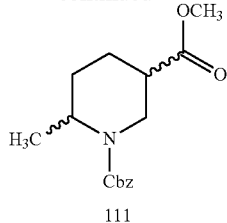

111

Mixture of cis and trans isomers

Seperation of diastereomers by column cromatography

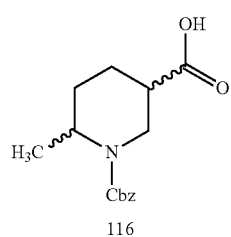
116
mixture of trans enantiomers

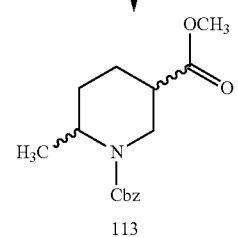
113
mixture of trans enantiomers

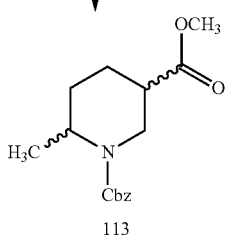
113
mixture of cis enantiomers

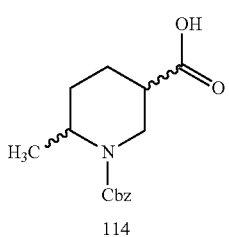
114
mixture of cis enantion

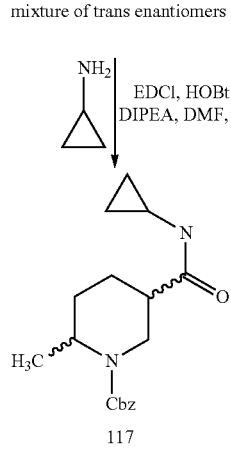
117
mixture of trans enantiomers

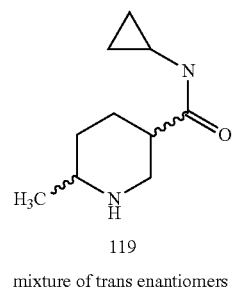
119
mixture of trans enantiomers

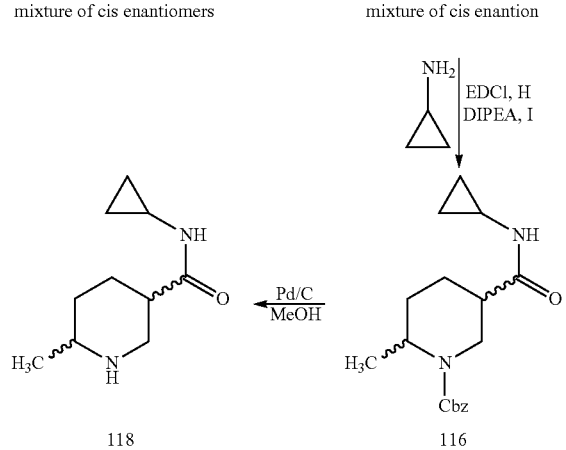
118
mixture of cis enantiomers 116
mixture of cis enantion

Step 1: benzyl 5-acetyl-2-methyl-piperidine-1-carboxylate (111)

A solution of compound 110 (2.5 g, 16.53 mmol) in $CH_3OH$ (50 mL) and conc. HCl (1.25 mL) was added to a slurry of platinum(IV) oxide (0.2 g) in 10 mL of $CH_3OH$/water (4/1) in a Parr bottle. The mixture was hydrogenated at room temperature under 60 psi of hydrogen gas for 7 h. The mixture was then filtered through celite. The filtrate was concentrated in vacuo, after chasing with 100 mL of toluene, to about 2.5 g of syrup. This residue was dissolved in $CH_2Cl_2$ (30 mL) and chilled in an ice bath. To this stirred solution was added DMAP (0.194 g, 1.59 mmol), followed by TEA (6.64 mL, 47.7 mmol) portion wise. A suspension formed when TEA was added. This mixture was chilled to 15° C. To the resulting suspension was added benzyl chloroformate (2.72 mL, 19 mmol) dropwise over a 15 min period such that the temperature of the mixture was kept at 15-20° C. After completion of benzyl chloroformate addition, the mixture was stirred chilled with an ice bath for another 30 min and then at ambient temperature for 1 h. This mixture was washed with 100 mL of cold 1N HCl. The organic was concentrated in vacuo. The residue was partitioned between toluene (100 mL), MTBE (100 mL), and water (50 mL). The organic was washed with brine, dried over MgSO4, filtered, and concentrated in vacuo to give an oil (2.5 g) as the crude (NMR showed ~3:1 cis/trans ratio of isomers). Isomer was separated by silica gel column chromatography using gradient elution of EtOAc in hexane and gave 840 mg cis isomer (112) and 450 mg trans isomer (113).

Step 2: cis benzyl 5-acetyl-2-methyl-piperidine-1-carboxylate (112)

$^1$HNMR (400 MHz, $CDCl_3$): δ 1.16 (d, J=6.8 Hz, 3H), 1.51-1.84 (m, 3H), 1.90-2.00 (m, 1H), 2.34-2.45 (m, 1H), 2.89-3.11 (m, 1H), 3.69 (s, 3H), 4.29 (br s, 1H), 4.51 (br s, 1H), 5.13 (s, 2H), 7.32-7.50 (m, 5H).

Step 3: trans benzyl 5-acetyl-2-methyl-piperidine-1-carboxylate (113)

$^1$HNMR (400 MHz, CDCl$_3$): δ 1.16 (d, J=6.8 Hz, 3H), 1.38 (d, J=12 Hz, 1H), 1.80-1.91 (m, 2H), 2.05 (d, J=13.2 Hz, 1H), 2.61 (br s, 1H), 3.13 (dd, J=13.6, 4.0 Hz, 1H), 3.61 (s, 3H), 4.44-4.52 (m, 2H), 5.08 (d, J=12.4 Hz, 1H), 5.19 (d, J=12.8 Hz, 1H), 7.25-7.40 (m, 5H).

Step 4: cis-1-benzyloxycarbonyl-6-methyl-piperidine-3-carboxylic acid (114)

To a solution of compound 112 (2 g, 6.86 mmol) in 20 mL of (THF: H$_2$O:MeOH=3:2:1) aq.LiOH (1 g, 5 ml, 24 mmol) was added at 0° C. and the reaction was stirred overnight. Organic solvents were removed by concentrating under vacuum. Residue was diluted with DCM and washed with water and brine. Organic layer was dried over sodium sulfate and concentrated under reduced pressure crude residue was afforded required compound 114 (1.7 g, 89%). $^1$HNMR (400 MHz, DMSO d$_6$): δ 1.08 (d, J=6.8 Hz, 3H), 1.51-1.70 (m, 3H), 1.75-1.85 (m, 1H), 2.22-2.35 (m, 1H), 2.80-2.95 (m, 1H), 4.00-4.15 (m, 1H), 4.28-4.40 (br s, 1H), 5.07 (s, 2H), 7.32-7.50 (m, 5H), 12.55 (br s, 1H).

Step 5: trans-1-benzyloxycarbonyl-6-methyl-piperidine-3-carboxylic acid (115)

The preparation of compound 115 was carried out in a manner similar to that described for the preparation of compound 114.

$^1$HNMR (400 MHz, DMSO d$_6$): δ 1.09 (d, J=6.8 Hz, 3H), 1.30-1.40 (m, 1H), 1.65-1.91 (m, 3H), 2.58 (br s, 1H), 3.05-3.13 (m, 1H), 4.20-4.35 (m, 2H), 5.05 (dd, J=14.8, 26.8 Hz, 2H), 7.25-7.40 (m, 5H), 12.38 (br s 1H).

Step 6: Cis-benzyl-5-(cyclopropylcarbamoyl)-2-methyl-piperidine-1-carboxylate (116)

The preparation of compound 116 was carried out in a manner similar to that described in Method: A2

$^1$HNMR (400 MHz, CDCl$_3$): δ 0.45-0.50 (m, 2H), 0.72-0.80 (m, 2H), 1.18 (d, J=6.8 Hz, 3H), 1.58-1.80 (m, 3H), 1.82-1.95 (m, 1H), 2.62-2.75 (m, 1H), 3.00-3.10 (m, 1H), 3.21-3.30 (m, 1H), 4.05-4.15 (m, 1H), 4.45-4.52 (m, 1H), 5.12 (d, J=2.0 Hz, 2H), 5.62 (br s, 1H), 7.32-7.50 (m, 5H).

Step 7: Trans-benzyl-5-(cyclopropylcarbamoyl)-2-methyl-piperidine-1-carboxylate (117)

The preparation of compound 117 was carried out in a manner similar to that described in Method: A2

$^1$HNMR (400 MHz, CDCl$_3$): δ 0.22-0.40 (m, 2H), 0.62-0.72 (m, 2H), 1.20 (m, 3H), 1.32-1.40 (m, 1H), 1.65-1.75 (m, 1H), 1.82-1.95 (m, 1H), 2.10-2.22 (m, 1H), 2.46-2.52 (m 1H), 2.66-2.75 (m, 1H), 3.12-3.20 (dd, J=15.2, 3.6, 1H), 4.16 (d, J=15.2 Hz, 1H), 4.32-4.42 (m, 1H), 5.16 (dd, J=25.6, 12.4 Hz, 2H), 6.84 (br s, 1H), 7.32-7.45 (m, 5H).

Step 8: Cis-N-cyclopropyl-6-methyl-piperidine-3-carboxamide (118)

A stirred solution of compound 116 (1.7 g, 5.37 mmol) in methanol (30 mL) was purged under vacuum/argon cycles to replace air inside the flask with argon gas by a suction adapter (fitted with a balloon).then added 10% palladium on charcoal (170 mg), the reaction mixture was purged under vacuum/H$_2$ cycles to replace air inside the flask with hydrogen gas by a suction adapter (fitted with a bladder) and continued stirring at room temperature for 4 h. The reaction mixture was filtered through a celite pad, washed with 10% methanol in DCM, and concentrated the solvent under reduced pressure to afford off white solid 0.9 g (92%). Then next step was performed without purification.

$^1$HNMR (400 MHz, DMSO d$_6$): δ 0.33-0.40 (m, 2H), 0.55-0.65 (m, 2H), 0.95 (d, J=6.4 Hz, 3H), 1.11-1.18 (m, 1H), 1.35-1.60 (m, 2H), 1.79-1.84 (m, 1H), 2.08-2.22 (m, 2H), 2.56-2.65 (m, 3H), 2.98-3.05 (m, 1H), 8.31 (br s, 1H).

Step 9: Trans-N-cyclopropyl-6-methyl-piperidine-3-carboxamide (119)

The preparation of compound 119 was carried out in a manner similar to that described for the preparation of compound 118.

$^1$HNMR (400 MHz, DMSO d$_6$): δ 0.30-0.40 (m, 2H), 0.50-0.60 (m, 2H), 0.90-1.00 (m, 4H), 1.38-1.60 (m, 2H), 1.64-1.74 (m, 1H), 1.82 (br s, 1H), 1.98-2.08 (m, 1H), 2.35-2.50 (m, 2H), 2.54-2.62 (m, 1H), 2.85-2.92 (m, 1H), 7.77 (br s, 1H).

The compounds in Table 7 were synthesized according to the above general method D

TABLE 7

| Ex | Structure | IUPAC Name | Amine Used | 1H NMR |
| --- | --- | --- | --- | --- |
| 54 | 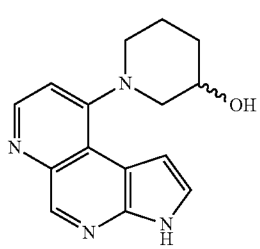 [SMILES: OC1CCCN(c2ccnc3cnc4[nH]ccc4c23)C1] | 1-(3H-pyrrolo[3,2-f][1,7]naphthyridin-9-yl)piperidin-3-ol | piperidin-3-ol | $^1$HNMR(400 MHz, DMSO-d6): δ 1.82-1.89 (m, 2H), 2.02-2.11 (m, 1H), 2.33-2.34 (m, 1H), 3.41-3.43 (m, 2H), 3.52-3.54 (m, 2H), 3.88-3.91 (m, 1H), 5.00 (d, J = 4 Hz, 1H), 7.05 (s, 1H), 7.28 (d, J= 6 Hz, 1H), 7.59 (s, 1H), 8.71 (d, J = 4.8 Hz, 1H), 8.93 (s, 1H), 12.22 (s, 1H) |

TABLE 7-continued

| Ex | Structure | IUPAC Name | Amine Used | 1H NMR |
|---|---|---|---|---|
| 55 | 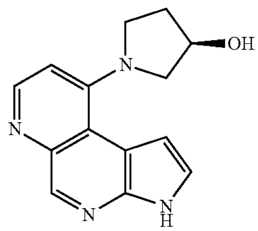 [SMILES: O[C@@H]1CCN(c2ccnc3cnc4[nH]ccc4c23)C1] | (3R)-1-(3H-pyrrolo[3,2-f][1,7]naphthyridin-9-yl)pyrrolidin-3-ol | Pyrrolidin-3-ol | $^1$HNMR (400 MHz, MeOH-d4): δ 2.06-2.09 (m, 1H), 2.31-2.39 (m, 1H), 3.37-3.41 (m, 2H), 3.72-3.76 (m, 1H), 3.79-3.85 (m, 1H), 4.60-4.68 (m, 1H), 7.02 (d, .7=3.6 Hz, 1H), 7.17 (d, J = 6 Hz, 1H), 7.59 (d, J = 3.2 Hz, 1H), 8.37 (s, 1H), 8.52 (d,J = 6 Hz, 1H), 8.87 (s, 1H) |
| 56 | 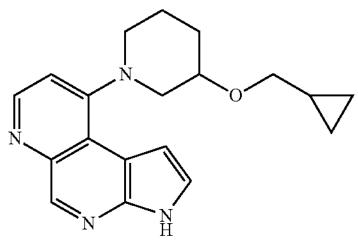 [SMILES: c1cc(N2CCCC(OCC3CC3)C2)c2c(cnc3[nH]ccc32)n1] | 9-[3-(cyclopropylmethoxy)-1-piperidyl]-3H pyrrolo[3,2f][1,7] naphthyridine | (cyclopropylmethoxy)piperidine (S27) | $^1$HNMR (400 MHz, MeOH-d4): δ 0.11-0.21 ( m, 2H), 0.48 (d, J = 7.6 Hz, 2H), 0.95-1.09 (m, 1H), 1.37-1.41 (m, 1H), 1.95-2.01 (m, 2H), 2.27-2.32 (m, 1H), 2.52-2.56 (m, 1H), 2.68-2.72 (m, 1H), 3.33-3.35 (m, 1H), 3.38-3.43 (m, 1H), 3.52-3.58 (m, 1H), 3.78-3.86 (m, 2H), 7.20 (s, 1H), 7.33 (s, 1H), 7.54 (s, 1H), 8.67 (s, 1H),8.93 (s, 1H) |
| 57 | 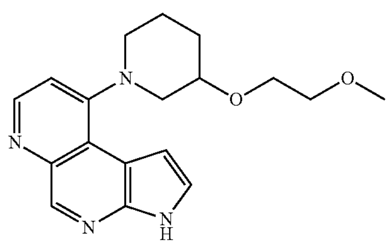 [SMILES: COCCOC1CCCN(c2ccnc3cnc4[nH]ccc4c23)C1] | 9-[3-(2-methoxyethoxy)-1-piperidyl]-3H-pyrrolo[3,2-f][1,7]naphthyridine | 3-(2-methoxyethoxy)piperidine (S29) | $^1$HNMR (400 MHz, MeOH d4): δ 1.37-1.42 (m, 1H), 1.66-1.77 (m, 1H), 1.95-1.98 (m, 1H), 2.29-2.33 (m, 1H), 2.51-2.55 (m, 1H), 2.67-2.71 (m, 1H), 3.32 (s, 3H), 3.49-3.69 (m, 6H), 3.79-3.89 (m, 1H), 7.21 (s, 1H), 7.34 (d, J = 4.4 Hz, 1H), 7.55 (s, 1H), 8.67 (d,J = 4.4 Hz, 1H), 8.93 (s, 1H) |
| 58 | 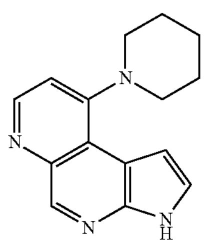 [SMILES: c1cc(N2CCCCC2)c2c(cnc3[nH]ccc32)n1] | 9-(1-piperidyl)-3H-pyrrolo[3,2-f][1,7]naphthyridine | Piperidine | $^1$HNMR(400 MHz, DMSO-d6): δ 12.20 (br s, 1H), 8.92 (s, 1H), 8.70 (d, J = 4.4 Hz, 1H), 7.58 (s, 1H), 7.26 (d, J = 4.8 Hz, 1H), 7.12 (d, J = 2.0 Hz, 1H), 3.50-3.47 (m, 2H), 2.68-2.66 (m, 2H), 1.88-1.83 (m, 4H), 1.38-1.37 (m, 2H) |
| 59 | 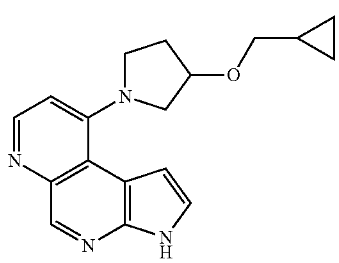 [SMILES: c1cc(N2CCC(OCC3CC3)C2)c2c(cnc3[nH]ccc32)n1] | 9-[3-(cyclopropylmethoxy)pyrrolidin-1-yl]-3H-pyrrolo[3,2-f][1,7]naphthyridine | 3-(cyclopropylmethoxy)pyrrolidine (S33) | $^1$HNMR (400 MHz, MeOH-d4): δ 0.22- 0.26 ( m, 2H), 0.51-0.56 (m, 2H), 1.05-1.11 (m, 1H), 2.08-2.16 (m, 1H), 2.34-2.43 (m, 1H), 3.19-3.25 (m, 1H), 3.33-3.36 (m, 3H), 3.53-3.61 (m, 2H), 4.32-4.35 (m, 1H), 7.11 (d, J = 3.2 Hz, 1H), 7.19 (d, J = 4.8 Hz, 1H), 7.51 (d, J = 3.6 Hz, 1H), 8.58 (d, J = 4.8 Hz, 1H), 8.89 (s, 1H) |
| 60 | 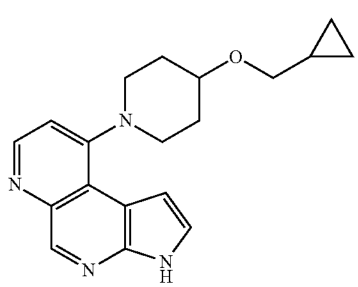 [SMILES: c1cc(N2CCC(OCC3CC3)CC2)c2c(cnc3[nH]ccc32)n1] | 9-[4-(cyclopropylmethoxy)-1-piperidyl]-3H-pyrrolo[3,2-f][1,7]naphthyridine | 4-(cyclopropylmethoxy)piperidine (S30) | $^1$HNMR(400 MHz, MeOH-d4): δ 0.22-0.26 ( m, 2H), 0.51-0.56 (m, 2H), 1.01-1.18 (m, 1H), 1.82-2.20 (m, 2H), 2.13-2.29 (m, 2H), 2.78 (t, J = 11.6 Hz, 2H), 3.12-3.22 (m, 1H), 3.33-3.43 (m, 3H), 3.51-3.69 (m, 1H), 7.24 (s, 1H), 7.31 (d, J = 4.4 Hz, 1H), 7.55 (s, 1H), 8.66 (d, J = 4.8 Hz, 1H), 8.92 (s, 1H) |

TABLE 7-continued

| Ex | Structure | IUPAC Name | Amine Used | 1H NMR |
|---|---|---|---|---|
| 61 | | N-cyclopropyl-1-(3H-pyrrolo[3,2-f][1,7]naphthyridin-9-yl)piperidine-3-carboxamide | N-cyclopropylpiperidine-3-carboxamide (S10) | $^1$HNMR (400 MHz, MeOH-d4): δ 8.93 (s, 1H), 8.69 (d, J = 4.4 Hz, 1H), 7.54 (d, J = 3.2 Hz, 1H), 7.34 (d, J = 5.2 Hz, 1H), 7.22 (br s, 1H), 3.64-3.58 (m, 2H), 2.93-2.84 (m, 2H), 2.65-2.58 (m, 2H), 2.09-1.94 (m, 3H), 1.69-1.66 (m, 1H), 0.72-0.71 (m, 2H), 0.48 (br s, 2H) |
| 61 A | 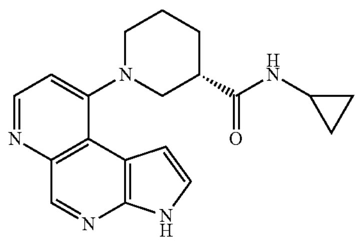 [SMILES: O=C(NC1CC1)[C@H]1CCCN(c2ccnc3cnc4[nH]ccc4c23)C1] | (3S)-N-cyclopropyl-1-(3H-pyrrolo[3,2-f][1,7]naphthyridin-9-yl)piperidine-3-carboxamide | (3S)-N-cyclopropylpiperidine-3-carboxamide (S10) | $^1$HNMR(400 MHz,MeOH-d4): δ 8.93 (s, 1H), 8.69 (d, J = 4.4 Hz, 1H), 7.54 (d, J = 3.2 Hz, 1H), 7.34 (d, J = 5.2 Hz, 1H), 7.22 (br s, 1H), 3.64-3.58 (m, 2H), 2.93-2.84 (m, 2H), 2.65-2.58 (m, 2H), 2.09-1.94 (m, 3H), 1.69-1.66 (m, 1H), 0.72-0.71 (m, 2H), 0.48 (br s, 2H) |
| 61 | | (3R)-N-cyclopropyl-1-(3H-pyrrolo[3,2-f][1,7]naphthyridin-9-yl)piperidine-3-carboxamide | (3R)-N-cyclopropylpiperidine-3-carboxamide (S10) | $^1$HNMR (400 MHz, MeOH-d4): δ 8.93 (s, 1H), 8.69 (d, J = 4.4 Hz, 1H), 7.54 (d, J = 3.2 Hz, 1H), 7.34 (d, J = 5.2 Hz, 1H), 7.22 (br s, 1H), 3.64-3.58 (m, 2H), 2.93-2.84 (m, 2H), 2.65-2.58 (m, 2H), 2.09-1.94 (m, 3H), 1.69-1.66 (m, 1H), 0.72-0.71 (m, 2H), 0.48 (br s, 2H) |
| 62 | 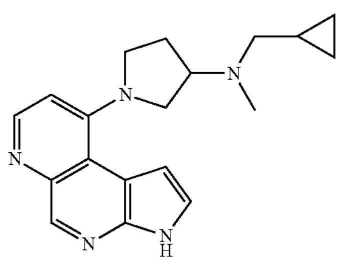 | N-(cyclopropylmethyl)-N-methyl-1-(3H-pyrrolo[3,2-f][1,7]naphthyridin-9-yl)pyrrolidin-3-amine | N-(cyclopropylmethyl)-N-methyl-pyrrolidin-3-amine (S35) | $^1$HNMR(400 MHz, MeOH-d4): δ 0.16-0.19- (m, 2H), 0.55-0.60 (m, 2H), 0.87-0.97 (m, 1H), 1.99-2.07 (m, 1H), 2.29-2.45 (m, 3H), 2.43 (s, 3H), 3.19-3.27 (m, 1H), 3.34-3.41 (m, 2H), 3.43-3.50 (m, 1 H), 3.57- 3.63 (m, 1H), 6.96 (d, J = 3.2 Hz, 1H), 7.21 (d, J = 5.2 Hz, 1H), 7.53 (d, J = 3.2 Hz, 1H), 8.59 (d, J = 5.2 Hz, 1H), 8.89 (s, 1H) |
| 63 | 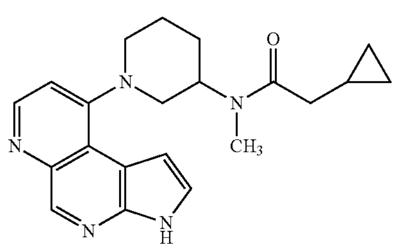 [SMILES: CN(C(=O)CC1CC1)C1CCCN(c2ccnc3cnc4[nH]ccc4c23)C1] | 2-cyclopropyl-N-methyl-N-[1-(3H-pyrrolo[3,2-f][1,7]naphthyridin-9-yl)-3-piperidyl]acetamide | 2-cyclopropyl-N-methyl-N-[3-piperidyl]acetamide (S21) | $^1$HNMR (400 MHz, MeOH-d4): δ 0.16-0.18 (m 2H), 0.52-0.55 (m 2H), 1.02-1.04 (m, 1H), 1.28-1.37 (m, 1H), 1.82-2.05 (m, 2H), 2.18-2.21 (m, 1H), 2.35(d, J = 6.8 Hz 1H), 2.43-2.67 (m, 2H), 2.84-2.91 (m, 1H), 2.99 (s, 3H), 3.48-3.61 (m, 2H), 5.0-5.05 (m, 1H), 7.30-7.39 (m, 2H), 7.55 (br s, 1H), 8.68-8.71 (m, 1H); 8.44-8.93 (m, 1H) |
| 64 | 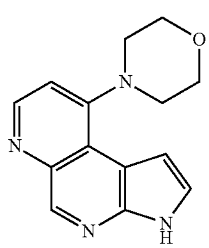 [SMILES: c1cc(N2CCOCC2)c2c(cnc3[nH]ccc32)n1] | 4-(3H-pyrrolo[3,2-f][1,7]naphthyridin-9-yl)morpholine | morpholine | $^1$HNMR (400 MHz, MeOH-d4): δ 8.94 (s, 1H), 8.69 (d, J = 3.2 Hz, 1H), 7.55 (d, J = 3.2 Hz, 1H), 7.32 (d, 7 = 4.8 Hz, 1H), 7.24 (d, J = 3.2 Hz, 1H), 4.04-4.03 (m, 4H), 3.48-3.46 (m, 2H), 2.99-2.97 (m, 2H) |

TABLE 7-continued

| Ex | Structure | IUPAC Name | Amine Used | 1H NMR |
|---|---|---|---|---|
| 65 | 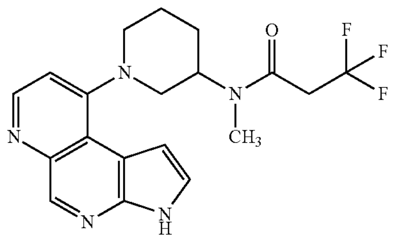 [SMILES: CN(C(=O)CC(F)(F)F)C1CCCN(c2ccnc3cnc4[nH]ccc4c23)C1] | 3,3,3-trifluoro-N-methyl-N-[1-(3H-pyrrolo[3,2-f][1,7]naphthyridin-9-yl)-3-piperidyl]propanamide | 3,3,3-trifluoro-N-methyl-N-[3-piperidyl]propanamide (S19) | ¹HNMR (400 MHz, DMSO-d6): δ 1.78-1.80 (m, 1H), 1.91-1.99 (m, 2H), 2.83-3.01 (m, 4H), 3.25-3.32 (m, 2H), 3.58-3.75 (m, 2H), 3.93-3.96 (m, 1H), 4.1-4.2 (m, 1H), 4.75-4.85 (m, 1H), 7.13 (s, 1H), 7.32 (d, J = 4.9 Hz, 1H), 7.58 (s, 1H), 8-8.73 (m, 1H), 8.93-8.94 (m, 1H), 12.24 (s, 1H) |
| 66 | | N-methyl-N-[1-(3H-pyrrolo[3,2-f][1,7]naphthyridin-9-yl)-3-piperidyl]cyclopentane-carboxamide | N-methyl-N-[3-piperidyl]cyclopentanecarboxamide (S22) | ¹HNMR (400 MHz, DMSO-d6): δ 1.52-1.63 (m, 5H), 1.67-1.78 (m, 4H), 1.87-1.95 (m, 3H), 2.51-2.61 (m, 1H), 2.78 (s, 1H), 2.86-2.97 (m, 3H), 3.16-3.24 (m, 1H), 3.32-3.34 (m, 1H), 3.48-3.5 (m, 1H), 4.75-4.85 (m, 1H), 7.13 (s, 1H), 7.32-7.37 (m, 1H), 7.58 (s, 1H), 8.72-8.74 (m, 1H); 8.94 (d, J = 4 Hz, 1H), 12.24 (br s, 1H) |
| 67 | 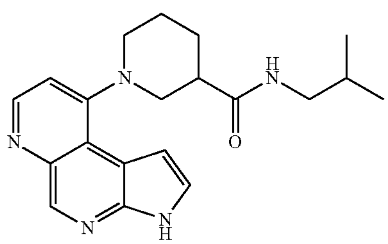 [SMILES: CC(C)CNC(=O)C1CCCN(c2ccnc3cnc4[nH]ccc4c23)C1] | N-isobutyl-1-(3H-pyrrolo[3,2-f][1,7]naphthyridin-9-yl)piperidine-3-carboxamide | N-isobutyl-piperidine-3-carboxamide (S6) | ¹HNMR (400 MHz, MeOH-d4): δ 8.93 (s, 1H), 8.69 (d, J = 4.8 Hz, 1H), 7.55-7.54 (m, 1H), 7.34 (d, J = 4.8 Hz, 1H), 7.26-7.25 (m, 1H), 3.65-3.62 (m, 2H), 3.01-2.86 (m, 4H), 2.67-2.63 (m, 1H), 2.18-2.0 (m, 3H), 1.78-1.69 (m, 3H), 0.90 (d, J = 4 Hz, 6H) |
| 68 | 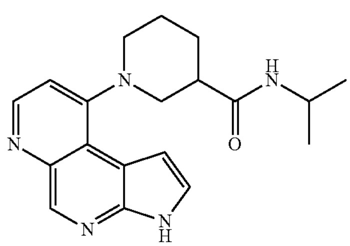 [SMILES: CC(C)NC(=O)C1CCCN(c2ccnc3cnc4[nH]ccc4c23)C1] | N-isopropyl-1-(3H-pyrrolo[3,2-f][1,7]naphthyridin-9-yl)piperidine-3-carboxamide | N-isopropylpiperidine-3-carboxamide (S1) | ¹HNMR (400 MHz, CDCl₃): δ 9.79 (br s, 1H), 9.19-9.15 (m, 1H,), 8.78 (d, J = 5.2Hz, 1H), 7.45 (s, 1H,), 7.21-7.20 (m, 2H), 5.38-5.36 (m, 1H), 4.12-4.05 (m, 1H), 3.86-3.83 (m, 1H), 3.65-3.62 (m, 2H), 3.0-2.94 (m, 1H), 2.74-2.68 (m, 1H), 2.60-2.55 (m, 1H), 2.16-1.99 (m, 2H), 1.85-1.76 (m, 1H), 1.77-1.09 (m, 6H) |
| 69 | 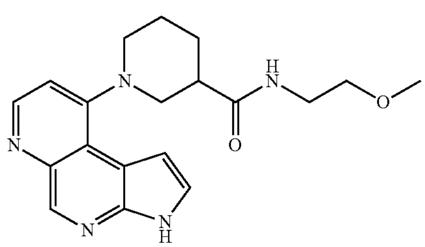 [SMILES: COCCNC(=O)C1CCCN(c2ccnc3cnc4[nH]ccc4c23)C1] | N-(2-methoxyethyl)-1-(3H-pyrrolo[3,2-f][1,7]naphthyridin-9-yl)piperidine-3-carboxamide | N-(2-methoxyethyl)-piperidine-3-carboxamide (S3) | ¹HNMR (400 MHz, CDCl₃): δ 10.0 (br s, 1H), 9.14 (s, 1H,), 8.77 (d, J = 4.8 Hz , 1H), 7.43 (s, 1H), 7.17 (s, 2H), 6.16 (br s, 1H), 3.63-3.61 (m, 2H), 3.48 (br s, 4H), 3.36 (s, 3H), 2.97-2.92 (m, 1H), 2.81-2.75 (m, 1H), 2.58-2.53 (m, 1H), 2.16-1.95 (m, 3H), 1.77-1.74 (m, 1H) |
| 70 | 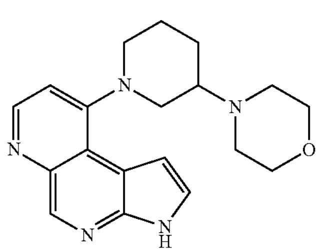 [SMILES: c1cc(N2CCCC(N3CCOCC3)C2)c2c(cnc3[nH]ccc32)n1] | 4-[1-(3H-pyrrolo[3,2-f][1,7]naphthyridin-9-yl)-3-piperidiyl]morpholine | 4-(3-iperidiyl)morpholine (S34) | ¹HNMR: (400 MHz, MeOH-d4) δ 8.94 (s, 1H), 8.69 (d, J = 4.8 Hz, 1H), 7.56 (d, J = 3.2 Hz, 1H), 7.37 (d, J = 5.2 Hz, 1H), 7.25 (d, J = 3.6 Hz, 1H), 3.87 (d, J = 10.4 Hz, 1H), 3.68 (t, J = 4.8 Hz, 4H), 3.57 (d, J = 12 Hz, 1H), 2.97-2.91 (m, 1H), 2.68-2.63 (m, 5H), 2.56 (t,J = 10.8 Hz, 1H), 2.2 (d, J = 12 Hz, 1H), 2.04-2.01 km (m, 2H), 1.49-1.44 (m, 1H) |

TABLE 7-continued

| Ex | Structure | IUPAC Name | Amine Used | 1H NMR |
|---|---|---|---|---|
| 71 | 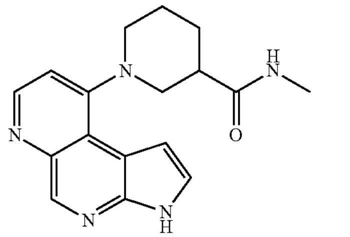 [SMILES: CNC(=O)C1CCCN(c2ccnc3cnc4[nH]ccc4c23)C1] | N-methyl-1-(3H-pyrrolo[3,2-f][1,7]naphthyridin-9-yl)piperidine-3-carboxamide | N-methylpiperidine-3-carboxamide (S4) | $^1$HNMR: (400 MHz, MeOH-d4) δ 8.93 (s, 1H), 8.69 (d, J = 5.2 Hz, 1H), 7.55 (d, J = 3.2 Hz, 1H), 7.34 (d, J = 4.8 Hz, 1H), 7.24 (d, J = 2.4 Hz, 1H), 3.64 (d, J = 7.6 Hz, 2H), 2.90-2.87 (m, 2H), 2.73 (s, 3H), 2.66-2.63 (m, H), 2.15-2.10 (m, 2H), 1.98-1.96 (m, 1H), 1.69-1.67 (m, 1H) |
| 72 | 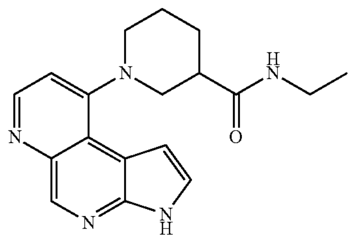 [SMILES: CCNC(=O)C1CCCN(c2ccnc3cnc4[nH]ccc4c23)C1] | N-ethyl-1-(3H-pyrrolo[3,2-f][1,7]naphthyridin-9-yl)piperidine-3-carboxamide | N-ethylpiperidine-3-carboxamide (S5) | $^1$HNMR: (400 MHz, DMSO-d6) δ 12.25 (s, 1H), 8.94 (s, 1H), 8.72 (d, J = 4.8 Hz, 1H), 7.96 (br s, 1H), 7.60 (s, 1H), 7.29 (d, J = 4.8 Hz, 1H), 7.08 (s, 1H), 3.52-3.46 (m, 2H), 3.08-3.05 (m, 2H), 2.82-2.67 (m, 2H), 2.02-1.89 (m, 3H), 1.60-1.53 (m, 2H), 1.00 (t, J = 7.2 Hz, 3H) |
| 73 | 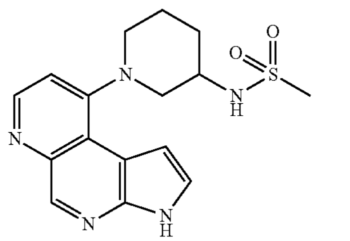 [SMILES: CS(=O)(=O)NC1CCCN(c2ccnc3cnc4[nH]ccc4c23)C1] | N-[1-(3H-pyrrolo[3,2-f][1,7]naphthyridin-9-yl)-3-piperidyl]methanesulfonamide | N-[3-piperidyl]methanesulfonamide (S25) | $^1$HNMR (400 MHz, DMSO-d6): δ 1.37-1.39 (m, 1H), 1.85-2.05 (m, 3H), 2.13-2.15 (m, 1H), 2.96 (s, 3H), 3.43-3.45 (m, 1H), 3.57-3.69 (m, 3H), 7.13 (s, 1H), 7.29 (br s, 1H), 7.59 (s, 1H), 8.29 (s, 1H), 8.73 (br s, 1H), 8.95 (s, 1H), 12.26 (br s, 1H) |
| 74 | 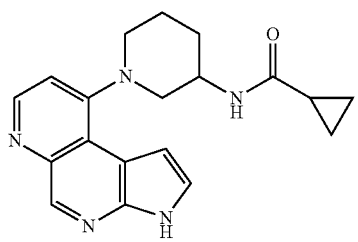 [SMILES: O=C(NC1CCCN(c2ccnc3cnc4[nH]ccc4c23)C1)C1CC1] | N-[1-(3H-pyrrolo[3,2-f][1,7]naphthyridin-9-yl)-3-piperidyl]cyclopropanecarboxamide | N-[3-piperidyl]cyclopropanecarboxamide (S18) | $^1$HNMR(400 MHz, DMSO-d6): δ 0.63-0.66 (m, 4H), 1.35-1.55 (m, 2H), 1.81-2.05 (m, 4H), 2.45-2.50 (m, 1H), 3.45-3.51 (m, 2H), 4.02-4.12 (m, 1H), 7.11 (br s, 1H), 7.28 (d, J = 4.4 Hz, 1H), 7.58 (br s, 1H), 8.16 (d, J = 6.8 Hz, 1H), 8.72 (d, J = 4.8 Hz, 1H), 8.93 (s, 1H), 12.22 (s, 1H) |
| 75 | 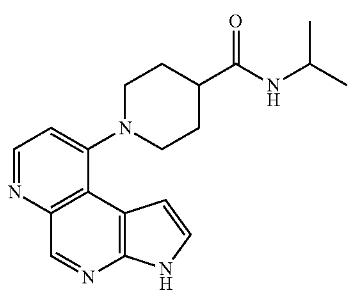 [SMILES: CC(C)NC(=O)C1CCN(c2ccnc3cnc4[nH]ccc4c23)CC1] | N-isopropyl-1-(3H-pyrrolo[3,2-f][1,7]naphthyridin-9-yl)piperidine-4-carboxamide | N-isopropylpiperidine-4-carboxamide (S9) | $^1$HNMR (400 MHz, MeOH-d4): δ 8.92 (s, 1H), 8.68 (d, J = 5.2 Hz, 1H), 7.56 (d, J = 3.2 Hz, 1H), 7.32 (d, J = 4.8 Hz, 2H), 4.03-4.00 (m, 1H), 3.68 (d, J = 12 Hz, 2H) 2.75 (t, J = 12 Hz, 2H), 2.41-2.37 (m, 1H), 2.22-2.19 (m, 1H), 2.15 (s, 1H), 1.96 (d, J = 11.4 Hz, 2H), 1.17 (d, J = 6.4 Hz, 6H) |
| 76 | 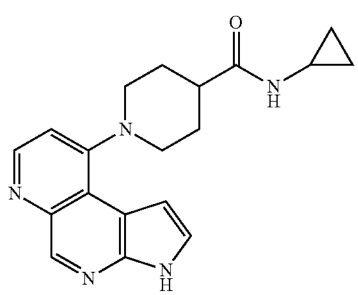 [SMILES: O=C(NC1CC1)C1CCN(c2ccnc3cnc4[nH]ccc4c23)CC1] | N-cyclopropyl-1-(3H-pyrrolo[3,2-f][1,7]naphthyridin-9-yl)piperidine-4-carboxamide | N-cyclopropylpiperidine-4-carboxamide (S2) | $^1$HNMR (400 MHz, DMSO-d6): δ 12.22 (br s, 1H), 8.93 (s, 1H), 8.71 (d, J - 4 Hz, 1H), 7.98 (s, 1H), 7.62 (s, 1H), 7.85 (d, J = 4.0 Hz, 1H), 7.11 (s, 1H), 3.53-3.52 (d, J = 10.8 Hz, 2H), 2.67-2.62 (m, 2H), 2.28-2.26 (m, 1H), 1.99-1.86 (m, 4H), 1.37-1.28 (m, 1H), 0.64-0.62 (m, 2H), 0.43-0.41 (m, 2H) |

TABLE 7-continued

| Ex | Structure | IUPAC Name | Amine Used | 1H NMR |
|---|---|---|---|---|
| 77 | 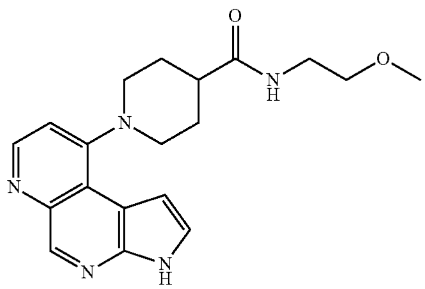 [SMILES: COCCNC(=O)C1CCN(c2ccnc3cnc4[nH]ccc4c23)CC1] | N-(2-methoxyethyl)-1-(3H-pyrrolo[3,2-f][1,7]naphthyridin-9-yl)piperidine-4-carboxamide | N-(2-methoxyethyl) piperidine-4-carboxamide (S12) | ¹HNMR (400 MHz, DMSO-d6): δ 12.21 (s, 1H), 8.93 (s, 1H), 8.72 (d, J = 4.4 Hz, 1H), 8.02 (br s, 1H), 7.62 (s, 1H), 7.29 (d, J = 4.8 Hz, 1H), 7.11 (s, 1H), 3.55-3.52 (m, 2H), 3.38-3.35 (m, 2H), 3.26-3.23 (m, 4H), 2.67-2.63 (m, 2H), 2.00-1.87 (m, 4H) |
| 78 | 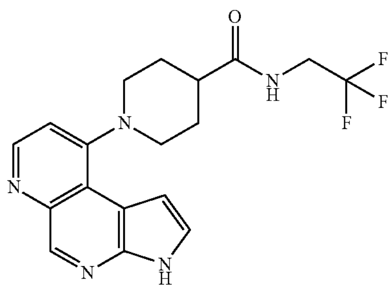 [SMILES: O=C(NCC(F)(F)F)C1CCN(c2ccnc3cnc4[nH]ccc4c23)CC1] | 1-(3H-pyrrolo[3,2-f][1,7]naphthyridin-9-yl)-N-(2,2,2-trifluoroethyl)piperidine-4-carboxamide | N-(2,2,2-trifluoroethyl) piperidine-4-carboxamide (S8) | ¹HNMR (400 MHz, DMSO-d6): δ 12.22 (s, 1H), 8.93 (s, 1H), 8.72 (d, J = 5.2 Hz, 1H), 8.63 (d, J = 6.4 Hz, 1H), 7.62 (s, 1H), 7.30 (d, J = 5.2 Hz, 1H), 7.10 (s, 1H), 4.11-4.10 (m, 1H), 3.97-3.93 (m, 2H), 3.56-3.53 (m, 2H), 3.16 (d, J = 4.4 Hz, 2H), 2.71-2.66 (m, 2H), 2.01-1.95 (m, 2H) |
| 79 | 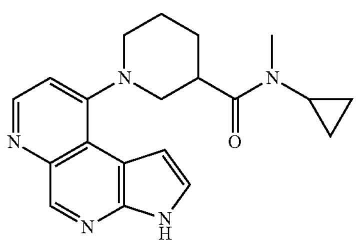 [SMILES: CN(C(=O)C1CCCN(c2ccnc3cnc4[nH]ccc4c23)C1)C1CC1] | N-cyclopropyl-N-methyl-1-(3H-pyrrolo[3,2-f][1,7]naphthyridin-9-yl)piperidine-3-carboxamide | N-cyclopropyl-N-methyl-piperidine-3-carboxamide (S16) | ¹HNMR (400 MHz, DMSO-d6): δ 12.23 (s, 1H), 8.93 (s, 1H), 8.72 (d, J = 4.8 Hz, 1H), 7.61 (s, 1H), 7.29 (d, J = 4.8 Hz, 1H), 7.15 (s, 1H), 3.72-3.71 (m, 1H), 3.48 (t, J = 12.8 Hz, 2H), 3.31 (s, 1H), 2.89-2.87 (m, 1H), 2.77 (s, 3H), 2.72-2.67 (m, 2H), 2.04-1.94 (m, 3H), 0.97-0.95 (m, 2H), 0.84-0.82 (m, 2H) |
| 80 | 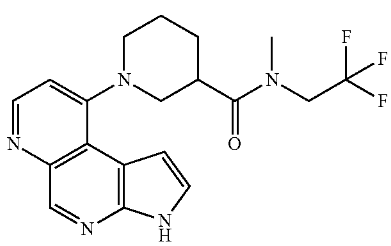 [SMILES: CN(CC(F)(F)F)C(=O)C1CCCN(c2ccnc3cnc4[nH]ccc4c23)C1] | N-methyl-1-(3H-pyrrolo[3,2-f][1,7]naphthyridin-9-yl)-N-(2,2,2-trifluoroethyl)piperidine-3-carboxamide | N-methyl-N-(2,2,2-trifluoroethyl) piperidine-3-carboxamide (S15) | ¹HNMR (400 MHz, CD₃OD): δ 8.94 (s,1H), 8.70 (d, J = 4.4Hz, 1H), 7.55-7.53 (m, 1H), 7.37-7.33 (m, 2H), 4.22-4.20 (m, 1H), 4.06-4.03 (m, 1H), 3.68-3.56(m, 2H), 3.51-3.42 (m, 1H), 3.38 (s, 3H), 3.01 (s, 1H), 2.94-2.88 (m, 1H), 2.70-2.67 (m, 1H), 2.16-2.13 (m, 1H), 2.01-1.98 (m, 1H), 1.69-1.66 (m, 1H) |
| 81 | 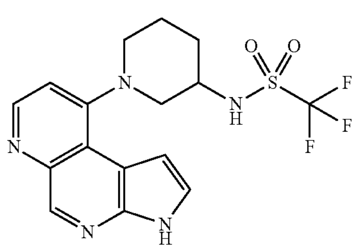 [SMILES: O=S(=O)(NC1CCCN(c2ccnc3cnc4[nH]ccc4c23)C1)C(F)(F)F] | 1,1,1-trifluoro-N-[1-(3H-pyrrolo[3,2-f][1,7]naphthyridin-9-yl)-3-piperidyl]methanesulfonamide | 1,1,1-trifluoro-N-[3-piperidyl]methanesulfonamide (S24) | ¹HNMR (400 MHz, DMSO-d6) δ 12.24(br s, 1H), 9.76 (br s, 1H), 8.95 (s, 1H),8.75 (d, J = 4.8 Hz, 1H), 7.59 (s, 1H),7.33 (d, J = 4.8 Hz, 1H), 7.07 (s, 1H),3.89-3.80 (m, 1H), 3.56-3.42 (m, 2H),2.63-2.54 (m, 2H), 2.15-2.12 (m, 1H),2.02-1.91 (m, 2H), 1.56-1.48 (m, 1H). |
| 82 | 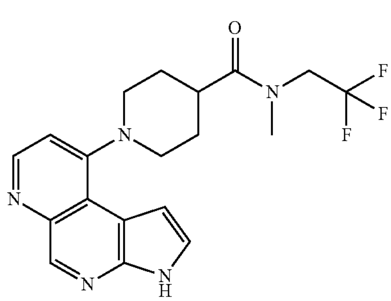 [SMILES: CN(CC(F)(F)F)C(=O)C1CCN(c2ccnc3cnc4[nH]ccc4c23)CC1] | N-methyl-1-(3H-yrrolo[3,2-f][1,7]naphthyridin-9-yl)-N-(2,2,2-trifluoroethyl)piperidine-4-carboxamide | N-methyl)-N-(2,2,2-trifluoroethyl) piperidine-4-carboxamide (S14) | ¹HNMR(400 MHz, DMSO-d6): δ 12.21 (br s, 1H), 8.93 (s, 1H), 8.73 (d, J = 4 Hz, IH), 7.62 (s, 1H), 7.28 (d, J = 4.8 Hz, 1H), 7.10 (br s, 1H), 4.47-4.16 (m, 2H), 3.56-3.50 (m, 2H), 3.22 (br s, 2H), 3.02-2.94 (m, 2H), 2.80-2.75 (m, 1H), 1.99-1.85 (m, 4H), 1.36-1.34 (m, 1H) |

TABLE 7-continued

| Ex | Structure | IUPAC Name | Amine Used | 1H NMR |
|---|---|---|---|---|
| 83 | 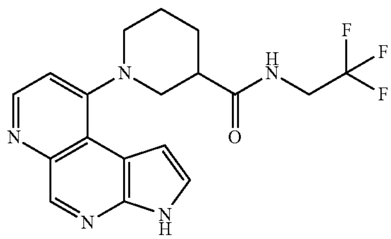 [SMILES: O=C(NCC(F)(F)F)C1CCCN(c2ccnc3cnc4[nH]ccc4c23)C1] | 1-(3H-pyrrolo[3,2-f][1,7]naphthyridin-9-yl)-N-(2,2,2-trifluoroethyl)piperidine-3-carboxamide | N-(2,2,2-trifluoroethyl)piperidine-3-carboxamide (S7) | $^1$HNMR (400 MHz, DMSO-d6): δ 12.26 (s, 1H), 8.94 (s, 1H), 8.73-8.68 (m, 2H), 7.60 (s, 1H), 7.30 (d, J = 4.9 Hz, 1H), 7.09 (s, 1H), 3.96-3.85 (m, 2H), 3.52-3.49 (m, 2H), 2.90-2.79 (m, 2H), 2.05-1.91 (m, 4H), 1.60-1.55 (m, 1H) |
| 84 | 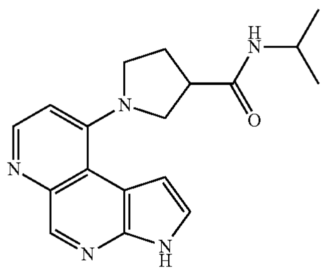 [SMILES: CC(C)NC(=O)C1CCN(c2ccnc3cnc4[nH]ccc4c23)C1] | N-isopropyl-1-(3H-pyrrolo[3,2-f][1,7]naphthyridin-9-yl)pyrrolidine-3-carboxamide | N-isopropyl-pyrrolidine-3-carboxamide (S13) | $^1$HNMR (400 MHz, DMSO-d6): δ 12.19 (s, 1H), 8.9 (s, 1H), 8.64 (d, J = 4.8 Hz, 1H), 7.89 (d, J = 7.6 Hz, 1H), 7.57 (s, 1H), 7.21 (d, J = 4.9 Hz, 1H), 6.95 (s, 1H), 3.89-3.84 (m, 1H), 3.30-3.26 (m, 2H), 3.09 (quin, J = 6.Hz, 1H), 2.19 (q, J = 6.8 Hz, 2H), 1.08-1.04 (m, 8H) |
| 85 | 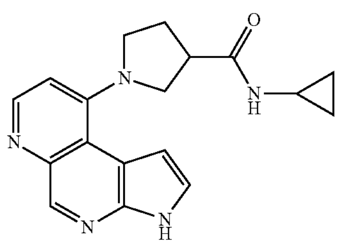 [SMILES: O=C(NC1CC1)C1CCN(c2ccnc3cnc4[nH]ccc4c23)C1] | N-cyclopropyl-1-(3H-pyrrolo[3,2-f][1,7]naphthyridin-9-yl)pyrrolidine-3-carboxamide | N-cyclopropyl-pyrrolidine-3-carboxamide (S12) | $^1$HNMR (400 MHz, DMSO-d6): δ 12.2 (br s, 1H), 8.88 (s, 1H), 8.62 (d, J = 5.2 Hz, 1H), 8.07 (d, J = 3.9 Hz, 1H), 7.56-7.54 (m, 1H), 7.18 (d, .7= 4.9 Hz, 1H), 6.92 (s, 1H), 3.38-3.37 (m, 2H), 3.28-3.24 (m, 1H), 3.04 (quin, J = 7.3 Hz, 1H), 2.65-2.61 (m, 2H), 2.19-2.16 (m, 2H), 0.60-0.58 (m, 2H), 0.39-0.36 (m, 2H) |
| 86 | 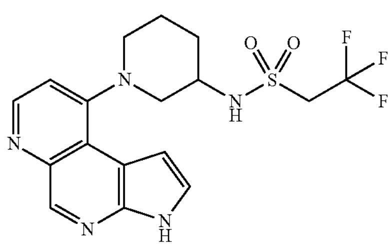 [SMILES: O=S(=O)(CC(F)(F)F)NC1CCCN(c2ccnc3cnc4[nH]ccc4c23)C1] | 2,2,2-trifluoro-N-[1-(3H-pyrrolo[3,2-f][1,7]naphthyridin-9-yl)-3-piperidyl]ethanesulfonamide | 2,2,2-trifluoro-N-[3-piperidyl]ethanesulfonamide (S23) | $^1$HNMR (400MHz, DMSO-d6): δ 12.2 (s, 1H), 8.92 (s, 1H), 8.72 (d, J = 4.4 Hz, 1H), 8.11 (d, J = 7.1 Hz, 1H), 7.56 (s, 1H), 7.27 (d, J = 4.6 Hz, 1H), 7.09 (s, 1H), 4.47 (q, J = 9.5 Hz, 2H), 3.78 (br s, 1H), 3.55-3.42 (m, 4H), 2.12-1.97 (m, 2H), 1.89-1.83 (m, 1H), 1.41-1.38 (m, 1H) |
| 87 | 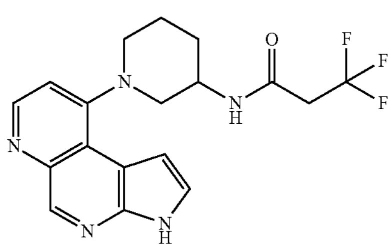 [SMILES: O=C(CC(F)(F)F)NC1CCCN(c2ccnc3cnc4[nH]ccc4c23)C1] | 3,3,3-trifluoro-N-[1-(3H-pyrrolo[3,2-f][1,7]naphthyridin-9-yl)-3-piperidyl]propanamide | 3,3,3-trifluoro-N-[3-piperidyl]propanamide (S17) | $^1$HNMR (400 MHz, DMSO-d6): δ 12.21 (br s, 1H), 8.92 (s, 1H), 8.71 (d, J = 4.4 Hz, 1H), 8.34 (d, J = 6.3 Hz, 1H), 7.57 (s, 1H), 7.26 (d, J = 4.4 Hz, 1H), 7.09 (s, 1H), 4.08-4.06 (m, 1H), 3.52-3.44 (m, 2H), 3.27-3.18 (m, 3H), 2.05-1.96 (m, 2H), 1.89-1.77 (m, 2H), 1.38-1.35 (m, 1H) |
| 88A | cis-isomer | cis-N-cyclopropyl-6-methyl-1-(3H-pyrrolo[3,2-f][1,7]naphthyridin-9-yl)piperidine-3-carboxamide | cis-N-cyclopropyl-6-methyl-piperidine-3-carboxamide (S36A) | $^1$HNMR (400 MHz, DMSO-d6): δ 0.40 (s, 2H), 0.61 (d,J = 4.8 Hz, 2H), 0.71 (d, J = 6.4 Hz, 3H), 1.65-1.90 (m, 3H), 2.10-2.25 (m, 1H), 2.55-2.70 (m, 2H), 3.09 (d, J = 11.2 Hz, 1H), 3.35-3.50 (m, 1H), 3.90-4.0 (m, 1H), 7.05 (s, 1H), 7.21 (d, J = 3.6 Hz, 1H), 7.59 (s, 1H), 8.02 (s, 1H), 8.69 (d, J = 4.0 Hz, 1H), 8.92 (s, 1H), 12.22 (br s, 1H) |

TABLE 7-continued

| Ex | Structure | IUPAC Name | Amine Used | 1H NMR |
|---|---|---|---|---|
| 88 B | [structure shown: trans-isomer of methyl-piperidine linked to pyrrolo[3,2-f][1,7]naphthyridine with cyclopropyl carboxamide] | trans-N-cyclopropyl-6-methyl-1-(3H-pyrrolo[3,2-f][1,7]naphthyridin-9-yl)piperidine-3-carboxamide | trans-N-cyclopropyl-6-methyl-piperidine-3-carboxamide (S36B) | $^1$HNMR (400 MHz, DMSO-d6): δ 0.25-0.35 (m, 2H), 0.50-0.61 (m, 2H), 0.90 (d, J = 5.6 Hz, 3H), 1.45-1.65 (m, 2H), 1.92-2.15 (m, 2H), 2.50-2.60 (m, 2H), 2.65-2.75 (m, 1H), 3.13 (d,J = 8.8 Hz, 1H), 3.20-3.30 (m, 1H), 7.31(d, J = 2.4 Hz, 1H), 7.52 (t, J = 2.8 Hz, 1H), 7.55 (d, J = 4.8 Hz, 1H), 7.92 (d, J = 4.0 Hz, 1H), 8.78 (d, J = 4.8 Hz, 1H), 8.93 (s, 1H), 12.22 (br s, 1H) |

Preparation 29: 1-(3H-pyrrolo[3,2-f][1,7]naphthyridin-9-yl)piperidin-3-ol (121) (Alternate process for Example 54)

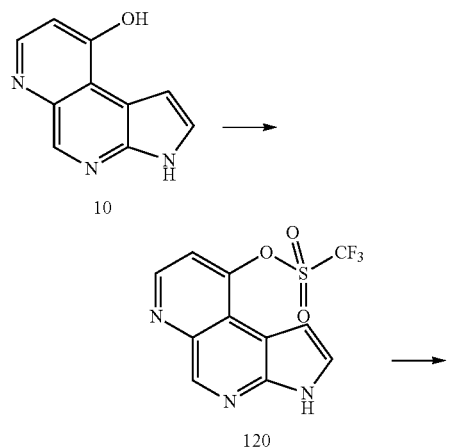

Step I: 3H-pyrrolo[3,2-f][1,7]naphthyridin-9-yl trifluoromethanesulfonate (120)

To a suspension of compound 10 (0.12 gm, 0.65 mmol) in pyridine (2 ml), trifluoromethanesulfonic anhydride (0.9 gm, 3.25 mmol) was added at 0° C. and the reaction mixture was stirred at room temperature overnight. Water was added into the reaction mixture when a light brown solid separated out. It was filtered and dried to obtain compound 120 (52 mg, 25%) as a brown solid.

Step II: 1-(3H-pyrrolo[3,2-f][1,7]naphthyridin-9-yl)piperidin-3-ol (121)

To a suspension of compound 120 (50 mg, 0.16 mmol) in N-methyl pyrrolidinone (2 ml), 3-hydroxy piperidine (160 mg, 1.6 mmol) was added and the reaction mixture was heated at 150° C. overnight. Water was added to the reaction mixture. It was further extracted with ethyl acetate, the organic layer was concentrated to obtain a residue which was purified by preparative HPLC to obtain compound 121 (3.3 mg) as a white solid.

$^1$HNMR (400 MHz, DMSO-d6): □$_1$□□$_1$□□ (m, 2H); 2.02-2.11 (m, 1H); 2.33-2.34 (m, 1H); 3.41-3.43 (m, 2H); 3.52-3.54 (1, 2H); 3.88-3.91 (m, 1H); 5.00 (d, J=4 Hz, 1H); 7.05 (s, 1H); 7.28 (d, J=6 Hz, 1H); 7.59 (s, 1H); 8.71 (d, J=4.8 Hz, 1H); 8.93 (s, 1H); 12.22 (br s, 1H).

Preparation 30: (3R)-1-(3H-pyrrolo[3,2-f][1,7]naphthyridin-9-yl)pyrrolidin-3-ol (122) (Alternate process for Example 55)

Compound 122 was prepared in an analogous manner of compound 121.

Example 89

3,3-Difluoro-N-[1-(3H-3,4,6,7-tetraaza-cyclopenta[a]naphthalen-9-yl)-piperidin-3-yl]-butyramide (123)

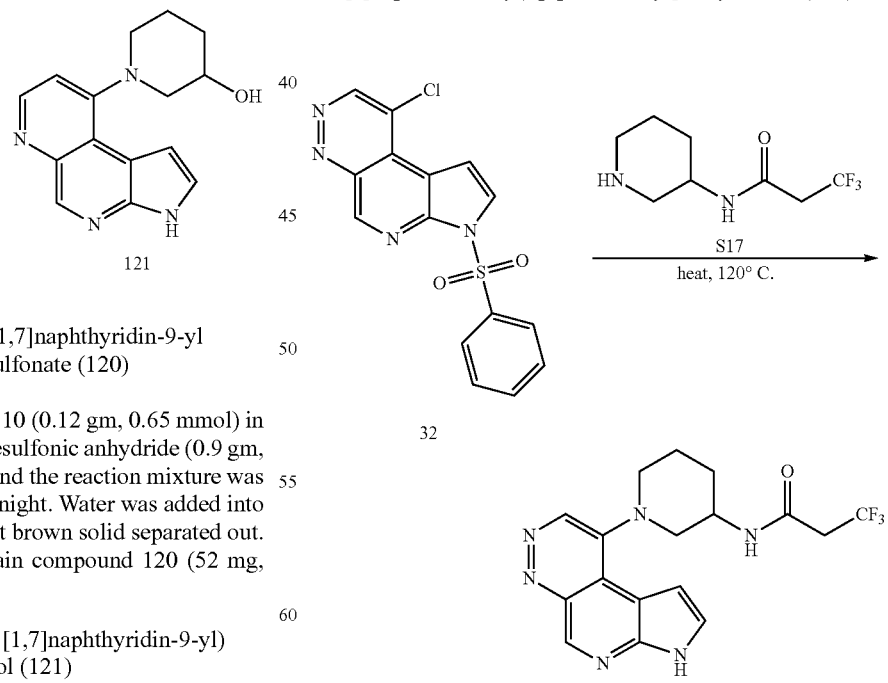

The compound 123 was synthesized according to the above general method D. $^1$HNMR (400 MHz, DMSO-d6): □ 1.61-

1.69 (m, 1H), 1.71-2.17 (m, 3H), 2.82-3.20 (m, 3H), 3.33-3.68 (m, 2H), 3.80-4.00 (m, 2H), 7.02 (s, 1H), 7.70 (s, 1H), 8.66 (t, J=6 Hz, 1H), 9.16 (s, 1H), 9.34 (s, 1H), 12.64 (br s, 1H)

Preparation 31: 1-(3H-pyrrolo[3,2-f][1,7]naphthyridin-9-yl)pyrrolidin-3-amine derivative (126)

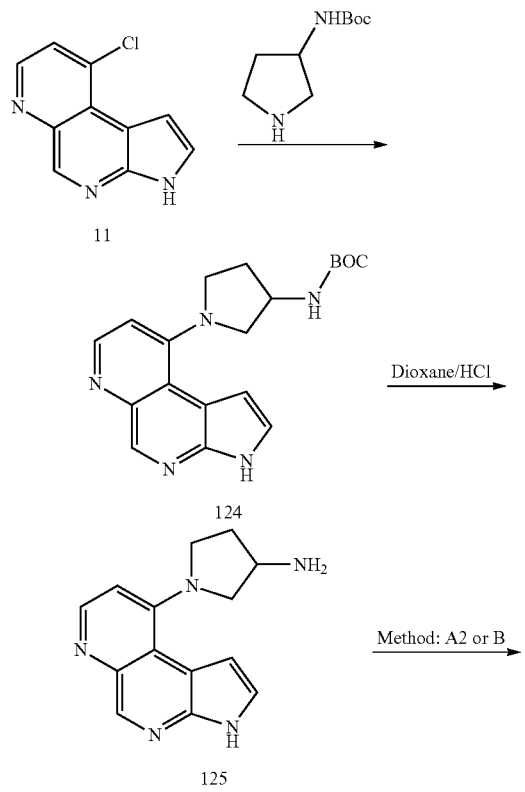

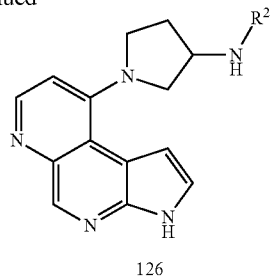

126

Step 1: tert-Butyl N-[1-(3H-pyrrolo[3,2-f][1,7]naphthyridin-9-yl)pyrrolidin-3-yl]carbamate (124)

The compound 124 was synthesized according to the above general method D. ¹H NMR (400 MHz, CDCl₃): δ 9.31 (br s, 1H), 9.11 (s, 1H), 8.71 (d, J=12. Hz, 1H), 7.43 (s, 1H), 7.05 (d, J=12 Hz, 1H), 6.96 (s, 1H), 4.87 (br s, 1H), 4.48 (br s, 1H), 3.60-3.58 (m, 2H), 3.22-3.21 (m, 1H), 3.14-3.12 (m, 1H), 2.56-2.52 (m, 1H), 1.92-1.90 (m, 1H), 1.46 (s, 9H).

Step 2: 1-(3H-pyrrolo[3,2-f][1,7]naphthyridin-9-yl)pyrrolidin-3-amine (125)

The preparation of compound 125 was carried out in a manner similar to that described for the preparation of compound 87. ¹HNMR (400 MHz, MeOH-d4): δ 8.92 (s, 1H), 8.65 (d, J=9.2 Hz, 1H), 7.57 (s, 1H), 7.26 (d, J=5.2 Hz, 1H), 7.03 (d, J=3.2 Hz, 1H), 4.08-4.07 (m, 1H), 3.81-3.77 (m, 1H), 3.71-3.66 (m, 1H), 3.34-3.32 (m, 2H), 2.63-2.58 (m, 1H), 2.11-2.01 (m, 1H)

Step 3: 1-(3H-pyrrolo[3,2-f][1,7]naphthyridin-9-yl)pyrrolidin-3-amine derivative (126)

The preparation of compound 126 was carried out in a manner similar to that described above in method A or method B. The compounds in Table 8 were synthesized according to the general method A, B or C

TABLE 8

| Ex | Structure | Method | IUPAC Name | NMR data |
|---|---|---|---|---|
| 90 | 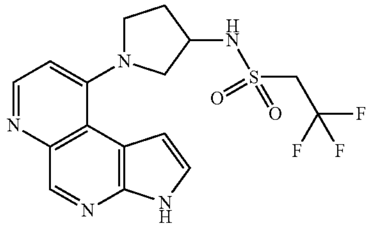 [SMILES: O=S(=O)(CC(F)(F)F)NC1CCN(c2ccnc3cnc4[nH]ccc4c23)C1] | B | 2,2,2-trifluoro-N-[1-(3H-pyrrolo[3,2-f][1,7]naphthyridin-9-yl)pyrrolidin-3-yl]ethanesulfonamide | ¹HNMR (400 MHz, DMSO-d6): δ 12.19 (s, 1H), 8.90 (s, 1H), 8.64 (d, J = 4.8 Hz, 1H), 8.38 (d, J = 4.8 Hz, 1H), 7.58 (m, 1H), 7.18 (d, J = 4.8 Hz, 1H), 6.96 (s, 1H), 4.54-4.46 (m, 2H), 4.26-4.24 (m, 1H), 3.58-3.54 (m, 2H), 3.27-3.16 (m, 2H), 2.01-1.97 (m, 2H) |
| 91 | 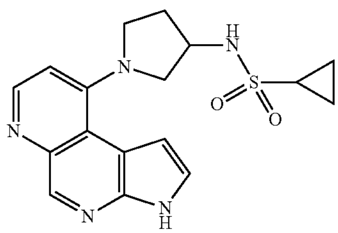 [SMILES: O=S(=O)(NC1CCN(c2ccnc3cnc4[nH]ccc4c23)C1)C1CC1] | B | N-[1-(3H-pyrrolo[3,2-f][1,7]naphthyridin-9-yl)pyrrolidin-3-yl]cyclopropanesulfonamide | ¹HNMR (400 MHz, DMSO-d6): δ 12.19 (br s, 1H), 8.90 (s, 1H), 8.64 (d, J = 8 Hz, 1H), 7.64-7.59 (m, 2H), 7.18 (d, J = 4 Hz, 1H), 6.96 (s, 1H), 4.19-4.17 (m, 1H), 3.62-3.58 (m, 1H), 3.28-3.17 (m, 3H), 2.61-2.50 (m, 2H), 2.01-1.99 (m, 1H), 1.05-0.89 (m, 4H) |

TABLE 8-continued

| Ex | Method | IUPAC Name | NMR data |
|---|---|---|---|
| 92 | B | N-[1-(3H-pyrrolo[3,2-f][1,7]naphthyridin-9-yl)pyrrolidin-3-yl]propane-2-sulfonamide | $^1$HNMR (400 MHz, DMSO-d6): δ 12.16 (br s, 1H), 8.90 (s, 1H), 8.63 (d; J = 4.4 Hz, 1H), 7.58 (s, 1H), 7.17 (d, J = 4.4 Hz, 1H), 6.96 (s, 1H), 4.14-4.13 (m, 1H), 3.55-3.51 (m, 1H), 3.27-3.19 (m, 4H), 2.44-2.42 (m, 1H), 2.00-1.99 (m, 1H), 1.26-1.23 (m, 6H) |
| 93 | B | 2-methyl-N-[1-(3H-pyrrolo[3,2-f][1,7]naphthyridin-9-yl)pyrrolidin-3-yl]propane-1-sulfonamide | $^1$HNMR (400 MHz, DMSO-d6): δ 12.16 (s, 1H), 8.87 (s, 1H), 8.67 (d, J = 4.8 Hz, 1H), 7.57 (d, J = 7.6 Hz, 2H), 7.15 (d, J = 4.8 Hz, 1H), 6.93 (s, 1H), 4.12-4.10 (m, 1H), 3.54-3.50 (m, 1H), 3.27-3.24 (m, 3H), 3.18-3.14 (m, 1H), 2.95-2.93 (m, 2H), 2.12-2.05 (m, 1H), 1.97-1.93 (m, 1H), 1.02-0.98 (m, 6H) |
| 94 | B | 1-cyano-N-[1-(3H-pyrrolo[3,2-f][1,7]naphthyridin-9-yl)pyrrolidin-3-yl]methanesulfonamide | $^1$HNMR (400 MHz, DMSO-d6): δ 12.20 (s, 1H), 8.90 (s, 1H), 8.68-8.64 (m, 2H), 7.59 (s, 1H), 7.18 (d, J = 5.2 Hz, 1H), 6.96 (s, 1H), 4.80 (s, 2H), 4.27-4.25 (m, 1H), 3.60-3.56 (m, 1H), 3.43-3.39 (m, 2H), 3.28-3.19 (m, 2H), 2.03-1.99 (m, 1H) |
| 95 | C | 1-isopropyl-3-[1-(3H-pyrrolo[3,2-f][1,7]naphthyridin-9-yl)pyrrolidin-3-yl]urea | $^1$HNMR (400 MHz, DMSO-d6): δ 12.20 (s, 1H), 8.88 (s, 1H), 8.61 (d, J = 4.4 Hz, 1H), 7.58 (s, 1H), 7.13 (d, J = 5.2 Hz, 1H), 6.89 (s, 1H), 6.14 (d, J = 6.8 Hz, 1H), 5.66 (d, J = 7.2 Hz, 1H), 4.30-4.28 (m, 1H), 3.66-3.62 (m, 1H), 3.49-3.43 (m, 2H), 3.18-3.13 (m, 2H), 2.35-2.31 (m, 1H), 1.79-1.77 (m, 1H), 1.02-1.0 (m, 6H) |
| 96 | A2 | N-[1-(3H-pyrrolo[3,2-f][1,7]naphthyridin-9-yl)pyrrolidin-3-yl]cyclopropanecarbox-amide | $^1$HNMR (400 MHz, DMSO-d6): δ 12.22 (s, 1H), 8.92 (s, 1H), 8.64 (d, J = 4.8 Hz , 1H), 8.56 (d, J = 6 Hz, 1H), 7.58 (s, 1H), 7.18 (d, J = 4.8 Hz, 1H), 6.97 (s, 1H), 4.48-4.40 (m, 1H), 3.50-3.49 (m, 1H), 3.39-3.37 (m, 1H), 3.21-3.18 (m, 2H), 2.41-2.36 (m, 1H), 1.98-1.94 (m, 1H), 1.65-1.62 (m, 1H), 0.71-0.68 (m, 4H) |
| 97 | A2 | 2-methyl-N-[1-(3H-pyrrolo[3,2-f][1,7]naphthyridin-9-yl)pyrrolidin-3-yl]propanamide | $^1$HNMR (400 MHz, DMSO-d6): δ 12.2 (s, 1H), 8.90 (s, 1H), 8.64 (d, J = 4.8 Hz, 1H), 8.18 (d, J = 6.4 Hz, 1H), 7.56 (s, 1H), 7.17 (d, J = 4.8 Hz, 1H), 6.95 (s, 1H), 4.2-4.15 (m, 1H), 4.03-4.0 (m, 1H), 3.49-3.35 (m, 1H), 3.19-3.16 (m, 2H), 2.50-2.34 (m, 2H), 1.99-1.92 (m, 1H), 1.03-1.01 (m, 6H) |

TABLE 8-continued

| Ex | Structure | Method | IUPAC Name | NMR data |
|---|---|---|---|---|
| 98 | 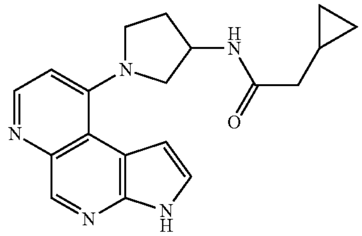 [SMILES: O=C(CC1CC1)NC1CCN(c2ccnc3cnc4[nH]ccc4c23)C1] | A2 | 2-cyclopropyl-N-[1-(3H-pyrrolo[3,2-f][1,7]naphthyridin-9-yl)pyrrolidin-3-yl]acetamide | ¹HNMR (400 MHz, DMSO-d6): δ 12.19 (s, 1H), 8.90 (s, 1H), 8.63 (d, J = 4.8 Hz, 1H), 8.17 (d, J = 6 Hz, 1H), 7.57 (s, 1H), 7.17 (d, J = 4.8 Hz, 1H), 6.94 (s, 1H), 4.45-4.40 (m, 1H), 3.49-3.40 (m, 2H), 3.17-3.16, (m, 2H), 2.38-2.34 (m, 1H), 2.03 (d, J = 6.8 Hz, 2H), 1.95-1.92 (m, 1H), 0.99-0.96 (m, 1H), 0.43-0.41 (m, 2H), 0.13-0.12 (m, 2H) |
| 99 | 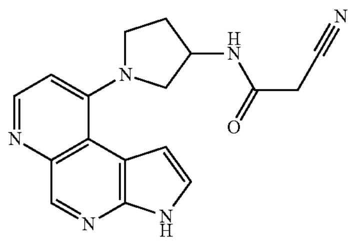 [SMILES: N#CCC(=O)NC1CCN(c2ccnc3cnc4[nH]ccc4c23)C1] | A2 | 2-cyano-N-[1-(3H-pyrrolo[3,2-f][1,7]naphthyridin-9-yl)pyrrolidin-3-yl]acetamide | ¹HNMR (400 MHz, DMSO-d6): δ 12.23 (s, 1H), 8.90 (s, 1H), 8.76 (d, J = 5.6 Hz, 1H), 7.63 (d, J = 4.8 Hz, 1H), 7.60 (s, 1H), 7.19 (d, J = 4.8 Hz, 1H), 6.93 (s, 1H), 4.4 (br s, 1H), 3.77 (s, 2H), 3.53-3.50 (m, 1H), 3.44-3.40 (m, 1H), 3.20-3.13 (m, 2H), 2.43-2.40 (m, 1H), 1.99-1.91 (m, 1H) |
| 100 | 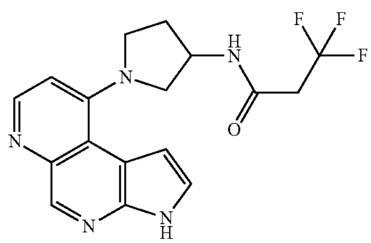 [SMILES: O=C(CC(F)(F)F)NC1CCN(c2ccnc3cnc4[nH]ccc4c23)C1] | A2 | 3,3,3-trifluoro-N-[1-(3H-pyrrolo[3,2-f][1,7]naphthyridin-9-yl)pyrrolidin-3-yl]propanamide | ¹HNMR (400 MHz, MeOH-d4): δ 8.90 (s, 1H), 8.61 (d, J = 4.4 Hz, 1H), 7.53 (s, 1H), 7.22 (d, J = 4.4 Hz, 1H), 7.02 (s, 1H), 4.6 (br s, 1H), 3.71-3.60 (m, 2H), 3.25-3.17 (m, 1H), 2.53-2.51 (m, 1H), 2.23 (s, 1H), 2.04-2.03 (m, 1H), 1.86-1.83 (m, 1H), 1.18-1.15 (m, 1H) |
| 101 | 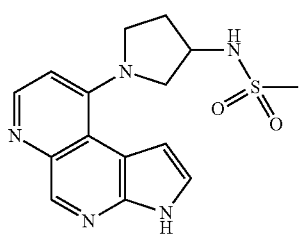 [SMILES: CS(=O)(=O)NC1CCN(c2ccnc3cnc4[nH]ccc4c23)C1] | B | N-[1-(3H-pyrrolo[3,2-f][1,7]naphthyridin-9-yl)pyrrolidin-3-yl]methanesulfonamide | ¹HNMR (400 MHz, DMSO-d6): δ 12.18(s, 1H), 8.90 (s, 1H), 8.64 (d, J = 4.8 Hz, 1H), 7.58-7.55 (m, 1H), 7.19 (d, J = 4.8 Hz, 1H), 6.95 (s, 1H), 4.17-4.15 (m, 1H), 3.59-3.54 (m, 1H), 3.35-3.19 (m, 4H), 2.97 (s, 3H), 1.98-1.96 (m, 1H) |

Preparation 32: 9-piperazin-1-yl-3H-pyrrolo[3,2-f][1,7]naphthyridine derivative (129)

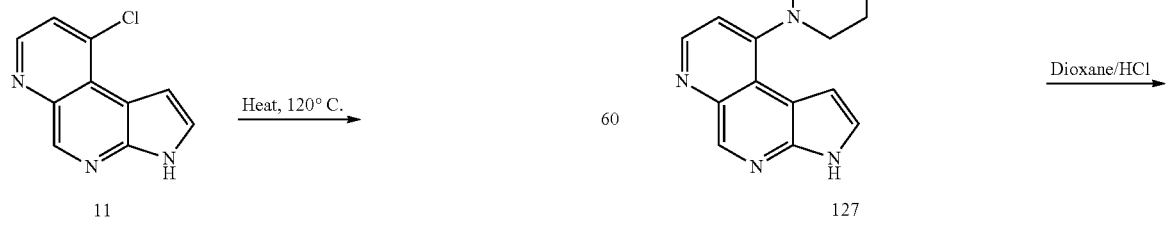

-continued

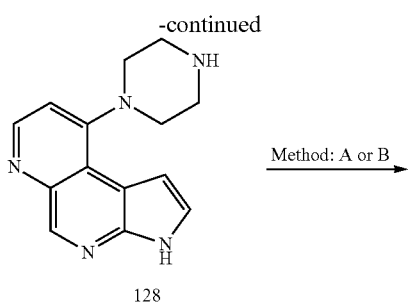

128 Method: A or B →

129

Step 1: tert-butyl 4-(3H-pyrrolo[3,2-f][1,7]naphthyridin-9-yl)piperazine-1-carboxylate (127)

The compound 127 was synthesized according to the above general method D. ¹HNMR (400 MHz, MeOH-d4): δ 1.48-1.51 (s, 9H), 2.78-2.86 (m, 2H), 3.35-3.62 (m, 4H), 4.08-4.12 (m, 2H), 7.27 (d, J=3.6 Hz, 1H), 7.34 (d, J=5.2 Hz, 1H), 7.56 (d, J=3.6 Hz, 1H), 8.70 (d, J=5.2 Hz, 1H), 8.94 (s, 1H)

Step 2: 9-piperazin-1-yl-3H-pyrrolo[3,2-f][1,7]naphthyridine (128)

The preparation of (128) was carried out in a manner similar to that described for the preparation of compound (87). This compound was used as the hydrochloride salt, without further purification.

Step 3: 9-piperazin-1-yl-3H-pyrrolo[3,2-f][1,7]naphthyridine derivative (129)

The preparation of 129 was carried out in a manner similar to that described above in method A or method B.

The compounds in Table 9 were synthesized according to the general method A or B

TABLE 9

| Ex | Structure | Method | IUPAC Name | 1H NMR |
|---|---|---|---|---|
| 102 | 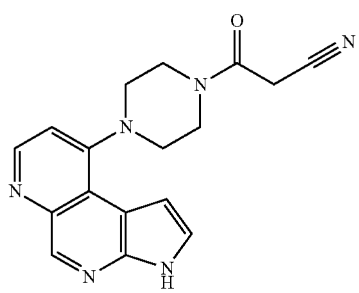 [SMILES: N#CCC(=O)N1CCN(c2ccnc3cnc4[nH]ccc4c23)CC1] | A2 | 3-oxo-3-[4-(3H-pyrrolo[3,2-f][1,7]naphthyridin-9-yl)piperazin-1-yl]propanenitrile | ¹HNMR (400 MHz, MeOH-d4): δ 8.95 (s,1H), 8.71 (d, J = 4.8 Hz, 1H), 7.57 (d, J = 3.6 Hz, 1H), 7.35 (d, J = 4.8 Hz, 1H), 7.27 (d, J = 3.2 Hz, IH), 4.89-4.62 (m, 1H), 4.01-3.91 (m, 2H), 3.78-3.76 (m, 1H), 3.62-3.61 (m, 2H), 3.40-3.38 (m, 1H), 2.93-2.86 (m, 3H) |
| 103 | 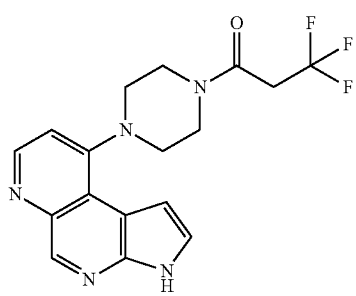 [SMILES: O=C(CC(F)(F)F)N1CCN(c2ccnc3cnc4[nH]ccc4c23)CC1] | A2 | 3,3,3-trifluoro-1-[4-(3H-pyrrolo[3,2-f][1,7]naphthyridin-9-yl)piperazin-1-yl]propan-1-one | ¹HNMR (400 MHz, MeOH-d4): δ 8.96 (s, 1H), 8.71 (d, J = 4.8 Hz, 1H), 7.57 (d, J = 2.0 Hz, 1H), 7.35 (d, J = 5.2 Hz, 1H), 7.27 (d, J = 3.2 Hz, 1H), 4.67-4.64 (m, 1H), 4.07-4.10 (m, 1H), 3.78-3.76 (m, 1H), 3.65-3.55 (m, 4H), 3.36-3.35 (m, 1H), 2.89-2.83 (m, 2H) |
| 104 | 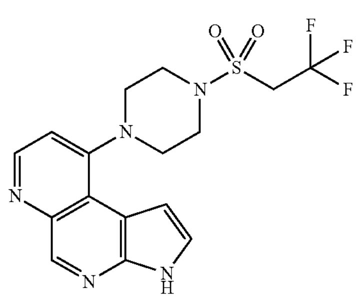 [SMILES: O=S(=O)(CC(F)(F)F)N1CCN(c2ccnc3cnc4[nH]ccc4c23)CC1] | B | 9-[4-(2,2,2-trifluoroethylsulfonyl)piperazin-1-yl]-3H-pyrrolo[3,2-f][1,7]naphthyridine | ¹HNMR (400 MHz, MeOH-d4): δ 8.95 (s, IH), 8.72-8.71 (m, 1H), 7.57 (d, J = 3.2 Hz, 1H), 7.38 (d, J = 4 Hz, 1H), 7.25 (d, J = 3.2 Hz, 1H), 4.32 (q, J = 9.6 Hz, 2H), 3.94-3.91 (m, 2H), 3.69-3.66 (m, 2H), 3.55-3.50 (m, 2H), 3.00-2.95 (m, 2H) |

TABLE 9-continued

| Ex | Structure | Method | IUPAC Name | 1H NMR |
|---|---|---|---|---|
| 105 | 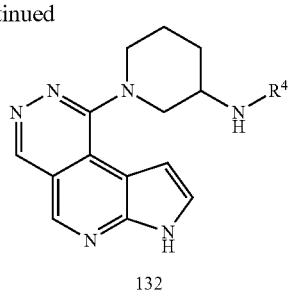 | B | 2-[4-(3H-pyrrolo[3,2-f][1,7]naphthyridin-9-yl)piperazin-1-yl]sulfonylacetonitrile | $^1$HNMR (400 MHz, DMSO-d6): δ 12.30 (s, 1H), 8.97 (s, 1H), 8.77 (d, J = 4.8 Hz, 1H), 7.63 (d, J = 2.8 Hz, 1H), 7.35 (d, J = 4.8 Hz, 1H), 7.14 (s, 1H), 5.05 (s, 2H), 3.80-3.77 (m, 2H), 3.58-3.56 (m, 4H), 2.91-2.89 (m, 2H) |

Preparation 33: 1-(3H-3,4,7,8-tetraaza-cyclopenta[a]naphthalen-9-yl)-piperidin-3-ylamine derivative (132)

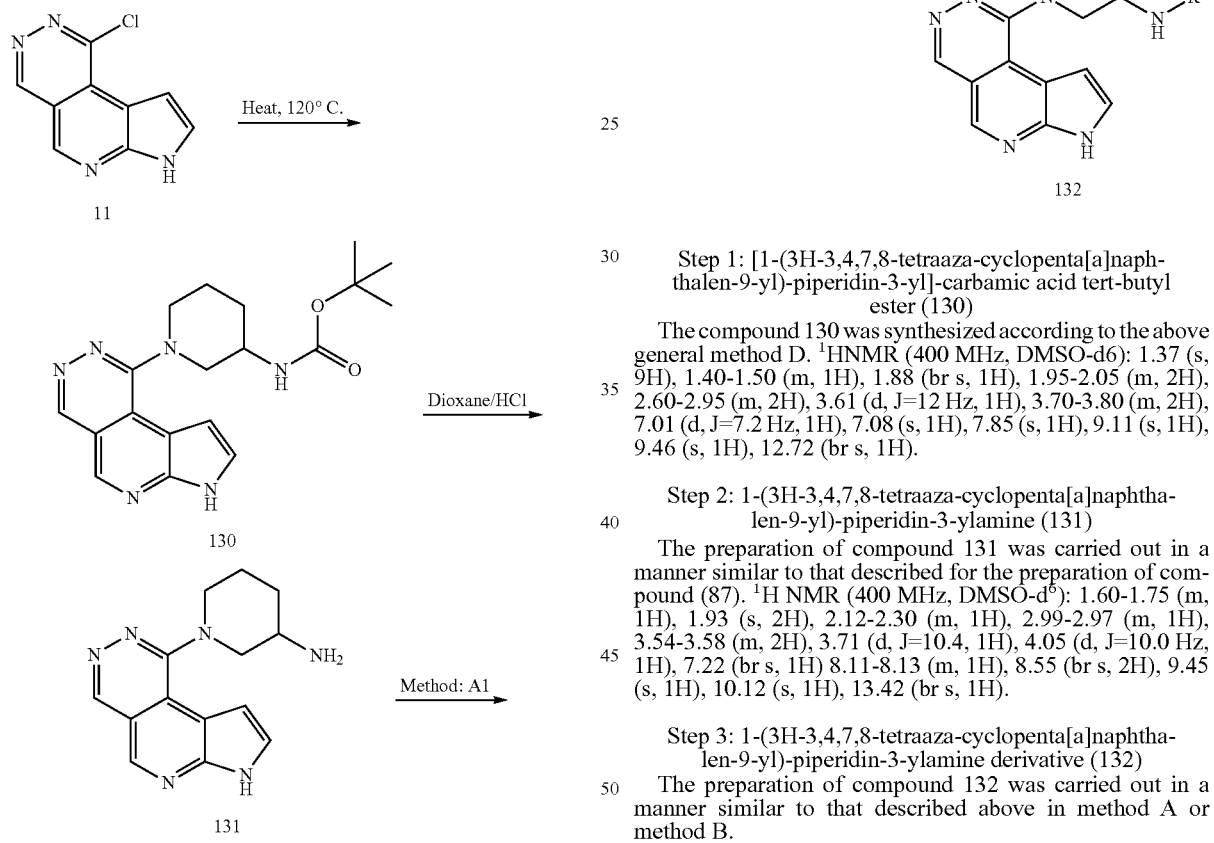

Step 1: [1-(3H-3,4,7,8-tetraaza-cyclopenta[a]naphthalen-9-yl)-piperidin-3-yl]-carbamic acid tert-butyl ester (130)

The compound 130 was synthesized according to the above general method D. $^1$HNMR (400 MHz, DMSO-d6): 1.37 (s, 9H), 1.40-1.50 (m, 1H), 1.88 (br s, 1H), 1.95-2.05 (m, 2H), 2.60-2.95 (m, 2H), 3.61 (d, J=12 Hz, 1H), 3.70-3.80 (m, 2H), 7.01 (d, J=7.2 Hz, 1H), 7.08 (s, 1H), 7.85 (s, 1H), 9.11 (s, 1H), 9.46 (s, 1H), 12.72 (br s, 1H).

Step 2: 1-(3H-3,4,7,8-tetraaza-cyclopenta[a]naphthalen-9-yl)-piperidin-3-ylamine (131)

The preparation of compound 131 was carried out in a manner similar to that described for the preparation of compound (87). $^1$H NMR (400 MHz, DMSO-d6): 1.60-1.75 (m, 1H), 1.93 (s, 2H), 2.12-2.30 (m, 1H), 2.99-2.97 (m, 1H), 3.54-3.58 (m, 2H), 3.71 (d, J=10.4, 1H), 4.05 (d, J=10.0 Hz, 1H), 7.22 (br s, 1H) 8.11-8.13 (m, 1H), 8.55 (br s, 2H), 9.45 (s, 1H), 10.12 (s, 1H), 13.42 (br s, 1H).

Step 3: 1-(3H-3,4,7,8-tetraaza-cyclopenta[a]naphthalen-9-yl)-piperidin-3-ylamine derivative (132)

The preparation of compound 132 was carried out in a manner similar to that described above in method A or method B.

The compounds in Table 10 were synthesized according to the general method A1

TABLE 10

| Ex | Structure | IUPAC Name | 1H NMR |
|---|---|---|---|
| 106 | 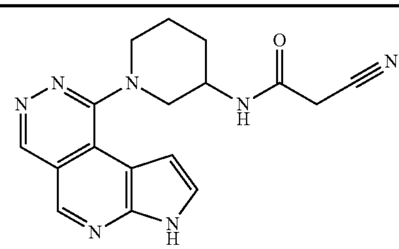 | 2-Cyano-N-[1-(3H-3,4,7,8-tetraaza-cyclopenta[a]naphthalen-9-yl)-piperidin-3-yl]-acetamide | $^1$HNMR (400 MHz, DMSO-d6): ☐ 1.40-1.60 (m, 1H), 1.86-2.08 (m, 3H), 2.60-3.10 (m, 2H), 3.45-3.59 (m, 1H), 3.64 (d, J = 2 Hz, 2H), 3.74 (d, J = 9.6 Hz, 1H), 4.03-4.12 (m, 1H), 7.11 (s, 1H), 7.86 (t, J = 2.4 Hz, 1H), 8.38 (d, J = 7.6 Hz, 1H), 9.11 (s, 1H), 9.47 (s, 1H), 12.37 (br s, 1H) |

TABLE 10-continued
| Ex | Structure | IUPAC Name | 1H NMR |
|---|---|---|---|
| 107 | 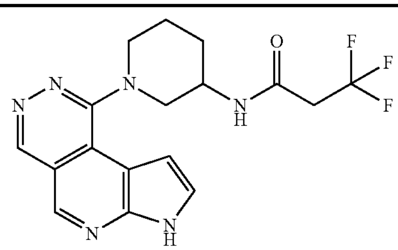 | 3,3,3-trifluoro-N-[1-(3H-3,4,7,8-tetraaza-cyclopenta[a]naphthalen-9-yl)-piperidin-3-yl]-propionamide | $^1$HNMR (400 MHz, DMSO-d6): ☐ 1.38-1.56 (m, 1H), 1.89-2.12 (m, 3H), 2.64-2.86 (m, 3H), 3.26 (q, J = 12.8 Hz, 2H), 3.34-3.56 (m, 1H), 3.72 (d, J = 11.2 Hz, 1H), 4.06-4.08 (m, 1H), 7.08 (d, J = 1.2 Hz, 1H), 7.8 (t, J = 3.2 Hz, 1H), 8.36 (d, J = 7.2 Hz, 1H), 9.08 (s, 1H), 9.44 (br s, 1H) |
Example 108
9-[4-[[3-[(4-fluorophenoxy)methyl]-1-piperidyl]sulfonylmethyl]-1-piperidyl]-3H-pyrrolo[3,2-f][1,7]naphthyridine (140)
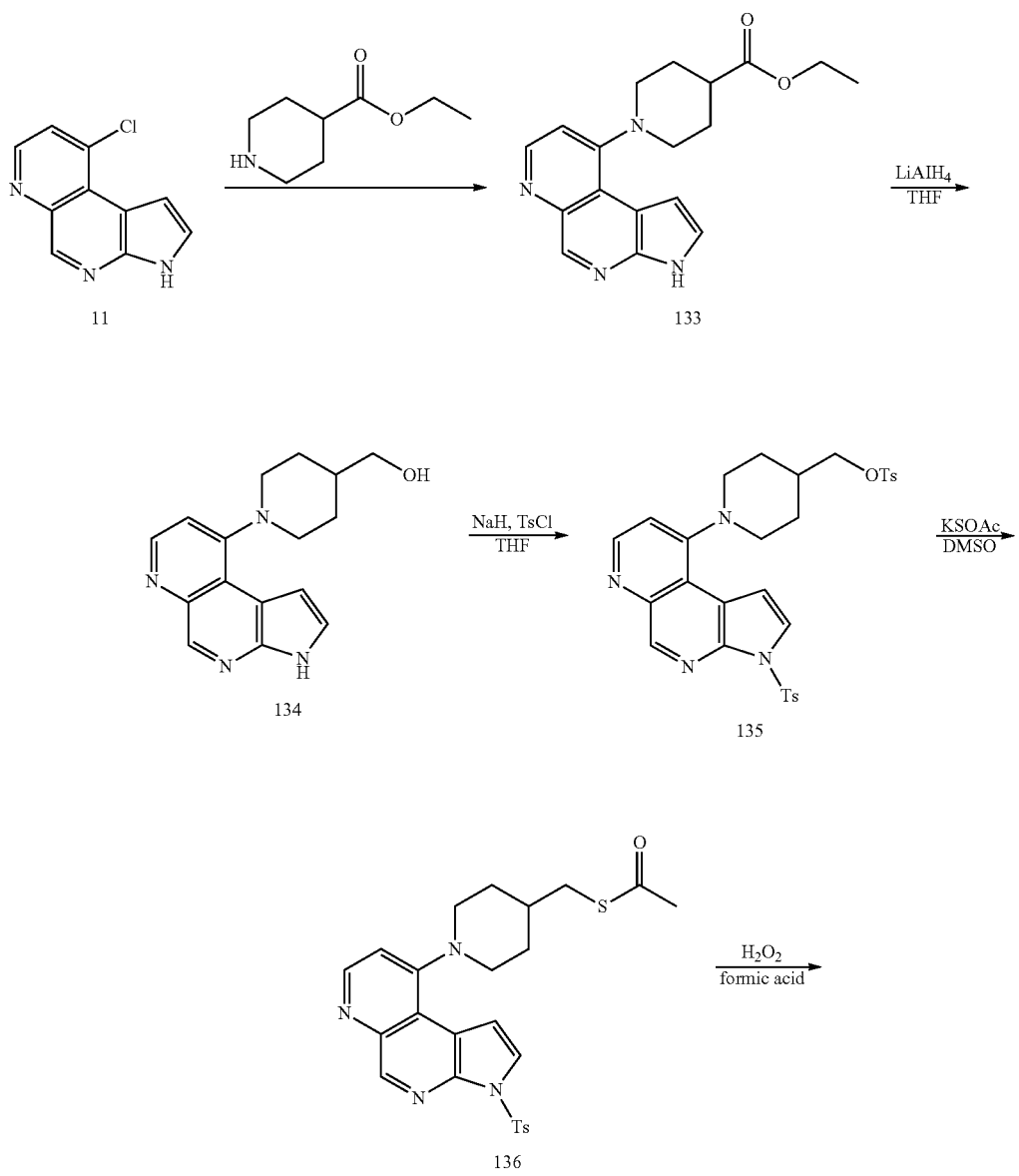

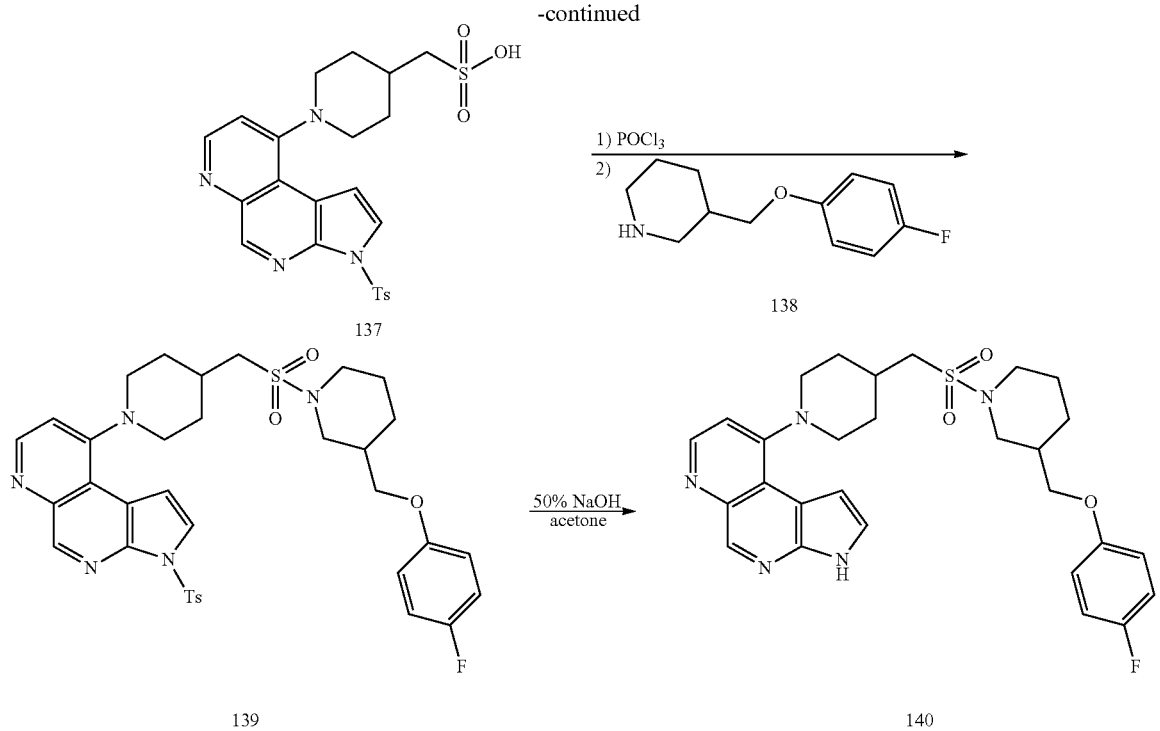

Step 1: Ethyl 1-(3H-pyrrolo[3,2-f][1,7]naphthyridin-9-yl)piperidine-4-carboxylate (133)

To compound 11 (2.5 g, 12.31 mmol) in a seal tube was added ethyl piperidine-4-carboxylate (9.6 g, 61.57 mmol). The tube was flushed with nitrogen and sealed with a teflon stopper. The reaction mixture was heated at 130° C. in an oil bath overnight. Following this, the reaction was diluted with $CH_2Cl_2$ (500 mL) and washed with brine. The organic layer was dried over sodium sulphate and concentrated to afford a crude residue which upon column chromatography yielded 2.8 g of the desired product. $^1$H-NMR (400 MHz, DMSO-d6): δ 1.21 (t, J=7.2 Hz, ☐3H), 1.89-2.09 (m, 4H), 2.48-2.55 (m, 1H), 2.68 (t, J=12 Hz, 2H), 3.51 (d, J=11.2 Hz, 2H), 4.12 (q, J=7.2 Hz, 2H), 7.05 (s, 1H), 7.24 (d, J=4.8 Hz, 1H), 7.59 (s, 1H), 8.69 (d, J=4.4 Hz, 1H), 8.92 (s, 1H), 12.20 (s, 1H).

Step 2: [1-(3H-pyrrolo[3,24-f][1,7]naphthyridin-9-yl)-4-piperidyl]methanol (134)

Compound 133 (2.5 g, 7.72 mmol) was taken in dry THF (20 mL) under an inert atmosphere. This was cooled to 0° C. followed by the addition of $LiAlH_4$ (0.88 g, 23.14 mmol). The suspension was warmed to room temperature and stirred at room temperature for 4 h. The reaction was quenched by addition saturated sodium sulphate solution. The solid was removed by filtration and the cake was washed with ethyl acetate (4×500 mL). The filtrate and washings were combined and concentrated to afford 2.2 g of the desired product. $^1$HNMR (400 MHz, DMSO-d6): δ 1.51-1.59 (m, 3H), ☐1.88 (d, J=8 Hz, 2H), 2.65 (t, J=10.4 Hz, 2H), 3.41 (t, J=4.4 Hz, 2H), 3.53 (d, J=10.8 Hz, 2H), 4.59 (t, J=5.2 Hz, 1H), 7.10 (s, 1H), 7.27 (d, J=4.8 Hz, 1H), 7.59 (s, 1H), 8.70 (d, J=4.4 Hz, 1H), 8.93 (s, 1H), 12.20 (s, 1H).

Step 3: [1-[3-(p-tolylsulfonyl)pyrrolo[3,2-f][1,7]naphthyridin-9-yl]-4-piperidyl]methyl 4-methylbenzenesulfonate (135)

Sodium hydride (0.13 g, 3.19 mmol) was taken in dry THF (5 mL) and cooled to 0° C. under an inert atmosphere. To this was added compound 134 (0.3 g, 1.06 mmol) in dry THF (1 mL). The resultant reaction was allowed to warm to room temperature and stirred for 1 h. Following this, the reaction was cooled in ice-water bath and tosyl chloride (0.61 g, 3.19 mmol) was slowly added. The reaction mixture was warmed to room temperature and stirred at room temperature overnight. Additional sodium hydride (0.13 g, 3.19 mmol) and tosyl chloride (0.61 g, 3.19 mmol) were added at 0° C. The reaction was further stirred at room temperature for 6 h. Following this, the reaction was quenched by drop-wise addition of $NH_4Cl$ solution. The THF was removed under vacuum and the residue diluted with water and extracted using $CH_2Cl_2$ (3×100 mL). The organics were combined, dried over sodium sulphate and concentrated to get oil, which upon column chromatography afforded 0.18 g of desired product. $^1$HNMR (400 MHz, CDCl3): δ 1.21-1.29 (m, 3H), 1.92 (d, J=10.4 Hz, 2H), 2.36 (s, 3H), 2.48 (s, 3H), 2.65 (t, J=11.6 Hz, 2H), 3.48 (d, J=10 Hz, 2H), 4.02 (d, J=5.6 Hz, 2H), 7.12 (d, J=5.2 Hz, 1H), 7.28 (d, J=4 Hz, 2H), 7.30-7.38 (m, 1H), 7.39 (d, J=8 Hz, 2H), 7.84 (d, J=6.8 Hz, 3H), 8.11 (d, J=8.4 Hz, 2H), 8.78 (d, J=4.8 Hz, 1H), 9.22 (s, 1H).

Step 4: S-[[1-[3-(p-tolylsulfonyl)pyrrolo[3,2-f][1,7]naphthyridin-9-yl]-4-piperidyl]methyl]ethanethioate (136)

Under a nitrogen atmosphere, compound 135 (0.5 g, 0.85 mmol) was dissolved in dry DMSO (3 mL) followed by the addition of potassium thioacetate (0.21 g, 1.87 mmol). The reaction was then heated at 40-44° C. overnight. The reaction mixture was diluted with aqueous $NaHCO_3$ solution (200 mL) and extracted with ethyl acetate (3×100 mL). The organic layers were combined, washed with brine, dried over sodium sulphate and concentrated to afford a crude residue. This was subjected to column chromatography to afford 0.38 g of the desired product. $^1$HNMR (400 MHz, DMSO-d6): δ 1.51-1.67 (m, 3H), 1.86-1.93 (m, 2H), 2.33 (s, 3H), 2.38 (s, 3H), 2.64 (t, J=10.8 Hz, 2H), 2.96 (s, 2H), 3.35-3.43 (m, 2H), 7.34 (d, J=3.6 Hz, 2H), 7.43 (d, J=8.4 Hz, 2H), 8.04 (d, J=8.4 Hz, 2H), 8.05-8.09 (m, 1H), 8.81 (d, J=4.4 Hz, 1H), 9.07 (s, 1H).

Step 5: [1-[3-(p-tolylsulfonyl)pyrrolo[3,2-f][1,7]naphthyridin-9-yl]-4-piperidyl]methanesulfonic acid (137)

Compound 136 (0.1 g, 0.20 mmol) was taken up in formic acid (0.5 mL) followed by addition of hydrogen peroxide (30% solution, 0.2 mL) at 0° C. The reaction mixture was stirred at room temperature for 4 h followed by addition of sodium metabisulphite (0.076 g, 0.40 mmol) in water (0.2 mL). The reaction mixture was neutralized to pH5 using 50% NaOH solution. The residue obtained was used as such without further purification. $^1$HNMR (400 MHz, DMSO-d6): δ 1.47-1.58 (m, 3H), 1.85-1.93 (m, 2H), 2.03-2.19 (m, 2H), 2.32 (s, 3H), 2.65 (t, J=12 Hz, 2H), 3.33-3.40 (m, 2H), 7.31-7.38 (m, 2H), 7.39-7.47 (m, 2H), 8.00-8.10 (m, 3H), 8.80 (d, J=4.8 Hz, 1H), 9.06 (s, 1H).

Step 6: 9-[4-[[3-[(4-fluorophenoxy)methyl]-1-piperidyl]sulfonylmethyl]-1-piperidyl]-3-(p-tolylsulfonyl)pyrrolo[3,2-f][1,7]naphthyridine (139)

To compound 137 (0.05 g, 0.1 mmol) was added POCl$_3$ (3 mL) and the resultant reaction mixture was heated under reflux for 4 h. The reaction mixture was then concentrated under vacuum and dried under high vacuum. The crude residue was taken up in dry CH$_2$Cl$_2$ (5 mL) followed by the addition of compound 138 (0.041 g, 0.2 mmol) and triethylamine (0.03 g, 0.3 mmol). The reaction was stirred overnight at room temperature. The reaction was diluted with CH$_2$Cl$_2$ (50 mL) and washed with brine (20 mL), dried over sodium sulphate and concentrated to an oil. This was subjected to purification via preparative TLC to afford 0.024 g of the desired product. $^1$HNMR (400 MHz, DMSO-d6): δ 1.66-1.81 (m, 3H), 1.82-1.94 (m, 3H), 2.21 (d, J=11.6 Hz, 4H), 2.35 (s, 3H), 2.67-2.81 (m, 3H), 2.81-2.89 (m, 1H), 2.93 (d, J=6 Hz, 1H), 3.49 (d, J=11.2 Hz, 3H), 3.73 (d, J=11.6 Hz, 1H), 3.80 (t, J=8.8 Hz, 1H), 3.86-3.93 (m, 2H), 6.80-6.85 (m, 2H), 6.96-7.00 (m, 2H), 7.13 (d, J=5.2 Hz, 1H), 7.26-7.32 (m, 3H), 7.84 (d, J=3.6 Hz, 1H), 8.11 (d, J=8.4 Hz, 2H), 8.80 (d, J=4.8 Hz, 1H), 9.22 (s, 1H).

Step 7: 9-[4-[[3-[(4-fluorophenoxy)methyl]-1-piperidyl]sulfonylmethyl]-1-piperidyl]-3H-pyrrolo[3,2-f][1,7]naphthyridine (140)

Compound 139 (0.02 g) was dissolved in acetone (5 mL) followed by the addition of 50% NaOH solution (0.1 mL). The reaction was then heated at 48-50° C. for 4 h. The reaction was concentrated and purified via preparative TLC to afford 5 mg of the desired product. $^1$HNMR (400 MHz, DMSO-d$_6$): δ 1.51-1.57 (m, 2H), 1.72-1.84 (m, 4H), 1.98-2.12 (m, 4H), 2.63-2.76 (m, 3H), 2.83 (t, J=9.2 Hz, 1H), 3.15 (d, J=4.8 Hz, 2H), 3.47-3.57 (m, 3H), 3.72 (d, J=8.4 Hz, 1H), 3.83 (t, J=8.8 Hz, 1H), 3.88-3.95 (m, 1H), 6.94-7.00 (m, 2H), 7.08-7.16 (m, 3H), 7.27 (d, J=4.8 Hz, 1H), 7.60 (s, 1H), 8.71 (d, J=4.8 Hz, 1H), 8.93 (s, 1H), 12.24 (s, 1H).

Preparation 34: 3-[(4-fluorophenoxy)methyl]piperidine (138)

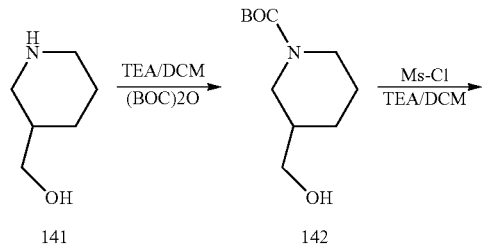

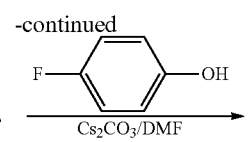

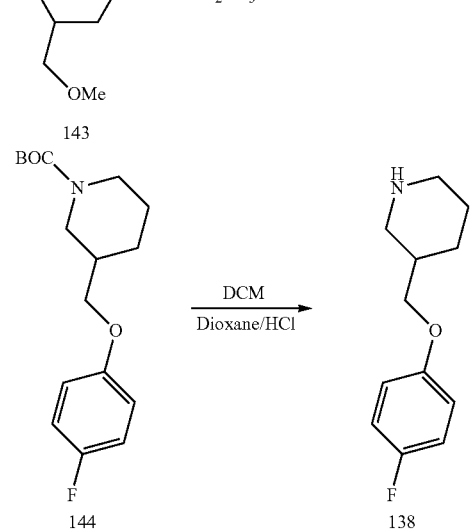

Step-I: tert-butyl 3-(hydroxymethyl)piperidine-1-carboxylate (142)

To a solution of Compound 141 (18 g, 156 mmol) and triethylamine (43 mL, 312 mmol) in DCM (200 mL) was added boc-anhydride (40 g, 187 mmol) at 0° C. under nitrogen atmosphere. It was stirred at room temperature for 4 h. To the reaction mixture water (200 mL) was added and extracted with DCM (2×200 mL) followed by washing with brine and organic layer was evaporated to get compound 142 (31 g, 92%) as white solid. $^1$HNMR (400 MHz, CDCl$_3$): δ 1.45 (s, 9H), 1.45-1.46 (m, 3H), 1.69-1.72 (m, 1H), 1.72-1.79 (m, 1H), 1.81-1.91 (m, 1H), 1.94-2.22 (m, 1H), 3.02-3.17 (m, 2H), 3.52 (bs, 1H), 3.70-3.76 (m, 2H).

Step-II: tert-butyl 3-(methylsulfonyloxymethyl)piperidine-1-carboxylate (143)

To a solution of compound 142 (30 g, 139 mmol) and triethylamine (29 mL, 208 mmol) in DCM (300 mL) was added Methane sulfonyl chloride (14 mL, 181 mmol) at 0° C. under nitrogen atmosphere. It was stirred at room temperature for 2 h. To the reaction mixture Aq.NaHCO$_3$ (200 mL) was added and extracted with DCM (2×200 mL) followed by washing with brine and organic layer was evaporated to get compound 143 (36 g, 88%) as white solid. $^1$HNMR (400 MHz, CDCl$_3$): δ 1.25-1.38 (m, 1H), 1.46 (s, 9H), 1.46-1.54 (m, 1H), 1.58-1.70 (m, 1H), 1.79-1.83 (m, 1H), 1.88-2.01 (m, 1H), 2.72-2.87 (m, 1H), 2.88-2.97 (m, 1H), 3.03 (s, 3H), 3.78-3.85 (m, 1H), 3.94 (bs, 1H), 4.03-4.16 (m, 2H).

Step-III: tert-butyl 3-[(4-fluorophenoxy)methyl]piperidine-1-carboxylate (144)

To a solution of compound 143 (3 g, 10.2 mmol) and Cs$_2$CO$_3$ (10 g, 30.6 mmol) in DMF (25 mL) was added 4-fluorophenol (1.37 mL, 12.2 mmol) at room temperature under nitrogen atmosphere. It was stirred at 60° C. for 6 h. Reaction mixture was diluted with water (200 mL) and extracted with ethylacetate (2×100 mL) followed by washing with brine and organic layer was evaporated to get compound 144 (2.5 g, 79%) as oil.

Step-IV: 3-[(4-fluorophenoxy)methyl]piperidine (138)

The preparation of compound 138 was carried out in a manner similar to that described for the preparation of compound (87). ¹HNMR (400 MHz, CDCl₃): δ 1.22-1.29 (m, 1H), 1.45-1.57 (m, 1H), 1.67-1.73 (m, 1H), 1.85-1.90 (m, 1H), 1.93-1.99 (m, 1H), 2.43-2.48 (m, 1H), 2.56-2.63 (m, 1H), 3.01-3.04 (m, 1H), 3.21-3.24 (m, 1H), 3.70-3.78 (m, 1H), 6.79-6.83 (m, 2H); 6.92-6.97 (m, 2H).

Example 109

1-[3-[(4-fluorophenoxy)methyl]-1-piperidyl]-2-[4-(3H-pyrrolo[3,2-f][1,7]naphthyridin-9-yl)piperazin-1-yl]ethanone (144)

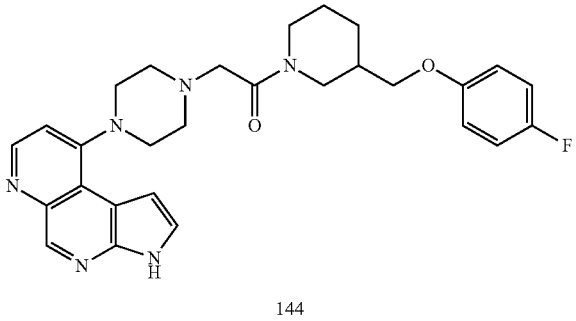

A mixture of compound 128 (40 mg, 0.088 mmol) and compound 145 (49 mg, 0.173 mmol) in DMF (2 ml) was added DIPEA (0.4 ml, 0.264 mmol) at room temperature under nitrogen atmosphere. It was heated at 50° C. for 16 hr. The reaction mixture was diluted with water (20 ml) and extracted with ethyl acetate (25 ml×2) followed by washing with brine and organic layer was evaporate. Residue obtained was purified by preparative TLC to get 1-[3-[(4-fluorophenoxy)methyl]-1-piperidyl]-2-[4-(3H-pyrrolo[3,2-f][1,7]naphthyridin-9-yl)piperazin-1-yl]ethanone (5 mg) as off white solid. ¹HNMR (400 MHz, CDCl₃): δ 1.21-1.31 (m, 2H), 1.34-1.74 (m, 3H), 1.75-2.17 (m, 3H), 2.64-2.80 (m, 2H), 2.86-3.16 (m, 4H), 3.21-3.62 (m, 4H), 3.79-3.95 (m, 1H), 4.00-4.62 (m, 2H); 6.78-6.84 (m, 2H), 6.92-7.00 (m, 2H), 7.07-7.10 (m, 1H), 7.13-7.17 (m, 1H), 7.43-7.47 (m, 1H), 8.75-8.81 (m, 1H), 9.13-9.16 (m, 1H), 9.82 (br s, 1H).

The compounds in Table 11 were synthesized according to the above synthetic procedure

TABLE 11

| Ex. | Structure | IUPAC Name | NMR data |
|---|---|---|---|
| 110 | 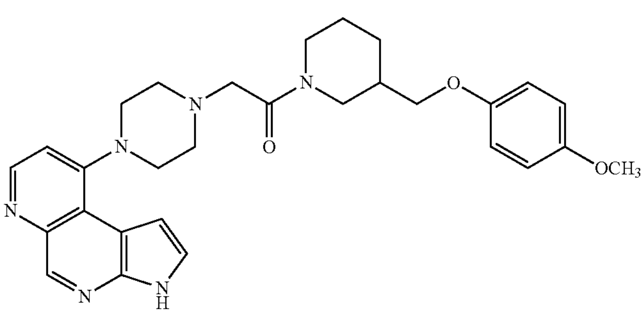 [SMILES: COc1ccc(OCC2CCCN(C(=O)CN3CCN(c4ccnc5cnc6[nH]ccc6c45)CC3)C2)cc1] | 1-[3-(4-Methoxy-phenoxymethyl)-piperidin-1-yl]-2-[4-(3H-3,4,6-triaza-cyclopenta[a]naphthalen-9-yl)-piper-azin-1-yl]-etha-none | ¹HNMR (400MHz, CDCl₃): δ 1.21-1.31 (m, 2H), 1.34-1.74 (m, 3H), 1.75-2.17 (m,3H), 2.64-2.80 (m, 2H), 2.86-3.16 (m, 4H), 3.21-3.62 (m, 4H), 3.71-3.76 (m, 3H), 3.79-3.91 (m, 1H), 4.00-4.62 (m, 2H); 6.82 (s, 4H), 7.07-7.10 (m, 1H), 7.13-7.17 (m, 1H), 7.43-7.47 (m, 1H), 8.75-8.81 (m, 1H), 9.13-9.16 (m, 1H), 9.72 (br s, 1H) |

TABLE 11-continued

| Ex. | Structure | IUPAC Name | NMR data |
|---|---|---|---|
| 111 | 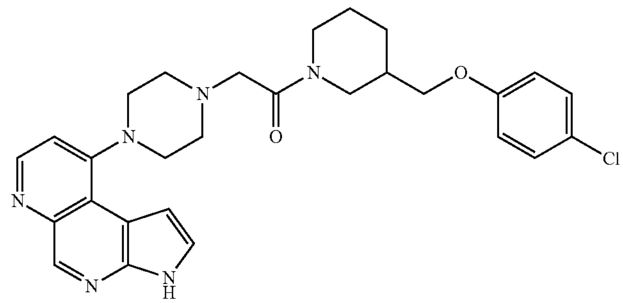 [SMILES: O=C(CN1CCN(c2ccnc3cnc4[nH]ccc4c23)CC1)N1CCCC(COc2ccc(Cl)cc2)C1] | 1-[3-(4-Chloro-phenoxymethyl)-piper-idin-1-yl]-2-[4-(3H-3,4,6-triaza-cyclopenta[a]naphthalen-9-yl)-piperazin-1-yl]ethanone | $^1$HNMR (400MHz, CDCl$_3$): δ 1.21-1.31 (m, 2H), 1.34-1.74 (m, 3H), 1.75-2.17 (m, 3H), 2.64-2.80 (m, 2H), 2.86-3.16 (m, 4H), 3.21-3.62 (m, 4H), 3.79-3.95 (m, 1H), 4.00-4.62 (m, 2H); 6.78-6.84 (m, 2H), 7.06-7.09 (m, 1H), 7.13-7.18 (m, 1H), 7.19-7.26 (m, 2H), 7.42-7.47 (m, 1H), 8.77-8.79 (m, 1H), 9.13-9.16 (m, 1H), 9.82 (br s, 1H) |
| 112 | 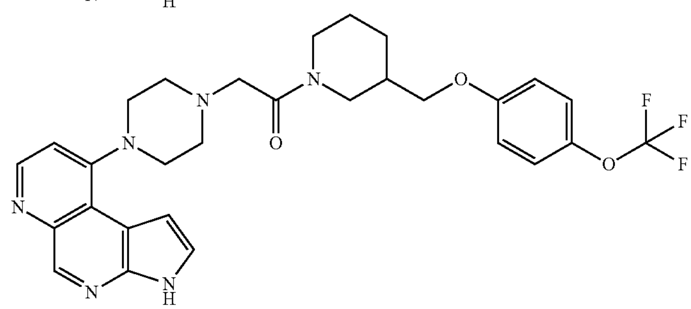 | 2-[4-(3H-pyrrolo[3,2-f][1,7]naphthyridin-9-yl)piperazin-1-yl]-1-[3-[[4-(trifluoromethoxy)phenoxy]methyl]-1-piperidyl]ethanone | $^1$HNMR (400MHz, DMSOd-6): δ 1.18-1.42 (m, 3H), 1.46-1.76 (m, 2H), 1.79-2.10 (m, 2H), 2.58-2.84 (m, 3H), 2.92-3.13 (m, 3H), 3.21-3.49 (m, 3H), 3.79-3.99 (m, 3H), 4.10-4.39 (m, 2H); 6.98-7.04 (m, 2H), 7.06-7.12 (m, 1H), 7.17-7.21 (m, 1H), 7.22-7.30 (m, 2H), 7.56-7.61 (m, 1H), 8.65-8.71 (m, 1H), 8.89-8.92 (m, 1H), 12.20 (br s, 1H) |

Preparation 35: 2-Chloro-1-[3-[(4-fluorophenoxy)methyl]-1-piperidyl]ethanone (145)

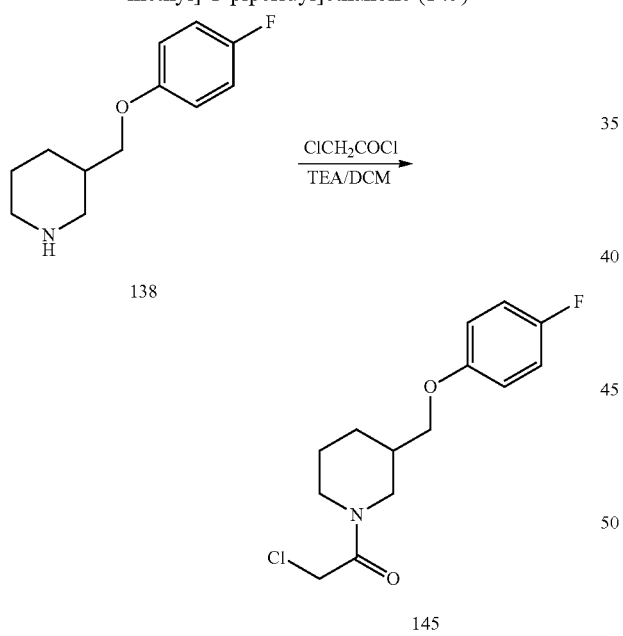

To a solution of compound 138 (200 mg, 0.957 mmol) and TEA (0.4 ml, 2.87 mmol) in DCM (5 ml) was added chloroacetylchloride (0.09 ml, 1.148 mmol) at room temperature under nitrogen atmosphere. After stirring at room temperature for 4 hr water (20 ml) was added and extracted with ethylacetate (25 ml×2) followed by washing with brine and organic layer was evaporate. Residue obtained was purified by column chromatography to get 2-chloro-1-[3-[(4-fluorophenoxy)methyl]-1-piperidyl]ethanone (90 mg, 33%) as oil. $^1$HNMR (400 MHz, CDCl$_3$): δ 1.41-1.51 (m, 1H), 1.51-1.71 (m, 1H), 1.74-1.88 (m, 1H), 1.90-2.00 (m, 1H), 2.01-2.21 (m, 1H), 2.69-2.99 (m, 1H), 3.09-3.21 (m, 1H), 3.75-3.86 (m, 2H), 3.87-3.96 (m, 1H), 4.02-4.16 (m, 2H); 4.20-4.55 (m, 1H) 6.78-6.84 (m, 2H), 7.20-7.25 (m, 2H)

The intermediates in Table 12 were synthesized according to the above synthetic procedure

TABLE 12

| Intermediate | Structure | IUPAC Name | NMR data |
| --- | --- | --- | --- |
| 1 | 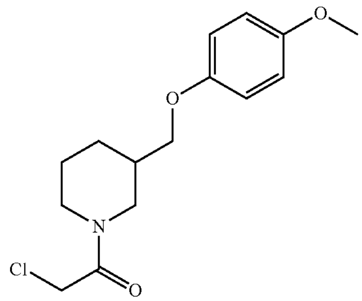 [SMILES: COc1ccc(OCC2CCCN(C(=O)CCl)C2)cc1] | 2-Chloro-1-[3-(4-methoxy-phenoxymethyl)-piperidin-1-yl]-ethanone | $^1$HNMR (400 MHz, CDCl$_3$): δ 1.41-1.51 (m, 1H), 1.51-1.71 (m, 1H), 1.74-1.88 (m, 1H), 1.90-2.00 (m, 1H), 2.01-2.21 (m, 1H), 2.69-2.99 (m, 1H), 3.09-3.21 (m, 1H), 3.75-3.86 (m, 2H), 3.87-3.96 (m, 1H), 4.02-4.16 (m, 2H); 4.20-4.55 (m, 1H) 6.81-6.84(m, 4H) |
| 2 | 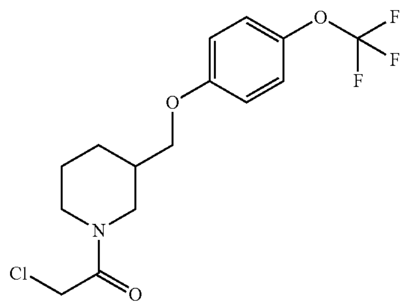 [SMILES: O=C(CCl)N1CCCC(COc2ccc(OC(F)(F)F)cc2)C1] | 2-chloro-1-[3-[[4-(trifluoromethoxy)phenoxy]methyl]-1-piperidyl]ethanone | $^1$HNMR (400 MHz, CDCl$_3$): δ 1.41-1.51 (m, 1H), 1.51-1.71 (m, 1H), 1.74-1.88 (m, 1H), 1.90-2.00 (m, 1H), 2.01-2.21 (m, 1H), 2.69-2.99 (m, 1H), 3.09-3.21 (m, 1H), 3.75-3.86 (m, 2H), 3.87-3.96 (m, 1H), 4.02-4.16 (m, 2H); 4.20-4.55 (m, 1H), 6.80-6.84 (m, 2H), 6.94-6.98 (m, 2H) |
| 3 | 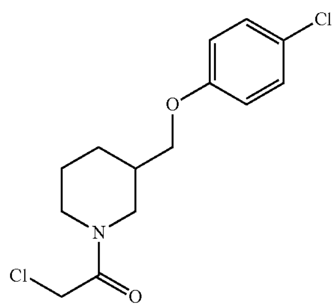 [SMILES: O=C(CCl)N1CCCC(COc2ccc(Cl)cc2)C1] | 2-Chloro-1-[3-(4-chloro-phenoxymethyl)-piperidin-1-yl]-ethanone | $^1$HNMR (400 MHz, CDCl$_3$): δ 1.41-1.51 (m, 1H), 1.51-1.71 (m, 1H), 1.74-1.88 (m, 1H), 1.90-2.00 (m, 1H), 2.01-2.21 (m, 1H), 2.69-2.99 (m, 1H), 3.09-3.21 (m, 1H), 3.75-3.86 (m, 2H), 3.87-3.96 (m, 1H), 4.02-4.16 (m, 2H); 4.20-4.55 (m, 1H) 6.78-6.84(m, 2H), 7.20-7.25(m, 2H) |

The below list of examples, but not to be limited to these numbers, can also be synthesized by following the general synthesis described above:

1-[3-(3H-pyrrolo[3,2-f][1,7]naphthyridin-9-yl)piperidine-1-carbonyl]cyclopropanecarbonitrile;
[3-(3H-pyrrolo[3,2-f][1,7]naphthyridin-9-yl)-1-piperidyl]-[1-(trifluoromethyl)cyclopropyl]methanone;
4-oxo-4-[3-(3H-pyrrolo[3,2-f][1,7]naphthyridin-9-yl)-1-piperidyl]butanenitrile;
4,4,4-trifluoro-1-[3-(3H-pyrrolo[3,2-f][1,7]naphthyridin-9-yl)-1-piperidyl]butan-1-one;
1-[3-(3H-pyrrolo[3,2-f][1,7]naphthyridin-9-yl)pyrrolidine-1-carbonyl]cyclopropanecarbonitrile;
[3-(3H-pyrrolo[3,2-f][1,7]naphthyridin-9-yl)pyrrolidin-1-yl]-[1-(trifluoromethyl)cyclopropyl]methanone;
4-oxo-4-[3-(3H-pyrrolo[3,2-f][1,7]naphthyridin-9-yl)pyrrolidin-1-yl]butanenitrile;
4,4,4-trifluoro-1-[3-(3H-pyrrolo[3,2-f][1,7]naphthyridin-9-yl)pyrrolidin-1-yl]butan-1-one;
[3-(3H-3,4,6,8-Tetraaza-cyclopenta[a]naphthalen-9-yl)-piperidine-1-sulfonyl]-acetonitrile;
9-[1-(2,2,2-Trifluoro-ethanesulfonyl)-piperidin-3-yl]-3H-3,4,6,8-tetraaza-cyclopenta[a]naphthalene;
9-(1-Methanesulfonyl-piperidin-3-yl)-3H-3,4,6,8-tetraaza-cyclopenta[a]naphthalene;
9-(1-Ethanesulfonyl-piperidin-3-yl)-3H-3,4,6,8-tetraaza-cyclopenta[a]naphthalene;
9-[1-(Propane-2-sulfonyl)-piperidin-3-yl]-3H-3,4,6,8-tetraaza-cyclopenta[a]naphthalene;
[3-(3H-3,4,6,8-Tetraaza-cyclopenta[a]naphthalen-9-yl)-pyrrolidine-1-sulfonyl]-acetonitrile;
9-[1-(2,2,2-Trifluoro-ethanesulfonyl)-pyrrolidin-3-yl]-3H-3,4,6,8-tetraaza-cyclopenta[a]naphthalene;
9-(1-Methanesulfonyl-pyrrolidin-3-yl)-3H-3,4,6,8-tetraaza-cyclopenta[a]naphthalene;
9-(1-Ethanesulfonyl-pyrrolidin-3-yl)-3H-3,4,6,8-tetraaza-cyclopenta[a]naphthalene;
9-[1-(Propane-2-sulfonyl)-pyrrolidin-3-yl]-3H-3,4,6,8-tetraaza-cyclopenta[a]naphthalene;
9-(1-Cyclopropanesulfonyl-pyrrolidin-3-yl)-3H-3,4,6,8-tetraaza-cyclopenta[a]naphthalene;
3-Oxo-3-[3-(3H-3,4,7,8-tetraaza-cyclopenta[a]naphthalen-9-yl)-piperidin-1-yl]-propionitrile;
3,3,3-Trifluoro-1-[3-(3H-3,4,7,8-tetraaza-cyclopenta[a]naphthalen-9-yl)-piperidin-1-yl]-propan-1-one;
2-Methyl-1-[3-(3H-3,4,7,8-tetraaza-cyclopenta[a]naphthalen-9-yl)-piperidin-1-yl]-propan-1-one;
Cyclopropyl-[3-(3H-3,4,7,8-tetraaza-cyclopenta[a]naphthalen-9-yl)-piperidin-1-yl]-methanone;
[3-(3H-3,4,7,8-Tetraaza-cyclopenta[a]naphthalen-9-yl)-piperidine-1-sulfonyl]-acetonitrile;

9-[1-(2,2,2-Trifluoro-ethanesulfonyl)-piperidin-3-yl]-3H-3,4,7,8-tetraaza-cyclopenta[a]naphthalene;
9-(1-Methanesulfonyl-piperidin-3-yl)-3H-3,4,7,8-tetraaza-cyclopenta[a]naphthalene;
9-(1-Ethanesulfonyl-piperidin-3-yl)-3H-3,4,7,8-tetraaza-cyclopenta[a]naphthalene;
9-[1-(Propane-2-sulfonyl)-piperidin-3-yl]-3H-3,4,7,8-tetraaza-cyclopenta[a]naphthalene;
9-(1-Cyclopropanesulfonyl-piperidin-3-yl)-3H-3,4,7,8-tetraaza-cyclopenta[a]naphthalene;
3-(3H-3,4,7,8-Tetraaza-cyclopenta[a]naphthalen-9-yl)-piperidine-1-carboxylic acid methylamide;
3-(3H-3,4,7,8-Tetraaza-cyclopenta[a]naphthalen-9-yl)-piperidine-1-carboxylic acid ethylamide;
3-(3H-3,4,7,8-Tetraaza-cyclopenta[a]naphthalen-9-yl)-piperidine-1-carboxylic acid isopropylamide;
3-Oxo-3-[3-(3H-3,4,7,8-tetraaza-cyclopenta[a]naphthalen-9-yl)-pyrrolidin-1-yl]-propionitrile;
3,3,3-Trifluoro-1-[3-(3H-3,4,7,8-tetraaza-cyclopenta[a]naphthalen-9-yl)-pyrrolidin-1-yl]-propan-1-one;
2-Methyl-1-[3-(3H-3,4,7,8-tetraaza-cyclopenta[a]naphthalen-9-yl)-pyrrolidin-1-yl]-propan-1-one;
Cyclopropyl-[3-(3H-3,4,7,8-tetraaza-cyclopenta[a]naphthalen-9-yl)-pyrrolidin-1-yl]-methanone;
[3-(3H-3,4,7,8-Tetraaza-cyclopenta[a]naphthalen-9-yl)-pyrrolidine-1-sulfonyl]-acetonitrile;
9-[1-(2,2,2-Trifluoro-ethanesulfonyl)-pyrrolidin-3-yl]-3H-3,4,7,8-tetraaza-cyclopenta[a]naphthalene;
9-(1-Methanesulfonyl-pyrrolidin-3-yl)-3H-3,4,7,8-tetraaza-cyclopenta[a]naphthalene;
9-(1-Ethanesulfonyl-pyrrolidin-3-yl)-3H-3,4,7,8-tetraaza-cyclopenta[a]naphthalene;
9-[1-(Propane-2-sulfonyl)-pyrrolidin-3-yl]-3H-3,4,7,8-tetraaza-cyclopenta[a]naphthalene;
9-(1-Cyclopropanesulfonyl-pyrrolidin-3-yl)-3H-3,4,7,8-tetraaza-cyclopenta[a]naphthalene;
3-(3H-3,4,7,8-Tetraaza-cyclopenta[a]naphthalen-9-yl)-pyrrolidine-1-carboxylic acid methylamide;
3-(3H-3,4,7,8-Tetraaza-cyclopenta[a]naphthalen-9-yl)-pyrrolidine-1-carboxylic acid ethylamide;
3-(3H-3,4,7,8-Tetraaza-cyclopenta[a]naphthalen-9-yl)-pyrrolidine-1-carboxylic acid isopropylamide;
3-oxo-3-[3-(7H-pyrrolo[2,3-h][2,6]naphthyridin-1-yl)-1-piperidyl]propanenitrile;
3,3,3-trifluoro-1-[3-(7H-pyrrolo[2,3-h][2,6]naphthyridin-1-yl)-1-piperidyl]propan-1-one;
2-methyl-1-[3-(7H-pyrrolo[2,3-h][2,6]naphthyridin-1-yl)-1-piperidyl]propan-1-one;
cyclopropyl-[3-(7H-pyrrolo[2,3-h][2,6]naphthyridin-1-yl)-1-piperidyl]methanone;
2-[[3-(7H-pyrrolo[2,3-h][2,6]naphthyridin-1-yl)-1-piperidyl]sulfonyl]acetonitrile;
1-[1-(2,2,2-trifluoroethylsulfonyl)-3-piperidyl]-7H-pyrrolo[2,3-c][2,6]naphthyridine;
1-(1-methylsulfonyl-3-piperidyl)-7H-pyrrolo[2,3-c][2,6]naphthyridine;
1-(1-ethylsulfonyl-3-piperidyl)-7H-pyrrolo[2,3-c][2,6]naphthyridine;
1-(1-isopropylsulfonyl-3-piperidyl)-7H-pyrrolo[2,3-c][2,6]naphthyridine;
1-(1-cyclopropylsulfonyl-3-piperidyl)-7H-pyrrolo[2,3-c][2,6]naphthyridine;
N-methyl-3-(7H-pyrrolo[2,3-h][2,6]naphthyridin-1-yl)piperidine-1-carboxamide;
N-ethyl-3-(7H-pyrrolo[2,3-h][2,6]naphthyridin-1-yl)piperidine-1-carboxamide;
N-isopropyl-3-(7H-pyrrolo[2,3-h][2,6]naphthyridin-1-yl)piperidine-1-carboxamide;
3-oxo-3-[3-(7H-pyrrolo[2,3-h][2,6]naphthyridin-1-yl)pyrrolidin-1-yl]propanenitrile;
3,3,3-trifluoro-1-[3-(7H-pyrrolo[2,3-h][2,6]naphthyridin-1-yl)pyrrolidin-1-yl]propan-1-one;
2-methyl-1-[3-(7H-pyrrolo[2,3-h][2,6]naphthyridin-1-yl)pyrrolidin-1-yl]propan-1-one;
cyclopropyl-[3-(7H-pyrrolo[2,3-h][2,6]naphthyridin-1-yl)pyrrolidin-1-yl]methanone;
2-[3-(7H-pyrrolo[2,3-h][2,6]naphthyridin-1-yl)pyrrolidin-1-yl]sulfonylacetonitrile;
1-[1-(2,2,2-trifluoroethylsulfonyl)pyrrolidin-3-yl]-7H-pyrrolo[2,3-c][2,6]naphthyridine;
1-(1-methylsulfonylpyrrolidin-3-yl)-7H-pyrrolo[2,3-c][2,6]naphthyridine;
1-(1-ethylsulfonylpyrrolidin-3-yl)-7H-pyrrolo[2,3-c][2,6]naphthyridine;
1-(1-isopropylsulfonylpyrrolidin-3-yl)-7H-pyrrolo[2,3-c][2,6]naphthyridine;
1-(1-cyclopropylsulfonylpyrrolidin-3-yl)-7H-pyrrolo[2,3-c][2,6]naphthyridine;
N-methyl-3-(7H-pyrrolo[2,3-h][2,6]naphthyridin-1-yl)pyrrolidine-1-carboxamide;
N-ethyl-3-(7H-pyrrolo[2,3-h][2,6]naphthyridin-1-yl)pyrrolidine-1-carboxamide;
N-isopropyl-3-(7H-pyrrolo[2,3-h][2,6]naphthyridin-1-yl)pyrrolidine-1-carboxamide;
3-oxo-3-[3-(3H-pyrrolo[2,3-c][2,7]naphthyridin-9-yl)-1-piperidyl]propanenitrile;
3,3,3-trifluoro-1-[3-(3H-pyrrolo[2,3-c][2,7]naphthyridin-9-yl)-1-piperidyl]propan-1-one;
2-methyl-1-[3-(3H-pyrrolo[2,3-c][2,7]naphthyridin-9-yl)-1-piperidyl]propan-1-one;
cyclopropyl-[3-(3H-pyrrolo[2,3-c][2,7]naphthyridin-9-yl)-1-piperidyl]methanone;
2-[[3-(3H-pyrrolo[2,3-c][2,7]naphthyridin-9-yl)-1-piperidyl]sulfonyl]acetonitrile;
9-[1-(2,2,2-trifluoroethylsulfonyl)-3-piperidyl]-3H-pyrrolo[2,3-c][2,7]naphthyridine;
9-(1-methylsulfonyl-3-piperidyl)-3H-pyrrolo[2,3-c][2,7]naphthyridine;
9-(1-ethylsulfonyl-3-piperidyl)-3H-pyrrolo[2,3-c][2,7]naphthyridine;
9-(1-isopropylsulfonyl-3-piperidyl)-3H-pyrrolo[2,3-c][2,7]naphthyridine;
9-(1-cyclopropylsulfonyl-3-piperidyl)-3H-pyrrolo[2,3-c][2,7]naphthyridine;
N-methyl-3-(3H-pyrrolo[2,3-c][2,7]naphthyridin-9-yl)piperidine-1-carboxamide;
N-ethyl-3-(3H-pyrrolo[2,3-c][2,7]naphthyridin-9-yl)piperidine-1-carboxamide;
N-isopropyl-3-(3H-pyrrolo[2,3-c][2,7]naphthyridin-9-yl)piperidine-1-carboxamide;
3-oxo-3-[3-(3H-pyrrolo[2,3-c][2,7]naphthyridin-9-yl)pyrrolidin-1-yl]propanenitrile;
3,3,3-trifluoro-1-[3-(3H-pyrrolo[2,3-c][2,7]naphthyridin-9-yl)pyrrolidin-1-yl]propan-1-one;
2-methyl-1-[3-(3H-pyrrolo[2,3-c][2,7]naphthyridin-9-yl)pyrrolidin-1-yl]propan-1-one;
cyclopropyl-[3-(3H-pyrrolo[2,3-c][2,7]naphthyridin-9-yl)pyrrolidin-1-yl]methanone;
2-[3-(3H-pyrrolo[2,3-c][2,7]naphthyridin-9-yl)pyrrolidin-1-yl]sulfonylacetonitrile;
9-[1-(2,2,2-trifluoroethylsulfonyl)pyrrolidin-3-yl]-3H-pyrrolo[2,3-c][2,7]naphthyridine;
9-(1-methylsulfonylpyrrolidin-3-yl)-3H-pyrrolo[2,3-c][2,7]naphthyridine;
9-(1-ethylsulfonylpyrrolidin-3-yl)-3H-pyrrolo[2,3-c][2,7]naphthyridine;
9-(1-isopropylsulfonylpyrrolidin-3-yl)-3H-pyrrolo[2,3-c][2,7]naphthyridine;
9-(1-cyclopropylsulfonylpyrrolidin-3-yl)-3H-pyrrolo[2,3-c][2,7]naphthyridine;
N-methyl-3-(3H-pyrrolo[2,3-c][2,7]naphthyridin-9-yl)pyrrolidine-1-carboxamide;
N-ethyl-3-(3H-pyrrolo[2,3-c][2,7]naphthyridin-9-yl)pyrrolidine-1-carboxamide;

N-isopropyl-3-(3H-pyrrolo[2,3-c][2,7]naphthyridin-9-yl)pyrrolidine-1-carboxamide;
3-[3-(7-Methyl-3H-3,4,6,8-tetraaza-cyclopenta[a]naphthalen-9-yl)-piperidin-1-yl]-3-oxo-propionitrile;
3,3,3-Trifluoro-1-[3-(7-methyl-3H-3,4,6,8-tetraaza-cyclopenta[a]naphthalen-9-yl)-piperidin-1-yl]-propan-1-one;
2-Methyl-1-[3-(7-methyl-3H-3,4,6,8-tetraaza-cyclopenta[a]naphthalen-9-yl)-piperidin-1-yl]-propan-1-one;
Cyclopropyl-[3-(7-methyl-3H-3,4,6,8-tetraaza-cyclopenta[a]naphthalen-9-yl)-piperidin-1-yl]-methanone;
[3-(7-Methyl-3H-3,4,6,8-tetraaza-cyclopenta[a]naphthalen-9-yl)-piperidine-1-sulfonyl]-acetonitrile;
7-Methyl-9-[1-(2,2,2-trifluoro-ethanesulfonyl)-piperidin-3-yl]-3H-3,4,6,8-tetraaza-cyclopenta[a]naphthalene;
9-(1-Methanesulfonyl-piperidin-3-yl)-7-methyl-3H-3,4,6,8-tetraaza-cyclopenta[a]naphthalene;
9-(1-Ethanesulfonyl-piperidin-3-yl)-7-methyl-3H-3,4,6,8-tetraaza-cyclopenta[a]naphthalene;
7-Methyl-9-[1-(propane-2-sulfonyl)-piperidin-3-yl]-3H-3,4,6,8-tetraaza-cyclopenta[a]naphthalene;
9-(1-Cyclopropanesulfonyl-piperidin-3-yl)-7-methyl-3H-3,4,6,8-tetraaza-cyclopenta[a]naphthalene;
3-(7-Methyl-3H-3,4,6,8-tetraaza-cyclopenta[a]naphthalen-9-yl)-piperidine-1-carboxylic acid methylamide;
3-(7-Methyl-3H-3,4,6,8-tetraaza-cyclopenta[a]naphthalen-9-yl)-piperidine-1-carboxylic acid ethylamide;
3-(7-Methyl-3H-3,4,6,8-tetraaza-cyclopenta[a]naphthalen-9-yl)-piperidine-1-carboxylic acid isopropylamide;
3-[3-(7-Methyl-3H-3,4,6,8-tetraaza-cyclopenta[a]naphthalen-9-yl)-pyrrolidin-1-yl]-3-oxo-propionitrile;
3,3,3-Trifluoro-1-[3-(7-methyl-3H-3,4,6,8-tetraaza-cyclopenta[a]naphthalen-9-yl)-pyrrolidin-1-yl]-propan-1-one;
2-Methyl-1-[3-(7-methyl-3H-3,4,6,8-tetraaza-cyclopenta[a]naphthalen-9-yl)-pyrrolidin-1-yl]-propan-1-one;
Cyclopropyl-[3-(7-methyl-3H-3,4,6,8-tetraaza-cyclopenta[a]naphthalen-9-yl)-pyrrolidin-1-yl]-methanone;
[3-(7-Methyl-3H-3,4,6,8-tetraaza-cyclopenta[a]naphthalen-9-yl)-pyrrolidine-1-sulfonyl]-acetonitrile;
7-Methyl-9-[1-(2,2,2-trifluoro-ethanesulfonyl)-pyrrolidin-3-yl]-3H-3,4,6,8-tetraaza-cyclopenta[a]naphthalene;
9-(1-Methanesulfonyl-pyrrolidin-3-yl)-7-methyl-3H-3,4,6,8-tetraaza-cyclopenta[a]naphthalene;
9-(1-Ethanesulfonyl-pyrrolidin-3-yl)-7-methyl-3H-3,4,6,8-tetraaza-cyclopenta[a]naphthalene;
7-Methyl-9-[1-(propane-2-sulfonyl)-pyrrolidin-3-yl]-3H-3,4,6,8-tetraaza-cyclopenta[a]naphthalene;
9-(1-Cyclopropanesulfonyl-pyrrolidin-3-yl)-7-methyl-3H-3,4,6,8-tetraaza-cyclopenta[a]naphthalene;
3-(7-Methyl-3H-3,4,6,8-tetraaza-cyclopenta[a]naphthalen-9-yl)-pyrrolidine-1-carboxylic acid methylamide;
3-(7-Methyl-3H-3,4,6,8-tetraaza-cyclopenta[a]naphthalen-9-yl)-pyrrolidine-1-carboxylic acid ethylamide;
3-(7-Methyl-3H-3,4,6,8-tetraaza-cyclopenta[a]naphthalen-9-yl)-pyrrolidine-1-carboxylic acid isopropylamide;
3-oxo-3-[5-(3H-pyrrolo[3,2-f][1,7]naphthyridin-9-yl)-3,6-dihydro-2H-pyridin-1-yl]propanenitrile;
3,3,3-trifluoro-1-[5-(3H-pyrrolo[3,2-f][1,7]naphthyridin-9-yl)-3,6-dihydro-2H-pyridin-1-yl]propan-1-one;
2-[[5-(3H-pyrrolo[3,2-f][1,7]naphthyridin-9-yl)-3,6-dihydro-2H-pyridin-1-yl]sulfonyl]acetonitrile;
9-[1-(2,2,2-trifluoroethylsulfonyl)-3,6-dihydro-2H-pyridin-5-yl]-3H-pyrrolo[3,2-f][1,7]naphthyridine;
9-(1-methylsulfonyl-3,6-dihydro-2H-pyridin-5-yl)-3H-pyrrolo[3,2-f][1,7]naphthyridine;
3-oxo-3-[5-(3H-pyrrolo[3,2-f][1,7]naphthyridin-9-yl)-3,4-dihydro-2H-pyridin-1-yl]propanenitrile;
3,3,3-trifluoro-1-[5-(3H-pyrrolo[3,2-f][1,7]naphthyridin-9-yl)-3,4-dihydro-2H-pyridin-1-yl]propan-1-one;
2-[[5-(3H-pyrrolo[3,2-f][1,7]naphthyridin-9-yl)-3,4-dihydro-2H-pyridin-1-yl]sulfonyl]acetonitrile;
9-[1-(2,2,2-trifluoroethylsulfonyl)-3,4-dihydro-2H-pyridin-5-yl]-3H-pyrrolo[3,2-f][1,7]naphthyridine;
9-(1-methylsulfonyl-3,4-dihydro-2H-pyridin-5-yl)-3H-pyrrolo[3,2-f][1,7]naphthyridine;
2-[[3-(3H-pyrrolo[3,2-f][1,7]naphthyridin-9-yl)-2,5-dihydropyrrol-1-yl]sulfonyl]acetonitrile;
9-[1-(2,2,2-trifluoroethylsulfonyl)-2,5-dihydropyrrol-3-yl]-3H-pyrrolo[3,2-f][1,7]naphthyridine;
9-(1-methylsulfonyl-2,5-dihydropyrrol-3-yl)-3H-pyrrolo[3,2f][1,7]naphthyridine;
3-[4-methyl-3-(3H-pyrrolo[3,2-f][1,7]naphthyridin-9-yl)-1-piperidyl]-3-oxo-propanenitrile;
3,3,3-trifluoro-1-[4-methyl-3-(3H-pyrrolo[3,2-f][1,7]naphthyridin-9-yl)-1-piperidyl]propan-1-one;
2-[[4-methyl-3-(3H-pyrrolo[3,2-f][1,7]naphthyridin-9-yl)-1-piperidyl]sulfonyl]acetonitrile;
9-[4-methyl-1-(2,2,2-trifluoroethylsulfonyl)-3-piperidyl]-3H-pyrrolo[3,2-f][1,7]naphthyridine;
9-(4-methyl-1-methylsulfonyl-3-piperidyl)-3H-pyrrolo[3,2-f][1,7]naphthyridine;
3-[3-methyl-4-(3H-pyrrolo[3,2-f][1,7]naphthyridin-9-yl)pyrrolidin-1-yl]-3-oxo-propanenitrile;
3,3,3-trifluoro-1-[3-methyl-4-(3H-pyrrolo[3,2-f][1,7]naphthyridin-9-yl)pyrrolidin-1-yl]propan-1-one;
2-[3-methyl-4-(3H-pyrrolo[3,2-f][1,7]naphthyridin-9-yl)pyrrolidin-1-yl]sulfonylacetonitrile;
9-[4-methyl-1-(2,2,2-trifluoroethylsulfonyl)pyrrolidin-3-yl]-3H-pyrrolo[3,2-f][1,7]naphthyridine;
9-(4-methyl-1-methylsulfonyl-pyrrolidin-3-yl)-3H-pyrrolo[3,2-f][1,7]naphthyridine;
3-[3-(2-methyl-3H-pyrrolo[3,2-f][1,7]naphthyridin-9-yl)-1-piperidyl]-3-oxo-propanenitrile;
3,3,3-trifluoro-1-[3-(2-methyl-3H-pyrrolo[3,2-f][1,7]naphthyridin-9-yl)-1-piperidyl]propan-1-one;
2-[[3-(2-methyl-3H-pyrrolo[3,2-f][1,7]naphthyridin-9-yl)-1-piperidyl]sulfonyl]acetonitrile;
2-methyl-9-[1-(2,2,2-trifluoroethylsulfonyl)-3-piperidyl]-3H-pyrrolo[3,2-f][1,7]naphthyridine;
2-methyl-9-(1-methylsulfonyl-3-piperidyl)-3H-pyrrolo[3,2-f][1,7]naphthyridine;
3-[3-(2-methyl-3H-pyrrolo[3,2-f][1,7]naphthyridin-9-yl)pyrrolidin-1-yl]-3-oxo-propanenitrile;
3,3,3-trifluoro-1-[3-(2-methyl-3H-pyrrolo[3,2-f][1,7]naphthyridin-9-yl)pyrrolidin-1-yl]propan-1-one;
2-[3-(2-methyl-3H-pyrrolo[3,2-f][1,7]naphthyridin-9-yl)pyrrolidin-1-yl]sulfonylacetonitrile;
2-methyl-9-[1-(2,2,2-trifluoroethylsulfonyl)pyrrolidin-3-yl]-3H-pyrrolo[3,2-f][1,7]naphthyridine;
2-methyl-9-(1-methylsulfonylpyrrolidin-3-yl)-3H-pyrrolo[3,2-f][1,7]naphthyridine;
3-oxo-3-[4-(3H-pyrrolo[3,2-f][1,7]naphthyridin-9-yl)-1-piperidyl]propanenitrile;
4-oxo-4-[4-(3H-pyrrolo[3,2-f][1,7]naphthyridin-9-yl)-1-piperidyl]butanenitrile;
4,4,4-trifluoro-1-[4-(3H-pyrrolo[3,2-f][1,7]naphthyridin-9-yl)-1-piperidyl]butan-1-one;
2-[[4-(3H-pyrrolo[3,2-f][1,7]naphthyridin-9-yl)-1-piperidyl]sulfonyl]acetonitrile;
9-[1-(2,2,2-trifluoroethylsulfonyl)-4-piperidyl]-3H-pyrrolo[3,2-f][1,7]naphthyridine;
9-(3-Morpholin-4-yl-piperidin-1-yl)-3H-3,4,6,7-tetraaza-cyclopenta[a]naphthalene;
9-(3-Cyclopropylmethoxy-piperidin-1-yl)-3H-3,4,6,7-tetraaza-cyclopenta[a]naphthalene;
2-Cyano-N-[1-(3H-3,4,6,7-tetraaza-cyclopenta[a]naphthalen-9-yl)-piperidin-3-yl]-acetamide;
1-(3H-3,4,6,7-Tetraaza-cyclopenta[a]naphthalen-9-yl)-piperidine-3-carboxylic acid cyanomethyl-amide;
2-Nitrilo-ethanesulfonic acid [1-(3H-3,4,6,7-tetraaza-cyclopenta[a]naphthalen-9-yl)-piperidin-3-yl]-amide;
1-(3H-3,4,6,7-Tetraaza-cyclopenta[a]naphthalen-9-yl)-piperidine-3-carboxylic acid cyanomethyl-methyl-amide;
2-Cyano-N-methyl-N-[1-(3H-3,4,6,7-tetraaza-cyclopenta[a]naphthalen-9-yl)-piperidin-3-yl]-acetamide;

1-(3H-3,4,6,7-Tetraaza-cyclopenta[a]naphthalen-9-yl)-pyrrolidine-3-carboxylic acid cyanomethyl-methyl-amide;
1-(3H-3,4,6,7-Tetraaza-cyclopenta[a]naphthalen-9-yl)-pyrrolidine-3-carboxylic acid methyl-(2,2,2-trifluoro-ethyl)-amide;
2-Cyano-N-methy 1-N-[1-(3H-3,4,6,7-tetraaza-cyclopenta[a]naphthalen-9-yl)-pyrrolidin-3-yl]-acetamide;
3,3,3-Trifluoro-N-methyl-N-[1-(3H-3,4,6,7-tetraaza-cyclopenta[a]naphthalen-9-yl)-pyrrolidin-3-yl]-propionamide;
1-(3H-3,4,6,7-Tetraaza-cyclopenta[a]naphthalen-9-yl)-pyrrolidine-3-carboxylic acid cyanomethyl-amide;
1-(3H-3,4,6,7-Tetraaza-cyclopenta[a]naphthalen-9-yl)-pyrrolidine-3-carboxylic acid (2,2,2-trifluoro-ethyl)-amide;
2,2,2-Trifluoro-ethanesulfonic acid [1-(3H-3,4,6,7-tetraaza-cyclopenta[a]naphthalen-9-yl)-pyrrolidin-3-yl]-amide;
2-Cyano-N-[1-(3H-3,4,6,7-tetraaza-cyclopenta[a]naphthalen-9-yl)-pyrrolidin-3-yl]-acetamide;
2-Nitrilo-ethanesulfonic acid [1-(3H-3,4,6,7-tetraaza-cyclopenta[a]naphthalen-9-yl)-pyrrolidin-3-yl]-amide;
3,3,3-Trifluoro-N-[1-(3H-3,4,6,7-tetraaza-cyclopenta[a]naphthalen-9-yl)-pyrrolidin-3-yl]-propionamide;
3,3,3-Trifluoro-N-[1-(3H-3,4,6,7-tetraaza-cyclopenta[a]naphthalen-9-yl)-piperidin-3-yl]-propionamide;
2,2,2-Trifluoro-ethanesulfonic acid [1-(3H-3,4,6,7-tetraaza-cyclopenta[a]naphthalen-9-yl)-piperidin-3-yl]-amide;
1-(3H-3,4,6,7-Tetraaza-cyclopenta[a]naphthalen-9-yl)-piperidine-4-carboxylic acid (2,2,2-trifluoro-ethyl)-amide;
1-(3H-3,4,6,7-Tetraaza-cyclopenta[a]naphthalen-9-yl)-piperidine-4-carboxylic acid methyl-(2,2,2-trifluoro-ethyl)-amide;
1-(3H-3,4,6,7-Tetraaza-cyclopenta[a]naphthalen-9-yl)-piperidine-4-carboxylic acid cyanomethyl-methyl-amide;
1-(3H-3,4,6,7-Tetraaza-cyclopenta[a]naphthalen-9-yl)-piperidine-4-carboxylic acid cyanomethyl-amide;
2-Cyano-N-[1-(3H-3,4,6,7-tetraaza-cyclopenta[a]naphthalen-9-yl)-piperidin-4-yl]-acetamide;
2-Cyano-N-methyl-N-[1-(3H-3,4,6,7-tetraaza-cyclopenta[a]naphthalen-9-yl)-piperidin-4-yl]-acetamide;
3,3,3-Trifluoro-N-methyl-N-[1-(3H-3,4,6,7-tetraaza-cyclopenta[a]naphthalen-9-yl)-piperidin-3-yl]-propionamide;
1-(3H-3,4,6,7-Tetraaza-cyclopenta[a]naphthalen-9-yl)-piperidine-3-carboxylic acid cyclopropylamide;
1-(3H-3,4,6,7-Tetraaza-cyclopenta[a]naphthalen-9-yl)-piperidine-3-carboxylic acid cyclopropyl-methyl-amide;
1-(3H-3,4,6,7-Tetraaza-cyclopenta[a]naphthalen-9-yl)-piperidine-3-carboxylic acid methyl-(2,2,2-trifluoro-ethyl)-amide;
6-Methyl-1-(3H-3,4,6,7-tetraaza-cyclopenta[a]naphthalen-9-yl)-piperidine-3-carboxylic acid cyclopropylamide;
1-(3H-3,4,6,7-Tetraaza-cyclopenta[a]naphthalen-9-yl)-piperidine-3-sulfonic acid (2,2,2-trifluoro-ethyl)-amide;
1-(3H-3,4,6,7-Tetraaza-cyclopenta[a]naphthalen-9-yl)-pyrrolidine-3-sulfonic acid (2,2,2-trifluoro-ethyl)-amide;
1-(3H-3,4,6,7-Tetraaza-cyclopenta[a]naphthalen-9-yl)-piperidine-3-carboxylic acid (2,2,2-trifluoro-ethyl)-amide;
2-Cyano-N-[1-(3H-3,4,6,8-tetraaza-cyclopenta[a]naphthalen-9-yl)-piperidin-3-yl]-acetamide;
2-Nitrilo-ethanesulfonic acid [1-(3H-3,4,6,8-tetraaza-cyclopenta[a]naphthalen-9-yl)-piperidin-3-yl]-amide;
1-(3H-3,4,6,8-Tetraaza-cyclopenta[a]naphthalen-9-yl)-piperidine-3-carboxylic acid cyanomethyl-methyl-amide;
2-Cyano-N-methyl-N-[1-(3H-3,4,6,8-tetraaza-cyclopenta[a]naphthalen-9-yl)-piperidin-3-yl]-acetamide;
1-(3H-3,4,6,8-Tetraaza-cyclopenta[a]naphthalen-9-yl)-pyrrolidine-3-carboxylic acid cyanomethyl-methyl-amide;
1-(3H-3,4,6,8-Tetraaza-cyclopenta[a]naphthalen-9-yl)-pyrrolidine-3-carboxylic acid methyl-(2,2,2-trifluoro-ethyl)-amide;
2-Cyano-N-methyl-N-[1-(3H-3,4,6,8-tetraaza-cyclopenta[a]naphthalen-9-yl)-pyrrolidin-3-yl]-acetamide;
3,3,3-Trifluoro-N-methyl-N-[1-(3H-3,4,6,8-tetraaza-cyclopenta[a]naphthalen-9-yl)-pyrrolidin-3-yl]-propionamide;
1-(3H-3,4,6,8-Tetraaza-cyclopenta[a]naphthalen-9-yl)-pyrrolidine-3-carboxylic acid cyanomethyl-amide;
1-(3H-3,4,6,8-Tetraaza-cyclopenta[a]naphthalen-9-yl)-pyrrolidine-3-carboxylic acid (2,2,2-trifluoro-ethyl)-amide;
1-(3H-3,4,6,8-Tetraaza-cyclopenta[a]naphthalen-9-yl)-piperidine-3-carboxylic acid cyanomethyl-amide;
2,2,2-Trifluoro-ethanesulfonic acid [1-(3H-3,4,6,8-tetraaza-cyclopenta[a]naphthalen-9-yl)-pyrrolidin-3-yl]-amide;
Cyclopropanesulfonic acid [1-(3H-3,4,6,8-tetraaza-cyclopenta[a]naphthalen-9-yl)-pyrrolidin-3-yl]-amide;
Propane-2-sulfonic acid [1-(3H-3,4,6,8-tetraaza-cyclopenta[a]naphthalen-9-yl)-pyrrolidin-3-yl]-amide;
2-Cyano-N-[1-(3H-3,4,6,8-tetraaza-cyclopenta[a]naphthalen-9-yl)-pyrrolidin-3-yl]-acetamide;
2-Nitrilo-ethanesulfonic acid [1-(3H-3,4,6,8-tetraaza-cyclopenta[a]naphthalen-9-yl)-pyrrolidin-3-yl]-amide;
1-Isopropyl-3-[1-(3H-3,4,6,8-tetraaza-cyclopenta[a]naphthalen-9-yl)-pyrrolidin-3-yl]urea;
N-[1-(3H-3,4,6,8-Tetraaza-cyclopenta[a]naphthalen-9-yl)-pyrrolidin-3-yl]-isobutyramide;
3,3,3-Trifluoro-N-[1-(3H-3,4,6,8-tetraaza-cyclopenta[a]naphthalen-9-yl)-pyrrolidin-3-yl]-propionamide;
1-(3H-3,4,6,8-Tetraaza-cyclopenta[a]naphthalen-9-yl)-pyrrolidine-3-carboxylic acid cyclopropylamide;
N-[1-(3H-3,4,6,8-Tetraaza-cyclopenta[a]naphthalen-9-yl)-piperidin-3-yl]-methanesulfonamide;
C,C,C-Trifluoro-N-[1-(3H-3,4,6,8-tetraaza-cyclopenta[a]naphthalen-9-yl)-piperidin-3-yl]-methanesulfonamide;
2,2,2-Trifluoro-ethanesulfonic acid [1-(3H-3,4,6,8-tetraaza-cyclopenta[a]naphthalen-9-yl)-piperidin-3-yl]-amide;
1-(3H-3,4,6,8-Tetraaza-cyclopenta[a]naphthalen-9-yl)-piperidine-4-carboxylic acid (2,2,2-trifluoro-ethyl)-amide;
1-(3H-3,4,6,8-Tetraaza-cyclopenta[a]naphthalen-9-yl)-piperidine-4-carboxylic acid methyl-(2,2,2-trifluoro-ethyl)-amide;
1-(3H-3,4,6,8-Tetraaza-cyclopenta[a]naphthalen-9-yl)-piperidine-4-carboxylic acid cyanomethyl-methyl-amide;
1-(3H-3,4,6,8-Tetraaza-cyclopenta[a]naphthalen-9-yl)-piperidine-4-carboxylic acid cyanomethyl-amide;
2-Cyano-N-[1-(3H-3,4,6,8-tetraaza-cyclopenta[a]naphthalen-9-yl)-piperidin-4-yl]-acetamide;
2-Cyano-N-methyl-N-[1-(3H-3,4,6,8-tetraaza-cyclopenta[a]naphthalen-9-yl)-piperidin-4-yl]-acetamide;
2-Cyclopropyl-N-methyl-N-[1-(3H-3,4,6,8-tetraaza-cyclopenta[a]naphthalen-9-yl)-piperidin-3-yl]-acetamide;
3,3,3-Trifluoro-N-methyl-N-[1-(3H-3,4,6,8-tetraaza-cyclopenta[a]naphthalen-9-yl)-piperidin-3-yl]-propionamide;
Cyclopentanecarboxylic acid methyl-[1-(3H-3,4,6,8-tetraaza-cyclopenta[a]naphthalen-9-yl)-piperidin-3-yl]-amide;
Cyclopropanecarboxylic acid [1-(3H-3,4,6,8-tetraaza-cyclopenta[a]naphthalen-9-yl)-piperidin-3-yl]-amide;
3,3,3-Trifluoro-N-[1-(3H-3,4,6,8-tetraaza-cyclopenta[a]naphthalen-9-yl)-piperidin-3-yl]-propionamide;
1-(3H-3,4,6,8-Tetraaza-cyclopenta[a]naphthalen-9-yl)-piperidine-4-carboxylic acid isopropylamide;
1-(3H-3,4,6,8-Tetraaza-cyclopenta[a]naphthalen-9-yl)-piperidine-4-carboxylic acid cyclopropylamide;
1-(3H-3,4,6,8-Tetraaza-cyclopenta[a]naphthalen-9-yl)-piperidine-4-carboxylic acid (2-methoxy-ethyl)-amide;
1-(3H-3,4,6,8-Tetraaza-cyclopenta[a]naphthalen-9-yl)-piperidine-3-carboxylic acid cyclopropylamide;
1-(3H-3,4,6,8-Tetraaza-cyclopenta[a]naphthalen-9-yl)-piperidine-3-carboxylic acid methyl-(2,2,2-trifluoro-ethyl)-amide;
1-(3H-3,4,6,8-Tetraaza-cyclopenta[a]naphthalen-9-yl)-piperidine-3-carboxylic acid (2,2,2-trifluoro-ethyl)-amide;
1-(3H-3,4,6,8-Tetraaza-cyclopenta[a]naphthalen-9-yl)-piperidine-3-carboxylic acid isopropylamide;
1-(3H-3,4,6,8-Tetraaza-cyclopenta[a]naphthalen-9-yl)-piperidine-3-carboxylic acid cyclopropyl-methyl-amide 6-Methyl-1-(3H-3,4,6,8-tetraaza-cyclopenta[a]naphthalen-9-yl)-piperidine-3-carboxylic acid cyclopropylamide;
1-(3H-3,4,6,8-Tetraaza-cyclopenta[a]naphthalen-9-yl)-piperidine-3-sulfonic acid (2,2,2-trifluoro-ethyl)-amide;
1-(3H-3,4,6,8-Tetraaza-cyclopenta[a]naphthalen-9-yl)-pyrrolidine-3-sulfonic acid (2,2,2-trifluoro-ethyl)-amide;
2-Cyano-N-[1-(7-methyl-3H-3,4,6,8-tetraaza-cyclopenta[a]naphthalen-9-yl)-piperidin-3-yl]-acetamide;
2-Nitrilo-ethanesulfonic acid [1-(7-methyl-3H-3,4,6,8-tetraaza-cyclopenta[a]naphthalen-9-yl)-piperidin-3-yl]-amide;
1-(7-Methyl-3H-3,4,6,8-tetraaza-cyclopenta[a]naphthalen-9-yl)-pyrrolidine-3-carboxylic acid cyanomethyl-amide;
1-(7-Methyl-3H-3,4,6,8-tetraaza-cyclopenta[a]naphthalen-9-yl)-pyrrolidine-3-carboxylic acid (2,2,2-trifluoro-ethyl)-amide;
1-(7-Methyl-3H-3,4,6,8-tetraaza-cyclopenta[a]naphthalen-9-yl)-piperidine-3-carboxylic acid cyanomethyl-amide;
1-(7-Methyl-3H-3,4,6,8-tetraaza-cyclopenta[a]naphthalen-9-yl)-piperidine-3-carboxylic acid cyanomethyl-methyl-amide;
2-Cyano-N-methyl-N-[1-(7-methyl-3H-3,4,6,8-tetraaza-cyclopenta[a]naphthalen-9-yl)-piperidin-3-yl]-acetamide;
1-(7-Methyl-3H-3,4,6,8-tetraaza-cyclopenta[a]naphthalen-9-yl)-pyrrolidine-3-carboxylic acid cyanomethyl-methyl-amide;
1-(7-Methyl-3H-3,4,6,8-tetraaza-cyclopenta[a]naphthalen-9-yl)-pyrrolidine-3-carboxylic acid methyl-(2,2,2-trifluoro-ethyl)-amide;
2-Cyano-N-methyl-N-[1-(7-methyl-3H-3,4,6,8-tetraaza-cyclopenta[a]naphthalen-9-yl)-pyrrolidin-3-yl]-acetamide;
3,3,3-Trifluoro-N-methyl-N-[1-(7-methyl-3H-3,4,6,8-tetraaza-cyclopenta[a]naphthalen-9-yl)-pyrrolidin-3-yl]-propionamide;
2,2,2-Trifluoro-ethanesulfonic acid [1-(7-methyl-3H-3,4,6,8-tetraaza-cyclopenta[a]naphthalen-9-yl)-pyrrolidin-3-yl]-amide;
2-Nitrilo-ethanesulfonic acid [1-(7-methyl-3H-3,4,6,8-tetraaza-cyclopenta[a]naphthalen-9-yl)-pyrrolidin-3-yl]-amide;
3,3,3-Trifluoro-N-[1-(7-methyl-3H-3,4,6,8-tetraaza-cyclopenta[a]naphthalen-9-yl)-pyrrolidin-3-yl]-propionamide;
N-[1-(7-Methyl-3H-3,4,6,8-tetraaza-cyclopenta[a]naphthalen-9-yl)-pyrrolidin-3-yl]-methanesulfonamide;
2-Cyano-N-[1-(7-methyl-3H-3,4,6,8-tetraaza-cyclopenta[a]naphthalen-9-yl)-pyrrolidin-3-yl]-acetamide;
N-[1-(7-Methyl-3H-3,4,6,8-tetraaza-cyclopenta[a]naphthalen-9-yl)-piperidin-3-yl]-methanesulfonamide;
1-(7-Methyl-3H-3,4,6,8-tetraaza-cyclopenta[a]naphthalen-9-yl)-piperidine-4-carboxylic acid methyl-(2,2,2-trifluoro-ethyl)-amide;
1-(7-Methyl-3H-3,4,6,8-tetraaza-cyclopenta[a]naphthalen-9-yl)-piperidine-4-carboxylic acid cyanomethyl-methyl-amide;
1-(7-Methyl-3H-3,4,6,8-tetraaza-cyclopenta[a]naphthalen-9-yl)-piperidine-4-carboxylic acid cyanomethyl-amide;
2-Cyano-N-[1-(7-methyl-3H-3,4,6,8-tetraaza-cyclopenta[a]naphthalen-9-yl)-piperidin-4-yl]-acetamide;
2-Cyano-N-methyl-N-[1-(7-methyl-3H-3,4,6,8-tetraaza-cyclopenta[a]naphthalen-9-yl)-piperidin-4-yl]-acetamide;
2,2,2-Trifluoro-ethanesulfonic acid [1-(7-methyl-3H-3,4,6,8-tetraaza-cyclopenta[a]naphthalen-9-yl)-piperidin-3-yl]-amide;
1-(7-Methyl-3H-3,4,6,8-tetraaza-cyclopenta[a]naphthalen-9-yl)-piperidine-4-carboxylic acid (2,2,2-trifluoro-ethyl)-amide;
3,3,3-Trifluoro-N-[1-(7-methyl-3H-3,4,6,8-tetraaza-cyclopenta[a]naphthalen-9-yl)-piperidin-3-yl]-propionamide;
3,3,3-Trifluoro-N-methyl-N-[1-(7-methyl-3H-3,4,6,8-tetraaza-cyclopenta[a]naphthalen-9-yl)-piperidin-3-yl]-propionamide;
1-(7-Methyl-3H-3,4,6,8-tetraaza-cyclopenta[a]naphthalen-9-yl)-piperidine-3-carboxylic acid cyclopropylamide;
1-(7-Methyl-3H-3,4,6,8-tetraaza-cyclopenta[a]naphthalen-9-yl)-piperidine-3-carboxylic acid isopropylamide;
1-(7-Methyl-3H-3,4,6,8-tetraaza-cyclopenta[a]naphthalen-9-yl)-piperidine-3-carboxylic acid cyclopropyl-methyl-amide;
1-(7-Methyl-3H-3,4,6,8-tetraaza-cyclopenta[a]naphthalen-9-yl)-piperidine-3-carboxylic acid methyl-(2,2,2-trifluoro-ethyl)-amide;
6-Methyl-1-(7-methyl-3H-3,4,6,8-tetraaza-cyclopenta[a]naphthalen-9-yl)-piperidine-3-carboxylic acid cycloPropylamide;
1-(7-Methyl-3H-3,4,6,8-tetraaza-cyclopenta[a]naphthalen-9-yl)-piperidine-3-sulfonic acid (2,2,2-trifluoro-ethyl)-amide;
1-(7-Methyl-3H-3,4,6,8-tetraaza-cyclopenta[a]naphthalen-9-yl)-pyrrolidine-3-sulfonic acid (2,2,2-trifluoro-ethyl)-amide;
1-(7-Methyl-3H-3,4,6,8-tetraaza-cyclopenta[a]naphthalen-9-yl)-piperidine-3-carboxylic acid (2,2,2-trifluoro-ethyl)-amide;
9-(3-Cyclopropylmethoxy-pyrrolidin-1-yl)-3H-3,4,7,8-tetraaza-cyclopenta[a]naphthalene;
9-(3-Morpholin-4-yl-piperidin-1-yl)-3H-3,4,7,8-tetraaza-cyclopenta[a]naphthalene;
Cyclopropylmethyl-methyl-[1-(3H-3,4,7,8-tetraaza-cyclopenta[a]naphthalen-9-yl)-pyrrolidin-3-yl]-amine;
2-Cyano-N-[1-(3H-3,4,7,8-tetraaza-cyclopenta[a]naphthalen-9-yl)-piperidin-3-yl]-acetamide;
9-Morpholin-4-yl-3H-3,4,7,8-tetraaza-cyclopenta[a]naphthalene;
1-(3H-3,4,7,8-tetraaza-cyclopenta[a]naphthalen-9-yl)-pyrrolidine-3-carboxylic acid (2,2,2-trifluoro-ethyl)-amide;
2-Nitrilo-ethanesulfonic acid [1-(3H-3,4,7,8-tetraaza-cyclopenta[a]naphthalen-9-yl)-piperidin-3-yl]-amide;
1-(3H-3,4,7,8-Tetraaza-cyclopenta[a]naphthalen-9-yl)-pyrrolidine-3-carboxylic acid cyanomethyl-amide;
1-(3H-3,4,7,8-Tetraaza-cyclopenta[a]naphthalen-9-yl)-piperidine-3-carboxylic acid cyanomethyl-amide;
1-(3H-3,4,7,8-Tetraaza-cyclopenta[a]naphthalen-9-yl)-piperidine-3-carboxylic acid cyanomethyl-methyl-amide;
2-Cyano-N-methyl-N-[1-(3H-3,4,7,8-tetraaza-cyclopenta[a]naphthalen-9-yl)-piperidin-3-yl]-acetamide;
1-(3H-3,4,7,8-Tetraaza-cyclopenta[a]naphthalen-9-yl)-pyrrolidine-3-carboxylic acid cyanomethyl-methyl-amide;
1-(3H-3,4,7,8-Tetraaza-cyclopenta[a]naphthalen-9-yl)-pyrrolidine-3-carboxylic acid methyl-(2,2,2-trifluoro-ethyl)-amide;
2-Cyano-N-methyl-N-[1-(3H-3,4,7,8-tetraaza-cyclopenta[a]naphthalen-9-yl)-pyrrolidin-3-yl]-acetamide;
3,3,3-Trifluoro-N-methyl-N-[1-(3H-3,4,7,8-tetraaza-cyclopenta[a]naphthalen-9-yl)-pyrrolidin-3-yl]-propionamide;
2,2,2-Trifluoro-ethanesulfonic acid [1-(3H-3,4,7,8-tetraaza-cyclopenta[a]naphthalen-9-yl)-pyrrolidin-3-yl]-amide;
Cyclopropanesulfonic acid [1-(3H-3,4,7,8-tetraaza-cyclopenta[a]naphthalen-9-yl)-pyrrolidin-3-yl]-amide;
1-Isopropyl-3-[1-(3H-3,4,7,8-tetraaza-cyclopenta[a]naphthalen-9-yl)-pyrrolidin-3-yl]-urea;
N-[1-(3H-3,4,7,8-Tetraaza-cyclopenta[a]naphthalen-9-yl)-pyrrolidin-3-yl]-methanesulfonamide;
2-Nitrilo-ethanesulfonic acid [1-(3H-3,4,7,8-tetraaza-cyclopenta[a]naphthalen-9-yl)-pyrrolidin-3-yl]-amide;
2-Cyano-N-[1-(3H-3,4,7,8-tetraaza-cyclopenta[a]naphthalen-9-yl)-pyrrolidin-3-yl]-acetamide;
3,3,3-Trifluoro-N-[1-(3H-3,4,7,8-tetraaza-cyclopenta[a]naphthalen-9-yl)-pyrrolidin-3-yl]-propionamide;
3,3,3-Trifluoro-N-[1-(3H-3,4,7,8-tetraaza-cyclopenta[a]naphthalen-9-yl)-piperidin-3-yl]-methanesulfonamide;
2,2,2-Trifluoro-ethanesulfonic acid [1-(3H-3,4,7,8-tetraaza-cyclopenta[a]naphthalen-9-yl)-piperidin-3-yl]-amide;

1-(3H-3,4,7,8-Tetraaza-cyclopenta[a]naphthalen-9-yl)-piperidine-4-carboxylic acid (2,2,2-trifluoro-ethyl)-amide;
1-(3H-3,4,7,8-Tetraaza-cyclopenta[a]naphthalen-9-yl)-piperidine-4-carboxylic acid methyl-(2,2,2-trifluoro-ethyl)-amide;
1-(3H-3,4,7,8-Tetraaza-cyclopenta[a]naphthalen-9-yl)-piperidine-4-carboxylic acid cyanomethyl-methyl-amide;
1-(3H-3,4,7,8-Tetraaza-cyclopenta[a]naphthalen-9-yl)-piperidine-4-carboxylic acid cyanomethyl-amide;
2-Cyano-N-[1-(3H-3,4,7,8-tetraaza-cyclopenta[a]naphthalen-9-yl)-piperidin-4-yl]-acetamide;
2-Cyano-N-methyl-N-[1-(3H-3,4,7,8-tetraaza-cyclopenta[a]naphthalen-9-yl)-piperidin-4-yl]-acetamide;
3,3,3-Trifluoro-N-methyl-N-[1-(3H-3,4,7,8-tetraaza-cyclopenta[a]naphthalen-9-yl)-piperidin-3-yl]-propionamide;
3,3,3-Trifluoro-N-[1-(3H-3,4,7,8-tetraaza-cyclopenta[a]naphthalen-9-yl)-piperidin-3-yl]-propionamide;
1-(3H-3,4,7,8-Tetraaza-cyclopenta[a]naphthalen-9-yl)-piperidine-3-carboxylic acid cyclopropylamide;
1-(3H-3,4,7,8-Tetraaza-cyclopenta[a]naphthalen-9-yl)-piperidine-3-carboxylic acid isopropylamide;
1-(3H-3,4,7,8-Tetraaza-cyclopenta[a]naphthalen-9-yl)-piperidine-3-carboxylic acid cyclopropyl-methyl-amide;
1-(3H-3,4,7,8-Tetraaza-cyclopenta[a]naphthalen-9-yl)-piperidine-3-carboxylic acid methyl-(2,2,2-trifluoro-ethyl)-amide;
6-Methyl-1-(3H-3,4,7,8-tetraaza-cyclopenta[a]naphthalen-9-yl)-piperidine-3-carboxylic acid cyclopropylamide;
1-(3H-3,4,7,8-Tetraaza-cyclopenta[a]naphthalen-9-yl)-pyrrolidine-3-sulfonic acid (2,2,2-trifluoro-ethyl)-amide;
1-(3H-3,4,7,8-Tetraaza-cyclopenta[a]naphthalen-9-yl)-piperidine-3-sulfonic acid (2,2,2-trifluoro-ethyl)-amide;
1-(3H-3,4,7,8-Tetraaza-cyclopenta[a]naphthalen-9-yl)-piperidine-3-carboxylic acid (2,2,2-trifluoro-ethyl)-amide;
9-(3-Cyclopropylmethoxy-pyrrolidin-1-yl)-3H-3,4,7-triaza-cyclopenta[a]naphthalene;
9-(3-Morpholin-4-yl-piperidin-1-yl)-3H-3,4,7-triaza-cyclopenta[a]naphthalene;
Cyclopropylmethyl-methyl-[1-(3H-3,4,7-triaza-cyclopenta[a]naphthalen-9-yl)-pyrrolidin-3-yl]-amine;
1-(3H-3,4,7-Triaza-cyclopenta[a]naphthalen-9-yl)-pyrrolidine-3-carboxylic acid (2,2,2-trifluoro-ethyl)-amide;
2-Cyano-N-[1-(3H-3,4,7-triaza-cyclopenta[a]naphthalen-9-yl)-piperidin-3-yl]-acetamide;
2-Nitrilo-ethanesulfonic acid [1-(3H-3,4,7-triaza-cyclopenta[a]naphthalen-9-yl)-piperidin-3-yl]-amide;
9-Morpholin-4-yl-3H-3,4,7-triaza-cyclopenta[a]naphthalene;
1-(3H-3,4,7-Triaza-cyclopenta[a]naphthalen-9-yl)-piperidine-3-carboxylic acid cyanomethyl-amide;
1-(3H-3,4,7-Triaza-cyclopenta[a]naphthalen-9-yl)-piperidine-3-carboxylic acid cyanomethyl-methyl-amide;
2-Cyano-N-methyl-N-[1-(3H-3,4,7-triaza-cyclopenta[a]naphthalen-9-yl)-piperidin-3-yl]-acetamide;
1-(3H-3,4,7-Triaza-cyclopenta[a]naphthalen-9-yl)-pyrrolidine-3-carboxylic acid cyanomethyl-methyl-amide;
1-(3H-3,4,7-Triaza-cyclopenta[a]naphthalen-9-yl)-pyrrolidine-3-carboxylic acid methyl-(2,2,2-trifluoro-ethyl)-amide;
2-Cyano-N-methyl-N-[1-(3H-3,4,7-triaza-cyclopenta[a]naphthalen-9-yl)-pyrrolidin-3-yl]-acetamide;
3,3,3-Trifluoro-N-methyl-N-[1-(3H-3,4,7-triaza-cyclopenta[a]naphthalen-9-yl)-pyrrolidin-3-yl]-propionamide;
1-(3H-3,4,7-Triaza-cyclopenta[a]naphthalen-9-yl)-pyrrolidine-3-carboxylic acid cyanomethyl-amide;
2,2,2-Trifluoro-ethanesulfonic acid [1-(3H-3,4,7-triaza-cyclopenta[a]naphthalen-9-yl)-pyrrolidin-3-yl]-amide;
Cyclopropanesulfonic acid [1-(3H-3,4,7-triaza-cyclopenta[a]naphthalen-9-yl)-pyrrolidin-3-yl]-amide;
N-[1-(3H-3,4,7-Triaza-cyclopenta[a]naphthalen-9-yl)-pyrrolidin-3-yl]-methanesulfonamide;
2-Nitrilo-ethanesulfonic acid [1-(3H-3,4,7-triaza-cyclopenta[a]naphthalen-9-yl)-pyrrolidin-3-yl]-amide;
3,3,3-Trifluoro-N-[1-(3H-3,4,7-triaza-cyclopenta[a]naphthalen-9-yl)-pyrrolidin-3-yl]-propionamide;
2-Cyano-N-[1-(3H-3,4,7-triaza-cyclopenta[a]naphthalen-9-yl)-pyrrolidin-3-yl]-acetamide;
1-Isopropyl-3-[1-(3H-3,4,7-triaza-cyclopenta[a]naphthalen-9-yl)-pyrrolidin-3-yl]-urea;
N-[1-(3H-3,4,7-Triaza-cyclopenta[a]naphthalen-9-yl)-piperidin-3-yl]-methanesulfonamide;
2,2,2-Trifluoro-ethanesulfonic acid [1-(3H-3,4,7-triaza-cyclopenta[a]naphthalen-9-yl)-piperidin-3-yl]-amide;
1-(3H-3,4,7-Triaza-cyclopenta[a]naphthalen-9-yl)-piperidine-4-carboxylic acid (2,2,2-trifluoro-ethyl)-amide;
1-(3H-3,4,7-Triaza-cyclopenta[a]naphthalen-9-yl)-piperidine-4-carboxylic acid cyanomethyl-methyl-amide;
1-(3H-3,4,7-Triaza-cyclopenta[a]naphthalen-9-yl)-piperidine-4-carboxylic acid cyanomethyl-amide;
2-Cyano-N-[1-(3H-3,4,7-triaza-cyclopenta[a]naphthalen-9-yl)-piperidin-4-yl]-acetamide;
2-Cyano-N-methyl-N-[1-(3H-3,4,7-triaza-cyclopenta[a]naphthalen-9-yl)-piperidin-4-yl]-acetamide;
3,3,3-Trifluoro-N-methyl-N-[1-(3H-3,4,7-triaza-cyclopenta[a]naphthalen-9-yl)-piperidin-3-yl]-propionamide;
3,3,3-Trifluoro-N-[1-(3H-3,4,7-triaza-cyclopenta[a]naphthalen-9-yl)-piperidin-3-yl]-propionamide;
1-(3H-3,4,7-Triaza-cyclopenta[a]naphthalen-9-yl)-piperidine-3-carboxylic acid cyclopropylamide;
1-(3H-3,4,7-Triaza-cyclopenta[a]naphthalen-9-yl)-piperidine-3-carboxylic acid isobutyl-amide;
1-(3H-3,4,7-Triaza-cyclopenta[a]naphthalen-9-yl)-piperidine-3-carboxylic acid (2,2,2-trifluoro-ethyl)-amide;
1-(3H-3,4,7-Triaza-cyclopenta[a]naphthalen-9-yl)-piperidine-3-carboxylic acid cyclopropyl-methyl-amide;
1-(3H-3,4,7-Triaza-cyclopenta[a]naphthalen-9-yl)-pyrrolidine-3-sulfonic acid (2,2,2-trifluoro-ethyl)-amide;
1-(3H-3,4,7-Triaza-cyclopenta[a]naphthalen-9-yl)-piperidine-3-sulfonic acid (2,2,2-trifluoro-ethyl)-amide;
1-(3H-3,4,7-Triaza-cyclopenta[a]naphthalen-9-yl)-piperidine-3-carboxylic acid methyl-(2,2,2-trifluoro-ethyl)-amide;
6-Methyl-1-(3H-3,4,7-triaza-cyclopenta[a]naphthalen-9-yl)-piperidine-3-carboxylic acid cyclopropylamide;
1-(3H-3,4,8-Triaza-cyclopenta[a]naphthalen-9-yl)-piperidin-3-ol;
9-(3-Morpholin-4-yl-piperidin-1-yl)-3H-3,4,8-triaza-cyclopenta[a]naphthalene;
Cyclopropylmethyl-methyl-[1-(3H-3,4,8-triaza-cyclopenta[a]naphthalen-9-yl)-pyrrolidin-3-yl]-amine;
9-Morpholin-4-yl-3H-3,4,8-triaza-cyclopenta[a]naphthalene;
2-Cyano-N-[1-(3H-3,4,8-triaza-cyclopenta[a]naphthalen-9-yl)-piperidin-3-yl]-acetamide;
2-Nitrilo-ethanesulfonic acid [1-(3H-3,4,8-triaza-cyclopenta[a]naphthalen-9-yl)-piperidin-3-yl]-amide;
1-(3H-3,4,8-Triaza-cyclopenta[a]naphthalen-9-yl)-pyrrolidine-3-carboxylic acid (2,2,2-trifluoro-ethyl)-amide;
1-(3H-3,4,8-Triaza-cyclopenta[a]naphthalen-9-yl)-piperidine-3-carboxylic acid cyanomethyl-amide;
1-(3H-3,4,8-Triaza-cyclopenta[a]naphthalen-9-yl)-piperidine-3-carboxylic acid cyanomethyl-methyl-amide;
2-Cyano-N-methyl-N-[1-(3H-3,4,8-triaza-cyclopenta[a]naphthalen-9-yl)-piperidin-3-yl]-acetamide;
1-(3H-3,4,8-Triaza-cyclopenta[a]naphthalene-9-yl)-pyrrolidine-3-carboxylic acid cyanomethyl-methyl-amide;
1-(3H-3,4,8-Triaza-cyclopenta[a]naphthalen-9-yl)-pyrrolidine-3-carboxylic acid methyl-(2,2,2-trifluoro-ethyl)-amide;
2-Cyano-N-methyl-N-[1-(3H-3,4,8-triaza-cyclopenta[a]naphthalen-9-yl)-pyrrolidin-3-yl]-acetamide;
3,3,3-Trifluoro-N-methyl-N-[1-(3H-3,4,8-triaza-cyclopenta[a]naphthalen-9-yl)-pyrrolidin-3-yl]-propionamide;

1-(3H-3,4,8-Triaza-cyclopenta[a]naphthalen-9-yl)-pyrrolidine-3-carboxylic acid cyanomethyl-amide;
2,2,2-Trifluoro-ethanesulfonic acid [1-(3H-3,4,8-triaza-cyclopenta[a]naphthalen-9-yl)-pyrrolidin-3-yl]-amide;
N-[1-(3H-3,4,8-Triaza-cyclopenta[a]naphthalen-9-yl)-pyrrolidin-3-yl]-methanesulfonamide;
2-Methyl-propane-1-sulfonic acid [1-(3H-3,4,8-triaza-cyclopenta[a]naphthalen-9-yl)-pyrrolidin-3-yl]-amide;
2-Nitrilo-ethanesulfonic acid [1-(3H-3,4,8-triaza-cyclopenta[a]naphthalen-9-yl)-pyrrolidin-3-yl]-amide;
1-Isopropyl-3-[1-(3H-3,4,8-triaza-cyclopenta[a]naphthalen-9-yl)-pyrrolidin-3-yl]-urea;
2-Cyano-N-[1-(3H-3,4,8-triaza-cyclopenta[a]naphthalen-9-yl)-pyrrolidin-3-yl]-acetamide;
Cyclopropanecarboxylic acid [1-(3H-3,4,8-triaza-cyclopenta[a]naphthalen-9-yl)-pyrrolidin-3-yl]-amide;
1-(3H-3,4,8-Triaza-cyclopenta[a]naphthalen-9-yl)-pyrrolidine-3-carboxylic acid cyclopropylamide;
3,3,3-Trifluoro-N-[1-(3H-3,4,8-triaza-cyclopenta[a]naphthalen-9-yl)-pyrrolidin-3-yl]-propionamide;
N-[1-(3H-3,4,8-Triaza-cyclopenta[a]naphthalen-9-yl)-piperidin-3-yl]-methanesulfonamide;
2,2,2-Trifluoro-ethanesulfonic acid [1-(3H-3,4,8-triaza-cyclopenta[a]naphthalen-9-yl)-piperidin-3-yl]-amide;
1-(3H-3,4,8-Triaza-cyclopenta[a]naphthalen-9-yl)-piperidine-4-carboxylic acid (2,2,2-trifluoro-ethyl)-amide;
1-(3H-3,4,8-Triaza-cyclopenta[a]naphthalen-9-yl)-piperidine-4-carboxylic acid methyl-(2,2,2-trifluoro-ethyl)-amide;
1-(3H-3,4,8-Triaza-cyclopenta[a]naphthalen-9-yl)-piperidine-4-carboxylic acid cyanomethyl-methyl-amide;
1-(3H-3,4,8-Triaza-cyclopenta[a]naphthalen-9-yl)-piperidine-4-carboxylic acid cyanomethyl-amide;
2-Cyano-N-[1-(3H-3,4,8-triaza-cyclopenta[a]naphthalen-9-yl)-piperidin-4-yl]-acetamide;
2-Cyano-N-methyl-N-[1-(3H-3,4,8-triaza-cyclopenta[a]naphthalen-9-yl)-piperidin-4-yl]-acetamide;
3,3,3-Trifluoro-N-methyl-N-[1-(3H-3,4,8-triaza-cyclopenta[a]naphthalen-9-yl)-piperidin-3-yl]-propionamide;
3,3,3-Trifluoro-N-[1-(3H-3,4,8-triaza-cyclopenta[a]naphthalen-9-yl)-piperidin-3-yl]-propionamide;
1-(3H-3,4,8-Triaza-cyclopenta[a]naphthalen-9-yl)-piperidine-3-carboxylic acid cyclopropylamide;
1-(3H-3,4,8-Triaza-cyclopenta[a]naphthalen-9-yl)-piperidine-3-carboxylic acid cyclopropyl-methyl-amide;
1-(3H-3,4,8-Triaza-cyclopenta[a]naphthalen-9-yl)-piperidine-3-carboxylic acid methyl-(2,2,2-trifluoro-ethyl)-amide;
6-Methyl-1-(3H-3,4,8-triaza-cyclopenta[a]naphthalen-9-yl)-piperidine-3-carboxylic acid cyclopropylamide;
1-(3H-3,4,8-Triaza-cyclopenta[a]naphthalen-9-yl)-pyrrolidine-3-sulfonic acid (2,2,2-trifluoro-ethyl)-amide;
1-(3H-3,4,8-Triaza-cyclopenta[a]naphthalen-9-yl)-piperidine-3-sulfonic acid (2,2,2-trifluoro-ethyl)-amide;
1-(3H-3,4,8-Triaza-cyclopenta[a]naphthalen-9-yl)-piperidine-3-carboxylic acid (2,2,2-trifluoro-ethyl)-amide;
2-Cyano-N-[1-(3H-3,4,6-triaza-cyclopenta[a]naphthalen-9-yl)-piperidin-3-yl]-acetamide;
2-Nitrilo-ethanesulfonic acid [1-(3H-3,4,6-triaza-cyclopenta[a]naphthalen-9-yl)-piperidin-3-yl]-amide;
1-(3H-3,4,6-Triaza-cyclopenta[a]naphthalen-9-yl)-pyrrolidine-3-carboxylic acid (2,2,2-trifluoro-ethyl)-amide;
1-(3H-3,4,6-Triaza-cyclopenta[a]naphthalen-9-yl)-piperidine-3-carboxylic acid cyanomethyl-amide;
1-(3H-3,4,6-Triaza-cyclopenta[a]naphthalen-9-yl)-pyrrolidine-3-carboxylic acid cyanomethyl-amide;
6-Methyl-1-(3H-3,4,6,7-tetraaza-cyclopenta[a]naphthalen-9-yl)-piperidine-3-carboxylic acid cyanomethyl-amide;
6-Methyl-1-(7-methyl-3H-3,4,6,8-tetraaza-cyclopenta[a]naphthalen-9-yl)-piperidine-3-carboxylic acid cyanomethyl-amide;
6-Methyl-1-(3H-3,4,7,8-tetraaza-cyclopenta[a]naphthalen-9-yl)-piperidine-3-carboxylic acid cyanomethyl-amide;
6-Methyl-1-(3H-3,4,7-triaza-cyclopenta[a]naphthalen-9-yl)-piperidine-3-carboxylic acid cyanomethyl-amide;
6-Methyl-1-(3H-3,4,8-triaza-cyclopenta[a]naphthalen-9-yl)-piperidine-3-carboxylic acid cyanomethyl-amide;
6-Methyl-1-(3H-3,4,6,7-tetraaza-cyclopenta[a]naphthalen-9-yl)-piperidine-3-carboxylic acid (2,2,2-trifluoro-ethyl)-amide;
6-Methyl-1-(7-methyl-3H-3,4,6,8-tetraaza-cyclopenta[a]naphthalen-9-yl)-piperidine-3-carboxylic acid (2,2,2-trifluoro-ethyl)-amide;
6-Methyl-1-(3H-3,4,7,8-tetraaza-cyclopenta[a]naphthalen-9-yl)-piperidine-3-carboxylic acid (2,2,2-trifluoro-ethyl)-amide;
6-Methyl-1-(3H-3,4,7-triaza-cyclopenta[a]naphthalen-9-yl)-piperidine-3-carboxylic acid (2,2,2-trifluoro-ethyl)-amide;
6-Methyl-1-(3H-3,4,8-triaza-cyclopenta[a]naphthalen-9-yl)-piperidine-3-carboxylic acid (2,2,2-trifluoro-ethyl)-amide;
2-Cyano-N-[6-methyl-1-(3H-3,4,6,7-tetraaza-cyclopenta[a]naphthalen-9-yl)-piperidin-3-yl]-acetamide;
2-Cyano-N-[6-methyl-1-(7-methyl-3H-3,4,6,8-tetraaza-cyclopenta[a]naphthalen-9-yl)-piperidin-3-yl]-acetamide;
2-Cyano-N-[6-methyl-1-(3H-3,4,7,8-tetraaza-cyclopenta[a]naphthalen-9-yl)-piperidin-3-yl]-acetamide;
2-Cyano-N-[6-methyl-1-(3H-3,4,7-triaza-cyclopenta[a]naphthalen-9-yl)-piperidin-3-yl]-acetamide;
2-Cyano-N-[6-methyl-1-(3H-3,4,8-triaza-cyclopenta[a]naphthalen-9-yl)-piperidin-3-yl]-acetamide;
3,3,3-Trifluoro-N-[6-methyl-1-(3H-3,4,6,7-tetraaza-cyclopenta[a]naphthalen-9-yl)-piperidin-3-yl]-propionamide;
3,3,3-Trifluoro-N-[6-methyl-1-(7-methyl-3H-3,4,6,8-tetraaza-cyclopenta[a]naphthalen-9-yl)-piperidin-3-yl]-propionamide;
3,3,3-Trifluoro-N-[6-methyl-1-(3H-3,4,7,8-tetraaza-cyclopenta[a]naphthalen-9-yl)-piperidin-3-yl]-propionamide;
3,3,3-Trifluoro-N[6-methyl-1-(3H-3,4,7-triaza-cyclopenta[a]naphthalen-9-yl)-piperidin-3-yl]-propionamide;
3,3,3-Trifluoro-N-[6-methyl-1-(3H-3,4,8-triaza-cyclopenta[a]naphthalen-9-yl)-piperidin-3-yl]-propionamide;
2-Nitrilo-ethanesulfonic acid [6-methyl-1-(3H-3,4,6,7-tetraaza-cyclopenta[a]naphthalen-9-yl)-piperidin-3-yl]-amide;
2-Nitrilo-ethanesulfonic acid [6-methyl-1-(7-methyl-3H-3,4,6,8-tetraaza-cyclopenta[a]naphthalen-9-yl)-piperidin-3-yl]-amide;
2-Nitrilo-ethanesulfonic acid [6-methyl-1-(3H-3,4,7,8-tetraaza-cyclopenta[a]naphthalen-9-yl)-piperidin-3-yl]-amide;
2-Nitrilo-ethanesulfonic acid [6-methyl-1-(3H-3,4,7-triaza-cyclopenta[a]naphthalen-9-yl)-piperidin-3-yl]-amide;
2-Nitrilo-ethanesulfonic acid [6-methyl-1-(3H-3,4,8-triaza-cyclopenta[a]naphthalen-9-yl)-piperidin-3-yl]-amide;
2,2,2-Trifluoro-ethanesulfonic acid [6-methyl-1-(3H-3,4,6,7-tetraaza-cyclopenta[a]naphthalen-9-yl)-piperidin-3-yl]-amide;
2,2,2-Trifluoro-ethanesulfonic acid [6-methyl-1-(7-methyl-3H-3,4,6,8-tetraaza-cyclopenta[a]naphthalen-9-yl)-piperidin-3-yl]-amide;
2,2,2-Trifluoro-ethanesulfonic acid [6-methyl-1-(3H-3,4,7,8-tetraaza-cyclopenta[a]naphthalen-9-yl)-piperidin-3-yl]-amide;
2,2,2-Trifluoro-ethanesulfonic acid [6-methyl-1-(3H-3,4,7-triaza-cyclopenta[a]naphthalen-9-yl)-piperidin-3-yl]-amide;
2,2,2-Trifluoro-ethanesulfonic acid [6-methyl-1-(3H-3,4,8-triaza-cyclopenta[a]naphthalen-9-yl)-piperidin-3-yl]-amide;
6-Methyl-1-(3H-3,4,6,7-tetraaza-cyclopenta[a]naphthalen-9-yl)-piperidine-3-sulfonic acid cyanomethyl-amide;

6-Methyl-1-(7-methyl-3H-3,4,6,8-tetraaza-cyclopenta[a]naphthalen-9-yl)-piperidine-3-sulfonic acid cyanomethyl-amide;
6-Methyl-1-(3H-3,4,7,8-tetraaza-cyclopenta[a]naphthalen-9-yl)-piperidine-3-sulfonic acid cyanomethyl-amide;
6-Methyl-1-(3H-3,4,7-triaza-cyclopenta[a]naphthalen-9-yl)-piperidine-3-sulfonic acid cyanomethyl-amide;
6-Methyl-1-(3H-3,4,8-triaza-cyclopenta[a]naphthalen-9-yl)-piperidine-3-sulfonic acid cyanomethyl-amide;
9-[4-[[3-(pyrrolidin-1-ylmethyl)-1-piperidyl]sulfonylmethyl]-1-piperidyl]-3H-pyrrolo[3,2-f][1,7]naphthyridine;
9-[4-[[3-(methoxymethyl) pyrrolidin-1-yl]sulfonylmethyl]-1-piperidyl]-3H-pyrrolo[3,2-f][1,7]naphthyridine;
3-methyl-1-[[1-(3H-pyrrolo[3,2-f][1,7]naphthyridin-9-yl)-4-piperidyl]methylsulfonyl]pyrrolidin-3-ol;
9-[4-[(3-methoxy-1-piperidyl)sulfonylmethyl]-1-piperidyl]-3H-pyrrolo[3,2-f][1,7]naphthyridine;
[1-[[1-(3H-pyrrolo[3,2-f][1,7]naphthyridin-9-yl)-4-piperidyl]methylsulfonyl]-3-piperidyl]methanesulfonamide;
9-[4-[(3-isobutoxy-1-piperidyl)sulfonylmethyl]-1-piperidyl]-3H-pyrrolo[3,2-f][1,7]naphthyridine;
9-[4-[[3-(2-methoxyethoxy)-1-piperidyl]sulfonylmethyl]-1-piperidyl]-3H-pyrrolo[3,2-f][1,7]naphthyridine;
N-(cyclopropylmethyl)-1-[1-(3H-pyrrolo[3,2-f][1,7]naphthyridin-9-yl)-4-piperidyl]methanesulfonamide;
N-cyclobutyl-1-[1-(3H-pyrrolo[3,2-f][1,7]naphthyridin-9-yl)-4-piperidyl]methanesulfonamide;
9-[4-[[3-[(4-fluorophenoxy)methyl]-1-piperidyl]sulfonylmethyl]-1-piperidyl]-3H-pyrrolo[3,2-f][1,7]naphthyridine;
9-[4-[[3-[(4-chlorophenoxy)methyl]-1-piperidyl]sulfonylmethyl]-1-piperidyl]-3H-pyrrolo[3,2-f][1,7]naphthyridine;
4-[[1-[[1-(3H-pyrrolo[3,2-f][1,7]naphthyridin-9-yl)-4-piperidyl]methylsulfonyl]-3-piperidyl]methoxy]benzonitrile;
4-[[1-[[4-(3H-pyrrolo[3,2-f][1,7]naphthyridin-9-yl)-1-piperidyl]methylsulfonyl]-3-piperidyl]methoxy]benzoic acid;
4-[[1-[[4-(3H-pyrrolo[3,2-f][1,7]naphthyridin-9-yl)-1-piperidyl]methylsulfonyl]-3-piperidyl]methoxy]benzamide;
9-[4-[[3-[(2,4-difluorophenoxy)methyl]-1-piperidyl]sulfonyl methyl]-1-piperidyl]-3H-pyrrolo[3,2-f][1,7]naphthyridine;
9-[4-[[3-[(4-methoxyphenoxy)methyl]-1-piperidyl]sulfonyl methyl]-1-piperidyl]-3H-pyrrolo[3,2-f][1,7]naphthyridine;
9-[4-[[3-[[4-(trifluoromethoxy)phenoxy]methyl]-1-piperidyl]sulfonylmethyl]-1-piperidyl]-3H-pyrrolo[3,2-f][1,7]naphthyridine;
9-[4-[[3-[[4-(trifluoromethyl)phenoxy]methyl]-1-piperidyl]sulfonylmethyl]-1-piperidyl]-3H-pyrrolo[3,2-f][1,7]naphthyridine;
9-[4-[(3-methyl-1-piperidyl)sulfonylmethyl]-1-piperidyl]-3H-pyrrolo[3,2-f][1,7]naphthyridine;
9-[4-[[3-(trifluoromethyl)-1-piperidyl]sulfonylmethyl]-1-piperidyl]-3H-pyrrolo[3,2-f][1,7]naphthyridine;
9-[4-[[3-(pyrrolidin-1-ylmethyl)-1-piperidyl]sulfonylmethyl]piperazin-1-yl]-3H-pyrrolo[3,2-f][1,7]naphthyridine;
9-[4-[[3-(methoxymethyl) pyrrolidin-1-yl]sulfonylmethyl]piperazin-1-yl]-3H-pyrrolo[3,2-f][1,7]naphthyridine;
3-methyl-1-[[4-(3H-pyrrolo[3,2-f][1,7]naphthyridin-9-yl)piperazin-1-yl]methylsulfonyl]pyrrolidin-3-ol;
9-[4-[(3-methoxy-1-piperidyl)sulfonylmethyl]piperazin-1-yl]-3H-pyrrolo[3,2-f][1,7]naphthyridine;
[1-[[4-(3H-pyrrolo[3,2-f][1,7]naphthyridin-9-yl)piperazin-1-yl]methylsulfonyl]-3-piperidyl]methanesulfonamide;
9-[4-[(3-isobutoxy-1-piperidyl)sulfonylmethyl]piperazin-1-yl]-3H-pyrrolo[3,2-f][1,7]naphthyridine;
9-[4-[[3-(2-methoxyethoxy)-1-piperidyl]sulfonylmethyl]piperazin-1-yl]-3H-pyrrolo[3,2-f][1,7]naphthyridine;
N-(cyclopropylmethyl)-1-[4-(3H-pyrrolo[3,2-f][1,7]naphthyridin-9-yl)piperazin-1-yl]methane sulfonamide;
N-cyclobutyl-1-[4-(3H-pyrrolo[3,2-f][1,7]naphthyridin-9-yl)piperazin-1-yl]methanesulfonamide;
9-[4-[[3-[(4-fluorophenoxy)methyl]-1-piperidyl]sulfonylmethyl]piperazin-1-yl]-3H-pyrrolo[3,2-f][1,7]naphthyridine;
9-[4-[[3-[(4-chlorophenoxy)methyl]-1-piperidyl]sulfonylmethyl]piperazin-1-yl]-3H-pyrrolo[3,2-f][1,7]naphthyridine;
4-[[1-[[4-(3H-pyrrolo[3,2-f][1,7]naphthyridin-9-yl)piperazin-1-yl]methylsulfonyl]-3-piperidyl]methoxy]benzonitrile;
4-[[1-[[4-(3H-pyrrolo[3,2-f][1,7]naphthyridin-9-yl)piperazin-1-yl]methylsulfonyl]-3-piperidyl]methoxy]benzoic acid;
4-[[1-[[4-(3H-pyrrolo[3,2-f][1,7]naphthyridin-9-yl)piperazin-1-yl]methylsulfonyl]-3-piperidyl]methoxy]benzamide;
9-[4-[[3-[(2,4-difluorophenoxy)methyl]-1-piperidyl]sulfonylmethyl]piperazin-1-yl]-3H-pyrrolo[3,2-f][1,7]naphthyridine;
9-[4-[[3-[(4-methoxyphenoxy)methyl]-1-piperidyl]sulfonylmethyl]piperazin-1-yl]-3H-pyrrolo[3,2-f][1,7]naphthyridine;
9-[4-[[3-[[4-(trifluoromethoxy)phenoxy]methyl]-1-piperidyl]sulfonylmethyl]piperazin-1-yl]-3H-pyrrolo[3,2-f][1,7]naphthyridine;
9-[4-[[3-[[4-(trifluoromethyl)phenoxy]methyl]-1-piperidyl]sulfonylmethyl]piperazin-1-yl]-3H-pyrrolo[3,2-f][1,7]naphthyridine;
9-[4-[(3-methyl-1-piperidyl)sulfonylmethyl]piperazin-1-yl]-3H-pyrrolo[3,2-f][1,7]naphthyridine;
9-[4-[[3-(trifluoromethyl)-1-piperidyl]sulfonylmethyl]piperazin-1-yl]-3H-pyrrolo[3,2-f][1,7]naphthyridine;
9-[1-[[3-(pyrrolidin-1-ylmethyl)-1-piperidyl]sulfonylmethyl]-4-piperidyl]-3H-pyrrolo[3,2-f][1,7]naphthyridine;
9-[1-[[3-(methoxymethyl) pyrrolidin-1-yl]sulfonylmethyl]-4-piperidyl]-3H-pyrrolo[3,2-f][1,7]naphthyridine;
3-methyl-1-[[4-(3H-pyrrolo[3,2-f][1,7]naphthyridin-9-yl)-1-piperidyl]methylsulfonyl]pyrrolidin-3-ol;
9-[1-[(3-methoxy-1-piperidyl)sulfonylmethyl]-4-piperidyl]-3H-pyrrolo[3,2-f][1,7]naphthyridine;
[1-[[4-(3H-pyrrolo[3,2-f][1,7]naphthyridin-9-yl)-1-piperidyl]methylsulfonyl]-3-piperidyl]methanesulfonamide;
9-[1-[(3-isobutoxy-1-piperidyl)sulfonylmethyl]-4-piperidyl]-3H-pyrrolo[3,2-f][1,7]naphthyridine;
9-[1-[[3-(2-methoxyethoxy)-1-piperidyl]sulfonylmethyl]-4-piperidyl]-3H-pyrrolo[3,2-f][1,7]naphthyridine;
N-(cyclopropylmethyl)-1-[4-(3H-pyrrolo[3,2-f][1,7]naphthyridin-9-yl)-1-piperidyl]methanesulfonamide;
N-cyclobutyl-1-[4-(3H-pyrrolo[3,2-f][1,7]naphthyridin-9-yl)-1-piperidyl]methanesulfonamide;
9-[1-[[3-[(4-fluorophenoxy)methyl]-1-piperidyl]sulfonylmethyl]-4-piperidyl]-3H-pyrrolo[3,2-f][1,7]naphthyridine;
9-[1-[[3-[(4-chlorophenoxy)methyl]-1-piperidyl]sulfonylmethyl]-4-piperidyl]-3H-pyrrolo[3,2-f][1,7]naphthyridine;
4-[[1-[[4-(3H-pyrrolo[3,2-f][1,7]naphthyridin-9-yl)-1-piperidyl]methylsulfonyl]-3-piperidyl]methoxy]benzonitrile;
4-[[1-[[4-(3H-pyrrolo[3,2-f][1,7]naphthyridin-9-yl)-1-piperidyl]methylsulfonyl]-3-piperidyl]methoxy]benzoic acid;
4-[[1-[[4-(3H-pyrrolo[3,2-f][1,7]naphthyridin-9-yl)-1-piperidyl]methylsulfonyl]-3-piperidyl]methoxy]benzamide;
9-[1-[[3-[(2,4-difluorophenoxy)methyl]-1-piperidyl]sulfonyl methyl]-4-piperidyl]-3H-pyrrolo[3,2-f][1,7]naphthyridine;
9-[1-[[3-[(4-methoxyphenoxy)methyl]-1-piperidyl]sulfonylmethyl]-4-piperidyl]-3H-pyrrolo[3,2-f][1,7]naphthyridine;

9-[1-[[3-[[(4-(trifluoromethoxy)phenoxy]methyl]-1-piperidyl]sulfonylmethyl]-4-piperidyl]-3H-pyrrolo[3,2-f][1,7]naphthyridine;
9-[1-[[3-[[4-(trifluoromethyl)phenoxy]methyl]-1-piperidyl]sulfonylmethyl]-4-piperidyl]-3H-pyrrolo[3,2-f][1,7]naphthyridine;
9-[1-[(3-methyl-1-piperidyl)sulfonylmethyl]-4-piperidyl]-3H-pyrrolo[3,2-f][1,7]naphthyridine;
9-[1-[[3-(trifluoromethyl)-1-piperidyl]sulfonylmethyl]-4-piperidyl]-3H-pyrrolo[3,2-f][1,7]naphthyridine;
9-[4-[[3-(pyrrolidin-1-ylmethyl)-1-piperidyl]sulfonylmethyl]cyclohexyl]-3H-pyrrolo[3,2-f][1,7]naphthyridine;
9-[4-[[3-(methoxymethyl)pyrrolidin-1-yl]sulfonylmethyl]cyclohexyl]-3H-pyrrolo[3,2-f][1,7]naphthyridine;
3-methyl-1-[[4-(3H-pyrrolo[3,2-f][1,7]naphthyridin-9-yl)cyclohexyl]methylsulfonyl]pyrrolidin-3-ol;
9-[4-[(3-methoxy-1-piperidyl) sulfonyl methyl]cyclohexyl]-3H-pyrrolo[3,2-f][1,7]naphthyridine;
[1-[[4-(3H-pyrrolo[3,2-f][1,7]naphthyridin-9-yl)cyclohexyl]methylsulfonyl]-3-piperidyl]methanesulfonamide
9-[4-[(3-isobutoxy-1-piperidyl)sulfonylmethyl]cyclohexyl]-3H-pyrrolo[3,2-f][1,7]naphthyridine;
9-[4-[[3-(2-methoxyethoxy)-1-piperidyl]sulfonylmethyl]cyclohexyl]-3H-pyrrolo[3,2-f][1,7]naphthyridine;
N-(cyclopropylmethyl)-1-[4-(3H-pyrrolo[3,2-f][1,7]naphthyridin-9-yl)cyclohexyl]methanesulfonamide;
N-cyclobutyl-1-[4-(3H-pyrrolo[3,2-f][1,7]naphthyridin-9-yl)cyclohexyl]methanesulfonamide;
9-[4-[[3-[(4-fluorophenoxy)methyl]-1-piperidyl]sulfonylmethyl]cyclohexyl]-3H-pyrrolo[3,2-f][1,7]naphthyridine;
9-[4-[[3-[(4-chlorophenoxy)methyl]-1-piperidyl]sulfonylmethyl]cyclohexyl]-3H-pyrrolo[3,2-f][1,7]naphthyridine;
4-[[1-[[4-(3H-pyrrolo[3,2-f][1,7]naphthyridin-9-yl)cyclohexyl]methylsulfonyl]-3-piperidyl]methoxy]benzonitrile;
4-[[1-[[4-(3H-pyrrolo[3,2-f][1,7]naphthyridin-9-yl)cyclohexyl]methylsulfonyl]-3-piperidyl]methoxy]benzoic acid;
4-[[1-[[4-(3H-pyrrolo[3,2-f][1,7]naphthyridin-9-yl)cyclohexyl]methylsulfonyl]-3-piperidyl]methoxy]benzamide;
9-[4-[[3-[(2,4-difluorophenoxy)methyl]-1-piperidyl]sulfonylmethyl]cyclohexyl]-3H-pyrrolo[3,2-f][1,7]naphthyridine;
9-[4-[[3-[(4-methoxyphenoxy)methyl]-1-piperidyl]sulfonylmethyl]cyclohexyl]-3H-pyrrolo[3,2-f][1,7]naphthyridine;
9-[4-[[3-[[4-(trifluoromethoxy)phenoxy]methyl]-1-piperidyl]sulfonylmethyl]cyclohexyl]-3H-pyrrolo[3,2-f][1,7]naphthyridine;
9-[4-[[3-[[4-(trifluoromethyl)phenoxy]methyl]-1-piperidyl]sulfonylmethyl]cyclohexyl]-3H-pyrrolo[3,2-f][1,7]naphthyridine;
9-[4-[(3-methyl-1-piperidyl)sulfonyl methyl]cyclohexyl]-3H-pyrrolo[3,2-f][1,7]naphthyridine;
9-[4-[[3-(trifluoromethyl)-1-piperidyl]sulfonylmethyl]cyclohexyl]-3H-pyrrolo[3,2-f][1,7]naphthyridine;
1-[3-(pyrrolidin-1-ylmethyl)-1-piperidyl]-2-[1-(3H-pyrrolo[3,2-f][1,7]naphthyridin-9-yl)-4-piperidyl]ethanone;
1-[3-(methoxymethyl)pyrrolidin-1-yl]-2-[1-(3H-pyrrolo[3,2-f][1,7]naphthyridin-9-yl)-4-piperidyl]ethanone;
1-(3-hydroxy-3-methyl-pyrrolidin-1-yl)-2-[1-(3H-pyrrolo[3,2-f][1,7]naphthyridin-9-yl)-4-piperidyl]ethanone;
1-(3-methoxy-1-piperidyl)-2-[1-(3H-pyrrolo[3,2-f][1,7]naphthyridin-9-yl)-4-piperidyl]ethanone;
[1-[2-[1-(3H-pyrrolo[3,2-f][1,7]naphthyridin-9-yl)-4-piperidyl]acetyl]-3-piperidyl]methane sulfonamide;
1-(3-isobutoxy-1-piperidyl)-2-[1-(3H-pyrrolo[3,2-f][1,7]naphthyridin-9-yl)-4-piperidyl]ethanone;
1-[3-(2-methoxyethoxy)-1-piperidyl]-2-[1-(3H-pyrrolo[3,2-f][1,7]naphthyridin-9-yl)-4-piperidyl]ethanone;
N-(cyclopropylmethyl)-2-[1-(3H-pyrrolo[3,2-f][1,7]naphthyridin-9-yl)-4-piperidyl]acetamide;
N-cyclobutyl-2-[1-(3H-pyrrolo[3,2-f][1,7]naphthyridin-9-yl)-4-piperidyl]acetamide;
1-[3-[(4-fluorophenoxy)methyl]-1-piperidyl]-2-[1-(3H-pyrrolo[3,2-f][1,7]naphthyridin-9-yl)-4-piperidyl]ethanone;
1-[3-[(4-chlorophenoxy)methyl]-1-piperidyl]-2-[1-(3H-pyrrolo[3,2-f][1,7]naphthyridin-9-yl)-4-piperidyl]ethanone;
4-[[1-[2-[1-(3H-pyrrolo[3,2-f][1,7]naphthyridin-9-yl)-4-piperidyl]acetyl]-3-piperidyl]methoxy]benzonitrile;
4-[[1-[2-[1-(3H-pyrrolo[3,2-f][1,7]naphthyridin-9-yl)-4-piperidyl]acetyl]-3-piperidyl]methoxy]benzoic acid;
4-[[1-[2-[1-(3H-pyrrolo[3,2-f][1,7]naphthyridin-9-yl)-4-piperidyl]acetyl]-3-piperidyl]methoxy]benzamide;
1-[3-[(2,4-difluorophenoxy)methyl]-1-piperidyl]-2-[1-(3H-pyrrolo[3,2-f][1,7]naphthyridin-9-yl)-4-piperidyl]ethanone;
1-[3-[(4-methoxyphenoxy)methyl]-1-piperidyl]-2-[1-(3H-pyrrolo[3,2-f][1,7]naphthyridin-9-yl)-4-piperidyl]ethanone;
2-[1-(3H-pyrrolo[3,2-f][1,7]naphthyridin-9-yl)-4-piperidyl]-1-[3-[[4-(trifluoromethoxy)phenoxy]methyl]-1-piperidyl]ethanone;
2-[1-(3H-pyrrolo[3,2-f][1,7]naphthyridin-9-yl)-4-piperidyl]-1-[3-[[4-(trifluoromethyl)phenoxy]methyl]-1-piperidyl]ethanone;
1-(3-methyl-1-piperidyl)-2-[1-(3H-pyrrolo[3,2-f][1,7]naphthyridin-9-yl)-4-piperidyl]ethanone;
2-[1-(3H-pyrrolo[3,2-f][1,7]naphthyridin-9-yl)-4-piperidyl]-1-[3-(trifluoromethyl)-1-piperidyl]ethanone;
1-[3-(pyrrolidin-1-ylmethyl)-1-piperidyl]-2-[4-(3H-pyrrolo[3,2-f][1,7]naphthyridin-9-yl)piperazin-1-yl]ethanone;
1-[3-(methoxymethyl)pyrrolidin-1-yl]-2-[4-(3H-pyrrolo[3,2-f][1,7]naphthyridin-9-yl)piperazin-1-yl]ethanone;
1-(3-hydroxy-3-methyl-pyrrolidin-1-yl)-2-[4-(3H-pyrrolo[3,2-f][1,7]naphthyridin-9-yl)piperazin-1-yl]ethanone;
1-(3-methoxy-1-piperidyl)-2-[4-(3H-pyrrolo[3,2-f][1,7]naphthyridin-9-yl)piperazin-1-yl]ethanone;
[1-[2-[4-(3H-pyrrolo[3,2-f][1,7]naphthyridin-9-yl)piperazin-1-yl]acetyl]-3-piperidyl]methane sulfonamide;
1-(3-isobutoxy-1-piperidyl)-2-[4-(3H-pyrrolo[3,2-f][1,7]naphthyridin-9-yl)piperazin-1-yl]ethanone;
1-[3-(2-methoxyethoxy)-1-piperidyl]-2-[4-(3H-pyrrolo[3,2-f][1,7]naphthyridin-9-yl)piperazin-1-yl]ethanone;
N-(cyclopropylmethyl)-2-[4-(3H-pyrrolo[3,2-f][1,7]naphthyridin-9-yl)piperazin-1-yl]acetamide;
N-cyclobutyl-2-[4-(3H-pyrrolo[3,2-f][1,7]naphthyridin-9-yl)piperazin-1-yl]acetamide;
1-[3-[(4-fluorophenoxy)methyl]-1-piperidyl]-2-[4-(3H-pyrrolo[3,2-f][1,7]naphthyridin-9-yl)piperazin-1-yl]ethanone;
1-[3-[(4-chlorophenoxy)methyl]-1-piperidyl]-2-[4-(3H-pyrrolo[3,2-f][1,7]naphthyridin-9-yl)piperazin-1-yl]ethanone;
4-[[1-[2-[4-(3H-pyrrolo[3,2-f][1,7]naphthyridin-9-yl)piperazin-1-yl]acetyl]-3-piperidyl]methoxy]benzonitrile;
4-[[1-[2-[4-(3H-pyrrolo[3,2-f][1,7]naphthyridin-9-yl)piperazin-1-yl]acetyl]-3-piperidyl]methoxy]benzoic acid;
4-[[1-[2-[4-(3H-pyrrolo[3,2-f][1,7]naphthyridin-9-yl)piperazin-1-yl]acetyl]-3-piperidyl]methoxy]benzamide;
1-[3-[(2,4-difluorophenoxy)methyl]-1-piperidyl]-2-[4-(3H-pyrrolo[3,2-f][1,7]naphthyridin-9-yl)piperazin-1-yl]ethanone;
1-[3-[(4-methoxyphenoxy)methyl]-1-piperidyl]-2-[4-(3H-pyrrolo[3,2-f][1,7]naphthyridin-9-yl)piperazin-1-yl]ethanone;
2-[4-(3H-pyrrolo[3,2-f][1,7]naphthyridin-9-yl)piperazin-1-yl]-1-[3-[[4-(trifluoromethoxy)phenoxy]methyl]-1-piperidyl]ethanone;
2-[4-(3H-pyrrolo[3,2-f][1,7]naphthyridin-9-yl)piperazin-1-yl]-1-[3-[[4-(trifluoromethyl)phenoxy]methyl]-1-piperidyl]ethanone;
1-(3-methyl-1-piperidyl)-2-[4-(3H-pyrrolo[3,2-f][1,7]naphthyridin-9-yl)piperazin-1-yl]ethanone;

2-[4-(3H-pyrrolo[3,2-f][1,7]naphthyridin-9-yl)piperazin-1-yl]-1-[3-(trifluoromethyl)-1-piperidyl]ethanone;
1-[3-(pyrrolidin-1-ylmethyl)-1-piperidyl]-2-[4-(3H-pyrrolo[3,2-f][1,7]naphthyridin-9-yl)-1-piperidyl]ethanone;
1-[3-(methoxymethyl)pyrrolidin-1-yl]-2-[4-(3H-pyrrolo[3,2-f][1,7]naphthyridin-9-yl)-1-piperidyl]ethanone;
1-(3-hydroxy-3-methyl-pyrrolidin-1-yl)-2-[4-(3H-pyrrolo[3,2-f][1,7]naphthyridin-9-yl)-1-piperidyl]ethanone;
1-(3-methoxy-1-piperidyl)-2-[4-(3H-pyrrolo[3,2-f][1,7]naphthyridin-9-yl)-1-piperidyl]ethanone;
[1-[2-[4-(3H-pyrrolo[3,2-f][1,7]naphthyridin-9-yl)-1-piperidyl]acetyl]-3-piperidyl]methane sulfonamide;
1-(3-isobutoxy-1-piperidyl)-2-[4-(3H-pyrrolo[3,2-f][1,7]naphthyridin-9-yl)-1-piperidyl]ethanone;
1-[3-(2-methoxyethoxy)-1-piperidyl]-2-[4-(3H-pyrrolo[3,2-f][1,7]naphthyridin-9-yl)-1-piperidyl]ethanone;
N-(cyclopropylmethyl)-2-[4-(3H-pyrrolo[3,2-f][1,7]naphthyridin-9-yl)-1-piperidyl]acetamide
N-cyclobutyl-2-[4-(3H-pyrrolo[3,2-f][1,7]naphthyridin-9-yl)-1-piperidyl]acetamide;
1-[3-[(4-fluorophenoxy)methyl]-1-piperidyl]-2-[4-(3H-pyrrolo[3,2-f][1,7]naphthyridin-9-yl)-1-piperidyl]ethanone;
1-[3-[(4-chlorophenoxy)methyl]-1-piperidyl]-2-[4-(3H-pyrrolo[3,2-f][1,7]naphthyridin-9-yl)-1-piperidyl]ethanone;
4-[[1-[2-[4-(3H-pyrrolo[3,2-f][1,7]naphthyridin-9-yl)-1-piperidyl]acetyl]-3-piperidyl]methoxy]benzonitrile;
4-[[1-[2-[4-(3H-pyrrolo[3,2-f][1,7]naphthyridin-9-yl)-1-piperidyl]acetyl]-3-piperidyl]methoxy]benzoic acid;
4-[[1-[2-[4-(3H-pyrrolo[3,2-f][1,7]naphthyridin-9-yl)-1-piperidyl]acetyl]-3-piperidyl]methoxy]benzamide;
1-[3-[(2,4-difluorophenoxy)methyl]-1-piperidyl]-2-[4-(3H-pyrrolo[3,2-f][1,7]naphthyridin-9-yl)-1-piperidyl]ethanone;
1-[3-[(4-methoxyphenoxy)methyl]-1-piperidyl]-2-[4-(3H-pyrrolo[3,2-f][1,7]naphthyridin-9-yl)-1-piperidyl]ethanone;
2-[4-(3H-pyrrolo[3,2-f][1,7]naphthyridin-9-yl)-1-piperidyl]-1-[3-[[4-(trifluoromethoxy)phenoxy]methyl]-1-piperidyl]ethanone;
2-[4-(3H-pyrrolo[3,2-f][1,7]naphthyridin-9-yl)-1-piperidyl]-1-[3-[[4-(trifluoromethyl)phenoxy]methyl]-1-piperidyl]ethanone;
1-(3-methyl-1-piperidyl)-2-[4-(3H-pyrrolo[3,2-f][1,7]naphthyridin-9-yl)-1-piperidyl]ethanone;
2-[4-(3H-pyrrolo[3,2-f][1,7]naphthyridin-9-yl)-1-piperidyl]-1-[3-(trifluoromethyl)-1-piperidyl]ethanone;
1-[3-(pyrrolidin-1-ylmethyl)-1-piperidyl]-2-[4-(3H-pyrrolo[3,2-f][1,7]naphthyridin-9-yl)cyclohexyl]ethanone;
1-[3-(methoxymethyl)pyrrolidin-1-yl]-2-[4-(3H-pyrrolo[3,2-f][1,7]naphthyridin-9-yl)cyclohexyl]ethanone;
1-(3-hydroxy-3-methyl-pyrrolidin-1-yl)-2-[4-(3H-pyrrolo[3,2-f][1,7]naphthyridin-9-yl)cyclohexyl]ethanone;
1-(3-methoxy-1-piperidyl)-2-[4-(3H-pyrrolo[3,2-f][1,7]naphthyridin-9-yl)cyclohexyl]ethanone;
[1-[2-[4-(3H-pyrrolo[3,2-f][1,7]naphthyridin-9-yl)cyclohexyl]acetyl]-3-piperidyl]methane sulfonamide;
1-(3-isobutoxy-1-piperidyl)-2-[4-(3H-pyrrolo[3,2-f][1,7]naphthyridin-9-yl)cyclohexyl]ethanone;
1-[3-(2-methoxyethoxy)-1-piperidyl]-2-[4-(3H-pyrrolo[3,2-f][1,7]naphthyridin-9-yl)cyclohexyl]ethanone;
N-(cyclopropylmethyl)-2-[4-(3H-pyrrolo[3,2-f][1,7]naphthyridin-9-yl)cyclohexyl]acetamide;
N-cyclobutyl-2-[4-(3H-pyrrolo[3,2-f][1,7]naphthyridin-9-yl)cyclohexyl]acetamide;
1-[3-[(4-fluorophenoxy)methyl]-1-piperidyl]-2-[4-(3H-pyrrolo[3,2-f][1,7]naphthyridin-9-yl)cyclohexyl]ethanone;
1-[3-[(4-chlorophenoxy)methyl]-1-piperidyl]-2-[4-(3H-pyrrolo[3,2-f][1,7]naphthyridin-9-yl)cyclohexyl]ethanone;
4-[[1-[2-[4-(3H-pyrrolo[3,2-f][1,7]naphthyridin-9-yl)cyclohexyl]acetyl]-3-piperidyl]methoxy]benzonitrile
4-[[1-[2-[4-(3H-pyrrolo[3,2-f][1,7]naphthyridin-9-yl)cyclohexyl]acetyl]-3-piperidyl]methoxy]benzoic acid;
4-[[1-[2-[4-(3H-pyrrolo[3,2-f][1,7]naphthyridin-9-yl)cyclohexyl]acetyl]-3-piperidyl]methoxy]benzamide;
1-[3-[(2,4-difluorophenoxy)methyl]-1-piperidyl]-2-[4-(3H-pyrrolo[3,2-f][1,7]naphthyridin-9-yl)cyclohexyl]ethanone;
1-[3-[(4-methoxyphenoxy)methyl]-1-piperidyl]-2-[4-(3H-pyrrolo[3,2-f][1,7]naphthyridin-9-yl)cyclohexyl]ethanone;
2-[4-(3H-pyrrolo[3,2-f][1,7]naphthyridin-9-yl)cyclohexyl]-1-[3-[[4-(trifluoromethoxy)phenoxy]methyl]-1-piperidyl]ethanone;
2-[4-(3H-pyrrolo[3,2-f][1,7]naphthyridin-9-yl)cyclohexyl]-1-[3-[[4-(trifluoromethyl)phenoxy]methyl]-1-piperidyl]ethanone;
1-(3-methyl-1-piperidyl)-2-[4-(3H-pyrrolo[3,2-f][1,7]naphthyridin-9-yl)cyclohexyl]ethanone;
2-[4-(3H-pyrrolo[3,2-f][1,7]naphthyridin-9-yl)cyclohexyl]-1-[3-(trifluoromethyl)-1-piperidyl]ethanone;
3-(pyrrolidin-1-ylmethyl)-N-[1-(3H-pyrrolo[3,2-f][1,7]naphthyridin-9-yl)-4-piperidyl]piperidine-1-carboxamide;
3-(methoxymethyl)-N-[1-(3H-pyrrolo[3,2-f][1,7]naphthyridin-9-yl)-4-piperidyl]pyrrolidine-1-carboxamide;
3-hydroxy-3-methyl-N-[1-(3H-pyrrolo[3,2-f][1,7]naphthyridin-9-yl)-4-piperidyl]pyrrolidine-1-carboxamide;
3-methoxy-N-[1-(3H-pyrrolo[3,2-f][1,7]naphthyridin-9-yl)-4-piperidyl]piperidine-1-carboxamide;
N-[1-(3H-pyrrolo[3,2-f][1,7]naphthyridin-9-yl)-4-piperidyl]-3-(sulfamoylmethyl)piperidine-1-carboxamide;
3-isobutoxy-N-[1-(3H-pyrrolo[3,2-f][1,7]naphthyridin-9-yl)-4-piperidyl]piperidine-1-carboxamide;
3-(2-methoxyethoxy)-N-[1-(3H-pyrrolo[3,2-f][1,7]naphthyridin-9-yl)-4-piperidyl]piperidine-1-carboxamide;
1-(cyclopropylmethyl)-3-[1-(3H-pyrrolo[3,2-f][1,7]naphthyridin-9-yl)-4-piperidyl]urea;
1-cyclobutyl-3-[1-(3H-pyrrolo[3,2-f][1,7]naphthyridin-9-yl)-4-piperidyl]urea;
3-[(4-fluorophenoxy)methyl]-N-[1-(3H-pyrrolo[3,2-f][1,7]naphthyridin-9-yl)-4-piperidyl]piperidine-1-carboxamide;
3-[(4-chlorophenoxy)methyl]-N-[1-(3H-pyrrolo[3,2-f][1,7]naphthyridin-9-yl)-4-piperidyl]piperidine-1-carboxamide;
3-[(4-cyanophenoxy)methyl]-N-[1-(3H-pyrrolo[3,2-f][1,7]naphthyridin-9-yl)-4-piperidyl]piperidine-1-carboxamide;
4-[[1-[[1-(3H-pyrrolo[3,2-f][1,7]naphthyridin-9-yl)-4-piperidyl]carbamoyl]-3-piperidyl]methoxy]benzoic acid;
3-[(4-carbamoylphenoxy)methyl]-N-[1-(3H-pyrrolo[3,2-f][1,7]naphthyridin-9-yl)-4-piperidyl]piperidine-1-carboxamide;
3-[(2,4-difluorophenoxy)methyl]-N-[1-(3H-pyrrolo[3,2-f][1,7]naphthyridin-9-yl)-4-piperidyl]piperidine-1-carboxamide;
3-[(4-methoxyphenoxy)methyl]-N-[1-(3H-pyrrolo[3,2-f][1,7]naphthyridin-9-yl)-4-piperidyl]piperidine-1-carboxamide;
N-[1-(3H-pyrrolo[3,2-f][1,7]naphthyridin-9-yl)-4-piperidyl]-3-[[4-(trifluoromethoxy)phenoxy]methyl]piperidine-1-carboxamide;
N-[1-(3H-pyrrolo[3,2-f][1,7]naphthyridin-9-yl)-4-piperidyl]-3-[[4-(trifluoromethyl)phenoxy]methyl]piperidine-1-carboxamide;
3-methyl-N-[1-(3H-pyrrolo[3,2-f][1,7]naphthyridin-9-yl)-4-piperidyl]piperidine-1-carboxamide;
N-[1-(3H-pyrrolo[3,2-f][1,7]naphthyridin-9-yl)-4-piperidyl]-3-(trifluoromethyl)piperidine-1-carboxamide;
[3-(pyrrolidin-1-ylmethyl)-1-piperidyl]-[4-(3H-pyrrolo[3,2-f][1,7]naphthyridin-9-yl)piperazin-1-yl]methanone;
[3-(methoxymethyl)pyrrolidin-1-yl]-[4-(3H-pyrrolo[3,2-f][1,7]naphthyridin-9-yl)piperazin-1-yl]methanone;

(3-hydroxy-3-methyl-pyrrolidin-1-yl)-[4-(3H-pyrrolo[3,2-f] [1,7]naphthyridin-9-yl)piperazin-1-yl]methanone;
(3-methoxy-1-piperidyl)-[4-(3H-pyrrolo[3,2-f][1,7]naphthyridin-9-yl)piperazin-1-yl]methanone;
[1-[4-(3H-pyrrolo[3,2-f][1,7]naphthyridin-9-yl)piperazine-1-carbonyl]-3-piperidyl]methane sulfonamide;
(3-isobutoxy-1-piperidyl)-[4-(3H-pyrrolo[3,2-f][1,7]naphthyridin-9-yl)piperazin-1-yl]methanone;
[3-(2-methoxyethoxy)-1-piperidyl]-[4-(3H-pyrrolo[3,2-f][1,7]naphthyridin-9-yl)piperazin-1-yl]methanone;
N-(cyclopropylmethyl)-4-(3H-pyrrolo[3,2-f][1,7]naphthyridin-9-yl)piperazine-1-carboxamide;
N-cyclobutyl-4-(3H-pyrrolo[3,2-f][1,7]naphthyridin-9-yl)piperazine-1-carboxamide;
[3-[(4-fluorophenoxy)methyl]-1-piperidyl]-[4-(3H-pyrrolo[3,2-f][1,7]naphthyridin-9-yl)piperazin-1-yl]methanone;
[3-[(4-chlorophenoxy)methyl]-1-piperidyl]-[4-(3H-pyrrolo[3,2-f][1,7]naphthyridin-9-yl)piperazin-1-yl]methanone;
4-[[1-[4-(3H-pyrrolo[3,2-f][1,7]naphthyridin-9-yl)piperazine-1-carbonyl]-3-piperidyl]methoxy]benzonitrile;
4-[[1-[4-(3H-pyrrolo[3,2-f][1,7]naphthyridin-9-yl)piperazine-1-carbonyl]-3-piperidyl]methoxy]benzoic acid;
4-[[1-[4-(3H-pyrrolo[3,2-f][1,7]naphthyridin-9-yl)piperazine-1-carbonyl]-3-piperidyl]methoxy]benzamide;
[3-[(2,4-difluorophenoxy)methyl]-1-piperidyl]-[4-(3H-pyrrolo[3,2-f][1,7]naphthyridin-9-yl)piperazin-1-yl]methanone;
[3-[(4-methoxyphenoxy)methyl]-1-piperidyl]-[4-(3H-pyrrolo[3,2-f][1,7]naphthyridin-9-yl)piperazin-1-yl]methanone;
[4-(3H-pyrrolo[3,2-f][1,7]naphthyridin-9-yl)-1-piperidyl]-[3-[[4-(trifluoromethoxy)phenoxy]methyl]-1-piperidyl]methanone;
[4-(3H-pyrrolo[3,2-f][1,7]naphthyridin-9-yl)piperazin-1-yl]-[3-[[4-(trifluoromethyl) phenoxy]methyl]-1-piperidyl]methanone;
(3-methyl-1-piperidyl)-[4-(3H-pyrrolo[3,2-f][1,7]naphthyridin-9-yl)piperazin-1-yl]methanone;
[4-(3H-pyrrolo[3,2-f][1,7]naphthyridin-9-yl)piperazin-1-yl]-[3-(trifluoromethyl)-1-piperidyl]methanone;
[3-(pyrrolidin-1-ylmethyl)-1-piperidyl]-[4-(3H-pyrrolo[3,2-f][1,7]naphthyridin-9-yl)-1-piperidyl]methanone;
[3-(methoxymethyl)pyrrolidin-1-yl]-[4-(3H-pyrrolo[3,2-f][1,7]naphthyridin-9-yl)-1-piperidyl]methanone;
(3-hydroxy-3-methyl-pyrrolidin-1-yl)-[4-(3H-pyrrolo[3,2-f][1,7]naphthyridin-9-yl)-1-piperidyl]methanone
(3-methoxy-1-piperidyl)-[4-(3H-pyrrolo[3,2-f][1,7]naphthyridin-9-yl)-1-piperidyl]methanone;
[1-[4-(3H-pyrrolo[3,2-f][1,7]naphthyridin-9-yl)piperidine-1-carbonyl]-3-piperidyl]methane sulfonamide;
(3-isobutoxy-1-piperidyl)-[4-(3H-pyrrolo[3,2-f][1,7]naphthyridin-9-yl)-1-piperidyl]methanone;
[3-(2-methoxyethoxy)-1-piperidyl]-[4-(3H-pyrrolo[3,2-f][1,7]naphthyridin-9-yl)-1-piperidyl]methanone;
N-(cyclopropylmethyl)-4-(3H-pyrrolo[3,2-f][1,7]naphthyridin-9-yl)piperidine-1-carboxamide;
N-cyclobutyl-4-(3H-pyrrolo[3,2-f][1,7]naphthyridin-9-yl)piperidine-1-carboxamide;
[3-[(4-fluorophenoxy)methyl]-1-piperidyl]-[4-(3H-pyrrolo[3,2-f][1,7]naphthyridin-9-yl)-1-piperidyl]methanone;
[3-[(4-chlorophenoxy)methyl]-1-piperidyl]-[4-(3H-pyrrolo[3,2-f][1,7]naphthyridin-9-yl)-1-piperidyl]methanone;
4-[[1-[4-(3H-pyrrolo[3,2-f][1,7]naphthyridin-9-yl)piperidine-1-carbonyl]-3-piperidyl]methoxy]benzonitrile;
4-[[1-[4-(3H-pyrrolo[3,2-f][1,7]naphthyridin-9-yl)piperidine-1-carbonyl]-3-piperidyl]methoxy]benzoic acid;
4-[[1-[4-(3H-pyrrolo[3,2-f][1,7]naphthyridin-9-yl)piperidine-1-carbonyl]-3-piperidyl]methoxy]benzamide;
[3-[(2,4-difluorophenoxy)methyl]-1-piperidyl]-[4-(3H-pyrrolo[3,2-f][1,7]naphthyridin-9-yl)-1-piperidyl]methanone;
[3-[(4-methoxyphenoxy)methyl]-1-piperidyl]-[4-(3H-pyrrolo[3,2-f][1,7]naphthyridin-9-yl)-1-piperidyl]methanone;
[4-(3H-pyrrolo[3,2-f][1,7]naphthyridin-9-yl)-1-piperidyl]-[3-[[4-(trifluoromethoxy)phenoxy]methyl]-1-piperidyl]methanone;
[4-(3H-pyrrolo[3,2-f][1,7]naphthyridin-9-yl)-1-piperidyl]-[3-[[4-(trifluoromethyl)phenoxy]methyl]-1-piperidyl]methanone;
(3-methyl-1-piperidyl)-[4-(3H-pyrrolo[3,2-f][1,7]naphthyridin-9-yl)-1-piperidyl]methanone;
[4-(3H-pyrrolo[3,2-f][1,7]naphthyridin-9-yl)-1-piperidyl]-[3-(trifluoromethyl)-1-piperidyl]methanone;
3-(pyrrolidin-1-ylmethyl)-N-[4-(3H-pyrrolo[3,2-f][1,7]naphthyridin-9-yl)cyclohexyl]piperidine-1-carboxamide;
3-(methoxymethyl)-N-[4-(3H-pyrrolo[3,2-f][1,7]naphthyridin-9-yl)cyclohexyl]pyrrolidine-1-carboxamide;
3-hydroxy-3-methyl-N-[4-(3H-pyrrolo[3,2-f][1,7]naphthyridin-9-yl)cyclohexyl]pyrrolidine-1-carboxamide;
3-methoxy-N-[4-(3H-pyrrolo[3,2f][1,7]naphthyridin-9-yl)cyclohexyl]piperidine-1-carboxamide;
N-[4-(3H-pyrrolo[3,2-f][1,7]naphthyridin-9-yl)cyclohexyl]-3-(sulfamoylmethyl)piperidine-1-carboxamide;
3-isobutoxy-N-[4-(3H-pyrrolo[3,2-f][1,7]naphthyridin-9-yl)cyclohexyl]piperidine-1-carboxamide;
3-(2-methoxyethoxy)-N-[4-(3H-pyrrolo[3,2-f][1,7]naphthyridin-9-yl)cyclohexyl]piperidine-1-carboxamide;
1-(cyclopropylmethyl)-3-[4-(3H-pyrrolo[3,2f][1,7]naphthyridin-9-yl)cyclohexyl]urea;
1-cyclobutyl-3-[4-(3H-pyrrolo[3,2-f][1,7]naphthyridin-9-yl)cyclohexyl]urea;
3-[(4-fluorophenoxy)methyl]-N-[4-(3H-pyrrolo[3,2-f][1,7]naphthyridin-9-yl)cyclohexyl]piperidine-1-carboxamide;
3-[(4-chlorophenoxy)methyl]-N-[4-(3H-pyrrolo[3,2-f][1,7]naphthyridin-9-yl)cyclohexyl]piperidine-1-carboxamide;
3-[(4-cyanophenoxy)methyl]-N-[4-(3H-pyrrolo[3,2-f][1,7]naphthyridin-9-yl)cyclohexyl]piperidine-1-carboxamide;
4-[[1-[[4-(3H-pyrrolo[3,2-f][1,7]naphthyridin-9-yl)cyclohexyl]carbamoyl]-3-piperidyl]methoxy]benzoic acid;
3-[(4-carbamoylphenoxy)methyl]-N-[4-(3H-pyrrolo[3,2-f][1,7]naphthyridin-9-yl)cyclohexyl]piperidine-1-carboxamide;
3-[(2,4-difluorophenoxy)methyl]-N-[4-(3H-pyrrolo[3,2-f][1,7]naphthyridin-9-yl)cyclohexyl]piperidine-1-carboxamide;
3-[(4-methoxyphenoxy)methyl]-N-[4-(3H-pyrrolo[3,2-f][1,7]naphthyridin-9-yl)cyclohexyl]piperidine-1-carboxamide;
N-[4-(3H-pyrrolo[3,2-f][1,7]naphthyridin-9-yl)cyclohexyl]-3-[[4-(trifluoromethoxy)phenoxy]methyl]piperidine-1-carboxamide;
N-[4-(3H-pyrrolo[3,2-f][1,7]naphthyridin-9-yl)cyclohexyl]-3-[[4-(trifluoromethyl)phenoxy]methyl]piperidine-1-carboxamide;
3-methyl-N-[4-(3H-pyrrolo[3,2-f][1,7]naphthyridin-9-yl)cyclohexyl]piperidine-1-carboxamide;
N-[4-(3H-pyrrolo[3,2-f][1,7]naphthyridin-9-yl)cyclohexyl]-3-(trifluoromethyl)piperidine-1-carboxamide;
9-[4-[[3-(pyrrolidin-1-ylmethyl)-1-piperidyl]methylsulfonyl]cyclohexyl]-3-pyrrolo[3,2-f][1,7]naphthyridine;
9-[4-[[3-(methoxymethyl) pyrrolidin-1-yl]methylsulfonyl]cyclohexyl]-3-pyrrolo[3,2-f][1,7]naphthyridine;
3-methyl-1-[[4-(3H-pyrrolo[3,2-f][1,7]naphthyridin-9-yl)cyclohexyl]sulfonylmethyl]pyrrolidin-3-ol;
9-[4-[(3-methoxy-1-piperidyl)methylsulfonyl]cyclohexyl]-3H-pyrrolo[3,2-f][1,7]naphthyridine;
[1-[[4-(3H-pyrrolo[3,2-f][1,7]naphthyridin-9-yl)cyclohexyl]sulfonylmethyl]-3-piperidyl]methanesulfonamide;
9-[4-[(3-isobutoxy-1-piperidyl)methylsulfonyl]cyclohexyl]-3H-pyrrolo[3,2-f][1,7]naphthyridine;
9-[4-[[3-(2-methoxyethoxy)-1-piperidyl]methylsulfonyl]cyclohexyl]-3H-pyrrolo[3,2-f][1,7]naphthyridine;

1-cyclopropyl-N-[[4-(3H-pyrrolo[3,2-f][1,7]naphthyridin-9-yl) cyclohexyl]sulfonylmethyl]methanamine;
N-[[4-(3H-pyrrolo[3,2-f][1,7]naphthyridin-9-yl)cyclohexyl]sulfonylmethyl]cyclobutanamine;
9-[4-[[3[(4-fluorophenoxy)methyl]-1-piperidyl]methylsulfonyl]cyclohexyl]-3H-pyrrolo[3,2-f][1,7]naphthyridine;
9-[4-[[3-[(4-chlorophenoxy)methyl]-1-piperidyl]methylsulfonyl]cyclohexyl]-3H-pyrrolo[3,2-f][1,7]naphthyridine;
4-[[3-[[4-(3H-pyrrolo[3,2-f][1,7]naphthyridin-9-yl)cyclohexyl]sulfonylmethyl]cyclohexyl]methoxy]benzonitrile;
4-[[3-[[4-(3H-pyrrolo[3,2-f][1,7]naphthyridin-9-yl)cyclohexyl]sulfonylmethyl]cyclohexyl]methoxy]benzoic acid;
4-[[3-[[4-(3H-pyrrolo[3,2-f][1,7]naphthyridin-9-yl)cyclohexyl]sulfonylmethyl]cyclohexyl]methoxy]benzamide;
9-[4-[[3-[(2,4-difluorophenoxy)methyl]-1-piperidyl]methylsulfonyl]cyclohexyl]-3H-pyrrolo[3,2-f][1,7]naphthyridine;
9-[4-[[3-[(4-methoxyphenoxy)methyl]-1-piperidyl]methylsulfonyl]cyclohexyl]-3H-pyrrolo[3,2-f][1,7]naphthyridine;
9-[4-[[3-[[4-(trifluoromethoxy)phenoxy]methyl]-1-piperidyl]methylsulfonyl]cyclohexyl]-3H-pyrrolo[3,2-f][1,7]naphthyridine;
9-[4-[[3-[[4-(trifluoromethyl)phenoxy]methyl]-1-piperidyl]methylsulfonyl]cyclohexyl]-3H-pyrrolo[3,2-f][1,7]naphthyridine;
9-[4-[(3-methyl-1-piperidyl)methylsulfonyl]cyclohexyl]-3H-pyrrolo[3,2-f][1,7]naphthyridine;
9-[4-[[3-(trifluoromethyl)-1-piperidyl]methylsulfonyl]cyclohexyl]-3H-pyrrolo[3,2-f][1,7]naphthyridine;
2-[3-(pyrrolidin-1-ylmethyl)-1-piperidyl]-1-[4-(3H-pyrrolo[3,2-f][1,7]naphthyridin-9-yl)cyclohexyl]ethanone;
2-[3-(methoxymethyl)pyrrolidin-1-yl]-1-[4-(3H-pyrrolo[3,2-f][1,7]naphthyridin-9-yl)cyclohexyl]ethanone;
2-(3-hydroxy-3-methyl-pyrrolidin-1-yl)-1-[4-(3H-pyrrolo[3,2-f][1,7]naphthyridin-9-yl)cyclohexyl]ethanone;
2-(3-methoxy-1-piperidyl)-1-[4-(3H-pyrrolo[3,2-f][1,7]naphthyridin-9-yl)cyclohexyl]ethanone;
[1-[2-oxo-2-[4-(3H-pyrrolo[3,2-f][1,7]naphthyridin-9-yl)cyclohexyl]ethyl]-3-piperidyl]methane sulfonamide;
2-(3-isobutoxy-1-piperidyl)-1-[4-(3H-pyrrolo[3,2-f][1,7]naphthyridin-9-yl)cyclohexyl]ethanone;
2-[3-(2-methoxyethoxy)-1-piperidyl]-1-[4-(3H-pyrrolo[3,2-f][1,7]naphthyridin-9-yl)cyclohexyl]ethanone;
2-(cyclopropylmethylamino)-1-[4-(3H-pyrrolo[3,2-f][1,7]naphthyridin-9-yl)cyclohexyl]ethanone;
2-(cyclobutylamino)-1-[4-(3H-pyrrolo[3,2-f][1,7]naphthyridin-9-yl)cyclohexyl]ethanone;
2-[3-[(4-fluorophenoxy)methyl]-1-piperidyl]-1-[4-(3H-pyrrolo[3,2-f][1,7]naphthyridin-9-yl)cyclohexyl]ethanone;
2-[3-[(4-chlorophenoxy)methyl]-1-piperidyl]-1-[4-(3H-pyrrolo[3,2-f][1,7]naphthyridin-9-yl)cyclohexyl]ethanone;
4-[[3-[2-oxo-2-[4-(3H-pyrrolo[3,2-f][1,7]naphthyridin-9-yl)cyclohexyl]ethyl]cyclohexyl]methoxy]benzonitrile;
4-[[3-[2-oxo-2-[4-(3H-pyrrolo[3,2-f][1,7]naphthyridin-9-yl)cyclohexyl]ethyl]cyclohexyl]methoxy]benzoic acid;
4-[[3-[2-oxo-2-[4-(3H-pyrrolo[3,2-f][1,7]naphthyridin-9-yl)cyclohexyl]ethyl]cyclohexyl]methoxy]benzamide;
2-[3-[(2,4-difluorophenoxy)methyl]-1-piperidyl]-1-[4-(3H-pyrrolo[3,2-f][1,7]naphthyridin-9-yl)cyclohexyl]ethanone;
2-[3-[(4-methoxyphenoxy)methyl]-1-piperidyl]-1-[4-(3H-pyrrolo[3,2-f][1,7]naphthyridin-9-yl)cyclohexyl]ethanone;
1-[4-(3H-pyrrolo[3,2-f][1,7]naphthyridin-9-yl)cyclohexyl]-2-[3-[[4-(trifluoromethoxy)phenoxy]methyl]-1-piperidyl]ethanone;
1-[4-(3H-pyrrolo[3,2-f][1,7]naphthyridin-9-yl)cyclohexyl]-2-[3-[[4-(trifluoromethyl)phenoxy]methyl]-1-piperidyl]ethanone;
2-(3-methyl-1-piperidyl)-1-[4-(3H-pyrrolo[3,2-f][1,7]naphthyridin-9-yl)cyclohexyl]ethanone;
1-[4-(3H-pyrrolo[3,2-f][1,7]naphthyridin-9-yl)cyclohexyl]-2-[3-(trifluoromethyl)-1-piperidyl]ethanone;
9-{4-[3-(4-Fluoro-phenoxymethyl)-piperidine-1-sulfonylmethyl]-cyclohexyl}-3H-3,4,6,7-tetraaza-cyclopenta[a]naphthalene;
9-{4-[3-(4-Chloro-phenoxymethyl)-piperidine-1-sulfonylmethyl]-cyclohexyl}-3H-3,4,6,7-tetraaza-cyclopenta[a]naphthalene;
4-{1-[4-(3H-3,4,6,7-Tetraaza-cyclopenta[a]naphthalen-9-yl)-cyclohexylmethanesulfonyl]piperidin-3-ylmethoxy}-benzonitrile;
4-{1-[4-(3H-3,4,6,7-Tetraaza-cyclopenta[a]naphthalen-9-yl)-cyclohexylmethanesulfonyl]-piperidin-3-ylmethoxy}-benzoic acid;
4-{1-[4-(3H-3,4,6,7-Tetraaza-cyclopenta[a]naphthalen-9-yl)-cyclohexylmethanesulfonyl]-piperidin-3-ylmethoxy}-benzamide;
9-[4-(3-Pyrrolidin-1-ylmethyl-piperidine-1-sulfonylmethyl)-cyclohexyl]-3H-3,4,6,7-tetraaza-cyclopenta[a]naphthalene;
9-[4-(3-Methoxymethyl-pyrrolidine-1-sulfonylmethyl)-cyclohexyl]-3H-3,4,6,7-tetraaza-cyclopenta[a]naphthalene;
3-Methyl-1-[4-(3H-3,4,6,7-tetraaza-cyclopenta[a]naphthalen-9-yl)-cyclohexylmethanesulfonyl]-pyrrolidin-3-ol;
9-[4-(3-Methoxy-piperidine-1-sulfonylmethyl)-cyclohexyl]-3H-3,4,6,7-tetraaza-cyclopenta[a]naphthalene;
{1-[4-(3H-3,4,6,7-Tetraaza-cyclopenta[a]naphthalen-9-yl)-cyclohexylmethanesulfonyl-piperidin-3-yl}-methanesulfonamide;
9-[4-(3-Isobutoxy-piperidine-1-sulfonylmethyl)-cyclohexyl]-3H-3,4,6,7-tetraaza-cyclopenta[a]naphthalene;
9-{4-[3-(2-Methoxy-ethoxy)-piperidine-1-sulfonylmethyl]-cyclohexyl}-3H-3,4,6,7-tetraaza-cyclopenta[a]naphthalene;
N-Cyclopropylmethyl-C-[4-(3H-3,4,6,7-tetraaza-cyclopenta[a]naphthalen-9-yl)-cyclohexyl]-methanesulfonamide;
N-Cyclobutyl-C-[4-(3H-3,4,6,7-tetraaza-cyclopenta[a]naphthalen-9-yl)-cyclohexyl]-methanesulfonamide;
9-{4-[3-(2,4-Difluoro-phenoxymethyl)-piperidine-1-sulfonylmethyl]-cyclohexyl}-3H-3,4,6,7-tetraaza-cyclopenta[a]naphthalene;
9-{4-[3-(4-Methoxy-phenoxymethyl)-piperidine-1-sulfonylmethyl]-cyclohexyl}-3H-3,4,6,7-tetraaza-cyclopenta[a]naphthalene;
9-{4-[3-(4-Trifluoromethoxy-phenoxymethyl)-piperidine-1-sulfonylmethyl]-cyclohexyl}-3H-3,4,6,7-tetraaza-cyclopenta[a]naphthalene;
9-{4-[3-(4-Trifluoromethyl-phenoxymethyl)-piperidine-1-sulfonylmethyl]-cyclohexyl}-3H-3,4,6,7-tetraaza-cyclopenta[a]naphthalene;
9-[4-(3-Methyl-piperidine-1-sulfonylmethyl)-cyclohexyl]-3H-3,4,6,7-tetraaza-cyclopenta[a]naphthalene;
9-[4-(3-Trifluoromethyl-piperidine-1-sulfonylmethyl)-cyclohexyl]-3H-3,4,6,7-tetraaza-cyclopenta[a]naphthalene;
9-{4-[3-(4-Fluoro-phenoxymethyl)-piperidine-1-sulfonylmethyl]-cyclohexyl}-3H-3,4,6,8-tetraaza-cyclopenta[a]naphthalene;
9-{4-[3-(4-Chloro-phenoxymethyl)-piperidine-1-sulfonylmethyl]-cyclohexyl}-3H-3,4,6,8-tetraaza-cyclopenta[a]naphthalene;
4-{1-[4-(3H-3,4,6,8-Tetraaza-cyclopenta[a]naphthalen-9-yl)-cyclohexylmethanesulfonyl]-piperidin-3-ylmethoxy}-benzonitrile;
4-{1-[4-(3H-3,4,6,8-Tetraaza-cyclopenta[a]naphthalen-9-yl)-cyclohexylmethanesulfonyl]-piperidin-3-ylmethoxy}-benzoic acid;
4-{1-[4-(3H-3,4,6,8-Tetraaza-cyclopenta[a]naphthalen-9-yl)-cyclohexylmethanesulfonyl]-piperidin-3-ylmethoxy}-benzamide;

9-[4-(3-Pyrrolidin-1-ylmethyl-piperidine-1-sulfonylmethyl)-cyclohexyl]-3H-3,4,6,8-tetraaza-cyclopenta[a]naphthalene;
9-[4-(3-Methoxymethyl-pyrrolidine-1-sulfonylmethyl)-cyclohexyl]-3H-3,4,6,8-tetraaza-cyclopenta[a]naphthalene;
3-Methyl-1-[4-(3H-3,4,6,8-tetraaza-cyclopenta[a]naphthalen-9-yl)-cyclohexylmethanesulfonyl]-pyrrolidin-3-ol;
9-[4-(3-Methoxy-piperidine-1-sulfonylmethyl)-cyclohexyl]-3H-3,4,6,8-tetraaza-cyclopenta[a]naphthalene;
{1-[4-(3H-3,4,6,8-Tetraaza-cyclopenta[a]naphthalen-9-yl)-cyclohexylmethanesulfonyl]-piperidin-3-yl}-methanesulfonamide;
9-[4-(3-Isobutoxy-piperidine-1-sulfonylmethyl)-cyclohexyl]-3H-3,4,6,8-tetraaza-cyclopenta[a]naphthalene;
9-{4-[3-(2-Methoxy-ethoxy)-piperidine-1-sulfonylmethyl]-cyclohexyl}-3H-3,4,6,8-tetraaza-cyclopenta[a]naphthalene;
N-Cyclopropylmethyl-C-[4-(3H-3,4,6,8-tetraaza-cyclopenta[a]naphthalen-9-yl)-cyclohexyl]-methanesulfonamide;
N-Cyclobutyl-C-[4-(3H-3,4,6,8-tetraaza-cyclopenta[a]naphthalen-9-yl)-cyclohexyl]-methanesulfonamide;
9-{4-[3-(2,4-Difluoro-phenoxymethyl)-piperidine-1-sulfonylmethyl]-cyclohexyl}-3H-3,4,6,8-tetraaza-cyclopenta[a]naphthalene;
9-{4-[3-(4-Methoxy-phenoxymethyl)-piperidine-1-sulfonylmethyl]-cyclohexyl}-3H-3,4,6,8-tetraaza-cyclopenta[a]naphthalene;
9-{4-[3-(4-Trifluoromethoxy-phenoxymethyl)-piperidine-1-sulfonylmethyl]-cyclohexyl}-3H-3,4,6,8-tetraaza-cyclopenta[a]naphthalene;
9-{4-[3-(4-Trifluoromethyl-phenoxymethyl)-piperidine-1-sulfonylmethyl]-cyclohexyl}-3H-3,4,6,8-tetraaza-cyclopenta[a]naphthalene;
9-[4-(3-Methyl-piperidine-1-sulfonylmethyl)-cyclohexyl]-3H-3,4,6,8-tetraaza-cyclopenta[a]naphthalene;
9-[4-(3-Trifluoromethyl-piperidine-1-sulfonylmethyl)-cyclohexyl]-3H-3,4,6,8-tetraaza-cyclopenta[a]naphthalene;
9-{4-[3-(4-Fluoro-phenoxymethyl)-piperidine-1-sulfonylmethyl]-cyclohexyl}-7-methyl-3H-3,4,6,8-tetraaza-cyclopenta[a]naphthalene;
9-{4-[3-(4-Chloro-phenoxymethyl)-piperidine-1-sulfonylmethyl]-cyclohexyl}-7-methyl-3H-3,4,6,8-tetraaza-cyclopenta[a]naphthalene;
4-{1-[4-(7-Methyl-3H-3,4,6,8-tetraaza-cyclopenta[a]naphthalen-9-yl)-cyclohexylmethanesulfonyl]-piperidin-3-ylmethoxy}-benzonitrile;
4-{1-[4-(7-Methyl-3H-3,4,6,8-tetraaza-cyclopenta[a]naphthalen-9-yl)-cyclohexylmethanesulfonyl]-piperidin-3-ylmethoxy}-benzoic acid;
4-{1-[4-(7-Methyl-3H-3,4,6,8-tetraaza-cyclopenta[a]naphthalen-9-yl)-cyclohexylmethanesulfonyl]-piperidin-3-ylmethoxy}-benzamide;
7-Methyl-9-[4-(3-pyrrolidin-1-ylmethyl-piperidine-1-sulfonylmethyl)-cyclohexyl]-3H-3,4,6,8-tetraaza-cyclopenta[a]naphthalene;
9-[4-(3-Methoxymethyl-pyrrolidine-1-sulfonylmethyl)-cyclohexyl]-7-methyl-3H-3,4,6,8-tetraaza-cyclopenta[a]naphthalene;
3-Methyl-1-[4-(7-methyl-3H-3,4,6,8-tetraaza-cyclopenta[a]naphthalen-9-yl)-cyclohexylmethanesulfonyl]-pyrrolidin-3-ol;
9-[4-(3-Methoxy-piperidine-1-sulfonylmethyl)-cyclohexyl]-7-methyl-3H-3,4,6,8-tetraaza-cyclopenta[a]naphthalene;
{1-[4-(7-Methyl-3H-3,4,6,8-tetraaza-cyclopenta[a]naphthalen-9-yl)-cyclohexylmethanesulfonyl]-piperidin-3-yl}-methanesulfonamide;
9-[4-(3-Isobutoxy-piperidine-1-sulfonylmethyl)-cyclohexyl]-7-methyl-3H-3,4,6,8-tetraaza-cyclopenta[a]naphthalene;
9-{4-[3-(2-Methoxy-ethoxy)-piperidine-1-sulfonylmethyl]-cyclohexyl}-7-methyl-3H-3,4,6,8-tetraaza-cyclopenta[a]naphthalene;
N-Cyclopropylmethyl-C-[4-(7-methyl-3H-3,4,6,8-tetraaza-cyclopenta[a]naphthalen-9-yl)-cyclohexyl]-methanesulfonamide;
N-Cyclobutyl-C-[4-(7-methyl-3H-3,4,6,8-tetraaza-cyclopenta[a]naphthalen-9-yl)-cyclohexyl]-methanesulfonamide;
9-{4-[3-(2,4-Difluoro-phenoxymethyl)-piperidine-1-sulfonylmethyl]-cyclohexyl}-7-methyl-3H-3,4,6,8-tetraaza-cyclopenta[a]naphthalene;
9-{4-[3-(4-Methoxy-phenoxymethyl)-piperidine-1-sulfonylmethyl]-cyclohexyl}-7-methyl-3H-3,4,6,8-tetraaza-cyclopenta[a]naphthalene;
7-Methyl-9-{4-[3-(4-trifluoromethoxy-phenoxymethyl)-piperidine-1-sulfonylmethyl]-cyclohexyl}-3H-3,4,6,8-tetraaza-cyclopenta[a]naphthalene;
7-Methyl-9-{4-[3-(4-trifluoromethyl-phenoxymethyl)-piperidine-1-sulfonylmethyl]-cyclohexyl}-3H-3,4,6,8-tetraaza-cyclopenta[a]naphthalene;
7-Methyl-9-[4-(3-methyl-piperidine-1-sulfonylmethyl)-cyclohexyl]-3H-3,4,6,8-tetraaza-cyclopenta[a]naphthalene;
7-Methyl-9-[4-(3-trifluoromethyl-piperidine-1-sulfonylmethyl)-cyclohexyl]-3H-3,4,6,8-tetraaza-cyclopenta[a]naphthalene;
9-{4-[3-(4-Fluoro-phenoxymethyl)-piperidine-1-sulfonylmethyl]-cyclohexyl}-3H-3,4,7,8-tetraaza-cyclopenta[a]naphthalene;
9-{4-[3-(4-Chloro-phenoxymethyl)-piperidine-1-sulfonylmethyl]-cyclohexyl}-3H-3,4,7,8-tetraaza-cyclopenta[a]naphthalene;
4-{1-[4-(3H-3,4,7,8-Tetraaza-cyclopenta[a]naphthalen-9-yl)-cyclohexylmethanesulfonyl]-piperidin-3-ylmethoxy}-benzonitrile;
4-{1-[4-(3H-3,4,7,8-Tetraaza-cyclopenta[a]naphthalen-9-yl)-cyclohexylmethanesulfonyl]-piperidin-3-ylmethoxy}-benzoic acid;
4-{1-[4-(3H-3,4,7,8-Tetraaza-cyclopenta[a]naphthalen-9-yl)-cyclohexylmethanesulfonyl]-piperidin-3-ylmethoxy}-benzamide;
9-[4-(3-Pyrrolidin-1-ylmethyl-piperidine-1-sulfonylmethyl)-cyclohexyl]-3H-3,4,7,8-tetraaza-cyclopenta[a]naphthalene;
9-[4-(3-Methoxymethyl-pyrrolidine-1-sulfonylmethyl)-cyclohexyl]-3H-3,4,7,8-tetraaza-cyclopenta[a]naphthalene;
3-Methyl-1-[4-(3H-3,4,7,8-tetraaza-cyclopenta[a]naphthalen-9-yl)-cyclohexylmethanesulfonyl]-pyrrolidin-3-ol;
9-[4-(3-Methoxy-piperidine-1-sulfonylmethyl)-cyclohexyl]-3H-3,4,7,8-tetraaza-cyclopenta[a]naphthalene;
{1-[4-(3H-3,4,7,8-Tetraaza-cyclopenta[a]naphthalen-9-yl)-cyclohexylmethanesulfonyl]-piperidin-3-yl}-methanesulfonamide;
9-[4-(3-Isobutoxy-piperidine-1-sulfonylmethyl)-cyclohexyl]-3H-3,4,7,8-tetraaza-cyclopenta[a]naphthalene;
9-{4-[3-(2-Methoxy-ethoxy)-piperidine-1-sulfonylmethyl]-cyclohexyl}-3H-3,4,7,8-tetraaza-cyclopenta[a]naphthalene;
N-Cyclopropylmethyl-C-[4-(3H-3,4,7,8-tetraaza-cyclopenta[a]naphthalen-9-yl)-cyclohexyl]-methanesulfonamide;
N-Cyclobutyl-C-[4-(3H-3,4,7,8-tetraaza-cyclopenta[a]naphthalen-9-yl)-cyclohexyl]-methanesulfonamide;
9-{4-[3-(2,4-Difluoro-phenoxymethyl)-piperidine-1-sulfonylmethyl]-cyclohexyl}-3H-3,4,7,8-tetraaza-cyclopenta[a]naphthalene;
9-{4-[3-(4-Methoxy-phenoxymethyl)-piperidine-1-sulfonylmethyl]-cyclohexyl}-3H-3,4,7,8-tetraaza-cyclopenta[a]naphthalene;
9-{4-[3-(4-Trifluoromethoxy-phenoxymethyl)-piperidine-1-sulfonylmethyl]-cyclohexyl}-3H-3,4,7,8-tetraaza-cyclopenta[a]naphthalene;

9-{4-[3-(4-Trifluoromethyl-phenoxymethyl)-piperidine-1-sulfonylmethyl]-cyclohexyl}-3H-3,4,7,8-tetraaza-cyclopenta[a]naphthalene;

9-[4-(3-Methyl-piperidine-1-sulfonylmethyl)-cyclohexyl]-3H-3,4,7,8-tetraaza-cyclopenta[a]naphthalene;

9-[4-(3-Trifluoromethyl-piperidine-1-sulfonylmethyl)-cyclohexyl]-3H-3,4,7,8-tetraaza-cyclopenta[a]naphthalene;

9-[4-[[3-[(4-fluorophenoxy)methyl]-1-piperidyl]sulfonylmethyl]cyclohexyl]-3H-pyrrolo[2,3c][2,7]naphthyridine;

9-[4-[[3-[(4-chlorophenoxy)methyl]-1-piperidyl]sulfonylmethyl]cyclohexyl]-3H-pyrrolo[2,3c][2,7]naphthyridine;

4-[[1-[[4-(3H-pyrrolo[2,3-c][2,7]naphthyridin-9-yl)cyclohexyl]methylsulfonyl]-3-piperidyl]methoxy]benzonitrile;

4-[[1-[[4-(3H-pyrrolo[2,3-c][2,7]naphthyridin-9-yl)cyclohexyl]methylsulfonyl]-3-piperidyl]methoxy]benzoic acid;

4-[[1-[[4-(3H-pyrrolo[2,3-c][2,7]naphthyridin-9-yl)cyclohexyl]methylsulfonyl]-3-piperidyl]methoxy]benzamide;

9-[4-[[3-(pyrrolidin-1-ylmethyl)-1-piperidyl]sulfonylmethyl]cyclohexyl]-3H-pyrrolo[2,3-c][2,7]naphthyridine;

9-[4-[[3-(methoxymethyl)pyrrolidin-1-yl]sulfonylmethyl]cyclohexyl]-3H-pyrrolo[2,3-c][2,7]naphthyridine;

3-methyl-1-[[4-(3H-pyrrolo[2,3-c][2,7]naphthyridin-9-yl)cyclohexyl]methylsulfonyl]pyrrolidin-3-ol;

9-[4-[(3-methoxy-1-piperidyl)sulfonylmethyl]cyclohexyl]-3H-pyrrolo[2,3-c][2,7]naphthyridine;

[1-[[4-(3H-pyrrolo[2,3-c][2,7]naphthyridin-9-yl)cyclohexyl]methylsulfonyl]-3-piperidyl]methanesulfonamide;

9-[4-[(3-isobutoxy-1-piperidyl)sulfonylmethyl]cyclohexyl]-3H-pyrrolo[2,3-c][2,7]naphthyridine;

9-[4-[[3-(2-methoxyethoxy)-1-piperidyl]sulfonylmethyl]cyclohexyl]-3H-pyrrolo[2,3-c][2,7]naphthyridine;

N-(cyclopropylmethyl)-1-[4-(3H-pyrrolo[2,3-c][2,7]naphthyridin-9-yl)cyclohexyl]methanesulfonamide;

N-cyclobutyl-1-[4-(3H-pyrrolo[2,3-c][2,7]naphthyridin-9-yl)cyclohexyl]methanesulfonamide;

9-[4-[[3-[(2,4-difluorophenoxy)methyl]-1-piperidyl]sulfonylmethyl]cyclohexyl]-3H-pyrrolo[2,3-c][2,7]naphthyridine;

9-[4-[[3-[(4-methoxyphenoxy)methyl]-1-piperidyl]sulfonylmethyl]cyclohexyl]-3H-pyrrolo[2,3-c][2,7]naphthyridine;

9-[4-[[3-[[4-(trifluoromethoxy)phenoxy]methyl]-1-piperidyl]sulfonylmethyl]cyclohexyl]-3H-pyrrolo[2,3-c][2,7]naphthyridine;

9-[4-[[3-[[4-(trifluoromethyl)phenoxy]methyl]-1-piperidyl]sulfonylmethyl]cyclohexyl]-3H-pyrrolo[2,3-c][2,7]naphthyridine;

9-[4-[(3-methyl-1-piperidyl)sulfonylmethyl]cyclohexyl]-3H-pyrrolo[2,3-c][2,7]naphthyridine;

9-[4-[[3-(trifluoromethyl)-1-piperidyl]sulfonylmethyl]cyclohexyl]-3H-pyrrolo[2,3-c][2,7]naphthyridine;

1-[4-[[3-[(4-fluorophenoxy)methyl]-1-piperidyl]sulfonylmethyl]cyclohexyl]-7H-pyrrolo[2,3-c][2,6]naphthyridine;

1-[4-[[3-[(4-chlorophenoxy)methyl]-1-piperidyl]sulfonylmethyl]cyclohexyl]-7H-pyrrolo[2,3-c][2,6]naphthyridine;

4-[[1-[[4-(7H-pyrrolo[2,3-h][2,6]naphthyridin-1-yl)cyclohexyl]methylsulfonyl]-3-piperidyl]methoxy]benzonitrile;

4-[[1-[[4-(7H-pyrrolo[2,3-h][2,6]naphthyridin-1-yl)cyclohexyl]methylsulfonyl]-3-piperidyl]methoxy]benzoic acid;

4-[[1-[[4-(7H-pyrrolo[2,3-h][2,6]naphthyridin-1-yl)cyclohexyl]methylsulfonyl]-3-piperidyl]methoxy]benzamide;

1-[4-[[3-(pyrrolidin-1-ylmethyl)-1-piperidyl]sulfonylmethyl]cyclohexyl]-7H-pyrrolo[2,3-c][2,6]naphthyridine;

1-[4-[[3-(methoxymethyl)pyrrolidin-1-yl]sulfonylmethyl]cyclohexyl]-7H-pyrrolo[2,3-c][2,6]naphthyridine;

3-methyl-1-[[4-(7H-pyrrolo[2,3-h][2,6]naphthyridin-1-yl)cyclohexyl]methylsulfonyl]pyrrolidin-3-ol;

1-[4-[(3-methoxy-1-piperidyl)sulfonylmethyl]cyclohexyl]-7H-pyrrolo[2,3-c][2,6]naphthyridine;

[1-[[4-(7H-pyrrolo[2,3-h][2,6]naphthyridin-1-yl)cyclohexyl]methylsulfonyl]-3-piperidyl]methanesulfonamide;

1-[4-[(3-isobutoxy-1-piperidyl)sulfonylmethyl]cyclohexyl]-7H-pyrrolo[2,3-c][2,6]naphthyridine;

1-[4-[[3-(2-methoxyethoxy)-1-piperidyl]sulfonylmethyl]cyclohexyl]-7H-pyrrolo[2,3-c][2,6]naphthyridine;

N-(cyclopropylmethyl)-1-[4-(7H-pyrrolo[2,3-h][2,6]naphthyridin-1-yl)cyclohexyl]methanesulfonamide;

N-cyclobutyl-1-[4-(7H-pyrrolo[2,3-h][2,6]naphthyridin-1-yl)cyclohexyl]methanesulfonamide;

1-[4-[[3-[(2,4-difluorophenoxy)methyl]-1-piperidyl]sulfonylmethyl]cyclohexyl]-7H-pyrrolo[2,3-c][2,6]naphthyridine;

1-[4-[[3-[(4-methoxyphenoxy)methyl]-1-piperidyl]sulfonylmethyl]cyclohexyl]-7H-pyrrolo[2,3-c][2,6]naphthyridine;

1-[4-[[3-[[4-(trifluoromethoxy)phenoxy]methyl]-1-piperidyl]sulfonylmethyl]cyclohexyl]-7H-pyrrolo[2,3-c][2,6]naphthyridine;

1-[4-[[3-[[4-(trifluoromethyl)phenoxy]methyl]-1-piperidyl]sulfonylmethyl]cyclohexyl]-7H-pyrrolo[2,3-c][2,6]naphthyridine;

1-[4-[(3-methyl-1-piperidyl)sulfonylmethyl]cyclohexyl]-7H-pyrrolo[2,3-c][2,6]naphthyridine;

1-[4-[[3-(trifluoromethyl)-1-piperidyl]sulfonylmethyl]cyclohexyl]-7H-pyrrolo[2,3-c][2,6]naphthyridine;

4,4,4-Trifluoro-1-[3-(3H-3,4,6-triaza-cyclopenta[a]naphthalen-9-yl)-2,5-dihydro-pyrrol-1-yl]-butan-1-one;

Cyclopropyl-[3-(3H-3,4,6-triaza-cyclopenta[a]naphthalen-9-yl)-2,5-dihydro-pyrrol-1-yl]-methanone;

3-Oxo-3-[3-(3H-3,4,6,8-tetraaza-cyclopenta[a]naphthalen-9-yl)-2,5-dihydro-pyrrol-1-yl]-propionitrile;

3,3,3-Trifluoro-1-[3-(3H-3,4,6,8-tetraaza-cyclopenta[a]naphthalen-9-yl)-2,5-dihydro-pyrrol-1-yl]-propan-1-one;

4,4,4-Trifluoro-1-[3-(3H-3,4,6,8-tetraaza-cyclopenta[a]naphthalen-9-yl)-2,5-dihydro-pyrrol-1-yl]-butan-1-one;

Cyclopropyl-[3-(3H-3,4,6,8-tetraaza-cyclopenta[a]naphthalen-9-yl)-2,5-dihydro-pyrrol-1-yl]-methanone;

[3-(3H-3,4,6,8-Tetraaza-cyclopenta[a]naphthalen-9-yl)-2,5-dihydro-pyrrole-1-sulfonyl]-acetonitrile;

9-[1-(2,2,2-Trifluoro-ethanesulfonyl)-2,5-dihydro-1H-pyrrol-3-yl]-3H-3,4,6,8-tetraaza-cyclopenta[a]naphthalene;

9-(1-Methanesulfonyl-2,5-dihydro-1H-pyrrol-3-yl)-3H-3,4,6,8-tetraaza-cyclopenta[a]naphthalene;

3-[3-(7-Methyl-3H-3,4,6,8-tetraaza-cyclopenta[a]naphthalen-9-yl)-2,5-dihydro-pyrrol-1-yl]-3-oxo-propionitrile;

3,3,3-Trifluoro-1-[3-(7-methyl-3H-3,4,6,8-tetraaza-cyclopenta[a]naphthalen-9-yl)-2,5-dihydro-pyrrol-1-yl]-propan-1-one;

4,4,4-Trifluoro-1-[3-(7-methyl-3H-3,4,6,8-tetraaza-cyclopenta[a]naphthalen-9-yl)-2,5-dihydro-pyrrol-1-yl]-butan-1-one;

Cyclopropyl-[3-(7-methyl-3H-3,4,6,8-tetraaza-cyclopenta[a]naphthalen-9-yl)-2,5-dihydro-pyrrol-1-yl]methanone;

[3-(7-Methyl-3H-3,4,6,8-tetraaza-cyclopenta[a]naphthalen-9-yl)-2,5-dihydro-pyrrole-1-sulfonyl]-acetonitrile;

7-Methyl-9-[1-(2,2,2-trifluoro-ethanesulfonyl)-2,5-dihydro-1H-pyrrol-3-yl]-3H-3,4,6,8-tetraaza-cyclopenta[a]naphthalene;

9-(1-Methanesulfonyl-2,5-dihydro-1H-pyrrol-3-yl)-7-methyl-3H-3,4,6,8-tetraaza-cyclopenta[a]naphthalene;

3-Oxo-3-[3-(3H-3,4,6,7-tetraaza-cyclopenta[a]naphthalen-9-yl)-2,5-dihydro-pyrrol-1-yl]-propionitrile;

3,3,3-Trifluoro-1-[3-(3H-3,4,6,7-tetraaza-cyclopenta[a]naphthalen-9-yl)-2,5-dihydro-pyrrol-1-yl]-propan-1-one 4,4,4-Trifluoro-1-[3-(3H-3,4,6,7-tetraaza-cyclopenta[a]naphthalen-9-yl)-2,5-dihydro-pyrrol-1-yl]-butan-1-one;

Cyclopropyl-[3-(3H-3,4,6,7-tetraaza-cyclopenta[a]naphthalen-9-yl)-2,5-dihydro-pyrrol-1-yl]-methanone;

[3-(3H-3,4,6,7-Tetraaza-cyclopenta[a]naphthalen-9-yl)-2,5-dihydro-pyrrole-1-sulfonyl]-acetonitrile;

9-[1-(2,2,2-Trifluoro-ethanesulfonyl)-2,5-dihydro-1H-pyrrol-3-yl]-3H-3,4,6,7-tetraaza-cyclopenta[a]naphthalene;
9-(1-Methanesulfonyl-2,5-dihydro-1H-pyrrol-3-yl)-3H-3,4,6,7-tetraaza-cyclopenta[a]naphthalene;
3-Oxo-3-[3-(3H-3,4,7,8-tetraaza-cyclopenta[a]naphthalen-9-yl)-2,5-dihydro-pyrrol-1-yl]-propionitrile;
3,3,3-Trifluoro-1-[3-(3H-3,4,7,8-tetraaza-cyclopenta[a]naphthalen-9-yl)-2,5-dihydro-pyrrol-1-yl]-propan-1-one;
4,4,4-Trifluoro-1-[3-(3H-3,4,7,8-tetraaza-cyclopenta[a]naphthalen-9-yl)-2,5-dihydro-pyrrol-1-yl]-butan-1-one;
Cyclopropyl-[3-(3H-3,4,7,8-tetraaza-cyclopenta[a]naphthalen-9-yl)-2,5-dihydro-pyrrol-1-yl]-methanone;
[3-(3H-3,4,7,8-Tetraaza-cyclopenta[a]naphthalen-9-yl)-2,5-dihydro-pyrrole-1-sulfonyl]-acetonitrile;
9-[1-(2,2,2-Trifluoro-ethanesulfonyl)-2,5-dihydro-1H-pyrrol-3-yl]-3H-3,4,7,8-tetraaza-cyclopenta[a]naphthalene;
9-(1-Methanesulfonyl-2,5-dihydro-1H-pyrrol-3-yl)-3H-3,4,7,8-tetraaza-cyclopenta[a]naphthalene;
3-Oxo-3-[3-(3H-3,4,8-triaza-cyclopenta[a]naphthalen-9-yl)-2,5-dihydro-pyrrol-1-yl]-propionitrile;
3,3,3-Trifluoro-1-[3-(3H-3,4,8-triaza-cyclopenta[a]naphthalen-9-yl)-2,5-dihydro-pyrrol-1-yl]-propan-1-one;
4,4,4-Trifluoro-1-[3-(3H-3,4,8-triaza-cyclopenta[a]naphthalen-9-yl)-2,5-dihydro-pyrrol-1-yl]-butan-1-one;
Cyclopropyl-[3-(3H-3,4,8-triaza-cyclopenta[a]naphthalen-9-yl)-2,5-dihydro-pyrrol-1-yl]-methanone;
[3-(3H-3,4,8-Triaza-cyclopenta[a]naphthalen-9-yl)-2,5-dihydro-pyrrole-1-sulfonyl]-acetonitrile;
9-[1-(2,2,2-Trifluoro-ethanesulfonyl)-2,5-dihydro-1H-pyrrol-3-yl]-3H-3,4,8-triaza-cyclopenta[a]naphthalene;
9-(1-Methanesulfonyl-2,5-dihydro-1H-pyrrol-3-yl)-3H-3,4,8-triaza-cyclopenta[a]naphthalene;
3-Oxo-3-[3-(3H-3,4,7-triaza-cyclopenta[a]naphthalen-9-yl)-2,5-dihydro-pyrrol-1-yl]-propionitrile
3,3,3-Trifluoro-1-[3-(3H-3,4,7-triaza-cyclopenta[a]naphthalen-9-yl)-2,5-dihydro-pyrrol-1-yl]-propan-1-one;
4,4,4-Trifluoro-1-[3-(3H-3,4,7-triaza-cyclopenta[a]naphthalen-9-yl)-2,5-dihydro-pyrrol-1-yl]-butan-1-one;
Cyclopropyl-[3-(3H-3,4,7-triaza-cyclopenta[a]naphthalen-9-yl)-2,5-dihydro-pyrrol-1-yl]-methanone;
[3-(3H-3,4,7-Triaza-cyclopenta[a]naphthalen-9-yl)-2,5-dihydro-pyrrole-1-sulfonyl]-acetonitrile;
9-[1-(2,2,2-Trifluoro-ethanesulfonyl)-2,5-dihydro-1H-pyrrol-3-yl]-3H-3,4,7-triaza-cyclopenta[a]naphthalene; and
9-(1-Methanesulfonyl-2,5-dihydro-1H-pyrrol-3-yl)-3H-3,4,7-triaza-cyclopenta[a]naphthalene.

Biological Activity

Materials

Recombinant JAK1 (Amino acids 850-1154; NM_002227.2), JAK2 (Amino acids 808-1132; NM_004972.3) and JAK3 (Amino acids 781-1124; NM_000215.3) used in the studies were expressed using Invitrogen's Bac-to-Bac baculovirus expression system according to manufacturer's instructions. Adenosine 5'-triphosphate was obtained from Sigma Aldrich chemicals (Cat # A7699). Poly Glu-Tyr (4:1) sodium salt was obtained from Sigma Aldrich (Cat # P0275), Kinase Glo® Luminescent Kinase assay kit was obtained from Promega (Cat # V6713)

Methods

Kinase activity was assessed by Promega Kinase-Glo® Luminescent Kinase Assay kit using 200 μg/ml Poly Glu-Tyr (4:1) as substrate and ATP at 1 uM concentration. The reactions were carried out in 384 well plates in total reaction volume of 20 uL. Reaction mixtures contained 50 mM HEPES pH 7.4, 5 mM MgCl2, 1 mM DTT, 0.01% BSA, 0.01% Tween 20. Kinase was pre-incubated with compounds or 1% DMSO for 5 min before addition of substrate and ATP to check for inhibition. Kinase reactions were carried out at room temperature for 90 min. The reactions were stopped by adding 5 μl of Kinase Glo® reagent & 10 μl of reaction mixture followed by measuring luminescence. The luminescent signal is correlated with the amount of ATP present at the end of kinase reaction and is inversely correlated with the amount of kinase activity.

For each data point, % inhibition is calculated based on uninhibited reaction (without compound) which is considered as 100% activity over no enzyme or substrate controls. Dose response data is then fit using a four parameter logistic equation using Graph-pad Prism 5 software to determine inhibition constant 50 ($IC_{50}$).

Using the above protocol the following results are generated:

(+)—1050 less than 1 nm; (++)—1050 more than 1 nm and less than 20 nm; (+++)—1050 more than 20 nm

| No. | JAK1 | JAK2 | JAK3 |
|---|---|---|---|
| Comp. 8 | − | − | +++ |
| Comp. 41 | ++ | − | ++ |
| Comp. 50 | ++ | − | +++ |
| Comp. 55 | ++ | +++ | +++ |
| Comp. 88 | +++ | − | +++ |
| Comp. 124 | − | +++ | +++ |
| Comp. 125 | − | − | +++ |
| Comp. 127 | +++ | − | +++ |
| Ex. 1 | ++ | ++ | ++ |
| Ex. 2 | ++ | − | ++ |
| Ex. 3 | +++ | | +++ |
| Ex. 4 | ++ | − | ++ |
| Ex. 5 | ++ | | +++ |
| Ex. 6 | ++ | − | ++ |
| Ex. 7 | ++ | − | ++ |
| Ex. 8 | ++ | − | ++ |
| Ex. 9 | ++ | ++ | ++ |
| Ex. 10 | ++ | ++ | ++ |
| Ex. 11 | +++ | +++ | +++ |
| Ex. 12 | ++ | ++ | +++ |
| Ex. 13 | +++ | +++ | +++ |
| Ex. 14 | ++ | ++ | +++ |
| Ex. 15 | ++ | ++ | +++ |
| Ex. 16 | ++ | ++ | +++ |
| Ex. 17 | +++ | ++ | +++ |
| Ex. 18 | ++ | ++ | +++ |
| Ex. 19 | ++ | ++ | +++ |
| Ex. 20 | ++ | ++ | +++ |
| Ex. 21 | +++ | +++ | +++ |
| Ex. 22 | +++ | +++ | +++ |
| Ex. 23 | ++ | ++ | ++ |
| Ex. 24 | ++ | ++ | +++ |
| Ex. 25 | ++ | +++ | +++ |
| Ex. 26 | ++ | +++ | +++ |
| Ex. 27 | +++ | +++ | +++ |
| Ex. 28 | ++ | ++ | +++ |
| Ex. 29 | +++ | +++ | +++ |
| Ex. 30 | +++ | +++ | +++ |
| Ex. 31 | +++ | +++ | +++ |
| Ex. 32 | +++ | +++ | +++ |
| Ex. 33 | − | − | +++ |
| Ex. 34 | − | − | +++ |
| Ex. 35 | − | − | +++ |
| Ex. 36 | − | − | +++ |
| Ex. 37 | − | − | +++ |
| Ex. 38 | − | − | +++ |
| Ex. 40 | − | − | +++ |
| Ex. 41 | − | − | +++ |
| Ex. 42 | − | − | +++ |
| Ex. 43 | +++ | ++ | ++ |
| Ex. 44 | ++ | ++ | +++ |
| Ex. 45 | ++ | ++ | +++ |
| Ex. 46 | | +++ | +++ |
| Ex. 47 | ++ | ++ | ++ |
| Ex. 48 | +++ | +++ | +++ |
| Ex. 49 | +++ | +++ | +++ |
| Ex. 50 | +++ | +++ | +++ |
| Ex. 51 | − | ++ | ++ |
| Ex. 52 | − | ++ | ++ |
| Ex. 56 | ++ | ++ | ++ |
| Ex. 57 | − | +++ | +++ |
| Ex. 58 | − | ++ | ++ |

-continued

| No. | JAK1 | JAK2 | JAK3 |
|---|---|---|---|
| Ex. 59 | − | +++ | ++ |
| Ex. 60 | +++ | +++ | ++ |
| Ex. 61 | − | +++ | +++ |
| Ex. 62 | − | +++ | +++ |
| Ex. 63 | +++ | − | +++ |
| Ex. 64 | − | − | +++ |
| Ex. 65 | +++ | +++ | +++ |
| Ex. 66 | − | − | +++ |
| Ex. 67 | +++ | − | +++ |
| Ex. 68 | +++ | +++ | +++ |
| Ex. 69 | − | − | +++ |
| Ex. 70 | − | − | +++ |
| Ex. 71 | +++ | +++ | +++ |
| Ex. 72 | +++ | +++ | +++ |
| Ex. 73 | +++ | − | ++ |
| Ex. 74 | +++ | +++ | +++ |
| Ex. 75 | +++ | − | +++ |
| Ex. 76 | +++ | − | +++ |
| Ex. 77 | +++ | − | +++ |
| Ex. 78 | +++ | − | +++ |
| Ex. 79 | ++ | − | +++ |
| Ex. 80 | ++ | − | ++ |
| Ex. 81 | ++ | ++ | ++ |
| Ex. 82 | +++ | − | ++ |
| Ex. 83 | ++ | ++ | ++ |
| Ex. 84 | ++ | +++ | +++ |
| Ex. 85 | +++ | +++ | +++ |
| Ex. 86 | − | ++ | ++ |
| Ex. 87 | +++ | ++ | +++ |
| Ex. 90 | − | ++ | ++ |
| Ex. 91 | − | ++ | +++ |
| Ex. 92 | − | ++ | +++ |
| Ex. 93 | − | − | +++ |
| Ex. 94 | − | − | ++ |
| Ex. 95 | − | − | +++ |
| Ex. 96 | − | − | +++ |
| Ex. 97 | − | − | +++ |
| Ex. 98 | − | − | +++ |
| Ex. 99 | − | − | +++ |
| Ex. 100 | − | − | ++ |
| Ex. 101 | − | − | ++ |
| Ex. 102 | +++ | +++ | +++ |
| Ex. 103 | +++ | − | +++ |
| Ex. 104 | +++ | − | +++ |
| Ex. 105 | ++ | +++ | +++ |
| Ex. 1A | +++ | +++ | +++ |
| Ex. 1B | ++ | ++ | + |
| Ex. 4A | ++ | ++ | ++ |
| Ex. 4B | − | − | +++ |
| Ex. 10A | − | +++ | +++ |
| Ex. 10B | ++ | ++ | ++ |
| Ex. 14A | +++ | +++ | +++ |
| Ex. 14B | ++ | ++ | +++ |
| Ex. 15A | +++ | +++ | +++ |
| Ex. 15B | − | ++ | +++ |
| Ex. 16A | − | ++ | +++ |
| Ex. 16B | − | +++ | +++ |
| Ex. 23A | +++ | +++ | +++ |
| Ex. 23B | − | ++ | ++ |
| Ex. 24A | +++ | +++ | +++ |
| Ex. 24B | − | ++ | ++ |
| Ex. 43A | +++ | +++ | +++ |
| Ex. 43B | ++ | ++ | ++ |
| Ex. 61A | − | +++ | +++ |
| Ex. 61B | +++ | +++ | +++ |
| Ex. 88A | +++ | − | ++ |
| Ex. 88B | +++ | − | ++ |
| Ex. 88B1 | +++ | − | +++ |
| Ex. 88B2 | ++ | ++ | ++ |

We claim:
1. A compound of formula (Ia):

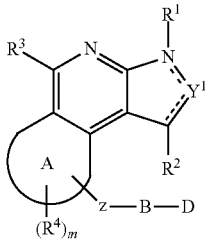

wherein,
$Y^1$ represents $CR'$ wherein $R'$ is H or alkyl;
A is selected from

[structures shown]

$R^1$ is selected from hydrogen or alkyl;
$R^2$ is selected from hydrogen or alkyl;
$R^3$ is selected from hydrogen or alkyl;
$R^4$ is selected from hydrogen, alkyl, alkoxy, cyano, halogen, hydroxy, hydroxyalkyl, haloalkyl, perhaloalkyl, carboxy, alkylcarboxy, carboxyalkyl, carboxyalkyloxy, alkylcarboxyalkyloxy or nitro;
Z is a bond or is a group selected from cycloalkylene, arylene, heterocyclylene, heterocyclylenealkyl, heteroarylene, spirocyclyl, $(C_{1-6})$alkylene, $(C_{1-6})$alkenylene or $(C_{1-6})$alkynylene wherein one or more than one methylene groups from alkylene, alkenylene or alkynylene are optionally replaced by hetero atoms or groups selected from —O—, —S(O)p-, —N($R^5$)—, or —C(O);
B is a bond or is a group selected from cycloalkylene, cycloalkenylene, arylene, heterocyclylene, heteroarylene, $(C_{1-6})$alkylene, $(C_{1-6})$alkenylene or $(C_{1-6})$alkynylene wherein one or more than one methylene groups from alkylene, alkenylene or alkynylene are optionally replaced by hetero atoms or groups selected from —O—, —S(O)p-, —N($R^5$)—, —C(O) or —C(=NR")— wherein R" is H, alkyl, cyano, hydroxy, hydroxyalkyl, haloalkyl or perhaloalkyl;
D is selected from hydroxy, alkoxy, alkoxyalkyl, cyano, halogen, haloalkyl, perhaloalkyl, alkyl, alkenyl, alkynyl, carboxy, carboxyalkyl, cyanoalkyl, acyl, cyanoalkylarbonyl, cyanoalkenylcarbonyl, —$(CR^aR^b)_n OR^5$, —$SR^5$, —$(CR^aR^b)_n COOR^5$, —$(CR^aR^b)_n NR^6R^7$, —$(CR^aR^b)_n C(O)NR^6R^7$, —$(CR^aR^b)_n NR^5C(O)NR^6R^7$, thiocarbonyl, $S(O)_2NR^6R^7$, —$NR^5S(O)_2R^5$, —$S(O)_p R^5$, —$SO_3H$, cycloalkyl, cycloalkenyl, cycloalkylalkyl, cycloalkyloxy, cycloalkylamino, aryl, arylalkyl, aryloxy, arylamino, heterocyclyl, heterocyclylalkyl, heterocyclyloxy, heterocycloalkylamino, heteroaryl, heteroarylalkyl, heteroaryloxy, or heteroarylamino;

$R^5$ is selected from the group consisting of hydrogen, halogen, haloalkyl, alkyl, alkenyl, alkynyl, aryl, arylalkyl, heteroaryl, heteroarylalkyl, cycloalkyl, cycloalkylalkyl, heterocyclyl and heterocyclylalkyl;

wherein alkyl, alkenyl, alkynyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy, or carboxyalkyl;

$R^6$ and $R^7$ are independently selected from the group consisting of hydrogen, —$(CR^aR^b)_n OR^5$, haloalkyl, —$(CR^aR^b)_n C(O)R^5$, alkyl, alkenyl, alkynyl, aryl, arylalkyl, heteroaryl, heteroarylalkyl, cycloalkyl, cycloalkylalkyl, heterocyclyl or heterocyclylalkyl, or $R^6$ and $R^7$ taken together form a monocyclic or a bicyclic ring system which is saturated or partially unsaturated and optionally have additional heteroatoms selected from O, N or S, the said ring system is further optionally substituted with 1 to 4 substituents independently selected from halo, alkyl, alkenyl, alkynyl, nitro, cyano, —$(CR^aR^b)_n OR^5$, —$SR^5$, oxo, alkylsulfonyl, —$(CR^aR^b)_n COOR^5$, cycloalkyl, cycloalkylalkyl, aryl, arylalkyl, heterocyclyl, heterocyclylalkyl, heteroaryl, and heteroarylalkyl;

Z, B and D may be optionally substituted with one or more substituents independently selected from cyano, nitro, keto, oxo, halogen, haloalkyl, perhaloalkyl, hydroxyamino, —$(CR^aR^b)_n OR^5$, —$(CR^aR^b)C(O)R^5 OC(O)R^5$, —$SR^5$, —$(CR^aR^b)_n COOR^5$, —$(CR^aR^b)_n NR^6R^7$, —$(CR^aR^b)_n C(O)NR^6R^7$, —$(CR^aR^b)_n NR^5C(O)NR^6R^7$, —$NR^5C(O)R^5$, thiocarbonyl, $S(O)_2 NR^6R^7$, —$NR^5$, —$S(O)_2 R^5$, —$S(O)_p R^5$, —$SO_3H$, —$OP(O)(R^8)_q$, alkyl, alkenyl, alkynyl, cycloalkyl, cycloalkenyl, cycloalkylalkyl, aryl, heterocyclyl or heteroaryl;

wherein alkyl, alkenyl, alkynyl, cycloalkyl, cycloalkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —$OC(O)R^5$, —$(CR^aR^b)_n C(O)NR^6R^7$, —$NR^5C(O)R^5$, —$SR^5$, —$S(O)_p R^5$, —$S(O)_2 NR^6R^7$ or —$NR^5S(O)_2 R^5$;

$R^8$ is selected from the group consisting of hydroxy and alkoxy;

$R^a$ and $R^b$ are independently selected from the group consisting of hydrogen, —$OR^5$, halogen, haloalkyl, perhaloalkyl and alkyl;

n is 0-6;

m is 0, 1 or 2;

p is 0, 1 or 2;

q is 1 or 2.

2. The compound of formula (Ia) as claimed in claim 1, wherein, $Y^1$ represents CR' wherein R' is H or alkyl;

A is selected from $R^1$ is selected from hydrogen or alkyl;
$R^2$ is selected from hydrogen or alkyl;
$R^3$ is selected from hydrogen or alkyl;
$R^4$ is selected from hydrogen, alkyl, alkoxy, cyano, halogen, hydroxy, hydroxyalkyl, haloalkyl, perhaloalkyl, carboxy, alkylcarboxy, carboxyalkyl, carboxyalkyloxy, alkylcarboxyalkyloxy or nitro;

Z is selected from

B is a bond or $(C_{1-6})$alkylene wherein one or more than one methylene groups are optionally replaced by hetero atoms or groups —O—, —S(O)p-, —N($R^5$)—, —C(O) or —C(=NR")— wherein R" is H, alkyl, cyano, hydroxy, hydroxyalkyl, haloalkyl or perhaloalkyl;

D is selected from alkoxy, alkoxyalkyl, cyano, halogen, haloalkyl, perhaloalkyl, alkyl, alkenyl, alkynyl, carboxy, carboxyalkyl, cyanoalkyl, acyl, cyanoalkylcarbonyl, cyanoalkenylcarbonyl, —$(CR^aR^b)_n OR^5$, —$SR^5$, —$(CR^aR^b)_n COOR^5$, —$(CR^aR^b)_n NR^6R^7$, —$(CR^aR^b)_n C(O)NR^6R^7$, —$(CR^aR^b)_n NR^5C(O)NR^6R^7$, thiocarbonyl, $S(O)_2 NR^6R^7$, —$NR^5S(O)_2 R^5$, —$S(O)_p R^5$, —$SO_3H$, cycloalkyl, cycloalkenyl, cycloalkylalkyl, cycloalkyloxy, cycloalkylamino, aryl, arylalkyl, aryloxy, arylamino, heterocyclyl, heterocyclylalkyl, heterocyclyloxy, heterocycloalkylamino, heteroaryl, heteroarylalkyl, heteroaryloxy, or heteroarylamino;

$R^5$ is selected from the group consisting of hydrogen, halogen, haloalkyl, alkyl, alkenyl, alkynyl, aryl, arylalkyl, heteroaryl, heteroarylalkyl, cycloalkyl, cycloalkylalkyl, heterocyclyl and heterocyclylalkyl;

wherein alkyl, alkenyl, alkynyl, aryl, arylalkyl, heteroaryl, heteroarylalkyl, cycloalkyl, cycloalkylalkyl, heterocyclyl or heterocyclylalkyl are optionally substituted with one or more substituents selected from hydroxy, alkyl, alkoxy, alkoxyalkyl, halogen, haloalkyl, perhaloalkyl, cyano, cyanoalkyl, amino, carboxy, or carboxyalkyl;

$R^6$ and $R^7$ are independently selected from the group consisting of hydrogen, —$(CR^aR^b)_n OR^5$, haloalkyl, —(CR$^a$R$^b$)$_n$C(O)R$^5$, alkyl, alkenyl, alkynyl, aryl, arylalkyl, heteroaryl, heteroarylalkyl, cycloalkyl, cycloalkylalkyl, heterocyclyl or heterocyclylalkyl, or R$^6$ and R$^7$ taken together form a monocyclic or a bicyclic ring system which is saturated or partially unsaturated and optionally have additional heteroatoms selected from O, N or S, the said ring system is further optionally substituted with 1 to 4 substituents independently selected from halo, alkyl, alkenyl, alkynyl, nitro, cyano, —(CR$^a$R$^b$)$_n$OR$^5$, —SR$^5$, oxo, alkylsulfonyl, —(CR$^a$R$^b$)$_n$COOR$^5$, cycloalkyl, cycloalkylalkyl, aryl, arylalkyl, heterocyclyl, heterocyclylalkyl, heteroaryl, or heteroarylalkyl;

Z, B and D may be optionally substituted with one or more substituents independently selected from cyano, nitro, keto, oxo, halogen, haloalkyl, perhaloalkyl, hydroxyamino, —(CR$^a$R$^b$)$_n$OR$^5$, —(CR$^a$R$^b$)$_n$C(O)R$^5$OC(O)R$^5$, —SR$^5$, —(CR$^a$R$^b$)$_n$COOR$^5$, —(CR$^a$R$^b$)$_n$NR$^6$R$^7$, —(CR$^a$R$^b$)$_n$C(O)NR$^6$R$^7$, —(CR$^a$R$^b$)$_n$NR$^5$C(O)NR$^6$R$^7$, —NR$^5$C(O)R$^5$, thiocarbonyl, S(O)$_2$NR$^6$R$^7$, —NR$^5$S(O)$_2$R$^5$, —S(O)$_p$R$^5$, —SO$_3$H, —OP(O)(R$^8$)$_q$, alkyl, alkenyl, alkynyl, cycloalkyl, cycloalkenyl, cycloalkylalkyl, aryl, heterocyclyl or heteroaryl;

wherein alkyl, alkenyl, alkynyl, cycloalkyl, cycloalkenyl, cycloalkylalkyl, aryl, heterocyclyl or heteroaryl are optionally substituted with one or more substituents selected from hydroxy, alkyl, alkoxy, alkoxyalkyl, halogen, haloalkyl, perhaloalkyl, cyano, cyanoalkyl, amino, carboxy, carboxyalkyl, —OC(O)R$^5$, —(CR$^a$R$^b$)$_n$C(O)NR$^6$R$^7$, —NR$^5$C(O)R$^5$, —SR$^5$, —S(O)$_p$R$^5$, —S(O)$_2$NR$^6$R$^7$ or —NR$^5$S(O)$_2$R$^5$;

R$^8$ is selected from the group consisting of hydroxy and alkoxy;

R$^a$ and R$^b$ are independently selected from the group consisting of hydrogen, —OR$^5$, halogen, haloalkyl, perhaloalkyl and alkyl;

n is 0-6;

m is 0, 1 or 2;

p is 0, 1 or 2; and q is 1 or 2.

3. A compound of formula (Ia) as claimed in claim 1 which is selected from a group consisting of:

1 tert-butyl 3-(3H-pyrrolo[3,2-f][1,7]naphthyridin-9-yl)piperidine-1-carboxylate;
1 tert-butyl 3-(3H-pyrrolo[3,2-f][1,7]naphthyridin-9-yl)pyrrolidine-1-carboxylate;
3-(3H-3,4,6,8-Tetraaza-cyclopenta[a]naphthalen-9-yl)-piperidine-1-carboxylic acid tert-butyl ester;
3-oxo-3-[3-(3H-pyrrolo[3,2-f][1,7]naphthyridin-9-yl)-1-piperidyl]propanenitrile;
(R)3-oxo-3-[3-(3H-pyrrolo[3,2-f][1,7]naphthyridin-9-yl)-1-piperidyl]propanenitrile;
(S)3-oxo-3-[3-(3H-pyrrolo[3,2-f][1,7]naphthyridin-9-yl)-1-piperidyl]propanenitrile;
cyclopropyl-[3-(3H-pyrrolo[3,2-f][1,7]naphthyridin-9-yl)-1-piperidyl]methanone;
2-methyl-1-[3-(3H-pyrrolo[3,2-f][1,7]naphthyridin-9-yl)-1-piperidyl]propan-1-one;
3,3,3-trifluoro-1-[3-(3H-pyrrolo[3,2-f][1,7]naphthyridin-9-yl)-1-piperidyl]propan-1-one;
(R)3,3,3-trifluoro-1-[3-(3H-pyrrolo[3,2-f][1,7]naphthyridin-9-yl)-1-piperidyl]propan-1-one;
(S)3,3,3-trifluoro-1-[3-(3H-pyrrolo[3,2-f][1,7]naphthyridin-9-yl)-1-piperidyl]propan-1-one;
3-methyl-1-[3-(3H-pyrrolo[3,2-f][1,7]naphthyridin-9-yl)-1-piperidyl]butan-1-one;
9-(1-cyclopropylsulfonyl-3-piperidyl)-3H-pyrrolo[3,2-f][1,7]naphthyridine;
2-[[3-(3H-pyrrolo[3,2-f][1,7]naphthyridin-9-yl)-1-piperidyl]sulfonyl]acetonitrile;
9-(1-isobutylsulfonyl-3-piperidyl)-3H-pyrrolo[3,2-f][1,7]naphthyridine;
9-(1-ethylsulfonyl-3-piperidyl)-3H-pyrrolo[3,2-f][1,7]naphthyridine;
9-(1-methylsulfonyl-3-piperidyl)-3H-pyrrolo[3,2-f][1,7]naphthyridine;
9-(1-methylsulfonyl-3-piperidyl)-3H-pyrrolo[3,2-f][1,7]naphthyridine;
(R)9-(1-methylsulfonyl-3-piperidyl)-3H-pyrrolo[3,2-f][1,7]naphthyridine;
(S)9-(1-isopropylsulfonyl-3-piperidyl)-3H-pyrrolo[3,2-][1,7]naphthyridine;
2-methylsulfonyl-1-[3-(3H-pyrrolo[3,2-f][1,7]naphthyridin-9-yl)-1-piperidyl]ethanone;
N-isopropyl-3-(3H-pyrrolo[3,2-f][1,7]naphthyridin-9-yl)piperidine-1-carboxamide;
3-oxo-3-[3-(3H-pyrrolo[3,2-f][1,7]naphthyridin-9-yl)pyrrolidin-1-yl]propanenitrile;
(R)3-oxo-3-[3-(3H-pyrrolo[3,2-f][1,7]naphthyridin-9-yl)pyrrolidin-1-yl]propanenitrile;
(S)3-oxo-3-[3-(3H-pyrrolo[3,2-f][1,7]naphthyridin-9-yl)pyrrolidin-1-yl]propanenitrile;
3,3,3-trifluoro-1-[3-(3H-pyrrolo[3,2-f][1,7]naphthyridin-9-yl)pyrrolidin-1-yl]propan-1-one;
(R)3,3,3-trifluoro-1-[3-(3H-pyrrolo[3,2-f][1,7]naphthyridin-9-yl)pyrrolidin-1-yl]propan-1-one;
(S)3,3,3-trifluoro-1-[3-(3H-pyrrolo[3,2-f][1,7]naphthyridin-9-yl)pyrrolidin-1-yl]propan-1-one;
2-[3-(3H-pyrrolo[3,2-f][1,7]naphthyridin-9-yl)pyrrolidin-1-yl]sulfonylacetonitrile;
(R)2-[3-(3H-pyrrolo[3,2-f][1,7]naphthyridin-9-yl)pyrrolidin-1-yl]sulfonylacetonitrile;
(S)2-[3-(3H-pyrrolo[3,2-f][1,7]naphthyridin-9-yl)pyrrolidin-1-yl]sulfonylacetonitrile;
9-[1-(trifluoromethylsulfonyl)pyrrolidin-3-yl]-3H-pyrrolo[3,2-f][1,7]naphthyridine;
9-(1-isobutylsulfonylpyrrolidin-3-yl)-3H-pyrrolo[3,2-f][1,7]naphthyridine;
9-(1-ethylsulfonylpyrrolidin-3-yl)-3H-pyrrolo[3,2-f][1,7]naphthyridine;
9-(1-methylsulfonylpyrrolidin-3-yl)-3H-pyrrolo[3,2-f][1,7]naphthyridine;
3-Methyl-1-[3-(3H-3,4,6,8-tetraaza-cyclopenta[a]naphthalen-9-yl)-piperidin-1-yl]-butan-1-one;
2-Methyl-1-[3-(3H-3,4,6,8-tetraaza-cyclopenta[a]naphthalen-9-yl)-piperidin-1-yl]-propan-1-one;
3-Oxo-3-[3-(3H-3,4,6,8-tetraaza-cyclopenta[a]naphthalen-9-yl)-piperidin-1-yl]-propionitrile;
(R)3-Oxo-3-[3-(3H-3,4,6,8-tetraaza-cyclopenta[a]naphthalen-9-yl)-piperidin-1-yl]-propionitrile;
(S)3-Oxo-3-[3-(3H-3,4,6,8-tetraaza-cyclopenta[a]naphthalen-9-yl)-piperidin-1-yl]-propionitrile;
3,3,3-Trifluoro-1-[3-(3H-3,4,6,8-tetraaza-cyclopenta[a]naphthalen-9-yl)-piperidin-1-yl]-propan-1-one;
(R)3,3,3-Trifluoro-1-[3-(3H-3,4,6,8-tetraaza-cyclopenta[a]naphthalen-9-yl)-piperidin-1-yl]-propan-1-one;
(S)3,3,3-Trifluoro-1-[3-(3H-3,4,6,8-tetraaza-cyclopenta[a]naphthalen-9-yl)-piperidin-1-yl]-propan-1-one;
2-Cyclopropyl-1-[3-(3H-3,4,6,8-tetraaza-cyclopenta[a]naphthalen-9-yl)-piperidin-1-yl]-ethanone;
[3-(3H-3,4,6,8-Tetraaza-cyclopenta[a]naphthalen-9-yl)-piperidin-1-yl]-(tetrahydro-furan-3-yl)-methanone;
1-[3-(3H-3,4,6,8-Tetraaza-cyclopenta[a]naphthalen-9-yl)-piperidin-1-yl]-propan-1-one;
2,2-Dimethyl-1-[3-(3H-3,4,6,8-tetraaza-cyclopenta[a]naphthalen-9-yl)-piperidin-1-yl]-propan-1-one;
Cyclopropyl-[3-(3H-3,4,6,8-tetraaza-cyclopenta[a]naphthalen-9-yl)-piperidin-1-yl]-methanone;
9-[1-(2-Methyl-propane-1-sulfonyl)-piperidin-3-yl]-3H-3,4,6,8-tetraaza-cyclopenta[a]naphthalene;
9-(1-Cyclopropanesulfonyl-piperidin-3-yl)-3H-3,4,6,8-tetraaza-cyclopenta[a]naphthalene;
3-(3H-3,4,6,8-Tetraaza-cyclopenta[a]naphthalen-9-yl)-piperidine-1-carboxylic acid isopropylamide;

3,3,3-Trifluoro-1-[3-(3H-3,4,6,8-tetraaza-cyclopenta[a] naphthalen-9-yl)-pyrrolidin-1-yl]-propan-1-one;
3-Oxo-3-[3-(3H-3,4,6,8-tetraaza-cyclopenta[a]naphthalen-9-yl)-pyrrolidin-1-yl]-propionitrile;
Cyclopropyl-[3-(3H-3,4,6,8-tetraaza-cyclopenta[a]naphthalen-9-yl)-pyrrolidin-1-yl]-methanone;
2-Methyl-1-[3-(3H-3,4,6,8-tetraaza-cyclopenta[a]naphthalen-9-yl)-pyrrolidin-1-yl]-propan-1-one;
4,4,4-Trifluoro-1-[3-(3H-3,4,6,8-tetraaza-cyclopenta[a] naphthalen-9-yl)-pyrrolidin-1-yl]-butan-1-one;
2,2-Dimethyl-1-[3-(3H-3,4,6,8-tetraaza-cyclopenta[a] naphthalen-9-yl)-pyrrolidin-1-yl]-propan-1-one;
[3-(3H-3,4,6,8-Tetraaza-cyclopenta[a]naphthalen-9-yl)-pyrrolidin-1-yl]-(1-trifluoromethyl-cyclopropyl)-methanone;
9-[1-(2-Methyl-propane-1-sulfonyl)-pyrrolidin-3-yl]-3H-3,4,6,8-tetraaza-cyclopenta[a]naphthalene;
3-oxo-3-[3-(3H-pyrrolo[3,2-f][1,7]naphthyridin-9-yl)-2,5-dihydropyrrol-1-yl]propanenitrile;
3,3,3-trifluoro-1-[3-(3H-pyrrolo[3,2-f][1,7]naphthyridin-9-yl)-2,5-dihydropyrrol-1-yl]propan-1-one;
(E)-[2-methyl-1-[3-(3H-pyrrolo[3,2-f][1,7]naphthyridin-9-yl)-1-piperidyl]propylidene]cyanamide;
(R)(E)-[2-methyl-1-[3-(3H-pyrrolo[3,2-f][1,7]naphthyridin-9-yl)-1-piperidyl]propylidene]cyanamide;
(S)(E)-[2-methyl-1-[3-(3H-pyrrolo[3,2-f][1,7]naphthyridin-9-yl)-1-piperidyl]propylidene]cyanamide;
(R)(E)-[3,3,3-trifluoro-1-[3-(3H-pyrrolo[3,2-f][1,7]naphthyridin-9-yl)-1-piperidyl]propylidene]cyanamide;
(S)(E)-[3,3,3-trifluoro-1-[3-(3H-pyrrolo[3,2-f][1,7]naphthyridin-9-yl)pyrrolidin-1-yl]propylidene]cyanamide;
N-cyclopropyl-3-(3H-pyrrolo[3,2-f][1,7]naphthyridin-9-yl)piperidine-1-carboxamide;
N,N-dimethyl-3-(3H-pyrrolo[3,2-f][1,7]naphthyridin-9-yl)piperidine-1-carboxamide;
N-ethyl-3-(3H-pyrrolo[3,2-f][1,7]naphthyridin-9-yl)piperidine-1-carboxamide;
N-isobutyl-3-(3H-pyrrolo[3,2-f][1,7]naphthyridin-9-yl) piperidine-1-carboxamide;
N-methyl-3-(3H-pyrrolo[3,2-f][1,7]naphthyridin-9-yl)piperidine-1-carboxamide;
2,2,2-trifluoroethyl 3-(3H-pyrrolo[3,2-f][1,7]naphthyridin-9-yl)piperidine-1-carboxylate;
Isopropyl 3-(3H-pyrrolo[3,2-f][1,7]naphthyridin-9-yl)piperidine-1-carboxylate;
3,3,3-trifluoro-1-[4-(3H-pyrrolo[3,2-f][1,7]naphthyridin-9-yl)-1-piperidyl]propan-1-one;
1-(3H-pyrrolo[3,2-f][1,7]naphthyridin-9-yl) piperidin-3-ol;
(3R)-1-(3H-pyrrolo[3,2-f][1,7]naphthyridin-9-yl)pyrrolidin-3-ol;
9-[3-(cyclopropylmethoxy)-1-piperidyl]-3H pyrrolo[3,2f][1,7]naphthyridine;
9-[3-(2-methoxyethoxy)-1-piperidyl]-3H-pyrrolo[3,2-f][1,7]naphthyridine;
9-(1-piperidyl)-3H-pyrrolo[3,2-f][1,7]naphthyridine;
9-[3-(cyclopropylmethoxy)pyrrolidin-1-yl]-3H-pyrrolo[3,2-f][1,7]naphthyridine;
9-[4-(cyclopropylmethoxy)-1-piperidyl]-3H-pyrrolo[3,2-f][1,7]naphthyridine;
N-cyclopropyl-1-(3H-pyrrolo[3,2-f][1,7]naphthyridin-9-yl)piperidine-3-carboxamide;
(3S)—N-cyclopropyl-1-(3H-pyrrolo[3,2-f][1,7]naphthyridin-9-yl)piperidine-3-carboxamide;
(3R)—N-cyclopropyl-1-(3H-pyrrolo[3,2-f][1,7]naphthyridin-9-yl)piperidine-3-carboxamide;
N-(cyclopropylmethyl)-N-methyl-1-(3H-pyrrolo[3,2-f][1,7]naphthyridin-9-yl)pyrrolidin-3-amine;
2-cyclopropyl-N-methyl-N-[1-(3H-pyrrolo[3,2-f][1,7] naphthyridin-9-yl)-3-piperidyl]acetamide;
4-(3H-pyrrolo[3,2-f][1,7]naphthyridin-9-yl)morpholine;
3,3,3-trifluoro-N-methyl-N-[1-(3H-pyrrolo[3,2-f][1,7] naphthyridin-9-yl)-3-piperidyl]propanamide;
N-methyl-N-[1-(3H-pyrrolo[3,2-f][1,7]naphthyridin-9-yl)-3-piperidyl]cyclopentane carboxamide;
N-isobutyl-1-(3H-pyrrolo[3,2-f][1,7]naphthyridin-9-yl) piperidine-3-carboxamide;
N-isopropyl-1-(3H-pyrrolo[3,2-f][1,7]naphthyridin-9-yl) piperidine-3-carboxamide;
N-(2-methoxyethyl)-1-(3H-pyrrolo[3,2-f][1,7]naphthyridin-9-yl)piperidine-3-carboxamide;
4-[1-(3H-pyrrolo[3,2-f][1,7]naphthyridin-9-yl)-3-piperidiyl]morpholine;
N-methyl-1-(3H-pyrrolo[3,2-f][1,7]naphthyridin-9-yl)piperidine-3-carboxamide;
N-ethyl-1-(3H-pyrrolo[3,2-f][1,7]naphthyridin-9-yl)piperidine-3-carboxamide;
N-[1-(3H-pyrrolo[3,2-f][1,7]naphthyridin-9-yl)-3-piperidyl]methanesulfonamide;
N-[1-(3H-pyrrolo[3,2-f][1,7]naphthyridin-9-yl)-3-piperidyl]cyclopropanecarboxamide;
N-isopropyl-1-(3H-pyrrolo[3,2-f][1,7]naphthyridin-9-yl) piperidine-4-carboxamide;
N-cyclopropyl-1-(3H-pyrrolo[3,2-f][1,7]naphthyridin-9-yl)piperidine-4-carboxamide;
N-(2-methoxyethyl)-1-(3H-pyrrolo[3,2-f][1,7]naphthyridin-9-yl)piperidine-4-carboxamide;
1-(3H-pyrrolo[3,2-f][1,7]naphthyridin-9-yl)-N-(2,2,2-trifluoroethyl)piperidine-4-carboxamide;
N-cyclopropyl-N-methyl-1-(3H-pyrrolo[3,2-f][1,7]naphthyridin-9-yl)piperidine-3-carboxamide;
N-methyl-1-(3H-pyrrolo[3,2-f][1,7]naphthyridin-9-yl)-N-(2,2,2-trifluoroethyl)piperidine-3-carboxamide;
1,1,1-trifluoro-N-[1-(3H-pyrrolo[3,2-f][1,7]naphthyridin-9-yl)-3-piperidyl]methane sulfonamide;
N-methyl-1-(3H-pyrrolo[3,2-f][1,7]naphthyridin-9-yl)-N-(2,2,2-trifluoroethyl) piperidine-4-carboxamide;
1-(3H-pyrrolo[3,2-f][1,7]naphthyridin-9-yl)-N-(2,2,2-trifluoroethyl)piperidine-3-carboxamide;
N-isopropyl-1-(3H-pyrrolo[3,2-f][1,7]naphthyridin-9-yl) pyrrolidine-3-carboxamide;
N-cyclopropyl-1-(3H-pyrrolo[3,2-f][1,7]naphthyridin-9-yl)pyrrolidine-3-carboxamide;
2,2,2-trifluoro-N-[1-(3H-pyrrolo[3,2-f][1,7]naphthyridin-9-yl)-3-piperidyl]ethanesulfonamide;
3,3,3-trifluoro-N-[1-(3H-pyrrolo[3,2-f][1,7]naphthyridin-9-yl)-3-piperidyl]propanamide;
cis-N-cyclopropyl-6-methyl-1-(3H-pyrrolo[3,2-f][1,7] naphthyridin-9-yl)piperidine-3-carboxamide;
trans-N-cyclopropyl-6-methyl-1-(3H-pyrrolo[3,2-f][1,7] naphthyridin-9-yl)piperidine-3-carboxamide;
(3S,6S)—N-cyclopropyl-6-methyl-1-(3H-pyrrolo[3,2-f] [1,7]naphthyridin-9-yl)piperidine-3-carboxamide;
3,3-Difluoro-N-[1-(3H-3,4,6,7-tetraaza-cyclopenta[a] naphthalen-9-yl)-piperidin-3-yl]-butyramide;
tert-Butyl N-[1-(3H-pyrrolo[3,2-f][1,7]naphthyridin-9-yl) pyrrolidin-3-yl]carbamate;
1-(3H-pyrrolo[3,2-f][1,7]naphthyridin-9-yl)pyrrolidin-3-amine;
2,2,2-trifluoro-N-[1-(3H-pyrrolo[3,2-f][1,7]naphthyridin-9-yl)pyrrolidin-3-yl]ethanesulfonamide;
N-[1-(3H-pyrrolo[3,2-f][1,7]naphthyridin-9-yl)pyrrolidin-3-yl]cyclopropanesulfonamide;
N-[1-(3H-pyrrolo[3,2-f][1,7]naphthyridin-9-yl)pyrrolidin-3-yl]propane-2-sulfonamide;
2-methyl-N-[1-(3H-pyrrolo[3,2-f][1,7]naphthyridin-9-yl)pyrrolidin-3-yl]propane-1-sulfonamide;
1-cyano-N-[1-(3H-pyrrolo[3,2-f][1,7]naphthyridin-9-yl) pyrrolidin-3-yl]methane sulfonamide;
1-isopropyl-3-[1-(3H-pyrrolo[3,2-f][1,7]naphthyridin-9-yl)pyrrolidin-3-yl]urea  N-[1-(3H-pyrrolo[3,2-f][1,7] naphthyridin-9-yl)pyrrolidin-3-yl]cyclopropanecarboxamide;

2-methyl-N-[1-(3H-pyrrolo[3,2-f][1,7]naphthyridin-9-yl)pyrrolidin-3-yl]propanamide;
2-cyclopropyl-N-[1-(3H-pyrrolo[3,2-f][1,7]naphthyridin-9-yl)pyrrolidin-3-yl]acetamide;
2-cyano-N-[1-(3H-pyrrolo[3,2-f][1,7]naphthyridin-9-yl)pyrrolidin-3-yl]acetamide;
3,3,3-trifluoro-N-[1-(3H-pyrrolo[3,2-f][1,7]naphthyridin-9-yl)pyrrolidin-3-yl]propanamide;
N-[1-(3H-pyrrolo[3,2-f][1,7]naphthyridin-9-yl)pyrrolidin-3-yl]methanesulfonamide;
tert-butyl 4-(3H-pyrrolo[3,2-f][1,7]naphthyridin-9-yl)piperazine-1-carboxylate;
3-oxo-3-[4-(3H-pyrrolo[3,2-f][1,7]naphthyridin-9-yl)piperazin-1-yl]propanenitrile;
3,3,3-trifluoro-1-[4-(3H-pyrrolo[3,2-f][1,7]naphthyridin-9-yl)piperazin-1-yl]propan-1-one;
9-[4-(2,2,2-trifluoroethylsulfonyl)piperazin-1-yl]-3H-pyrrolo[3,2-f][1,7]naphthyridine;
2-[4-(3H-pyrrolo[3,2-f][1,7]naphthyridin-9-yl)piperazin-1-yl]sulfonylacetonitrile;
2-Cyano-N-[1-(3H-3,4,7,8-tetraaza-cyclopenta[a]naphthalen-9-yl)-piperidin-3-yl]-acetamide;
3,3,3-trifluoro-N-[1-(3H-3,4,7,8-tetraaza-cyclopenta[a]naphthalen-9-yl)-piperidin-3-yl]-propionamide;
9-[4-[[3-[(4-fluorophenoxy)methyl]-1-piperidyl]sulfonylmethyl]-1-piperidyl]-3H-pyrrolo[3,2-f][1,7]naphthyridine;
1-[3-(3H-pyrrolo[3,2-f][1,7]naphthyridin-9-yl)piperidine-1-carbonyl]cyclopropanecarbonitrile;
[3-(3H-pyrrolo[3,2-f][1,7]naphthyridin-9-yl)-1-piperidyl]-[1-(trifluoromethyl)cyclopropyl]methanone;
4-oxo-4-[3-(3H-pyrrolo[3,2-f][1,7]naphthyridin-9-yl)-1-piperidyl]butanenitrile;
4,4,4-trifluoro-1-[3-(3H-pyrrolo[3,2-f][1,7]naphthyridin-9-yl)-1-piperidyl]butan-1-one;
1-[3-(3H-pyrrolo[3,2-f][1,7]naphthyridin-9-yl)pyrrolidine-1-carbonyl]cyclopropanecarbonitrile;
[3-(3H-pyrrolo[3,2-f][1,7]naphthyridin-9-yl)pyrrolidin-1-yl]-[1-(trifluoromethyl)cyclopropyl]methanone;
4-oxo-4-[3-(3H-pyrrolo[3,2-f][1,7]naphthyridin-9-yl)pyrrolidin-1-yl]butanenitrile;
4,4,4-trifluoro-1-[3-(3H-pyrrolo[3,2-f][1,7]naphthyridin-9-yl)pyrrolidin-1-yl]butan-1-one;
[3-(3H-3,4,6,8-Tetraaza-cyclopenta[a]naphthalen-9-yl)-piperidine-1-sulfonyl]-acetonitrile;
9-[1-(2,2,2-Trifluoro-ethanesulfonyl)-piperidin-3-yl]-3H-3,4,6,8-tetraaza-cyclopenta[a]naphthalene;
9-(1-Methanesulfonyl-piperidin-3-yl)-3H-3,4,6,8-tetraaza-cyclopenta[a]naphthalene;
9-(1-Ethanesulfonyl-piperidin-3-yl)-3H-3,4,6,8-tetraaza-cyclopenta[a]naphthalene;
9-[1-(Propane-2-sulfonyl)-piperidin-3-yl]-3H-3,4,6,8-tetraaza-cyclopenta[a]naphthalene;
[3-(3H-3,4,6,8-Tetraaza-cyclopenta[a]naphthalen-9-yl)-pyrrolidine-1-sulfonyl]-acetonitrile;
9-[1-(2,2,2-Trifluoro-ethanesulfonyl)-pyrrolidin-3-yl]-3H-3,4,6,8-tetraaza-cyclopenta[a]naphthalene;
9-(1-Methanesulfonyl-pyrrolidin-3-yl)-3H-3,4,6,8-tetraaza-cyclopenta[a]naphthalene;
9-(1-Ethanesulfonyl-pyrrolidin-3-yl)-3H-3,4,6,8-tetraaza-cyclopenta[a]naphthalene;
9-[1-(Propane-2-sulfonyl)-pyrrolidin-3-yl]-3H-3,4,6,8-tetraaza-cyclopenta[a]naphthalene;
9-(1-Cyclopropanesulfonyl-pyrrolidin-3-yl)-3H-3,4,6,8-tetraaza-cyclopenta[a]naphthalene;
3-Oxo-3-[3-(3H-3,4,7,8-tetraaza-cyclopenta[a]naphthalen-9-yl)-piperidin-1-yl]-propionitrile;
3,3,3-Trifluoro-1-[3-(3H-3,4,7,8-tetraaza-cyclopenta[a]naphthalen-9-yl)-piperidin-1-yl]-propan-1-one;
2-Methyl-1-[3-(3H-3,4,7,8-tetraaza-cyclopenta[a]naphthalen-9-yl)-piperidin-1-yl]-propan-1-one;
Cyclopropyl-[3-(3H-3,4,7,8-tetraaza-cyclopenta[a]naphthalen-9-yl)-piperidin-1-yl]-methanone;
[3-(3H-3,4,7,8-Tetraaza-cyclopenta[a]naphthalen-9-yl)-piperidine-1-sulfonyl]-acetonitrile;
9-[1-(2,2,2-Trifluoro-ethanesulfonyl)-piperidin-3-yl]-3H-3,4,7,8-tetraaza-cyclopenta[a]naphthalene;
9-(1-Methanesulfonyl-piperidin-3-yl)-3H-3,4,7,8-tetraaza-cyclopenta[a]naphthalene;
9-(1-Ethanesulfonyl-piperidin-3-yl)-3H-3,4,7,8-tetraaza-cyclopenta[a]naphthalene;
9-[1-(Propane-2-sulfonyl)-piperidin-3-yl]-3H-3,4,7,8-tetraaza-cyclopenta[a]naphthalene;
9-(1-Cyclopropanesulfonyl-piperidin-3-yl)-3H-3,4,7,8-tetraaza-cyclopenta[a]naphthalene;
3-(3H-3,4,7,8-Tetraaza-cyclopenta[a]naphthalen-9-yl)-piperidine-1-carboxylic acid methylamide;
3-(3H-3,4,7,8-Tetraaza-cyclopenta[a]naphthalen-9-yl)-piperidine-1-carboxylic acid ethylamide;
3-(3H-3,4,7,8-Tetraaza-cyclopenta[a]naphthalen-9-yl)-piperidine-1-carboxylic acid isopropylamide;
3-Oxo-3-[3-(3H-3,4,7,8-tetraaza-cyclopenta[a]naphthalen-9-yl)-pyrrolidin-1-yl]-propionitrile;
3,3,3-Trifluoro-1-[3-(3H-3,4,7,8-tetraaza-cyclopenta[a]naphthalen-9-yl)-pyrrolidin-1-yl]-propan-1-one;
2-Methyl-1-[3-(3H-3,4,7,8-tetraaza-cyclopenta[a]naphthalen-9-yl)-pyrrolidin-1-yl]-propan-1-one;
Cyclopropyl-[3-(3H-3,4,7,8-tetraaza-cyclopenta[a]naphthalen-9-yl)-pyrrolidin-1-yl]-methanone;
[3-(3H-3,4,7,8-Tetraaza-cyclopenta[a]naphthalen-9-yl)-pyrrolidine-1-sulfonyl]-acetonitrile;
9-[1-(2,2,2-Trifluoro-ethanesulfonyl)-pyrrolidin-3-yl]-3H-3,4,7,8-tetraaza-cyclopenta[a]naphthalene;
9-(1-Methanesulfonyl-pyrrolidin-3-yl)-3H-3,4,7,8-tetraaza-cyclopenta[a]naphthalene;
9-(1-Ethanesulfonyl-pyrrolidin-3-yl)-3H-3,4,7,8-tetraaza-cyclopenta[a]naphthalene;
9-[1-(Propane-2-sulfonyl)-pyrrolidin-3-yl]-3H-3,4,7,8-tetraaza-cyclopenta[a]naphthalene;
9-(1-Cyclopropanesulfonyl-pyrrolidin-3-yl)-3H-3,4,7,8-tetraaza-cyclopenta[a]naphthalene;
3-(3H-3,4,7,8-Tetraaza-cyclopenta[a]naphthalen-9-yl)-pyrrolidine-1-carboxylic acid methylamide;
3-(3H-3,4,7,8-Tetraaza-cyclopenta[a]naphthalen-9-yl)-pyrrolidine-1-carboxylic acid ethylamide;
3-(3H-3,4,7,8-Tetraaza-cyclopenta[a]naphthalen-9-yl)-pyrrolidine-1-carboxylic acid isopropylamide;
3-oxo-3-[3-(7H-pyrrolo[2,3-h][2,6]naphthyridin-1-yl)-1-piperidyl]propanenitrile;
3,3,3-trifluoro-1-[3-(7H-pyrrolo[2,3-h][2,6]naphthyridin-1-yl)-1-piperidyl]propan-1-one;
2-methyl-1-[3-(7H-pyrrolo[2,3-h][2,6]naphthyridin-1-yl)-1-piperidyl]propan-1-one;
cyclopropyl-[3-(7H-pyrrolo[2,3-h][2,6]naphthyridin-1-yl)-1-piperidyl]methanone;
2-[[3-(7H-pyrrolo[2,3-h][2,6]naphthyridin-1-yl)-1-piperidyl]sulfonyl]acetonitrile;
1-[1-(2,2,2-trifluoroethylsulfonyl)-3-piperidyl]-7H-pyrrolo[2,3-c][2,6]naphthyridine;
1-(1-methylsulfonyl-3-piperidyl)-7H-pyrrolo[2,3-c][2,6]naphthyridine;
1-(1-ethylsulfonyl-3-piperidyl)-7H-pyrrolo[2,3-c][2,6]naphthyridine;
1-(1-isopropylsulfonyl-3-piperidyl)-7H-pyrrolo[2,3-c][2,6]naphthyridine;
1-(1-cyclopropylsulfonyl-3-piperidyl)-7H-pyrrolo[2,3-c][2,6]naphthyridine;
N-methyl-3-(7H-pyrrolo[2,3-h][2,6]naphthyridin-1-yl)piperidine-1-carboxamide;
N-ethyl-3-(7H-pyrrolo[2,3-h][2,6]naphthyridin-1-yl)piperidine-1-carboxamide;
N-isopropyl-3-(7H-pyrrolo[2,3-h][2,6]naphthyridin-1-yl)piperidine-1-carboxamide;

3-oxo-3-[3-(7H-pyrrolo[2,3-h][2,6]naphthyridin-1-yl)
  pyrrolidin-1-yl]propanenitrile;
3,3,3-trifluoro-1-[3-(7H-pyrrolo[2,3-h][2,6]naphthyridin-
  1-yl)pyrrolidin-1-yl]propan-1-one;
2-methyl-1-[3-(7H-pyrrolo[2,3-h][2,6]naphthyridin-1-yl)
  pyrrolidin-1-yl]propan-1-one;
cyclopropyl-[3-(7H-pyrrolo[2,3-h][2,6]naphthyridin-1-
  yl)pyrrolidin-1-yl]methanone;
2-[3-(7H-pyrrolo[2,3-h][2,6]naphthyridin-1-yl)pyrroli-
  din-1-yl]sulfonylacetonitrile;
1-[1-(2,2,2-trifluoroethylsulfonyl)pyrrolidin-3-yl]-7H-
  pyrrolo[2,3-c][2,6]naphthyridine;
1-(1-methylsulfonylpyrrolidin-3-yl)-7H-pyrrolo[2,3-c][2,
  6]naphthyridine;
1-(1-ethylsulfonylpyrrolidin-3-yl)-7H-pyrrolo[2,3-c][2,6]
  naphthyridine;
1-(1-isopropylsulfonylpyrrolidin-3-yl)-7H-pyrrolo[2,3-c]
  [2,6]naphthyridine;
1-(1-cyclopropylsulfonylpyrrolidin-3-yl)-7H-pyrrolo[2,
  3-c][2,6]naphthyridine;
N-methyl-3-(7H-pyrrolo[2,3-h][2,6]naphthyridin-1-yl)
  pyrrolidine-1-carboxamide;
N-ethyl-3-(7H-pyrrolo[2,3-h][2,6]naphthyridin-1-yl)pyr-
  rolidine-1-carboxamide;
N-isopropyl-3-(7H-pyrrolo[2,3-h][2,6]naphthyridin-1-yl)
  pyrrolidine-1-carboxamide;
3-oxo-3-[3-(3H-pyrrolo[2,3-c][2,7]naphthyridin-9-yl)-1-
  piperidyl]propanenitrile;
3,3,3-trifluoro-1-[3-(3H-pyrrolo[2,3-c][2,7]naphthyridin-
  9-yl)-1-piperidyl]propan-1-one;
2-methyl-1-[3-(3H-pyrrolo[2,3-c][2,7]naphthyridin-9-
  yl)-1-piperidyl]propan-1-one;
cyclopropyl-[3-(3H-pyrrolo[2,3-c][2,7]naphthyridin-9-
  yl)-1-piperidyl]methanone;
2-[[3-(3H-pyrrolo[2,3-c][2,7]naphthyridin-9-yl)-1-pip-
  eridyl]sulfonyl]acetonitrile;
9-[1-(2,2,2-trifluoro ethylsulfonyl)-3-piperidyl]-3H-pyr-
  rolo[2,3-c][2,7]naphthyridine;
9-(1-methylsulfonyl-3-piperidyl)-3H-pyrrolo[2,3-c][2,7]
  naphthyridine;
9-(1-ethylsulfonyl-3-piperidyl)-3H-pyrrolo[2,3-c][2,7]
  naphthyridine;
9-(1-isopropylsulfonyl-3-piperidyl)-3H-pyrrolo[2,3-c][2,
  7]naphthyridine;
9-(1-cyclopropylsulfonyl-3-piperidyl)-3H-pyrrolo[2,3-c]
  [2,7]naphthyridine;
N-methyl-3-(3H-pyrrolo[2,3-c][2,7]naphthyridin-9-yl)pi-
  peridine-1-carboxamide;
N-ethyl-3-(3H-pyrrolo[2,3-c][2,7]naphthyridin-9-yl)pip-
  eridine-1-carboxamide;
N-isopropyl-3-(3H-pyrrolo[2,3-c][2,7]naphthyridin-9-yl)
  piperidine-1-carboxamide;
3-oxo-3-[3-(3H-pyrrolo[2,3-c][2,7]naphthyridin-9-yl)
  pyrrolidin-1-yl]propanenitrile;
3,3,3-trifluoro-1-[3-(3H-pyrrolo[2,3-c][2,7]naphthyridin-
  9-yl)pyrrolidin-1-yl]propan-1-one;
2-methyl-1-[3-(3H-pyrrolo[2,3-c][2,7]naphthyridin-9-yl)
  pyrrolidin-1-yl]propan-1-one;
cyclopropyl-[3-(3H-pyrrolo[2,3-c][2,7]naphthyridin-9-
  yl)pyrrolidin-1-yl]methanone;
2-[3-(3H-pyrrolo[2,3-c][2,7]naphthyridin-9-yl)pyrroli-
  din-1-yl]sulfonylacetonitrile;
9-[1-(2,2,2-trifluoroethylsulfonyl)pyrrolidin-3-yl]-3H-
  pyrrolo[2,3-c][2,7]naphthyridine;
9-(1-methylsulfonylpyrrolidin-3-yl)-3H-pyrrolo[2,3-c][2,
  7]naphthyridine;
9-(1-ethylsulfonylpyrrolidin-3-yl)-3H-pyrrolo[2,3-c][2,7]
  naphthyridine;
9-(1-isopropylsulfonylpyrrolidin-3-yl)-3H-pyrrolo[2,3-c]
  [2,7]naphthyridine;
9-(1-cyclopropylsulfonylpyrrolidin-3-yl)-3H-pyrrolo[2,
  3-c][2,7]naphthyridine;
N-methyl-3-(3H-pyrrolo[2,3-c][2,7]naphthyridin-9-yl)
  pyrrolidine-1-carboxamide;
N-ethyl-3-(3H-pyrrolo[2,3-c][2,7]naphthyridin-9-yl)pyr-
  rolidine-1-carboxamide;
N-isopropyl-3-(3H-pyrrolo[2,3-c][2,7]naphthyridin-9-yl)
  pyrrolidine-1-carboxamide;
3-[3-(7-Methyl-3H-3,4,6,8-tetraaza-cyclopenta[a]naph-
  thalen-9-yl)-piperidin-1-yl]-3-oxo-propionitrile;
3,3,3-Trifluoro-1-[3-(7-methyl-3H-3,4,6,8-tetraaza-cy-
  clopenta[a]naphthalen-9-yl)-piperidin-1-yl]-propan-1-
  one;
2-Methyl-1-[3-(7-methyl-3H-3,4,6,8-tetraaza-cyclopenta
  [a]naphthalen-9-yl)-piperidin-1-yl]-propan-1-one;
Cyclopropyl-[3-(7-methyl-3H-3,4,6,8-tetraaza-cyclo-
  penta[a]naphthalen-9-yl)-piperidin-1-yl]-methanone;
[3-(7-Methyl-3H-3,4,6,8-tetraaza-cyclopenta[a]naphtha-
  len-9-yl)-piperidine-1-sulfonyl]-acetonitrile;
7-Methyl-9-[1-(2,2,2-trifluoro-ethanesulfonyl)-piperidin-
  3-yl]-3H-3,4,6,8-tetraaza-cyclopenta[a]naphthalene;
9-(1-Methanesulfonyl-piperidin-3-yl)-7-methyl-3H-3,4,
  6,8-tetraaza-cyclopenta[a]naphthalene;
9-(1-Ethanesulfonyl-piperidin-3-yl)-7-methyl-3H-3,4,6,
  8-tetraaza-cyclopenta[a]naphthalene;
7-Methyl-9-[1-(propane-2-sulfonyl)-piperidin-3-yl]-3H-
  3,4,6,8-tetraaza-cyclopenta[a]naphthalene;
9-(1-Cyclopropanesulfonyl-piperidin-3-yl)-7-methyl-3H-
  3,4,6,8-tetraaza-cyclopenta[a]naphthalene;
3-(7-Methyl-3H-3,4,6,8-tetraaza-cyclopenta[a]naphtha-
  len-9-yl)-piperidine-1-carboxylic acid methylamide;
3-(7-Methyl-3H-3,4,6,8-tetraaza-cyclopenta[a]naphtha-
  len-9-yl)-piperidine-1-carboxylic acid ethylamide;
3-(7-Methyl-3H-3,4,6,8-tetraaza-cyclopenta[a]naphtha-
  len-9-yl)-piperidine-1-carboxylic acid isopropylamide;
3-[3-(7-Methyl-3H-3,4,6,8-tetraaza-cyclopenta[a]naph-
  thalen-9-yl)-pyrrolidin-1-yl]-3-oxo-propionitrile;
3,3,3-Trifluoro-1-[3-(7-methyl-3H-3,4,6,8-tetraaza-cy-
  clopenta[a]naphthalen-9-yl)-pyrrolidin-1-yl]-propan-
  1-one;
2-Methyl-1-[3-(7-methyl-3H-3,4,6,8-tetraaza-cyclopenta
  [a]naphthalen-9-yl)-pyrrolidin-1-yl]-propan-1-one;
Cyclopropyl-[3-(7-methyl-3H-3,4,6,8-tetraaza-cyclo-
  penta[a]naphthalen-9-yl)-pyrrolidin-1-yl]-methanone;
[3-(7-Methyl-3H-3,4,6,8-tetraaza-cyclopenta[a]naphtha-
  len-9-yl)-pyrrolidine-1-sulfonyl]-acetonitrile;
7-Methyl-9-[1-(2,2,2-trifluoro-ethanesulfonyl)-pyrroli-
  din-3-yl]-3H-3,4,6,8-tetraaza-cyclopenta[a]naphtha-
  lene;
9-(1-Methanesulfonyl-pyrrolidin-3-yl)-7-methyl-3H-3,4,
  6,8-tetraaza-cyclopenta[a]naphthalene;
9-(1-Ethanesulfonyl-pyrrolidin-3-yl)-7-methyl-3H-3,4,6,
  8-tetraaza-cyclopenta[a]naphthalene;
7-Methyl-9-[1-(propane-2-sulfonyl)-pyrrolidin-3-yl]-3H-
  3,4,6,8-tetraaza-cyclopenta[a]naphthalene;
9-(1-Cyclopropanesulfonyl-pyrrolidin-3-yl)-7-methyl-
  3H-3,4,6,8-tetraaza-cyclopenta[a]naphthalene;
3-(7-Methyl-3H-3,4,6,8-tetraaza-cyclopenta[a]naphtha-
  len-9-yl)-pyrrolidine-1-carboxylic acid methylamide;
3-(7-Methyl-3H-3,4,6,8-tetraaza-cyclopenta[a]naphtha-
  len-9-yl)-pyrrolidine-1-carboxylic acid ethylamide;
3-(7-Methyl-3H-3,4,6,8-tetraaza-cyclopenta[a]naphtha-
  len-9-yl)-pyrrolidine-1-carboxylic acid isopropyla-
  mide;
3-oxo-3-[5-(3H-pyrrolo[3,2-f][1,7]naphthyridin-9-yl)-3,
  6-dihydro-2H-pyridin-1-yl]propanenitrile;
3,3,3-trifluoro-1-[5-(3H-pyrrolo[3,2-f][1,7]naphthyridin-
  9-yl)-3,6-dihydro-2H-pyridin-1-yl]propan-1-one;
2-[[5-(3H-pyrrolo[3,2-f][1,7]naphthyridin-9-yl)-3,6-di-
  hydro-2H-pyridin-1-yl]sulfonyl]acetonitrile;
9-[1-(2,2,2-trifluoroethylsulfonyl)-3,6-dihydro-2H-pyri-
  din-5-yl]-3H-pyrrolo[3,2-f][1,7]naphthyridine;
9-(1-methylsulfonyl-3,6-dihydro-2H-pyridin-5-yl)-3H-
  pyrrolo[3,2-f][1,7]naphthyridine;

3-oxo-3-[5-(3H-pyrrolo[3,2-f][1,7]naphthyridin-9-yl)-3,4-dihydro-2H-pyridin-1-yl]propanenitrile;
3,3,3-trifluoro-1-[5-(3H-pyrrolo[3,2-f][1,7]naphthyridin-9-yl)-3,4-dihydro-2H-pyridin-1-yl]propan-1-one;
2-[[5-(3H-pyrrolo[3,2-f][1,7]naphthyridin-9-yl)-3,4-dihydro-2H-pyridin-1-yl]sulfonyl]acetonitrile;
9-[1-(2,2,2-trifluoroethylsulfonyl)-3,4-dihydro-2H-pyridin-5-yl]-3H-pyrrolo[3,2-f][1,7]naphthyridine;
9-(1-methylsulfonyl-3,4-dihydro-2H-pyridin-5-yl)-3H-pyrrolo[3,2-f][1,7]naphthyridine;
2-[[3-(3H-pyrrolo[3,2-f][1,7]naphthyridin-9-yl)-2,5-dihydropyrrol-1-yl]sulfonyl]acetonitrile;
9-[1-(2,2,2-trifluoroethylsulfonyl)-2,5-dihydropyrrol-3-yl]-3H-pyrrolo[3,2-f][1,7]naphthyridine;
9-(1-methylsulfonyl-2,5-dihydropyrrol-3-yl)-3H-pyrrolo[3,2-f][1,7]naphthyridine;
3-[4-methyl-3-(3H-pyrrolo[3,2-f][1,7]naphthyridin-9-yl)-1-piperidyl]-3-oxo-propanenitrile;
3,3,3-trifluoro-1-[4-methyl-3-(3H-pyrrolo[3,2-f][1,7]naphthyridin-9-yl)-1-piperidyl]propan-1-one;
2-[[4-methyl-3-(3H-pyrrolo[3,2-f][1,7]naphthyridin-9-yl)-1-piperidyl]sulfonyl]acetonitrile;
9-[4-methyl-1-(2,2,2-trifluoroethylsulfonyl)-3-piperidyl]-3H-pyrrolo[3,2-f][1,7]naphthyridine;
9-(4-methyl-1-methylsulfonyl-3-piperidyl)-3H-pyrrolo[3,2-f][1,7]naphthyridine;
3-[3-methyl-4-(3H-pyrrolo[3,2-f][1,7]naphthyridin-9-yl)pyrrolidin-1-yl]-3-oxo-propanenitrile;
3,3,3-trifluoro-1-[3-methyl-4-(3H-pyrrolo[3,2-f][1,7]naphthyridin-9-yl)pyrrolidin-1-yl]propan-1-one;
2-[3-methyl-4-(3H-pyrrolo[3,2-f][1,7]naphthyridin-9-yl)pyrrolidin-1-yl]sulfonylacetonitrile;
9-[4-methyl-1-(2,2,2-trifluoroethylsulfonyl)pyrrolidin-3-yl]-3H-pyrrolo[3,2-f][1,7]naphthyridine;
9-(4-methyl-1-methylsulfonyl-pyrrolidin-3-yl)-3H-pyrrolo[3,2-f][1,7]naphthyridine;
3-[3-(2-methyl-3H-pyrrolo[3,2-f][1,7]naphthyridin-9-yl)-1-piperidyl]-3-oxo-propanenitrile;
3,3,3-trifluoro-1-[3-(2-methyl-3H-pyrrolo[3,2-f][1,7]naphthyridin-9-yl)-1-piperidyl]propan-1-one;
2-[[3-(2-methyl-3H-pyrrolo[3,2-f][1,7]naphthyridin-9-yl)-1-piperidyl]sulfonyl]acetonitrile;
2-methyl-9-[1-(2,2,2-trifluoroethylsulfonyl)-3-piperidyl]-3H-pyrrolo[3,2-f][1,7]naphthyridine;
2-methyl-9-(1-methylsulfonyl-3-piperidyl)-3H-pyrrolo[3,2-f][1,7]naphthyridine;
3-[3-(2-methyl-3H-pyrrolo[3,2-f][1,7]naphthyridin-9-yl)pyrrolidin-1-yl]-3-oxo-propanenitrile;
3,3,3-trifluoro-1-[3-(2-methyl-3H-pyrrolo[3,2-f][1,7]naphthyridin-9-yl)pyrrolidin-1-yl]propan-1-one;
2-[3-(2-methyl-3H-pyrrolo[3,2-f][1,7]naphthyridin-9-yl)pyrrolidin-1-yl]sulfonylacetonitrile;
2-methyl-9-[1-(2,2,2-trifluoroethylsulfonyl)pyrrolidin-3-yl]-3H-pyrrolo[3,2-f][1,7]naphthyridine;
2-methyl-9-(1-methylsulfonylpyrrolidin-3-yl)-3H-pyrrolo[3,2-f][1,7]naphthyridine;
3-oxo-3-[4-(3H-pyrrolo[3,2-f][1,7]naphthyridin-9-yl)-1-piperidyl]propanenitrile;
4-oxo-4-[4-(3H-pyrrolo[3,2-f][1,7]naphthyridin-9-yl)-1-piperidyl]butanenitrile;
4,4,4-trifluoro-1-[4-(3H-pyrrolo[3,2-f][1,7]naphthyridin-9-yl)-1-piperidyl]butan-1-one;
2-[[4-(3H-pyrrolo[3,2-f][1,7]naphthyridin-9-yl)-1-piperidyl]sulfonyl]acetonitrile;
9-[1-(2,2,2-trifluoroethylsulfonyl)-4-piperidyl]-3H-pyrrolo[3,2-f][1,7]naphthyridine;
9-(3-Morpholin-4-yl-piperidin-1-yl)-3H-3,4,6,7-tetraaza-cyclopenta[a]naphthalene;
9-(3-Cyclopropylmethoxy-piperidin-1-yl)-3H-3,4,6,7-tetraaza-cyclopenta[a]naphthalene;
2-Cyano-N-[1-(3H-3,4,6,7-tetraaza-cyclopenta[a]naphthalen-9-yl)-piperidin-3-yl]-acetamide;
1-(3H-3,4,6,7-Tetraaza-cyclopenta[a]naphthalen-9-yl)-piperidine-3-carboxylic acid cyanomethyl-amide;
2-Nitrilo-ethanesulfonic acid [1-(3H-3,4,6,7-tetraaza-cyclopenta[a]naphthalen-9-yl)-piperidin-3-yl]-amide;
1-(3H-3,4,6,7-Tetraaza-cyclopenta[a]naphthalen-9-yl)-piperidine-3-carboxylic acid cyanomethyl-methyl-amide;
2-Cyano-N-methyl-N-[1-(3H-3,4,6,7-tetraaza-cyclopenta[a]naphthalen-9-yl)-piperidin-3-yl]-acetamide;
1-(3H-3,4,6,7-Tetraaza-cyclopenta[a]naphthalen-9-yl)-pyrrolidine-3-carboxylic acid cyanomethyl-methyl-amide;
1-(3H-3,4,6,7-Tetraaza-cyclopenta[a]naphthalen-9-yl)-pyrrolidine-3-carboxylic acid methyl-(2,2,2-trifluoro-ethyl)-amide;
2-Cyano-N-methyl-N-[1-(3H-3,4,6,7-tetraaza-cyclopenta[a]naphthalen-9-yl)-pyrrolidin-3-yl]-acetamide;
3,3,3-Trifluoro-N-methyl-N-[1-(3H-3,4,6,7-tetraaza-cyclopenta[a]naphthalen-9-yl)-pyrrolidin-3-yl]-propionamide;
1-(3H-3,4,6,7-Tetraaza-cyclopenta[a]naphthalen-9-yl)-pyrrolidine-3-carboxylic acid cyanomethyl-amide;
1-(3H-3,4,6,7-Tetraaza-cyclopenta[a]naphthalen-9-yl)-pyrrolidine-3-carboxylic acid (2,2,2-trifluoro-ethyl)-amide;
2,2,2-Trifluoro-ethanesulfonic acid [1-(3H-3,4,6,7-tetraaza-cyclopenta[a]naphthalen-9-yl)-pyrrolidin-3-yl]-amide;
2-Cyano-N-[1-(3H-3,4,6,7-tetraaza-cyclopenta[a]naphthalen-9-yl)-pyrrolidin-3-yl]-acetamide;
2-Nitrilo-ethanesulfonic acid [1-(3H-3,4,6,7-tetraaza-cyclopenta[a]naphthalen-9-yl)-pyrrolidin-3-yl]-amide;
3,3,3-Trifluoro-N-[1-(3H-3,4,6,7-tetraaza-cyclopenta[a]naphthalen-9-yl)-pyrrolidin-3-yl]-propionamide;
3,3,3-Trifluoro-N-[1-(3H-3,4,6,7-tetraaza-cyclopenta[a]naphthalen-9-yl)-piperidin-3-yl]-propionamide;
2,2,2-Trifluoro-ethanesulfonic acid [1-(3H-3,4,6,7-tetraaza-cyclopenta[a]naphthalen-9-yl)-piperidin-3-yl]-amide;
1-(3H-3,4,6,7-Tetraaza-cyclopenta[a]naphthalen-9-yl)-piperidine-4-carboxylic acid (2,2,2-trifluoro-ethyl)-amide;
1-(3H-3,4,6,7-Tetraaza-cyclopenta[a]naphthalen-9-yl)-piperidine-4-carboxylic acid methyl-(2,2,2-trifluoro-ethyl)-amide;
1-(3H-3,4,6,7-Tetraaza-cyclopenta[a]naphthalen-9-yl)-piperidine-4-carboxylic acid cyanomethyl-methyl-amide;
1-(3H-3,4,6,7-Tetraaza-cyclopenta[a]naphthalen-9-yl)-piperidine-4-carboxylic acid cyanomethyl-amide;
2-Cyano-N-[1-(3H-3,4,6,7-tetraaza-cyclopenta[a]naphthalen-9-yl)-piperidin-4-yl]-acetamide;
2-Cyano-N-methyl-N-[1-(3H-3,4,6,7-tetraaza-cyclopenta[a]naphthalen-9-yl)-piperidin-4-yl]-acetamide;
3,3,3-Trifluoro-N-methyl-N-[1-(3H-3,4,6,7-tetraaza-cyclopenta[a]naphthalen-9-yl)-piperidin-3-yl]-propionamide;
1-(3H-3,4,6,7-Tetraaza-cyclopenta[a]naphthalen-9-yl)-piperidine-3-carboxylic acid cyclopropylamide;
1-(3H-3,4,6,7-Tetraaza-cyclopenta[a]naphthalen-9-yl)-piperidine-3-carboxylic acid cyclopropyl-methyl-amide;
1-(3H-3,4,6,7-Tetraaza-cyclopenta[a]naphthalen-9-yl)-piperidine-3-carboxylic acid methyl-(2,2,2-trifluoro-ethyl)-amide;
6-Methyl-1-(3H-3,4,6,7-tetraaza-cyclopenta[a]naphthalen-9-yl)-piperidine-3-carboxylic acid cyclopropylamide;
1-(3H-3,4,6,7-Tetraaza-cyclopenta[a]naphthalen-9-yl)-piperidine-3-sulfonic acid (2,2,2-trifluoro-ethyl)-amide;

1-(3H-3,4,6,7-Tetraaza-cyclopenta[a]naphthalen-9-yl)-pyrrolidine-3-sulfonic acid (2,2,2-trifluoro-ethyl)-amide;
1-(3H-3,4,6,7-Tetraaza-cyclopenta[a]naphthalen-9-yl)-piperidine-3-carboxylic acid (2,2,2-trifluoro-ethyl)-amide;
2-Cyano-N-[1-(3H-3,4,6,8-tetraaza-cyclopenta[a]naphthalen-9-yl)-piperidin-3-yl]-acetamide;
2-Nitrilo-ethanesulfonic acid [1-(3H-3,4,6,8-tetraaza-cyclopenta[a]naphthalen-9-yl)-piperidin-3-yl]-amide;
1-(3H-3,4,6,8-tetraaza-cyclopenta[a]naphthalen-9-yl)-piperidine-3-carboxylic acid cyanomethyl-methyl-amide;
2-Cyano-N-methyl-N-[1-(3H-3,4,6,8-tetraaza-cyclopenta[a]naphthalen-9-yl)-piperidin-3-yl]-acetamide;
1-(3H-3,4,6,8-Tetraaza-cyclopenta[a]naphthalen-9-yl)-pyrrolidine-3-carboxylic acid cyanomethyl-methyl-amide;
1-(3H-3,4,6,8-Tetraaza-cyclopenta[a]naphthalen-9-yl)-pyrrolidine-3-carboxylic acid methyl-(2,2,2-trifluoro-ethyl)-amide;
2-Cyano-N-methyl-N-[1-(3H-3,4,6,8-tetraaza-cyclopenta[a]naphthalen-9-yl)-pyrrolidin-3-yl]-acetamide;
3,3,3-Trifluoro-N-methyl-N-[1-(3H-3,4,6,8-tetraaza-cyclopenta[a]naphthalen-9-yl)-pyrrolidin-3-yl]-propionamide;
1-(3H-3,4,6,8-Tetraaza-cyclopenta[a]naphthalen-9-yl)-pyrrolidine-3-carboxylic acid cyanomethyl-amide;
1-(3H-3,4,6,8-Tetraaza-cyclopenta[a]naphthalen-9-yl)-pyrrolidine-3-carboxylic acid (2,2,2-trifluoro-ethyl)-amide;
1-(3H-3,4,6,8-Tetraaza-cyclopenta[a]naphthalen-9-yl)-piperidine-3-carboxylic acid cyanomethyl-amide;
2,2,2-Trifluoro-ethanesulfonic acid [1-(3H-3,4,6,8-tetraaza-cyclopenta[a]naphthalen-9-yl)-pyrrolidin-3-yl]-amide;
Cyclopropanesulfonic acid [1-(3H-3,4,6,8-tetraaza-cyclopenta[a]naphthalen-9-yl)-pyrrolidin-3-yl]-amide;
Propane-2-sulfonic acid [1-(3H-3,4,6,8-tetraaza-cyclopenta[a]naphthalen-9-yl)-pyrrolidin-3-yl]-amide;
2-Cyano-N-[1-(3H-3,4,6,8-tetraaza-cyclopenta[a]naphthalen-9-yl)-pyrrolidin-3-yl]-acetamide;
2-Nitrilo-ethanesulfonic acid [1-(3H-3,4,6,8-tetraaza-cyclopenta[a]naphthalen-9-yl)-pyrrolidin-3-yl]-amide;
1-Isopropyl-3-[1-(3H-3,4,6,8-tetraaza-cyclopenta[a]naphthalen-9-yl)-pyrrolidin-3-yl]-urea;
N-[1-(3H-3,4,6,8-Tetraaza-cyclopenta[a]naphthalen-9-yl)-pyrrolidin-3-yl]-isobutyramide;
3,3,3-Trifluoro-N-[1-(3H-3,4,6,8-tetraaza-cyclopenta[a]naphthalen-9-yl)-pyrrolidin-3-yl]-propionamide;
1-(3H-3,4,6,8-Tetraaza-cyclopenta[a]naphthalen-9-yl)-pyrrolidine-3-carboxylic acid cyclopropylamide;
N-[1-(3H-3,4,6,8-Tetraaza-cyclopenta[a]naphthalen-9-yl)-piperidin-3-yl]-methanesulfonamide;
C,C,C-Trifluoro-N-[1-(3H-3,4,6,8-tetraaza-cyclopenta[a]naphthalen-9-yl)-piperidin-3-yl]-methanesulfonamide;
2,2,2-Trifluoro-ethanesulfonic acid [1-(3H-3,4,6,8-tetraaza-cyclopenta[a]naphthalen-9-yl)-piperidin-3-yl]-amide;
1-(3H-3,4,6,8-Tetraaza-cyclopenta[a]naphthalen-9-yl)-piperidine-4-carboxylic acid (2,2,2-trifluoro-ethyl)-amide;
1-(3H-3,4,6,8-Tetraaza-cyclopenta[a]naphthalen-9-yl)-piperidine-4-carboxylic acid methyl-(2,2,2-trifluoro-ethyl)-amide;
1-(3H-3,4,6,8-Tetraaza-cyclopenta[a]naphthalen-9-yl)-piperidine-4-carboxylic acid cyanomethyl-methyl-amide;
1-(3H-3,4,6,8-Tetraaza-cyclopenta[a]naphthalen-9-yl)-piperidine-4-carboxylic acid cyanomethyl-amide;
2-Cyano-N-[1-(3H-3,4,6,8-tetraaza-cyclopenta[a]naphthalen-9-yl)-piperidin-4-yl]-acetamide;
2-Cyano-N-methyl-N-[1-(3H-3,4,6,8-tetraaza-cyclopenta[a]naphthalen-9-yl)-piperidin-4-yl]-acetamide;
2-Cyclopropyl-N-methyl-N-[1-(3H-3,4,6,8-tetraaza-cyclopenta[a]naphthalen-9-yl)-piperidin-3-yl]-acetamide;
3,3,3-Trifluoro-N-methyl-N-[1-(3H-3,4,6,8-tetraaza-cyclopenta[a]naphthalen-9-yl)-piperidin-3-yl]-propionamide;
Cyclopentanecarboxylic acid methyl-[1-(3H-3,4,6,8-tetraaza-cyclopenta[a]naphthalen-9-yl)-piperidin-3-yl]-amide;
Cyclopropanecarboxylic acid [1-(3H-3,4,6,8-tetraaza-cyclopenta[a]naphthalen-9-yl)-piperidin-3-yl]-amide;
3,3,3-Trifluoro-N-[1-(3H-3,4,6,8-tetraaza-cyclopenta[a]naphthalen-9-yl)-piperidin-3-yl]-propionamide;
1-(3H-3,4,6,8-Tetraaza-cyclopenta[a]naphthalen-9-yl)-piperidine-4-carboxylic acid isopropylamide;
1-(3H-3,4,6,8-Tetraaza-cyclopenta[a]naphthalen-9-yl)-piperidine-4-carboxylic acid cyclopropylamide;
1-(3H-3,4,6,8-Tetraaza-cyclopenta[a]naphthalen-9-yl)-piperidine-4-carboxylic acid (2-methoxy-ethyl)-amide;
1-(3H-3,4,6,8-Tetraaza-cyclopenta[a]naphthalen-9-yl)-piperidine-3-carboxylic acid cyclopropylamide;
1-(3H-3,4,6,8-Tetraaza-cyclopenta[a]naphthalen-9-yl)-piperidine-3-carboxylic acid methyl-(2,2,2-trifluoro-ethyl)-amide;
1-(3H-3,4,6,8-Tetraaza-cyclopenta[a]naphthalen-9-yl)-piperidine-3-carboxylic acid (2,2,2-trifluoro-ethyl)-amide;
1-(3H-3,4,6,8-Tetraaza-cyclopenta[a]naphthalen-9-yl)-piperidine-3-carboxylic acid isopropylamide;
1-(3H-3,4,6,8-Tetraaza-cyclopenta[a]naphthalen-9-yl)-piperidine-3-carboxylic acid cyclopropyl-methyl-amide
6-Methyl-1-(3H-3,4,6,8-tetraaza-cyclopenta[a]naphthalen-9-yl)-piperidine-3-carboxylic acid cyclopropylamide;
1-(3H-3,4,6,8-Tetraaza-cyclopenta[a]naphthalen-9-yl)-piperidine-3-sulfonic acid (2,2,2-trifluoro-ethyl)-amide;
1-(3H-3,4,6,8-Tetraaza-cyclopenta[a]naphthalen-9-yl)-pyrrolidine-3-sulfonic acid (2,2,2-trifluoro-ethyl)-amide;
2-Cyano-N-[1-(7-methyl-3H-3,4,6,8-tetraaza-cyclopenta[a]naphthalen-9-yl)-piperidin-3-yl]-acetamide;
2-Nitrilo-ethanesulfonic acid [1-(7-methyl-3H-3,4,6,8-tetraaza-cyclopenta[a]naphthalen-9-yl)-piperidin-3-yl]-amide;
1-(7-Methyl-3H-3,4,6,8-tetraaza-cyclopenta[a]naphthalen-9-yl)-pyrrolidine-3-carboxylic acid cyanomethyl-amide;
1-(7-Methyl-3H-3,4,6,8-tetraaza-cyclopenta[a]naphthalen-9-yl)-pyrrolidine-3-carboxylic acid (2,2,2-trifluoro-ethyl)-amide;
1-(7-Methyl-3H-3,4,6,8-tetraaza-cyclopenta[a]naphthalen-9-yl)-piperidine-3-carboxylic acid cyanomethyl-amide;
1-(7-Methyl-3H-3,4,6,8-tetraaza-cyclopenta[a]naphthalen-9-yl)-piperidine-3-carboxylic acid cyanomethyl-methyl-amide;
2-Cyano-N-methyl-N-[1-(7-methyl-3H-3,4,6,8-tetraaza-cyclopenta[a]naphthalen-9-yl)-piperidin-3-yl]-acetamide;
1-(7-Methyl-3H-3,4,6,8-tetraaza-cyclopenta[a]naphthalen-9-yl)-pyrrolidine-3-carboxylic acid cyanomethyl-methyl-amide;
1-(7-Methyl-3H-3,4,6,8-tetraaza-cyclopenta[a]naphthalen-9-yl)-pyrrolidine-3-carboxylic acid methyl-(2,2,2-trifluoro-ethyl)-amide;
2-Cyano-N-methyl-N-[1-(7-methyl-3H-3,4,6,8-tetraaza-cyclopenta[a]naphthalen-9-yl)-pyrrolidin-3-yl]-acetamide;

3,3,3-Trifluoro-N-methyl-N-[1-(7-methyl-3H-3,4,6,8-tetraaza-cyclopenta[a]naphthalen-9-yl)-pyrrolidin-3-yl]-propionamide;
2,2,2-Trifluoro-ethanesulfonic acid [1-(7-methyl-3H-3,4,6,8-tetraaza-cyclopenta[a]naphthalen-9-yl)-pyrrolidin-3-yl]-amide;
2-Nitrilo-ethanesulfonic acid [1-(7-methyl-3H-3,4,6,8-tetraaza-cyclopenta[a]naphthalen-9-yl)-pyrrolidin-3-yl]-amide;
3,3,3-Trifluoro-N-[1-(7-methyl-3H-3,4,6,8-tetraaza-cyclopenta[a]naphthalen-9-yl)-pyrrolidin-3-yl]-propionamide;
N-[1-(7-Methyl-3H-3,4,6,8-tetraaza-cyclopenta[a]naphthalen-9-yl)-pyrrolidin-3-yl]-methanesulfonamide;
2-Cyano-N-[1-(7-methyl-3H-3,4,6,8-tetraaza-cyclopenta[a]naphthalen-9-yl)-pyrrolidin-3-yl]-acetamide;
N-[1-(7-Methyl-3H-3,4,6,8-tetraaza-cyclopenta[a]naphthalen-9-yl)-piperidin-3-yl]-methanesulfonamide;
1-(7-Methyl-3H-3,4,6,8-tetraaza-cyclopenta[a]naphthalen-9-yl)-piperidine-4-carboxylic acid methyl-(2,2,2-trifluoro-ethyl)-amide;
1-(7-Methyl-3H-3,4,6,8-tetraaza-cyclopenta[a]naphthalen-9-yl)-piperidine-4-carboxylic acid cyanomethyl-methyl-amide;
1-(7-Methyl-3H-3,4,6,8-tetraaza-cyclopenta[a]naphthalen-9-yl)-piperidine-4-carboxylic acid cyanomethyl-amide;
2-Cyano-N-[1-(7-methyl-3H-3,4,6,8-tetraaza-cyclopenta[a]naphthalen-9-yl)-piperidin-4-yl]-acetamide;
2-Cyano-N-methyl-N-[1-(7-methyl-3H-3,4,6,8-tetraaza-cyclopenta[a]naphthalen-9-yl)-piperidin-4-yl]-acetamide;
2,2,2-Trifluoro-ethanesulfonic acid [1-(7-methyl-3H-3,4,6,8-tetraaza-cyclopenta[a]naphthalen-9-yl)-piperidin-3-yl]-amide;
1-(7-Methyl-3H-3,4,6,8-tetraaza-cyclopenta[a]naphthalen-9-yl)-piperidine-4-carboxylic acid (2,2,2-trifluoro-ethyl)-amide;
3,3,3-Trifluoro-N-[1-(7-methyl-3H-3,4,6,8-tetraaza-cyclopenta[a]naphthalen-9-yl)-piperidin-3-yl]-propionamide;
3,3,3-Trifluoro-N-methyl-N-[1-(7-methyl-3H-3,4,6,8-tetraaza-cyclopenta[a]naphthalen-9-yl)-piperidin-3-yl]-propionamide;
1-(7-Methyl-3H-3,4,6,8-tetraaza-cyclopenta[a]naphthalen-9-yl)-piperidine-3-carboxylic acid cyclopropylamide;
1-(7-Methyl-3H-3,4,6,8-tetraaza-cyclopenta[a]naphthalen-9-yl)-piperidine-3-carboxylic acid isopropylamide;
1-(7-Methyl-3H-3,4,6,8-tetraaza-cyclopenta[a]naphthalen-9-yl)-piperidine-3-carboxylic acid cyclopropyl-methyl-amide;
1-(7-Methyl-3H-3,4,6,8-tetraaza-cyclopenta[a]naphthalen-9-yl)-piperidine-3-carboxylic acid methyl-(2,2,2-trifluoro-ethyl)-amide;
6-Methyl-1-(7-methyl-3H-3,4,6,8-tetraaza-cyclopenta[a]naphthalen-9-yl)-piperidine-3-carboxylic acid cyclo-Propylamide;
1-(7-Methyl-3H-3,4,6,8-tetraaza-cyclopenta[a]naphthalen-9-yl)-piperidine-3-sulfonic acid (2,2,2-trifluoro-ethyl)-amide;
1-(7-Methyl-3H-3,4,6,8-tetraaza-cyclopenta[a]naphthalen-9-yl)-pyrrolidine-3-sulfonic acid (2,2,2-trifluoro-ethyl)-amide;
1-(7-Methyl-3H-3,4,6,8-tetraaza-cyclopenta[a]naphthalen-9-yl)-piperidine-3-carboxylic acid (2,2,2-trifluoro-ethyl)-amide;
9-(3-Cyclopropylmethoxy-pyrrolidin-1-yl)-3H-3,4,7,8-tetraaza-cyclopenta[a]naphthalene;
9-(3-Morpholin-4-yl-piperidin-1-yl)-3H-3,4,7,8-tetraaza-cyclopenta[a]naphthalene;
Cyclopropylmethyl-methyl-[1-(3H-3,4,7,8-tetraaza-cyclopenta[a]naphthalen-9-yl)-pyrrolidin-3-yl]-amine;
2-Cyano-N-[1-(3H-3,4,7,8-tetraaza-cyclopenta[a]naphthalen-9-yl)-piperidin-3-yl]-acetamide;
9-Morpholin-4-yl-3H-3,4,7,8-tetraaza-cyclopenta[a]naphthalene;
1-(3H-3,4,7,8-tetraaza-cyclopenta[a]naphthalen-9-yl)-pyrrolidine-3-carboxylic acid (2,2,2-trifluoro-ethyl)-amide;
2-Nitrilo-ethanesulfonic acid [1-(3H-3,4,7,8-tetraaza-cyclopenta[a]naphthalen-9-yl)-piperidin-3-yl]-amide;
1-(3H-3,4,7,8-Tetraaza-cyclopenta[a]naphthalen-9-yl)-pyrrolidine-3-carboxylic acid cyanomethyl-amide;
1-(3H-3,4,7,8-Tetraaza-cyclopenta[a]naphthalen-9-yl)-piperidine-3-carboxylic acid cyanomethyl-amide;
1-(3H-3,4,7,8-Tetraaza-cyclopenta[a]naphthalen-9-yl)-piperidine-3-carboxylic acid cyanomethyl-methyl-amide;
2-Cyano-N-methyl-N-[1-(3H-3,4,7,8-tetraaza-cyclopenta[a]naphthalen-9-yl)-piperidin-3-yl]-acetamide;
1-(3H-3,4,7,8-Tetraaza-cyclopenta[a]naphthalen-9-yl)-pyrrolidine-3-carboxylic acid cyanomethyl-methyl-amide;
1-(3H-3,4,7,8-Tetraaza-cyclopenta[a]naphthalen-9-yl)-pyrrolidine-3-carboxylic acid methyl-(2,2,2-trifluoro-ethyl)-amide;
2-Cyano-N-methyl-N-[1-(3H-3,4,7,8-tetraaza-cyclopenta[a]naphthalen-9-yl)-pyrrolidin-3-yl]-acetamide;
3,3,3-Trifluoro-N-methyl-N-[1-(3H-3,4,7,8-tetraaza-cyclopenta[a]naphthalen-9-yl)-pyrrolidin-3-yl]-propionamide;
2,2,2-Trifluoro-ethanesulfonic acid [1-(3H-3,4,7,8-tetraaza-cyclopenta[a]naphthalen-9-yl)-pyrrolidin-3-yl]-amide;
Cyclopropanesulfonic acid [1-(3H-3,4,7,8-tetraaza-cyclopenta[a]naphthalen-9-yl)-pyrrolidin-3-yl]-amide;
1-Isopropyl-3-[1-(3H-3,4,7,8-tetraaza-cyclopenta[a]naphthalen-9-yl)-pyrrolidin-3-yl]-urea;
N-[1-(3H-3,4,7,8-Tetraaza-cyclopenta[a]naphthalen-9-yl)-pyrrolidin-3-yl]-methanesulfonamide;
2-Nitrilo-ethanesulfonic acid [1-(3H-3,4,7,8-tetraaza-cyclopenta[a]naphthalen-9-yl)-pyrrolidin-3-yl]-amide;
2-Cyano-N-[1-(3H-3,4,7,8-tetraaza-cyclopenta[a]naphthalen-9-yl)-pyrrolidin-3-yl]-acetamide;
3,3,3-Trifluoro-N-[1-(3H-3,4,7,8-tetraaza-cyclopenta[a]naphthalen-9-yl)-pyrrolidin-3-yl]-propionamide;
3,3,3-Trifluoro-N-[1-(3H-3,4,7,8-tetraaza-cyclopenta[a]naphthalen-9-yl)-piperidin-3-yl]-methanesulfonamide;
2,2,2-Trifluoro-ethanesulfonic acid [1-(3H-3,4,7,8-tetraaza-cyclopenta[a]naphthalen-9-yl)-piperidin-3-yl]-amide;
1-(3H-3,4,7,8-Tetraaza-cyclopenta[a]naphthalen-9-yl)-piperidine-4-carboxylic acid (2,2,2-trifluoro-ethyl)-amide;
1-(3H-3,4,7,8-Tetraaza-cyclopenta[a]naphthalen-9-yl)-piperidine-4-carboxylic acid methyl-(2,2,2-trifluoro-ethyl)-amide;
1-(3H-3,4,7,8-Tetraaza-cyclopenta[a]naphthalen-9-yl)-piperidine-4-carboxylic acid cyanomethyl-methyl-amide;
1-(3H-3,4,7,8-Tetraaza-cyclopenta[a]naphthalen-9-yl)-piperidine-4-carboxylic acid cyanomethyl-amide;
2-Cyano-N-[1-(3H-3,4,7,8-tetraaza-cyclopenta[a]naphthalen-9-yl)-piperidin-4-yl]-acetamide;
2-Cyano-N-methyl-N-[1-(3H-3,4,7,8-tetraaza-cyclopenta[a]naphthalen-9-yl)-piperidin-4-yl]-acetamide;
3,3,3-Trifluoro-N-methyl-N-[1-(3H-3,4,7,8-tetraaza-cyclopenta[a]naphthalen-9-yl)-piperidin-3-yl]-propionamide;
3,3,3-Trifluoro-N-[1-(3H-3,4,7,8-tetraaza-cyclopenta[a]naphthalen-9-yl)-piperidin-3-yl]-propionamide;

1-(3H-3,4,7,8-Tetraaza-cyclopenta[a]naphthalen-9-yl)-piperidine-3-carboxylic acid cyclopropylamide;
1-(3H-3,4,7,8-Tetraaza-cyclopenta[a]naphthalen-9-yl)-piperidine-3-carboxylic acid isopropylamide;
1-(3H-3,4,7,8-Tetraaza-cyclopenta[a]naphthalen-9-yl)-piperidine-3-carboxylic acid cyclopropyl-methyl-amide;
1-(3H-3,4,7,8-Tetraaza-cyclopenta[a]naphthalen-9-yl)-piperidine-3-carboxylic acid methyl-(2,2,2-trifluoro-ethyl)-amide;
6-Methyl-1-(3H-3,4,7,8-tetraaza-cyclopenta[a]naphthalen-9-yl)-piperidine-3-carboxylic acid cyclopropylamide;
1-(3H-3,4,7,8-Tetraaza-cyclopenta[a]naphthalen-9-yl)-pyrrolidine-3-sulfonic acid (2,2,2-trifluoro-ethyl)-amide;
1-(3H-3,4,7,8-Tetraaza-cyclopenta[a]naphthalen-9-yl)-piperidine-3-sulfonic acid (2,2,2-trifluoro-ethyl)-amide;
1-(3H-3,4,7,8-Tetraaza-cyclopenta[a]naphthalen-9-yl)-piperidine-3-carboxylic acid (2,2,2-trifluoro-ethyl)-amide;
9-(3-Cyclopropylmethoxy-pyrrolidin-1-yl)-3H-3,4,7-triaza-cyclopenta[a]naphthalene;
9-(3-Morpholin-4-yl-piperidin-1-yl)-3H-3,4,7-triaza-cyclopenta[a]naphthalene;
Cyclopropylmethyl-methyl-[1-(3H-3,4,7-triaza-cyclopenta[a]naphthalen-9-yl)-pyrrolidin-3-yl]-amine;
1-(3H-3,4,7-Triaza-cyclopenta[a]naphthalen-9-yl)-pyrrolidine-3-carboxylic acid (2,2,2-trifluoro-ethyl)-amide;
2-Cyano-N-[1-(3H-3,4,7-triaza-cyclopenta[a]naphthalen-9-yl)-piperidin-3-yl]-acetamide;
2-Nitrilo-ethanesulfonic acid [1-(3H-3,4,7-triaza-cyclopenta[a]naphthalen-9-yl)-piperidin-3-yl]-amide;
9-Morpholin-4-yl-3H-3,4,7-triaza-cyclopenta[a]naphthalene;
1-(3H-3,4,7-Triaza-cyclopenta[a]naphthalen-9-yl)-piperidine-3-carboxylic acid cyanomethyl-amide;
1-(3H-3,4,7-Triaza-cyclopenta[a]naphthalen-9-yl)-piperidine-3-carboxylic acid cyanomethyl-methyl-amide;
2-Cyano-N-methyl-N-[1-(3H-3,4,7-triaza-cyclopenta[a]naphthalen-9-yl)-piperidin-3-yl]-acetamide;
1-(3H-3,4,7-Triaza-cyclopenta[a]naphthalen-9-yl)-pyrrolidine-3-carboxylic acid cyanomethyl-methyl-amide;
1-(3H-3,4,7-Triaza-cyclopenta[a]naphthalen-9-yl)-pyrrolidine-3-carboxylic acid methyl-(2,2,2-trifluoro-ethyl)-amide;
2-Cyano-N-methyl-N-[1-(3H-3,4,7-triaza-cyclopenta[a]naphthalen-9-yl)-pyrrolidin-3-yl]-acetamide;
3,3,3-Trifluoro-N-methyl-N-[1-(3H-3,4,7-triaza-cyclopenta[a]naphthalen-9-yl)-pyrrolidin-3-yl]-propionamide;
1-(3H-3,4,7-Triaza-cyclopenta[a]naphthalen-9-yl)-pyrrolidine-3-carboxylic acid cyanomethyl-amide;
2,2,2-Trifluoro-ethanesulfonic acid [1-(3H-3,4,7-triaza-cyclopenta[a]naphthalen-9-yl)-pyrrolidin-3-yl]-amide;
Cyclopropanesulfonic acid [1-(3H-3,4,7-triaza-cyclopenta[a]naphthalen-9-yl)-pyrrolidin-3-yl]-amide;
N-[1-(3H-3,4,7-Triaza-cyclopenta[a]naphthalen-9-yl)-pyrrolidin-3-yl]-methanesulfonamide;
2-Nitrilo-ethanesulfonic acid [1-(3H-3,4,7-triaza-cyclopenta[a]naphthalen-9-yl)-pyrrolidin-3-yl]-amide;
3,3,3-Trifluoro-N-[1-(3H-3,4,7-triaza-cyclopenta[a]naphthalen-9-yl)-pyrrolidin-3-yl]-propionamide;
2-Cyano-N-[1-(3H-3,4,7-triaza-cyclopenta[a]naphthalen-9-yl)-pyrrolidin-3-yl]-acetamide;
1-Isopropyl-3-[1-(3H-3,4,7-triaza-cyclopenta[a]naphthalen-9-yl)-pyrrolidin-3-yl]-urea;
N-[1-(3H-3,4,7-Triaza-cyclopenta[a]naphthalen-9-yl)-piperidin-3-yl]-methanesulfonamide;
2,2,2-Trifluoro-ethanesulfonic acid [1-(3H-3,4,7-triaza-cyclopenta[a]naphthalen-9-yl)-piperidin-3-yl]-amide;
1-(3H-3,4,7-Triaza-cyclopenta[a]naphthalen-9-yl)-piperidine-4-carboxylic acid (2,2,2-trifluoro-ethyl)-amide;
1-(3H-3,4,7-Triaza-cyclopenta[a]naphthalen-9-yl)-piperidine-4-carboxylic acid cyanomethyl-methyl-amide;
1-(3H-3,4,7-Triaza-cyclopenta[a]naphthalen-9-yl)-piperidine-4-carboxylic acid cyanomethyl-amide;
2-Cyano-N-[1-(3H-3,4,7-triaza-cyclopenta[a]naphthalen-9-yl)-piperidin-4-yl]-acetamide;
2-Cyano-N-methyl-N-[1-(3H-3,4,7-triaza-cyclopenta[a]naphthalen-9-yl)-piperidin-4-yl]-acetamide;
3,3,3-Trifluoro-N-methyl-N-[1-(3H-3,4,7-triaza-cyclopenta[a]naphthalen-9-yl)-piperidin-3-yl]-propionamide;
3,3,3-Trifluoro-N-[1-(3H-3,4,7-triaza-cyclopenta[a]naphthalen-9-yl)-piperidin-3-yl]-propionamide;
1-(3H-3,4,7-Triaza-cyclopenta[a]naphthalen-9-yl)-piperidine-3-carboxylic acid cyclopropylamide;
1-(3H-3,4,7-Triaza-cyclopenta[a]naphthalen-9-yl)-piperidine-3-carboxylic acid isobutyl-amide;
1-(3H-3,4,7-Triaza-cyclopenta[a]naphthalen-9-yl)-piperidine-3-carboxylic acid (2,2,2-trifluoro-ethyl)-amide;
1-(3H-3,4,7-Triaza-cyclopenta[a]naphthalen-9-yl)-piperidine-3-carboxylic acid cyclopropyl-methyl-amide;
1-(3H-3,4,7-Triaza-cyclopenta[a]naphthalen-9-yl)-pyrrolidine-3-sulfonic acid (2,2,2-trifluoro-ethyl)-amide;
1-(3H-3,4,7-Triaza-cyclopenta[a]naphthalen-9-yl)-piperidine-3-sulfonic acid (2,2,2-trifluoro-ethyl)-amide;
1-(3H-3,4,7-Triaza-cyclopenta[a]naphthalen-9-yl)-piperidine-3-carboxylic acid methyl-(2,2,2-trifluoro-ethyl)-amide;
6-Methyl-1-(3H-3,4,7-triaza-cyclopenta[a]naphthalen-9-yl)-piperidine-3-carboxylic acid cyclopropylamide;
1-(3H-3,4,8-Triaza-cyclopenta[a]naphthalen-9-yl)-piperidin-3-ol;
9-(3-Morpholin-4-yl-piperidin-1-yl)-3H-3,4,8-triaza-cyclopenta[a]naphthalene;
Cyclopropylmethyl-methyl-[1-(3H-3,4,8-triaza-cyclopenta[a]naphthalen-9-yl)-pyrrolidin-3-yl]-amine;
9-Morpholin-4-yl-3H-3,4,8-triaza-cyclopenta[a]naphthalene;
2-Cyano-N-[1-(3H-3,4,8-triaza-cyclopenta[a]naphthalen-9-yl)-piperidin-3-yl]-acetamide;
2-Nitrilo-ethanesulfonic acid [1-(3H-3,4,8-triaza-cyclopenta[a]naphthalen-9-yl)-piperidin-3-yl]-amide;
1-(3H-3,4,8-Triaza-cyclopenta[a]naphthalen-9-yl)-pyrrolidine-3-carboxylic acid (2,2,2-trifluoro-ethyl)-amide;
1-(3H-3,4,8-Triaza-cyclopenta[a]naphthalen-9-yl)-piperidine-3-carboxylic acid cyanomethyl-amide;
1-(3H-3,4,8-Triaza-cyclopenta[a]naphthalen-9-yl)-piperidine-3-carboxylic acid cyanomethyl-methyl-amide;
2-Cyano-N-methyl-N-[1-(3H-3,4,8-triaza-cyclopenta[a]naphthalen-9-yl)-piperidin-3-yl]-acetamide;
1-(3H-3,4,8-Triaza-cyclopenta[a]naphthalene-9-yl)-pyrrolidine-3-carboxylic acid cyanomethyl-methyl-amide;
1-(3H-3,4,8-Triaza-cyclopenta[a]naphthalen-9-yl)-pyrrolidine-3-carboxylic acid methyl-(2,2,2-trifluoro-ethyl)-amide;
2-Cyano-N-methyl-N-[1-(3H-3,4,8-triaza-cyclopenta[a]naphthalen-9-yl)-pyrrolidin-3-yl]-acetamide;
3,3,3-Trifluoro-N-methyl-N-[1-(3H-3,4,8-triaza-cyclopenta[a]naphthalen-9-yl)-pyrrolidin-3-yl]-propionamide;
1-(3H-3,4,8-Triaza-cyclopenta[a]naphthalen-9-yl)-pyrrolidine-3-carboxylic acid cyanomethyl-amide;
2,2,2-Trifluoro-ethanesulfonic acid [1-(3H-3,4,8-triaza-cyclopenta[a]naphthalen-9-yl)-pyrrolidin-3-yl]-amide;
N-[1-(3H-3,4,8-Triaza-cyclopenta[a]naphthalen-9-yl)-pyrrolidin-3-yl]-methanesulfonamide;
2-Methyl-propane-1-sulfonic acid [1-(3H-3,4,8-triaza-cyclopenta[a]naphthalen-9-yl)-pyrrolidin-3-yl]-amide;
2-Nitrilo-ethanesulfonic acid [1-(3H-3,4,8-triaza-cyclopenta[a]naphthalen-9-yl)-pyrrolidin-3-yl]-amide;

1-Isopropyl-3-[1-(3H-3,4,8-triaza-cyclopenta[a]naphthalen-9-yl)-pyrrolidin-3-yl]-urea;
2-Cyano-N-[1-(3H-3,4,8-triaza-cyclopenta[a]naphthalen-9-yl)-pyrrolidin-3-yl]-acetamide;
Cyclopropanecarboxylic acid [1-(3H-3,4,8-triaza-cyclopenta[a]naphthalen-9-yl)-pyrrolidin-3-yl]-amide;
1-(3H-3,4,8-Triaza-cyclopenta[a]naphthalen-9-yl)-pyrrolidine-3-carboxylic acid cyclopropylamide;
3,3,3-Trifluoro-N-[1-(3H-3,4,8-triaza-cyclopenta[a]naphthalen-9-yl)-pyrrolidin-3-yl]-propionamide;
N-[1-(3H-3,4,8-Triaza-cyclopenta[a]naphthalen-9-yl)-piperidin-3-yl]-methanesulfonamide;
2,2,2-Trifluoro-ethanesulfonic acid [1-(3H-3,4,8-triaza-cyclopenta[a]naphthalen-9-yl)-piperidin-3-yl]-amide;
1-(3H-3,4,8-Triaza-cyclopenta[a]naphthalen-9-yl)-piperidine-4-carboxylic acid (2,2,2-trifluoro-ethyl)-amide;
1-(3H-3,4,8-Triaza-cyclopenta[a]naphthalen-9-yl)-piperidine-4-carboxylic acid methyl-(2,2,2-trifluoro-ethyl)-amide;
1-(3H-3,4,8-Triaza-cyclopenta[a]naphthalen-9-yl)-piperidine-4-carboxylic acid cyanomethyl-methyl-amide;
1-(3H-3,4,8-Triaza-cyclopenta[a]naphthalen-9-yl)-piperidine-4-carboxylic acid cyanomethyl-amide;
2-Cyano-N-[1-(3H-3,4,8-triaza-cyclopenta[a]naphthalen-9-yl)-piperidin-4-yl]-acetamide;
2-Cyano-N-methyl-N-[1-(3H-3,4,8-triaza-cyclopenta[a]naphthalen-9-yl)-piperidin-4-yl]-acetamide;
3,3,3-Trifluoro-N-methyl-N-[1-(3H-3,4,8-triaza-cyclopenta[a]naphthalen-9-yl)-piperidin-3-yl]-propionamide;
3,3,3-Trifluoro-N-[1-(3H-3,4,8-triaza-cyclopenta[a]naphthalen-9-yl)-piperidin-3-yl]-propionamide;
1-(3H-3,4,8-Triaza-cyclopenta[a]naphthalen-9-yl)-piperidine-3-carboxylic acid cyclopropylamide;
1-(3H-3,4,8-Triaza-cyclopenta[a]naphthalen-9-yl)-piperidine-3-carboxylic acid cyclopropyl-methyl-amide;
1-(3H-3,4,8-Triaza-cyclopenta[a]naphthalen-9-yl)-piperidine-3-carboxylic acid methyl-(2,2,2-trifluoro-ethyl)-amide;
6-Methyl-1-(3H-3,4,8-triaza-cyclopenta[a]naphthalen-9-yl)-piperidine-3-carboxylic acid cyclopropylamide;
1-(3H-3,4,8-Triaza-cyclopenta[a]naphthalen-9-yl)-pyrrolidine-3-sulfonic acid (2,2,2-trifluoro-ethyl)-amide;
1-(3H-3,4,8-Triaza-cyclopenta[a]naphthalen-9-yl)-piperidine-3-sulfonic acid (2,2,2-trifluoro-ethyl)-amide;
1-(3H-3,4,8-Triaza-cyclopenta[a]naphthalen-9-yl)-piperidine-3-carboxylic acid (2,2,2-trifluoro-ethyl)-amide;
2-Cyano-N-[1-(3H-3,4,6-triaza-cyclopenta[a]naphthalen-9-yl)-piperidin-3-yl]-acetamide;
2-Nitrilo-ethanesulfonic acid [1-(3H-3,4,6-triaza-cyclopenta[a]naphthalen-9-yl)-piperidin-3-yl]-amide;
1-(3H-3,4,6-Triaza-cyclopenta[a]naphthalen-9-yl)-pyrrolidine-3-carboxylic acid (2,2,2-trifluoro-ethyl)-amide;
1-(3H-3,4,6-Triaza-cyclopenta[a]naphthalen-9-yl)-piperidine-3-carboxylic acid cyanomethyl-amide;
1-(3H-3,4,6-Triaza-cyclopenta[a]naphthalen-9-yl)-pyrrolidine-3-carboxylic acid cyanomethyl-amide;
6-Methyl-1-(3H-3,4,6,7-tetraaza-cyclopenta[a]naphthalen-9-yl)-piperidine-3-carboxylic acid cyanomethyl-amide;
6-Methyl-1-(7-methyl-3H-3,4,6,8-tetraaza-cyclopenta[a]naphthalen-9-yl)-piperidine-3-carboxylic acid cyanomethyl-amide;
6-Methyl-1-(3H-3,4,7,8-tetraaza-cyclopenta[a]naphthalen-9-yl)-piperidine-3-carboxylic acid cyanomethyl-amide;
6-Methyl-1-(3H-3,4,7-triaza-cyclopenta[a]naphthalen-9-yl)-piperidine-3-carboxylic acid cyanomethyl-amide;
6-Methyl-1-(3H-3,4,8-triaza-cyclopenta[a]naphthalen-9-yl)-piperidine-3-carboxylic acid cyanomethyl-amide;
6-Methyl-1-(3H-3,4,6,7-tetraaza-cyclopenta[a]naphthalen-9-yl)-piperidine-3-carboxylic acid (2,2,2-trifluoro-ethyl)-amide;
6-Methyl-1-(7-methyl-3H-3,4,6,8-tetraaza-cyclopenta[a]naphthalen-9-yl)-piperidine-3-carboxylic acid (2,2,2-trifluoro-ethyl)-amide;
6-Methyl-1-(3H-3,4,7,8-tetraaza-cyclopenta[a]naphthalen-9-yl)-piperidine-3-carboxylic acid (2,2,2-trifluoro-ethyl)-amide;
6-Methyl-1-(3H-3,4,7-triaza-cyclopenta[a]naphthalen-9-yl)-piperidine-3-carboxylic acid (2,2,2-trifluoro-ethyl)-amide;
6-Methyl-1-(3H-3,4,8-triaza-cyclopenta[a]naphthalen-9-yl)-piperidine-3-carboxylic acid (2,2,2-trifluoro-ethyl)-amide;
2-Cyano-N-[6-methyl-1-(3H-3,4,6,7-tetraaza-cyclopenta[a]naphthalen-9-yl)-piperidin-3-yl]-acetamide;
2-Cyano-N-[6-methyl-1-(7-methyl-3H-3,4,6,8-tetraaza-cyclopenta[a]naphthalen-9-yl)-piperidin-3-yl]-acetamide;
2-Cyano-N-[6-methyl-1-(3H-3,4,7,8-tetraaza-cyclopenta[a]naphthalen-9-yl)-piperidin-3-yl]-acetamide;
2-Cyano-N-[6-methyl-1-(3H-3,4,7-triaza-cyclopenta[a]naphthalen-9-yl)-piperidin-3-yl]-acetamide;
2-Cyano-N-[6-methyl-1-(3H-3,4,8-triaza-cyclopenta[a]naphthalen-9-yl)-piperidin-3-yl]-acetamide;
3,3,3-Trifluoro-N-[6-methyl-1-(3H-3,4,6,7-tetraaza-cyclopenta[a]naphthalen-9-yl)-piperidin-3-yl]-propionamide;
3,3,3-Trifluoro-N-[6-methyl-1-(7-methyl-3H-3,4,6,8-tetraaza-cyclopenta[a]naphthalen-9-yl)-piperidin-3-yl]-propionamide;
3,3,3-Trifluoro-N-[6-methyl-1-(3H-3,4,7,8-tetraaza-cyclopenta[a]naphthalen-9-yl)-piperidin-3-yl]-propionamide;
3,3,3-Trifluoro-N-[6-methyl-1-(3H-3,4,7-triaza-cyclopenta[a]naphthalen-9-yl)-piperidin-3-yl]-propionamide;
3,3,3-Trifluoro-N-[6-methyl-1-(3H-3,4,8-triaza-cyclopenta[a]naphthalen-9-yl)-piperidin-3-yl]-propionamide;
2-Nitrilo-ethanesulfonic acid [6-methyl-1-(3H-3,4,6,7-tetraaza-cyclopenta[a]naphthalen-9-yl)-piperidin-3-yl]-amide;
2-Nitrilo-ethanesulfonic acid [6-methyl-1-(7-methyl-3H-3,4,6,8-tetraaza-cyclopenta[a]naphthalen-9-yl)-piperidin-3-yl]-amide;
2-Nitrilo-ethanesulfonic acid [6-methyl-1-(3H-3,4,7,8-tetraaza-cyclopenta[a]naphthalen-9-yl)-piperidin-3-yl]-amide;
2-Nitrilo-ethanesulfonic acid [6-methyl-1-(3H-3,4,7-triaza-cyclopenta[a]naphthalen-9-yl)-piperidin-3-yl]-amide;
2-Nitrilo-ethanesulfonic acid [6-methyl-1-(3H-3,4,8-triaza-cyclopenta[a]naphthalen-9-yl)-piperidin-3-yl]-amide;
2,2,2-Trifluoro-ethanesulfonic acid [6-methyl-1-(3H-3,4,6,7-tetraaza-cyclopenta[a]naphthalen-9-yl)-piperidin-3-yl]-amide;
2,2,2-Trifluoro-ethanesulfonic acid [6-methyl-1-(7-methyl-3H-3,4,6,8-tetraaza-cyclopenta[a]naphthalen-9-yl)-piperidin-3-yl]-amide;
2,2,2-Trifluoro-ethanesulfonic acid [6-methyl-1-(3H-3,4,7,8-tetraaza-cyclopenta[a]naphthalen-9-yl)-piperidin-3-yl]-amide;
2,2,2-Trifluoro-ethanesulfonic acid [6-methyl-1-(3H-3,4,7-triaza-cyclopenta[a]naphthalen-9-yl)-piperidin-3-yl]-amide;
2,2,2-Trifluoro-ethanesulfonic acid [6-methyl-1-(3H-3,4,8-triaza-cyclopenta[a]naphthalen-9-yl)-piperidin-3-yl]-amide;

6-Methyl-1-(3H-3,4,6,7-tetraaza-cyclopenta[a]naphthalen-9-yl)-piperidine-3-sulfonic acid cyanomethyl-amide;
6-Methyl-1-(7-methyl-3H-3,4,6,8-tetraaza-cyclopenta[a]naphthalen-9-yl)-piperidine-3-sulfonic acid cyanomethyl-amide;
6-Methyl-1-(3H-3,4,7,8-tetraaza-cyclopenta[a]naphthalen-9-yl)-piperidine-3-sulfonic acid cyanomethyl-amide;
6-Methyl-1-(3H-3,4,7-triaza-cyclopenta[a]naphthalen-9-yl)-piperidine-3-sulfonic acid cyanomethyl-amide;
6-Methyl-1-(3H-3,4,8-triaza-cyclopenta[a]naphthalen-9-yl)-piperidine-3-sulfonic acid cyanomethyl-amide;
9-[4-[[3-(pyrrolidin-1-ylmethyl)-1-piperidyl]sulfonylmethyl]-1-piperidyl]-3H-pyrrolo[3,2-f][1,7]naphthyridine;
9-[4-[[3-(methoxymethyl) pyrrolidin-1-yl]sulfonylmethyl]-1-piperidyl]-3H-pyrrolo[3,2-f][1,7]naphthyridine;
3-methyl-1-[[1-(3H-pyrrolo[3,2-f][1,7]naphthyridin-9-yl)-4-piperidyl]methylsulfonyl]pyrrolidin-3-ol;
9-[4-[(3-methoxy-1-piperidyl)sulfonylmethyl]-1-piperidyl]-3H-pyrrolo[3,2-f][1,7]naphthyridine;
[1-[[1-(3H-pyrrolo[3,2-f][1,7]naphthyridin-9-yl)-4-piperidyl]methylsulfonyl]-3-piperidyl]methanesulfonamide;
9-[4-[(3-isobutoxy-1-piperidyl)sulfonylmethyl]-1-piperidyl]-3H-pyrrolo[3,2-f][1,7]naphthyridine;
9-[4-[[3-(2-methoxyethoxy)-1-piperidyl]sulfonylmethyl]-1-piperidyl]-3H-pyrrolo[3,2-f][1,7]naphthyridine;
N-(cyclopropylmethyl)-1-[1-(3H-pyrrolo[3,2-f][1,7]naphthyridin-9-yl)-4-piperidyl]methanesulfonamide;
N-cyclobutyl-1-[1-(3H-pyrrolo[3,2-f][1,7]naphthyridin-9-yl)-4-piperidyl]methanesulfonamide;
9-[4-[[3-[(4-fluorophenoxy)methyl]-1-piperidyl]sulfonylmethyl]-1-piperidyl]-3H-pyrrolo[3,2-f][1,7]naphthyridine;
9-[4-[[3-[(4-chlorophenoxy)methyl]-1-piperidyl]sulfonylmethyl]-1-piperidyl]-3H-pyrrolo[3,2-f][1,7]naphthyridine;
4-[[1-[[1-(3H-pyrrolo[3,2-f][1,7]naphthyridin-9-yl)-4-piperidyl]methylsulfonyl]-3-piperidyl]methoxy]benzonitrile;
4-[[1-[[4-(3H-pyrrolo[3,2-f][1,7]naphthyridin-9-yl)-1-piperidyl]methylsulfonyl]-3-piperidyl]methoxy]benzoic acid;
4-[[1-[[4-(3H-pyrrolo[3,2-f][1,7]naphthyridin-9-yl)-1-piperidyl]methylsulfonyl]-3-piperidyl]methoxy]benzamide;
9-[4-[[3-[(2,4-difluorophenoxy)methyl]-1-piperidyl]sulfonyl methyl]-1-piperidyl]-3H-pyrrolo[3,2-f][1,7]naphthyridine;
9-[4-[[3-[(4-methoxyphenoxy)methyl]-1-piperidyl]sulfonyl methyl]-1-piperidyl]-3H-pyrrolo[3,2-f][1,7]naphthyridine;
9-[4-[[3-[[4-(trifluoromethoxy)phenoxy]methyl]-1-piperidyl]sulfonylmethyl]-1-piperidyl]-3H-pyrrolo[3,2-f][1,7]naphthyridine;
9-[4-[[3-[[4-(trifluoromethyl)phenoxy]methyl]-1-piperidyl]sulfonylmethyl]-1-piperidyl]-3H-pyrrolo[3,2-f][1,7]naphthyridine;
9-[4-[(3-methyl-1-piperidyl)sulfonylmethyl]-1-piperidyl]-3H-pyrrolo[3,2-f][1,7]naphthyridine;
9-[4-[[3-(trifluoromethyl)-1-piperidyl]sulfonylmethyl]-1-piperidyl]-3H-pyrrolo[3,2-f][1,7]naphthyridine;
9-[4-[[3-(pyrrolidin-1-ylmethyl)-1-piperidyl]sulfonylmethyl]piperazin-1-yl]-3H-pyrrolo[3,2-f][1,7]naphthyridine;
9-[4-[[3-(methoxymethyl) pyrrolidin-1-yl]sulfonylmethyl]piperazin-1-yl]-3H-pyrrolo[3,2-f][1,7]naphthyridine;
3-methyl-1-[[4-(3H-pyrrolo[3,2-f][1,7]naphthyridin-9-yl)piperazin-1-yl]methylsulfonyl]pyrrolidin-3-ol;
9-[4-[(3-methoxy-1-piperidyl)sulfonylmethyl]piperazin-1-yl]-3H-pyrrolo[3,2-f][1,7]naphthyridine;
[1-[[4-(3H-pyrrolo[3,2-f][1,7]naphthyridin-9-yl)piperazin-1-yl]methylsulfonyl]-3-piperidyl]methanesulfonamide;
9-[4-[(3-isobutoxy-1-piperidyl)sulfonylmethyl]piperazin-1-yl]-3H-pyrrolo[3,2-f][1,7]naphthyridine;
9-[4-[[3-(2-methoxyethoxy)-1-piperidyl]sulfonylmethyl]piperazin-1-yl]-3H-pyrrolo[3,2-f][1,7]naphthyridine;
N-(cyclopropylmethyl)-1-[4-(3H-pyrrolo[3,2-f][1,7]naphthyridin-9-yl)piperazin-1-yl]methane sulfonamide;
N-cyclobutyl-1-[4-(3H-pyrrolo[3,2-f][1,7]naphthyridin-9-yl)piperazin-1-yl]methanesulfonamide;
9-[4-[[3-[(4-fluorophenoxy)methyl]-1-piperidyl]sulfonylmethyl]piperazin-1-yl]-3H-pyrrolo[3,2-f][1,7]naphthyridine;
9-[4-[[3-[(4-chlorophenoxy)methyl]-1-piperidyl]sulfonyl methyl]piperazin-1-yl]-3H-pyrrolo[3,2-f][1,7]naphthyridine;
4-[[1-[[4-(3H-pyrrolo[3,2-f][1,7]naphthyridin-9-yl)piperazin-1-yl]methylsulfonyl]-3-piperidyl]methoxy]benzonitrile;
4-[[1-[[4-(3H-pyrrolo[3,2-f][1,7]naphthyridin-9-yl)piperazin-1-yl]methylsulfonyl]-3-piperidyl]methoxy]benzoic acid;
4-[[1-[[4-(3H-pyrrolo[3,2-f][1,7]naphthyridin-9-yl)piperazin-1-yl]methylsulfonyl]-3-piperidyl]methoxy]benzamide;
9-[4-[[3-[(2,4-difluorophenoxy)methyl]-1-piperidyl]sulfonylmethyl]piperazin-1-yl]-3H-pyrrolo[3,2-f][1,7]naphthyridine;
9-[4-[[3-[(4-methoxyphenoxy)methyl]-1-piperidyl]sulfonylmethyl]piperazin-1-yl]-3H-pyrrolo[3,2-f][1,7]naphthyridine;
9-[4-[[3-[[4-(trifluoromethoxy)phenoxy]methyl]-1-piperidyl]sulfonylmethyl]piperazin-1-yl]-3H-pyrrolo[3,2-f][1,7]naphthyridine;
9-[4-[[3-[[4-(trifluoromethyl)phenoxy]methyl]-1-piperidyl]sulfonylmethyl]piperazin-1-yl]-3H-pyrrolo[3,2-f][1,7]naphthyridine;
9-[4-[(3-methyl-1-piperidyl)sulfonylmethyl]piperazin-1-yl]-3H-pyrrolo[3,2-f][1,7]naphthyridine;
9-[4-[(3-(trifluoromethyl)-1-piperidyl]sulfonylmethyl]piperazin-1-yl]-3H-pyrrolo[3,2-f][1,7]naphthyridine;
9-[1-[[3-(pyrrolidin-1-ylmethyl)-1-piperidyl]sulfonylmethyl]-4-piperidyl]-3H-pyrrolo[3,2-f][1,7]naphthyridine;
9-[1-[ [3-(methoxymethyl) pyrrolidin-1-yl]sulfonylmethyl]-4-piperidyl]-3H-pyrrolo[3,2-f][1,7]naphthyridine;
3-methyl-1-[[4-(3H-pyrrolo[3,2-f][1,7]naphthyridin-9-yl)-1-piperidyl]methylsulfonyl]pyrrolidin-3-ol;
9-[1-[(3-methoxy-1-piperidyl)sulfonylmethyl]-4-piperidyl]-3H-pyrrolo[3,2-f][1,7]naphthyridine;
[1-[[4-(3H-pyrrolo[3,2-f][1,7]naphthyridin-9-yl)-1-piperidyl]methylsulfonyl]-3-piperidyl]methanesulfonamide;
9-[1-[(3-isobutoxy-1-piperidyl)sulfonylmethyl]-4-piperidyl]-3H-pyrrolo[3,2-f][1,7]naphthyridine;
9-[1-[[3-(2-methoxyethoxy)-1-piperidyl]sulfonylmethyl]-4-piperidyl]-3H-pyrrolo[3,2-f][1,7]naphthyridine;
N-(cyclopropylmethyl)-1-[4-(3H-pyrrolo[3,2-f][1,7]naphthyridin-9-yl)-1-piperidyl]methanesulfonamide;
N-cyclobutyl-1-[4-(3H-pyrrolo[3,2-f][1,7]naphthyridin-9-yl)-1-piperidyl]methanesulfonamide;
9-[1-[[3-[(4-fluorophenoxy)methyl]-1-piperidyl]sulfonylmethyl]-4-piperidyl]-3H-pyrrolo[3,2-f][1,7]naphthyridine;

9-[1-[[3-[(4-chlorophenoxy)methyl]-1-piperidyl]sulfonylmethyl]-4-piperidyl]-3H-pyrrolo[3,2-f][1,7]naphthyridine;

4-[[1-[[4-(3H-pyrrolo[3,2-f][1,7]naphthyridin-9-yl)-1-piperidyl]methylsulfonyl]-3-piperidyl]methoxy]benzonitrile;

4-[[1-[[4-(3H-pyrrolo[3,2-f][1,7]naphthyridin-9-yl)-1-piperidyl]methylsulfonyl]-3-piperidyl]methoxy]benzoic acid;

4-[[1-[[4-(3H-pyrrolo[3,2-f][1,7]naphthyridin-9-yl)-1-piperidyl]methylsulfonyl]-3-piperidyl]methoxy]benzamide;

9-[1-[[3-[(2,4-difluorophenoxy)methyl]-1-piperidyl]sulfonyl methyl]-4-piperidyl]-3H-pyrrolo[3,2-f][1,7]naphthyridine;

9-[1-[[3-[(4-methoxyphenoxy)methyl]-1-piperidyl]sulfonylmethyl]-4-piperidyl]-3H-pyrrolo[3,2-f][1,7]naphthyridine;

9-[1-[[3-[[4-(trifluoromethoxy)phenoxy]methyl]-1-piperidyl]sulfonylmethyl]-4-piperidyl]-3H-pyrrolo[3,2-f][1,7]naphthyridine;

9-[1-[[3-[[4-(trifluoromethyl)phenoxy]methyl]-1-piperidyl]sulfonylmethyl]-4-piperidyl]-3H-pyrrolo[3,2-f][1,7]naphthyridine;

9-[1-[(3-methyl-1-piperidyl)sulfonylmethyl]-4-piperidyl]-3H-pyrrolo[3,2-f][1,7]naphthyridine;

9-[1-[[3-(trifluoromethyl)-1-piperidyl]sulfonylmethyl]-4-piperidyl]-3H-pyrrolo[3,2-f][1,7]naphthyridine;

9-[4-[[3-(pyrrolidin-1-ylmethyl)-1-piperidyl]sulfonylmethyl]cyclohexyl]-3H-pyrrolo[3,2-f][1,7]naphthyridine;

9-[4-[[3-(methoxymethyl)pyrrolidin-1-yl]sulfonylmethyl]cyclohexyl]-3H-pyrrolo[3,2-f][1,7]naphthyridine;

3-methyl-1-[[4-(3H-pyrrolo[3,2-f][1,7]naphthyridin-9-yl)cyclohexyl]methylsulfonyl]pyrrolidin-3-ol;

9-[4-[(3-methoxy-1-piperidyl) sulfonyl methyl]cyclohexyl]-3H-pyrrolo[3,2-f][1,7]naphthyridine;

[1-[[4-(3H-pyrrolo[3,2-f][1,7]naphthyridin-9-yl)cyclohexyl]methylsulfonyl]-3-piperidyl]methanesulfonamide 9-[4-[(3-isobutoxy-1-piperidyl)sulfonylmethyl]cyclohexyl]-3H-pyrrolo[3,2-f][1,7]naphthyridine;

9-[4-[[3-(2-methoxyethoxy)-1-piperidyl]sulfonylmethyl]cyclohexyl]-3H-pyrrolo[3,2-f][1,7]naphthyridine;

N-(cyclopropylmethyl)-1-[4-(3H-pyrrolo[3,2-f][1,7]naphthyridin-9-yl)cyclohexyl]methanesulfonamide;

N-cyclobutyl-1-[4-(3H-pyrrolo[3,2-f][1,7]naphthyridin-9-yl)cyclohexyl]methanesulfonamide;

9-[4-[[3-(4-fluorophenoxy)methyl]-1-piperidyl]sulfonylmethyl]cyclohexyl]-3H-pyrrolo[3,2-f][1,7]naphthyridine;

9-[4-[[3-[(4-chlorophenoxy)methyl]-1-piperidyl]sulfonylmethyl]cyclohexyl]-3H-pyrrolo[3,2-f][1,7]naphthyridine;

4-[[1-[[4-(3H-pyrrolo[3,2-f][1,7]naphthyridin-9-yl)cyclohexyl]methylsulfonyl]-3-piperidyl]methoxy]benzonitrile;

4-[[1-[[4-(3H-pyrrolo[3,2-f][1,7]naphthyridin-9-yl)cyclohexyl]methylsulfonyl]-3-piperidyl]methoxy]benzoic acid;

4-[[1-[[4-(3H-pyrrolo[3,2-f][1,7]naphthyridin-9-yl)cyclohexyl]methylsulfonyl]-3-piperidyl]methoxy]benzamide;

9-[4-[[3-[(2,4-difluorophenoxy)methyl]-1-piperidyl]sulfonylmethyl]cyclohexyl]-3H-pyrrolo[3,2-f][1,7]naphthyridine;

9-[4-[[3-[(4-methoxyphenoxy)methyl]-1-piperidyl]sulfonylmethyl]cyclohexyl]-3H-pyrrolo[3,2-f][1,7]naphthyridine;

9-[4-[[3-[[4-(trifluoromethoxy)phenoxy]methyl]-1-piperidyl]sulfonylmethyl]cyclohexyl]-3H-pyrrolo[3,2-f][1,7]naphthyridine;

9-[4-[[3-[[4-(trifluoromethyl)phenoxy]methyl]-1-piperidyl]sulfonylmethyl]cyclohexyl]-3H-pyrrolo[3,2-f][1,7]naphthyridine;

9-[4-[(3-methyl-1-piperidyl)sulfonyl methyl]cyclohexyl]-3H-pyrrolo[3,2-f][1,7]naphthyridine;

9-[4-[[3-(trifluoromethyl)-1-piperidyl]sulfonylmethyl cyclohexyl]-3H-pyrrolo[3,2-f][1,7]naphthyridine;

1-[3-(pyrrolidin-1-ylmethyl)-1-piperidyl]-2-[1-(3H-pyrrolo[3,2-f][1,7]naphthyridin-9-yl)-4-piperidyl]ethanone;

1-[3-(methoxymethyl)pyrrolidin-1-yl]-2-[1-(3H-pyrrolo[3,2-f][1,7]naphthyridin-9-yl)-4-piperidyl]ethanone;

1-(3-hydroxy-3-methyl-pyrrolidin-1-yl)-2-[ 1-(3H-pyrrolo[3,2-f][1,7]naphthyridin-9-yl)-4-piperidyl]ethanone;

1-(3-methoxy-1-piperidyl)-2-[1-(3H-pyrrolo[3,2-f][1,7]naphthyridin-9-yl)-4-piperidyl]ethanone;

[1-[2-[1-(3H-pyrrolo[3,2-f][1,7]naphthyridin-9-yl)-4-piperidyl]acetyl]-3-piperidyl]methane sulfonamide;

1-(3-isobutoxy-1-piperidyl)-2-[1-(3H-pyrrolo[3,2-f][1,7]naphthyridin-9-yl)-4-piperidyl]ethanone;

1-[3-(2-methoxyethoxy)-1-piperidyl]-2-[1-(3H-pyrrolo[3,2-f][1,7]naphthyridin-9-yl)-4-piperidyl]ethanone;

N-(cyclopropylmethyl)-2-[1-(3H-pyrrolo[3,2-f][1,7]naphthyridin-9-yl)-4-piperidyl]acetamide;

N-cyclobutyl-2-[1-(3H-pyrrolo[3,2-f][1,7]naphthyridin-9-yl)-4-piperidyl]acetamide;

1-[3-[(4-fluorophenoxy)methyl]-1-piperidyl]-2-[1-(3H-pyrrolo[3,2-f][1,7]naphthyridin-9-yl)-4-piperidyl]ethanone;

1-[3-[(4-chlorophenoxy)methyl]-1-piperidyl]-2-[1-(3H-pyrrolo[3,2-f][1,7]naphthyridin-9-yl)-4-piperidyl]ethanone;

4-[[1-[2-[1-(3H-pyrrolo[3,2-f][1,7]naphthyridin-9-yl)-4-piperidyl]acetyl]-3-piperidyl]methoxy]benzonitrile;

4-[[1-[2-[1-(3H-pyrrolo[3,2-f][1,7]naphthyridin-9-yl)-4-piperidyl]acetyl]-3-piperidyl]methoxy]benzoic acid;

4-[[1-[2-[1-(3H-pyrrolo[3,2-f][1,7]naphthyridin-9-yl)-4-piperidyl]acetyl]-3-piperidyl]methoxy]benzamide;

1-[3-[(2,4-difluorophenoxy)methyl]-1-piperidyl]-2-[1-(3H-pyrrolo[3,2-f][1,7]naphthyridin-9-yl)-4-piperidyl]ethanone;

1-[3-[(4-methoxyphenoxy)methyl]-1-piperidyl]-2-[1-(3H-pyrrolo[3,2-f][1,7]naphthyridin-9-yl)-4-piperidyl]ethanone;

2-[1-(3H-pyrrolo[3,2-f][1,7]naphthyridin-9-yl)-4-piperidyl]-1-[3-[[4-(trifluoromethoxy)phenoxy]methyl]-1-piperidyl]ethanone;

2-[1-(3H-pyrrolo[3,2-f][1,7]naphthyridin-9-yl)-4-piperidyl]-1-[3-[[4-(trifluoromethyl)phenoxy]methyl]-1-piperidyl]ethanone;

1-(3-methyl-1-piperidyl)-2-[1-(3H-pyrrolo[3,2-f][1,7]naphthyridin-9-yl)-4-piperidyl]ethanone;

2-[1-(3H-pyrrolo[3,2-f][1,7]naphthyridin-9-yl)-4-piperidyl]-1-[3-(trifluoromethyl)-1-piperidyl]ethanone;

1-[3-(pyrrolidin-1-ylmethyl)-1-piperidyl]-2-[4-(3H-pyrrolo[3,2-f][1,7]naphthyridin-9-yl)piperazin-1-yl]ethanone;

1-[3-(methoxymethyl)pyrrolidin-1-yl]-2-[4-(3H-pyrrolo[3,2-f][1,7]naphthyridin-9-yl)piperazin-1-yl]ethanone;

1-(3-hydroxy-3-methyl-pyrrolidin-1-yl)-2-[4-(3H-pyrrolo[3,2-f][1,7]naphthyridin-9-yl)piperazin-1-yl]ethanone;

1-(3-methoxy-1-piperidyl)-2-[4-(3H-pyrrolo[3,2-f][1,7]naphthyridin-9-yl)piperazin-1-yl]ethanone;

[1-[2-[4-(3H-pyrrolo[3,2-f][1,7]naphthyridin-9-yl)piperazin-1-yl]acetyl]-3-piperidyl]methane sulfonamide;

1-(3-isobutoxy-1-piperidyl)-2-[4-(3H-pyrrolo[3,2-f][1,7]naphthyridin-9-yl)piperazin-1-yl]ethanone;

1-[3-(2-methoxyethoxy)-1-piperidyl]-2-[4-(3H-pyrrolo[3,2-f][1,7]naphthyridin-9-yl)piperazin-1-yl]ethanone;
N-(cyclopropylmethyl)-2-[4-(3H-pyrrolo[3,2-f][1,7]naphthyridin-9-yl)piperazin-1-yl]acetamide;
N-cyclobutyl-2-[4-(3H-pyrrolo[3,2-f][1,7]naphthyridin-9-yl)piperazin-1-yl]acetamide;
1-[3-[(4-fluorophenoxy)methyl]-1-piperidyl]-2-[4-(3H-pyrrolo[3,2-f][1,7]naphthyridin-9-yl)piperazin-1-yl]ethanone;
1-[3-[(4-chlorophenoxy)methyl]-1-piperidyl]-2-[4-(3H-pyrrolo[3,2-f][1,7]naphthyridin-9-yl)piperazin-1-yl]ethanone;
4-[[1-[2-[4-(3H-pyrrolo[3,2-f][1,7]naphthyridin-9-yl)piperazin-1-yl]acetyl]-3-piperidyl]methoxy]benzonitrile;
4-[[1-[2-[4-(3H-pyrrolo[3,2-f][1,7]naphthyridin-9-yl)piperazin-1-yl]acetyl]-3-piperidyl]methoxy]benzoic acid;
4-[[1-[2-[4-(3H-pyrrolo[3,2-f][1,7]naphthyridin-9-yl)piperazin-1-yl]acetyl]-3-piperidyl]methoxy]benzamide;
1-[3-[(2,4-difluorophenoxy)methyl]-1-piperidyl]-2-[4-(3H-pyrrolo[3,2-f][1,7]naphthyridin-9-yl)piperazin-1-yl]ethanone;
1-[3-[(4-methoxyphenoxy)methyl]-1-piperidyl]-2-[4-(3H-pyrrolo[3,2-f][1,7]naphthyridin-9-yl)piperazin-1-yl]ethanone;
2-[4-(3H-pyrrolo[3,2-f][1,7]naphthyridin-9-yl)piperazin-1-yl]-1-[3-[[4-(trifluoromethoxy)phenoxy]methyl]-1-piperidyl]ethanone;
2-[4-(3H-pyrrolo[3,2-f][1,7]naphthyridin-9-yl)piperazin-1-yl]-1-[3-[[4-(trifluoromethyl)phenoxy]methyl]-1-piperidyl]ethanone;
1-(3-methyl-1-piperidyl)-2-[4-(3H-pyrrolo[3,2-f][1,7]naphthyridin-9-yl)piperazin-1-yl]ethanone;
2-[4-(3H-pyrrolo[3,2-f][1,7]naphthyridin-9-yl)piperazin-1-yl]-1-[3-(trifluoromethyl)-1-piperidyl]ethanone;
1-[3-(pyrrolidin-1-ylmethyl)-1-piperidyl]-2-[4-(3H-pyrrolo[3,2-f][1,7]naphthyridin-9-yl)-1-piperidyl]ethanone;
1-[3-(methoxymethyl)pyrrolidin-1-yl]-2-[4-(3H-pyrrolo[3,2-f][1,7]naphthyridin-9-yl)-1-piperidyl]ethanone;
1-(3-hydroxy-3-methyl-pyrrolidin-1-yl)-2-[4-(3H-pyrrolo[3,2-f][1,7]naphthyridin-9-yl)-1-piperidyl]ethanone;
1-(3-methoxy-1-piperidyl)-2-[4-(3H-pyrrolo[3,2-f][1,7]naphthyridin-9-yl)-1-piperidyl]ethanone;
[1-[2-[4-(3H-pyrrolo[3,2-f][1,7]naphthyridin-9-yl)-1-piperidyl]acetyl]-3-piperidyl]methane sulfonamide;
1-(3-isobutoxy-1-piperidyl)-2-[4-(3H-pyrrolo[3,2-f][1,7]naphthyridin-9-yl)-1-piperidyl]ethanone;
1-[3-(2-methoxyethoxy)-1-piperidyl]-2-[4-(3H-pyrrolo[3,2-f][1,7]naphthyridin-9-yl)-1-piperidyl]ethanone;
N-(cyclopropylmethyl)-2-[4-(3H-pyrrolo[3,2-f][1,7]naphthyridin-9-yl)-1-piperidyl]acetamide
N-cyclobutyl-2-[4-(3H-pyrrolo[3,2-f][1,7]naphthyridin-9-yl)-1-piperidyl]acetamide;
1-[3-[(4-fluorophenoxy)methyl]-1-piperidyl]-2-[4-(3H-pyrrolo[3,2-f][1,7]naphthyridin-9-yl)-1-piperidyl]ethanone;
1-[3-[(4-chlorophenoxy)methyl]-1-piperidyl]-2-[4-(3H-pyrrolo[3,2-f][1,7]naphthyridin-9-yl)-1-piperidyl]ethanone;
4-[[1-[2-[4-(3H-pyrrolo[3,2-f][1,7]naphthyridin-9-yl)-1-piperidyl]acetyl]-3-piperidyl]methoxy]benzonitrile;
4-[[1-[2-[4-(3H-pyrrolo[3,2-f][1,7]naphthyridin-9-yl)-1-piperidyl]acetyl]-3-piperidyl]methoxy]benzoic acid;
4-[[1-[2-[4-(3H-pyrrolo[3,2-f][1,7]naphthyridin-9-yl)-1-piperidyl]acetyl]-3-piperidyl]methoxy]benzamide;
1-[3-[(2,4-difluorophenoxy)methyl]-1-piperidyl]-2-[4-(3H-pyrrolo[3,2-f][1,7]naphthyridin-9-yl)-1-piperidyl]ethanone;
1-[3-[(4-methoxyphenoxy)methyl]-1-piperidyl]-2-[4-(3H-pyrrolo[3,2-f][1,7]naphthyridin-9-yl)-1-piperidyl]ethanone;

2-[4-(3H-pyrrolo[3,2-f][1,7]naphthyridin-9-yl)-1-piperidyl]-1-[3-[[4-(trifluoromethoxy)phenoxy]methyl]-1-piperidyl]ethanone;
2-[4-(3H-pyrrolo[3,2-f][1,7]naphthyridin-9-yl)-1-piperidyl]-1-[3-[[4-(trifluoromethyl)phenoxy]methyl]-1-piperidyl]ethanone;
1-(3-methyl-1-piperidyl)-2-[4-(3H-pyrrolo[3,2-f][1,7]naphthyridin-9-yl)-1-piperidyl]ethanone;
2-[4-(3H-pyrrolo[3,2-f][1,7]naphthyridin-9-yl)-1-piperidyl]-1-[3-(trifluoromethyl)-1-piperidyl]ethanone;
1-[3-(pyrrolidin-1-ylmethyl)-1-piperidyl]-2-[4-(3H-pyrrolo[3,2-f][1,7]naphthyridin-9-yl)cyclohexyl]ethanone;
1-[3-(methoxymethyl)pyrrolidin-1-yl]-2-[4-(3H-pyrrolo[3,2-f][1,7]naphthyridin-9-yl)cyclohexyl]ethanone;
1-(3-hydroxy-3-methyl-pyrrolidin-1-yl)-2-[4-(3H-pyrrolo[3,2-f][1,7]naphthyridin-9-yl)cyclohexyl]ethanone;
1-(3-methoxy-1-piperidyl)-2-[4-(3H-pyrrolo[3,2-f][1,7]naphthyridin-9-yl)cyclohexyl]ethanone;
[1-[2-[4-(3H-pyrrolo[3,2-f][1,7]naphthyridin-9-yl)cyclohexyl]acetyl]-3-piperidyl]methane sulfonamide;
1-(3-isobutoxy-1-piperidyl)-2-[4-(3H-pyrrolo[3,2-f][1,7]naphthyridin-9-yl)cyclohexyl]ethanone;
1-[3-(2-methoxyethoxy)-1-piperidyl]-2-[4-(3H-pyrrolo[3,2-f][1,7]naphthyridin-9-yl)cyclohexyl]ethanone;
N-(cyclopropylmethyl)-2-[4-(3H-pyrrolo[3,2-f][1,7]naphthyridin-9-yl)cyclohexyl]acetamide;
N-cyclobutyl-2-[4-(3H-pyrrolo[3,2-f][1,7]naphthyridin-9-yl)cyclohexyl]acetamide;
1-[3-[(4-fluorophenoxy)methyl]-1-piperidyl]-2-[4-(3H-pyrrolo[3,2-f][1,7]naphthyridin-9-yl)cyclohexyl]ethanone;
1-[3-[(4-chlorophenoxy)methyl]-1-piperidyl]-2-[4-(3H-pyrrolo[3,2-f][1,7]naphthyridin-9-yl)cyclohexyl]ethanone;
4-[[1-[2-[4-(3H-pyrrolo[3,2-f][1,7]naphthyridin-9-yl)cyclohexyl]acetyl]-3-piperidyl]methoxy]benzonitrile
4-[[1-[2-[4-(3H-pyrrolo[3,2-f][1,7]naphthyridin-9-yl)cyclohexyl]acetyl]-3-piperidyl]methoxy]benzoic acid;
4-[[1-[2-[4-(3H-pyrrolo[3,2-f][1,7]naphthyridin-9-yl)cyclohexyl]acetyl]-3-piperidyl]methoxy]benzamide;
1-[3-[(2,4-difluorophenoxy)methyl]-1-piperidyl]-2-[4-(3H-pyrrolo[3,2-f][1,7]naphthyridin-9-yl)cyclohexyl]ethanone;
1-[3-[(4-methoxyphenoxy)methyl]-1-piperidyl]-2-[4-(3H-pyrrolo[3,2-f][1,7]naphthyridin-9-yl)cyclohexyl]ethanone;
2-[4-(3H-pyrrolo[3,2-f][1,7]naphthyridin-9-yl)cyclohexyl]-1-[3-[[4-(trifluoromethoxy)phenoxy]methyl]-1-piperidyl]ethanone;
2-[4-(3H-pyrrolo[3,2-f][1,7]naphthyridin-9-yl)cyclohexyl]-1-[3-[[4-(trifluoromethyl)phenoxy]methyl]-1-piperidyl]ethanone;
1-(3-methyl-1-piperidyl)-2-[4-(3H-pyrrolo[3,2-f][1,7]naphthyridin-9-yl)cyclohexyl]ethanone;
2-[4-(3H-pyrrolo[3,2-f][1,7]naphthyridin-9-yl)cyclohexyl]-1-[3-(trifluoromethyl)-1-piperidyl]ethanone;
3-(pyrrolidin-1-ylmethyl)-N-[1-(3H-pyrrolo[3,2-f][1,7]naphthyridin-9-yl)-4-piperidyl]piperidine-1-carboxamide;
3-(methoxymethyl)-N-[1-(3H-pyrrolo[3,2-f][1,7]naphthyridin-9-yl)-4-piperidyl]pyrrolidine-1-carboxamide;
3-hydroxy-3-methyl-N-[1-(3H-pyrrolo[3,2-f][1,7]naphthyridin-9-yl)-4-piperidyl]pyrrolidine-1-carboxamide;
3-methoxy-N-[1-(3H-pyrrolo[3,2-f][1,7]naphthyridin-9-yl)-4-piperidyl]piperidine-1-carboxamide;
N-[1-(3H-pyrrolo[3,2-f][1,7]naphthyridin-9-yl)-4-piperidyl]-3-(sulfamoylmethyl)piperidine-1-carboxamide;
3-isobutoxy-N-[1-(3H-pyrrolo[3,2-f][1,7]naphthyridin-9-yl)-4-piperidyl]piperidine-1-carboxamide;

3-(2-methoxyethoxy)-N-[1-(3H-pyrrolo[3,2-f][1,7]naphthyridin-9-yl)-4-piperidyl]piperidine-1-carboxamide;
1-(cyclopropylmethyl)-3-[1-(3H-pyrrolo[3,2-f][1,7]naphthyridin-9-yl)-4-piperidyl]urea;
1-cyclobutyl-3-[1-(3H-pyrrolo[3,2-f][1,7]naphthyridin-9-yl)-4-piperidyl]urea;
3-[(4-fluorophenoxy)methyl]-N-[1-(3H-pyrrolo[3,2-f][1,7]naphthyridin-9-yl)-4-piperidyl]piperidine-1-carboxamide;
3-[(4-chlorophenoxy)methyl]-N-[1-(3H-pyrrolo[3,2-f][1,7]naphthyridin-9-yl)-4-piperidyl]piperidine-1-carboxamide;
3-[(4-cyanophenoxy)methyl]-N-[1-(3H-pyrrolo[3,2-f][1,7]naphthyridin-9-yl)-4-piperidyl]piperidine-1-carboxamide;
4-[[1-[[1-(3H-pyrrolo[3,2-f][1,7]naphthyridin-9-yl)-4-piperidyl]carbamoyl]-3-piperidyl]methoxy]benzoic acid;
3-[(4-carbamoylphenoxy)methyl]-N-[1-(3H-pyrrolo[3,2-f][1,7]naphthyridin-9-yl)-4-piperidyl]piperidine-1-carboxamide;
3-[(2,4-difluorophenoxy)methyl]-N-[1-(3H-pyrrolo[3,2-f][1,7]naphthyridin-9-yl)-4-piperidyl]piperidine-1-carboxamide;
3-[(4-methoxyphenoxy)methyl]-N-[1-(3H-pyrrolo[3,2-f][1,7]naphthyridin-9-yl)-4-piperidyl]piperidine-1-carboxamide;
N-[1-(3H-pyrrolo[3,2-f][1,7]naphthyridin-9-yl)-4-piperidyl]-3-[[4-(trifluoromethoxy)phenoxy]methyl]piperidine-1-carboxamide;
N-[1-(3H-pyrrolo[3,2-f][1,7]naphthyridin-9-yl)-4-piperidyl]-3-[[4-(trifluoromethyl)phenoxy]methyl]piperidine-1-carboxamide;
3-methyl-N-[1-(3H-pyrrolo[3,2-f][1,7]naphthyridin-9-yl)-4-piperidyl]piperidine-1-carboxamide;
N-[1-(3H-pyrrolo[3,2-f][1,7]naphthyridin-9-yl)-4-piperidyl]-3-(trifluoromethyl)piperidine-1-carboxamide;
[3-(pyrrolidin-1-ylmethyl)-1-piperidyl]-[4-(3H-pyrrolo[3,2-f][1,7]naphthyridin-9-yl)piperazin-1-yl]methanone;
[3-(methoxymethyl)pyrrolidin-1-yl]-[4-(3H-pyrrolo[3,2-f][1,7]naphthyridin-9-yl)piperazin-1-yl]methanone;
(3-hydroxy-3-methyl-pyrrolidin-1-yl)-[4-(3H-pyrrolo[3,2-f][1,7]naphthyridin-9-yl)piperazin-1-yl]methanone;
(3-methoxy-1-piperidyl)-[4-(3H-pyrrolo[3,2-f][1,7]naphthyridin-9-yl)piperazin-1-yl]methanone;
[1-[4-(3H-pyrrolo[3,2-f][1,7]naphthyridin-9-yl)piperazine-1-carbonyl]-3-piperidyl]methane sulfonamide;
(3-isobutoxy-1-piperidyl)-[4-(3H-pyrrolo[3,2-f][1,7]naphthyridin-9-yl)piperazin-1-yl]methanone;
[3-(2-methoxyethoxy)-1-piperidyl]-[4-(3H-pyrrolo[3,2-f][1,7]naphthyridin-9-yl)piperazin-1-yl]methanone;
N-(cyclopropylmethyl)-4-(3H-pyrrolo[3,2-f][1,7]naphthyridin-9-yl)piperazine-1-carboxamide;
N-cyclobutyl-4-(3H-pyrrolo[3,2-f][1,7]naphthyridin-9-yl)piperazine-1-carboxamide;
[3-[(4-fluorophenoxy)methyl]-1-piperidyl]-[4-(3H-pyrrolo[3,2-f][1,7]naphthyridin-9-yl)piperazin-1-yl]methanone;
[3-[(4-chlorophenoxy)methyl]-1-piperidyl]-[4-(3H-pyrrolo[3,2-f][1,7]naphthyridin-9-yl)piperazin-1-yl]methanone;
4-[[1-[4-(3H-pyrrolo[3,2-f][1,7]naphthyridin-9-yl)piperazine-1-carbonyl]-3-piperidyl]methoxy]benzonitrile;
4-[[1-[4-(3H-pyrrolo[3,2-f][1,7]naphthyridin-9-yl)piperazine-1-carbonyl]-3-piperidyl]methoxy]benzoic acid;
4-[[1-[4-(3H-pyrrolo[3,2-f][1,7]naphthyridin-9-yl)piperazine-1-carbonyl]-3-piperidyl]methoxy]benzamide;
[3-[(2,4-difluorophenoxy)methyl]-1-piperidyl]-[4-(3H-pyrrolo[3,2-f][1,7]naphthyridin-9-yl)piperazin-1-yl]methanone;
[3-[(4-methoxyphenoxy)methyl]-1-piperidyl]-[4-(3H-pyrrolo[3,2-f][1,7]naphthyridin-9-yl)piperazin-1-yl]methanone;
[4-(3H-pyrrolo[3,2-f][1,7]naphthyridin-9-yl)-1-piperidyl]-[3-[[4-(trifluoromethoxy)phenoxy]methyl]-1-piperidyl]methanone;
[4-(3H-pyrrolo[3,2-f][1,7]naphthyridin-9-yl)piperazin-1-yl]-[3-[[4-(trifluoromethyl) phenoxy]methyl]-1-piperidyl]methanone;
(3-methyl-1-piperidyl)-[4-(3H-pyrrolo[3,2-f][1,7]naphthyridin-9-yl)piperazin-1-yl]methanone;
[4-(3H-pyrrolo[3,2-f][1,7]naphthyridin-9-yl)piperazin-1-yl]-[3-(trifluoromethyl)-1-piperidyl]methanone;
[3-(pyrrolidin-1-ylmethyl)-1-piperidyl]-[4-(3H-pyrrolo[3,2-f][1,7]naphthyridin-9-yl)-1-piperidyl]methanone;
[3-(methoxymethyl)pyrrolidin-1-yl]-[4-(3H-pyrrolo[3,2-f][1,7]naphthyridin-9-yl)-1-piperidyl]methanone;
(3-hydroxy-3-methyl-pyrrolidin-1-yl)-[4-(3H-pyrrolo[3,2-f][1,7]naphthyridin-9-yl)-1-piperidyl]methanone
(3-methoxy-1-piperidyl)-[4-(3H-pyrrolo[3,2-f][1,7]naphthyridin-9-yl)-1-piperidyl]methanone;
[1-[4-(3H-pyrrolo[3,2-f][1,7]naphthyridin-9-yl)piperidine-1-carbonyl]-3-piperidyl]methane sulfonamide;
(3-isobutoxy-1-piperidyl)-[4-(3H-pyrrolo[3,2-f][1,7]naphthyridin-9-yl)-1-piperidyl]methanone;
[3-(2-methoxyethoxy)-1-piperidyl]-[4-(3H-pyrrolo[3,2-f][1,7]naphthyridin-9-yl)-1-piperidyl]methanone;
N-(cyclopropylmethyl)-4-(3H-pyrrolo[3,2-f][1,7]naphthyridin-9-yl)piperidine-1-carboxamide;
N-cyclobutyl-4-(3H-pyrrolo[3,2-f][1,7]naphthyridin-9-yl)piperidine-1-carboxamide;
[3-[(4-fluorophenoxy)methyl]-1-piperidyl]-[4-(3H-pyrrolo[3,2-f][1,7]naphthyridin-9-yl)-1-piperidyl]methanone;
[3-[(4-chlorophenoxy)methyl]-1-piperidyl]-[4-(3H-pyrrolo[3,2-f][1,7]naphthyridin-9-yl)-1-piperidyl]methanone;
4-[[1-[4-(3H-pyrrolo[3,2-f][1,7]naphthyridin-9-yl)piperidine-1-carbonyl]-3-piperidyl]methoxy]benzonitrile;
4-[[1-[4-(3H-pyrrolo[3,2-f][1,7]naphthyridin-9-yl)piperidine-1-carbonyl]-3-piperidyl]methoxy]benzoic acid;
4-[[1-[4-(3H-pyrrolo[3,2-f][1,7]naphthyridin-9-yl)piperidine-1-carbonyl]-3-piperidyl]methoxy]benzamide;
[3-[(2,4-difluorophenoxy)methyl]-1-piperidyl]-[4-(3H-pyrrolo[3,2-f][1,7]naphthyridin-9-yl)-1-piperidyl]methanone;
[3-[(4-methoxyphenoxy)methyl]-1-piperidyl]-[4-(3H-pyrrolo[3,2-f][1,7]naphthyridin-9-yl)-1-piperidyl]methanone;
[4-(3H-pyrrolo[3,2-f][1,7]naphthyridin-9-yl)-1-piperidyl]-[3-[[4-(trifluoromethoxy)phenoxy]methyl]-1-piperidyl]methanone;
[4-(3H-pyrrolo[3,2-f][1,7]naphthyridin-9-yl)-1-piperidyl]-[[3-[4-(trifluoromethyl)phenoxy]methyl]-1-piperidyl]methanone;
(3-methyl-1-piperidyl)-[4-(3H-pyrrolo[3,2-f][1,7]naphthyridin-9-yl)-1-piperidyl]methanone;
[4-(3H-pyrrolo[3,2-f][1,7]naphthyridin-9-yl)-1-piperidyl]-[3-(trifluoromethyl)-1-piperidyl]methanone;
3-(pyrrolidin-1-ylmethyl)-N-[4-(3H-pyrrolo[3,2-f][1,7]naphthyridin-9-yl)cyclohexyl]piperidine-1-carboxamide;
3-(methoxymethyl)-N-[4-(3H-pyrrolo[3,2-f][1,7]naphthyridin-9-yl)cyclohexyl]pyrrolidine-1-carboxamide;
3-hydroxy-3-methyl-N-[4-(3H-pyrrolo[3,2-f][1,7]naphthyridin-9-yl)cyclohexyl]pyrrolidine-1-carboxamide;
3-methoxy-N-[4-(3H-pyrrolo[3,2-f][1,7]naphthyridin-9-yl)cyclohexyl]piperidine-1-carboxamide;
N-[4-(3H-pyrrolo[3,2-f][1,7]naphthyridin-9-yl)cyclohexyl]-3-(sulfamoylmethyl)piperidine-1-carboxamide;
3-isobutoxy-N-[4-(3H-pyrrolo[3,2-f][1,7]naphthyridin-9-yl)cyclohexyl]piperidine-1-carboxamide;

3-(2-methoxyethoxy)-N-[4-(3H-pyrrolo[3,2-f][1,7]naphthyridin-9-yl)cyclohexyl]piperidine-1-carboxamide;
1-(cyclopropylmethyl)-3-[4(3H-pyrrolo[3,2-f][1,7]naphthyridin-9-yl)cyclohexyl]urea;
1-cyclobutyl-3-[4-(3H-pyrrolo[3,2-f][1,7]naphthyridin-9-yl)cyclohexyl]urea;
3-[(4-fluorophenoxy)methyl]-N-[4(3H-pyrrolo[3,2-f][1,7]naphthyridin-9-yl)cyclohexyl]piperidine-1-carboxamide;
3-[(4-chlorophenoxy)methyl]-N-[4(3H-pyrrolo[3,2-f][1,7]naphthyridin-9-yl)cyclohexyl]piperidine-1-carboxamide;
3-[(4-cyanophenoxy)methyl]-N-[4-(3H-pyrrolo[3,2-f][1,7]naphthyridin-9-yl)cyclohexyl]piperidine-1-carboxamide;
4-[[1-[[4-(3H-pyrrolo[3,2-f][1,7]naphthyridin-9-yl)cyclohexyl]carbamoyl]-3-piperidyl]methoxy]benzoic acid;
3-[(4-carbamoylphenoxy)methyl]-N-[4(3H-pyrrolo[3,2-f][1,7]naphthyridin-9-yl)cyclohexyl]piperidine-1-carboxamide;
3-[(2,4-difluorophenoxy)methyl]-N-[4-(3H-pyrrolo[3,2-f][1,7]naphthyridin-9-yl)cyclohexyl]piperidine-1-carboxamide;
3-[(4-methoxyphenoxy)methyl]-N-[4(3H-pyrrolo[3,2-f][1,7]naphthyridin-9-yl)cyclohexyl]piperidine-1-carboxamide;
N-[4-(3H-pyrrolo[3,2-f][1,7]naphthyridin-9-yl)cyclohexyl]-3-[[4-(trifluoromethoxy)phenoxy]methyl]piperidine-1-carboxamide;
N-[4-(3H-pyrrolo[3,2-f][1,7]naphthyridin-9-yl)cyclohexyl]-3-[[4-(trifluoromethyl)phenoxy]methyl]piperidine-1-carboxamide;
3-methyl-N-[4-(3H-pyrrolo[3,2-f][1,7]naphthyridin-9-yl)cyclohexyl]piperidine-1-carboxamide;
N-[4-(3H-pyrrolo[3,2-f][1,7]naphthyridin-9-yl)cyclohexyl]-3-(trifluoromethyl)piperidine-1-carboxamide;
9-[4-[[3-(pyrrolidin-1-ylmethyl)-1-piperidyl]methylsulfonyl]cyclohexyl]-3H-pyrrolo[3,2-f][1,7]naphthyridine;
9-[4-[[3-(methoxymethyl) pyrrolidin-1-yl]methylsulfonyl]cyclohexyl]-3H-pyrrolo[3,2-f][1,7]naphthyridine;
3-methyl-1-[[4-(3H-pyrrolo[3,2-f][1,7]naphthyridin-9-yl)cyclohexyl]sulfonylmethyl]pyrrolidin-3-ol;
9-[4-[(3-methoxy-1-piperidyl)methylsulfonyl]cyclohexyl]-3H-pyrrolo[3,2-f][1,7]naphthyridine;
[1-[[4-(3H-pyrrolo[3,2-f][1,7]naphthyridin-9-yl)cyclohexyl]sulfonylmethyl]-3-piperidyl]methanesulfonamide;
9-[4-[(3-isobutoxy-1-piperidyl)methylsulfonyl]cyclohexyl]-3H-pyrrolo[3,2-f][1,7]naphthyridine;
9-[4-[[3-(2-methoxyethoxy)-1-piperidyl]methylsulfonyl]cyclohexyl]-3H-pyrrolo[3,2-f][1,7]naphthyridine;
1-cyclopropyl-N-[[4-(3H-pyrrolo[3,2-f][1,7]naphthyridin-9-yl)cyclohexyl]sulfonylmethyl]methanamine;
N-[[4-(3H-pyrrolo[3,2-f][1,7]naphthyridin-9-yl)cyclohexyl]sulfonylmethyl]cyclobutanamine;
9-[4-[[3-[(4-fluorophenoxy)methyl]-1-piperidyl]methylsulfonyl]cyclohexyl]-3H-pyrrolo[3,2-f][1,7]naphthyridine;
9-[4-[[3-[(4-chlorophenoxy)methyl]-1-piperidyl]methylsulfonyl]cyclohexyl]-3H-pyrrolo[3,2-f][1,7]naphthyridine;
4-[[3-[[4-(3H-pyrrolo[3,2-f][1,7]naphthyridin-9-yl)cyclohexyl]sulfonylmethyl]cyclohexyl]methoxy]benzonitrile;
4-[[3-[[4-(3H-pyrrolo[3,2-f][1,7]naphthyridin-9-yl)cyclohexyl]sulfonylmethyl]cyclohexyl]methoxy]benzoic acid;
4-[[3-[[4-(3H-pyrrolo[3,2-f][1,7]naphthyridin-9-yl)cyclohexyl]sulfonylmethyl]cyclohexyl]methoxy]benzamide;
9-[4-[[3-[(2,4-difluorophenoxy)methyl]-1-piperidyl]methylsulfonyl]cyclohexyl]-3H-pyrrolo[3,2-f][1,7]naphthyridine;
9-[4-[[3-[(4-methoxyphenoxy)methyl]-1-piperidyl]methylsulfonyl]cyclohexyl]-3H-pyrrolo[3,2-f][1,7]naphthyridine;
9-[4-[[3-[[4-(trifluoromethoxy)phenoxy]methyl]-1-piperidyl]methylsulfonyl]cyclohexyl]-3H-pyrrolo[3,2-f][1,7]naphthyridine;
9-[4-[[3-[[4-(trifluoromethyl)phenoxy]methyl]-1-piperidyl]methylsulfonyl]cyclohexyl]-3H-pyrrolo[3,2-f][1,7]naphthyridine;
9-[4-[[(3-methyl-1-piperidyl)methylsulfonyl]cyclohexyl]-3H-pyrrolo[3,2-f][1,7]naphthyridine;
9-[4-[[3-(trifluoromethyl)-1-piperidyl]methylsulfonyl]cyclohexyl]-3H-pyrrolo[3,2-f][1,7]naphthyridine;
2-[3-(pyrrolidin-1-ylmethyl)-1-piperidyl]-1-[4-(3H-pyrrolo[3,2-f][1,7]naphthyridin-9-yl)cyclohexyl]ethanone;
2-[3-(methoxymethyl)pyrrolidin-1-yl]-1-[4-(3H-pyrrolo[3,2-f][1,7]naphthyridin-9-yl)cyclohexyl]ethanone;
2-(3-hydroxy-3-methyl-pyrrolidin-1-yl)-1-[4-(3H-pyrrolo[3,2-f][1,7]naphthyridin-9-yl)cyclohexyl]ethanone;
2-(3-methoxy-1-piperidyl)-1-[4-(3H-pyrrolo[3,2-f][1,7]naphthyridin-9-yl)cyclohexyl]ethanone;
[1-[2-oxo-2-[4-(3H-pyrrolo[3,2-f][1,7]naphthyridin-9-yl)cyclohexyl]ethyl]-3-piperidyl]methane sulfonamide;
2-(3-isobutoxy-1-piperidyl)-1-[4-(3H-pyrrolo[3,2-f][1,7]naphthyridin-9-yl)cyclohexyl]ethanone;
2-[3-(2-methoxyethoxy)-1-piperidyl]-1-[4-(3H-pyrrolo[3,2-f][1,7]naphthyridin-9-yl)cyclohexyl]ethanone;
2-(cyclopropylmethylamino)-1-[4-(3H-pyrrolo[3,2-f][1,7]naphthyridin-9-yl)cyclohexyl]ethanone;
2-(cyclobutylamino)-1-[4-(3H-pyrrolo[3,2-f][1,7]naphthyridin-9-yl)cyclohexyl]ethanone;
2-[3-[(4-fluorophenoxy)methyl]-1-piperidyl]-1-[4-(3H-pyrrolo[3,2-f][1,7]naphthyridin-9-yl)cyclohexyl]ethanone;
2-[3-[(4-chlorophenoxy)methyl]-1-piperidyl]-1-[4-(3H-pyrrolo[3,2-f][1,7]naphthyridin-9-yl)cyclohexyl]ethanone;
4-[[3-[2-oxo-2-[4-(3H-pyrrolo[3,2-f][1,7]naphthyridin-9-yl)cyclohexyl]ethyl]cyclohexyl]methoxy]benzonitrile;
4-[[3-[2-oxo-2-[4-(3H-pyrrolo[3,2-f][1,7]naphthyridin-9-yl)cyclohexyl]ethyl]cyclohexyl]methoxy]benzoic acid;
4-[[3-[2-oxo-2-[4-(3H-pyrrolo[3,2-f][1,7]naphthyridin-9-yl)cyclohexyl]ethyl]cyclohexyl]methoxy]benzamide;
2-[3-[(2,4-difluorophenoxy)methyl]-1-piperidyl]-1-[4-(3H-pyrrolo[3,2-f][1,7]naphthyridin-9-yl)cyclohexyl]ethanone;
2-[3-[(4-methoxyphenoxy)methyl]-1-piperidyl]-1-[4-(3H-pyrrolo[3,2-f][1,7]naphthyridin-9-yl)cyclohexyl]ethanone;
1-[4-(3H-pyrrolo[3,2-f][1,7]naphthyridin-9-yl)cyclohexyl]-2-[3-[[4-(trifluoromethoxy)phenoxy]methyl]-1-piperidyl]ethanone;
1-[4-(3H-pyrrolo[3,2-f][1,7]naphthyridin-9-yl)cyclohexyl]-2-[3-[[4-(trifluoromethyl)phenoxy]methyl]-1-piperidyl]ethanone;
2-(3-methyl-1-piperidyl)-1-[4-(3H-pyrrolo[3,2-f][1,7]naphthyridin-9-yl)cyclohexyl]ethanone;
1-[4-(3H-pyrrolo[3,2-f][1,7]naphthyridin-9-yl)cyclohexyl]-2-[3-(trifluoromethyl)-1-piperidyl]ethanone;
9-{4-[3-(4-Fluoro-phenoxymethyl)-piperidine-1-sulfonylmethyl]-cyclohexyl}-3H-3,4,6,7-tetraaza-cyclopenta[a]naphthalene;
9-{4-[3-(4-Chloro-phenoxymethyl)-piperidine-1-sulfonylmethyl]-cyclohexyl}-3H-3,4,6,7-tetraaza-cyclopenta[a]naphthalene;

4-{1-[4-(3H-3,4,6,7-Tetraaza-cyclopenta[a]naphthalen-9-yl)-cyclohexylmethanesulfonyl]-piperidin-3-ylmethoxy}-benzonitrile;
4-{1-[4-(3H-3,4,6,7-Tetraaza-cyclopenta[a]naphthalen-9-yl)-cyclohexylmethanesulfonyl]-piperidin-3-ylmethoxy}-benzoic acid;
4-{1-[4-(3H-3,4,6,7-Tetraaza-cyclopenta[a]naphthalen-9-yl)-cyclohexylmethanesulfonyl]-piperidin-3-ylmethoxy}-benzamide;
9-[4-(3-Pyrrolidin-1-ylmethyl-piperidine-1-sulfonylmethyl)-cyclohexyl]-3H-3,4,6,7-tetraaza-cyclopenta[a]naphthalene;
9-[4-(3-Methoxymethyl-pyrrolidine-1-sulfonylmethyl)-cyclohexyl]-3H-3,4,6,7-tetraaza-cyclopenta[a]naphthalene;
3-Methyl-1-[4-(3H-3,4,6,7-tetraaza-cyclopenta[a]naphthalen-9-yl)-cyclohexylmethanesulfonyl]-pyrrolidin-3-ol;
9-[4-(3-Methoxy-piperidine-1-sulfonylmethyl)-cyclohexyl]-3H-3,4,6,7-tetraaza-cyclopenta[a]naphthalene;
{1-[4-(3H-3,4,6,7-Tetraaza-cyclopenta[a]naphthalen-9-yl)-cyclohexylmethanesulfonyl]-piperidin-3-yl}-methanesulfonamide;
9-[4-(3-Isobutoxy-piperidine-1-sulfonylmethyl)-cyclohexyl]-3H-3,4,6,7-tetraaza-cyclopenta[a]naphthalene;
9-{4-[3-(2-Methoxy-ethoxy)-piperidine-1-sulfonylmethyl]-cyclohexyl}-3H-3,4,6,7-tetraaza-cyclopenta[a]naphthalene;
N-Cyclopropylmethyl-C-[4-(3H-3,4,6,7-tetraaza-cyclopenta[a]naphthalen-9-yl)-cyclohexyl]-methanesulfonamide;
N-Cyclobutyl-C-[4-(3H-3,4,6,7-tetraaza-cyclopenta[a]naphthalen-9-yl)-cyclohexyl]-methanesulfonamide
9-{4-[3-(2,4-Difluoro-phenoxymethyl)-piperidine-1-sulfonylmethyl]-cyclohexyl}-3H-3,4,6,7-tetraaza-cyclopenta[a]naphthalene;
9-{4-[3-(4-Methoxy-phenoxymethyl)-piperidine-1-sulfonylmethyl]-cyclohexyl}-3H-3,4,6,7-tetraaza-cyclopenta[a]naphthalene;
9-{4-[3-(4-Trifluoromethoxy-phenoxymethyl)-piperidine-1-sulfonylmethyl]-cyclohexyl}-3H-3,4,6,7-tetraaza-cyclopenta[a]naphthalene;
9-{4-[3-(4-Trifluoromethyl-phenoxymethyl)-piperidine-1-sulfonylmethyl]-cyclohexyl}-3H-3,4,6,7-tetraaza-cyclopenta[a]naphthalene;
9-[4-(3-Methyl-piperidine-1-sulfonylmethyl)-cyclohexyl]-3H-3,4,6,7-tetraaza-cyclopenta[a]naphthalene;
9-[4-(3-Trifluoromethyl-piperidine-1-sulfonylmethyl)-cyclohexyl]-3H-3,4,6,7-tetraaza-cyclopenta[a]naphthalene;
9-{4-[3-(4-Fluoro-phenoxymethyl)-piperidine-1-sulfonylmethyl]-cyclohexyl}-3H-3,4,6,8-tetraaza-cyclopenta[a]naphthalene;
9-{4-[3-(4-Chloro-phenoxymethyl)-piperidine-1-sulfonylmethyl]-cyclohexyl}-3H-3,4,6,8-tetraaza-cyclopenta[a]naphthalene;
4-{1-[4-(3H-3,4,6,8-Tetraaza-cyclopenta[a]naphthalen-9-yl)-cyclohexylmethanesulfonyl]-piperidin-3-ylmethoxy}-benzonitrile;
4-{1-[4-(3H-3,4,6,8-Tetraaza-cyclopenta[a]naphthalen-9-yl)-cyclohexylmethanesulfonyl]-piperidin-3-ylmethoxy}-benzoic acid;
4-{1-[4-(3H-3,4,6,8-Tetraaza-cyclopenta[a]naphthalen-9-yl)-cyclohexylmethanesulfonyl]-piperidin-3-ylmethoxy}-benzamide;
9-[4-(3-Pyrrolidin-1-ylmethyl-piperidine-1-sulfonylmethyl)-cyclohexyl]-3H-3,4,6,8-tetraaza-cyclopenta[a]naphthalene;
9-[4-(3-Methoxymethyl-pyrrolidine-1-sulfonylmethyl)-cyclohexyl]-3H-3,4,6,8-tetraaza-cyclopenta[a]naphthalene;
3-Methyl-1-[4-(3H-3,4,6,8-tetraaza-cyclopenta[a]naphthalen-9-yl)-cyclohexylmethanesulfonyl]-pyrrolidin-3-ol;
9-[4-(3-Methoxy-piperidine-1-sulfonylmethyl)-cyclohexyl]-3H-3,4,6,8-tetraaza-cyclopenta[a]naphthalene;
{1-[4-(3H-3,4,6,8-Tetraaza-cyclopenta[a]naphthalen-9-yl)-cyclohexylmethanesulfonyl]-piperidin-3-yl}-methanesulfonamide;
9-[4-(3-Isobutoxy-piperidine-1-sulfonylmethyl)-cyclohexyl]-3H-3,4,6,8-tetraaza-cyclopenta[a]naphthalene;
9-{4-[3-(2-Methoxy-ethoxy)-piperidine-1-sulfonylmethyl]-cyclohexyl}-3H-3,4,6,8-tetraaza-cyclopenta[a]naphthalene;
N-Cyclopropylmethyl-C-[4-(3H-3,4,6,8-tetraaza-cyclopenta[a]naphthalen-9-yl)-cyclohexyl]-methanesulfonamide;
N-Cyclobutyl-C-[4-(3H-3,4,6,8-tetraaza-cyclopenta[a]naphthalen-9-yl)-cyclohexyl]-methanesulfonamide;
9-{4-[3-(2,4-Difluoro-phenoxymethyl)-piperidine-1-sulfonylmethyl]-cyclohexyl}-3H-3,4,6,8-tetraaza-cyclopenta[a]naphthalene;
9-{4-[3-(4-Methoxy-phenoxymethyl)-piperidine-1-sulfonylmethyl]-cyclohexyl}-3H-3,4,6,8-tetraaza-cyclopenta[a]naphthalene;
9-{4-[3-(4-Trifluoromethoxy-phenoxymethyl)-piperidine-1-sulfonylmethyl]-cyclohexyl}-3H-3,4,6,8-tetraaza-cyclopenta[a]naphthalene;
9-{4-[3-(4-Trifluoromethyl-phenoxymethyl)-piperidine-1-sulfonylmethyl]-cyclohexyl}-3H-3,4,6,8-tetraaza-cyclopenta[a]naphthalene;
9-[4-(3-Methyl-piperidine-1-sulfonylmethyl)-cyclohexyl]-3H-3,4,6,8-tetraaza-cyclopenta[a]naphthalene;
9-[4-(3-Trifluoromethyl-piperidine-1-sulfonylmethyl)-cyclohexyl]-3H-3,4,6,8-tetraaza-cyclopenta[a]naphthalene;
9-{4-[3-(4-Fluoro-phenoxymethyl)-piperidine-1-sulfonylmethyl]-cyclohexyl}-7-methyl-3H-3,4,6,8-tetraaza-cyclopenta[a]naphthalene;
9-{4-[3-(4-Chloro-phenoxymethyl)-piperidine-1-sulfonylmethyl]-cyclohexyl}-7-methyl-3H-3,4,6,8-tetraaza-cyclopenta[a]naphthalene;
4-{1-[4-(7-Methyl-3H-3,4,6,8-tetraaza-cyclopenta[a]naphthalen-9-yl)-cyclohexylmethanesulfonyl]-piperidin-3-ylmethoxy}-benzonitrile;
4-{1-[4-(7-Methyl-3H-3,4,6,8-tetraaza-cyclopenta[a]naphthalen-9-yl)-cyclohexylmethanesulfonyl]-piperidin-3-ylmethoxy}-benzoic acid;
4-{1-[4-(7-Methyl-3H-3,4,6,8-tetraaza-cyclopenta[a]naphthalen-9-yl)-cyclohexylmethanesulfonyl]-piperidin-3-ylmethoxy}-benzamide;
7-Methyl-9-[4-(3-pyrrolidin-1-ylmethyl-piperidine-1-sulfonylmethyl)-cyclohexyl]-3H-3,4,6,8-tetraaza-cyclopenta[a]naphthalene;
9-[4-(3-Methoxymethyl-pyrrolidine-1-sulfonylmethyl)-cyclohexyl]-7-methyl-3H-3,4,6,8-tetraaza-cyclopenta[a]naphthalene;
3-Methyl-1-[4-(7-methyl-3H-3,4,6,8-tetraaza-cyclopenta[a]naphthalen-9-yl)-cyclohexylmethanesulfonyl]-pyrrolidin-3-ol;
9-[4-(3-Methoxy-piperidine-1-sulfonylmethyl)-cyclohexyl]-7-methyl-3H-3,4,6,8-tetraaza-cyclopenta[a]naphthalene;
{1-[4-(7-Methyl-3H-3,4,6,8-tetraaza-cyclopenta[a]naphthalen-9-yl)-cyclohexylmethanesulfonyl]-piperidin-3-yl}-methanesulfonamide;
9-[4-(3-Isobutoxy-piperidine-1-sulfonylmethyl)-cyclohexyl]-7-methyl-3H-3,4,6,8-tetraaza-cyclopenta[a]naphthalene;
9-{4-[3-(2-Methoxy-ethoxy)-piperidine-1-sulfonylmethyl]-cyclohexyl}-7-methyl-3H-3,4,6,8-tetraaza-cyclopenta[a]naphthalene;

N-Cyclopropylmethyl-C-[4-(7-methyl-3H-3,4,6,8-tetraaza-cyclopenta[a]naphthalen-9-yl)-cyclohexyl]-methanesulfonamide;
N-Cyclobutyl-C-[4-(7-methyl-3H-3,4,6,8-tetraaza-cyclopenta[a]naphthalen-9-yl)-cyclohexyl]-methanesulfonamide;
9-{4-[3-(2,4-Difluoro-phenoxymethyl)-piperidine-1-sulfonylmethyl]-cyclohexyl}-7-methyl-3H-3,4,6,8-tetraaza-cyclopenta[a]naphthalene;
9-{4-[3-(4-Methoxy-phenoxymethyl)-piperidine-1-sulfonylmethyl]-cyclohexyl}-7-methyl-3H-3,4,6,8-tetraaza-cyclopenta[a]naphthalene;
7-Methyl-9-{4-[3-(4-trifluoromethoxy-phenoxymethyl)-piperidine-1-sulfonylmethyl]-cyclohexyl}-3H-3,4,6,8-tetraaza-cyclopenta[a]naphthalene;
7-Methyl-9-{4-[3-(4-trifluoromethyl-phenoxymethyl)-piperidine-1-sulfonylmethyl]-cyclohexyl}-3H-3,4,6,8-tetraaza-cyclopenta[a]naphthalene;
7-Methyl-9-[4-(3-methyl-piperidine-1-sulfonylmethyl)-cyclohexyl]-3H-3,4,6,8-tetraaza-cyclopenta[a]naphthalene;
7-Methyl-9-[4-(3-trifluoromethyl-piperidine-1-sulfonylmethyl)-cyclohexyl]-3H-3,4,6,8-tetraaza-cyclopenta[a]naphthalene;
9-{4-[3-(4-Fluoro-phenoxymethyl)-piperidine-1-sulfonylmethyl]-cyclohexyl}-3H-3,4,7,8-tetraaza-cyclopenta[a]naphthalene;
9-{4-[3-(4-Chloro-phenoxymethyl)-piperidine-1-sulfonylmethyl]-cyclohexyl}-3H-3,4,7,8-tetraaza-cyclopenta[a]naphthalene;
4-{1-[4-(3H-3,4,7,8-Tetraaza-cyclopenta[a]naphthalen-9-yl)-cyclohexylmethanesulfonyl]-piperidin-3-ylmethoxy}-benzonitrile;
4-{1-[4-(3H-3,4,7,8-Tetraaza-cyclopenta[a]naphthalen-9-yl)-cyclohexylmethanesulfonyl]-piperidin-3-ylmethoxy}-benzoic acid;
4-{1-[4-(3H-3,4,7,8-Tetraaza-cyclopenta[a]naphthalen-9-yl)-cyclohexylmethanesulfonyl]-piperidin-3-ylmethoxy}-benzamide;
9-[4-(3-Pyrrolidin-1-ylmethyl-piperidine-1-sulfonylmethyl)-cyclohexyl]-3H-3,4,7,8-tetraaza-cyclopenta[a]naphthalene;
9-[4-(3-Methoxymethyl-pyrrolidine-1-sulfonylmethyl)-cyclohexyl]-3H-3,4,7,8-tetraaza-cyclopenta[a]naphthalene;
3-Methyl-1-[4-(3H-3,4,7,8-tetraaza-cyclopenta[a]naphthalen-9-yl)-cyclohexylmethanesulfonyl]-pyrrolidin-3-ol;
9-[4-(3-Methoxy-piperidine-1-sulfonylmethyl)-cyclohexyl]-3H-3,4,7,8-tetraaza-cyclopenta[a]naphthalene;
{1-[4-(3H-3,4,7,8-Tetraaza-cyclopenta[a]naphthalen-9-yl)-cyclohexylmethanesulfonyl]-piperidin-3-yl}-methanesulfonamide;
9-[4-(3-Isobutoxy-piperidine-1-sulfonylmethyl)-cyclohexyl]-3H-3,4,7,8-tetraaza-cyclopenta[a]naphthalene;
9-{4-[3-(2-Methoxy-ethoxy)-piperidine-1-sulfonylmethyl]-cyclohexyl}-3H-3,4,7,8-tetraaza-cyclopenta[a]naphthalene;
N-Cyclopropylmethyl-C-[4-(3H-3,4,7,8-tetraaza-cyclopenta[a]naphthalen-9-yl)-cyclohexyl]-methanesulfonamide;
N-Cyclobutyl-C-[4-(3H-3,4,7,8-tetraaza-cyclopenta[a]naphthalen-9-yl)-cyclohexyl]-methanesulfonamide;
9-{4-[3-(2,4-Difluoro-phenoxymethyl)-piperidine-1-sulfonylmethyl]-cyclohexyl}-3H-3,4,7,8-tetraaza-cyclopenta[a]naphthalene;
9-{4-[3-(4-Methoxy-phenoxymethyl)-piperidine-1-sulfonylmethyl]-cyclohexyl}-3H-3,4,7,8-tetraaza-cyclopenta[a]naphthalene;
9-{4-[3-(4-Trifluoromethoxy-phenoxymethyl)-piperidine-1-sulfonylmethyl]-cyclohexyl}-3H-3,4,7,8-tetraaza-cyclopenta[a]naphthalene;
9-{4-[3-(4-Trifluoromethyl-phenoxymethyl)-piperidine-1-sulfonylmethyl]-cyclohexyl}-3H-3,4,7,8-tetraaza-cyclopenta[a]naphthalene;
9-[4-(3-Methyl-piperidine-1-sulfonylmethyl)-cyclohexyl]-3H-3,4,7,8-tetraaza-cyclopenta[a]naphthalene;
9-[4-(3-Trifluoromethyl-piperidine-1-sulfonylmethyl)-cyclohexyl]-3H-3,4,7,8-tetraaza-cyclopenta[a]naphthalene;
9-[4-[[3-[(4-fluorophenoxy)methyl]-1-piperidyl]sulfonylmethyl]cyclohexyl]-3H-pyrrolo[2,3c][2,7]naphthyridine;
9-[4-[[3-[(4-chlorophenoxy)methyl]-1-piperidyl]sulfonylmethyl]cyclohexyl]-3H-pyrrolo[2,3c][2,7]naphthyridine;
4-[[1-[[4-(3H-pyrrolo[2,3-c][2,7]naphthyridin-9-yl)cyclohexyl]methylsulfonyl]-3-piperidyl]methoxy]benzonitrile;
4-[[1-[[4-(3H-pyrrolo[2,3-c][2,7]naphthyridin-9-yl)cyclohexyl]methylsulfonyl]-3-piperidyl]methoxy]benzoic acid;
4-[[1-[[4-(3H-pyrrolo[2,3-c][2,7]naphthyridin-9-yl)cyclohexyl]methylsulfonyl]-3-piperidyl]methoxy]benzamide;
9-[4-[[3-(pyrrolidin-1-ylmethyl)-1-piperidyl]sulfonylmethyl]cyclohexyl]-3H-pyrrolo[2,3-c][2,7]naphthyridine;
9-[4-[[3-(methoxymethyl)pyrrolidin-1-yl]sulfonylmethyl]cyclohexyl]-3H-pyrrolo[2,3-c][2,7]naphthyridine;
3-methyl-1-[[4-(3H-pyrrolo[2,3-c][2,7]naphthyridin-9-yl)cyclohexyl]methylsulfonyl]pyrrolidin-3-ol;
9-[4-[(3-methoxy-1-piperidyl)sulfonylmethyl]cyclohexyl]-3H-pyrrolo[2,3-c][2,7]naphthyridine;
[1-[[4-(3H-pyrrolo[2,3-c][2,7]naphthyridin-9-yl)cyclohexyl]methylsulfonyl]-3-piperidyl]methanesulfonamide;
9-[4-[(3-isobutoxy-1-piperidyl)sulfonylmethyl]cyclohexyl]-3H-pyrrolo[2,3-c][2,7]naphthyridine;
9-[4-[[3-(2-methoxyethoxy)-1-piperidyl]sulfonylmethyl]cyclohexyl]-3H-pyrrolo[2,3-c][2,7]naphthyridine;
N-(cyclopropylmethyl)-1-[4-(3H-pyrrolo[2,3-c][2,7]naphthyridin-9-yl)cyclohexyl]methanesulfonamide;
N-cyclobutyl-1-[4-(3H-pyrrolo[2,3-c][2,7]naphthyridin-9-yl)cyclohexyl]methanesulfonamide;
9-[4-[[3-[(2,4-difluorophenoxy)methyl]-1-piperidyl]sulfonylmethyl]cyclohexyl]-3H-pyrrolo[2,3-c][2,7]naphthyridine;
9-[4-[[3-[(4-methoxyphenoxy)methyl]-1-piperidyl]sulfonylmethyl]cyclohexyl]-3H-pyrrolo[2,3-c][2,7]naphthyridine;
9-[4-[[3-[[4-(trifluoromethoxy)phenoxy]methyl]-1-piperidyl]sulfonylmethyl]cyclohexyl]-3H-pyrrolo[2,3-c][2,7]naphthyridine;
9-[4-[[3-[[4-(trifluoromethyl)phenoxy]methyl]-1-piperidyl]sulfonylmethyl]cyclohexyl]-3H-pyrrolo[2,3-c][2,7]naphthyridine;
9-[4-[(3-methyl-1-piperidyl)sulfonylmethyl]cyclohexyl]-3H-pyrrolo[2,3-c][2,7]naphthyridine;
9-[4-[[3-(trifluoromethyl)-1-piperidyl]sulfonylmethyl]cyclohexyl]-3H-pyrrolo[2,3-c][2,7]naphthyridine;
1-[4-[[3-[(4-fluorophenoxy)methyl]-1-piperidyl]sulfonylmethyl]cyclohexyl]-7H-pyrrolo[2,3-c][2,6]naphthyridine;
1-[4-[[3-[(4-chlorophenoxy)methyl]-1-piperidyl]sulfonylmethyl]cyclohexyl]-7H-pyrrolo[2,3-c][2,6]naphthyridine;
4-[[1-[[4-(7H-pyrrolo[2,3-h][2,6]naphthyridin-1-yl)cyclohexyl]methylsulfonyl]-3-piperidyl]methoxy]benzonitrile;
4-[[1-[[4-(7H-pyrrolo[2,3-h][2,6]naphthyridin-1-yl)cyclohexyl]methylsulfonyl]-3-piperidyl]methoxy]benzoic acid;

4-[[1-[[4-(7H-pyrrolo[2,3-h][2,6]naphthyridin-1-yl)cyclohexyl]methylsulfonyl]-3-piperidyl]methoxy]benzamide;
1-[4-[[3-(pyrrolidin-1-ylmethyl)-1-piperidyl]sulfonylmethyl]cyclohexyl]-7H-pyrrolo[2,3-c][2,6]naphthyridine;
1-[4-[[3-(methoxymethyl)pyrrolidin-1-yl]sulfonylmethyl]cyclohexyl]-7H-pyrrolo[2,3-c][2,6]naphthyridine;
3-methyl-1-[[4-(7H-pyrrolo[2,3-h][2,6]naphthyridin-1-yl)cyclohexyl]methylsulfonyl]pyrrolidin-3-ol;
1-[4-[(3-methoxy-1-piperidyl)sulfonylmethyl]cyclohexyl]-7H-pyrrolo[2,3-c][2,6]naphthyridine;
[1-[[4-(7H-pyrrolo[2,3-h][2,6]naphthyridin-1-yl)cyclohexyl]methylsulfonyl]-3-piperidyl]methanesulfonamide;
1-[4-[(3-isobutoxy-1-piperidyl)sulfonylmethyl]cyclohexyl]-7H-pyrrolo[2,3-c][2,6]naphthyridine;
1-[4-[[3-(2-methoxyethoxy)-1-piperidyl]sulfonylmethyl]cyclohexyl]-7H-pyrrolo[2,3-c][2,6]naphthyridine;
N-(cyclopropylmethyl)-1-[4-(7H-pyrrolo[2,3-h][2,6]naphthyridin-1-yl)cyclohexyl]methanesulfonamide;
N-cyclobutyl-1-[4-(7H-pyrrolo[2,3-h][2,6]naphthyridin-1-yl)cyclohexyl]methanesulfonamide;
1-[4-[[3-[(2,4-difluorophenoxy)methyl]-1-piperidyl]sulfonylmethyl]cyclohexyl]-7H-pyrrolo[2,3-c][2,6]naphthyridine;
1-[4-[[3-[(4-methoxyphenoxy)methyl]-1-piperidyl]sulfonylmethyl]cyclohexyl]-7H-pyrrolo[2,3-c][2,6]naphthyridine;
1-[4-[[3-[[4-(trifluoromethoxy)phenoxy]methyl]-1-piperidyl]sulfonylmethyl]cyclohexyl]-7H-pyrrolo[2,3-c][2,6]naphthyridine;
1-[4-[[3-[[4-(trifluoromethyl)phenoxy]methyl]-1-piperidyl]sulfonylmethyl]cyclohexyl]-7H-pyrrolo[2,3-c][2,6]naphthyridine;
1-[4-[(3-methyl-1-piperidyl)sulfonylmethyl]cyclohexyl]-7H-pyrrolo[2,3-c][2,6]naphthyridine;
1-[4-[[3-(trifluoromethyl)-1-piperidyl]sulfonylmethyl]cyclohexyl]-7H-pyrrolo[2,3-c][2,6]naphthyridine;
4,4,4-Trifluoro-1-[3-(3H-3,4,6-triaza-cyclopenta[a]naphthalen-9-yl)-2,5-dihydro-pyrrol-1-yl]-butan-1-one;
Cyclopropyl-[3-(3H-3,4,6-triaza-cyclopenta[a]naphthalen-9-yl)-2,5-dihydro-pyrrol-1-yl]-methanone;
3-Oxo-3-[3-(3H-3,4,6,8-tetraaza-cyclopenta[a]naphthalen-9-yl)-2,5-dihydro-pyrrol-1-yl]-propionitrile;
3,3,3-Trifluoro-1-[3-(3H-3,4,6,8-tetraaza-cyclopenta[a]naphthalen-9-yl)-2,5-dihydro-pyrrol-1-yl]-propan-1-one;
4,4,4-Trifluoro-1-[3-(3H-3,4,6,8-tetraaza-cyclopenta[a]naphthalen-9-yl)-2,5-dihydro-pyrrol-1-yl]-butan-1-one;
Cyclopropyl-[3-(3H-3,4,6,8-tetraaza-cyclopenta[a]naphthalen-9-yl)-2,5-dihydro-pyrrol-1-yl]-methanone;
[3-(3H-3,4,6,8-Tetraaza-cyclopenta[a]naphthalen-9-yl)-2,5-dihydro-pyrrole-1-sulfonyl]-acetonitrile;
9-[1-(2,2,2-Trifluoro-ethanesulfonyl)-2,5-dihydro-1H-pyrrol-3-yl]-3H-3,4,6,8-tetraaza-cyclopenta[a]naphthalene;
9-(1-Methanesulfonyl-2,5-dihydro-1H-pyrrol-3-yl)-3H-3,4,6,8-tetraaza-cyclopenta[a]naphthalene;
3-[3-(7-Methyl-3H-3,4,6,8-tetraaza-cyclopenta[a]naphthalen-9-yl)-2,5-dihydro-pyrrol-1-yl]-3-oxo-propionitrile;
3,3,3-Trifluoro-1-[3-(7-methyl-3H-3,4,6,8-tetraaza-cyclopenta[a]naphthalen-9-yl)-2,5-dihydro-pyrrol-1-yl]-propan-1-one;
4,4,4-Trifluoro-1-[3-(7-methyl-3H-3,4,6,8-tetraaza-cyclopenta[a]naphthalen-9-yl)-2,5-dihydro-pyrrol-1-yl]-butan-1-one;
Cyclopropyl-[3-(7-methyl-3H-3,4,6,8-tetraaza-cyclopenta[a]naphthalen-9-yl)-2,5-dihydro-pyrrol-1-yl]-methanone;
[3-(7-Methyl-3H-3,4,6,8-tetraaza-cyclopenta[a]naphthalen-9-yl)-2,5-dihydro-pyrrole-1-sulfonyl]-acetonitrile;
7-Methyl-9-[1-(2,2,2-trifluoro-ethanesulfonyl)-2,5-dihydro-1H-pyrrol-3-yl]-3H-3,4,6,8-tetraaza-cyclopenta[a]naphthalene;
9-(1-Methanesulfonyl-2,5-dihydro-1H-pyrrol-3-yl)-7-methyl-3H-3,4,6,8-tetraaza-cyclopenta[a]naphthalene;
3-Oxo-3-[3-(3H-3,4,6,7-tetraaza-cyclopenta[a]naphthalen-9-yl)-2,5-dihydro-pyrrol-1-yl]-propionitrile;
3,3,3-Trifluoro-1-[3-(3H-3,4,6,7-tetraaza-cyclopenta[a]naphthalen-9-yl)-2,5-dihydro-pyrrol-1-yl]-propan-1-one;
4,4,4-Trifluoro-1-[3-(3H-3,4,6,7-tetraaza-cyclopenta[a]naphthalen-9-yl)-2,5-dihydro-pyrrol-1-yl]-butan-1-one;
Cyclopropyl-[3-(3H-3,4,6,7-tetraaza-cyclopenta[a]naphthalen-9-yl)-2,5-dihydro-pyrrol-1-yl]-methanone;
[3-(3H-3,4,6,7-Tetraaza-cyclopenta[a]naphthalen-9-yl)-2,5-dihydro-pyrrole-1-sulfonyl]-acetonitrile;
9-[1-(2,2,2-Trifluoro-ethanesulfonyl)-2,5-dihydro-1H-pyrrol-3-yl]-3H-3,4,6,7-tetraaza-cyclopenta[a]naphthalene;
9-(1-Methanesulfonyl-2,5-dihydro-1H-pyrrol-3-yl)-3H-3,4,6,7-tetraaza-cyclopenta[a]naphthalene;
3-Oxo-3-[3-(3H-3,4,7,8-tetraaza-cyclopenta[a]naphthalen-9-yl)-2,5-dihydro-pyrrol-1-yl]-propionitrile;
3,3,3-Trifluoro-1-[3-(3H-3,4,7,8-tetraaza-cyclopenta[a]naphthalen-9-yl)-2,5-dihydro-pyrrol-1-yl]-propan-1-one;
4,4,4-Trifluoro-1-[3-(3H-3,4,7,8-tetraaza-cyclopenta[a]naphthalen-9-yl)-2,5-dihydro-pyrrol-1-yl]-butan-1-one;
Cyclopropyl-[3-(3H-3,4,7,8-tetraaza-cyclopenta[a]naphthalen-9-yl)-2,5-dihydro-pyrrol-1-yl]-methanone;
[3-(3H-3,4,7,8-Tetraaza-cyclopenta[a]naphthalen-9-yl)-2,5-dihydro-pyrrole-1-sulfonyl]-acetonitrile;
9-[1-(2,2,2-Trifluoro-ethanesulfonyl)-2,5-dihydro-1H-pyrrol-3-yl]-3H-3,4,7,8-tetraaza-cyclopenta[a]naphthalene;
9-(1-Methanesulfonyl-2,5-dihydro-1H-pyrrol-3-yl)-3H-3,4,7,8-tetraaza-cyclopenta[a]naphthalene;
3-Oxo-3-[3-(3H-3,4,8-triaza-cyclopenta[a]naphthalen-9-yl)-2,5-dihydro-pyrrol-1-yl]-propionitrile;
3,3,3-Trifluoro-1-[3-(3H-3,4,8-triaza-cyclopenta[a]naphthalen-9-yl)-2,5-dihydro-pyrrol-1-yl]-propan-1-one;
4,4,4-Trifluoro-1-[3-(3H-3,4,8-triaza-cyclopenta[a]naphthalen-9-yl)-2,5-dihydro-pyrrol-1-yl]-butan-1-one;
Cyclopropyl-[3-(3H-3,4,8-triaza-cyclopenta[a]naphthalen-9-yl)-2,5-dihydro-pyrrol-1-yl]-methanone;
[3-(3H-3,4,8-Triaza-cyclopenta[a]naphthalen-9-yl)-2,5-dihydro-pyrrole-1-sulfonyl]-acetonitrile;
9-[1-(2,2,2-Trifluoro-ethanesulfonyl)-2,5-dihydro-1H-pyrrol-3-yl]-3H-3,4,8-triaza-cyclopenta[a]naphthalene;
9-(1-Methanesulfonyl-2,5-dihydro-1H-pyrrol-3-yl)-3H-3,4,8-triaza-cyclopenta[a]naphthalene;
3-Oxo-3-[3-(3H-3,4,7-triaza-cyclopenta[a]naphthalen-9-yl)-2,5-dihydro-pyrrol-1-yl]-propionitrile
3,3,3-Trifluoro-1-[3-(3H-3,4,7-triaza-cyclopenta[a]naphthalen-9-yl)-2,5-dihydro-pyrrol-1-yl]-propan-1-one;
4,4,4-Trifluoro-1-[3-(3H-3,4,7-triaza-cyclopenta[a]naphthalen-9-yl)-2,5-dihydro-pyrrol-1-yl]-butan-1-one;
Cyclopropyl-[3-(3H-3,4,7-triaza-cyclopenta[a]naphthalen-9-yl)-2,5-dihydro-pyrrol-1-yl]-methanone;
[3-(3H-3,4,7-Triaza-cyclopenta[a]naphthalen-9-yl)-2,5-dihydro-pyrrole-1-sulfonyl]-acetonitrile;
9-[1-(2,2,2-Trifluoro-ethanesulfonyl)-2,5-dihydro-1H-pyrrol-3-yl]-3H-3,4,7-triaza-cyclopenta[a]naphthalene; and 9-(1-Methanesulfonyl-2,5-dihydro-1H-pyrrol-3-yl)-3H-3,4,7-triaza-cyclopenta[a]naphthalene.

4. A pharmaceutical composition comprising a compound of formula (Ia) as claimed in claim 1 together with a pharmaceutically acceptable carrier, optionally in combination with one or more other pharmaceutical compositions.

5. A pharmaceutical composition comprising a compound of formula (Ia) as claimed in claim 1 together with a pharmaceutically acceptable carrier, optionally in combination with one or more additional therapeutic agent selected from the group consisting of cytokine suppressive anti-inflammatory drugs, antibodies to or antagonists of other human cytokines or growth factors, IL-1, IL-2, IL-3, IL-4, IL-5, IL-6, IL-7, IL-8, IL-12, IL-15, IL-16, IL-21, IL-23, interferons, EMAP-II, GM-CSF, FGF, PDGF, CTLA or their ligands including CD 154, AdalimumaB, Infliximab, golimumab, Certolizumab Pegol, Tocilizumab, CDP 571, soluble p55 or p75 TNF receptors, Etanercept, Lenercept, TNFa converting enzyme inhibitors, IL-1 inhibitors, Interleukin 11, IL-18 antagonists, IL-12 antagonists, IL-12 antibodies, soluble IL-12 receptors, IL-12 binding proteins, non-depleting anti-CD4 inhibitors FK506, rapamycin, mycophenolate mofetil, leflunomide, NSAIDs, ibuprofen, corticosteroids, phosphodiesterase inhibitors, adenosine agonists, antithrombotic agents, complement inhibitors, adrenergic agents, IL-Iβ converting enzyme inhibitors, T-cell signalling kinase inhibitors, metalloproteinase inhibitors, sulfasalazine, 6-mercaptopurines, derivatives p75TNFRIgG, sIL-1RI, sIL-1RII, sIL-6R, celecoxib, hydroxychloroquine sulfate, rofecoxib, infliximab, naproxen, valdecoxib, sulfasalazine, meloxicam, acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, anti-ILLS, VX-740, Roflumilast, IC-485, CDC-801, S1P1 agonists, FTY720, PKC family inhibitors, Ruboxistaurin, AEB-071, Mesopram, methotrexate, leflunomide, corticosteroids, budenoside, dexamethasone, sulfasalazine, 5-aminosalicylic acid, olsalazine, IL-1β converting enzyme inhibitors, IL-1ra, T cell signaling inhibitors, tyrosine kinase inhibitors, 6-mercaptopurines, IL-11, mesalamine, prednisone, azathioprine, mercaptopurine, infliximab, methylprednisolone sodium succinate, diphenoxylate/atrop sulfate, loperamide hydrochloride, omeprazole, folate, ciprofloxacin/dextrose-water, hydrocodone, bitartrate/apap, tetracycline hydrochloride, fluocinonide, metronidazole, thimerosal/boric acid, cholestyramine/sucrose, ciprofloxacin hydrochloride, hyoscyamine sulfate, meperidine hydrochloride, midazolam hydrochloride, oxycodone HCl/acetaminophen, promethazine hydrochloride, sodium phosphate, sulfamethoxazole/trimethoprim, polycarbophil, propoxyphene napsylate, hydrocortisone, multivitamins, balsalazide disodium, codeine phosphate/apap, colesevelam HCl, cyanocobalamin, folic acid, levofloxacin, natalizumab, interferon-gamma, methylprednisolone, azathioprine, cyclophosphamide, cyclosporine, methotrexate, 4-aminopyridine, tizanidine, interferon-ia, Interferon Beta-1A, interferon-ib, Interferon Beta-1B, interferon a-n3, interferon-a, interferon βIA-IF, Peginterferon a 2b, Copolymer 1, Glatiramer Acetate, hyperbaric oxygen, intravenous immunoglobulin, cladribine, cyclosporine, FK506, mycophenolate mofetil, leflunomide, NSAIDs, corticosteroids, prednisolone, phosphodiesterase inhibitors, adensosine agonists, antithrombotic agents, complement inhibitors, adrenergic agents, antiinflammatory cytokines, interferon-β, IFN ia, IFN ib, Copaxone, corticosteroids, caspase inhibitors, inhibitors of caspase-1, antibodies to CD40 ligand and CD80, alemtuzumab, dronabinol, daclizumab, mitoxantrone, xaliproden hydrochloride, fampridine, glatiramer acetate, natalizumab, sinnabidol, a-immunokine NNS03, ABR-215062, AnergiX.MS, chemokine receptor antagonists, BBR-2778, calagualine, CPI-1189, liposome encapsulated mitoxantrone, THC.CBD, cannabinoid agonists, MBP-8298, mesopram, MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists, interferon gamma antagonist, IL-4 agonists, Diclofenac, Misoprostol, naproxen, Meloxicam, indomethacin, Diclofenac, Methotrexate, Azathioprine, Minocycline, prednisone, etanercept, Rofecoxib, Sulfasalazine, naproxen, leflunomide, methylprednisolone acetate, indomethacin, hydroxychloroquine sulfate, prednisone, sulindac, betamethasone diprop augmented, infliximab, Methotrexate, folate, Triamcinolone acetonide, Diclofenac, dimethylsulfoxide, Piroxicam, Diclofenac Sodium, ketoprofen, Meloxicam, methylprednisolone, nabumetone, tolmetin Sodium, calcipotriene, cyclosporine, Diclofenac Sodium/Misoprostol, fluocinonide, glucosamine sulfate, Sodium gold thiomalate, hydrocodone bitartrate/Apap, Sodium risedronate, sulfadiazine, thioguanine, valdecoxib, alefacept, and efalizumab, Diclofenac, naproxen, ibuprofen, Piroxicam, indomethacin, COX2 Inhibitors, Rofecoxib, valdecoxib, hydroxychloroquine, Steroids, Prednisolone, budenoside, Dexamethasone, cytotoxics, Azathioprine, cyclophosphamide, mycophenolate mofetil, Inhibitors of PDE4, purine synthesis Inhibitor, Sulfasalazine, 5-aminosalicylic acid, olsalazine, Azathioprine, CTLA-4-IgG, anti-B7 family antibodies, anti-PD-1 family antibodies, anti-cytokine antibodies, fonotolizumab, Antibody anti-IFNg, anti-receptor receptor antibodies, anti-IL-6 receptor Antibody, antibodies to B-cell Surface molecules, LJP 394, rituximab, anti-CD20 Antibody and B-lymphostat.

* * * * *